(12) United States Patent
Robichaud et al.

(10) Patent No.: US 7,081,455 B2
(45) Date of Patent: Jul. 25, 2006

(54) SUBSTITUTED HETEROCYCLE FUSED GAMMA-CARBOLINES

(75) Inventors: Albert J. Robichaud, Ringoes, NJ (US); Taekyu Lee, Doylestown, PA (US); Wei Deng, Lexington, MA (US); Ian S. Mitchell, Lafayette, CO (US); Wenting Chen, Langhorne, PA (US); Christopher D. McClung, Chicago, IL (US); Emilie J. Calvello, Baltimore, MD (US); David M. Zawrotny, Ann Arbor, MI (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/786,935

(22) Filed: Feb. 25, 2004

(65) Prior Publication Data

US 2004/0209864 A1 Oct. 21, 2004

Related U.S. Application Data

(60) Continuation-in-part of application No. 10/370,872, filed on Feb. 20, 2003, now abandoned, which is a division of application No. 09/594,008, filed on Jun. 15, 2000, now Pat. No. 6,548,493.

(60) Provisional application No. 60/139,321, filed on Jun. 15, 1999.

(51) Int. Cl.
*A61P 25/00* (2006.01)
(52) U.S. Cl. .............................. 514/212.05; 514/212.06; 514/214.02; 514/214.03; 514/286; 514/288
(58) Field of Classification Search .......... 514/212.05, 514/212.06, 214.02, 214.03, 286, 288
See application file for complete search history.

(56) References Cited

U.S. PATENT DOCUMENTS

| | | | |
|---|---|---|---|
| 3,299,078 | A | 1/1967 | Pachter |
| 5,512,575 | A | 4/1996 | Jacobs et al. |
| 5,654,139 | A | 8/1997 | Lappalainen et al. |
| 5,902,815 | A | 5/1999 | Olney et al. |
| 5,908,830 | A | 6/1999 | Smith et al. |
| 6,107,324 | A | 8/2000 | Behan et al. |
| 6,140,509 | A | 10/2000 | Behan et al. |

OTHER PUBLICATIONS

Bickerdike MJ, Vickers, SP, Dourish CT, (1999) 5-HT2C receptor modulation and the treatment of obesity. Diabetes, Obesity and Metabolism 1:207-2140.
Tecott LH, et al. (1995) Eating disorder and epilepsy in mice lacking 5-HT2C serotonin receptors. Nature (London) 374:542-546.
Cryan JF, Lucki I, (2000) Antidepressant-like behavioral effects mediated by 5-hydroxytryptamine2C receptors. J. Pharmacol. Exper. Ther. 295:1120-1126.
Millan MJ, Peglion JL, Lavielle G, Perrin-Monneyron S, (1997) 5-HT2C receptors mediate penile erection in rats: actions of novel and selective agonists and antagonists. Eur. J. Pharmacol. 325:9-12.
Martin JR, et al. (1998) 5-HT2C receptor agonists: Pharmacological characteristics and therapeutic potential. J. Pharmacol. Exper. Ther. 286:913-924.
Meltzer HY. (1999) The role of serotonin in antipsychotic drug action. Neuropsychopharmacology 21(2):1065-1155.
Curzon et al, Appetite suppression by commonly used drugs depends on 5-HT receptors but not on 5-HT availability, TiPS, vol. 18, 1997; 21-25.
Mora et al, Role of 5-HT2A and 5-HT2C Receptor subtypes in the Two Types of Fear Generated by the Elevated T-Maze, Pharma. Biolchem. & Behavior, vol. 58, No. 4, 1997; 1051-1057.
Jenck et al, Antiaversive effects of 5HT2C receptor agonists and fluoxetine in a model of panic-like anxiety in rats, European Neuropsychopharmacology, 8, 1998; 161-168.
Leysen, Selective 5-HT2c agonists as potential antidepressants, Drugs, 1999, 2(2); 109-120.
Jenck et al, The role of 5-HT2c receptors in affective disorders, Exp. Opin. Invest. Drugs, 1998, 7(10); 1587-1599.

(Continued)

*Primary Examiner*—Bruck Kifle
(74) *Attorney, Agent, or Firm*—Sammy G. Duncan, Jr.

(57) ABSTRACT

The present invention is directed to methods of treating addictive behavior and sleep disorders by administering compounds represented by structural Formula (I)

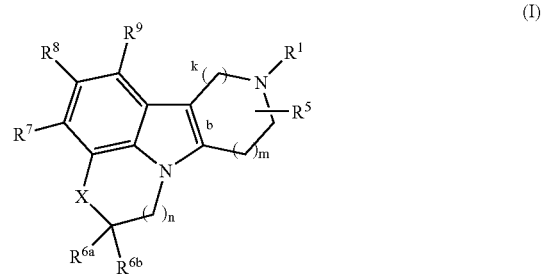

(I)

or pharmaceutically acceptable salt forms thereof, wherein $R^1$, $R^5$, $R^{6a}$, $R^{6b}$, $R^7$, $R^8$, $R^9$, X, b, k, m, and n, and the dashed lines are described herein. The compounds used in the method of treatment of this invention are serotonin agonists and antagonists and are useful in the control or prevention of central nervous system disorders including addictive behavior and sleep disorders.

17 Claims, No Drawings

OTHER PUBLICATIONS

Kennett, 5-HT drugs and eating disorders, I Drugs, 1998, vol. 1, No. 4; 456-470.

Brewerton, Induction of migrainelike headaches by the serotonin agonist m-chlorophenylpiperazine, Clin. Pharmacol. Ther., 1988, 605-609.

Kahn et al, m-Chlorophenylpiperazine as a probe of serotonin function, Biol. Psychiatry, 1991; 30: 1139-1166.

Gibson et al, Evidence that mCPP-induced Anxiety in the Plus-maze is mediated by Postsynaptic 5-Ht2c receptors but not by sympathomimetic effects, Neuropharmacology, vol. 33, No. 3, 4, 1994; 457-465.

SUBSTITUTED HETEROCYCLE FUSED GAMMA-CARBOLINES

CROSS-REFERENCE TO RELATED APPLICATIONS

This application is a continuation-in-part of U.S. patent application Ser. No. 10/370,872 filed on Feb. 20, 2003 now abandoned which is a divisional of U.S. patent application Ser. No. 09/594,008 filed on Jun. 15, 2000, now U.S. Pat. No. 6,548,493, which claims priority from U.S. Provisional Application No. 60/139,321 filed Jun. 15, 1999.

FIELD OF THE INVENTION

The present invention is directed to certain novel compounds represented by structural Formula (I)

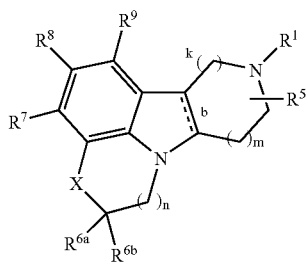

or pharmaceutically acceptable salt forms thereof, wherein $R^1$, $R^5$, $R^{6a}$, $R^{6b}$, $R^7$, $R^8$, $R^9$, X, b, k, m, and n, and the dashed lines are described herein. The invention is also concerned with pharmaceutical formulations comprising these novel compounds as active ingredients and the use of the novel compounds and their formulations in the treatment of certain disorders. The compounds of this invention are serotonin agonists and antagonists and are useful in the control or prevention of central nervous system disorders including obesity, anxiety, depression, psychosis, schizophrenia, sleep disorders, sexual disorders, migraine, conditions associated with cephalic pain, social phobias, and gastrointestinal disorders such as dysfunction of the gastrointestinal tract motility.

BACKGROUND OF THE INVENTION

There exists a substantial correlation for the relationship between 5-HT2 receptor modulation and a variety of diseases and therapies. To date, three subtypes of the 5-HT2 receptor class have been identified, 5-HT2A, 5-HT2B, and 5-HT2C. Prior to the early 1990's the 5-HT2C and 5-HT2A receptors were referred to as 5-HT1C and 5-HT2, respectively.

The agonism or antagonism of 5-HT2 receptors, either selectively or nonselectively, has been associated with the treatment of various central nervous system (CNS) disorders. Ligands possessing affinity for the 5-HT2 receptors have been shown to have numerous physiological and behavioral effects (Trends in Pharmacological Sciences, 11, 181, 1990). In the recent past the contribution of serotonergic activity to the mode of action of antidepressant drugs has been well documented. Compounds that increase the overall basal tone of serotonin in the CNS have been successfully developed as antidepressants. The serotonin selective reuptake inhibitors (SSRI) function by increasing the amount of serotonin present in the nerve synapse. These breakthrough treatments, however, are not without side effects and suffer from delayed onset of action (Leonard, J. Clin. Psychiatry, 54(suppl), 3, 1993). Due to the mechanism of action of the SSRIS, they effect the activity of a number of serotonin receptor subtypes. This non-specific modulation of the serotonin family of receptors most likely plays a significant role in the side effect profile. In addition, these compounds often have a high affinity for a number of the serotonin receptors as well as a multitude of other monoamine neurotransmitters and nuisance receptors. Removing some of the receptor cross reactivity would allow for the examination and possible development of potent therapeutic ligands with an improved side effect profile.

There is ample evidence to support the role of selective 5-HT2 receptor ligands in a number of disease therapies. Modulation of 5-HT2 receptors has been associated with the treatment of schizophrenia and psychoses (Ugedo, L., et. al., Psychopharmacology, 98, 45, 1989). Mood, behavior and hallucinogenesis can be affected by 5-HT2 receptors in the limbic system and cerebral cortex. 5-HT2 receptor modulation in the hypothalamus can influence appetite, thermoregulation, sleep, sexual behavior, motor activity, and neuroendocrine function (Hartig, P., et. al., Annals New York Academy of Science, 149, 159). There is also evidence indicating that 5-HT2 receptors mediate hypoactivity, effect feeding in rats, and mediate penile erections (Pyschopharmacology, 101, 57, 1990).

Compounds exhibiting selectivity for the 5-HT2B receptor are useful in treating conditions such as tachygastria, hypermotility associated with irritable bowel disorder, constipation, dyspepsia, and other peripherally mediated conditions.

5-HT2A antagonists have been shown to be effective in the treatment of schizophrenia, anxiety, depression, and migraines (Koek, W., Neuroscience and Behavioral reviews, 16, 95, 1996). Aside from the beneficial antipsychotic effects, classical neuroleptic are frequently responsible for eliciting acute extrapyramidal side effects and neuroendocrine disturbances. These compounds generally possess signifcant dopamine D2 receptor affinity (as well as other nuisance receptor affinity) which frequently is associated with extra pyramidal symptoms and tardive dyskinesia, thus detracting from their efficacy as front line treatments in schizophrenia and related disorders. Compounds possessing a more favorable selectivity profile would represent a possible improvement for the treatment of CNS disorders.

Serotonin (5HT) may have a critical role in the regulation of some drug-induced addictive behaviors. Serotonin is involved in neuronal processes related to inhibitory control and impulsivity. (Roy et al., Acta Psychiotr. Scand. 78 (1988) 529–535; Soubrie et al., Behav. Brain. Sci. 9 (1986) 319–364) Some studies have implicated serotonergic mechanisms in the development or expression of drug-induced sensitization (King et al., Psychopharmacology 130 (1997) 159–165; Olausson et al., Psychopharmacology 142 (1999) 111–119) The relationship between 5HT and impulsive behavior as well as drug intake has been described, and manipulations that attenuate 5HT neurotransmission both increase impulsive behavior (Roy et al., Acta Psychiotr. Scand. 78 (1988) 529–535; Soubrie et al., Behav. Brain. Sci. 9 (1986) 319–364) and elevate the intake of various drugs of abuse (Engel et al., in Naranjo, C. A., Sellers, E. M. (Eds.). Novel Pharmacological Interventions for Alcoholism, Springer, N.Y., pp. 68–82 (1999); Roberts et al., Pharmacol. Biochem. Behav. 49 (1994) 177–182)

A series of animal investigations have reported that central 5HT2 receptors are related to the many symptoms associated with drug-dependent withdrawal. Withdrawal from chronic exposure to low doses of cocaine causes reversible supersensitivity of 5HT2 receptors in mice. (Baumann et al., Neuropharmacology 35 (1996) 295–301; Darmani et al., Neurotoxicol. Tertol. 22 (2000) 61–69) Moreover, the 5HT2 receptor antagonists, ketanserin and mianserin, block or attenuate morphine withdrawal syndrome in rats. (Neal et al., J. Pharmacol. Exp. Ther. 236 (1986) 157–165; Neal et al., Eur. J. Pharmacol. 132 (1986) 299–304) The effects of 5HT receptor agonists on the behavioral and neurochemical consequences of repeated nicotine treatment have also been studied. (Olausson et al., Eur. J. Pharmacol. 420 (2001) 45–54) The results of that study provided evidence that repeated daily nicotine treatment is associated with both locomotor sensitization and behavioral disinhibition, and that the expression of those behaviors can be modulated by specific agonists at 5HT receptor subtypes.

Studies with experimental animals have shown that nicotine withdrawal leads to increased sensitivity of serotonergic neurons in the dorsal raphe to 5HT1A agonists in rats. (Rasmussen et al., Psychopharmacology (Berl) 133 (1997) 343–346) Other findings suggest that cessation of chronic nicotine increases the sensitivity to 5HT2 receptor systems, and that the 5HT2 receptor systems may be related to some aspect of the nicotine withdrawal syndrome. (Suemaru et al., Psychopharmacology (Berl) 159 (2001) 31–38) Other studies have also examined the effect of nicotine cessation on the central serotonergic systems in mice and the involvement of 5HT2 receptors. (Yasuda et al., Naunyn-Schmiedeberg's Arch. Pharmacol. 366 (2002) 276–281) The studies by Yasuda et al. suggested that cessation of repeated nicotine administration resulted in increased sensitivity to 5HT2 receptor systems and decreased 5HT2 turnover, and that these phenomena may be related to the manifestation of nicotine withdrawal symptoms.

Modulation of the 5-HT2 receptors has been observed to play a role in sleep disorders. Ritanserin, a selective 5HT2 receptor antagonist, massively enhances slow save sleep (stage 3 and 4) in humans (Declerck et al., Curr. Ther. Res. 41 (1987)427–432; Idzikowsky et al., Psychopharmacology 93 (1987) 416–420; Ikzikowsky et al., Brain Res. 378 (1986) 164–168) and increases deep slow wave sleep in rats. (Detari et al., Psychopharmacology 142 (1999) 318–326; Dugovic et al., Eur. J. Pharmaol. 137 (1987) 145–146; Kantor et al., J. Physiol. 526 (2000) 66–67) Ritanserin and other 5HT2 receptor antagonists increase low frequency EEG activity administered at the beginning of the passive phase of sleep, that is in the light period in rats (Borbely et al., Eur. J. Pharmacol. 156 (1988) 275–278) and in the dark period in humans (Dijk et al., Eur. J. Pharmacol. 171 (1989) 207–218).

The effects of the 5HT2 receptor antagonist ritanserin on electroencephalogram (EEG) power spectra, sleep and motor activity have also been studied. (Kantor et al., Brain Research 943 (2002) 105–111) The studies by Kantor et al. showed that the 5HT2 receptor antagonist ritanserin has longterm effects on EEG power spectra, sleep and motility. Kantor et al. concluded that because ritanserin is a 5HT2 receptor antagonist, under physiological conditions, serotonin increases electroencephalogram (EEG) synchronization and produces an increase in vigilance level and motor activity by tonic activation of 5HT2 receptors. The proposed regulatory mechanism plays an important role in the waking process and the appearances of its effects in the light and dark phases were markedly different.

U.S. Pat. Nos. 3,914,421; 4,013,652; 4,115,577; 4,183,936; and 4,238,607 disclose pyridopyrrolobenz-heterocycles of formula:

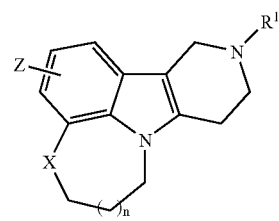

where X is O, S, S(═O), or $SO_2$; n is 0 or 1; $R^1$ is various carbon substituents, and Z is a monosubstituent of H, methyl, or chloro.

U.S. Pat. No. 4,219,550 discloses pyridopyrrolo-benzheterocycles of formula:

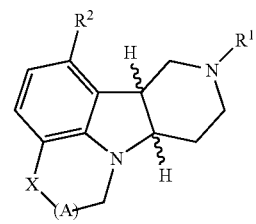

where X is O or S; $R^1$ is $C_{1-4}$ alkyl or cyclopropyl; $R^2$ is H, $CH_3$, $OCH_3$, Cl, Br, F, or $CF_3$; and (A) is —$CH_2$—, —$CH(CH_3)$—, or —$CH_2CH_2$—.

SUMMARY OF THE INVENTION

One object of the present invention is to provide methods for treating central nervous system disorders including addictive behavior and sleep disorders, comprising administering to a host in need of such treatment a therapeutically effective amount of compounds which are useful as agonists or antagonists of 5-HT2 receptors, more specifically 5-HT2A and 5-HT2C receptors, or pharmaceutically acceptable salts or prodrugs thereof.

This and other objects, which will become apparent during the following detailed description, have been achieved by the inventors' discovery that compounds of Formula (I):

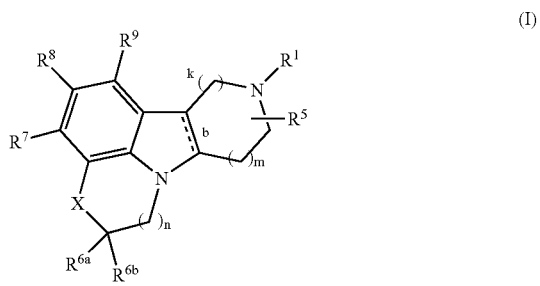

or pharmaceutically acceptable salt or prodrug forms thereof, wherein $R^1$, $R^5$, $R^{6a}$, $R^{6b}$, $R^7$, $R^8$, $R^9$, X, b, k, m, and n are defined below, are effective agonists or antagonists of 5-HT2 receptors and can be used in the treatment of central nervous system disorders including addictive behavior and sleep disorders.

DETAILED DESCRIPTION OF THE EMBODIMENTS

Thus, in a first embodiment, the present invention provides a method for treating a human suffering from addictive behavior associated with 5HT2C receptor modulation, comprising administering to a patient in need thereof a therapeutically effective amount of a compound of formula (I):

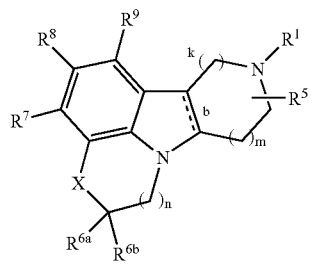

(I)

or stereoisomers or pharmaceutically acceptable salt forms thereof, wherein:
b is a single bond;
X is —$CHR^{10}$— or —C(=O)—;
$R^1$ is selected from
  H,
  C(=O)$R^2$,
  C(=O)O$R^2$,
  $C_{1-8}$ alkyl,
  $C_{2-8}$ alkenyl,
  $C_{2-8}$ alkynyl,
  $C_{3-7}$ cycloalkyl,
  $C_{1-6}$ alkyl substituted with Z,
  $C_{2-6}$ alkenyl substituted with Z,
  $C_{2-6}$ alkynyl substituted with Z,
  $C_{3-6}$ cycloalkyl substituted with Z,
  aryl substituted with Z,
  5–6 membered heterocyclic ring system containing at least one heteroatom selected from the group consisting of N, O, and S, said heterocyclic ring system substituted with Z;
  $C_{1-3}$ alkyl substituted with Y,
  $C_{2-3}$ alkenyl substituted with Y,
  $C_{2-3}$ alkynyl substituted with Y,
  $C_{1-6}$ alkyl substituted with 0–2 $R^2$,
  $C_{2-6}$ alkenyl substituted with 0–2 $R^2$,
  $C_{2-6}$ alkynyl substituted with 0–2 $R^2$,
  aryl substituted with 0–2 $R^2$, and
  5–6 membered heterocyclic ring system containing at least one heteroatom selected from the group consisting of N, O, and S, said heterocyclic ring system substituted with 0–2 $R^2$;
Y is selected from
  $C_{3-6}$ cycloalkyl substituted with Z,
  aryl substituted with Z,
  5–6 membered heterocyclic ring system containing at least one heteroatom selected from the group consisting of N, O, and S, said heterocyclic ring system substituted with Z;
  $C_{3-6}$ cycloalkyl substituted with —($C_{1-3}$ alkyl)-Z,
  aryl substituted with —($C_{1-3}$ alkyl)-Z, and
  5–6 membered heterocyclic ring system containing at least one heteroatom selected from the group consisting of N, O, and S, said heterocyclic ring system substituted with —($C_{1-3}$ alkyl)-Z;
Z is selected from H,
  —CH(OH)$R^2$,
  —C(ethylenedioxy)$R^2$,
  —O$R^2$,
  —S$R^2$,
  —N$R^2R^3$,
  —C(O)$R^2$,
  —C(O)N$R^2R^3$,
  —$NR^3$C(O)$R^2$,
  —C(O)O$R^2$,
  —OC(O)$R^2$,
  —CH(=N$R^4$)N$R^2R^3$,
  —NHC(=N$R^4$)N$R^2R^3$,
  —S(O)$R^2$,
  —S(O)$_2R^2$,
  —S(O)$_2$N$R^2R^3$, and —$NR^3$S(O)$_2R^2$;
$R^2$, at each occurrence, is independently selected from
  halo,
  $C_{1-3}$ haloalkyl,
  $C_{1-4}$ alkyl,
  $C_{2-4}$ alkenyl,
  $C_{2-4}$ alkynyl,
  $C_{3-6}$ cycloalkyl,
  aryl substituted with 0–5 $R^{42}$;
  $C_{3-10}$ carbocyclic group substituted with 0–3 $R^{41}$, and
  5–10 membered heterocyclic ring system containing from 1–4 heteroatoms selected from the group consisting of N, O, and S substituted with 0–3 $R^{41}$;
$R^3$, at each occurrence, is independently selected from
  H, $C_{1-4}$ alkyl, $C_{2-4}$ alkenyl, $C_{2-4}$ alkynyl, and
  $C_{1-4}$ alkoxy;
alternatively, $R^2$ and $R^3$ join to form a 5- or 6-membered ring optionally substituted with —O— or —N($R^4$)—;
$R^4$, at each occurrence, is independently selected from H and $C_{1-4}$ alkyl;
$R^5$ is H or $C_{1-4}$ alkyl;
$R^{6a}$ and $R^{6b}$, at each occurrence, are independently selected from
  H, —OH, —N$R^{46}R^{47}$, —$CF_3$, $C_{1-4}$ alkyl, $C_{2-4}$ alkenyl, $C_{2-4}$ alkynyl, $C_{1-4}$ alkoxy, $C_{1-4}$ haloalkyl, $C_{3-6}$ cycloalkyl, and
  aryl substituted with 0–3 $R^{44}$;
$R^7$ and $R^9$, at each occurrence, are independently selected from
  H, halo, —$CF_3$, —$OCF_3$, —OH, —CN, —$NO_2$, —N$R^{46}R^{47}$,
  $C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy,
  $C_{3-10}$ cycloalkyl substituted with 0–2 $R^{33}$,
  $C_{1-4}$ alkyl substituted with 0–2 $R^{11}$,
  $C_{3-10}$ carbocyclic group substituted with 0–3 $R^{33}$,
  aryl substituted with 0–5 $R^{33}$,
  5–10 membered heterocyclic ring system containing from 1–4 heteroatoms selected from the group consisting of N, O, and S substituted with 0–3 $R^{31}$;
  O$R^{12}$, S$R^{12}$, N$R^{12}R^{13}$, C(O)H, C(O)$R^{12}$, C(O)N$R^{12}R^{13}$, $NR^{14}$C(O)$R^{12}$, C(O)O$R^{12}$, OC(O)$R^{12}$, OC(O)O$R^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(O)OR$^{15}$, NR$^{12}$S(O)$_2$R$^{15}$, and NR$^{12}$C(O)NHR$^{15}$;

R$^8$ is selected from
H, halo, —CF$_3$, —OCF$_3$, —OH, —CN, —NO$_2$,
C$_{1-8}$ alkyl, C$_{2-8}$ alkenyl, C$_{2-8}$ alkynyl, C$_{1-4}$ haloalkyl, C$_{1-8}$ alkoxy, (C$_{1-4}$ haloalkyl)oxy,
C$_{3-10}$ cycloalkyl substituted with 0–2 R$^{33}$,
C$_{1-4}$ alkyl substituted with 0–2 R$^{11}$,
C$_{2-4}$ alkenyl substituted with 0–2 R$^{11}$,
C$_{2-4}$ alkynyl substituted with 0–1 R$^{11}$,
C$_{3-10}$ carbocyclic group substituted with 0–3 R$^{33}$,
aryl substituted with 0–5 R$^{33}$,
5–10 membered heterocyclic ring system containing from 1–4 heteroatoms selected from the group consisting of N, O, and S substituted with 0–3 R$^{31}$;
OR$^{12}$, SR$^{12}$, NR$^{12}$R$^{13}$, C(O)H, C(O)R$^{12}$, C(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(O)OR$^{15}$, NR$^{12}$S(O)$_2$R$^{15}$, and NR$^{12}$C(O)NHR$^{15}$;

R$^{10}$ is selected from H, —OH,
C$_{1-6}$ alkyl substituted with 0–1 R$^{10B}$,
C$_{2-6}$ alkenyl substituted with 0–1 R$^{10B}$,
C$_{2-6}$ alkynyl substituted with 0–1 R$^{10B}$, and
C$_{1-6}$ alkoxy;

R$^{10B}$ is selected from
C$_{1-4}$ alkoxy,
C$_{3-6}$ cycloalkyl,
C$_{3-10}$ carbocyclic group substituted with 0–3 R$^{33}$,
phenyl substituted with 0–3 R$^{33}$, and
5–6 membered heterocyclic ring system containing 1, 2, or 3 heteroatoms selected from the group consisting of N, O, and S substituted with 0–2 R$^{44}$;

R$^{11}$ is selected from
H, halo, —CF$_3$, —CN, —NO$_2$,
C$_{1-8}$ alkyl, C$_{2-8}$ alkenyl, C$_{2-8}$ alkynyl, C$_{1-4}$ haloalkyl, C$_{1-8}$ alkoxy, C$_{3-10}$ cycloalkyl,
C$_{3-10}$ carbocyclic group substituted with 0–3 R$^{33}$,
aryl substituted with 0–5 R$^{33}$,
5–10 membered heterocyclic ring system containing from 1–4 heteroatoms selected from the group consisting of N, O, and S substituted with 0–3 R$^{31}$;
OR$^{12}$, SR$^{12}$, NR$^{12}$R$^{13}$, C(O)H, C(O)R$^{12}$, C(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(O)OR$^{15}$, NR$^{12}$S(O)$_2$R$^{15}$, and NR$^{12}$C(O)NHR$^{15}$;

R$^{12}$, at each occurrence, is independently selected from
C$_{1-4}$ alkyl substituted with 0–1 R$^{12a}$,
C$_{2-4}$ alkenyl substituted with 0–1 R$^{12a}$,
C$_{2-4}$ alkynyl substituted with 0–1 R$^{12a}$,
C$_{3-6}$ cycloalkyl substituted with 0–3 R$^{33}$,
phenyl substituted with 0–5 R$^{33}$;
C$_{3-10}$ carbocyclic group substituted with 0–3 R$^{33}$, and
5–10 membered heterocyclic ring system containing from 1–4 heteroatoms selected from the group consisting of N, O, and S substituted with 0–3 R$^{31}$;

R$^{12a}$, at each occurrence, is independently selected from
phenyl substituted with 0–5 R$^{33}$;
C$_{3-10}$ carbocyclic group substituted with 0–3 R$^{33}$, and
5–10 membered heterocyclic ring system containing from 1–4 heteroatoms selected from the group consisting of N, O, and S substituted with 0–3 R$^{31}$;

R$^{13}$, at each occurrence, is independently selected from
H, C$_{1-4}$ alkyl, C$_{2-4}$ alkenyl, and C$_{2-4}$ alkynyl;
alternatively, R$^{12}$ and R$^{13}$ join to form a 5- or 6-membered ring optionally substituted with —O— or —N(R$^{14}$)—;
alternatively, R$^{12}$ and R$^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 R$^{16}$;

R$^{14}$, at each occurrence, is independently selected from H and C$_{1-4}$ alkyl;

R$^{15}$, at each occurrence, is independently selected from H, C$_{1-4}$ alkyl, C$_{2-4}$ alkenyl, and C$_{2-4}$ alkynyl;

R$^{16}$, at each occurrence, is independently selected from
H, OH, halo, CN, NO$_2$, CF$_3$, SO$_2$R$^{45}$, NR$^{46}$R$^{47}$, —C(=O)H, C$_{1-4}$ alkyl, C$_{2-4}$ alkenyl, C$_{2-4}$ alkynyl, C$_{1-4}$ haloalkyl, C$_{1-3}$ haloalkyl-oxy-, and C$_{1-3}$ alkyloxy-;

R$^{31}$, at each occurrence, is independently selected from
H, OH, halo, CF$_3$, SO$_2$R$^{45}$, NR$^{46}$R$^{47}$, and C$_{1-4}$ alkyl;

R$^{33}$, at each occurrence, is independently selected from
H, OH, halo, CN, NO$_2$, CF$_3$, SO$_2$R$^{45}$, NR$^{46}$R$^{47}$, —C(=O)H,
C$_{1-6}$ alkyl, C$_{2-6}$ alkenyl, C$_{2-6}$ alkynyl,
C$_{3-6}$ cycloalkyl, C$_{1-4}$ haloalkyl, C$_{1-4}$ haloalkyl-oxy-, C$_{1-4}$ alkyloxy-,
C$_{1-4}$ alkylthio-, C$_{1-4}$ alkyl-C(=O)—, C$_{1-4}$ alkyl-C(=O)NH—, C$_{1-4}$ alkyl-OC(=O)—,
C$_{1-14}$ alkyl-C(=O)O—, C$_{3-6}$ cycloalkyl-oxy-, C$_{3-6}$ cycloalkylmethyl-oxy-;
C$_{1-6}$ alkyl substituted with OH, methoxy, ethoxy, propoxy, or butoxy; and
C$_{2-6}$ alkenyl substituted with OH, methoxy, ethoxy, propoxy, or butoxy;

R$^{41}$, at each occurrence, is independently selected from
H, CF$_3$, halo, OH, CO$_2$H, SO$_2$R$^{45}$, NR$^{46}$R$^{47}$, NO$_2$, CN, =O;
C$_{2-8}$ alkenyl, C$_{2-8}$ alkynyl, C$_{1-4}$ alkoxy, C$_{1-4}$ haloalkyl
C$_{1-4}$ alkyl substituted with 0–1 R$^{43}$,
aryl substituted with 0–3 R$^{42}$, and
5–10 membered heterocyclic ring system containing from 1–4 heteroatoms selected from the group consisting of N, O, and S substituted with 0–3 R$^{44}$;

R$^{42}$, at each occurrence, is independently selected from
H, CF$_3$, halo, OH, CO$_2$H, SO$_2$R$^{45}$, SOR$^{45}$, SR$^{45}$, NR$^{46}$SO$_2$R$^{45}$, NR$^{46}$COR$^{45}$, NR$^{46}$R$^{47}$, NO$_2$, CN, CH(=NH)NH$_2$, NHC(=NH)NH$_2$,
C$_{2-6}$ alkenyl, C$_{2-6}$ alkynyl, C$_{1-4}$ alkoxy, C$_{1-4}$ haloalkyl, C$_{3-6}$ cycloalkyl,
C$_{1-4}$ alkyl substituted with 0–1 R$^{43}$,
aryl substituted with 0–3 R$^{44}$, and
5–10 membered heterocyclic ring system containing from 1–4 heteroatoms selected from the group consisting of N, O, and S substituted with 0–3 R$^{44}$;

R$^{43}$ is C$_{3-6}$ cycloalkyl or aryl substituted with 0–3 R$^{44}$;

R$^{44}$, at each occurrence, is independently selected from H, halo, —OH, NR$^{46}$R$^{47}$,
CO$_2$H, SO$_2$R$^{45}$, —CF$_3$, —OCF$_3$, —CN, —NO$_2$, C$_{1-4}$ alkyl, and C$_{1-4}$ alkoxy;

R$^{45}$ is C$_{1-4}$ alkyl;

R$^{46}$, at each occurrence, is independently selected from H and C$_{1-4}$ alkyl;

R$^{47}$, at each occurrence, is independently selected from H, C$_{1-4}$ alkyl, —C(=O)NH($C_{1-4}$ alkyl), —SO$_2$($C_{1-4}$ alkyl), —C(=O)O($C_{1-4}$ alkyl), —C(=O)($C_{1-4}$ alkyl), and —C(=O)H;

k is 1 or 2;
m is 0, 1, or 2;
n is 0, 1, 2, or 3;
provided when m is 0 or 1 then k is 1 or 2;
provided when m is 2 then k is 1;
provided that when $R^6$ or $R^{6a}$ is NH$_2$, then X is not —CH($R^{10}$); and provided that when n=0, then $R^6$ or $R^{6a}$ is not NH$_2$ or —OH.

In a preferred embodiment, the present invention provides the method as defined in claim 1 where in the compound administered:

X is —CHR$^{10}$— or —C(=O)—;
$R^1$ is selected from
  H,
  C(=O)R$^2$,
  C(=O)OR$^2$,
  $C_{1-8}$ alkyl,
  $C_{2-8}$ alkenyl,
  $C_{2-8}$ alkynyl,
  $C_{3-7}$ cycloalkyl,
  $C_{1-6}$ alkyl substituted with 0–2 R$^2$,
  $C_{2-6}$ alkenyl substituted with 0–2 R$^2$,
  $C_{2-6}$ alkynyl substituted with 0–2 R$^2$,
  aryl substituted with 0–2 R$^2$, and
  5–6 membered heterocyclic ring system containing at least one heteroatom selected from the group consisting of N, O, and S, said heterocyclic ring system substituted with 0–2 R$^2$;
$R^2$, at each occurrence, is independently selected from
  F, Cl, CH$_2$F, CHF$_2$, CF$_3$,
  $C_{1-4}$ alkyl,
  $C_{2-4}$ alkenyl,
  $C_{2-4}$ alkynyl,
  $C_{3-6}$ cycloalkyl,
  phenyl substituted with 0–5 R$^{42}$;
  $C_{3-10}$ carbocyclic group substituted with 0–3 R$^{41}$, and
  5–10 membered heterocyclic ring system containing from 1–4 heteroatoms selected from the group consisting of N, O, and S substituted with 0–3 R$^{41}$;
$R^5$ is H, methyl, ethyl, propyl, or butyl;
$R^{6a}$ is selected from
  H, —OH, —NR$^{46}$R$^{47}$, —CF$_3$,
  $C_{1-4}$ alkyl, $C_{1-4}$ alkoxy, $C_{1-4}$ haloalkyl, and
  aryl substituted with 0–3 R$^{44}$;
$R^{6b}$ is H;
$R^7$ and $R^9$, at each occurrence, are independently selected from
  H, halo, —CF$_3$, —OCF$_3$, —OH, —CN, —NO$_2$, —NR$^{46}$R$^{47}$,
  $C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy,
  $C_{3-10}$ cycloalkyl substituted with 0–2 R$^{33}$,
  $C_{1-4}$ alkyl substituted with 0–2 R$^{11}$,
  $C_{3-10}$ carbocyclic group substituted with 0–3 R$^{33}$,
  aryl substituted with 0–5 R$^{33}$,
  5–10 membered heterocyclic ring system containing from 1–4 heteroatoms selected from the group consisting of N, O, and S substituted with 0–3 R$^{31}$;
  OR$^{12}$, SR$^{12}$, NR$^{12}$R$^{13}$, C(O)H, C(O)R$^{12}$, C(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(O)OR$^{15}$, NR$^{12}$S(O)$_2$R$^{15}$, and NR$^{12}$C(O)NHR$^{15}$;

$R^8$ is selected from
  H, halo, —CF$_3$, —OCF$_3$, —OH, —CN, —NO$_2$,
  $C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy,
  $C_{3-10}$ cycloalkyl substituted with 0–2 R$^{33}$,
  $C_{1-4}$ alkyl substituted with 0–2 R$^{11}$,
  $C_{2-4}$ alkenyl substituted with 0–2 R$^{11}$,
  $C_{2-4}$ alkynyl substituted with 0–1 R$^{11}$,
  $C_{3-10}$ carbocyclic group substituted with 0–3 R$^{33}$,
  aryl substituted with 0–5 R$^{33}$,
  5–10 membered heterocyclic ring system containing from 1–4 heteroatoms selected from the group consisting of N, O, and S substituted with 0–3 R$^{31}$;
  OR$^{12}$, SR$^{12}$, NR$^{12}$R$^{13}$, C(O)H, C(O)R$^{12}$, C(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(O)OR$^{15}$, NR$^{12}$S(O)$_2$R$^{15}$, and NR$^{12}$C(O)NHR$^{15}$;
$R^{10}$ is selected from H, —OH,
  $C_{1-6}$ alkyl substituted with 0–1 R$^{10B}$,
  $C_{2-6}$ alkenyl substituted with 0–1 R$^{10B}$,
  $C_{2-6}$ alkynyl substituted with 0–1 R$^{10B}$, and
  $C_{1-6}$ alkoxy;
$R^{10B}$ is selected from
  $C_{1-4}$ alkoxy,
  $C_{3-6}$ cycloalkyl,
  $C_{3-10}$ carbocyclic group substituted with 0–3 R$^{33}$,
  phenyl substituted with 0–3 R$^{33}$, and
  5–6 membered heterocyclic ring system containing 1, 2, or 3 heteroatoms selected from the group consisting of N, O, and S substituted with 0–2 R$^{44}$;
$R^{11}$ is selected from
  H, halo, —CF$_3$, —CN, —NO$_2$,
  $C_{1-8}$ alkyl, $C_{2-8}$ alkenyl, $C_{2-8}$ alkynyl, $C_{1-14}$ haloalkyl, $C_{1-8}$ alkoxy, $C_{3-10}$ cycloalkyl,
  $C_{3-10}$ carbocyclic group substituted with 0–3 R$^{33}$,
  aryl substituted with 0–5 R$^{33}$,
  5–10 membered heterocyclic ring system containing from 1–4 heteroatoms selected from the group consisting of N, O, and S substituted with 0–3 R$^{31}$;
  OR$^{12}$, SR$^{12}$, NR$^{12}$R$^{13}$, C(O)H, C(O)R$^{12}$, C(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(O)OR$^{15}$, NR$^{12}$S(O)$_2$R$^{15}$, and NR$^{12}$C(O)NHR$^{15}$;
$R^{12}$, at each occurrence, is independently selected from
  $C_{1-4}$ alkyl substituted with 0–1 R$^{12a}$,
  $C_{2-4}$ alkenyl substituted with 0–1 R$^{12a}$,
  $C_{2-4}$ alkynyl substituted with 0–1 R$^{12a}$,
  $C_{3-6}$ cycloalkyl substituted with 0–3 R$^{33}$,
  phenyl substituted with 0–5 R$^{33}$;
  $C_{3-10}$ carbocyclic group substituted with 0–3 R$^{33}$, and
  5–10 membered heterocyclic ring system containing from 1–4 heteroatoms selected from the group consisting of N, O, and S substituted with 0–3 R$^{31}$;
$R^{12a}$, at each occurrence, is independently selected from
  phenyl substituted with 0–5 R$^{33}$;
  $C_{3-10}$ carbocyclic group substituted with 0–3 R$^{33}$, and
  5–10 membered heterocyclic ring system containing from 1–4 heteroatoms selected from the group consisting of N, O, and S substituted with 0–3 R$^{31}$;
$R^{13}$, at each occurrence, is independently selected from
  H, $C_{1-4}$ alkyl, $C_{2-4}$ alkenyl, and $C_{2-4}$ alkynyl;
alternatively, $R^{12}$ and $R^{13}$ join to form a 5- or 6-membered ring optionally substituted with —O— or —N(R$^{14}$)—;

alternatively, $R^{12}$ and $R^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;

$R^{14}$, at each occurrence, is independently selected from H and $C_{1-4}$ alkyl;

$R^{15}$, at each occurrence, is independently selected from H, $C_{1-4}$ alkyl, $C_{2-4}$ alkenyl, and $C_{2-4}$ alkynyl;

$R^{16}$, at each occurrence, is independently selected from
  H, OH, halo, CN, $NO_2$, $CF_3$, $SO_2R^{45}$, $NR^{46}R^{47}$, —C(=O)H,
  $C_{1-4}$ alkyl, $C_{2-4}$ alkenyl, $C_{2-4}$ alkynyl, $C_{1-4}$ haloalkyl, $C_{1-3}$ haloalkyl-oxy-, and $C_{1-3}$ alkyloxy-;

$R^{31}$, at each occurrence, is independently selected from
  H, OH, halo, $CF_3$, $SO_2R^{45}$, $NR^{46}R^{47}$, and $C_{1-4}$ alkyl;

$R^{33}$, at each occurrence, is independently selected from
  H, OH, halo, CN, $NO_2$, $CF_3$, $SO_2R^{45}$, $NR^{46}R^{47}$, —C(=O)H,
  $C_{1-6}$ alkyl, $C_{2-6}$ alkenyl, $C_{2-6}$ alkynyl,
  $C_{3-6}$ cycloalkyl, $C_{1-4}$ haloalkyl, $C_{1-4}$ haloalkyl-oxy-, $C_{1-4}$ alkyloxy-,
  $C_{1-4}$ alkylthio-, $C_{1-4}$ alkyl-C(=O)—, $C_{1-4}$ alkyl-C(=O)NH—, $C_{1-4}$ alkyl-OC(=O)—,
  $C_{1-4}$ alkyl-C(=O)O—, $C_{3-6}$ cycloalkyl-oxy-, $C_{3-6}$ cycloalkylmethyl-oxy-;
  $C_{1-6}$ alkyl substituted with OH, methoxy, ethoxy, propoxy, or butoxy; and
  $C_{2-6}$ alkenyl substituted with OH, methoxy, ethoxy, propoxy, or butoxy;

$R^{41}$, at each occurrence, is independently selected from
  H, $CF_3$, halo, OH, $CO_2H$, $SO_2R^{45}$, $NR^{46}R^{47}$, $NO_2$, CN;
  $C_{2-8}$ alkenyl, $C_{2-8}$ alkynyl, $C_{1-14}$ alkoxy, $C_{1-4}$ haloalkyl
  $C_{1-4}$ alkyl substituted with 0–1 $R^{43}$,
  aryl substituted with 0–3 $R^{42}$, and
  5–10 membered heterocyclic ring system containing from 1–4 heteroatoms selected from the group consisting of N, O, and S substituted with 0–3 $R^{44}$;

$R^{42}$, at each occurrence, is independently selected from
  H, $CF_3$, halo, OH, $CO_2H$, $SO_2R^{45}$, $NR^{46}R^{47}$, $NO_2$, CN, CH(=NH)$NH_2$, NHC(=NH)$NH_2$,
  $C_{2-6}$ alkenyl, $C_{2-6}$ alkynyl, $C_{1-4}$ alkoxy, $C_{1-4}$ haloalkyl, $C_{3-6}$ cycloalkyl,
  $C_{1-4}$ alkyl substituted with 0–1 $R^{43}$,
  aryl substituted with 0–3 $R^{44}$, and
  5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$,
  $CO_2H$, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-4}$ alkyl;

$R^{47}$, at each occurrence, is independently selected from H and $C_{1-4}$ alkyl;

k is 1 or 2;

m is 0, 1, or 2; and n is 0, 1, 2, or 3.

In a more preferred embodiment, the present invention provides the method as defined in claim 2 where in the compound administered:

X is —$CHR^{10}$—;

$R^1$ is selected from
  H,
  C(=O)$R^2$,
  C(=O)$OR^2$,
  $C_{1-6}$ alkyl,
  $C_{2-6}$ alkenyl,
  $C_{2-6}$ alkynyl,
  $C_{3-6}$ cycloalkyl,
  $C_{1-4}$ alkyl substituted with 0–2 $R^2$,
  $C_{2-4}$ alkenyl substituted with 0–2 $R^2$, and
  $C_{2-4}$ alkynyl substituted with 0–2 $R^2$;

$R^2$, at each occurrence, is independently selected from
  $C_{1-4}$ alkyl,
  $C_{2-4}$ alkenyl,
  $C_{2-4}$ alkynyl,
  $C_{3-6}$ cycloalkyl,
  phenyl substituted with 0–5 $R^{42}$;
  $C_{3-10}$ carbocyclic group substituted with 0–3 $R^{41}$, and
  5–10 membered heterocyclic ring system containing from 1–4 heteroatoms selected from the group consisting of N, O, and S substituted with 0–3 $R^{41}$;

$R^5$ is H, methyl, ethyl, propyl, or butyl;

$R^{6a}$ is selected independently from
  H, —OH, —$NR^{46}R^{47}$, —$CF_3$, $C_{1-3}$ alkyl, and $C_{1-3}$ alkoxy;

$R^{6b}$ is H;

$R^7$ and $R^9$, at each occurrence, are independently selected from
  H, halo, —$CF_3$, —$OCF_3$, —OH, —CN, —$NO_2$, —$NR^{46}R^{47}$,
  $C_{1-6}$ alkyl, $C_{2-6}$ alkenyl, $C_{2-6}$ alkynyl, $C_{1-6}$ haloalkyl, $C_{1-6}$ alkoxy, ($C_{1-4}$ haloalkyl)oxy,
  $C_{3-10}$ cycloalkyl substituted with 0–2 $R^{33}$,
  $C_{1-4}$ alkyl substituted with 0–2 $R^{11}$,
  $C_{3-10}$ carbocyclic group substituted with 0–3 $R^{33}$,
  aryl substituted with 0–5 $R^{33}$,
  5–10 membered heterocyclic ring system containing from 1–4 heteroatoms selected from the group consisting of N, O, and S substituted with 0–3 $R^{31}$;
  $OR^{12}$, $SR^{12}$, $NR^{12}R^{13}$, C(O)H, C(O)$R^{12}$, C(O)$NR^{12}R^{13}$, $NR^{14}C(O)R^{12}$, C(O)$OR^{12}$, OC(O)$R^{12}$, OC(O)$OR^{12}$, CH(=$NR^{14}$)$NR^{12}R^{13}$, NHC(=$NR^{14}$)$NR^{12}R^{13}$, S(O)$R^{12}$, $S(O)_2R^{12}$, S(O)$NR^{12}R^{13}$, $S(O)_2NR^{12}R^{13}$, $NR^{14}S(O)R^{12}$, and $NR^{14}S(O)_2R^{12}$;

$R^8$ is selected from
  H, halo, —$CF_3$, —$OCF_3$, —OH, —CN, —$NO_2$,
  $C_{1-6}$ alkyl, $C_{2-6}$ alkenyl, $C_{2-6}$ alkynyl, $C_{1-6}$ haloalkyl, $C_{1-6}$ alkoxy, ($C_{1-4}$ haloalkyl)oxy,
  $C_{3-10}$ cycloalkyl substituted with 0–2 $R^{33}$,
  $C_{1-4}$ alkyl substituted with 0–2 $R^{11}$,
  $C_{2-4}$ alkenyl substituted with 0–2 $R^{11}$,
  $C_{2-4}$ alkynyl substituted with 0–1 $R^{11}$,
  $C_{3-10}$ carbocyclic group substituted with 0–3 $R^{33}$,
  aryl substituted with 0–5 $R^{33}$,
  5–10 membered heterocyclic ring system containing from 1–4 heteroatoms selected from the group consisting of N, O, and S substituted with 0–3 $R^{31}$;
  $OR^{12}$, $SR^{12}$, $NR^{12}R^{13}$, C(O)H, C(O)$R^{12}$, C(O)$NR^{12}R^{13}$, $NR^{14}C(O)R^{12}$, C(O)$OR^{12}$, OC(O)$R^{12}$, OC(O)$OR^{12}$, CH(=$NR^{14}$)$NR^{12}R^{13}$, NHC(=$NR^{14}$)$NR^{12}R^{13}$, S(O)$R^{12}$, $S(O)_2R^{12}$, S(O)$NR^{12}R^{13}$, $S(O)_2NR^{12}R^{13}$, $NR^{14}S(O)R^{12}$, $NR^{14}S(O)_2R^{12}$, $NR^{12}C(O)R^{15}$, $NR^{12}C(O)OR^{15}$, $NR^{12}S(O)_2R^{15}$, and $NR^{12}C(O)NHR^{15}$;

$R^{10}$ is selected from H, —OH,
  $C_{1-6}$ alkyl substituted with 0–1 $R^{10B}$,
  $C_{2-6}$ alkenyl substituted with 0–1 $R^{10B}$, $C_{2-6}$ alkynyl substituted with 0–1 $R^{10B}$, and
$C_{1-6}$ alkoxy;

$R^{10B}$ is selected from
$C_{1-4}$ alkoxy,
$C_{3-6}$ cycloalkyl,
$C_{3-10}$ carbocyclic group substituted with 0–3 $R^{33}$,
phenyl substituted with 0–3 $R^{33}$, and
5–6 membered heterocyclic ring system containing 1, 2, or 3 heteroatoms selected from the group consisting of N, O, and S substituted with 0–2 $R^{44}$;

$R^{11}$ is selected from
H, halo, —$CF_3$, —CN, —$NO_2$, $C_{1-6}$ alkyl,
$C_{2-6}$ alkenyl, $C_{2-6}$ alkynyl, $C_{1-4}$ haloalkyl, $C_{1-6}$ alkoxy, $C_{3-10}$ cycloalkyl,
$C_{3-10}$ carbocyclic group substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, $C(O)H$, $C(O)R^{12}$, $C(O)NR^{12}R^{13}$, $NR^{14}C(O)R^{12}$, $C(O)OR^{12}$, $OC(O)R^{12}$, $OC(O)OR^{12}$, $CH(=NR^{14})NR^{12}R^{13}$, $NHC(=NR^{14})NR^{12}R^{13}$, $S(O)R^{12}$, $S(O)_2R^{12}$, $S(O)NR^{12}R^{13}$, $S(O)_2NR^{12}R^{13}$, $NR^{14}S(O)R^{12}$, and $NR^{14}S(O)_2R^{12}$;

$R^{12}$, at each occurrence, is independently selected from
$C_{1-4}$ alkyl substituted with 0–1 $R^{12a}$,
$C_{2-4}$ alkenyl substituted with 0–1 $R^{12a}$,
$C_{2-4}$ alkynyl substituted with 0–1 $R^{12a}$,
$C_{3-6}$ cycloalkyl substituted with 0–3 $R^{33}$,
phenyl substituted with 0–5 $R^{33}$;
$C_{3-10}$ carbocyclic group substituted with 0–3 $R^{33}$, and
5–10 membered heterocyclic ring system containing from 1–4 heteroatoms selected from the group consisting of N, O, and S substituted with 0–3 $R^{31}$;

$R^{12a}$, at each occurrence, is independently selected from
phenyl substituted with 0–5 $R^{33}$;
$C_{3-10}$ carbocyclic group substituted with 0–3 $R^{33}$, and
5–10 membered heterocyclic ring system containing from 1–4 heteroatoms selected from the group consisting of N, O, and S substituted with 0–3 $R^{31}$;

$R^{13}$, at each occurrence, is independently selected from
H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —N($R^{14}$)—;

alternatively, $R^{12}$ and $R^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;

$R^{14}$, at each occurrence, is independently selected from H, methyl, ethyl, propyl, and butyl;

$R^{15}$, at each occurrence, is independently selected from H, $C_{1-4}$ alkyl, $C_{2-4}$ alkenyl, and $C_{2-4}$ alkynyl;

$R^{16}$, at each occurrence, is independently selected from
H, OH, F, Cl, CN, $NO_2$, $CF_3$, $SO_2R^{45}$, $NR^{46}R^{47}$, —C(=O)H,
methyl, ethyl, methoxy, ethoxy, trifluoromethyl, and trifluoromethoxy;

$R^{31}$, at each occurrence, is independently selected from
H, OH, halo, $CF_3$, $SO_2R^{45}$, $NR^{46}R^{47}$, and $C_{1-4}$ alkyl;

$R^{33}$, at each occurrence, is independently selected from
H, OH, halo, CN, $NO_2$, $CF_3$, $SO_2R^{45}$, $NR^{46}R^{47}$, —C(=O)H,
$C_{1-6}$ alkyl, $C_{2-6}$ alkenyl, $C_{2-6}$ alkynyl,
$C_{3-6}$ cycloalkyl, $C_{1-4}$ haloalkyl, $C_{1-4}$ haloalkyl-oxy-, $C_{1-4}$ alkyloxy-,
$C_{1-4}$ alkylthio-, $C_{1-4}$ alkyl-C(=O)—, $C_{1-4}$ alkyl-C(=O)NH—, $C_{1-4}$ alkyl-OC(=O)—,
$C_{1-4}$ alkyl-C(=O)O—, $C_{3-6}$ cycloalkyl-oxy-, $C_{3-6}$ cycloalkylmethyl-oxy-;
$C_{1-6}$ alkyl substituted with OH, methoxy, ethoxy, propoxy, or butoxy; and
$C_{2-6}$ alkenyl substituted with OH, methoxy, ethoxy, propoxy, or butoxy;

$R^{41}$, at each occurrence, is independently selected from
H, $CF_3$, halo, OH, $CO_2H$, $SO_2R^{45}$, $NR^{46}R^{47}$, $NO_2$, CN,
$C_{2-8}$ alkenyl, $C_{2-8}$ alkynyl, $C_{1-4}$ alkoxy, $C_{1-4}$ haloalkyl
$C_{1-4}$ alkyl substituted with 0–1 $R^{43}$,
aryl substituted with 0–3 $R^{42}$, and
5–10 membered heterocyclic ring system containing from 1–4 heteroatoms selected from the group consisting of N, O, and S substituted with 0–3 $R^{44}$;

$R^{42}$, at each occurrence, is independently selected from
H, $CF_3$, halo, OH, $CO_2H$, $SO_2R^{45}$, $NR^{46}R^{47}$, $NO_2$, CN,
$CH(=NH)NH_2$, $NHC(=NH)NH_2$,
$C_{2-6}$ alkenyl, $C_{2-6}$ alkynyl, $C_{1-4}$ alkoxy, $C_{1-4}$ haloalkyl, $C_{3-6}$ cycloalkyl,
$C_{1-4}$ alkyl substituted with 0–1 $R^{43}$,
aryl substituted with 0–3 $R^{44}$, and
5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$,
$CO_2H$, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-4}$ alkyl;

$R^{47}$, at each occurrence, is independently selected from H and $C_{1-4}$ alkyl;

k is 1 or 2;
m is 0 or 1; and
n is 0, 1 or 2.

In a more preferred embodiment, the present invention provides the method as defined in claim 2 where in the compound administered:

X is —$CH_2$—;

$R^1$ is selected from
H,
$C_{1-4}$ alkyl,
$C_{2-4}$ alkenyl,
$C_{2-4}$ alkynyl,
$C_{3-4}$ cycloalkyl,
$C_{1-3}$ alkyl substituted with 0–1 $R^2$,
$C_{2-3}$ alkenyl substituted with 0–1 $R^2$, and
$C_{2-3}$ alkynyl substituted with 0–1 $R^2$;

$R^2$, at each occurrence, is independently selected from
$C_{1-4}$ alkyl,
$C_{2-4}$ alkenyl,
$C_{2-4}$ alkynyl,
$C_{3-6}$ cycloalkyl,
phenyl substituted with 0–5 $R^{42}$;
$C_{3-6}$ carbocyclic group substituted with 0–3 $R^{41}$, and
5–6 membered heterocyclic ring system containing 1, 2, or 3 heteroatoms selected from the group consisting of N, O, and S substituted with 0–3 $R^{41}$;

$R^5$ is H, methyl, ethyl, propyl, or butyl;
$R^{6a}$ is H, methyl, ethyl, methoxy, —OH, or —$CF_3$;
$R^{6b}$ is H;

$R^7$ and $R^9$, at each occurrence, are independently selected from
  H, halo, —CF$_3$, —OCF$_3$, —OH, —CN, —NO$_2$, —NR$^{46}$R$^{47}$,
  C$_{1-4}$ alkyl, C$_{2-4}$ alkenyl, C$_{2-4}$ alkynyl, C$_{1-4}$ haloalkyl, C$_{1-4}$ alkoxy, (C$_{1-4}$ haloalkyl)oxy,
  C$_{3-10}$ cycloalkyl substituted with 0–2 R$^{33}$,
  C$_{1-4}$ alkyl substituted with 0–2 R$^{11}$,
  C$_{3-10}$ carbocyclic group substituted with 0–3 R$^{33}$,
  aryl substituted with 0–5 R$^{33}$, and
  5–6 membered heterocyclic ring system containing 1, 2, or 3 heteroatoms selected from the group consisting of N, O, and S substituted with 0–3 R$^{31}$;

$R^8$ is selected from
  H, halo, —CF$_3$, —OCF$_3$, —OH, —CN, —NO$_2$,
  C$_{1-4}$ alkyl, C$_{2-4}$ alkenyl, C$_{2-4}$ alkynyl, C$_{1-4}$ haloalkyl, C$_{1-4}$ alkoxy, (C$_{1-4}$ haloalkyl)oxy,
  C$_{3-10}$ cycloalkyl substituted with 0–2 R$^{33}$,
  C$_{1-4}$ alkyl substituted with 0–2 R$^{11}$,
  C$_{2-4}$ alkenyl substituted with 0–2 R$^{11}$,
  C$_{2-4}$ alkynyl substituted with 0–1 R$^{11}$,
  C$_{3-10}$ carbocyclic group substituted with 0–3 R$^{33}$,
  aryl substituted with 0–5 R$^{33}$,
  5–6 membered heterocyclic ring system containing 1, 2, or 3 heteroatoms selected from the group consisting of N, O, and S substituted with 0–3 R$^{31}$;
  OR$^{12}$, SR$^{12}$, NR$^{12}$R$^{13}$, NR$^{12}$C(O)R$^{15}$, NR$^{12}$C(O)OR$^{15}$, NR$^{12}$S(O)$_2$R$^{15}$, and NR$^{12}$C(O)NHR$^{15}$;

$R^{11}$ is selected from
  H, halo, —CF$_3$, —CN, —NO$_2$,
  C$_{1-4}$ alkyl, C$_{2-4}$ alkenyl, C$_{2-4}$ alkynyl, C$_{1-4}$ haloalkyl, C$_{1-4}$ alkoxy, (C$_{1-4}$ haloalkyl)oxy,
  C$_{3-10}$ cycloalkyl substituted with 0–2 R$^{33}$,
  C$_{3-10}$ carbocyclic group substituted with 0–3 R$^{33}$,
  aryl substituted with 0–5 R$^{33}$, and
  5–6 membered heterocyclic ring system containing 1, 2, or 3 heteroatoms selected from the group consisting of N, O, and S substituted with 0–3 R$^{31}$;

$R^{12}$, at each occurrence, is independently selected from
  C$_{1-4}$ alkyl substituted with 0–1 R$^{12a}$,
  C$_{2-4}$ alkenyl substituted with 0–1 R$^{12a}$,
  C$_{2-4}$ alkynyl substituted with 0–1 R$^{12a}$,
  C$_{3-6}$ cycloalkyl substituted with 0–3 R$^{33}$,
  phenyl substituted with 0–5 R$^{33}$;
  C$_{3-10}$ carbocyclic group substituted with 0–3 R$^{33}$, and
  5–10 membered heterocyclic ring system containing from 1–4 heteroatoms selected from the group consisting of N, O, and S substituted with 0–3 R$^{31}$;

$R^{12a}$, at each occurrence, is independently selected from
  phenyl substituted with 0–5 R$^{33}$;
  C$_{3-10}$ carbocyclic group substituted with 0–3 R$^{33}$, and
  5–10 membered heterocyclic ring system containing from 1–4 heteroatoms selected from the group consisting of N, O, and S substituted with 0–3 R$^{31}$;

$R^{13}$, at each occurrence, is independently selected from
  H, C$_{1-4}$ alkyl, C$_{2-4}$ alkenyl, and C$_{2-4}$ alkynyl;
alternatively, $R^{12}$ and $R^{13}$ join to form a 5- or 6-membered ring optionally substituted with —O— or —N(R$^{14}$)—;
alternatively, $R^{12}$ and $R^{13}$ when attached to N may be combined to form a 9- or 10-membered bicyclic heterocyclic ring system containing from 1–3 heteroatoms selected from the group consisting of one N, two N, three N, one N one O, and one N one S; wherein said bicyclic heterocyclic ring system is unsaturated or partially saturated, wherein said bicyclic heterocyclic ring system is substituted with 0–2 R$^{16}$;

$R^{14}$, at each occurrence, is independently selected from H, methyl, ethyl, propyl, and butyl;

$R^{15}$, at each occurrence, is independently selected from H, methyl, ethyl, propyl, and butyl;

$R^{16}$, at each occurrence, is independently selected from H, OH, F, Cl, CN, NO$_2$, methyl, ethyl, methoxy, ethoxy, trifluoromethyl, and trifluoromethoxy;

$R^{31}$, at each occurrence, is independently selected from H, OH, halo, CF$_3$, methyl, ethyl, and propyl;

$R^{33}$, at each occurrence, is independently selected from
  H, OH, halo, CN, NO$_2$, CF$_3$, SO$_2$R$^{45}$, NR$^{46}$R$^{47}$, —C(═O)H,
  C$_{1-6}$ alkyl, C$_{2-6}$ alkenyl, C$_{2-6}$ alkynyl,
  C$_{3-6}$ cycloalkyl, C$_{1-4}$ haloalkyl, C$_{1-4}$ haloalkyl-oxy-, C$_{1-4}$ alkyloxy-,
  C$_{1-4}$ alkylthio-, C$_{1-4}$ alkyl-C(═O)—, C$_{1-4}$ alkyl-C(═O)NH—, C$_{1-4}$ alkyl-OC(═O)—,
  C$_{1-4}$ alkyl-C(═O)O—, C$_{3-6}$ cycloalkyl-oxy-, C$_{3-6}$ cycloalkylmethyl-oxy-;
  C$_{1-6}$ alkyl substituted with OH, methoxy, ethoxy, propoxy, or butoxy; and
  C$_{2-6}$ alkenyl substituted with OH, methoxy, ethoxy, propoxy, or butoxy;

$R^{41}$, at each occurrence, is independently selected from
  H, CF$_3$, halo, OH, CO$_2$H, SO$_2$R$^{45}$, NR$^{46}$R$^{47}$, NO$_2$, CN,
  C$_{2-4}$ alkenyl, C$_{2-4}$ alkynyl, C$_{1-3}$ alkoxy, C$_{1-3}$ haloalkyl, and
  C$_{1-3}$ alkyl;

$R^{42}$, at each occurrence, is independently selected from
  H, CF$_3$, halo, OH, CO$_2$H, SO$_2$R$^{45}$, NR$^{46}$R$^{47}$, NO$_2$, CN, CH(═NH)NH$_2$, NHC(═NH)NH$_2$,
  C$_{2-4}$ alkenyl, C$_{2-4}$ alkynyl, C$_{1-3}$ alkoxy, C$_{1-3}$ haloalkyl, C$_{3-6}$ cycloalkyl, and
  C$_{1-3}$ alkyl;

$R^{43}$ is cyclopropyl, cyclobutyl, cyclopentyl, cyclohexyl, phenyl, or pyridyl, each substituted with 0–3 R$^{44}$;

$R^{44}$, at each occurrence, is independently selected from H, halo, —OH, NR$^{46}$R$^{47}$, CO$_2$H, SO$_2$R$^{45}$, —CF$_3$, —OCF$_3$, —CN, —NO$_2$, methyl, ethyl, propyl, butyl, methoxy, ethoxy, propoxy, and butoxy;

$R^{45}$ is methyl, ethyl, propyl, or butyl;

$R^{46}$, at each occurrence, is independently selected from H, methyl, ethyl, propyl, and butyl;

$R^{47}$, at each occurrence, is independently selected from from H, methyl, ethyl, propyl, and butyl;

k is 1;
m is 1; and
n is 0, 1 or 2.

In a more preferred embodiment, the present invention provides the method as defined in claim 2 where in the compound administered:

X is —CH$_2$—;

$R^1$ is selected from
  H,
  C$_{1-4}$ alkyl,
  C$_{2-4}$ alkenyl,
  C$_{2-4}$ alkynyl,
  C$_{3-4}$ cycloalkyl,
  C$_{1-3}$ alkyl substituted with 0–1 R$^2$,
  C$_{2-3}$ alkenyl substituted with 0–1 R$^2$, and
  C$_{2-3}$ alkynyl substituted with 0–1 R$^2$;

$R^2$, at each occurrence, is independently selected from
  C$_{1-4}$ alkyl,
  C$_{2-4}$ alkenyl,
  C$_{2-4}$ alkynyl,
  C$_{3-6}$ cycloalkyl,
  phenyl substituted with 0–5 R$^{42}$;
  C$_{3-6}$ carbocyclic group substituted with 0–3 R$^{41}$, and 5–6 membered heterocyclic ring system containing 1, 2, or 3 heteroatoms selected from the group consisting of N, O, and S substituted with 0–3 $R^{41}$;

$R^5$ is H, methyl, ethyl, propyl, or butyl;

$R^{6a}$ is H, methyl, ethyl, methoxy, —OH, or —$CF_3$;

$R^{6b}$ is H;

$R^7$ and $R^9$, at each occurrence, are independently selected from
H, F, Cl, —$CH_3$, —$OCH_3$, —$CF_3$, —$OCF_3$, —CN, and —$NO_2$, $R^8$ is selected from
H, F, Cl, Br, —$CF_3$, —$OCF_3$, —OH, —CN, —$NO_2$,
$C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{2-4}$ alkenyl substituted with 0–2 $R^{11}$,
$C_{2-4}$ alkynyl substituted with 0–1 $R^{11}$,
$C_{3-10}$ carbocyclic group substituted with 0–3 $R^{33}$,
aryl substituted with 0–5 $R^{33}$,
5–6 membered heterocyclic ring system containing 1, 2, or 3 heteroatoms selected from the group consisting of N, O, and S substituted with 0–3 $R^{31}$;
$OR^{12}$, $SR^{12}$, $NR^{12}R^{13}$, $NR^{12}C(O)R^{15}$, $NR^{12}C(O)OR^{15}$, $NR^{12}S(O)_2R^{15}$, and $NR^{12}C(O)NHR^{15}$;

$R^{11}$ is selected from
H, halo, —$CF_3$, —CN, —$NO_2$,
$C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
$C_{3-10}$ cycloalkyl substituted with 0–2 $R^{33}$,
$C_{3-10}$ carbocyclic group substituted with 0–3 $R^{33}$,
aryl substituted with 0–5 $R^{33}$, and
5–6 membered heterocyclic ring system containing 1, 2, or 3 heteroatoms selected from the group consisting of N, O, and S substituted with 0–3 $R^{31}$;

$R^{12}$, at each occurrence, is independently selected from
$C_{1-4}$ alkyl substituted with 0–1 $R^{12a}$,
$C_{2-4}$ alkenyl substituted with 0–1 $R^{12a}$,
$C_{2-4}$ alkynyl substituted with 0–1 $R^{12a}$,
$C_{3-6}$ cycloalkyl substituted with 0–3 $R^{33}$,
phenyl substituted with 0–5 $R^{33}$;
$C_{3-10}$ carbocyclic group substituted with 0–3 $R^{33}$, and
5–10 membered heterocyclic ring system containing from 1–4 heteroatoms selected from the group consisting of N, O, and S substituted with 0–3 $R^{31}$;

$R^{12a}$, at each occurrence, is independently selected from
phenyl substituted with 0–5 $R^{33}$;
$C_{3-10}$ carbocyclic group substituted with 0–3 $R^{33}$, and
5–10 membered heterocyclic ring system containing from 1–4 heteroatoms selected from the group consisting of N, O, and S substituted with 0–3 $R^{31}$;

$R^{13}$, at each occurrence, is independently selected from
H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —$N(R^{14})$—;

alternatively, $R^{12}$ and $R^{13}$ when attached to N may be combined to form a 9- or 10-membered bicyclic heterocyclic ring system containing from 1–3 heteroatoms selected from the group consisting of N, O, and S; wherein said bicyclic heterocyclic ring system is selected from indolyl, indolinyl, indazolyl, benzimidazolyl, benzimidazolinyl, benztriazolyl, benzoxazolyl, benzoxazolinyl, benzthiazolyl, and dioxobenzthiazolyl; wherein said bicyclic heterocyclic ring system is substituted with 0–1 $R^{16}$;

$R^{14}$, at each occurrence, is independently selected from H, methyl, ethyl, propyl, and butyl;

$R^{15}$, at each occurrence, is independently selected from H, methyl, ethyl, propyl, and butyl;

$R^{16}$, at each occurrence, is independently selected from
H, OH, F, Cl, CN, $NO_2$, methyl, ethyl, methoxy, ethoxy, trifluoromethyl, and trifluoromethoxy;

$R^{31}$, at each occurrence, is independently selected from
H, OH, halo, $CF_3$, methyl, ethyl, and propyl;

$R^{33}$, at each occurrence, is independently selected from
H, OH, halo, CN, $NO_2$, $CF_3$, $SO_2R^{45}$, $NR^{46}R^{47}$, —C(=O)H,
$C_{1-6}$ alkyl, $C_{2-6}$ alkenyl, $C_{2-6}$ alkynyl,
$C_{3-6}$ cycloalkyl, $C_{1-4}$ haloalkyl, $C_{1-4}$ haloalkyl-oxy-, $C_{1-4}$ alkyloxy-,
$C_{1-4}$ alkylthio-, $C_{1-4}$ alkyl-C(=O)—, $C_{1-4}$ alkyl-C(=O)NH—, $C_{1-4}$ alkyl-OC(=O)—,
$C_{1-4}$ alkyl-C(=O)O—, $C_{3-6}$ cycloalkyl-oxy-, $C_{3-6}$ cycloalkylmethyl-oxy-;
$C_{1-6}$ alkyl substituted with OH, methoxy, ethoxy, propoxy, or butoxy; and
$C_{2-6}$ alkenyl substituted with OH, methoxy, ethoxy, propoxy, or butoxy;

$R^{41}$, at each occurrence, is independently selected from
H, $CF_3$, halo, OH, $CO_2H$, $SO_2R^{45}$, $NR^{46}R^{47}$, $NO_2$, CN,
$C_{2-4}$ alkenyl, $C_{2-4}$ alkynyl, $C_{1-3}$ alkoxy, $C_{1-3}$ haloalkyl, and $C_{1-3}$ alkyl;

$R^{42}$, at each occurrence, is independently selected from
H, $CF_3$, halo, OH, $CO_2H$, $SO_2R^{45}$, $NR^{46}R^{47}$, $NO_2$, CN, CH(=NH)$NH_2$, NHC(=NH)$NH_2$,
$C_{2-4}$ alkenyl, $C_{2-4}$ alkynyl, $C_{1-3}$ alkoxy, $C_{1-3}$ haloalkyl, $C_{3-6}$ cycloalkyl, and $C_{1-3}$ alkyl;

$R^{43}$ is cyclopropyl, cyclobutyl, cyclopentyl, cyclohexyl, phenyl, or pyridyl, each substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, methyl, ethyl, propyl, butyl, methoxy, ethoxy, propoxy, and butoxy;

$R^{45}$ is methyl, ethyl, propyl, or butyl;

$R^{46}$, at each occurrence, is independently selected from H, methyl, ethyl, propyl, and butyl;

$R^{47}$, at each occurrence, is independently selected from from H, methyl, ethyl, propyl, and butyl;

k is 1;

m is 1; and n is 0, 1 or 2.

In a more preferred embodiment, the present invention provides the method as defined in claim 2 where in the compound administered:

X is —$CH_2$—;

$R^1$ is selected from H,
$C_{1-5}$ alkyl substituted with 0–1 $R^2$,
$C_{2-5}$ alkenyl substituted with 0–1 $R^2$, and
$C_{2-3}$ alkynyl substituted with 0–1 $R^2$;

$R^2$ is $C_{3-6}$ cycloalkyl;

$R^5$ is H, methyl, ethyl, or propyl;

$R^{6a}$ is H, methyl, or ethyl;

$R^{6b}$ is H;

$R^7$ and $R^9$, at each occurrence, are independently selected from
H, F, Cl, —$CH_3$, —$OCH_3$, —$CF_3$, —$OCF_3$, —CN, and —$NO_2$, $R^8$ is selected from
methyl substituted with $R^{11}$;
ethenyl substituted with $R^{11}$;
$OR^{12}$, $SR^{12}$, $NR^{12}R^{13}$, $NR^{12}C(O)R^{15}$, $NR^{12}C(O)OR^{15}$, $NR^{12}S(O)_2R^{15}$, and $NR^{12}C(O)NHR^{15}$;

$R^{11}$ is selected from
phenyl-substituted with 0–5 fluoro;
2-($H_3CCH_2C(=O)$)-phenyl-substituted with $R^{33}$;
2-($H_3CC(=O)$)-phenyl-substituted with $R^{33}$;
2-(HC(=O))-phenyl-substituted with $R^{33}$;
2-($H_3CCH(OH)$)-phenyl-substituted with $R^{33}$;
2-($H_3CCH_2CH(OH)$)-phenyl-substituted with $R^{33}$;
2-($HOCH_2$)-phenyl-substituted with $R^{33}$;
2-($HOCH_2CH_2$)-phenyl-substituted with $R^{33}$;
2-($H_3COCH_2$)-phenyl-substituted with $R^{33}$;
2-($H_3COCH_2CH_2$)-phenyl-substituted with $R^{33}$;
2-($H_3CCH(OMe)$)-phenyl-substituted with $R^{33}$;
2-($H_3COC(=O)$)-phenyl-substituted with $R^{33}$;
2-($HOCH_2CH=CH$)-phenyl-substituted with $R^{33}$;
2-((MeOC=O)CH=CH)-phenyl-substituted with $R^{33}$;
2-(methyl)-phenyl-substituted with $R^{33}$;
2-(ethyl)-phenyl-substituted with $R^{33}$;
2-(i-propyl)-phenyl-substituted with $R^{33}$;
2-($F_3C$)-phenyl-substituted with $R^{33}$;
2-(NC)-phenyl-substituted with $R^{33}$;
2-($H_3CO$)-phenyl-substituted with $R^{33}$;
2-(fluoro)-phenyl-substituted with $R^{33}$;
2-(chloro)-phenyl-substituted with $R^{33}$;
3-(NC)-phenyl-substituted with $R^{33}$;
3-($H_3CO$)-phenyl-substituted with $R^{33}$;
3-(fluoro)-phenyl-substituted with $R^{33}$;
3-(chloro)-phenyl-substituted with $R^{33}$;
4-(NC)-phenyl-substituted with $R^{33}$;
4-(fluoro)-phenyl-substituted with $R^{33}$;
4-(chloro)-phenyl-substituted with $R^{33}$;
4-($H_3CS$)-phenyl-substituted with $R^{33}$;
4-($H_3CO$)-phenyl-substituted with $R^{33}$;
4-(ethoxy)-phenyl-substituted with $R^{33}$;
4-(i-propoxy)-phenyl-substituted with $R^{33}$;
4-(i-butoxy)-phenyl-substituted with $R^{33}$;
4-($H_3CCH_2CH_2C(=O)$)-phenyl-substituted with $R^{33}$;
4-(($H_3C)_2CHC(=O)$)-phenyl-substituted with $R^{33}$;
4-($H_3CCH_2C(=O)$)-phenyl-substituted with $R^{33}$;
4-($H_3CC(=O)$)-phenyl-substituted with $R^{33}$;
4-($H_3CCH_2CH_2CH(OH)$)-phenyl-substituted with $R^{33}$;
4-(($H_3C)_2CHCH(OH)$)-phenyl-substituted with $R^{33}$;
4-($H_3CCH_2CH(OH)$)-phenyl-substituted with $R^{33}$;
4-($H_3CCH(OH)$)-phenyl-substituted with $R^{33}$;
4-(cyclopropyloxy)-phenyl-substituted with $R^{33}$;
4-(cyclobutyloxy)-phenyl-substituted with $R^{33}$; and
4-(cyclopentyloxy)-phenyl-substituted with $R^{33}$;

$R^{12}$ is selected from
phenyl-substituted with 0–5 fluoro;
2-($H_3CCH_2C(=O)$)-phenyl-substituted with $R^{33}$;
2-($H_3CC(=O)$)-phenyl-substituted with $R^{33}$;
2-(HC(=O))-phenyl-substituted with $R^{33}$;
2-($H_3CCH(OH)$)-phenyl-substituted with $R^{33}$;
2-($H_3CCH_2CH(OH)$)-phenyl-substituted with $R^{33}$;
2-($HOCH_2$)-phenyl-substituted with $R^{33}$;
2-($HOCH_2CH_2$)-phenyl-substituted with $R^{33}$;
2-($H_3COCH_2$)-phenyl-substituted with $R^{33}$;
2-($H_3COCH_2CH_2$)-phenyl-substituted with $R^{33}$;
2-($H_3CCH(OMe)$)-phenyl-substituted with $R^{33}$;
2-($H_3COC(=O)$)-phenyl-substituted with $R^{33}$;
2-($HOCH_2CH=CH$)-phenyl-substituted with $R^{33}$;
2-((MeOC=O)CH=CH)-phenyl-substituted with $R^{33}$;
2-(methyl)-phenyl-substituted with $R^{33}$;
2-(ethyl)-phenyl-substituted with $R^{33}$;
2-(i-propyl)-phenyl-substituted with $R^{33}$;
2-($F_3C$)-phenyl-substituted with $R^{33}$;
2-(NC)-phenyl-substituted with $R^{33}$;
2-($H_3CO$)-phenyl-substituted with $R^{33}$;
2-(fluoro)-phenyl-substituted with $R^{33}$;
2-(chloro)-phenyl-substituted with $R^{33}$;
3-(NC)-phenyl-substituted with $R^{33}$;
3-($H_3CO$)-phenyl-substituted with $R^{33}$;
3-(fluoro)-phenyl-substituted with $R^{33}$;
3-(chloro)-phenyl-substituted with $R^{33}$;
4-(NC)-phenyl-substituted with $R^{33}$;
4-(fluoro)-phenyl-substituted with $R^{33}$;
4-(chloro)-phenyl-substituted with $R^{33}$;
4-($H_3CS$)-phenyl-substituted with $R^{33}$;
4-($H_3CO$)-phenyl-substituted with $R^{33}$;
4-(ethoxy)-phenyl-substituted with $R^{33}$;
4-(i-propoxy)-phenyl-substituted with $R^{33}$;
4-(i-butoxy)-phenyl-substituted with $R^{33}$;
4-($H_3CCH_2CH_2C(=O)$)-phenyl-substituted with $R^{33}$;
4-(($H_3C)_2CHC(=O)$)-phenyl-substituted with $R^{33}$;
4-($H_3CCH_2C(=O)$)-phenyl-substituted with $R^{33}$;
4-($H_3CC(=O)$)-phenyl-substituted with $R^{33}$;
4-($H_3CCH_2CH_2CH(OH)$)-phenyl-substituted with $R^{33}$;
4-(($H_3C)_2CHCH(OH)$)-phenyl-substituted with $R^{33}$;
4-($H_3CCH_2CH(OH)$)-phenyl-substituted with $R^{33}$;
4-($H_3CCH(OH)$)-phenyl-substituted with $R^{33}$;
4-(cyclopropyloxy)-phenyl-substituted with $R^{33}$;
4-(cyclobutyloxy)-phenyl-substituted with $R^{33}$; and
4-(cyclopentyloxy)-phenyl-substituted with $R^{33}$;

$R^{13}$ is H, methyl, or ethyl;

alternatively, $R^{12}$ and $R^{13}$ join to form a 5- or 6-membered ring selected from pyrrolyl, pyrrolidinyl, imidazolyl, piperidinyl, piperizinyl, methylpiperizinyl, and morpholinyl;

alternatively, $R^{12}$ and $R^{13}$ when attached to N may be combined to form a 9- or 10-membered bicyclic heterocyclic ring system containing from 1–3 heteroatoms selected from the group consisting of N, O, and S; wherein said bicyclic heterocyclic ring system is selected from indolyl, indolinyl, indazolyl, benzimidazolyl, benzimidazolinyl, benztriazolyl, benzoxazolyl, benzoxazolinyl, benzthiazolyl, and dioxobenzthiazolyl; wherein said bicyclic heterocyclic ring system is substituted with 0–1 $R^{16}$;

$R^{15}$ is H, methyl, ethyl, propyl, or butyl;

$R^{16}$, at each occurrence, is independently selected from H, OH, F, Cl, CN, $NO_2$, methyl, ethyl, methoxy, ethoxy, trifluoromethyl, and trifluoromethoxy;

$R^{33}$, at each occurrence, is independently selected from H, F, Cl, —$CH_3$, —$OCH_3$, —$CF_3$, —$OCF_3$, —CN, and —$NO_2$;

k is 1;
m is 1; and
n is 1 or 2.

In a more preferred embodiment, the present invention provides the method as defined in claim 2 where the compound administered is a compound of Formula (I-a):

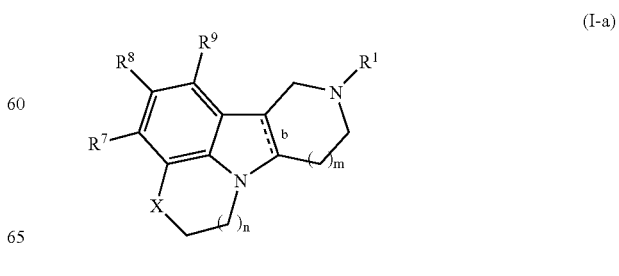

(I-a)

wherein:

b is a single bond;

X is —CH$_2$—, —CH(OH)—, or —C(=O)—;

R$^1$ is selected from
- hydrogen, methyl, ethyl, n-propyl, n-butyl, s-butyl, t-butyl, n-pentyl, n-hexyl, 2-propyl, 2-butyl, 2-pentyl, 2-hexyl, 2-methylpropyl, 2-methylbutyl, 2-methylpentyl, 2-ethylbutyl, 3-methylpentyl, 3-methylbutyl, 4-methylpentyl, 2-fluoroethyl, 2,2-difluoroethyl, 2,2,2-trifluoroethyl,
- 2-propenyl, 2-methyl-2-propenyl, trans-2-butenyl, 3-methyl-butenyl, 3-butenyl, trans-2-pentenyl, cis-2-pentenyl, 4-pentenyl, 4-methyl-3-pentenyl, 3,3-dichloro-2-propenyl, trans-3-phenyl-2-propenyl,
- cyclopropyl, cyclobutyl, cyclopentyl, cyclohexyl, cyclopropylmethyl, cyclobutylmethyl, cyclopentylmethyl, cyclohexylmethyl,
- benzyl, 2-methylbenzyl, 3-methylbenzyl, 4-methylbenzyl, 2,5-dimethylbenzyl, 2,4-dimethylbenzyl, 3,5-dimethylbenzyl,
- 2,4,6-trimethyl-benzyl, 3-methoxy-benzyl, 3,5-dimethoxy-benzyl, pentafluorobenzyl, 2-phenylethyl, 1-phenyl-2-propyl, 4-phenylbutyl, 4-phenylbenzyl, 2-phenylbenzyl,
- (2,3-dimethoxy-phenyl)C(=O)—, (2,5-dimethoxy-phenyl)C(=O)—, (3,4-dimethoxy-phenyl)C(=O)—, (3,5-dimethoxy-phenyl)C(=O)—, cyclopropyl-C(=O)—,
- isopropyl-C(=O)—, ethyl-CO$_2$—, propyl-CO$_2$—, t-butyl-CO$_2$—,
- 2,6-dimethoxy-benzyl, 2,4-dimethoxy-benzyl, 2,4,6-trimethoxy-benzyl, 2,3-dimethoxy-benzyl, 2,4,5-trimethoxy-benzyl, 2,3,4-trimethoxy-benzyl, 3,4-dimethoxy-benzyl, 3,4,5-trimethoxy-benzyl, (4-fluoro-phenyl)ethyl,
- —CH=CH$_2$, —CH$_2$—CH=CH$_2$, —CH=CH—CH$_3$, —C≡CH, —C≡C—CH$_3$, and —CH$_2$—C≡CH;

R$^7$, R$^8$, and R$^9$, at each occurrence, are independently selected from
- hydrogen, fluoro, chloro, bromo, cyano, methyl, ethyl, propyl, isopropyl, butyl, t-butyl, nitro, trifluoromethyl, methoxy, ethoxy, isopropoxy, trifluoromethoxy, phenyl,
- methylC(=O)—, ethylC(=O)—, propylC(=O)—, isopropylC(=O)—, butylC(=O)—, phenylC(=O)—,
- methylCO$_2$—, ethylCO$_2$—, propylCO$_2$—, isopropylCO$_2$—, butylCO$_2$—, phenylCO$_2$—,
- dimethylamino-S(=O)—, diethylamino-S(=O)—, dipropylamino-S(=O)—, di-isopropylamino-S(=O)—, dibutylamino-S(=O)—, diphenylamino-S(=O)—,
- dimethylamino-SO$_2$—, diethylamino-SO$_2$—, dipropylamino-SO$_2$—, di-isopropylamino-SO$_2$—, dibutylamino-SO$_2$—,
- diphenylamino-SO$_2$—,
- dimethylamino-C(=O)—, diethylamino-C(=O)—, dipropylamino-C(=O)—, di-isopropylamino-C(=O)—, dibutylamino-C(=O)—, diphenylamino-C(=O)—,
- 2-chlorophenyl, 2-fluorophenyl, 2-bromophenyl, 2-cyanophenyl, 2-methylphenyl, 2-trifluoromethylphenyl,
- 2-methoxyphenyl, 2-trifluoromethoxyphenyl,
- 3-chlorophenyl, 3-fluorophenyl, 3-bromophenyl, 3-cyanophenyl, 3-methylphenyl, 3-ethylphenyl, 3-propylphenyl, 3-isopropylphenyl, 3-butylphenyl, 3-trifluoromethylphenyl, 3-methoxyphenyl, 3-isopropoxyphenyl, 3-trifluoromethoxyphenyl, 3-thiomethoxyphenyl,
- 4-chlorophenyl, 4-fluorophenyl, 4-bromophenyl, 4-cyanophenyl, 4-methylphenyl, 4-ethylphenyl, 4-propylphenyl, 4-isopropylphenyl, 4-butylphenyl, 4-trifluoromethylphenyl, 4-methoxyphenyl, 4-isopropoxyphenyl, 4-trifluoromethoxyphenyl, 4-thiomethoxyphenyl,
- 2,3-dichlorophenyl, 2,3-difluorophenyl, 2,3-dimethylphenyl, 2,3-ditrifluoromethylphenyl, 2,3-dimethoxyphenyl, 2,3-ditrifluoromethoxyphenyl,
- 2,4-dichlorophenyl, 2,4-difluorophenyl, 2,4-dimethylphenyl, 2,4-ditrifluoromethylphenyl, 2,4-dimethoxyphenyl, 2,4-ditrifluoromethoxyphenyl,
- 2,5-dichlorophenyl, 2,5-difluorophenyl, 2,5-dimethylphenyl, 2,5-ditrifluoromethylphenyl, 2,5-dimethoxyphenyl, 2,5-ditrifluoromethoxyphenyl,
- 2,6-dichlorophenyl, 2,6-difluorophenyl, 2,6-dimethylphenyl, 2,6-ditrifluoromethylphenyl, 2,6-dimethoxyphenyl, 2,6-ditrifluoromethoxyphenyl,
- 3,4-dichlorophenyl, 3,4-difluorophenyl, 3,4-dimethylphenyl, 3,4-ditrifluoromethylphenyl, 3,4-dimethoxyphenyl, 3,4-ditrifluoromethoxyphenyl,
- 2,4,6-trichlorophenyl, 2,4,6-trifluorophenyl, 2,4,6-trimethylphenyl, 2,4,6-tritrifluoromethylphenyl, 2,4,6-trimethoxyphenyl, 2,4,6-tritrifluoromethoxyphenyl,
- 2-chloro-4-CF$_3$-phenyl, 2-fluoro-3-chloro-phenyl, 2-chloro-4-CF$_3$-phenyl, 2-chloro-4-methoxy-phenyl, 2-methoxy-4-isopropyl-phenyl, 2-CF$_3$-4-methoxy-phenyl,
- 2-methyl-4-methoxy-5-fluoro-phenyl,
- 2-methyl-4-methoxy-phenyl, 2-chloro-4-CF$_3$O-phenyl, 2,4,5-trimethyl-phenyl, 2-methyl-4-chloro-phenyl,
- methyl-C(=O)NH—, ethyl-C(=O)NH—, propyl-C(=O)NH—, isopropyl-C(=O)NH—, butyl-C(=O)NH—, phenyl-C(=O)NH—,
- 4-acetylphenyl, 3-acetamidophenyl, 4-pyridyl, 2-furanyl, 2-thiophenyl, 2-naphthyl;
- 2-Me-5-F-phenyl, 2-F-5-Me-phenyl, 2-MeO-5-F-phenyl, 2-Me-3-Cl-phenyl, 3-NO$_2$-phenyl, 2-NO$_2$-phenyl, 2-Cl-3-Me-phenyl, 2-Me-4-EtO-phenyl, 2-Me-4-F-phenyl,
- 2-Cl-6-F-phenyl, 2-Cl-4-(CHF$_2$)O-phenyl, 2,4-diMeO-6-F-phenyl, 2-CF$_3$-6-F-phenyl, 2-MeS-phenyl, 2,6-diCl-4-MeO-phenyl, 2,3,4-triF-phenyl, 2,6-diF-4-Cl-phenyl, 2,3,4,6-tetraF-phenyl, 2,3,4,5,6-pentaF-phenyl, 2-CF$_3$-4-EtO-phenyl, 2-CF$_3$-4-iPrO-phenyl, 2-CF$_3$-4-Cl-phenyl, 2-CF$_3$-4-F-phenyl, 2-Cl-4-EtO-phenyl,
- 2-Cl-4-iPrO-phenyl, 2-Et-4-MeO-phenyl,
- 2-CHO-4-MeO-phenyl, 2-CH(OH)Me-4-MeO-phenyl, 2-CH(OMe)Me-4-MeO-phenyl, 2-C(=O)Me-4-MeO-phenyl,
- 2-CH$_2$(OH)-4-MeO-phenyl, 2-CH$_2$(OMe)-4-MeO-phenyl,
- 2-CH(OH)Et-4-MeO-phenyl, 2-C(=O)Et-4-MeO-phenyl,
- (Z)-2-CH=CHCO$_2$Me-4-MeO-phenyl, 2-CH$_2$CH$_2$CO$_2$Me-4-MeO-phenyl, (Z)-2-CH=CHCH$_2$(OH)-4-MeO-phenyl, (E)-2-CH=CHCO$_2$Me-4-MeO-phenyl, (E)-2-CH=CHCH$_2$(OH)-4-MeO-phenyl, 2-CH$_2$CH$_2$OMe-4-MeO-phenyl, 2-F-4-MeO-phenyl, 2-Cl-4-F-phenyl,
(2-Cl-phenyl)-CH=CH—, (3-Cl-phenyl)-CH=CH—,
(2,6-diF-phenyl)-CH=CH—, —CH$_2$CH=CH$_2$,
phenyl-CH=CH—, (2-Me-4-MeO-phenyl)-CH=CH—,
cyclohexyl, cyclopentyl, cyclohexylmethyl,
—CH$_2$CH$_2$CO$_2$Et, —(CH$_2$)$_3$CO$_2$Et, —(CH$_2$)$_4$CO$_2$Et,
benzyl, 2-F-benzyl, 3-F-benzyl, 4-F-benzyl,
3-MeO-benzyl, 3-OH-benzyl, 2-MeO-benzyl,
2-OH-benzyl, 2-CO$_2$Me-3-MeO-phenyl,
2-Me-4-CN-phenyl, 2-Me-3-CN-phenyl, 2-CF$_3$-4-CN-phenyl,
3-CHO-phenyl, 3-CH$_2$(OH)-phenyl, 3-CH$_2$(OMe)-phenyl,
3-CH$_2$(NMe$_2$)-phenyl, 3-CN-4-F-phenyl,
3-CONH$_2$-4-F-phenyl, 2-CH$_2$(NH$_2$)-4-MeO-phenyl-,
phenyl-NH—, (4-F-phenyl)-NH—, (2,4-diCl-phenyl)-NH—,
phenyl-C(=O)NH—, benzyl-NH—, (2-Me-4-MeO-phenyl)-NH—,
(2-F-4-MeO-phenyl)-NH—, (2-Me-4-F-phenyl)-NH—,
phenyl-S—, —NMe$_2$, 1-pyrrolidinyl, and
—N(tosylate)$_2$,
provided that two of R$^7$, R$^8$, and R$^9$, are independently
selected from hydrogen, fluoro, chloro, bromo, cyano,
methyl, ethyl, propyl, isopropyl, butyl, t-butyl, nitro,
trifluoromethyl, methoxy, ethoxy, isopropoxy, and trifluoromethoxy;
m is 1; and
n is 0, 1 or 2.

In a more preferred embodiment, the present invention provides the method as defined in claim 7 where the compound administered is a compound of Formula (V):

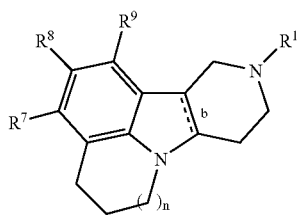

(V)

wherein:
b is a single bond, wherein the bridge hydrogens are in a cis position;
R$^1$ is selected from
hydrogen, methyl, ethyl, n-propyl, n-butyl, s-butyl,
t-butyl, n-pentyl, n-hexyl, 2-propyl, 2-butyl, 2-pentyl,
2-hexyl, 2-methylpropyl, 2-methylbutyl, 2-methylpentyl, 2-ethylbutyl, 3-methylpentyl, 3-methylbutyl,
4-methylpentyl, 2-fluoroethyl, 2,2-difluoroethyl,
2,2,2-trifluoroethyl, 2-propenyl, 2-methyl-2-propenyl,
trans-2-butenyl, 3-methyl-butenyl, 3-butenyl,
trans-2-pentenyl, cis-2-pentenyl, 4-pentenyl,
4-methyl-3-pentenyl, 3,3-dichloro-2-propenyl,
trans-3-phenyl-2-propenyl, cyclopropyl, cyclobutyl,
cyclopentyl, cyclohexyl, cyclopropylmethyl, cyclobutylmethyl, cyclopentylmethyl, cyclohexylmethyl,
—CH=CH$_2$, —CH$_2$—CH=CH$_2$, —CH=CH—CH$_3$,
—C≡CH, —C≡C—CH$_3$,
and —CH$_2$—C≡CH;
R$^7$ and R$^9$, at each occurrence, are independently selected
from hydrogen, fluoro, methyl, trifluoromethyl, and methoxy;

R$^8$ is selected from
hydrogen, fluoro, chloro, bromo, cyano, methyl, ethyl,
propyl, isopropyl, butyl, t-butyl, nitro, trifluoromethyl,
methoxy, ethoxy, isopropoxy, trifluoromethoxy, phenyl,
methylC(=O)—, ethylC(=O)—, propylC(=O)—, isopropylC(=O)—, butylC(=O)—, phenylC(=O)—,
methylCO$_2$—, ethylCO$_2$—, propylCO$_2$—, isopropylCO$_2$—, butylCO$_2$—, phenylCO$_2$—,
dimethylamino-S(=O)—, diethylamino-S(=O)—,
dipropylamino-S(=O)—, di-isopropylamino-S(=O)—,
dibutylamino-S(=O)—, diphenylamino-S(=O)—,
dimethylamino-SO$_2$—, diethylamino-SO$_2$—, dipropylamino-SO$_2$—, di-isopropylamino-SO$_2$—, dibutylamino-SO$_2$—,
diphenylamino-SO$_2$—,
dimethylamino-C(=O)—, diethylamino-C(=O)—,
dipropylamino-C(=O)—, di-isopropylamino-C(=O)—,
dibutylamino-C(=O)—, diphenylamino-C(=O)—,
2-chlorophenyl, 2-fluorophenyl, 2-bromophenyl, 2-cyanophenyl, 2-methylphenyl, 2-trifluoromethylphenyl,
2-methoxyphenyl, 2-trifluoromethoxyphenyl,
3-chlorophenyl, 3-fluorophenyl, 3-bromophenyl,
3-cyanophenyl, 3-methylphenyl, 3-ethylphenyl,
3-propylphenyl, 3-isopropylphenyl, 3-butylphenyl,
3-trifluoromethylphenyl, 3-methoxyphenyl,
3-isopropoxyphenyl, 3-trifluoromethoxyphenyl,
3-thiomethoxyphenyl,
4-chlorophenyl, 4-fluorophenyl, 4-bromophenyl,
4-cyanophenyl, 4-methylphenyl, 4-ethylphenyl,
4-propylphenyl, 4-isopropylphenyl, 4-butylphenyl,
4-trifluoromethylphenyl, 4-methoxyphenyl,
4-isopropoxyphenyl, 4-trifluoromethoxyphenyl,
4-thiomethoxyphenyl,
2,3-dichlorophenyl, 2,3-difluorophenyl, 2,3-dimethylphenyl,
2,3-ditrifluoromethylphenyl, 2,3-dimethoxyphenyl,
2,3-ditrifluoromethoxyphenyl,
2,4-dichlorophenyl, 2,4-difluorophenyl, 2,4-dimethylphenyl,
2,4-ditrifluoromethylphenyl, 2,4-dimethoxyphenyl,
2,4-ditrifluoromethoxyphenyl,
2,5-dichlorophenyl, 2,5-difluorophenyl, 2,5-dimethylphenyl,
2,5-ditrifluoromethylphenyl, 2,5-dimethoxyphenyl,
2,5-ditrifluoromethoxyphenyl,
2,6-dichlorophenyl, 2,6-difluorophenyl, 2,6-dimethylphenyl,
2,6-ditrifluoromethylphenyl, 2,6-dimethoxyphenyl,
2,6-ditrifluoromethoxyphenyl,
3,4-dichlorophenyl, 3,4-difluorophenyl, 3,4-dimethylphenyl,
3,4-ditrifluoromethylphenyl, 3,4-dimethoxyphenyl,
3,4-ditrifluoromethoxyphenyl,
2,4,6-trichlorophenyl, 2,4,6-trifluorophenyl,
2,4,6-trimethylphenyl, 2,4,6-tritrifluoromethylphenyl,
2,4,6-trimethoxyphenyl, 2,4,6-tritrifluoromethoxyphenyl,
2-chloro-4-CF$_3$-phenyl, 2-fluoro-3-chloro-phenyl,
2-chloro-4-CF$_3$-phenyl, 2-chloro-4-methoxy-phenyl,
2-methoxy-4-isopropyl-phenyl, 2-CF$_3$-4-methoxy-phenyl,
2-methyl-4-methoxy-5-fluoro-phenyl,
2-methyl-4-methoxy-phenyl, 2-chloro-4-CF$_3$O-phenyl,
2,4,5-trimethyl-phenyl, 2-methyl-4-chloro-phenyl,
methyl-C(=O)NH—, ethyl-C(=O)NH—, propyl-C(=O)NH—, isopropyl-C(=O)NH—, butyl-C(=O)NH—, phenyl-C(=O)NH—,
4-acetylphenyl, 3-acetamidophenyl, 4-pyridyl, 2-furanyl, 2-thiophenyl, 2-naphthyl;
2-Me-5-F-phenyl, 2-F-5-Me-phenyl, 2-MeO-5-F-phenyl, 2-Me-3-Cl-phenyl, 3-NO$_2$-phenyl, 2-NO$_2$-phenyl,
2-Cl-3-Me-phenyl, 2-Me-4-EtO-phenyl, 2-Me-4-F-phenyl,
2-Cl-6-F-phenyl, 2-Cl-4-(CHF$_2$)O-phenyl,
2,4-diMeO-6-F-phenyl, 2-CF$_3$-6-F-phenyl,
2-MeS-phenyl, 2,6-diCl-4-MeO-phenyl,
2,3,4-triF-phenyl, 2,6-diF-4-Cl-phenyl,
2,3,4,6-tetraF-phenyl, 2,3,4,5,6-pentaF-phenyl,
2-CF$_3$-4-EtO-phenyl, 2-CF$_3$-4-iPrO-phenyl,
2-CF$_3$-4-Cl-phenyl, 2-CF$_3$-4-F-phenyl, 2-Cl-4-EtO-phenyl,
2-Cl-4-iPrO-phenyl, 2-Et-4-MeO-phenyl,
2-CHO-4-MeO-phenyl, 2-CH(OH)Me-4-MeO-phenyl,
2-CH(OMe)Me-4-MeO-phenyl, 2-C(=O)Me-4-MeO-phenyl,
2-CH$_2$(OH)-4-MeO-phenyl, 2-CH$_2$(OMe)-4-MeO-phenyl,
2-CH(OH)Et-4-MeO-phenyl, 2-C(=O)Et-4-MeO-phenyl,
(Z)-2-CH=CHCO$_2$Me-4-MeO-phenyl,
2-CH$_2$CH$_2$CO$_2$Me-4-MeO-phenyl,
(Z)-2-CH=CHCH$_2$(OH)-4-MeO-phenyl,
(E)-2-CH=CHCO$_2$Me-4-MeO-phenyl,
(E)-2-CH=CHCH$_2$(OH)-4-MeO-phenyl,
2-CH$_2$CH$_2$OMe-4-MeO-phenyl,
2-F-4-MeO-phenyl, 2-Cl-4-F-phenyl,
(2-Cl-phenyl)-CH=CH—, (3-Cl-phenyl)-CH=CH—, (2,6-diF-phenyl)-CH=CH—, —CH$_2$CH=CH$_2$,
phenyl-CH=CH—, (2-Me-4-MeO-phenyl)-CH=CH—,
cyclohexyl, cyclopentyl, cyclohexylmethyl,
—CH$_2$CH$_2$CO$_2$Et, —(CH$_2$)$_3$CO$_2$Et, —(CH$_2$)$_4$CO$_2$Et,
benzyl, 2-F-benzyl, 3-F-benzyl, 4-F-benzyl,
3-MeO-benzyl, 3-OH-benzyl, 2-MeO-benzyl,
2-OH-benzyl, 2-CO$_2$Me-3-MeO-phenyl,
2-Me-4-CN-phenyl, 2-Me-3-CN-phenyl, 2-CF$_3$-4-CN-phenyl,
3-CHO-phenyl, 3-CH$_2$(OH)-phenyl, 3-CH$_2$(OMe)-phenyl,
3-CH$_2$(NMe$_2$)-phenyl, 3-CN-4-F-phenyl,
3-CONH$_2$-4-F-phenyl, 2-CH$_2$(NH$_2$)-4-MeO-phenyl-, phenyl-NH—, (4-F-phenyl)-NH—, (2,4-diCl-phenyl)-NH—,
phenyl-C(=O)NH—, benzyl-NH—, (2-Me-4-MeO-phenyl)-NH—,
(2-F-4-MeO-phenyl)-NH—, (2-Me-4-F-phenyl)-NH—, phenyl-S—, —NMe$_2$, 1-pyrrolidinyl, and —N(tosylate)$_2$; and
n is 0, 1 or 2.

In a more preferred embodiment, the present invention provides the method as defined in claim 1 where in the compound administered:
X is —CHR$^{10}$— or —C(=O)—;
R$^1$ is selected from
  C$_{1-6}$ alkyl substituted with Z,
  C$_{2-6}$ alkenyl substituted with Z,
  C$_{2-6}$ alkynyl substituted with Z,
  C$_{3-6}$ cycloalkyl substituted with Z,
  aryl substituted with Z,
  5–6 membered heterocyclic ring system containing at least one heteroatom selected from the group consisting of N, O, and S, said heterocyclic ring system substituted with Z;
  C$_{1-6}$ alkyl substituted with 0–2 R$^2$,
  C$_{2-6}$ alkenyl substituted with 0–2 R$^2$,
  C$_{2-6}$ alkynyl substituted with 0–2 R$^2$,
  aryl substituted with 0–2 R$^2$, and
  5–6 membered heterocyclic ring system containing at least one heteroatom selected from the group consisting of N, O, and S, said heterocyclic ring system substituted with 0–2 R$^2$;
Z is selected from H,
  —CH(OH)R$^2$,
  —C(ethylenedioxy)R$^2$,
  —SR$^2$,
  —NR$^2$R$^3$,
  —C(O)R$^2$,
  —C(O)NR$^2$R$^3$,
  —NR$^3$C(O)R$^2$,
  —C(O)OR$^2$,
  —OC(O)R$^2$,
  —CH(=NR$^4$)NR$^2$R$^3$,
  —NHC(=NR$^4$)NR$^2$R$^3$,
  —S(O)R$^2$,
  —S(O)$_2$R$^2$,
  —S(O)$_2$NR$^2$R$^3$, and —NR$^3$S(O)$_2$R$^2$;
R$^2$, at each occurrence, is independently selected from
  C$_{1-4}$ alkyl,
  C$_{2-4}$ alkenyl,
  C$_{2-4}$ alkynyl,
  C$_{3-6}$ cycloalkyl,
  aryl substituted with 0–5 R$^{42}$;
  C$_{3-10}$ carbocyclic group substituted with 0–3 R$^{41}$, and
  5–10 membered heterocyclic ring system containing from 1–4 heteroatoms selected from the group consisting of N, O, and S substituted with 0–3 R$^{41}$;
R$^3$, at each occurrence, is independently selected from
  H, C$_{1-4}$ alkyl, C$_{2-4}$ alkenyl, C$_{2-4}$ alkynyl, and
  C$_{1-4}$ alkoxy;
alternatively, R$^2$ and R$^3$ join to form a 5- or 6-membered ring optionally substituted with —O— or —N(R$^4$)—;
R$^4$, at each occurrence, is independently selected from H, methyl, ethyl, propyl, and butyl;
R$^5$ is H, methyl, ethyl, propyl, or butyl;
R$^{6a}$ is selected from
  H, —OH, —NR$^{46}$R$^{47}$, —CF$_3$,
  C$_{1-4}$ alkyl, C$_{2-4}$ alkenyl, C$_{2-4}$ alkynyl, C$_{1-4}$ alkoxy, C$_{1-4}$ haloalkyl, C$_{3-6}$ cycloalkyl, and
  aryl substituted with 0–3 R$^{44}$;
R$^{6b}$ is H;
R$^7$, R$^8$, and R$^9$, at each occurrence, are independently selected from
  H, halo, —CF$_3$, —OCF$_3$, —OH, —CN, —NO$_2$, —NR$^{46}$R$^{47}$,
  C$_{1-8}$ alkyl, C$_{2-8}$ alkenyl, C$_{2-8}$ alkynyl, C$_{1-4}$ haloalkyl, C$_{1-8}$ alkoxy, (C$_{1-4}$ haloalkyl)oxy,
  C$_{1-4}$ alkyl substituted with 0–2 R$^{11}$,
  C$_{3-10}$ carbocyclic group substituted with 0–3 R$^{33}$,
  aryl substituted with 0–5 R$^{33}$,
  5–10 membered heterocyclic ring system containing from 1–4 heteroatoms selected from the group consisting of N, O, and S substituted with 0–3 R$^{31}$;
  OR$^{12}$, SR$^{12}$, NR$^{12}$R$^{13}$, C(O)H, C(O)R$^{12}$, C(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(O)OR$^{15}$, NR$^{12}$S(O)$_2$R$^{15}$, and NR$^{12}$C(O)NHR$^{15}$;

$R^{10}$ is selected from H, —OH,
  $C_{1-6}$ alkyl substituted with 0–1 $R^{10B}$,
  $C_{2-6}$ alkenyl substituted with 0–1 $R^{10B}$,
  $C_{2-6}$ alkynyl substituted with 0–1 $R^{10B}$, and
  $C_{1-6}$ alkoxy;
$R^{10B}$ is selected from
  $C_{1-4}$ alkoxy,
  $C_{3-6}$ cycloalkyl,
  $C_{3-10}$ carbocyclic group substituted with 0–3 $R^{33}$,
  phenyl substituted with 0–3 $R^{33}$, and
  5–6 membered heterocyclic ring system containing 1, 2, or 3 heteroatoms selected from the group consisting of N, O, and S substituted with 0–2 $R^{44}$;
$R^{11}$ is selected from
  H, halo, —$CF_3$, —CN, —$NO_2$,
  $C_{1-8}$ alkyl, $C_{2-8}$ alkenyl, $C_{2-8}$ alkynyl, $C_{1-4}$ haloalkyl, $C_{1-8}$ alkoxy, $C_{3-10}$ cycloalkyl,
  $C_{3-10}$ carbocyclic group substituted with 0–3 $R^{33}$,
  aryl substituted with 0–5 $R^{33}$,
  5–10 membered heterocyclic ring system containing from 1–4 heteroatoms selected from the group consisting of N, O, and S substituted with 0–3 $R^{31}$;
  $OR^{12}$, $SR^{12}$, $NR^{12}R^{13}$, C(O)H, $C(O)R^{12}$, $C(O)NR^{12}R^{13}$, $NR^{14}C(O)R^{12}$, $C(O)OR^{12}$, $OC(O)R^{12}$, $OC(O)OR^{12}$, $CH(=NR^{14})NR^{12}R^{13}$, $NHC(=NR^{14})NR^{12}R^{13}$, $S(O)R^{12}$, $S(O)_2R^{12}$, $S(O)NR^{12}R^{13}$, $S(O)_2NR^{12}R^{13}$, $NR^{14}S(O)R^{12}$, and $NR^{14}S(O)_2R^{12}$;
$R^{12}$, at each occurrence, is independently selected from
  $C_{1-4}$ alkyl,
  $C_{2-4}$ alkenyl,
  $C_{2-4}$ alkynyl,
  $C_{3-6}$ cycloalkyl,
  phenyl substituted with 0–5 $R^{33}$;
  $C_{3-10}$ carbocyclic group substituted with 0–3 $R^{33}$, and
  5–10 membered heterocyclic ring system containing from 1–4 heteroatoms selected from the group consisting of N, O, and S substituted with 0–3 $R^{31}$;
$R^{13}$, at each occurrence, is independently selected from
  H, $C_{1-4}$ alkyl, $C_{2-4}$ alkenyl, and $C_{2-4}$ alkynyl;
alternatively, $R^{12}$ and $R^{13}$ join to form a 5- or 6-membered ring optionally
  substituted with —O— or —N($R^{14}$)—;
$R^{14}$, at each occurrence, is independently selected from H and $C_{1-4}$ alkyl;
$R^{31}$, at each occurrence, is independently selected from
  H, OH, halo, $CF_3$, $SO_2R^{45}$, $NR^{46}R^{47}$, methyl, ethyl, and propyl;
$R^{33}$, at each occurrence, is independently selected from
  H, OH, halo, CN, $NO_2$, $CF_3$, $SO_2R^{45}$, $NR^{46}R^{47}$,
  $C_{1-3}$ alkyl, $C_{2-3}$ alkenyl, $C_{2-3}$ alkynyl, $C_{3-5}$ cycloalkyl, $C_{1-3}$ haloalkyl, $C_{1-3}$ haloalkyl-oxy-, $C_{1-3}$ alkyloxy-, $C_{1-3}$ alkylthio-, $C_{1-3}$ alkyl-C(=O)—, and $C_{1-3}$ alkyl-C(=O)NH—;
$R^{41}$, at each occurrence, is independently selected from
  H, $CF_3$, halo, OH, $CO_2H$, $SO_2R^{45}$, $NR^{46}R^{47}$, $NO_2$, CN, =O,
  $C_{2-8}$ alkenyl, $C_{2-8}$ alkynyl, $C_{1-4}$ alkoxy, $C_{1-4}$ haloalkyl
  $C_{1-4}$ alkyl substituted with 0–1 $R^{43}$,
  aryl substituted with 0–3 $R^{42}$, and
  5–10 membered heterocyclic ring system containing from 1–4 heteroatoms selected from the group consisting of N, O, and S substituted with 0–3 $R^{44}$;
$R^{42}$, at each occurrence, is independently selected from
  H, $CF_3$, halo, OH, $CO_2H$, $SO_2R^{45}$, $SR^{45}$, $NR^{46}R^{47}$, $OR^{48}$, $NO_2$, CN, $CH(=NH)NH_2$, $NHC(=NH)NH_2$,
  $C_{2-6}$ alkenyl, $C_{2-6}$ alkynyl, $C_{1-4}$ alkoxy, $C_{1-4}$ haloalkyl, $C_{3-6}$ cycloalkyl,
  $C_{1-4}$ alkyl substituted with 0–1 $R^{43}$,
  aryl substituted with 0–3 $R^{44}$, and
  5–10 membered heterocyclic ring system containing from 1–4 heteroatoms selected from the group consisting of N, O, and S substituted with 0–3 $R^{44}$;
$R^{43}$ is $C_{3-6}$ cycloalkyl or aryl substituted with 0–3 $R^{44}$;
$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;
$R^{45}$ is $C_{1-4}$ alkyl;
$R^{46}$, at each occurrence, is independently selected from H and $C_{1-4}$ alkyl;
$R^{47}$, at each occurrence, is independently selected from H, $C_{1-4}$ alkyl,
  —C(=O)NH($C_{1-4}$ alkyl), —$SO_2$($C_{1-4}$ alkyl),
  —$SO_2$(phenyl), —C(=O)O($C_{1-4}$ alkyl), —C(=O)($C_{1-4}$ alkyl), and —C(=O)H;
$R^{48}$, at each occurrence, is independently selected from H, $C_{1-4}$ alkyl,
  —C(=O)NH($C_{1-4}$ alkyl), —C(=O)O($C_{1-4}$ alkyl), —C(=O)($C_{1-4}$ alkyl), and —C(=O)H;
k is 1 or 2;
m is 0, 1, or 2; and
n is 0, 1 or 2.

In a more preferred embodiment, the present invention provides the method as defined in claim 9 where in the compound administered:

X is —$CHR^{10}$— or —C(=O)—;
$R^1$ is selected from
  $C_{2-5}$ alkyl substituted with Z,
  $C_{2-5}$ alkenyl substituted with Z,
  $C_{2-5}$ alkynyl substituted with Z,
  $C_{3-6}$ cycloalkyl substituted with Z,
  aryl substituted with Z,
  5–6 membered heterocyclic ring system containing at least one heteroatom selected from the group consisting of N, O, and S, said heterocyclic ring system substituted with Z;
  $C_{1-5}$ alkyl substituted with 0–2 $R^2$,
  $C_{2-5}$ alkenyl substituted with 0–2 $R^2$, and
  $C_{2-5}$ alkynyl substituted with 0–2 $R^2$;
Z is selected from H,
  —CH(OH)$R^2$,
  —C(ethylenedioxy)$R^2$,
  —$SR^2$,
  —$NR^2R^3$,
  —C(O)$R^2$,
  —C(O)$NR^2R^3$,
  —$NR^3C(O)R^2$,
  —C(O)O$R^2$,
  —OC(O)$R^2$,
  —CH(=$NR^4$)$NR^2R^3$,
  —NHC(=$NR^4$)$NR^2R^3$,
  —S(O)$R^2$,
  —S(O)$_2R^2$,
  —S(O)$_2NR^2R^3$, and —$NR^3S(O)_2R^2$;
$R^2$, at each occurrence, is independently selected from
  $C_{1-4}$ alkyl,
  $C_{2-4}$ alkenyl,
  $C_{2-4}$ alkynyl,
  $C_{3-6}$ cycloalkyl,
  aryl substituted with 0–5 $R^{42}$;
  $C_{3-10}$ carbocyclic group substituted with 0–3 $R^{41}$, and
  5–10 membered heterocyclic ring system containing from 1–4 heteroatoms selected from the group consisting of N, O, and S substituted with 0–3 $R^{41}$;

$R^3$, at each occurrence, is independently selected from
H, $C_{1-4}$ alkyl, $C_{2-4}$ alkenyl, $C_{2-4}$ alkynyl, and
$C_{1-4}$ alkoxy;
alternatively, $R^2$ and $R^3$ join to form a 5- or 6-membered ring
optionally substituted with —O— or —N($R^4$)—;
$R^4$, at each occurrence, is independently selected from H,
methyl, ethyl, propyl, and butyl;
$R^5$ is H, methyl, or ethyl;
$R^{6a}$ is selected from
H, —OH, —N$R^{46}R^{47}$, —CF$_3$,
$C_{1-4}$ alkyl, $C_{2-4}$ alkenyl, $C_{2-4}$ alkynyl, $C_{1-4}$ alkoxy, $C_{1-4}$ haloalkyl, and $C_{3-6}$ cycloalkyl;
$R^{6b}$ is H;
$R^7$, $R^8$, and $R^9$, at each occurrence, are independently selected from
H, halo, —CF$_3$, —OCF$_3$, —OH, —OCH$_3$, —CN, —NO$_2$, —N$R^{46}R^{47}$,
$C_{1-6}$ alkyl, $C_{2-6}$ alkenyl, $C_{2-6}$ alkynyl, $C_{1-4}$ haloalkyl, $C_{1-6}$ alkoxy, ($C_{1-4}$ haloalkyl)oxy,
$C_{1-4}$ alkyl substituted with 0–2 $R^{11}$,
$C_{3-10}$ carbocyclic group substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
O$R^{12}$, S$R^{12}$, N$R^{12}R^{13}$, C(O)H, C(O)$R^{12}$, C(O)N$R^{12}R^{13}$, N$R^{14}$C(O)$R^{12}$, C(O)O$R^{12}$, OC(O)$R^{12}$, CH(=N$R^{14}$)N$R^{12}R^{13}$, NHC(=N$R^{14}$)N$R^{12}R^{13}$, S(O)$R^{12}$, S(O)$_2R^{12}$, S(O)$_2$N$R^{12}R^{13}$, N$R^{14}$S(O)$_2R^{12}$, N$R^{14}$S(O)$R^{12}$, N$R^{14}$S(O)$_2R^{12}$, N$R^{12}$C(O)$R^{15}$, N$R^{12}$C(O)O$R^{15}$, N$R^{12}$S(O)$_2R^{15}$, and N$R^{12}$C(O)NH$R^{15}$;
$R^{10}$ is selected from H, —OH, $C_{1-6}$ alkyl, $C_{1-4}$ alkoxy, and $C_{1-2}$ alkyl substituted with 0–1 $R^{10B}$;
$R^{10B}$ is $C_{3-6}$ cycloalkyl or
phenyl substituted with 0–3 $R^{33}$;
$R^{11}$ is selected from
H, halo, —CF$_3$, —OCF$_3$, —OH, —OCH$_3$, —CN, —NO$_2$, —N$R^{46}R^{47}$,
$C_{1-6}$ alkyl, $C_{2-6}$ alkenyl, $C_{2-6}$ alkynyl, $C_{1-4}$ haloalkyl, $C_{1-6}$ alkoxy, ($C_{1-4}$ haloalkyl)oxy,
$C_{3-10}$ carbocyclic group substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
O$R^{12}$, S$R^{12}$, N$R^{12}R^{13}$, C(O)H, C(O)$R^{12}$, C(O)N$R^{12}R^{13}$, N$R^{14}$C(O)$R^{12}$, C(O)O$R^{12}$, OC(O)$R^{12}$, CH(=N$R^{14}$)N$R^{12}R^{13}$, NHC(=N$R^{14}$)N$R^{12}R^{13}$, S(O)$R^{12}$, S(O)$_2R^{12}$, S(O)$_2$N$R^{12}R^{13}$, and N$R^{14}$S(O)$_2R^{12}$;
$R^{12}$, at each occurrence, is independently selected from
$C_{1-4}$ alkyl,
$C_{2-4}$ alkenyl,
$C_{2-4}$ alkynyl,
$C_{3-6}$ cycloalkyl,
phenyl substituted with 0–5 $R^{33}$;
$C_{3-10}$ carbocyclic group substituted with 0–3 $R^{33}$, and
5–10 membered heterocyclic ring system containing from 1–4 heteroatoms selected from the group consisting of N, O, and S substituted with 0–3 $R^{31}$;
$R^{13}$, at each occurrence, is independently selected from
H, $C_{1-4}$ alkyl, $C_{2-4}$ alkenyl, and $C_{2-4}$ alkynyl;
alternatively, $R^{12}$ and $R^{13}$ join to form a 5- or 6-membered ring optionally substituted with —O— or —N($R^{14}$)—;
$R^{14}$, at each occurrence, is independently selected from H and $C_{1-4}$ alkyl;

$R^{31}$, at each occurrence, is independently selected from
H, OH, halo, CF$_3$, methyl, and ethyl;
$R^{33}$, at each occurrence, is independently selected from
H, OH, halo, CN, NO$_2$, CF$_3$, methyl, and ethyl;
$R^{41}$, at each occurrence, is independently selected from
H, CF$_3$, halo, OH, CO$_2$H, SO$_2R^{45}$, N$R^{46}R^{47}$, NO$_2$, CN, =O,
$C_{2-8}$ alkenyl, $C_{2-8}$ alkynyl, $C_{1-4}$ alkoxy, $C_{1-4}$ haloalkyl,
$C_{1-4}$ alkyl substituted with 0–1 $R^{43}$,
aryl substituted with 0–3 $R^{42}$, and
5–10 membered heterocyclic ring system containing from 1–4 heteroatoms selected from the group consisting of N, O, and S substituted with 0–3 $R^{44}$;
$R^{42}$, at each occurrence, is independently selected from
H, CF$_3$, halo, OH, CO$_2$H, SO$_2R^{45}$, S$R^{45}$, N$R^{46}R^{47}$, O$R^{48}$, NO$_2$, CN, CH(=NH)NH$_2$, NHC(=NH)NH$_2$,
$C_{2-6}$ alkenyl, $C_{2-6}$ alkynyl, $C_{1-4}$ alkoxy, $C_{1-4}$ haloalkyl, $C_{3-6}$ cycloalkyl,
$C_{1-4}$ alkyl substituted with 0–1 $R^{43}$,
aryl substituted with 0–3 $R^{44}$, and
5–10 membered heterocyclic ring system containing from 1–4 heteroatoms selected from the group consisting of N, O, and S substituted with 0–3 $R^{44}$;
$R^{43}$ is $C_{3-6}$-cycloalkyl or aryl substituted with 0–3 $R^{44}$;
$R^{44}$, at each occurrence, is independently selected from H, halo, —OH, N$R^{46}R^{47}$, CO$_2$H, SO$_2R^{45}$, —CF$_3$, —OCF$_3$, —CN, —NO$_2$, $C_{1-4}$ alkyl, and $C_{1-4}$ alkoxy;
$R^{45}$ is $C_{1-4}$ alkyl;
$R^{46}$, at each occurrence, is independently selected from H and $C_{1-3}$ alkyl;
$R^{47}$, at each occurrence, is independently selected from H, $C_{1-4}$ alkyl,
—C(=O)NH($C_{1-4}$ alkyl), —SO$_2$($C_{1-4}$ alkyl),
—SO$_2$(phenyl), —C(=O)O($C_{1-4}$ alkyl), —C(=O)($C_{1-4}$ alkyl), and —C(=O)H;
$R^{48}$, at each occurrence, is independently selected from H, $C_{1-4}$ alkyl, —C(=O)NH($C_{1-4}$ alkyl), —C(=O)O($C_{1-4}$ alkyl), —C(=O)($C_{1-4}$ alkyl), and —C(=O)H;
k is 1 or 2;
m is 0, 1, 2; and
n is 0, 1 or 2.
In a more preferred embodiment, the present invention provides the method as defined in claim 9 where in the compound administered:
X is —CH$_2$—;
$R^1$ is selected from
$C_{2-4}$ alkyl substituted with Z,
$C_{2-4}$ alkenyl substituted with Z,
$C_{2-4}$ alkynyl substituted with Z,
$C_{3-6}$ cycloalkyl substituted with Z,
aryl substituted with Z,
5–6 membered heterocyclic ring system containing at least one heteroatom selected from the group consisting of N, O, and S, said heterocyclic ring system substituted with Z;
$C_{2-4}$ alkyl substituted with 0–2 $R^2$, and
$C_{2-4}$ alkenyl substituted with 0–2 $R^2$;
Z is selected from H,
—CH(OH)$R^2$,
—C(ethylenedioxy)$R^2$,
—O$R^2$,
—S$R^2$,
—N$R^2R^3$,
—C(O)$R^2$,
—C(O)N$R^2R^3$,
—N$R^3$C(O)$R^2$,
—C(O)O$R^2$, —S(O)R², 
—S(O)₂R², 
—S(O)₂NR²R³, and —NR³S(O)₂R²;

R², at each occurrence, is independently selected from
  phenyl substituted with 0–5 R⁴²;
  C$_{3-10}$ carbocyclic group substituted with 0–3 R⁴¹, and
  5–10 membered heterocyclic ring system containing from 1–4 heteroatoms selected from the group consisting of N, O, and S substituted with 0–3 R⁴¹;

R³, at each occurrence, is independently selected from
  H, C$_{1-4}$ alkyl, C$_{2-4}$ alkenyl, C$_{2-4}$ alkynyl, and
  C$_{1-4}$ alkoxy;
alternatively, R² and R³ join to form a 5- or 6-membered ring
  optionally substituted with —O— or —N(R⁴)—;

R⁴, at each occurrence, is independently selected from H, methyl, ethyl, propyl, and butyl;

R⁵ is H;

R$^{6a}$ is selected from H, —OH, —CF₃, methyl, ethyl, propyl, butyl, methoxy, and, ethoxy;

R$^{6b}$ is H;

R⁷, R⁸, and R⁹, at each occurrence, are independently selected from
  H, halo, —CF₃, —OCF₃, —OH, —OCH₃, —CN, —NO₂,
  C$_{1-4}$ alkyl, C$_{1-4}$ haloalkyl, C$_{1-4}$ alkoxy, (C$_{1-3}$ haloalkyl)oxy, and
  C$_{1-4}$ alkyl substituted with 0–2 R¹¹;

R¹¹ is selected from
  H, halo, —CF₃, —OCF₃, —OH, —OCH₃, —CN, —NO₂,
  C$_{1-4}$ alkyl, C$_{1-4}$ haloalkyl, C$_{1-4}$ alkoxy, and (C$_{1-3}$ haloalkyl)oxy;

R³³, at each occurrence, is independently selected from
  H, OH, halo, CF₃, and methyl;

R⁴¹, at each occurrence, is independently selected from
  H, CF₃, halo, OH, CO₂H, SO₂R⁴⁵, NR⁴⁶R⁴⁷, NO₂, CN, =O,
  C$_{2-8}$ alkenyl, C$_{2-8}$ alkynyl, C$_{1-4}$ alkoxy, C$_{1-4}$ haloalkyl,
  C$_{1-4}$ alkyl substituted with 0–1 R⁴³,
  aryl substituted with 0–3 R⁴², and
  5–10 membered heterocyclic ring system containing from 1–4 heteroatoms selected from the group consisting of N, O, and S substituted with 0–3 R⁴⁴;

R⁴², at each occurrence, is independently selected from
  H, CF₃, halo, OH, CO₂H, SO₂R⁴⁵, SR⁴⁵, NR⁴⁶R⁴⁷, OR⁴⁸,
  NO₂, CN, CH(=NH)NH₂, NHC(=NH)NH₂,
  C$_{2-6}$ alkenyl, C$_{2-6}$ alkynyl, C$_{1-4}$ alkoxy, C$_{1-4}$ haloalkyl,
  C$_{3-6}$ cycloalkyl,
  C$_{1-4}$ alkyl substituted with 0–1 R⁴³,
  aryl substituted with 0–3 R⁴⁴, and
  5–10 membered heterocyclic ring system containing from 1–4 heteroatoms selected from the group consisting of N, O, and S substituted with 0–3 R⁴⁴;

R⁴³ is cyclopropyl, cyclobutyl, cyclopentyl, cyclohexyl, phenyl, or pyridyl, each substituted with 0–3 R⁴⁴;

R⁴⁴, at each occurrence, is independently selected from H, halo, —OH, NR⁴⁶R⁴⁷, CO₂H, SO₂R⁴⁵, —CF₃, —OCF₃, —CN, —NO₂, methyl, ethyl, propyl, butyl, methoxy, ethoxy, propoxy, and butoxy;

R⁴⁵ is methyl, ethyl, propyl, or butyl;

R⁴⁶, at each occurrence, is independently selected from H, methyl, ethyl, propyl, and butyl;

R⁴⁷, at each occurrence, is independently selected from
  H, methyl, ethyl, n-propyl, i-propyl, n-butyl,
  i-butyl, —C(=O)NH(methyl), —C(=O)NH(ethyl),
  —SO₂(methyl), —SO₂(ethyl), —SO₂(phenyl),
  —C(=O)O(methyl), —C(=O)O(ethyl), —C(=O)(methyl),
  —C(=O)(ethyl), and —C(=O)H;

R⁴⁸, at each occurrence, is independently selected from
  H, methyl, ethyl, n-propyl, i-propyl, —C(=O)NH(methyl), —C(=O)NH(ethyl),
  —C(=O)O(methyl), —C(=O)O(ethyl), —C(=O)(methyl), —C(=O)(ethyl), and
  —C(=O)H;

k is 1;
m is 0, 1, or 2; and
n is 0, 1 or 2.

In a more preferred embodiment, the present invention provides the method as defined in claim 9 where in the compound administered:

X is —CH₂—;

R¹ is selected from
  ethyl substituted with Z,
  propyl substituted with Z,
  butyl substituted with Z,
  propenyl substituted with Z,
  butenyl substituted with Z,
  ethyl substituted with R²,
  propyl substituted with R²,
  butyl substituted with R²,
  propenyl substituted with R², and
  butenyl substituted with R²;

Z is selected from H,
  —CH(OH)R²,
  —OR²,
  —SR²,
  —NR²R³,
  —C(O)R²,
  —C(O)NR²R³,
  —NR³C(O)R²,
  —C(O)OR²,
  —S(O)R²,
  —S(O)₂R²,
  —S(O)₂NR²R³, and —NR³S(O)₂R²;

R², at each occurrence, is independently selected from
  phenyl substituted with 0–3 R⁴²;
  naphthyl substituted with 0–3 R⁴²;
  cyclopropyl substituted with 0–3 R⁴¹;
  cyclobutyl substituted with 0–3 R⁴¹;
  cyclopentyl substituted with 0–3 R⁴¹;
  cyclohexyl substituted with 0–3 R⁴¹;
  pyridyl substituted with 0–3 R⁴¹;
  indolyl substituted with 0–3 R⁴¹;
  indolinyl substituted with 0–3 R⁴¹;
  benzimidazolyl substituted with 0–3 R⁴¹;
  benzotriazolyl substituted with 0–3 R⁴¹;
  benzothienyl substituted with 0–3 R⁴¹;
  benzofuranyl substituted with 0–3 R⁴¹;
  phthalimid-1-yl substituted with 0–3 R⁴¹;
  inden-2-yl substituted with 0–3 R⁴¹;
  2,3-dihydro-1H-inden-2-yl substituted with 0–3 R⁴¹;
  indazolyl substituted with 0–3 R⁴¹;
  tetrahydroquinolinyl substituted with 0–3 R⁴¹; and
  tetrahydro-isoquinolinyl substituted with 0–3 R⁴¹;

R³, at each occurrence, is independently selected from
  H, methyl, and ethyl;

R⁵ is H;

R$^{6a}$ is selected from H, —OH, methyl, and methoxy;

R$^{6b}$ is H;

R⁷, R⁸, and R⁹, at each occurrence, are independently selected from H, F, Cl, methyl, ethyl, methoxy, —CF₃, and —OCF₃;

R⁴¹, at each occurrence, is independently selected from
  H, F, Cl, Br, OH, CF₃, NO₂, CN, =O, methyl, ethyl, propyl, butyl, methoxy, and ethoxy;

R$^{42}$, at each occurrence, is independently selected from
H, F, Cl, Br, OH, CF$_3$, SO$_2$R$^{45}$, SR$^{45}$, NR$^{46}$R$^{47}$, OR$^{48}$,
NO$_2$, CN, =O, methyl, ethyl, propyl, butyl, methoxy,
and ethoxy;

R$^{45}$ is methyl, ethyl, propyl, or butyl;

R$^{46}$, at each occurrence, is independently selected from H,
methyl, ethyl, propyl, and butyl;

R$^{47}$, at each occurrence, is independently selected from
H, methyl, ethyl, n-propyl, i-propyl, n-butyl,
i-butyl, —C(=O)NH(methyl), —C(=O)NH(ethyl),
—SO$_2$(methyl), —SO$_2$(ethyl), —SO$_2$(phenyl),
—C(=O)O(methyl), —C(=O)O(ethyl), —C(=O)(methyl),
—C(=O)(ethyl), and —C(=O)H;

R$^{48}$, at each occurrence, is independently selected from
H, methyl, ethyl, n-propyl, i-propyl, —C(=O)NH(methyl), —C(=O)NH(ethyl),
—C(=O)O(methyl), —C(=O)O(ethyl), —C(=O)(methyl), —C(=O)(ethyl), and
—C(=O)H;

k is 1;

m is 0, 1, or 2; and n is 0, 1 or 2.

In a more preferred embodiment, the present invention provides the method as defined in claim 9 where the compound administered is a compound of Formula (I-a):

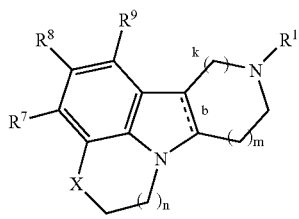

wherein:
b is a single bond;
X is —CH$_2$—, CH(OH)—, or —C(=O)—
R$^1$ is selected from
—(CH$_2$)$_3$C(=O)(4-fluoro-phenyl),
—(CH$_2$)$_3$C(=O)(4-bromo-phenyl),
—(CH$_2$)$_3$C(=O)(4-methyl-phenyl),
—(CH$_2$)$_3$C(=O)(4-methoxy-phenyl),
—(CH$_2$)$_3$C(=O)(4-(3,4-dichloro-phenyl)phenyl),
—(CH$_2$)$_3$C(=O)(3-methyl-4-fluoro-phenyl),
—(CH$_2$)$_3$C(=O)(2,3-dimethoxy-phenyl),
—(CH$_2$)$_3$C(=O)(phenyl),
—(CH$_2$)$_3$C(=O)(4-chloro-phenyl),
—(CH$_2$)$_3$C(=O)(3-methyl-phenyl),
—(CH$_2$)$_3$C(=O)(4-t-butyl-phenyl),
—(CH$_2$)$_3$C(=O)(3,4-difluoro-phenyl),
—(CH$_2$)$_3$C(=O)(2-methoxy-5-fluoro-phenyl),
—(CH$_2$)$_3$C(=O)(4-fluoro-1-naphthyl),
—(CH$_2$)$_3$C(=O)(benzyl),
—(CH$_2$)$_3$C(=O)(4-pyridyl),
—(CH$_2$)$_3$C(=O)(3-pyridyl),
—(CH$_2$)$_3$CH(OH)(4-fluoro-phenyl),
—(CH$_2$)$_3$CH(OH)(4-pyridyl),
—(CH$_2$)$_3$CH(OH)(2,3-dimethoxy-phenyl),
—(CH$_2$)$_3$S(3-fluoro-phenyl),
—(CH$_2$)$_3$S(4-fluoro-phenyl),
—(CH$_2$)$_3$S(=O)(4-fluoro-phenyl),
—(CH$_2$)$_3$SO$_2$(3-fluoro-phenyl),
—(CH$_2$)$_3$SO$_2$(4-fluoro-phenyl),
—(CH$_2$)$_3$O(4-fluoro-phenyl),
—(CH$_2$)$_3$O(phenyl),
—(CH$_2$)$_3$O(3-pyridyl),
—(CH$_2$)$_3$O(4-pyridyl),
—(CH$_2$)$_3$O(2-NH$_2$-phenyl),
—(CH$_2$)$_3$O(2-NH$_2$-5-F-phenyl),
—(CH$_2$)$_3$O(2-NH$_2$-4-F-phenyl),
—(CH$_2$)$_3$O(2-NH$_2$-3-F-phenyl),
—(CH$_2$)$_3$O(2-NH$_2$-4-Cl-phenyl),
—(CH$_2$)$_3$O(2-NH$_2$-4-OH-phenyl),
—(CH$_2$)$_3$O(2-NH$_2$-4-Br-phenyl),
—(CH$_2$)$_3$O(2-NHC(=O)Me-4-F-phenyl),
—(CH$_2$)$_3$O(2-NHC(=O)Me-phenyl),
—(CH$_2$)$_3$NH(4-fluoro-phenyl),
—(CH$_2$)$_3$N(methyl)(4-fluoro-phenyl),
—(CH$_2$)$_3$CO$_2$(ethyl),
—(CH$_2$)$_3$C(=O)N(methyl)(methoxy),
—(CH$_2$)$_3$C(=O)NH(4-fluoro-phenyl),
—(CH$_2$)$_2$NHC(=O)(phenyl),
—(CH$_2$)$_2$NMeC(=O)(phenyl),
—(CH$_2$)$_2$NHC(=O)(2-fluoro-phenyl),
—(CH$_2$)$_2$NMeC(=O)(2-fluoro-phenyl),
—(CH$_2$)$_2$NHC(=O)(4-fluoro-phenyl),
—(CH$_2$)$_2$NMeC(=O)(4-fluoro-phenyl),
—(CH$_2$)$_2$NHC(=O)(2,4-difluoro-phenyl),
—(CH$_2$)$_2$NMeC(=O)(2,4-difluoro-phenyl),
—(CH$_2$)$_3$(3-indolyl),
—(CH$_2$)$_3$(1-methyl-3-indolyl),
—(CH$_2$)$_3$(1-indolyl),
—(CH$_2$)$_3$(1-indolinyl),
—(CH$_2$)$_3$(1-benzimidazolyl),
—(CH$_2$)$_3$(1H-1,2,3-benzotriazol-1-yl),
—(CH$_2$)$_3$(1H-1,2,3-benzotriazol-2-yl),
—(CH$_2$)$_2$(1H-1,2,3-benzotriazol-1-yl),
—(CH$_2$)$_2$(1H-1,2,3-benzotriazol-2-yl),
—(CH$_2$)$_3$(3,4 dihydro-1 (2H)-quinolinyl),
—(CH$_2$)$_2$C(=O)(4-fluoro-phenyl),
—(CH$_2$)$_2$C(=O)NH(4-fluoro-phenyl),
—CH$_2$CH$_2$(3-indolyl),
—CH$_2$CH$_2$(1-phthalimidyl),
—(CH$_2$)$_4$C(=O)N(methyl)(methoxy),
—(CH$_2$)$_4$CO$_2$(ethyl),
—(CH$_2$)$_4$C(=O)(phenyl),
—(CH$_2$)$_4$(cyclohexyl),
—(CH$_2$)$_4$CH(phenyl)$_2$,
—CH$_2$CH$_2$CH=C(phenyl)$_2$,
—CH$_2$CH$_2$CH=CMe(4-F-phenyl),
—(CH$_2$)$_3$CH(4-fluoro-phenyl)$_2$,
—CH$_2$CH$_2$CH=C(4-fluoro-phenyl)$_2$,
—(CH$_2$)$_2$(2,3-dihydro-1H-inden-2-yl),
—(CH$_2$)$_3$C(=O)(2-NH$_2$-phenyl),
—(CH$_2$)$_3$C(=O)(2-NH$_2$-5-F-phenyl),
—(CH$_2$)$_3$C(=O)(2-NH$_2$-4-F-phenyl),
—(CH$_2$)$_3$C(=O)(2-NH$_2$-3-F-phenyl),
—(CH$_2$)$_3$C(=O)(2-NH$_2$-4-Cl-phenyl),
—(CH$_2$)$_3$C(=O)(2-NH$_2$-4-OH-phenyl),
—(CH$_2$)$_3$C(=O)(2-NH$_2$-4-Br-phenyl),
—(CH$_2$)$_3$(1H-indazol-3-yl),
—(CH$_2$)$_3$(5-F-1H-indazol-3-yl),
—(CH$_2$)$_3$(7-F-1H-indazol-3-yl),
—(CH$_2$)$_3$(6-Cl-1H-indazol-3-yl),
—(CH$_2$)$_3$(6-Br-1H-indazol-3-yl),
—(CH$_2$)$_3$C(=O)(2-NHMe-phenyl),
—(CH$_2$)$_3$(1-benzothien-3-yl),
—(CH$_2$)$_3$(6-F-1H-indol-1-yl),
—(CH$_2$)$_3$(5-F-1H-indol-1-yl), —(CH$_2$)$_3$(6-F-2,3-dihydro-1H-indol-1-yl),
—(CH$_2$)$_3$(5-F-2,3-dihydro-1H-indol-1-yl),
—(CH$_2$)$_3$(6-F-1H-indol-3-yl),
—(CH$_2$)$_3$(5-F-1H-indol-3-yl),
—(CH$_2$)$_3$(5-F-1H-indol-3-yl),
—(CH$_2$)$_3$(9H-purin-9-yl),
—(CH$_2$)$_3$(7H-purin-7-yl),
—(CH$_2$)$_3$(6-F-1H-indazol-3-yl),
—(CH$_2$)$_2$C(=O)(2-NHSO$_2$Me-4-F-phenyl),
—(CH$_2$)$_2$C(=O)(2-NHC(=O)Me-4-F-phenyl),
—(CH$_2$)$_2$C(=O)(2-NHC(=O)Me-phenyl),
—(CH$_2$)$_2$C(=O)(2-NHCO$_2$Et-4-F-phenyl),
—(CH$_2$)$_2$C(=O)(2-NHC(=O)NHEt-4-F-phenyl),
—(CH$_2$)$_2$C(=O)(2-NHCHO-4-F-phenyl),
—(CH$_2$)$_2$C(=O)(2-OH-4-F-phenyl),
—(CH$_2$)$_2$C(=O)(2-MeS-4-F-phenyl),
—(CH$_2$)$_2$C(=O)(2-NHSO$_2$Me-4-F-phenyl),
—(CH$_2$)$_2$C(Me)CO$_2$Me,
—(CH$_2$)$_2$C(Me)CH(OH)(4-F-phenyl)$_2$,
—(CH$_2$)$_2$C(Me)CH(OH)(4-Cl-phenyl)$_2$,
—(CH$_2$)$_2$C(Me)C(=O)(4-F-phenyl),
—(CH$_2$)$_2$C(Me)C(=O)(2-MeO-4-F-phenyl),
—(CH$_2$)$_2$C(Me)C(=O)(3-Me-4-F-phenyl),
—(CH$_2$)$_2$C(Me)C(=O)(2-Me-phenyl),
—(CH$_2$)$_2$C(Me)C(=O)phenyl,

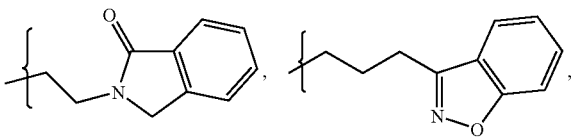

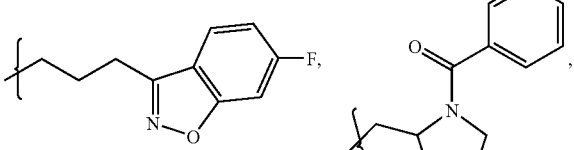

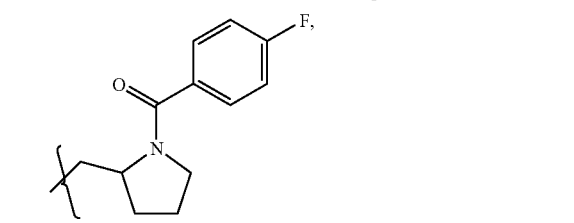

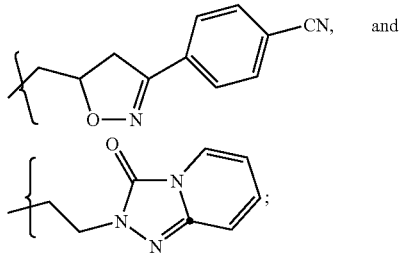

$R^7$, $R^8$, and $R^9$, at each occurrence, are independently selected from
hydrogen, fluoro, chloro, bromo, cyano, methyl, ethyl, propyl, isopropyl, butyl, t-butyl, nitro, trifluoromethyl, methoxy, ethoxy, isopropoxy, trifluoromethoxy, phenyl, benzyl,
HC(=O)—, methylC(=O)—, ethylC(=O)—, propylC(=O)—, isopropylC(=O)—, n-butylC(=O)—, isobutylC(=O)—, secbutylC(=O)—, tertbutylC(=O)—, phenylC(=O)—,
methylC(=O)NH—, ethylC(=O)NH—, propylC(=O)NH—, isopropylC(=O)NH—, n-butylC(=O)NH—, isobutylC(=O)NH—, secbutylC(=O)NH—, tertbutylC(=O)NH—, phenylC(=O)NH—,
methylamino-, ethylamino-, propylamino-, isopropylamino-, n-butylamino-, isobutylamino-, secbutylamino-, tertbutylamino-, phenylamino-,
provided that two of substituents $R^7$, $R^8$, and $R^9$, are independently selected from hydrogen, fluoro, chloro, bromo, cyano, methyl, ethyl, propyl, isopropyl, butyl, t-butyl, nitro, trifluoromethyl, methoxy, ethoxy, isopropoxy, and trifluoromethoxy;

k is 1 or 2;
m is 1 or 2; and
n is 0, 1 or 2.

In a more preferred embodiment, the present invention provides the method as defined in claim 13 where the compound administered is a compound of Formula (V-a):

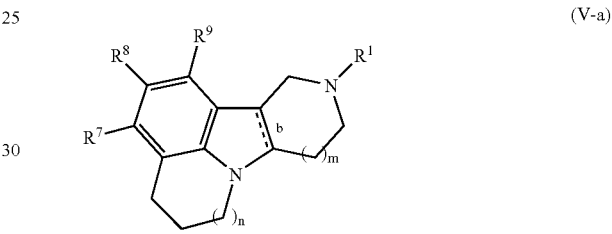

(V-a)

wherein:
b is a single bond, wherein the bridge hydrogens are in a cis position;
$R^1$ is selected from
—(CH$_2$)$_3$C(=O)(4-fluoro-phenyl),
—(CH$_2$)$_3$C(=O)(4-bromo-phenyl),
—(CH$_2$)$_3$C(=O)(4-methyl-phenyl),
—(CH$_2$)$_3$C(=O)(4-methoxy-phenyl),
—(CH$_2$)$_3$C(=O)(4-(3,4-dichloro-phenyl)phenyl),
—(CH$_2$)$_3$C(=O)(3-methyl-4-fluoro-phenyl),
—(CH$_2$)$_3$C(=O)(2,3-dimethoxy-phenyl),
—(CH$_2$)$_3$C(=O)(phenyl),
—(CH$_2$)$_3$C(=O)(4-chloro-phenyl),
—(CH$_2$)$_3$C(=O)(3-methyl-phenyl),
—(CH$_2$)$_3$C(=O)(4-t-butyl-phenyl),
—(CH$_2$)$_3$C(=O)(3,4-difluoro-phenyl),
—(CH$_2$)$_3$C(=O)(2-methoxy-5-fluoro-phenyl),
—(CH$_2$)$_3$C(=O)(4-fluoro-1-naphthyl),
—(CH$_2$)$_3$C(=O)(benzyl),
—(CH$_2$)$_3$C(=O)(4-pyridyl),
—(CH$_2$)$_3$C(=O)(3-pyridyl),
—(CH$_2$)$_3$CH(OH)(4-fluoro-phenyl),
—(CH$_2$)$_3$CH(OH)(4-pyridyl),
—(CH$_2$)$_3$CH(OH)(2,3-dimethoxy-phenyl),
—(CH$_2$)$_3$S(3-fluoro-phenyl),
—(CH$_2$)$_3$S(4-fluoro-phenyl),
—(CH$_2$)$_3$S(=O)(4-fluoro-phenyl),
—(CH$_2$)$_3$SO$_2$(3-fluoro-phenyl),
—(CH$_2$)$_3$SO$_2$(4-fluoro-phenyl),
—(CH$_2$)$_3$O(4-fluoro-phenyl),
—(CH$_2$)$_3$O(phenyl),
—(CH$_2$)$_3$NH(4-fluoro-phenyl), —(CH$_2$)$_3$N(methyl)(4-fluoro-phenyl),
—(CH$_2$)$_3$CO$_2$(ethyl),
—(CH$_2$)$_3$C(=O)N(methyl)(methoxy),
—(CH$_2$)$_3$C(=O)NH(4-fluoro-phenyl),
—(CH$_2$)$_2$NHC(=O)(phenyl),
—(CH$_2$)$_2$NMeC(=O)(phenyl),
—(CH$_2$)$_2$NHC(=O)(2-fluoro-phenyl),
—(CH$_2$)$_2$NMeC(=O)(2-fluoro-phenyl),
—(CH$_2$)$_2$NHC(=O)(4-fluoro-phenyl),
—(CH$_2$)$_2$NMeC(=O)(4-fluoro-phenyl),
—(CH$_2$)$_2$NHC(=O)(2,4-difluoro-phenyl),
—(CH$_2$)$_2$NMeC(=O)(2,4-difluoro-phenyl),
—(CH$_2$)$_3$(3-indolyl),
—(CH$_2$)$_3$(1-methyl-3-indolyl),
—(CH$_2$)$_3$(1-indolyl),
—(CH$_2$)$_3$(1-indolinyl),
—(CH$_2$)$_3$(1-benzimiidazolyl),
—(CH$_2$)$_3$(1H-1,2,3-benzotriazol-1-yl),
—(CH$_2$)$_3$(1H-1,2,3-benzotriazol-2-yl),
—(CH$_2$)$_3$(1H-1,2,3-benzotriazol-1-yl),
—(CH$_2$)$_3$(1H-1,2,3-benzotriazol-2-yl),
—(CH$_2$)$_3$(3,4 dihydro-1(2H)-quinolinyl),
—(CH$_2$)$_2$C(=O)(4-fluoro-phenyl),
—(CH$_2$)$_2$C(=O)NH(4-fluoro-phenyl),
—CH$_2$CH$_2$(3-indolyl),
—CH$_2$CH$_2$(1-phthaiimidyl),
—(CH$_2$)$_4$C(=O)N(methyl)(methoxy),
—(CH$_2$)$_4$CO$_2$(ethyl),
—(CH$_2$)$_4$C(=O)(phenyl),
—(CH$_2$)$_4$(cyclohexyl),
—(CH$_2$)$_3$CH(phenyl)$_2$,
—CH$_2$CH$_2$CH=C(phenyl)$_2$,
—CH$_2$CH$_2$CH=CMe(4-F-phenyl),
—(CH$_2$)$_3$CH(4-fluoro-phenyl)$_2$,
—CH$_2$CH$_2$CH=C(4-fluoro-phenyl)$_2$,
—(CH$_2$)$_2$(2,3-dihydro-1H-inden-2-yl),
—(CH$_2$)$_3$C(=O)(2-NH$_2$-phenyl),
—(CH$_2$)$_3$C(=O)(2-NH$_2$-5-F-phenyl),
—(CH$_2$)$_3$C(=O)(2-NH$_2$-4-F-phenyl),
—(CH$_2$)$_3$C(=O)(2-NH$_2$-3-F-phenyl),
—(CH$_2$)$_3$C(=O)(2-NH$_2$-4-Cl-phenyl),
—(CH$_2$)$_3$C(=O)(2-NH$_2$-4-OH-phenyl),
—(CH$_2$)$_3$C(=O)(2-NH$_2$-4-Br-phenyl),
—(CH$_2$)$_3$(1H-indazol-3-yl),
—(CH$_2$)$_3$(5-F-1H-indazol-3-yl),
—(CH$_2$)$_3$(7-F-1H-indazol-3-yl),
—(CH$_2$)$_3$(6-Cl-1H-indazol-3-yl),
—(CH$_2$)$_3$(6-Br-1H-indazol-3-yl),
—(CH$_2$)$_3$C(=O)(2-NHMe-phenyl),
—(CH$_2$)$_3$(1-benzothien-3-yl),
—(CH$_2$)$_3$(6-F-1H-indol-1-yl),
—(CH$_2$)$_3$(5-F-1H-indol-1-yl),
—(CH$_2$)$_3$(6-F-2,3-dihydro-1H-indol-1-yl),
—(CH$_2$)$_3$(5-F-2,3-dihydro-11H-indol-1-yl),
—(CH$_2$)$_3$(6-F-1H-indol-3-yl),
—(CH$_2$)$_3$(5-F-1H-indol-3-yl),
—(CH$_2$)$_3$(5-F-1H-indol-3-yl),
—(CH$_2$)$_3$(9H-purin-9-yl),
—(CH$_2$)$_3$(7H-purin-7-yl),
—(CH$_2$)$_3$(6-F-1H-indazol-3-yl),
—(CH$_2$)$_3$C(=O)(2-NHSO$_2$Me-4-F-phenyl),
—(CH$_2$)$_3$C(=O)(2-NHC(=O)Me-4-F-phenyl),
—(CH$_2$)$_3$C(=O)(2-NHC(=O)Me-4-F-phenyl),
—(CH$_2$)$_3$C(=O)(2-NHCO$_2$Et-4-F-phenyl),
—(CH$_2$)$_3$C(=O)(2-NHC(=O)NHEt-4-F-phenyl),
—(CH$_2$)$_3$C(=O)(2-NHCHO-4-F-phenyl),
—(CH$_2$)$_3$C(=O)(2-OH-4-F-phenyl),
—(CH$_2$)$_3$C(=O)(2-MeS-4-F-phenyl),
—(CH$_2$)$_3$C(=O)(2-NHSO$_2$Me-4-F-phenyl),
—(CH$_2$)$_2$C(Me)CO$_2$Me,
—(CH$_2$)$_2$C(Me)CH(OH)(4-F-phenyl)$_2$,
—(CH$_2$)$_2$C(Me)CH(OH)(4-Cl-phenyl)$_2$,
—(CH$_2$)$_2$C(Me)C(=O)(4-F-phenyl),
—(CH$_2$)$_2$C(Me)C(=O)(2-MeO-4-F-phenyl),
—(CH$_2$)$_2$C(Me)C(=O)(3-Me-4-F-phenyl),
—(CH$_2$)$_2$C(Me)C(=O)(2-Me-phenyl),
—(CH$_2$)$_2$C(Me)C(=O)phenyl,

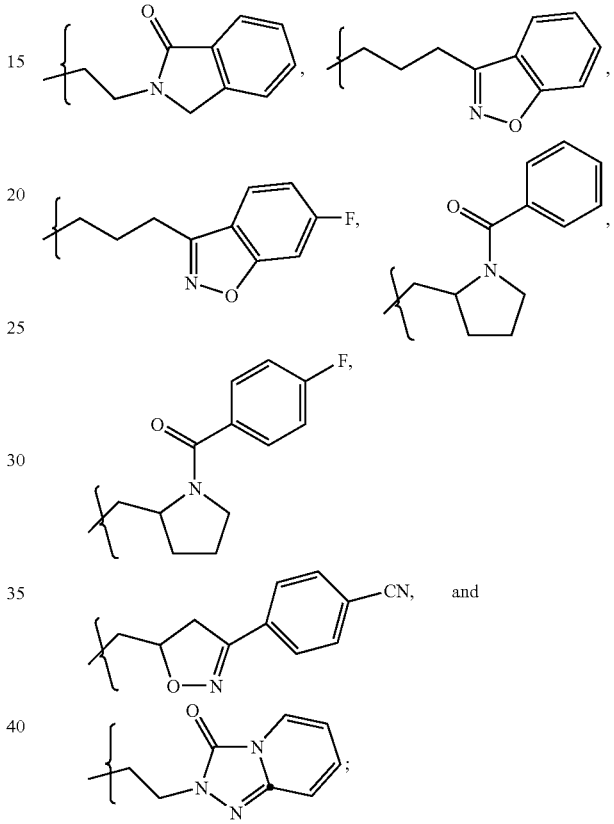

R$^7$, R$^8$, and R$^9$, at each occurrence, are independently selected from hydrogen, fluoro, chloro, bromo, cyano, methyl, ethyl, propyl, isopropyl, butyl, t-butyl, nitro, trifluoromethyl, methoxy, ethoxy, isopropoxy, trifluoromethoxy, methylC(=O)—, ethylC(=O)—, propylC(=O)—, isopropylC(=O)—, methylC(=O)NH—, ethylC(=O)NH—, propylC(=O)NH—, isopropylC(=O)NH, methylamino-, ethylamino-, propylamino-, and isopropylamino-,
provided that two of substituents R$^7$, R$^8$, and R$^9$, are independently selected from hydrogen, fluoro, chloro, methyl, trifluoromethyl, methoxy, and trifluoromethoxy;
m is 1 or 2; and
n is 0, 1 or 2.
In a more preferred embodiment, the present invention provides the method as defined in claim 1 where the compound administered is selected from the group:
(±)-cis-9-(cyclopropylcarbonyl)-4,5,6a,7,8,9,10,10a-octahydropyrido[4,3-b]pyrrolo[3,2,1-hi]indole;
(±)-cis-9-isobutyryl-4,5,6a,7,8,9,10,10a-octahydropyrido[4,3-b]pyrrolo[3,2,1-hi]indole;

tert-butyl(±)-cis-2-(2-chlorophenyl)-4,5,7,8,10,10a-hexahydropyrido[4,3-b]pyrrolo[3,2,1-hi]indole-9(6aH)-carboxylate;
tert-butyl(±)-cis-2-(2,4-dichlorophenyl)-4,5,7,8,10,10a-hexahydropyrido[4,3-b]pyrrolo[3,2,1-hi]indole-9(6aH)-carboxylate;
tert-butyl(±)-cis-2-(3,4-dichlorophenyl)-4,5,7,8,10,10a-hexahydropyrido[4,3-b]pyrrolo[3,2,1-hi]indole-9(6aH)-carboxylate;
tert-butyl(±)-cis-2-(2,3-dichlorophenyl)-4,5,7,8,10,10a-hexahydropyrido[4,3-b]pyrrolo[3,2,1-hi]indole-9(6aH)-carboxylate;
tert-butyl(±)-cis-2-[2-chloro-4-(trifluoromethyl)phenyl]-4,5,7,8,10,10a-hexahydropyrido[4,3-b]pyrrolo[3,2,1-hi]indole-9(6aH)-carboxylate;
tert-butyl(±)-cis-2-(2-chloro-4-methoxyphenyl)-4,5,7,8,10,10a-hexahydropyrido[4,3-b]pyrrolo[3,2,1-hi]indole-9(6aH)-carboxylate;
tert-butyl(±)-cis-2-(5-isopropyl-2-methoxyphenyl)-4,5,7,8,10,10a-hexahydropyrido[4,3-b]pyrrolo[3,2,1-hi]indole-9(6aH)-carboxylate;
tert-butyl(±)-cis-2-(3-fluorophenyl)-4,5,7,8,10,10a-hexahydropyrido[4,3-b]pyrrolo[3,2,1-hi]indole-9(6aH)-carboxylate;
tert-butyl(±)-cis-2-(2,4-dimethoxyphenyl)-4,5,7,8,10,10a-hexahydropyrido[4,3-b]pyrrolo[3,2,1-hi]indole-9(6aH)-carboxylate;
(±)-cis-2-(2-chlorophenyl)-4,5,6a,7,8,9,10,10a-octahydropyrido[4,3-b]pyrrolo[3,2,1-hi]indole;
(±)-cis-2-(2,4-dichlorophenyl)-4,5,6a,7,8,9,10,10a-octahydropyrido[4,3-b]pyrrolo[3,2,1-hi]indole;
(±)-cis-2-(3,4-dichlorophenyl)-4,5,6a,7,8,9,10,10a-octahydropyrido[4,3-b]pyrrolo[3,2,1-hi]indole;
(±)-cis-2-(2,3-dichlorophenyl)-4,5,6a,7,8,9,10,10a-octahydropyrido[4,3-b]pyrrolo[3,2,1-hi]indole;
(±)-cis-2-[2-chloro-4-(trifluoromethyl)phenyl]-4,5,6a,7,8,9,10,10a-octahydropyrido[4,3-b]pyrrolo[3,2,1-hi]indole;
(±)-cis-2-(2-chloro-4-methoxyphenyl)-4,5,6a,7,8,9,10,10a-octahydropyrido[4,3-b]pyrrolo[3,2,1-hi]indole;
(±)-cis-2-(4-isopropyl-2-methoxyphenyl)-4,5,6a,7,8,9,10,10a-octahydropyrido[4,3-b]pyrrolo[3,2,1-hi]indole;
(±)-cis-2-(3-fluorophenyl)-4,5,6a, 7,8,9,10,10a-octahydropyrido[4,3-b]pyrrolo[3,2,1-hi]indole;
(±)-cis-2-(2,4-dimethoxyphenyl)-4,5,6a, 7,8,9,10,10a-octahydropyrido[4,3-b]pyrrolo[3,2,1-hi]indole;
tert-butyl(±)-cis-5,6,8,9,11,11a-hexahydro-4H-pyrido[3',4':4,5]pyrrolo[3,2,1-ij]quinoline-10(7aH)-carboxylate;
tert-butyl(±)-cis-2-bromo-5,6,8,9,11,11a-hexahydro-4H-pyrido[3',4':4,5]pyrrolo[3,2,1-ij]quinoline-10(7aH1)-carboxylate;
tert-butyl(±)-cis-2-(2,3-dichlorophenyl)-5,6,8,9,11,11a-hexahydro-4H-pyrido[3',4':4,5]pyrrolo[3,2,1-q]quinoline-10(7aH)-carboxylate;
tert-butyl(±)-cis-2-(3,4-dichlorophenyl)-5,6,8,9,11,11a-hexahydro-4H-pyrido[3',4':4,5]pyrrolo[3,2,1-ij]quinoline-10(7aH)-carboxylate;
tert-butyl(±)-cis-2-[2-chloro-4-(trifluoromethyl)phenyl]-5,6,8,9,11,11a-hexahydro-4H-pyrido[3',4':4,5]pyrrolo[3,2,1-ij]quinoline-10(7aH)-carboxylate;
(±)-cis-2-(2,3-dichlorophenyl)-5,6,7a,8,9,10,11,11a-octahydro-4H-pyrido[3',4':4,5]pyrrolo[3,2,1-ij]quinoline;
(±)-cis-2-(3,4-dichlorophenyl)-5,6,7a,8,9,10,11,11a-octahydro-4H-pyrido[3',4':4,5]pyrrolo[3,2,1-ij]quinoline;
(±)-cis-2-[2-chloro-4-(trifluoromethyl)phenyl]-5,6,7a,8,9,10,11,11a-octahydro-4H-pyrido[3',4':4,5]pyrrolo[3,2,1-ij]quinoline;
4-((±)-cis-2-(2-chlorophenyl)-4,5,7,8,10,10a-hexahydropyrido[4,3-b]pyrrolo[3,2,1-hi]indol-9(6aH)-yl)-1-(4-fluorophenyl)-1-butanone;
4-((±)-cis-2-(2,4-dichlorophenyl)-4,5,7,8,10,10a-hexahydropyrido[4,3-b]pyrrolo[3,2,1-hi]indol-9(6aH)-yl)-1-(4-fluorophenyl)-1-butanone;
4-((±)-cis-5,6,8,9,11,11a-hexahydro-4H-pyrido[3',4':4,5]pyrrolo[3,2,1-ij]qionolin-10(7aH)-yl)-1-(4-fluorophenyl)-1-butanone;
4-((±)-cis-4,5,7,8,10,10a-hexahydropyrido[4.3-b]pyrrolo[3,2,1-hi]indol-9(6aH)-yl)-1-(4-fluorophenyl)-1-butanone;
(6aS,10aR)-2-(2-fluoro-4-methoxyphenyl)-4,5,6a,7,8,9,10,10a-octahydropyrido[4,3-b]pyrrolo[3,2,1-hi]indole;
tert-butyl(6aS,10aR)-2-[4-ethoxy-2-(trifluoromethyl)phenyl]-4,5,7,8,10,10a-hexahydropyrido[4,3-b]pyrrolo[3,2,1-hi]indole-9(6aH)-carboxylate;
(6aS,10aR)-2-[4-ethoxy-2-(trifluoromethyl)phenyl]-4,5,6a,7,8,9,10,10a-octahydropyrido[4,3-b]pyrrolo[3,2,1-hi]indole;
tert-butyl(6aS,10aR)-2-(4-chloro-2-fluorophenyl)-4,5,7,8,10,10a-hexahydropyrido[4,3-b]pyrrolo[3,2,1-hi]indole-9(6aH)-carboxylate;
(6aS,10aR)-2-(4-chloro-2-fluorophenyl)-4,5,6a,7,8,9,10,10a-octahydropyrido[4,3-b]pyrrolo[3,2,1-hi]indole;
tert-butyl(6aS,10aR)-2-[4-isopropoxy-2-(trifluoromethyl)phenyl]-4,5,7,8,10,10a-hexahydropyrido[4,3-b]pyrrolo[3,2,1-hi]indole-9(6aH)-carboxylate;
(6aS,10aR)-2-[4-isopropoxy-2-(trifluoromethyl)phenyl]-4,5,6a,7,8,9,10,10a-octahydropyrido[4,3-b]pyrrolo[3,2,1-hi]indole;
tert-butyl(6aS,10aR)-2-[4-methoxy-2-(trifluoromethyl)phenyl]-4,5,7,8,10,10a-hexahydropyrido[4,3-b]pyrrolo[3,2,1-hi]indole-9(6aH)-carboxylate;
(6aS,10aR)-2-[4-methoxy-2-(trifluoromethyl)phenyl]-4,5,6a,7,8,9,10,10a-octahydropyrido[4,3-b]pyrrolo[3,2,1-hi]indole;
tert-butyl(6aS,10aR)-2-phenyl-4,5,7,8,10,10a-hexahydropyrido[4,3-b]pyrrolo[3,2,1-hi]indole-9(6aH)-carboxylate;
(6aS,10aR)-2-phenyl-4,5,6a,7,8,9,10,10a-octahydropyrido[4,3-b]pyrrolo[3,2,1-hi]indole;
tert-butyl(6aS,10aR)-2-(2-methylphenyl)-4,5,7,8,10,10a-hexahydropyrido[4,3-b]pyrrolo[3,2,1-hi]indole-9(6aH)-carboxylate;
(6aS,10aR)-2-(2-methylphenyl)-4,5,6a,7,8,9,10,10a-octahydropyrido[4,3-b]pyrrolo[3,2,1-hi]indole;
tert-butyl(6aS,10aR)-2-[2-(trifluoromethyl)phenyl]-4,5,7,8,10,10a-hexahydropyrido[4,3-b]pyrrolo[3,2,1-hi]indole-9(6aH)-carboxylate;
(6aS,10aR)-2-[2-(trifluoromethyl)phenyl]-4,5,6a,7,8,9,10,10a-octahydropyrido[4,3-b]pyrrolo[3,2,1-hi]indole;
tert-butyl(6aS,10aR)-2-(3,4-dimethoxyphenyl)-4,5,7,8,10,10a-hexahydropyrido[4,3-b]pyrrolo[3,2,1-hi]indole-9(6aH)-carboxylate;
(6aS,10aR)-2-(3,4-dimethoxyphenyl)-4,5,6a,7,8,9,10,10a-octahydropyrido[4,3-b]pyrrolo[3,2,1-hi]indole;
tert-butyl(6aS,10aR)-2-(2,5-dichlorophenyl)-4,5,7,8,10,10a-hexahydropyrido[4,3-b]pyrrolo[3,2,1-hi]indole-9(6aH)-carboxylate;
(6aS,10aR)-2-(2,5-dichlorophenyl)-4,5,6a,7,8,9,10,10a-octahydropyrido[4,3-b]pyrrolo[3,2,1-hi]indole;
tert-butyl(6aS,10aR)-2-(3,5-dichlorophenyl)-4,5,7,8,10,10a-hexahydropyrido[4,3-b]pyrrolo[3,2,1-hi]indole-9(6aH)-carboxylate;
(6aS,10aR)-2-(3,5-dichlorophenyl)-4,5,6a,7,8,9,10,10a-octahydropyrido[4,3-b]pyrrolo[3,2,1-hi]indole;

tert-butyl(6aS,10aR)-2-(2-isopropyl-4-methoxyphenyl)-4,5,7,8,10,10a-hexahydropyrido[4,3-b]pyrrolo[3,2,1-hi]indole-9(6aH)-carboxylate;
(6aS,10aR)-2-(2-isopropyl-4-methoxyphenyl)-4,5,6a,7,8,9,10,10a-octahydropyrido[4,3-b]pyrrolo[3,2,1-hi]indole;
tert-butyl(6aS,10aR)-2-(5-fluoro-4-methoxy-2-methylphenyl)-4,5,7,8,10,10a-hexahydropyrido[4,3-b]pyrrolo[3,2,1-hi]indole-9(6aH)-carboxylate;
(6aS,10aR)-2-(5-fluoro-4-methoxy-2-methylphenyl)-4,5,6a,7,8,9,10,10a-octahydropyrido[4,3-b]pyrrolo[3,2,1-hi]indole;
tert-butyl(6aS,10aR)-2-(4-methoxy-2-methylphenyl)-4,5,7,8,10,10a-hexahydropyrido[4,3-b]pyrrolo[3,2,1-hi]indole-9(6aH)-carboxylate;
(6aS,10aR)-2-(4-methoxy-2-methylphenyl)-4,5,6a,7,8,9,10,10a-octahydropyrido[4,3-b]pyrrolo[3,2,1-hi]indole;
tert-butyl(6aS,10aR)-2-(2-chloro-4-methoxyphenyl)-4,5,7,8,10,10a-hexahydropyrido[4,3-b]pyrrolo[3,2,1-hi]indole-9(6aH)-carboxylate;
(6aS,10aR)-2-(2-chloro-4-methoxyphenyl)-4,5,6a,7,8,9,10,10a-octahydropyrido[4,3-b]pyrrolo[3,2,1-hi]indole;
tert-butyl(6aS,10aR)-2-(3-chloro-2-methylphenyl)-4,5,7,8,10,10a-hexahydropyrido[4,3-b]pyrrolo[3,2,1-hi]indole-9(6aH)-carboxylate;
(6aS,10aR)-2-(3-chloro-2-methylphenyl)-4,5,6a,7,8,9,10,10a-octahydropyrido[4,3-b]pyrrolo[3,2,1-hi]indole;
2-[(6aS,10aR)-4,5,6a,7,8,9,10,10a-octahydropyrido[4,3-b]pyrrolo[3,2,1-hi]-2-yl]-5-methoxybenzaldehyde;
(6aS,10aR)-2-(2,6-dichlorophenyl)-4,5,6a,7,8,9,10,10a-octahydropyrido[4,3-b]pyrrolo[3,2,1-hi]indole;
N-[4-[(6aS,10aR)-4,5,6a,7,8,9,10,10a-octahydropyrido[4,3-b]pyrrolo[3,2,1-hi]indol-2-yl]-3-(trifluoromethyl)phenyl]-N-methylamine;
4-[(6aS,10aR)-4,5,6a,7,8,9,10,10a-octahydropyrido[4,3-b]pyrrolo[3,2,1-hi]indol-2-yl]-3-(trifluoromethyl)phenylamine;
1-(2-[(6aS,10aR)-4,5,6a,7,8,9,10,10a-octahydropyrido[4,3-b]pyrrolo[3,2,1-hi]indol-2-yl]-5-methoxyphenyl)ethanol;
tert-butyl(±)-cis-4,5,6,7,8a,9,10,11,12,12a-decahydroazepino[3,2,1-hi]pyrido[4,3-b]indole-11(8aH)-carboxylate;
tert-butyl(8aS,12aR)-2-bromo-4,5,6,7,8a,9,10,11,12,12a-decahydroazepino[3,2,1-hi]pyrido[4,3-b]indole-11(8aH)-carboxylate;
(8aS,12aR)-2-(2,4-dichlorophenyl)-4,5,6,7,8a,9,10,11,12,12a-decahydroazepino[3,2,1-hi]pyrido[4,3-b]indole;
(8aS,12aR)-2-(2,3-dichlorophenyl)-4,5,6,7,8a,9,10,11,12,12a-decahydroazepino[3,2,1-hi]pyrido[4,3-b]indole;
(8aS,12aR)-2-(3,4-dichlorophenyl)-4,5,6,7,8a,9,10,11,12,12a-decahydroazepino[3,2,1-hi]pyrido[4,3-b]indole;
(8aS,12aR)-2-(3,5-dichlorophenyl)-4,5,6,7,8a,9,10,11,12,12a-decahydroazepino[3,2,1-hi]pyrido[4,3-b]indole;
(8aS,12aR)-2-(2,5-dichlorophenyl)-4,5,6,7,8a,9,10,11,12,12a-decahydroazepino[3,2,1-hi]pyrido[4,3-b]indole;
(8aS,12aR)-2-(2,6-dichlorophenyl)-4,5,6,7,8a,9,10,11,12,12a-decahydroazepino[3,2,1-hi]pyrido[4,3-b]indole;
(8aS,12aR)-2-(2-chlorophenyl)-4,5,6,7,8a,9,10,11,12,12a-decahydroazepino[3,2,1-hi]pyrido[4,3-b]indole;
(8aS,12aR)-2-(3-chlorophenyl)-4,5,6,7,8a,9,10,11,12,12a-decahydroazepino[3,2,1-hi]pyrido[4,3-b]indole;
(8aS,12aR)-2-(4-chlorophenyl)-4,5,6,7,8a,9,10,11,12,12a-decahydroazepino[3,2,1-hi]pyrido[4,3-b]indole;
(±)-cis-2-(2,6-difluorophenyl)-4,5,6,7,8a,9,10,11,12,12a-decahydroazepino[3,2,1-hi]pyrido[4,3-b]indole;
(8aS,12aR)-2-(2,6-difluorophenyl)-4,5,6,7,8a,9,10,11,12,12a-decahydroazepino[3,2,1-hi]pyrido[4,3-b]indole;
(8aS,12aR)-2-(2,3-difluorophenyl)-4,5,6,7,8a,9,10,11,12,12a-decahydroazepino[3,2,1-hi]pyrido[4,3-b]indole;
(8aS,12aR)-2-(3,4-difluorophenyl)-4,5,6,7,8a,9,10,11,12,12a-decahydroazepino[3,2,1-hi]pyrido[4,3-b]indole;
(8aS,12aR)-2-(3-fluorophenyl)-4,5,6,7,8a,9,10,11,12,12a-decahydroazepino[3,2,1-hi]pyrido[4,3-b]indole;
(8aS,12aR)-2-[2-chloro-4-(trifluoromethyl)phenyl]-4,5,6,7,8a,9,10,11,12,12a-decahydroazepino[3,2,1-hi]pyrido[4,3-b]indole;
(8aS,12aR)-2-(2-chloro-4-methoxyphenyl)-4,5,6,7,8a,9,10,11,12,12a-decahydroazepino[3,2,1-hi]pyrido[4,3-b]indole;
(8aS,12aR)-2-(2-fluoro-4-methoxyphenyl)-4,5,6,7,8a,9,10,11,12,12a-decahydroazepino[3,2,1-hi]pyrido[4,3-b]indole;
(8aS,12aR)-2-(4-methoxy-2-methylphenyl)-4,5,6,7,8a,9,10,11,12,12a-decahydroazepino[3,2,1-hi]pyrido[4,3-b]indole;
(8aS,12aR)-2-[4-methoxy-2-(trifluoromethyl)phenyl]-4,5,6,7,8a,9,10,11,12,12a-decahydroazepino[3,2,1-hi]pyrido[4,3-b]indole;
(8aS,12aR)-2-[2-(trifluoromethyl)phenyl]-4,5,6,7,8a,9,10,11,12,12a-decahydroazepino[3,2,1-hi]pyrido[4,3-b]indole;
(8aS,12aR)-2-[4-isopropoxy-2-(trifluoromethyl)phenyl]-4,5,6,7,8a,9,10,11,12,12a-decahydroazepino[3,2,1-hi]pyrido[4,3-b]indole;
(8aS,12aR)-2-[2,4-bis(trifluoromethyl)phenyl]-4,5,6,7,8a,9,10,11,12,12a-decahydroazepino[3,2,1-hi]pyrido[4,3-b]indole;
(8aS,12aR)-2-[4-fluoro-2-(trifluoromethyl)phenyl]-4,5,6,7,8a,9,10,11,12,12a-decahydroazepino[3,2,1-hi]pyrido[4,3-b]indole;
4-[(8aS,12aR)-4,5,6,7,8a,9,10,11,12,12a-decahydroazepino[3,2,1-hi]pyrido[4,3-b]indol-2-yl]-3-(trifluoromethyl)aniline;
4-[(8aS,12aR)-4,5,6,7,8a,9,10,11,12,12a-decahydroazepino[3,2,1-hi]pyrido[4,3-b]indol-2-yl]-N-methyl-3-(trifluoromethyl)aniline;
2-[(8aS,12aR)-4,5,6,7,8a,9,10,11,12,12a-decahydroazepino[3,2,1-hi]pyrido[4,3-b]indol-2-yl]benzaldehyde;
{2-[(8aS,12aR)-4,5,6,7,8a,9,10,11,12,12a-decahydroazepino[3,2,1-hi]pyrido[4,3-b]indol-2-yl]phenyl}methanol;
2-[(8aS,12aR)-4,5,6,7,8a,9,10,11,12,12a-decahydroazepino[3,2,1-hi]pyrido[4,3-b]indol-2-yl]-5-methoxybenzaldehyde;
{2-[(8aS,12aR)-4,5,6,7,8a,9,10,11,12,12a-decahydroazepino[3,2,1-hi]pyrido[4,3-b]indol-2-yl]-5-methoxyphenyl}methanol;
4-[(8aS,12aR)-4,5,6,7,8a,9,10,11,12,12a-decahydroazepino[3,2,1-hi]pyrido[4,3-b]indol-2-yl]-3-methylbenzonitrile;
1-{2-[(8aS,12aR)-4,5,6,7,8a,9,10,11,12,12a-decahydroazepino[3,2,1-hi]pyrido[4,3-b]indol-2-yl]-5-methoxyphenyl}ethanol;
tert-butyl(7aS,11aR)-2-bromo-5,6,7a,8,9,10,11,11a-octahydro-4H-pyrido[3',4':4,5]pyrrolo[3,2,1-ij]quinoline-10(7aH)-carboxylate;
(7aS,11aR)-2-(2,4-dichlorophenyl)-5,6,7a,8,9,10,11,11a-octahydro-4H-pyrido[3',4':4,5]pyrrolo[3,2,1-ij]quinoline;
(7aS,11aR)-2-(3,4-dichlorophenyl)-5,6,7a,8,9,10,11,11a-octahydro-4H-pyrido[3',4':4,5]pyrrolo[3,2,1-ij]quinoline;
(7aS,11aR)-2-(3,5-dichlorophenyl)-5,6,7a,8,9,10,11,11a-octahydro-4H-pyrido[3',4':4,5]pyrrolo[3,2,1-ij]quinoline;
(7aS,11aR)-2-(2,5-dichlorophenyl)-5,6,7a,8,9,10,11,11a-octahydro-4H-pyrido[3',4':4,5]pyrrolo[3,2,1-ij]quinoline;
(7aS,11aR)-2-(2,6-dichlorophenyl)-5,6,7a,8,9,10,11,11a-octahydro-4H-pyrido[3',4':4,5]pyrrolo[3,2,1-q]quinoline;
(7aS,11aR)-2-(2-chlorophenyl)-5,6,7a,8,9,10,11,11a-octahydro-4H-pyrido[3',4':4,5]pyrrolo[3,2,1-ij]quinoline;

(7aS,11aR)-2-(3-chlorophenyl)-5,6,7a,8,9,10,11,11a-octahydro-4H-pyrido[3',4':4,5]pyrrolo[3,2,1-ij]quinoline;

(7aS,11aR)-2-(4-chlorophenyl)-5,6,7a,8,9,10,11,11a-octahydro-4H-pyrido[3',4':4,5]pyrrolo[3,2,1-ij]quinoline;

(7aS,11aR)-2-(2,6-difluorophenyl)-5,6,7a,8,9,10,11,11a-octahydro-4H-pyrido[3',4':4,5]pyrrolo[3,2,1-ij]quinoline;

(7aS,11aR)-2-(2,6-difluorophenyl)-10-methyl-5,6,7a,8,9,10,11,11a-octahydro-4H-pyrido[3',4':4,5]pyrrolo[3,2,1-ij]quinoline;

(7aS,11aR)-2-(2,3-difluorophenyl)-5,6,7a,8,9,10,11,11a-octahydro-4H-pyrido[3',4':4,5]pyrrolo[3,2,1-ij]quinoline;

(7aS,11aR)-2-(3,4-difluorophenyl)-5,6,7a,8,9,10,11,11a-octahydro-4H-pyrido[3',4':4,5]pyrrolo[3,2,1-ij]quinoline;

(7aS,11aR)-2-(3-fluorophenyl)-5,6,7a,8,9,10,11,11a-octahydro-4H-pyrido[3',4':4,5]pyrrolo[3,2,1-ij]quinoline;

(7aS,11aR)-2-(2-chloro-4-methoxyphenyl)-5,6,7a,8,9,10,11,11a-octahydro-4H-pyrido[3',4':4,5]pyrrolo[3,2,1-ij]quinoline;

(7aS,11aR)-2-(2-fluoro-4-methoxyphenyl)-5,6,7a,8,9,10,11,11a-octahydro-4H-pyrido[3',4':4,5]pyrrolo[3,2,1-ij]quinoline;

(7aS,11aR)-2-(4-methoxy-2-methylphenyl)-5,6,7a,8,9,10,11,11a-octahydro-4H-pyrido[3',4':4,5]pyrrolo[3,2,1-ij]quinoline;

(7aS,11aR)-2-[4-methoxy-2-(trifluoromethyl)phenyl]-5,6,7a,8,9,10,11,11a-octahydro-4H-pyrido[3',4':4,5]pyrrolo[3,2,1-ij]quinoline;

4-[(7aS,11aR)-5,6,7a,8,9,10,11,11a-octahydro-4H-pyrido[3',4':4,5]pyrrolo[3,2,1-ij]quinolin-2-yl]-3-(trifluoromethyl)phenol;

(7aS,11aR)-2-[2-(trifluoromethyl)phenyl]-5,6,7a,8,9,10,11,11a-octahydro-4H-pyrido[3',4':4,5]pyrrolo[3,2,1-ij]quinoline;

(7aS,11aR)-2-[4-isopropoxy-2-(trifluoromethyl)phenyl]-5,6,7a,8,9,10,11,11a-octahydro-4H-pyrido[3',4':4,5]pyrrolo[3,2,1-ij]quinoline;

(7aS,11aR)-2-[2,4-bis(trifluoromethyl)phenyl]-5,6,7a,8,9,10,11,11a-octahydro-4H-pyrido[3',4':4,5]pyrrolo[3,2,1-ij]quinoline;

(7aS,11aR)-2-[4-fluoro-2-(trifluoromethyl)phenyl]-5,6,7a,8,9,10,11,11a-octahydro-4H-pyrido[3',4':4,5]pyrrolo[3,2,1-ij]quinoline;

4-[(7aS,11aR)-5,6,7a,8,9,10,11,11a-octahydro-4H-pyrido[3',4':4,5]pyrrolo[3,2,1-ij]quinolin-2-yl]-3-(trifluoromethyl)aniline;

4-[(7aS,11aR)-5,6,7a,8,9,10,11,11a-octahydro-4H-pyrido[3',4':4,5]pyrrolo[3,2,1-ij]quinolin-2-yl]-N-methyl-3-(trifluoromethyl)aniline;

4-[(7aS,11aR)-5,6,7a,8,9,10,11,11a-octahydro-4H-pyrido[3',4':4,5]pyrrolo[3,2,1-ij]quinolin-2-yl]-3-methylbenzonitrile;

2-[(7aS,11aR)-5,6,7a,8,9,10,11,11a-octahydro-4H-pyrido[3',4':4,5]pyrrolo[3,2,1-ij]quinolin-2-yl]benzaldehyde;

{2-[(7aS,11aR)-5,6,7a,8,9,10,11,11a-octahydro-4H-pyrido[3',4':4,5]pyrrolo[3,2,1-ij]quinolin-2-yl]phenyl}methanol;

2-[(7aS,11aR)-5,6,7a,8,9,10,11,11a-octahydro-4H-pyrido[3',4':4,5]pyrrolo[3,2,1-ij]quinolin-2-yl]-5-methoxybenzaldehyde;

{2-[(7aS,11aR)-5,6,7a,8,9,10,11,11a-octahydro-4H-pyrido[3',4':4,5]pyrrolo[3,2,1-ij]quinolin-2-yl]-5-methoxyphenyl}methanol;

(8aS,12aR)-2-[4-ethoxy-2-(trifluoromethyl)phenyl]-4,5,6,7,8a,9,10,11,12,12a-decahydroazepino[3,2,1-hi]pyrido[4,3b]indole;

(7aS,11aR)-2-[4-ethoxy-2-(trifluoromethyl)phenyl]-5,6,7a,8,9,10,11,11a-octahydro-4H-pyrido[3',4':4,5]pyrrolo[3,2,1-ij]quinoline;

(8aS,12aR)-2-[3-chloro-2-methylphenyl]-4,5,6,7,8a,9,10,11,12,12a-decahydroazepino[3,2,1-hi]pyrido[4,3b]indole;

(7aS,11aR)-2-[3-chloro-2-methylphenyl]-5,6,7a,8,9,10,11,11a-octahydro-4H-pyrido[3',4':4,5]pyrrolo[3,2,1-ij]quinoline;

(7aS,11aR)-2-[5-fluoro-2-methylphenyl]-5,6,7a,8,9,10,11,11a-octahydro-4H-pyrido[3',4':4,5]pyrrolo[3,2,1-ij]quinoline;

(±)-cis-2-(2,3-dichlorophenyl)-10-propyl-5,6,7a,8,9,10,11,11a-octahydro-4H-pyrido[3',4':4,5]pyrrolo[3,2,1-ij]quinoline;

(7aS,11aR)-2-(2,3-dichlorophenyl)-10-propyl-5,6,7a,8,9,10,11,11a-octahydro-4H-pyrido[3',4':4,5]pyrrolo[3,2,1-ij]quinoline;

(±)-cis-10-butyl-2-(2,3-dichlorophenyl)-5,6,7a,8,9,10,11,11a-octahydro-4H-pyrido[3',4':4,5]pyrrolo[3,2,1-ij]quinoline;

(7aS,11aR)-10-butyl-2-(2,3-dichlorophenyl)-5,6,7a,8,9,10,11,11a-octahydro-4H-pyrido[3',4':4,5]pyrrolo[3,2,1-ij]quinoline;

(7aS,11aR)-2-(2,3-dichlorophenyl)-10-(4-pentenyl)-5,6,7a,8,9,10,11,11a-octahydro-4H-pyrido[3',4':4,5]pyrrolo[3,2,1-ij]quinoline;

(7aS,11aR)-2-(2,3-dichlorophenyl)-10-(3-methyl-2-butenyl)-5,6,7a,8,9,10,11,11a-octahydro-4H-pyrido[3',4':4,5]pyrrolo[3,2,1-ij]quinoline;

(7aS,11aR)-2-(2,4-dichlorophenyl)-10-propyl-5,6,7a,8,9,10,11,11a-octahydro-4H-pyrido[3',4':4,5]pyrrolo[3,2,1-ij]quinoline;

(7aS,11aR)-10-butyl-2-(2,4-dichlorophenyl)-5,6,7a,8,9,10,11,11a-octahydro-4H-pyrido[3',4':4,5]pyrrolo[3,2,1-ij]quinoline;

(7aS,11aR)-2-(2,4-dichlorophenyl)-10-(4-pentenyl)-5,6,7a,8,9,10,11,11a-octahydro-4H-pyrido[3',4':4,5]pyrrolo[3,2,1-ij]quinoline;

(7aS,11aR)-2-(2,4-dichlorophenyl)-10-(3-methyl-2-butenyl)-5,6,7a,8,9,10,11,11a-octahydro-4H-pyrido[3',4':4,5]pyrrolo[3,2,1-ij]quinoline;

(7aS,11aR)-10-(cyclobutylmethyl)-2-(2,3-dichlorophenyl)-5,6,7a,8,9,10,11,11a-octahydro-4H-pyrido[3',4':4,5]pyrrolo[3,2,1-ij]quinoline;

(7aS,11aR)-2-[4-methoxy-2-(trifluoromethyl)phenyl]-10-methyl-5,6,7a,8,9,10,11,11a-octahydro-4H-pyrido[3',4':4,5]pyrrolo[3,2,1-ij]quinoline;

(7aS,11aR)-10-ethyl-2-[4-methoxy-2-(trifluoromethyl)phenyl]-5,6,7a,8,9,10,11,11a-octahydro-4H-pyrido[3',4':4,5]pyrrolo[3,2,1-ij]quinoline;

(7aS,11aR)-2-[4-methoxy-2-(trifluoromethyl)phenyl]-10-propyl-5,6,7a,8,9,10,11,11a-octahydro-4H-pyrido[3',4':4,5]pyrrolo[3,2,1-ij]quinoline;

(7aS,11aR)-10-butyl-2-[4-methoxy-2-(trifluoromethyl)phenyl]-10-methyl-5,6,7a,8,9,10,11,11a-octahydro-4H-pyrido[3',4':4,5]pyrrolo[3,2,1-ij]quinoline;

(7aS,11aR)-2-[4-methoxy-2-(trifluoromethyl)phenyl]-10-(4-pentenyl)-5,6,7a,8,9,10,11,11a-octahydro-4H-pyrido[3',4':4,5]pyrrolo[3,2,1-ij]quinoline;

(7aS,11aR)-2-[4-methoxy-2-(trifluoromethyl)phenyl]-10-(3-methyl-2-butenyl)-5,6,7a,8,9,11,11a-octahydro-4H-pyrido[3',4':4,5]pyrrolo[3,2,1-ij]quinoline;

(7aS,11aR)-10-(2-fluoroethyl)-2-[4-methoxy-2-(trifluoromethyl)phenyl]-5,6,7a,8,9,10,11,11a-octahydro-4H-pyrido[3',4':4,5]pyrrolo[3,2,1-ij]quinoline;

(7aS,11aR)-110-(2,2-difluoroethyl)-2-[4-methoxy-2-(trifluoromethyl)phenyl]-5,6,7a,8,9,10, 11,11a-octahydro-4H-pyrido[3',4':4,5]pyrrolo[3,2,1-ij]quinoline;

(7aS,11aR)-10-(cyclobutylmethyl)-2-[4-methoxy-2-(trifluoromethyl)phenyl]-5,6,7a,8,9,10,11,11a-octahydro-4H-pyrido[3',4':4,5]pyrrolo[3,2,1-ij]quinoline;

4-((7aS,11aR)-5,6,8,9,11,11a-hexahydro-4H-pyrido[3',4':4,5]pyrrolo[3,2,1-ij]quinolin-10(7aH)-yl)-1-(4-fluorophenyl)-1-butanone;

4-((7aR,11aS)-5,6,8,9,11,11a-hexahydro-4H-pyrido[3',4':4,5]pyrrolo[3,2,1-ij]quinolin-10(7aH)-yl)-1-(4-fluorophenyl)-1-butanone;

4-((7aS,11aR)-5,6,8,9,11,11a-hexahydro-4H-pyrido[3',4':4,5]pyrrolo[3,2,1-ij]quinolin-10(7aH)-yl)-1-(2-aminophenyl)-1-butanone;

4-((7aR,11aS)-5,6,8,9,11,11a-hexahydro-4H-pyrido[3',4':4,5]pyrrolo[3,2,1-ij]quinolin-10(7aH)-yl)-1-(2-aminophenyl)-1-butanone;

(±)-cis-3-(5,6,8,9,11,11a-hexahydro-4H-pyrido[3',4':4,5]pyrrolo[3,2,1-ij]quinolin-10(7aH)-yl)propyl 4-fluorophenyl ether;

4-((±)-cis-5,6,8,9,11,11a-hexahydro-4H-pyrido[3',4':4,5]pyrrolo[3,2,1-ij]quinolin-10(7aH)-yl)-1-(4-pyridinyl)-1-butanone;

(±)-cis-10-[3-(6-fluoro-1,2-benzisoxazol-3-yl)propyl]-5,6,7a,8,9,10,11,11a-octahydro-4H-pyrido[3',4':4,5]pyrrolo[3,2,1-ij]quinoline;

(7aS,11aR)-10-[3-(6-fluoro-1,2-benzisoxazol-3-yl)propyl]-5,6,7a,8,9,10,11,11a-octahydro-4H-pyrido[3',4':4,5]pyrrolo[3,2,1-ij]quinoline;

(±)-cis-4-(4,5,6,7,9,10,12,12a-octahydroazepino[3,2,1-hi]pyrido[4,3-b]indol-11(8aH)-yl)-1-(4-fluorophenyl)-1-butanone;

4-((8aS,12aR)-4,5,6,7,9,10,12,12a-octahydroazepino[3,2,1-hi]pyrido[4,3-b]indol-11(8aH)-yl)-1-(4-fluorophenyl)-1-butanone;

4-((8aR,12aR)-5,6,7,9,10,12,12a-octahydroazepino[3,2,1-hi]pyrido[4,3-b]indol-11(8aH)-yl)-1-(4-fluorophenyl)-1-butanone;

4-(±)-4,5,6,7,9,10,12,12a-octahydroazepino[3,2,1-hi]pyrido[4,3-b]indol-11(8aH)-yl)-1-(2-amino-4-fluorophenyl)-1-butanone;

4-((±)-cis-5,6,8,9,11,11a-hexahydro-4H-pyrido[3',4':4,5]pyrrolo[3,2,1-ij]quinolin-10(7aH)-yl)-1-(2-amino-4-fluorophenyl)-1-butanone;

4-((7aS,11aR)-5,6,8,9,11,11a-hexahydro-4H-pyrido[3',4':4,5]pyrrolo[3,2,1-ij]quinolin-10(7aH)-yl)-1-(2-amino-4-fluorophenyl)-1-butanone; and 4-((7aR,11aS)-5,6,8,9,11,11a-hexahydro-4H-pyrido[3',4':4,5]pyrrolo[3,2,1-ij]quinolin-10(7aH)-yl)-1-(2-amino-4-fluorophenyl)-1-butanone.

In a more preferred embodiment, the present invention provides the method as defined in claim 1 where the compound administered is selected from the group:

4-[(±)-5,6,8,9,10,11,12,12a-octahydro-4H,7aH-azepino[4',5':4,5]pyrrolo[3,2,1-ij]quinolin-10-yl]-1-(4-fluorophenyl)-1-butanone;

4-[(±)-5,6,8,9,10,11,12,12a-octahydro-4H,7aH-azepino[4',5':4,5]pyrrolo[3,2,1-ij]quinolin-10-yl]-1-(2-amino-4-fluorophenyl)-1-butanone;

4-[(±)-4,5,6,7,9,10,11,12,13,13a-decahydro-11H-diazepino[4,5-b:3,2,1-hi]indol-11-yl]-1-(4-fluorophenyl)-1-butanone;

4-[(±)-4,5,6,7,9,10,11,12,13,13a-decahydro-11H-diazepino[4,5-b:3,2,1-hi]indol-11-yl]-1-(2-amino-4-fluorophenyl)-1-butanone;

tert-butyl(±)-cis-5,6,8,9,10,11,12,12a-octahydro-4H,7aH-azepino[3',4':4,5]pyrrolo[3,2,1-ij]quinoline-11-carboxylate;

tert-butyl(±)-cis-2-bromo-5,6,8,9,10,11,12,12a-octahydro-4H,7aH-azepino[3',4':4,5]pyrrolo[3,2,1-ij]quinoline-11-carboxylate; and (±)-cis-2-[4-methoxy-2-(trifluoromethyl)phenyl]-5,6,8,9,10,11,12,12a-octahydro-4H,7aH-azepino[3',4':4,5]pyrrolo[3,2,1-ij]quinoline.

In a more preferred embodiment, the present invention provides the method as defined in claim 1 where the compound administered is selected from the group:

tert-butyl(±)-cis-2-bromo-4-oxo-4,5,6,7,9,10,12,12a-octahydroazepino[3,2,1-hi]pyrido[4,3-b]indole-11(8aH)-carboxylate;

tert-butyl(±)-cis-2-(2,4-dichlorophenyl)-4-oxo-4,5,6,7,9,10,12,12a-octahydroazepino[3,2,1-hi]pyrido[4,3-b]indole-11(8aH)-carboxylate;

(±)-cis-2-(2,4-dichlorophenyl)-6,7,8a,9,10,11,12,12a-octahydroazepino[3,2,1-hi]pyrido[4,3-b]indol-4(5H)-one;

(8aS,12aR)-2-(2,4-dichlorophenyl)-6,7,8a,9,10,11,12,12a-octahydroazepino[3,2,1-hi]pyrido[4,3-b]indol-4(5H)-one;

(8aR,12aS)-2-(2,4-dichlorophenyl)-6,7,8a,9,10,11,12,12a-octahydroazepino[3,2,1-hi]pyrido[4,3-b]indol-4(5H)-one;

(8aS,12aR)-2-(2,4-dichlorophenyl)-6,7,8a,9,10,11,12,12a-decahydroazepino[3,2,1-hi]pyrido[4,3-b]indol-4-ol; and (8aR,12aS)-2-(2,4-dichlorophenyl)-6,7,8a,9,10,11,12,12a-decahydroazepino[3,2,1-hi]pyrido[4,3-b]indol-4-ol.

Thus, in a second embodiment, the present invention provides a method for treating a human suffering from sleep disorders associated with 5HT2A receptor modulation, comprising administering to a patient in need thereof a therapeutically effective amount of a compound of formula (I):

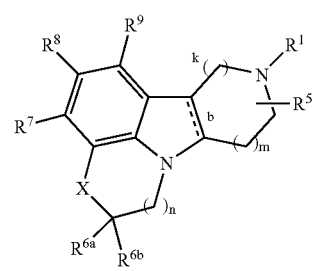

or stereoisomers or pharmaceutically acceptable salt forms thereof, wherein:
b is a single bond;
X is —CHR$^{10}$— or —C(═O)—;
R$^1$ is selected from
H,
C(═O)R$^2$,
C(═O)OR$^2$,
C$_{1-8}$ alkyl,
C$_{2-8}$ alkenyl,
C$_{2-8}$ alkynyl,
C$_{3-7}$ cycloalkyl,
C$_{1-6}$ alkyl substituted with Z,
C$_{2-6}$ alkenyl substituted with Z,
C$_{2-6}$ alkynyl substituted with Z,
C$_{3-6}$ cycloalkyl substituted with Z,
aryl substituted with Z, 5–6 membered heterocyclic ring system containing at least one heteroatom selected from the group consisting of N, O, and S, said heterocyclic ring system substituted with Z;
$C_{1-3}$ alkyl substituted with Y,
$C_{2-3}$ alkenyl substituted with Y,
$C_{2-3}$ alkynyl substituted with Y,
$C_{1-6}$ alkyl substituted with 0–2 $R^2$,
$C_{2-6}$ alkenyl substituted with 0–2 $R^2$,
$C_{2-6}$ alkynyl substituted with 0–2 $R^2$,
aryl substituted with 0–2 $R^2$, and
5–6 membered heterocyclic ring system containing at least one heteroatom selected from the group consisting of N, O, and S, said heterocyclic ring system substituted with 0–2 $R^2$;

Y is selected from
$C_{3-6}$ cycloalkyl substituted with Z,
aryl substituted with Z,
5–6 membered heterocyclic ring system containing at least one heteroatom selected from the group consisting of N, O, and S, said heterocyclic ring system substituted with Z;
$C_{3-6}$ cycloalkyl substituted with —($C_{1-3}$ alkyl)-Z,
aryl substituted with —($C_{1-3}$ alkyl)-Z, and
5–6 membered heterocyclic ring system containing at least one heteroatom selected from the group consisting of N, O, and S, said heterocyclic ring system substituted with —($C_{1-3}$ alkyl)-Z;

Z is selected from H,
—CH(OH)$R^2$,
—C(ethylenedioxy)$R^2$,
—O$R^2$,
—S$R^2$,
—N$R^2R^3$,
—C(O)$R^2$,
—C(O)N$R^2R^3$,
—N$R^3$C(O)$R^2$,
—C(O)O$R^2$,
—OC(O)$R^2$,
—CH(=N$R^4$)N$R^2R^3$,
—NHC(=N$R^4$)N$R^2R^3$,
—S(O)$R^2$,
—S(O)$_2R^2$,
—S(O)$_2$N$R^2R^3$, and —N$R^3$S(O)$_2R^2$;

$R^2$, at each occurrence, is independently selected from
halo,
$C_{1-3}$ haloalkyl,
$C_{1-4}$ alkyl,
$C_{2-4}$ alkenyl,
$C_{2-4}$ alkynyl,
$C_{3-6}$ cycloalkyl,
aryl substituted with 0–5 $R^{42}$;
$C_{3-10}$ carbocyclic group substituted with 0–3 $R^{41}$, and
5–10 membered heterocyclic ring system containing from 1–4 heteroatoms selected from the group consisting of N, O, and S substituted with 0–3 $R^{41}$;

$R^3$, at each occurrence, is independently selected from
H, $C_{1-4}$ alkyl, $C_{2-4}$ alkenyl, $C_{2-4}$ alkynyl, and $C_{1-4}$ alkoxy;
alternatively, $R^2$ and $R^3$ join to form a 5- or 6-membered ring optionally substituted with —O— or —N($R^4$)—;
$R^4$, at each occurrence, is independently selected from H and $C_{1-4}$ alkyl;
$R^5$ is H or $C_{1-4}$ alkyl;

$R^{6a}$ and $R^{6b}$, at each occurrence, are independently selected from
H, —OH, —N$R^{46}R^{47}$, —CF$_3$, $C_{1-4}$ alkyl, $C_{2-4}$ alkenyl, $C_{2-4}$ alkynyl, $C_{1-4}$ alkoxy, $C_{1-4}$ haloalkyl, $C_{3-6}$ cycloalkyl, and
aryl substituted with 0–3 $R^{44}$;

$R^7$ and $R^9$, at each occurrence, are independently selected from
H, halo, —CF$_3$, —OCF$_3$, —OH, —CN, —NO$_2$, —N$R^{46}R^{47}$,
$C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{3-10}$ carbocyclic group substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
O$R^{12}$, S$R^{12}$, N$R^{12}R^{13}$, C(O)H, C(O)$R^{12}$, C(O)N$R^{12}R^{13}$, N$R^{14}$C(O)$R^{12}$, C(O)O$R^{12}$, OC(O)$R^{12}$, OC(O)O$R^{12}$, CH(=N$R^{14}$)N$R^{12}R^{13}$, NHC(=N$R^{14}$)N$R^{12}R^{13}$, S(O)$R^{12}$, S(O)$_2R^{12}$, S(O)N$R^{12}R^{13}$, S(O)$_2$N$R^{12}R^{13}$, N$R^{14}$S(O)$R^{12}$, N$R^{14}$S(O)$_2R^{12}$, N$R^{12}$C(O)$R^{15}$, N$R^{12}$C(O)O$R^{15}$, N$R^{12}$S(O)$_2R^{15}$, and N$R^{12}$C(O)NH$R^{15}$;

$R^8$ is selected from
H, halo, —CF$_3$, —OCF$_3$, —OH, —CN, —NO$_2$,
$C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{2-4}$ alkenyl substituted with 0–2 $R^{11}$,
$C_{2-4}$ alkynyl substituted with 0–1 $R^{11}$,
$C_{3-10}$ carbocyclic group substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
O$R^{12}$, S$R^{12}$, N$R^{12}R^{13}$, C(O)H, C(O)$R^{12}$, C(O)N$R^{12}R^{13}$, N$R^{14}$C(O)$R^{12}$, C(O)O$R^{12}$, OC(O)$R^{12}$, OC(O)O$R^{12}$, CH(=N$R^{14}$)N$R^{12}R^{13}$, NHC(=N$R^{14}$)N$R^{12}R^{13}$, S(O)$R^{12}$, S(O)$_2R^{12}$, S(O)N$R^{12}R^{13}$, S(O)$_2$N$R^{12}R^{13}$, N$R^{14}$S(O)$R^{12}$, N$R^{14}$S(O)$_2R^{12}$, N$R^{12}$C(O)$R^{15}$, N$R^{12}$C(O)O$R^{15}$, N$R^{12}$S(O)$_2R^{15}$, and N$R^{12}$C(O)NH$R^{15}$;

$R^{10}$ is selected from H, —OH,
$C_{1-6}$ alkyl substituted with 0–1 $R^{10B}$,
$C_{2-6}$ alkenyl substituted with 0–1 $R^{10B}$,
$C_{2-6}$ alkynyl substituted with 0–1 $R^{10B}$, and
$C_{1-6}$ alkoxy;

$R^{10B}$ is selected from
$C_{1-4}$ alkoxy,
$C_{3-6}$ cycloalkyl,
$C_{3-10}$ carbocyclic group substituted with 0–3 $R^{33}$,
phenyl substituted with 0–3 $R^{33}$, and
5–6 membered heterocyclic ring system containing 1, 2, or 3 heteroatoms selected from the group consisting of N, O, and S substituted with 0–2 $R^{44}$;

$R^{11}$ is selected from
H, halo, —CF$_3$, —CN, —NO$_2$,
$C_{1-8}$ alkyl, $C_{2-8}$ alkenyl, $C_{2-8}$ alkynyl, $C_{1-4}$ haloalkyl, $C_{1-8}$ alkoxy, $C_{3-10}$ cycloalkyl,
$C_{3-10}$ carbocyclic group substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;

OR$^{12}$, SR$^{12}$, NR$^{12}$R$^{13}$, C(O)H, C(O)R$^{12}$, C(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O) R$^{12}$, S(O)$_2$R$^{12}$, S(O)NR$^{12}$R$^{13}$, S(O)$_2$NR$^{12}$R$^{13}$, NR$^{14}$S (O)R$^{12}$, NR$^{14}$S(O)$_2$R$^{12}$, NR$^{12}$C(O)R$^{15}$, NR$^{12}$C(O) OR$^{15}$, NR$^{12}$S(O)$_2$R$^{15}$, and NR$^{12}$C(O)NHR$^{15}$;

R$^{12}$, at each occurrence, is independently selected from
C$_{1-4}$ alkyl substituted with 0–1 R$^{12a}$,
C$_{2-4}$ alkenyl substituted with 0–1 R$^{12a}$,
C$_{2-4}$ alkynyl substituted with 0–1 R$^{12a}$,
C$_{3-6}$ cycloalkyl substituted with 0–3 R$^{33}$,
phenyl substituted with 0–5 R$^{33}$;
C$_{3-10}$ carbocyclic group substituted with 0–3 R$^{33}$, and
5–10 membered heterocyclic ring system containing from 1–4 heteroatoms selected from the group consisting of N, O, and S substituted with 0–3 R$^{31}$;

R$^{12a}$, at each occurrence, is independently selected from
phenyl substituted with 0–5 R$^{33}$;
C$_{3-10}$ carbocyclic group substituted with 0–3 R$^{33}$, and
5–10 membered heterocyclic ring system containing from 1–4 heteroatoms selected from the group consisting of N, O, and S substituted with 0–3 R$^{31}$;

R$^{13}$, at each occurrence, is independently selected from
H, C$_{1-4}$ alkyl, C$_{2-4}$ alkenyl, and C$_{2-4}$ alkynyl;
alternatively, R$^{12}$ and R$^{13}$ join to form a 5- or 6-membered ring optionally substituted with —O— or —N(R$^{14}$)—;
alternatively, R$^{12}$ and R$^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 R$^{16}$;

R$^{14}$, at each occurrence, is independently selected from H and C$_{1-4}$ alkyl;

R$^{15}$, at each occurrence, is independently selected from H, C$_{1-4}$ alkyl, C$_{2-4}$ alkenyl, and C$_{2-4}$ alkynyl;

R$^{16}$, at each occurrence, is independently selected from
H, OH, halo, CN, NO$_2$, CF$_3$, SO$_2$R$^{45}$, NR$^{46}$R$^{47}$, —C(=O)H, C$_{1-4}$ alkyl, C$_{2-4}$ alkenyl, C$_{2-4}$ alkynyl, C$_{1-4}$ haloalkyl, C$_{1-3}$ haloalkyl-oxy-, and C$_{1-3}$ alkyloxy-;

R$^{31}$, at each occurrence, is independently selected from
H, OH, halo, CF$_3$, SO$_2$R$^{45}$, NR$^{46}$R$^{47}$, and C$_{1-14}$ alkyl;

R$^{33}$, at each occurrence, is independently selected from
H, OH, halo, CN, NO$_2$, CF$_3$, SO$_2$R$^{45}$, NR$^{46}$R$^{47}$, —C(=O)H,
C$_{1-6}$ alkyl, C$_{2-6}$ alkenyl, C$_{2-6}$ alkynyl,
C$_{3-6}$ cycloalkyl, C$_{1-4}$ haloalkyl, C$_{1-4}$ haloalkyl-oxy-, C$_{1-4}$ alkyloxy-,
C$_{1-4}$ alkylthio-, C$_{1-4}$ alkyl-C(=O)—, C$_{1-4}$ alkyl-C(=O)NH—, C$_{1-4}$ alkyl-OC(=O)—,
C$_{1-4}$ alkyl-C(=O)O—, C$_{3-6}$ cycloalkyl-oxy-, C$_{3-6}$ cycloalkylmethyl-oxy-;
C$_{1-6}$ alkyl substituted with OH, methoxy, ethoxy, propoxy, or butoxy; and
C$_{2-6}$ alkenyl substituted with OH, methoxy, ethoxy, propoxy, or butoxy;

R$^{41}$, at each occurrence, is independently selected from
H, CF$_3$, halo, OH, CO$_2$H, SO$_2$R$^{45}$, NR$^{46}$R$^{47}$, NO$_2$, CN, =O;
C$_{2-8}$ alkenyl, C$_{2-8}$ alkynyl, C$_{1-4}$ alkoxy, C$_{1-4}$ haloalkyl
C$_{1-4}$ alkyl substituted with 0–1 R$^{43}$,
aryl substituted with 0–3 R$^{42}$, and
5–10 membered heterocyclic ring system containing from 1–4 heteroatoms selected from the group consisting of N, O, and S substituted with 0–3 R$^{44}$;

R$^{42}$, at each occurrence, is independently selected from
H, CF$_3$, halo, OH, CO$_2$H, SO$_2$R$^{45}$, SOR$^{45}$, SR$^{45}$, NR$^{46}$SO$_2$R$^{45}$, NR$^{46}$COR$^{45}$, NR$^{46}$R$^{47}$, NO$_2$, CN, CH(=NH)NH$_2$, NHC(=NH)NH$_2$,
C$_{2-6}$ alkenyl, C$_{2-6}$ alkynyl, C$_{1-4}$ alkoxy, C$_{1-4}$ haloalkyl, C$_{3-6}$ cycloalkyl,
C$_{1-4}$ alkyl substituted with 0–1 R$^{43}$,
aryl substituted with 0–3 R$^{44}$, and
5–10 membered heterocyclic ring system containing from 1–4 heteroatoms selected from the group consisting of N, O, and S substituted with 0–3 R$^{44}$;

R$^{43}$ is C$_{3-6}$ cycloalkyl or aryl substituted with 0–3 R$^{44}$;

R$^{44}$, at each occurrence, is independently selected from H, halo, —OH, NR$^{46}$R$^{47}$, CO$_2$H, SO$_2$R$^{45}$, —CF$_3$, —OCF$_3$, —CN, —NO$_2$, C$_{1-4}$ alkyl, and C$_{1-4}$ alkoxy;

R$^{45}$ is C$_{1-4}$alkyl;

R$^{46}$, at each occurrence, is independently selected from H and C$_{1-4}$ alkyl;

R$^{47}$, at each occurrence, is independently selected from H, C$_{1-4}$ alkyl,
—C(=O)NH(C$_{1-4}$ alkyl), —SO$_2$(C$_{1-4}$ alkyl),
—C(=O)O(C$_{1-4}$ alkyl), —C(=O)(C$_{1-4}$ alkyl), and
—C(=O)H;

k is 1 or 2;
m is 0, 1, or 2;
n is 0, 1, 2, or 3;
provided when m is 0 or 1 then k is 1 or 2;
provided when m is 2 then k is 1;
provided that when R$^6$ or R$^{6a}$ is NH$_2$, then X is not —CH(R$^{10}$); and
provided that when n=0, then R$^6$ or R$^{6a}$ is not NH$_2$ or —OH.

In a preferred embodiment, the present invention provides the method as defined in claim 1 where in the compound administered:

X is —CHR$^{10}$— or —C(=O)—;

R$^1$ is selected from
H,
C(=O)R$^2$,
C(=O)OR$^2$,
C$_{1-8}$ alkyl,
C$_{2-8}$ alkenyl,
C$_{2-8}$ alkynyl,
C$_{3-7}$ cycloalkyl,
C$_{1-6}$ alkyl substituted with 0–2 R$^2$,
C$_{2-6}$ alkenyl substituted with 0–2 R$^2$,
C$_{2-6}$ alkynyl substituted with 0–2 R$^2$,
aryl substituted with 0–2 R$^2$, and
5–6 membered heterocyclic ring system containing at least one heteroatom selected from the group consisting of N, O, and S, said heterocyclic ring system substituted with 0–2 R$^2$;

R$^2$, at each occurrence, is independently selected from
F, Cl, CH$_2$F, CHF2, CF$_3$,
C$_{1-4}$ alkyl,
C$_{2-4}$ alkenyl,
C$_{2-4}$ alkynyl,
C$_{3-6}$ cycloalkyl,
phenyl substituted with 0–5 R$^{42}$;
C$_{3-10}$ carbocyclic group substituted with 0–3 R$^{41}$, and
5–10 membered heterocyclic ring system containing from 1–4 heteroatoms selected from the group consisting of N, O, and S substituted with 0–3 R$^{41}$;

R$^5$ is H, methyl, ethyl, propyl, or butyl;

R$^{6a}$ is selected from
H, —OH, —NR$^{46}$R$^{47}$, —CF$_3$,
C$_{1-4}$ alkyl, C$_{1-4}$ alkoxy, C$_{1-4}$ haloalkyl, and
aryl substituted with 0–3 R$^{44}$;

$R^{6b}$ is H;

$R^7$ and $R^9$, at each occurrence, are independently selected from
- H, halo, —$CF_3$, —$OCF_3$, —OH, —CN, —$NO_2$, —$NR^{46}R^{47}$,
- $C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy,
- $C_{3-10}$ cycloalkyl substituted with 0–2 $R^{33}$,
- $C_{1-4}$ alkyl substituted with 0–2 $R^{11}$,
- $C_{3-10}$ carbocyclic group substituted with 0–3 $R^{33}$,
- aryl substituted with 0–5 $R^{33}$,
- 5–10 membered heterocyclic ring system containing from 1–4 heteroatoms selected from the group consisting of N, O, and S substituted with 0–3 $R^{31}$;
- $OR^{12}$, $SR^{12}$, $NR^{12}R^{13}$, C(O)H, C(O)$R^{12}$, C(O)$NR^{12}R^{13}$, $NR^{14}$C(O)$R^{12}$, C(O)$OR^{12}$, OC(O)$R^{12}$, OC(O)$OR^{12}$, CH(=$NR^{14}$)$NR^{12}R^{13}$, NHC(=$NR^{14}$)$NR^{12}R^{13}$, S(O)$R^{12}$, S(O)$_2R^{12}$, S(O)$NR^{12}R^{13}$, S(O)$_2NR^{12}R^{13}$, $NR^{14}$S(O)$R^{12}$, $NR^{14}$S(O)$_2R^{12}$, $NR^{12}$C(O)$R^{15}$, $NR^{12}$C(O)$OR^{15}$, $NR^{12}$S(O)$_2R^{15}$, and $NR^{12}$C(O)$NHR^{15}$;

$R^8$ is selected from
- H, halo, —$CF_3$, —$OCF_3$, —OH, —CN, —$NO_2$,
- $C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy,
- $C_{3-10}$ cycloalkyl substituted with 0–2 $R^{33}$,
- $C_{1-4}$ alkyl substituted with 0–2 $R^{11}$,
- $C_{2-4}$ alkenyl substituted with 0–2 $R^{11}$,
- $C_{2-4}$ alkynyl substituted with 0–1 $R^{11}$,
- $C_{3-10}$ carbocyclic group substituted with 0–3 $R^{33}$,
- aryl substituted with 0–5 $R^{33}$,
- 5–10 membered heterocyclic ring system containing from 1–4 heteroatoms selected from the group consisting of N, O, and S substituted with 0–3 $R^{31}$;
- $OR^{12}$, $SR^{12}$, $NR^{12}R^{13}$, C(O)H, C(O)$R^{12}$, C(O)$NR^{12}R^{13}$, $NR^{14}$C(O)$R^{12}$, C(O)$OR^{12}$, OC(O)$R^{12}$, OC(O)$OR^{12}$, CH(=$NR^{14}$)$NR^{12}R^{13}$, NHC(=$NR^{14}$)$NR^{12}R^{13}$, S(O)$R^{12}$, S(O)$_2R^{12}$, S(O)$NR^{12}R^{13}$, S(O)$_2NR^{12}R^{13}$, $NR^{14}$S(O)$R^{12}$, $NR^{14}$S(O)$_2R^{12}$, $NR^{12}$C(O)$R^5$, $NR^{12}$C(O)$OR^{15}$, $NR^{12}$S(O)$_2R^{15}$, and $NR^{12}$C(O)$NHR^{15}$;

$R^{10}$ is selected from H, —OH,
- $C_{1-6}$ alkyl substituted with 0–1 $R^{10B}$,
- $C_{2-6}$ alkenyl substituted with 0–1 $R^{10B}$,
- $C_{2-6}$ alkynyl substituted with 0–1 $R^{10B}$, and
- $C_{1-6}$ alkoxy;

$R^{10B}$ is selected from
- $C_{1-4}$ alkoxy,
- $C_{3-6}$ cycloalkyl,
- $C_{3-10}$ carbocyclic group substituted with 0–3 $R^{33}$,
- phenyl substituted with 0–3 $R^{33}$, and
- 5–6 membered heterocyclic ring system containing 1, 2, or 3 heteroatoms selected from the group consisting of N, O, and S substituted with 0–2 $R^{44}$;

$R^{11}$ is selected from
- H, halo, —$CF_3$, —CN, —$NO_2$,
- $C_{1-8}$ alkyl, $C_{2-8}$ alkenyl, $C_{2-8}$ alkynyl, $C_{1-4}$ haloalkyl, $C_{1-8}$ alkoxy, $C_{3-10}$ cycloalkyl,
- $C_{3-10}$ carbocyclic group substituted with 0–3 $R^{33}$,
- aryl substituted with 0–5 $R^{33}$,
- 5–10 membered heterocyclic ring system containing from 1–4 heteroatoms selected from the group consisting of N, O, and S substituted with 0–3 $R^{31}$;
- $OR^{12}$, $SR^{12}$, $NR^{12}R^{13}$, C(O)H, C(O)$R^{12}$, C(O)$NR^{12}R^{13}$, $NR^{14}$C(O)$R^{12}$, C(O)$OR^{12}$, OC(O)$R^{12}$, OC(O)$OR^{12}$, CH(=$NR^{14}$)$NR^{12}R^{13}$, NHC(=$NR^{14}$)$NR^{12}R^{13}$, S(O)$R^{12}$, S(O)$_2R^{12}$, S(O)$NR^{12}R^{13}$, S(O)$_2NR^{12}R^{13}$, $NR^{14}$S(O)$R^{12}$, $NR^{14}$S(O)$_2R^{12}$, $NR^{12}$C(O)$R^{15}$, $NR^{12}$C(O)$OR^{15}$, $NR^{12}$S(O)$_2R^{15}$, and $NR^{12}$C(O)$NHR^{15}$;

$R^{12}$, at each occurrence, is independently selected from
- $C_{1-4}$ alkyl substituted with 0–1 $R^{12a}$,
- $C_{2-4}$ alkenyl substituted with 0–1 $R^{12a}$,
- $C_{2-4}$ alkynyl substituted with 0–1 $R^{12a}$,
- $C_{3-6}$ cycloalkyl substituted with 0–3 $R^{33}$,
- phenyl substituted with 0–5 $R^{33}$;
- $C_{3-10}$ carbocyclic group substituted with 0–3 $R^{33}$, and
- 5–10 membered heterocyclic ring system containing from 1–4 heteroatoms selected from the group consisting of N, O, and S substituted with 0–3 $R^{31}$;

$R^{12a}$, at each occurrence, is independently selected from
- phenyl substituted with 0–5 $R^{33}$;
- $C_{3-10}$ carbocyclic group substituted with 0–3 $R^{33}$, and
- 5–10 membered heterocyclic ring system containing from 1–4 heteroatoms selected from the group consisting of N, O, and S substituted with 0–3 $R^{31}$;

$R^{13}$, at each occurrence, is independently selected from
- H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —N($R^{14}$)—;

alternatively, $R^{12}$ and $R^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;

$R^{14}$, at each occurrence, is independently selected from H and $C_{1-4}$ alkyl;

$R^{15}$, at each occurrence, is independently selected from H, $C_{1-4}$ alkyl, $C_{2-4}$ alkenyl, and $C_{2-4}$ alkynyl;

$R^{16}$, at each occurrence, is independently selected from
- H, OH, halo, CN, $NO_2$, $CF_3$, $SO_2R^{45}$, $NR^{46}R^{47}$, —C(=O)H,
- $C_{1-4}$ alkyl, $C_{2-4}$ alkenyl, $C_{2-4}$ alkynyl, $C_{1-4}$ haloalkyl, $C_{1-3}$ haloalkyl-oxy-, and $C_{1-3}$ alkyloxy-;

$R^{31}$, at each occurrence, is independently selected from
- H, OH, halo, $CF_3$, $SO_2R^{45}$, $NR^{46}R^{47}$, and $C_{1-4}$ alkyl;

$R^{33}$, at each occurrence, is independently selected from
- H, OH, halo, CN, $NO_2$, $CF_3$, $SO_2R^{45}$, $NR^{46}R^{47}$, —C(=O)H,
- $C_{1-6}$ alkyl, $C_{2-6}$ alkenyl, $C_{2-6}$ alkynyl,
- $C_{3-6}$ cycloalkyl, $C_{1-4}$ haloalkyl, $C_{1-4}$ haloalkyl-oxy-, $C_{1-4}$ alkyloxy-,
- $C_{1-4}$ alkylthio-, $C_{1-4}$ alkyl-C(=O)—, $C_{1-4}$ alkyl-C(=O)NH—, $C_{1-4}$ alkyl-OC(=O)—,
- $C_{1-4}$ alkyl-C(=O)O—, $C_{3-6}$ cycloalkyl-oxy-, $C_{3-6}$ cycloalkylmethyl-oxy-;
- $C_{1-6}$ alkyl substituted with OH, methoxy, ethoxy, propoxy, or butoxy; and
- $C_{2-6}$ alkenyl substituted with OH, methoxy, ethoxy, propoxy, or butoxy;

$R^{41}$, at each occurrence, is independently selected from
- H, $CF_3$, halo, OH, $CO_2H$, $SO_2R^{45}$, $NR^{46}R^{47}$, $NO_2$, CN;
- $C_{2-8}$ alkenyl, $C_{2-8}$ alkynyl, $C_{1-4}$ alkoxy, $C_{1-4}$ haloalkyl
- $C_{1-4}$ alkyl substituted with 0–1 $R^{43}$,
- aryl substituted with 0–3 $R^{42}$, and
- 5–10 membered heterocyclic ring system containing from 1–4 heteroatoms selected from the group consisting of N, O, and S substituted with 0–3 $R^{44}$;

$R^{42}$, at each occurrence, is independently selected from
- H, $CF_3$, halo, OH, $CO_2H$, $SO_2R^{45}$, $NR^{46}R^{47}$, $NO_2$, CN, CH(=NH)$NH_2$, NHC(=NH)$NH_2$,
- $C_{2-6}$ alkenyl, $C_{2-6}$ alkynyl, $C_{1-4}$ alkoxy, $C_{1-4}$ haloalkyl, $C_{3-6}$ cycloalkyl,
- $C_{1-4}$ alkyl substituted with 0–1 $R^{43}$,
- aryl substituted with 0–3 $R^{44}$, and 5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-4}$ alkyl;

$R^{47}$, at each occurrence, is independently selected from H and $C_{1-4}$ alkyl;

k is 1 or 2;

m is 0, 1, or 2; and n is 0, 1, 2, or 3.

In a more preferred embodiment, the present invention provides the method as defined in claim 2 where in the compound administered:

X is —$CHR^{10}$—;

$R^1$ is selected from
H,
$C(\!=\!O)R^2$,
$C(\!=\!O)OR^2$,
$C_{1-6}$ alkyl,
$C_{2-6}$ alkenyl,
$C_{2-6}$ alkynyl,
$C_{3-6}$ cycloalkyl,
$C_{1-4}$ alkyl substituted with 0–2 $R^2$,
$C_{2-4}$ alkenyl substituted with 0–2 $R^2$, and
$C_{2-4}$ alkynyl substituted with 0–2 $R^2$;

$R^2$, at each occurrence, is independently selected from
$C_{1-4}$ alkyl,
$C_{2-4}$ alkenyl,
$C_{2-4}$ alkynyl,
$C_{3-6}$ cycloalkyl,
phenyl substituted with 0–5 $R^{42}$;
$C_{3-10}$ carbocyclic group substituted with 0–3 $R^{41}$, and
5–10 membered heterocyclic ring system containing from 1–4 heteroatoms selected from the group consisting of N, O, and S substituted with 0–3 $R^{41}$;

$R^5$ is H, methyl, ethyl, propyl, or butyl;

$R^{6a}$ is selected independently from
H, —OH, —$NR^{46}R^{47}$, —$CF_3$, $C_{1-3}$ alkyl, and $C_{1-3}$ alkoxy;

$R^{6b}$ is H;

$R^7$ and $R^9$, at each occurrence, are independently selected from
H, halo, —$CF_3$, —$OCF_3$, —OH, —CN, —$NO_2$, —$NR^{46}R^{47}$,
$C_{1-6}$ alkyl, $C_{2-6}$ alkenyl, $C_{2-6}$ alkynyl, $C_{1-6}$ haloalkyl, $C_{1-6}$ alkoxy, $(C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{3-10}$ carbocyclic group substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, $C(O)H$, $C(O)R^{12}$, $C(O)NR^{12}R^{13}$, $NR^{14}C(O)R^{12}$, $C(O)OR^{12}$, $OC(O)R^{12}$, $OC(O)OR^{12}$, $CH(\!=\!NR^{14})NR^{12}R^{13}$, $NHC(\!=\!NR^{14})NR^{12}R^{13}$, $S(O)R^{12}$, $S(O)_2R^{12}$, $S(O)NR^{12}R^{13}$, $S(O)_2NR^{12}R^{13}$, $NR^{14}S(O)R^{12}$, and $NR^{14}S(O)_2R^{12}$;

$R^8$ is selected from
H, halo, —$CF_3$, —$OCF_3$, —OH, —CN, —$NO_2$,
$C_{1-6}$ alkyl, $C_{2-6}$ alkenyl, $C_{2-6}$ alkynyl, $C_{1-6}$ haloalkyl, $C_{1-6}$ alkoxy, $(C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{2-4}$ alkenyl substituted with 0–2 $R^{11}$,
$C_{2-4}$ alkynyl substituted with 0–1 $R^{11}$,
$C_{3-10}$ carbocyclic group substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, $C(O)H$, $C(O)R^{12}$, $C(O)NR^{12}R^{13}$, $NR^{14}C(O)R^{12}$, $C(O)OR^{12}$, $OC(O)R^{12}$, $OC(O)OR^{12}$, $CH(\!=\!NR^{14})NR^{12}R^{13}$, $NHC(\!=\!NR^{14})NR^{12}R^{13}$, $S(O)R^{12}$, $S(O)_2R^{12}$, $S(O)NR^{12}R^{13}$, $S(O)_2NR^{12}R^{13}$, $NR^{14}S(O)R^{12}$, $NR^{14}S(O)_2R^{12}$, $NR^{12}C(O)R^{15}$, $NR^{12}C(O)OR^{15}$, $NR^{12}S(O)_2R^{15}$, and $NR^{12}C(O)NHR^{15}$;

$R^{10}$ is selected from H, —OH,
$C_{1-6}$ alkyl substituted with 0–1 $R^{10B}$,
$C_{2-6}$ alkenyl substituted with 0–1 $R^{10B}$,
$C_{2-6}$ alkynyl substituted with 0–1 $R^{10B}$, and
$C_{1-6}$ alkoxy;

$R^{10B}$ is selected from
$C_{1-4}$ alkoxy,
$C_{3-6}$ cycloalkyl,
$C_{3-10}$ carbocyclic group substituted with 0–3 $R^{33}$,
phenyl substituted with 0–3 $R^{33}$, and
5–6 membered heterocyclic ring system containing 1, 2, or 3 heteroatoms selected from the group consisting of N, O, and S substituted with 0–2 $R^{44}$;

$R^{11}$ is selected from
H, halo, —$CF_3$, —CN, —$NO_2$, $C_{1-6}$ alkyl,
$C_{2-6}$ alkenyl, $C_{2-6}$ alkynyl, $C_{1-4}$ haloalkyl, $C_{1-6}$ alkoxy, $C_{3-10}$ cycloalkyl,
$C_{3-10}$ carbocyclic group substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, $C(O)H$, $C(O)R^{12}$, $C(O)NR^{12}R^{13}$, $NR^{14}C(O)R^{12}$, $C(O)OR^{12}$, $OC(O)R^{12}$, $OC(O)OR^{12}$, $CH(\!=\!NR^{14})NR^{12}R^{13}$, $NHC(\!=\!NR^{14})NR^{12}R^{13}$, $S(O)R^{12}$, $S(O)_2R^{12}$, $S(O)NR^{12}R^{13}$, $S(O)_2NR^{12}R^{13}$, $NR^{14}S(O)R^{12}$, and $NR^{14}S(O)_2R^{12}$;

$R^{12}$, at each occurrence, is independently selected from
$C_{1-4}$ alkyl substituted with 0–1 $R^{12a}$,
$C_{2-4}$ alkenyl substituted with 0–1 $R^{12a}$,
$C_{2-4}$ alkynyl substituted with 0–1 $R^{12a}$,
$C_{3-6}$ cycloalkyl substituted with 0–3 $R^{33}$,
phenyl substituted with 0–5 $R^{33}$;
$C_{3-10}$ carbocyclic group substituted with 0–3 $R^{33}$, and
5–10 membered heterocyclic ring system containing from 1–4 heteroatoms selected from the group consisting of N, O, and S substituted with 0–3 $R^{31}$;

$R^{12a}$, at each occurrence, is independently selected from
phenyl substituted with 0–5 $R^{33}$;
$C_{3-10}$ carbocyclic group substituted with 0–3 $R^{33}$, and
5–10 membered heterocyclic ring system containing from 1–4 heteroatoms selected from the group consisting of N, O, and S substituted with 0–3 $R^{31}$;

$R^{13}$, at each occurrence, is independently selected from
H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —$N(R^{14})$—;

alternatively, $R^{12}$ and $R^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;

$R^{14}$, at each occurrence, is independently selected from H, methyl, ethyl, propyl, and butyl;

$R^{15}$, at each occurrence, is independently selected from H, $C_{1-4}$ alkyl, $C_{2-4}$ alkenyl, and $C_{2-4}$ alkynyl;

$R^{16}$, at each occurrence, is independently selected from
H, OH, F, Cl, CN, $NO_2$, $CF_3$, $SO_2R^{45}$, $NR^{46}R^{47}$, —C(=O)H,
methyl, ethyl, methoxy, ethoxy, trifluoromethyl, and trifluoromethoxy;

$R^{31}$, at each occurrence, is independently selected from
H, OH, halo, $CF_3$, $SO_2R^{45}$, $NR^{46}R^{47}$, and $C_{1-4}$ alkyl;

$R^{33}$, at each occurrence, is independently selected from
H, OH, halo, CN, $NO_2$, $CF_3$, $SO_2R^{45}$, $NR^{46}R^{47}$, —C(=O)H,
$C_{1-6}$ alkyl, $C_{2-6}$ alkenyl, $C_{2-6}$ alkynyl,
$C_{3-6}$ cycloalkyl, $C_{1-4}$ haloalkyl, $C_{1-4}$ haloalkyl-oxy-, $C_{1-4}$ alkyloxy-,
$C_{1-4}$ alkylthio-, $C_{1-4}$ alkyl-C(=O)—, $C_{1-4}$ alkyl-C(=O)NH—, $C_{1-4}$ alkyl-OC(=O)—,
$C_{1-4}$ alkyl-C(=O)O—, $C_{3-6}$ cycloalkyl-oxy-, $C_{3-6}$ cycloalkylmethyl-oxy-;
$C_{1-6}$ alkyl substituted with OH, methoxy, ethoxy, propoxy, or butoxy; and
$C_{2-6}$ alkenyl substituted with OH, methoxy, ethoxy, propoxy, or butoxy;

$R^{41}$, at each occurrence, is independently selected from
H, $CF_3$, halo, OH, $CO_2H$, $SO_2R^{45}$, $NR^{46}R^{47}$, $NO_2$, CN,
$C_{2-8}$ alkenyl, $C_{2-8}$ alkynyl, $C_{1-4}$ alkoxy, $C_{1-4}$ haloalkyl
$C_{1-4}$ alkyl substituted with 0–1 $R^{43}$,
aryl substituted with 0–3 $R^{42}$, and
5–10 membered heterocyclic ring system containing from 1–4 heteroatoms selected from the group consisting of N, O, and S substituted with 0–3 $R^{44}$;

$R^{42}$, at each occurrence, is independently selected from
H, $CF_3$, halo, OH, $CO_2H$, $SO_2R^{45}$, $NR^{46}R^{47}$, $NO_2$, CN, CH(=NH)$NH_2$, NHC(=NH)$NH_2$,
$C_{2-6}$ alkenyl, $C_{2-6}$ alkynyl, $C_{1-4}$ alkoxy, $C_{1-4}$ haloalkyl, $C_{3-6}$ cycloalkyl,
$C_{1-4}$ alkyl substituted with 0–1 $R^{43}$,
aryl substituted with 0–3 $R^{44}$, and
5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-4}$ alkyl;

$R^{47}$, at each occurrence, is independently selected from H and $C_{1-4}$ alkyl;

k is 1 or 2;
m is 0 or 1; and
n is 0, 1 or 2.

In a more preferred embodiment, the present invention provides the method as defined in claim 2 where in the compound administered:

X is —$CH_2$—;

$R^1$ is selected from
H,
$C_{1-4}$ alkyl,
$C_{2-4}$ alkenyl,
$C_{2-4}$ alkynyl,
$C_{3-4}$ cycloalkyl,
$C_{1-3}$ alkyl substituted with 0–1 $R^2$,
$C_{2-3}$ alkenyl substituted with 0–1 $R^2$, and
$C_{2-3}$ alkynyl substituted with 0–1 $R^2$;

$R^2$, at each occurrence, is independently selected from
$C_{1-4}$ alkyl,
$C_{2-4}$ alkenyl,
$C_{2-4}$ alkynyl,
$C_{3-6}$ cycloalkyl,
phenyl substituted with 0–5 $R^{42}$;
$C_{3-6}$ carbocyclic group substituted with 0–3 $R^{41}$, and
5–6 membered heterocyclic ring system containing 1, 2, or 3 heteroatoms selected from the group consisting of N, O, and S substituted with 0–3 $R^{41}$;

$R^5$ is H, methyl, ethyl, propyl, or butyl;

$R^{6a}$ is H, methyl, ethyl, methoxy, —OH, or —$CF_3$;

$R^{6b}$ is H;

$R^7$ and $R^9$, at each occurrence, are independently selected from
H, halo, —$CF_3$, —$OCF_3$, —OH, —CN, —$NO_2$, —$NR^{46}R^{47}$,
$C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{3-10}$ carbocyclic group substituted with 0–3 $R^{33}$,
aryl substituted with 0–5 $R^{33}$, and
5–6 membered heterocyclic ring system containing 1, 2, or 3 heteroatoms selected from the group consisting of N, O, and S substituted with 0–3 $R^{31}$;

$R^8$ is selected from
H, halo, —$CF_3$, —$OCF_3$, —OH, —CN, —$NO_2$,
$C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{2-4}$ alkenyl substituted with 0–2 $R^{11}$,
$C_{2-4}$ alkynyl substituted with 0–1 $R^{11}$,
$C_{3-10}$ carbocyclic group substituted with 0–3 $R^{33}$,
aryl substituted with 0–5 $R^{33}$,
5–6 membered heterocyclic ring system containing 1, 2, or 3 heteroatoms selected from the group consisting of N, O, and S substituted with 0–3 $R^{31}$,
$OR^{12}$, $SR^{12}$, $NR^{12}R^{13}$, $NR^{12}C(O)R^{15}$, $NR^{12}C(O)OR^{15}$, $NR^{12}S(O)_2R^{15}$, and $NR^{12}C(O)NHR^{15}$;

$R^{11}$ is selected from
H, halo, —$CF_3$, —CN, —$NO_2$,
$C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
$C_{3-10}$ cycloalkyl substituted with 0–2 $R^{33}$,
$C_{3-10}$ carbocyclic group substituted with 0–3 $R^{33}$,
aryl substituted with 0–5 $R^{33}$, and
5–6 membered heterocyclic ring system containing 1, 2, or 3 heteroatoms selected from the group consisting of N, O, and S substituted with 0–3 $R^{31}$;

$R^{12}$, at each occurrence, is independently selected from
$C_{1-4}$ alkyl substituted with 0–1 $R^{12a}$,
$C_{2-4}$ alkenyl substituted with 0–1 $R^{12a}$,
$C_{2-4}$ alkynyl substituted with 0–1 $R^{12a}$,
$C_{3-6}$ cycloalkyl substituted with 0–3 $R^{33}$,
phenyl substituted with 0–5 $R^{33}$;
$C_{3-10}$ carbocyclic group substituted with 0–3 $R^{33}$, and
5–10 membered heterocyclic ring system containing from 1–4 heteroatoms selected from the group consisting of N, O, and S substituted with 0–3 $R^{31}$;

$R^{12a}$, at each occurrence, is independently selected from
phenyl substituted with 0–5 $R^{33}$;
$C_{3-10}$ carbocyclic group substituted with 0–3 $R^{33}$, and 5–10 membered heterocyclic ring system containing from 1–4 heteroatoms selected from the group consisting of N, O, and S substituted with 0–3 $R^{31}$;

$R^{13}$, at each occurrence, is independently selected from H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —N($R^{14}$)—;

alternatively, $R^{12}$ and $R^{13}$ when attached to N may be combined to form a 9- or 10-membered bicyclic heterocyclic ring system containing from 1–3 heteroatoms selected from the group consisting of one N, two N, three N, one N one O, and one N one S; wherein said bicyclic heterocyclic ring system is unsaturated or partially saturated, wherein said bicyclic heterocyclic ring system is substituted with 0–2 $R^{16}$;

$R^{14}$, at each occurrence, is independently selected from H, methyl, ethyl, propyl, and butyl;

$R^{15}$, at each occurrence, is independently selected from H, methyl, ethyl, propyl, and butyl;

$R^{16}$, at each occurrence, is independently selected from
H, OH, F, Cl, CN, $NO_2$, methyl, ethyl, methoxy, ethoxy, trifluoromethyl, and trifluoromethoxy;

$R^{31}$, at each occurrence, is independently selected from
H, OH, halo, $CF_3$, methyl, ethyl, and propyl;

$R^{33}$, at each occurrence, is independently selected from
H, OH, halo, CN, $NO_2$, $CF_3$, $SO_2R^{45}$, $NR^{46}R^{47}$, —C(=O)H,
$C_{1-6}$ alkyl, $C_{2-6}$ alkenyl, $C_{2-6}$ alkynyl,
$C_{3-6}$ cycloalkyl, $C_{1-4}$ haloalkyl, $C_{1-4}$ haloalkyl-oxy-, $C_{1-4}$ alkyloxy-,
$C_{1-4}$ alkylthio-, $C_{1-4}$ alkyl-C(=O)—, $C_{1-4}$ alkyl-C(=O)NH—, $C_{1-4}$ alkyl-OC(=O)—,
$C_{1-4}$ alkyl-C(=O)O—, $C_{3-6}$ cycloalkyl-oxy-, $C_{3-6}$ cycloalkylmethyl-oxy-;
$C_{1-6}$ alkyl substituted with OH, methoxy, ethoxy, propoxy, or butoxy; and
$C_{2-6}$ alkenyl substituted with OH, methoxy, ethoxy, propoxy, or butoxy;

$R^{41}$, at each occurrence, is independently selected from
H, $CF_3$, halo, OH, $CO_2H$, $SO_2R^{45}$, $NR^{46}R^{47}$, $NO_2$, CN,
$C_{2-4}$ alkenyl, $C_{2-4}$ alkynyl, $C_{1-3}$ alkoxy, $C_{1-3}$ haloalkyl, and $C_{1-3}$ alkyl;

$R^{42}$, at each occurrence, is independently selected from
H, $CF_3$, halo, OH, $CO_2H$, $SO_2R^{45}$, $NR^{46}R^{47}$, $NO_2$, CN, CH(=NH)$NH_2$, NHC(=NH)$NH_2$,
$C_{2-4}$ alkenyl, $C_{2-4}$ alkynyl, $C_{1-3}$ alkoxy, $C_{1-3}$ haloalkyl, $C_{3-6}$ cycloalkyl, and $C_{1-3}$ alkyl;

$R^{43}$ is cyclopropyl, cyclobutyl, cyclopentyl, cyclohexyl, phenyl, or pyridyl, each substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, methyl, ethyl, propyl, butyl, methoxy, ethoxy, propoxy, and butoxy;

$R^{45}$ is methyl, ethyl, propyl, or butyl;

$R^{46}$, at each occurrence, is independently selected from H, methyl, ethyl, propyl, and butyl;

$R^{47}$, at each occurrence, is independently selected from from H, methyl, ethyl, propyl, and butyl;

k is 1;
m is 1; and
n is 0, 1 or 2.

In a more preferred embodiment, the present invention provides the method as defined in claim 2 where in the compound administered:

X is —$CH_2$—;
$R^1$ is selected from
H,
$C_{1-4}$ alkyl,
$C_{2-4}$ alkenyl,
$C_{2-4}$ alkynyl,
$C_{3-4}$ cycloalkyl,
$C_{1-3}$ alkyl substituted with 0–1 $R^2$,
$C_{2-3}$ alkenyl substituted with 0–1 $R^2$, and
$C_{2-3}$ alkynyl substituted with 0–1 $R^2$;

$R^2$, at each occurrence, is independently selected from
$C_{1-4}$ alkyl,
$C_{2-4}$ alkenyl,
$C_{2-4}$ alkynyl,
$C_{3-6}$ cycloalkyl,
phenyl substituted with 0–5 $R^{42}$;
$C_{3-6}$ carbocyclic group substituted with 0–3 $R^{41}$, and
5–6 membered heterocyclic ring system containing 1, 2, or 3 heteroatoms selected from the group consisting of N, O, and S substituted with 0–3 $R^{41}$;

$R^5$ is H, methyl, ethyl, propyl, or butyl;
$R^{6a}$ is H, methyl, ethyl, methoxy, —OH, or —$CF_3$;
$R^{6b}$ is H;

$R^7$ and $R^9$, at each occurrence, are independently selected from
H, F, Cl, —$CH_3$, —$OCH_3$, —$CF_3$, —$OCF_3$, —CN, and —$NO_2$, $R^8$ is selected from
H, F, Cl, Br, —$CF_3$, —$OCF_3$, —OH, —CN, —$NO_2$,
$C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{2-4}$ alkenyl substituted with 0–2 $R^{11}$,
$C_{2-4}$ alkynyl substituted with 0–1 $R^{11}$,
$C_{3-10}$ carbocyclic group substituted with 0–3 $R^{33}$,
aryl substituted with 0–5 $R^{33}$,
5–6 membered heterocyclic ring system containing 1, 2, or 3 heteroatoms selected from the group consisting of N, O, and S substituted with 0–3 $R^{31}$;
$OR^{12}$, $SR^{12}$, $NR^{12}R^{13}$, $NR^{12}C(O)R^{15}$, $NR^{12}C(O)OR^{15}$, $NR^{12}S(O)_2R^{15}$,
and $NR^{12}C(O)NHR^{15}$;

$R^{11}$ is selected from
H, halo, —$CF_3$, —CN, —$NO_2$,
$C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
$C_{3-10}$ cycloalkyl substituted with 0–2 $R^{33}$,
$C_{3-10}$ carbocyclic group substituted with 0–3 $R^{33}$,
aryl substituted with 0–5 $R^{33}$, and
5–6 membered heterocyclic ring system containing 1, 2, or 3 heteroatoms selected from the group consisting of N, O, and S substituted with 0–3 $R^{31}$;

$R^{12}$, at each occurrence, is independently selected from
$C_{1-4}$ alkyl substituted with 0–1 $R^{12a}$,
$C_{2-4}$ alkenyl substituted with 0–1 $R^{12a}$,
$C_{2-4}$ alkynyl substituted with 0–1 $R^{12a}$,
$C_{3-6}$ cycloalkyl substituted with 0–3 $R^{33}$,
phenyl substituted with 0–5 $R^{33}$;
$C_{3-10}$ carbocyclic group substituted with 0–3 $R^{33}$, and
5–10 membered heterocyclic ring system containing from 1–4 heteroatoms selected from the group consisting of N, O, and S substituted with 0–3 $R^{31}$;

$R^{12a}$, at each occurrence, is independently selected from
phenyl substituted with 0–5 $R^{33}$;
$C_{3-10}$ carbocyclic group substituted with 0–3 $R^{33}$, and 5–10 membered heterocyclic ring system containing from 1–4 heteroatoms selected from the group consisting of N, O, and S substituted with 0–3 $R^{31}$;

$R^{13}$, at each occurrence, is independently selected from H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —N($R^{14}$)—;

alternatively, $R^{12}$ and $R^{13}$ when attached to N may be combined to form a 9- or 10-membered bicyclic heterocyclic ring system containing from 1–3 heteroatoms selected from the group consisting of N, O, and S; wherein said bicyclic heterocyclic ring system is selected from indolyl, indolinyl, indazolyl, benzimidazolyl, benzimidazolinyl, benztriazolyl, benzoxazolyl, benzoxazolinyl, benzthiazolyl, and dioxobenzthiazolyl; wherein said bicyclic heterocyclic ring system is substituted with 0–1 $R^{16}$;

$R^{14}$, at each occurrence, is independently selected from H, methyl, ethyl, propyl, and butyl;

$R^{15}$, at each occurrence, is independently selected from H, methyl, ethyl, propyl, and butyl;

$R^{16}$, at each occurrence, is independently selected from H, OH, F, Cl, CN, $NO_2$, methyl, ethyl, methoxy, ethoxy, trifluoromethyl, and trifluoromethoxy;

$R^{31}$, at each occurrence, is independently selected from H, OH, halo, $CF_3$, methyl, ethyl, and propyl;

$R^{33}$, at each occurrence, is independently selected from
H, OH, halo, CN, $NO_2$, $CF_3$, $SO_2R^{45}$, $NR^{46}R^{47}$, —C(=O)H,
$C_{1-6}$ alkyl, $C_{2-6}$ alkenyl, $C_{2-6}$ alkynyl,
$C_{3-6}$ cycloalkyl, $C_{1-4}$ haloalkyl, $C_{1-4}$ haloalkyl-oxy-, $C_{1-4}$ alkyloxy-,
$C_{1-4}$ alkylthio-, $C_{1-4}$ alkyl-C(=O)—, $C_{1-4}$ alkyl-C(=O)NH—, $C_{1-4}$ alkyl-OC(=O)—,
$C_{1-4}$ alkyl-C(=O)O—, $C_{3-6}$ cycloalkyl-oxy-, $C_{3-6}$ cycloalkylmethyl-oxy-;
$C_{1-6}$ alkyl substituted with OH, methoxy, ethoxy, propoxy, or butoxy; and
$C_{2-6}$ alkenyl substituted with OH, methoxy, ethoxy, propoxy, or butoxy;

$R^{41}$, at each occurrence, is independently selected from
H, $CF_3$, halo, OH, $CO_2H$, $SO_2R^{45}$, $NR^{46}R^{47}$, $NO_2$, CN, $C_{2-4}$ alkenyl, $C_{2-4}$ alkynyl, $C_{1-3}$ alkoxy, $C_{1-3}$ haloalkyl, and $C_{1-3}$ alkyl;

$R^{42}$, at each occurrence, is independently selected from
H, $CF_3$, halo, OH, $CO_2H$, $SO_2R^{45}$, $NR^{46}R^{47}$, $NO_2$, CN, CH(=NH)$NH_2$, NHC(=NH)$NH_2$,
$C_{2-4}$ alkenyl, $C_{2-4}$ alkynyl, $C_{1-3}$ alkoxy, $C_{1-3}$ haloalkyl, $C_{3-6}$ cycloalkyl, and $C_{1-3}$ alkyl;

$R^{43}$ is cyclopropyl, cyclobutyl, cyclopentyl, cyclohexyl, phenyl, or pyridyl, each substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, methyl, ethyl, propyl, butyl, methoxy, ethoxy, propoxy, and butoxy;

$R^{45}$ is methyl, ethyl, propyl, or butyl;

$R^{46}$, at each occurrence, is independently selected from H, methyl, ethyl, propyl, and butyl;

$R^{47}$, at each occurrence, is independently selected from from H, methyl, ethyl, propyl, and butyl;

k is 1;
m is 1; and
n is 0, 1 or 2.

In a more preferred embodiment, the present invention provides the method as defined in claim 2 where in the compound administered:

X is —$CH_2$—;
$R^1$ is selected from H,
$C_{1-5}$ alkyl substituted with 0–1 $R^2$,
$C_{2-5}$ alkenyl substituted with 0–1 $R^2$, and
$C_{2-3}$ alkynyl substituted with 0–1 $R^2$;
$R^2$ is $C_{3-6}$ cycloalkyl;
$R^5$ is H, methyl, ethyl, or propyl;
$R^{6a}$ is H, methyl, or ethyl;
$R^{6b}$ is H;
$R^7$ and $R^9$, at each occurrence, are independently selected from
H, F, Cl, —$CH_3$, —$OCH_3$, —$CF_3$, —$OCF_3$, —CN, and —$NO_2$,
$R^8$ is selected from
methyl substituted with $R^{11}$;
ethenyl substituted with $R^{11}$;
$OR^{12}$, $SR^{12}$, $NR^{12}R^{13}$, $NR^{12}C(O)R^{15}$, $NR^{12}C(O)OR^{15}$, $NR^{12}S(O)_2R^{15}$, and $NR^{12}C(O)NHR^{15}$;
$R^{11}$ is selected from
phenyl-substituted with 0–5 fluoro;
2-($H_3CCH_2C$(=O))-phenyl-substituted with $R^{33}$;
2-($H_3CC$(=O))-phenyl-substituted with $R^{33}$;
2-(HC(=O))-phenyl-substituted with $R^{33}$;
2-($H_3CCH$(OH))-phenyl-substituted with $R^{33}$;
2-($H_3CCH_2CH$(OH))-phenyl-substituted with $R^{33}$;
2-($HOCH_2$)-phenyl-substituted with $R^{33}$;
2-($HOCH_2CH_2$)-phenyl-substituted with $R^{33}$;
2-($H_3COCH_2$)-phenyl-substituted with $R^{33}$;
2-($H_3COCH_2CH_2$)-phenyl-substituted with $R^{33}$;
2-($H_3CCH$(OMe))-phenyl-substituted with $R^{33}$;
2-($H_3COC$(=O))-phenyl-substituted with $R^{33}$;
2-($HOCH_2CH$=CH)-phenyl-substituted with $R^{33}$;
2-((MeOC(=O)CH=CH)-phenyl-substituted with $R^{33}$;
2-(methyl)-phenyl-substituted with $R^{33}$;
2-(ethyl)-phenyl-substituted with $R^{33}$;
2-(i-propyl)-phenyl-substituted with $R^{33}$;
2-($F_3C$)-phenyl-substituted with $R^{33}$;
2-(NC)-phenyl-substituted with $R^{33}$;
2-($H_3CO$)-phenyl-substituted with $R^{33}$;
2-(fluoro)-phenyl-substituted with $R^{33}$;
2-(chloro)-phenyl-substituted with $R^{33}$;
3-(NC)-phenyl-substituted with $R^{33}$;
3-($H_3CO$)-phenyl-substituted with $R^{33}$;
3-(fluoro)-phenyl-substituted with $R^{33}$;
3-(chloro)-phenyl-substituted with $R^{33}$;
4-(NC)-phenyl-substituted with $R^{33}$;
4-(fluoro)-phenyl-substituted with $R^{33}$;
4-(chloro)-phenyl-substituted with $R^{33}$;
4-($H_3CS$)-phenyl-substituted with $R^{33}$;
4-($H_3CO$)-phenyl-substituted with $R^{33}$;
4-(ethoxy)-phenyl-substituted with $R^{33}$;
4-(i-propoxy)-phenyl-substituted with $R^{33}$;
4-(i-butoxy)-phenyl-substituted with $R^{33}$;
4-($H_3CCH_2CH_2C$(=O))-phenyl-substituted with $R^{33}$;
4-(($H_3C)_2CHC$(=O))-phenyl-substituted with $R^{33}$;
4-($H_3CCH_2C$(=O))-phenyl-substituted with $R^{33}$;
4-($H_3CC$(=O))-phenyl-substituted with $R^{33}$;
4-($H_3CCH_2CH_2CH$(OH))-phenyl-substituted with $R^{33}$;
4-(($H_3C)_2CHCH$(OH))-phenyl-substituted with $R^{33}$;
4-($H_3CCH_2CH$(OH))-phenyl-substituted with $R^{33}$;
4-($H_3CCH$(OH))-phenyl-substituted with $R^{33}$;
4-(cyclopropyloxy)-phenyl-substituted with $R^{33}$;
4-(cyclobutyloxy)-phenyl-substituted with $R^{33}$; and
4-(cyclopentyloxy)-phenyl-substituted with $R^{33}$;
$R^{12}$ is selected from
phenyl-substituted with 0–5 fluoro;
2-($H_3CCH_2C$(=O))-phenyl-substituted with $R^{33}$;

2-(H₃CC(=O))-phenyl-substituted with R³³;
2-(HC(=O))-phenyl-substituted with R³³;
2-(H₃CCH(OH))-phenyl-substituted with R³³;
2-(H₃CCH₂CH(OH))-phenyl-substituted with R³³;
2-(HOCH₂)-phenyl-substituted with R³³;
2-(HOCH₂CH₂)-phenyl-substituted with R³³;
2-(H₃COCH₂)-phenyl-substituted with R³³;
2-(H₃COCH₂CH₂)-phenyl-substituted with R³³;
2-(H₃CCH(OMe))-phenyl-substituted with R³³;
2-(H₃COC(=O))-phenyl-substituted with R³³;
2-(HOCH₂CH=CH)-phenyl-substituted with R³³;
2-((MeOC=O)CH=CH)-phenyl-substituted with R³³;
2-(methyl)-phenyl-substituted with R³³;
2-(ethyl)-phenyl-substituted with R³³;
2-(i-propyl)-phenyl-substituted with R³³;
2-(F₃C)-phenyl-substituted with R³³;
2-(NC)-phenyl-substituted with R³³;
2-(H₃CO)-phenyl-substituted with R³³;
2-(fluoro)-phenyl-substituted with R³³;
2-(chloro)-phenyl-substituted with R³³;
3-(NC)-phenyl-substituted with R³³;
3-(H₃CO)-phenyl-substituted with R³³;
3-(fluoro)-phenyl-substituted with R³³;
3-(chloro)-phenyl-substituted with R³³;
4-(NC)-phenyl-substituted with R³³;
4-(fluoro)-phenyl-substituted with R³³;
4-(chloro)-phenyl-substituted with R³³;
4-(H₃CS)-phenyl-substituted with R³³;
4-(H₃CO)-phenyl-substituted with R³³;
4-(ethoxy)-phenyl-substituted with R³³;
4-(i-propoxy)-phenyl-substituted with R³³;
4-(i-butoxy)-phenyl-substituted with R³³;
4-(H₃CCH₂CH₂C(=O))-phenyl-substituted with R³³;
4-((H₃C)₂CHC(=O))-phenyl-substituted with R³³;
4-(H₃CCH₂C(=O))-phenyl-substituted with R³³;
4-(H₃CC(=O))-phenyl-substituted with R³³;
4-(H₃CCH₂CH₂CH(OH))-phenyl-substituted with R³³;
4-((H₃C)₂CHCH(OH))-phenyl-substituted with R³³;
4-(H₃CCH₂CH(OH))-phenyl-substituted with R³³;
4-(H₃CCH(OH))-phenyl-substituted with R³³;
4-(cyclopropyloxy)-phenyl-substituted with R³³;
4-(cyclobutyloxy)-phenyl-substituted with R³³; and
4-(cyclopentyloxy)-phenyl-substituted with R³³;

$R^{13}$ is H, methyl, or ethyl;

alternatively, $R^{12}$ and $R^{13}$ join to form a 5- or 6-membered ring selected from pyrrolyl, pyrrolidinyl, imidazolyl, piperidinyl, piperizinyl, methylpiperizinyl, and morpholinyl;

alternatively, $R^{12}$ and $R^{13}$ when attached to N may be combined to form a 9- or 10-membered bicyclic heterocyclic ring system containing from 1–3 heteroatoms selected from the group consisting of N, O, and S; wherein said bicyclic heterocyclic ring system is selected from indolyl, indolinyl, indazolyl, benzimidazolyl, benzimidazolinyl, benztriazolyl, benzoxazolyl, benzoxazolinyl, benzthiazolyl, and dioxobenzthiazolyl; wherein said bicyclic heterocyclic ring system is substituted with 0–1 $R^{16}$;

$R^{15}$ is H, methyl, ethyl, propyl, or butyl;

$R^{16}$, at each occurrence, is independently selected from H, OH, F, Cl, CN, NO₂, methyl, ethyl, methoxy, ethoxy, trifluoromethyl, and trifluoromethoxy;

$R^{33}$, at each occurrence, is independently selected from H, F, Cl, —CH₃, —OCH₃, —CF₃, —OCF₃, —CN, and —NO₂;

k is 1;
m is 1; and
n is 1 or 2.

In a more preferred embodiment, the present invention provides the method as defined in claim 2 where the compound administered is a compound of Formula (I-a):

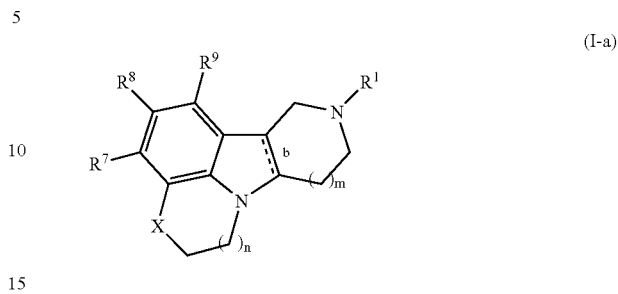

(I-a)

wherein:
b is a single bond;
X is —CH₂—, —CH(OH)—, or —C(=O)—;
$R^1$ is selected from
hydrogen, methyl, ethyl, n-propyl, n-butyl, s-butyl, t-butyl, n-pentyl, n-hexyl, 2-propyl, 2-butyl, 2-pentyl, 2-hexyl, 2-methylpropyl, 2-methylbutyl, 2-methylpentyl, 2-ethylbutyl, 3-methylpentyl, 3-methylbutyl, 4-methylpentyl, 2-fluoroethyl, 2,2-difluoroethyl, 2,2,2-trifluoroethyl,
2-propenyl, 2-methyl-2-propenyl, trans-2-butenyl, 3-methyl-butenyl, 3-butenyl, trans-2-pentenyl, cis-2-pentenyl, 4-pentenyl, 4-methyl-3-pentenyl, 3,3-dichloro-2-propenyl, trans-3-phenyl-2-propenyl,
cyclopropyl, cyclobutyl, cyclopentyl, cyclohexyl, cyclopropylmethyl, cyclobutylmethyl, cyclopentylmethyl, cyclohexylmethyl,
benzyl, 2-methylbenzyl, 3-methylbenzyl, 4-methylbenzyl, 2,5-dimethylbenzyl, 2,4-dimethylbenzyl, 3,5-dimethylbenzyl,
2,4,6-trimethyl-benzyl, 3-methoxy-benzyl, 3,5-dimethoxy-benzyl, pentafluorobenzyl, 2-phenylethyl, 1-phenyl-2-propyl, 4-phenylbutyl, 4-phenylbenzyl, 2-phenylbenzyl,
(2,3-dimethoxy-phenyl)C(=O)—, (2,5-dimethoxy-phenyl)C(=O)—, (3,4-dimethoxy-phenyl)C(=O)—, (3,5-dimethoxy-phenyl)C(=O)—, cyclopropyl-C(=O)—,
isopropyl-C(=O)—, ethyl-CO₂—, propyl-CO₂—, t-butyl-CO₂—,
2,6-dimethoxy-benzyl, 2,4-dimethoxy-benzyl, 2,4,6-trimethoxy-benzyl, 2,3-dimethoxy-benzyl, 2,4,5-trimethoxy-benzyl, 2,3,4-trimethoxy-benzyl, 3,4-dimethoxy-benzyl, 3,4,5-trimethoxy-benzyl, (4-fluoro-phenyl)ethyl,
—CH=CH₂, —CH₂—CH=CH₂, —CH=CH—CH₃, —C≡CH, —C≡C—CH₃, and —CH₂—C≡CH;

$R^7$, $R^8$, and $R^9$, at each occurrence, are independently selected from
hydrogen, fluoro, chloro, bromo, cyano, methyl, ethyl, propyl, isopropyl, butyl, t-butyl, nitro, trifluoromethyl, methoxy, ethoxy, isopropoxy, trifluoromethoxy, phenyl,
methylC(=O)—, ethylC(=O)—, propylC(=O)—, isopropylC(=O)—, butylC(=O)—, phenylC(=O)—,
methylCO₂—, ethylCO₂—, propylCO₂—, isopropylCO₂—, butylCO₂—, phenylCO₂—,
dimethylamino-S(=O)—, diethylamino-S(=O)—, dipropylamino-S(=O)—, di-isopropylamino-S(=O)—, dibutylamino-S(=O)—, diphenylamino-S(=O)—, dimethylamino-SO$_2$—, diethylamino-SO$_2$—, dipropylamino-SO$_2$—, di-isopropylamino-SO$_2$—, dibutylamino-SO$_2$—, diphenylamino-SO$_2$—,
dimethylamino-C(=O)—, diethylamino-C(=O)—, dipropylamino-C(=O)—, di-isopropylamino-C(=O)—, dibutylamino-C(=O)—, diphenylamino-C(=O)—,
2-chlorophenyl, 2-fluorophenyl, 2-bromophenyl, 2-cyanophenyl, 2-methylphenyl, 2-trifluoromethylphenyl, 2-methoxyphenyl, 2-trifluoromethoxyphenyl,
3-chlorophenyl, 3-fluorophenyl, 3-bromophenyl, 3-cyanophenyl, 3-methylphenyl, 3-ethylphenyl, 3-propylphenyl, 3-isopropylphenyl, 3-butylphenyl, 3-trifluoromethylphenyl, 3-methoxyphenyl, 3-isopropoxyphenyl, 3-trifluoromethoxyphenyl, 3-thiomethoxyphenyl,
4-chlorophenyl, 4-fluorophenyl, 4-bromophenyl, 4-cyanophenyl, 4-methylphenyl, 4-ethylphenyl, 4-propylphenyl, 4-isopropylphenyl, 4-butylphenyl, 4-trifluoromethylphenyl, 4-methoxyphenyl, 4-isopropoxyphenyl, 4-trifluoromethoxyphenyl, 4-thiomethoxyphenyl,
2,3-dichlorophenyl, 2,3-difluorophenyl, 2,3-dimethylphenyl,
2,3-ditrifluoromethylphenyl, 2,3-dimethoxyphenyl, 2,3-ditrifluoromethoxyphenyl,
2,4-dichlorophenyl, 2,4-difluorophenyl, 2,4-dimethylphenyl,
2,4-ditrifluoromethylphenyl, 2,4-dimethoxyphenyl, 2,4-ditrifluoromethoxyphenyl,
2,5-dichlorophenyl, 2,5-difluorophenyl, 2,5-dimethylphenyl,
2,5-ditrifluoromethylphenyl, 2,5-dimethoxyphenyl, 2,5-ditrifluoromethoxyphenyl,
2,6-dichlorophenyl, 2,6-difluorophenyl, 2,6-dimethylphenyl,
2,6-ditrifluoromethylphenyl, 2,6-dimethoxyphenyl, 2,6-ditrifluoromethoxyphenyl,
3,4-dichlorophenyl, 3,4-difluorophenyl, 3,4-dimethylphenyl,
3,4-ditrifluoromethylphenyl, 3,4-dimethoxyphenyl, 3,4-ditrifluoromethoxyphenyl,
2,4,6-trichlorophenyl, 2,4,6-trifluorophenyl, 2,4,6-trimethylphenyl, 2,4,6-tritrifluoromethylphenyl, 2,4,6-trimethoxyphenyl, 2,4,6-tritrifluoromethoxyphenyl,
2-chloro-4-CF$_3$-phenyl, 2-fluoro-3-chloro-phenyl, 2-chloro-4-CF$_3$-phenyl, 2-chloro-4-methoxy-phenyl,
2-methoxy-4-isopropyl-phenyl, 2-CF$_3$-4-methoxy-phenyl,
2-methyl-4-methoxy-5-fluoro-phenyl,
2-methyl-4-methoxy-phenyl, 2-chloro-4-CF$_3$O-phenyl,
2,4,5-trimethyl-phenyl, 2-methyl-4-chloro-phenyl,
methyl-C(=O)NH—, ethyl-C(=O)NH—, propyl-C(=O)NH—,
isopropyl-C(=O)NH—, butyl-C(=O)NH—, phenyl-C(=O)NH—,
4-acetylphenyl, 3-acetamidophenyl, 4-pyridyl, 2-furanyl, 2-thiophenyl, 2-naphthyl;
2-Me-5-F-phenyl, 2-F-5-Me-phenyl, 2-MeO-5-F-phenyl, 2-Me-3-Cl-phenyl, 3-NO$_2$-phenyl, 2-NO$_2$-phenyl,
2-Cl-3-Me-phenyl, 2-Me-4-EtO-phenyl, 2-Me-4-F-phenyl,
2-Cl-6-F-phenyl, 2-Cl-4-(CHF$_2$)O-phenyl,
2,4-diMeO-6-F-phenyl, 2-CF$_3$-6-F-phenyl,
2-MeS-phenyl, 2,6-diCl-4-MeO-phenyl,
2,3,4-triF-phenyl, 2,6-diF-4-Cl-phenyl,
2,3,4,6-tetraF-phenyl, 2,3,4,5,6-pentaF-phenyl,
2-CF$_3$-4-EtO-phenyl, 2-CF$_3$-4-iPrO-phenyl,
2-CF$_3$-4-Cl-phenyl, 2-CF$_3$-4-F-phenyl, 2-Cl-4-EtO-phenyl,
2-Cl-4-iPrO-phenyl, 2-Et-4-MeO-phenyl,
2-CHO-4-MeO-phenyl, 2-CH(OH)Me-4-MeO-phenyl,
2-CH(OMe)Me-4-MeO-phenyl, 2-C(=O)Me-4-MeO-phenyl,
2-CH$_2$(OH)-4-MeO-phenyl, 2-CH$_2$(OMe)-4-MeO-phenyl,
2-CH(OH)Et-4-MeO-phenyl, 2-C(=O)Et-4-MeO-phenyl,
(Z)-2-CH=CHCO$_2$Me-4-MeO-phenyl,
2-CH$_2$CH$_2$CO$_2$Me-4-MeO-phenyl,
(Z)-2-CH=CHCH$_2$(OH)-4-MeO-phenyl,
(E)-2-CH=CHCO$_2$Me-4-MeO-phenyl,
(E)-2-CH=CHCH$_2$(OH)-4-MeO-phenyl,
2-CH$_2$CH$_2$OMe-4-MeO-phenyl,
2-F-4-MeO-phenyl, 2-Cl-4-F-phenyl,
(2-Cl-phenyl)-CH=CH—, (3-Cl-phenyl)-CH=CH—,
(2,6-diF-phenyl)-CH=CH—, —CH$_2$CH=CH$_2$,
phenyl-CH=CH—, (2-Me-4-MeO-phenyl)-CH=CH—,
cyclohexyl, cyclopentyl, cyclohexylmethyl,
—CH$_2$CH$_2$CO$_2$Et, —(CH$_2$)$_3$CO$_2$Et, —(CH$_2$)$_4$CO$_2$Et,
benzyl, 2-F-benzyl, 3-F-benzyl, 4-F-benzyl,
3-MeO-benzyl, 3-OH-benzyl, 2-MeO-benzyl,
2-OH-benzyl, 2-CO$_2$Me-3-MeO-phenyl,
2-Me-4-CN-phenyl, 2-Me-3-CN-phenyl, 2-CF$_3$-4-CN-phenyl,
3-CHO-phenyl, 3-CH$_2$(OH)-phenyl, 3-CH$_2$(OMe)-phenyl,
3-CH$_2$(NMe2)-phenyl, 3-CN-4-F-phenyl,
3-CONH$_2$-4-F-phenyl, 2-CH$_2$(NH$_2$)-4-MeO-phenyl-,
phenyl-NH—, (4-F-phenyl)-NH—, (2,4-diCl-phenyl)-NH—,
phenyl-C(=O)NH—, benzyl-NH—, (2-Me-4-MeO-phenyl)-NH—,
(2-F-4-MeO-phenyl)-NH—, (2-Me-4-F-phenyl)-NH—,
phenyl-S—, —NMe$_2$, 1-pyrrolidinyl, and
—N(tosylate)$_2$,
provided that two of R$^7$, R$^8$, and R$^9$, are independently selected from hydrogen, fluoro, chloro, bromo, cyano, methyl, ethyl, propyl, isopropyl, butyl, t-butyl, nitro, trifluoromethyl, methoxy, ethoxy, isopropoxy, and trifluoromethoxy;

m is 1; and n is 0, 1 or 2.

In a more preferred embodiment, the present invention provides the method as defined in claim 7 where the compound administered is a compound of Formula (V):

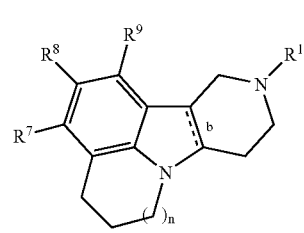

(V)

wherein:

b is a single bond, wherein the bridge hydrogens are in a cis position;

$R^1$ is selected from
hydrogen, methyl, ethyl, n-propyl, n-butyl, s-butyl,
t-butyl, n-pentyl, n-hexyl, 2-propyl, 2-butyl, 2-pentyl, 2-hexyl, 2-methylpropyl, 2-methylbutyl, 2-methylpentyl, 2-ethylbutyl, 3-methylpentyl, 3-methylbutyl, 4-methylpentyl, 2-fluoroethyl, 2,2-difluoroethyl, 2,2,2-trifluoroethyl, 2-propenyl, 2-methyl-2-propenyl, trans-2-butenyl, 3-methyl-butenyl, 3-butenyl, trans-2-pentenyl, cis-2-pentenyl, 4-pentenyl, 4-methyl-3-pentenyl, 3,3-dichloro-2-propenyl, trans-3-phenyl-2-propenyl, cyclopropyl, cyclobutyl, cyclopentyl, cyclohexyl, cyclopropylmethyl, cyclobutylmethyl, cyclopentylmethyl, cyclohexylmethyl,
—CH=CH$_2$, —CH$_2$—CH=CH$_2$, —CH=CH—CH$_3$, —C≡CH, —C≡C—CH$_3$,
and —CH$_2$—C≡CH;

$R^7$ and $R^9$, at each occurrence, are independently selected from hydrogen, fluoro, methyl, trifluoromethyl, and methoxy;

$R^8$ is selected from
hydrogen, fluoro, chloro, bromo, cyano, methyl, ethyl, propyl, isopropyl, butyl, t-butyl, nitro, trifluoromethyl, methoxy, ethoxy, isopropoxy, trifluoromethoxy, phenyl,
methylC(=O)—, ethylC(=O)—, propylC(=O)—, isopropylC(=O)—, butylC(=O)—, phenylC(=O)—,
methylCO$_2$—, ethylCO$_2$—, propylCO$_2$—, isopropylCO$_2$—, butylCO$_2$—, phenylCO$_2$—,
dimethylamino-S(=O)—, diethylamino-S(=O)—, dipropylamino-S(=O)—, di-isopropylamino-S(=O)—, dibutylamino-S(=O)—, diphenylamino-S(=O)—,
dimethylamino-SO$_2$—, diethylamino-SO$_2$—, dipropylamino-SO$_2$—, di-isopropylamino-SO$_2$—, dibutylamino-SO$_2$—,
diphenylamino-SO$_2$—,
dimethylamino-C(=O)—, diethylamino-C(=O)—, dipropylamino-C(=O)—, di-isopropylamino-C(=O)—, dibutylamino-C(=O)—, diphenylamino-C(=O)—,
2-chlorophenyl, 2-fluorophenyl, 2-bromophenyl, 2-cyanophenyl, 2-methylphenyl, 2-trifluoromethylphenyl, 2-methoxyphenyl, 2-trifluoromethoxyphenyl,
3-chlorophenyl, 3-fluorophenyl, 3-bromophenyl, 3-cyanophenyl, 3-methylphenyl, 3-ethylphenyl, 3-propylphenyl, 3-isopropylphenyl, 3-butylphenyl, 3-trifluoromethylphenyl, 3-methoxyphenyl, 3-isopropoxyphenyl, 3-trifluoromethoxyphenyl, 3-thiomethoxyphenyl,
4-chlorophenyl, 4-fluorophenyl, 4-bromophenyl, 4-cyanophenyl, 4-methylphenyl, 4-ethylphenyl, 4-propylphenyl, 4-isopropylphenyl, 4-butylphenyl, 4-trifluoromethylphenyl, 4-methoxyphenyl, 4-isopropoxyphenyl, 4-trifluoromethoxyphenyl, 4-thiomethoxyphenyl,
2,3-dichlorophenyl, 2,3-difluorophenyl, 2,3-dimethylphenyl, 2,3-ditrifluoromethylphenyl, 2,3-dimethoxyphenyl, 2,3-ditrifluoromethoxyphenyl,
2,4-dichlorophenyl, 2,4-difluorophenyl, 2,4-dimethylphenyl, 2,4-ditrifluoromethylphenyl, 2,4-dimethoxyphenyl, 2,4-ditrifluoromethoxyphenyl,
2,5-dichlorophenyl, 2,5-difluorophenyl, 2,5-dimethylphenyl, 2,5-ditrifluoromethylphenyl, 2,5-dimethoxyphenyl, 2,5-ditrifluoromethoxyphenyl,
2,6-dichlorophenyl, 2,6-difluorophenyl, 2,6-dimethylphenyl, 2,6-ditrifluoromethylphenyl, 2,6-dimethoxyphenyl, 2,6-ditrifluoromethoxyphenyl,
3,4-dichlorophenyl, 3,4-difluorophenyl, 3,4-dimethylphenyl, 3,4-ditrifluoromethylphenyl, 3,4-dimethoxyphenyl, 3,4-ditrifluoromethoxyphenyl,
2,4,6-trichlorophenyl, 2,4,6-trifluorophenyl, 2,4,6-trimethylphenyl, 2,4,6-tritrifluoromethylphenyl, 2,4,6-trimethoxyphenyl, 2,4,6-tritrifluoromethoxyphenyl,
2-chloro-4-CF$_3$-phenyl, 2-fluoro-3-chloro-phenyl, 2-chloro-4-CF$_3$-phenyl, 2-chloro-4-methoxy-phenyl, 2-methoxy-4-isopropyl-phenyl, 2-CF$_3$-4-methoxy-phenyl,
2-methyl-4-methoxy-5-fluoro-phenyl,
2-methyl-4-methoxy-phenyl, 2-chloro-4-CF$_3$O-phenyl, 2,4,5-trimethyl-phenyl, 2-methyl-4-chloro-phenyl,
methyl-C(=O)NH—, ethyl-C(=O)NH—, propyl-C(=O)NH—,
isopropyl-C(=O)NH—, butyl-C(=O)NH—, phenyl-C(=O)NH—,
4-acetylphenyl, 3-acetamidophenyl, 4-pyridyl, 2-furanyl, 2-thiophenyl, 2-naphthyl;
2-Me-5-F-phenyl, 2-F-5-Me-phenyl, 2-MeO-5-F-phenyl, 2-Me-3-Cl-phenyl, 3-NO$_2$-phenyl, 2-NO$_2$-phenyl, 2-Cl-3-Me-phenyl, 2-Me-4-EtO-phenyl, 2-Me-4-F-phenyl,
2-Cl-6-F-phenyl, 2-Cl-4-(CHF$_2$)O-phenyl, 2,4-diMeO-6-F-phenyl, 2-CF$_3$-6-F-phenyl, 2-MeS-phenyl, 2,6-diCl-4-MeO-phenyl, 2,3,4-triF-phenyl, 2,6-diF-4-Cl-phenyl, 2,3,4,6-tetraF-phenyl, 2,3,4,5,6-pentaF-phenyl, 2-CF$_3$-4-EtO-phenyl, 2-CF$_3$-4-iPrO-phenyl, 2-CF$_3$-4-Cl-phenyl, 2-CF$_3$-4-F-phenyl, 2-Cl-4-EtO-phenyl,
2-Cl-4-iPrO-phenyl, 2-Et-4-MeO-phenyl, 2-CHO-4-MeO-phenyl, 2-CH(OH)Me-4-MeO-phenyl, 2-CH(OMe)Me-4-MeO-phenyl, 2-C(=O)Me-4-MeO-phenyl,
2-CH$_2$(OH)-4-MeO-phenyl, 2-CH$_2$(OMe)-4-MeO-phenyl,
2-CH(OH)Et-4-MeO-phenyl, 2-C(=O)Et-4-MeO-phenyl,
(Z)-2-CH=CHCO$_2$Me-4-MeO-phenyl, 2-CH$_2$CH$_2$CO$_2$Me-4-MeO-phenyl,
(Z)-2-CH=CHCH$_2$(OH)-4-MeO-phenyl,
(E)-2-CH=CHCO$_2$Me-4-MeO-phenyl,
(E)-2-CH=CHCH$_2$(OH)-4-MeO-phenyl,
2-CH$_2$CH$_2$OMe-4-MeO-phenyl,
2-F-4-MeO-phenyl, 2-Cl-4-F-phenyl,
(2-Cl-phenyl)-CH=CH—, (3-Cl-phenyl)-CH=CH—, (2,6-diF-phenyl)-CH=CH—, —CH$_2$CH=CH$_2$,
phenyl-CH=CH—, (2-Me-4-MeO-phenyl)-CH=CH—, cyclohexyl, cyclopentyl, cyclohexylmethyl,
—CH$_2$CH$_2$CO$_2$Et, —(CH$_2$)$_3$CO$_2$Et, —(CH$_2$)$_4$CO$_2$Et, benzyl, 2-F-benzyl, 3-F-benzyl, 4-F-benzyl,
3-MeO-benzyl, 3-OH-benzyl, 2-MeO-benzyl, 2-OH-benzyl, 2-CO$_2$Me-3-MeO-phenyl,
2-Me-4-CN-phenyl, 2-Me-3-CN-phenyl, 2-CF$_3$-4-CN-phenyl,
3-CHO-phenyl, 3-CH$_2$(OH)-phenyl, 3-CH$_2$(OMe)-phenyl,
3-CH$_2$(NMe2)-phenyl, 3-CN-4-F-phenyl,
3-CONH$_2$-4-F-phenyl, 2-CH$_2$(NH$_2$)-4-MeO-phenyl-, phenyl-NH—, (4-F-phenyl)-NH—, (2,4-diCl-phenyl)-NH—, phenyl-C(=O)NH—, benzyl-NH—, (2-Me-4-MeO-phenyl)-NH—,
(2-F-4-MeO-phenyl)-NH—, (2-Me-4-F-phenyl)-NH—,
phenyl-S—, —NMe$_2$, 1-pyrrolidinyl, and
—N(tosylate)$_2$; and n is 0, 1 or 2.

In a more preferred embodiment, the present invention provides the method as defined in claim 1 where in the compound administered:

X is —CHR$^{10}$— or —C(=O)—;

R$^1$ is selected from
  C$_{1-6}$ alkyl substituted with Z,
  C$_{2-6}$ alkenyl substituted with Z,
  C$_{2-6}$ alkynyl substituted with Z,
  C$_{3-6}$ cycloalkyl substituted with Z,
  aryl substituted with Z,
  5–6 membered heterocyclic ring system containing at least one heteroatom selected from the group consisting of N, O, and S, said heterocyclic ring system substituted with Z;
  C$_{1-6}$ alkyl substituted with 0–2 R$^2$,
  C$_{2-6}$ alkenyl substituted with 0–2 R$^2$,
  C$_{2-6}$ alkynyl substituted with 0–2 R$^2$,
  aryl substituted with 0–2 R$^2$, and
  5–6 membered heterocyclic ring system containing at least one heteroatom selected from the group consisting of N, O, and S, said heterocyclic ring system substituted with 0–2 R$^2$;

Z is selected from H,
  —CH(OH)R$^2$,
  —C(ethylenedioxy)R$^2$,
  —SR$^2$,
  —NR$^2$R$^3$,
  —C(O)R$^2$,
  —C(O)NR$^2$R$^3$,
  —NR$^3$C(O)R$^2$,
  —C(O)OR$^2$,
  —OC(O)R$^2$,
  —CH(=NR$^4$)NR$^2$R$^3$,
  —NHC(=NR$^4$)NR$^2$R$^3$,
  —S(O)R$^2$,
  —S(O)$_2$R$^2$,
  —S(O)$_2$NR$^2$R$^3$, and —NR$^3$S(O)$_2$R$^2$;

R$^2$, at each occurrence, is independently selected from
  C$_{1-4}$ alkyl,
  C$_{2-4}$ alkenyl,
  C$_{2-4}$ alkynyl,
  C$_{3-6}$ cycloalkyl,
  aryl substituted with 0–5 R$^{42}$;
  C$_{3-10}$ carbocyclic group substituted with 0–3 R$^{41}$, and
  5–10 membered heterocyclic ring system containing from 1–4 heteroatoms selected from the group consisting of N, O, and S substituted with 0–3 R$^{41}$;

R$^3$, at each occurrence, is independently selected from
  H, C$_{1-4}$ alkyl, C$_{2-4}$ alkenyl, C$_{2-4}$ alkynyl, and
  C$_{1-4}$ alkoxy;
alternatively, R$^2$ and R$^3$ join to form a 5- or 6-membered ring optionally substituted with —O— or —N(R$^4$)—;

R$^4$, at each occurrence, is independently selected from H, methyl, ethyl, propyl, and butyl;

R$^5$ is H, methyl, ethyl, propyl, or butyl;

R$^{6a}$ is selected from
  H, —OH, —NR$^{46}$R$^{47}$, —CF$_3$,
  C$_{1-4}$ alkyl, C$_{2-4}$ alkenyl, C$_{2-4}$ alkynyl, C$_{1-4}$ alkoxy, C$_{1-4}$ haloalkyl, C$_{3-6}$ cycloalkyl, and
  aryl substituted with 0–3 R$^{44}$;

R$^{6b}$ is H;

R$^7$, R$^8$, and R$^9$, at each occurrence, are independently selected from
  H, halo, —CF$_3$, —OCF$_3$, —OH, —CN, —NO$_2$,
  —NR$^{46}$R$^{47}$,
  C$_{1-8}$ alkyl, C$_{2-8}$ alkenyl, C$_{2-8}$ alkynyl, C$_{1-4}$ haloalkyl, C$_{1-8}$ alkoxy, (C$_{1-4}$ haloalkyl)oxy,
  C$_{1-4}$ alkyl substituted with 0–2 R$^{11}$,
  C$_{3-10}$ carbocyclic group substituted with 0–3 R$^{33}$,
  aryl substituted with 0–5 R$^{33}$,
  5–10 membered heterocyclic ring system containing from 1–4 heteroatoms selected from the group consisting of N, O, and S substituted with 0–3 R$^{31}$;
  OR$^{12}$, SR$^{12}$, NR$^{12}$R$^{13}$, C(O)H, C(O)R$^{12}$, C(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(O)OR$^{15}$, NR$^{12}$S(O)$_2$R$^{15}$, and NR$^{12}$C(O)NHR$^{15}$;

R$^{10}$ is selected from H, —OH,
  C$_{1-6}$ alkyl substituted with 0–1 R$^{10B}$,
  C$_{2-6}$ alkenyl substituted with 0–1 R$^{10B}$,
  C$_{2-6}$ alkynyl substituted with 0–1 R$^{10B}$, and
  C$_{1-6}$ alkoxy;

R$^{10B}$ is selected from
  C$_{1-4}$ alkoxy,
  C$_{3-6}$ cycloalkyl,
  C$_{3-10}$ carbocyclic group substituted with 0–3 R$^{33}$,
  phenyl substituted with 0–3 R$^{33}$, and
  5–6 membered heterocyclic ring system containing 1, 2, or 3 heteroatoms selected from the group consisting of N, O, and S substituted with 0–2 R$^{44}$;

R$^{11}$ is selected from
  H, halo, —CF$_3$, —CN, —NO$_2$,
  C$_{1-8}$ alkyl, C$_{2-8}$ alkenyl, C$_{2-8}$ alkynyl, C$_{1-4}$ haloalkyl, C$_{1-8}$ alkoxy, C$_{3-10}$ cycloalkyl,
  C$_{3-10}$ carbocyclic group substituted with 0–3 R$^{33}$,
  aryl substituted with 0–5 R$^{33}$,
  5–10 membered heterocyclic ring system containing from 1–4 heteroatoms selected from the group consisting of N, O, and S substituted with 0–3 R$^{31}$;
  OR$^{12}$, SR$^{12}$, NR$^{12}$R$^{13}$, C(O)H, C(O)R$^{12}$, C(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, and NR$^{14}$S(O)$_2$R$^{12}$;

R$^{12}$, at each occurrence, is independently selected from
  C$_{1-4}$ alkyl,
  C$_{2-4}$ alkenyl,
  C$_{2-4}$ alkynyl,
  C$_{3-6}$ cycloalkyl,
  phenyl substituted with 0–5 R$^{33}$;
  C$_{3-10}$ carbocyclic group substituted with 0–3 R$^{33}$, and
  5–10 membered heterocyclic ring system containing from 1–4 heteroatoms selected from the group consisting of N, O, and S substituted with 0–3 R$^{31}$;

R$^{13}$, at each occurrence, is independently selected from
  H, C$_{1-4}$ alkyl, C$_{2-4}$ alkenyl, and C$_{2-4}$ alkynyl;
alternatively, R$^{12}$ and R$^{13}$ join to form a 5- or 6-membered ring optionally substituted with —O— or —N(R$^{14}$)—;

R$^{14}$, at each occurrence, is independently selected from H and C$_{1-4}$ alkyl;

R$^{31}$, at each occurrence, is independently selected from
  H, OH, halo, CF$_3$, SO$_2$R$^{45}$, NR$^{46}$R$^{47}$, methyl, ethyl, and propyl;

$R^{33}$, at each occurrence, is independently selected from
  H, OH, halo, CN, $NO_2$, $CF_3$, $SO_2R^{45}$, $NR^{46}R^{47}$,
  $C_{1-3}$ alkyl, $C_{2-3}$ alkenyl, $C_{2-3}$ alkynyl, $C_{3-5}$ cycloalkyl, $C_{1-3}$ haloalkyl, $C_{1-3}$ haloalkyl-oxy-, $C_{1-3}$ alkyloxy-, $C_{1-3}$ alkylthio-, $C_{1-3}$ alkyl-C(=O)—, and $C_{1-3}$ alkyl-C(=O)NH—;
$R^{41}$, at each occurrence, is independently selected from
  H, $CF_3$, halo, OH, $CO_2H$, $SO_2R^{45}$, $NR^{46}R^{47}$, $NO_2$, CN, =O,
  $C_{2-8}$ alkenyl, $C_{2-8}$ alkynyl, $C_{1-4}$ alkoxy, $C_{1-4}$ haloalkyl
  $C_{1-4}$ alkyl substituted with 0–1 $R^{43}$,
  aryl substituted with 0–3 $R^{42}$, and
  5–10 membered heterocyclic ring system containing from 1–4 heteroatoms selected from the group consisting of N, O, and S substituted with 0–3 $R^{44}$;
$R^{42}$, at each occurrence, is independently selected from
  H, $CF_3$, halo, OH, $CO_2H$, $SO_2R^{45}$, $SR^{45}$, $NR^{46}R^{47}$, $OR^{48}$, $NO_2$, CN, CH(=NH)$NH_2$, NHC(=NH)$NH_2$,
  $C_{2-6}$ alkenyl, $C_{2-6}$ alkynyl, $C_{1-4}$ alkoxy, $C_{1-4}$ haloalkyl, $C_{3-6}$ cycloalkyl,
  $C_{1-4}$ alkyl substituted with 0–1 $R^{43}$,
  aryl substituted with 0–3 $R^{44}$, and
  5–10 membered heterocyclic ring system containing from 1–4 heteroatoms selected from the group consisting of N, O, and S substituted with 0–3 $R^{44}$;
$R^{43}$ is $C_{3-6}$ cycloalkyl or aryl substituted with 0–3 $R^{44}$;
$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;
$R^{45}$ is $C_{1-4}$ alkyl;
$R^{46}$, at each occurrence, is independently selected from H and $C_{1-4}$ alkyl;
$R^{47}$, at each occurrence, is independently selected from H, $C_{1-4}$ alkyl,
  —C(=O)NH($C_{1-4}$ alkyl), —$SO_2$($C_{1-4}$ alkyl),
  —$SO_2$(phenyl), —C(=O)O($C_{1-4}$ alkyl), —C(=O)($C_{1-4}$ alkyl), and —C(=O)H;
$R^{48}$, at each occurrence, is independently selected from H, $C_{1-4}$ alkyl,
  —C(=O)NH($C_{1-4}$ alkyl), —C(=O)O($C_{1-4}$ alkyl), —C(=O)($C_{1-4}$ alkyl), and —C(=O)H;
k is 1 or 2;
m is 0, 1, or 2; and
n is 0, 1 or 2.

In a more preferred embodiment, the present invention provides the method as defined in claim 9 where in the compound administered:
X is —$CHR^{10}$— or —C(=O)—;
$R^1$ is selected from
  $C_{2-5}$ alkyl substituted with Z,
  $C_{2-5}$ alkenyl substituted with Z,
  $C_{2-5}$ alkynyl substituted with Z,
  $C_{3-6}$ cycloalkyl substituted with Z,
  aryl substituted with Z,
  5–6 membered heterocyclic ring system containing at least one heteroatom selected from the group consisting of N, O, and S, said heterocyclic ring system substituted with Z;
  $C_{1-5}$ alkyl substituted with 0–2 $R^2$,
  $C_{2-5}$ alkenyl substituted with 0–2 $R^2$, and
  $C_{2-5}$ alkynyl substituted with 0–2 $R^2$;
Z is selected from H,
  —CH(OH)$R^2$,
  —C(ethylenedioxy)$R^2$,
  —$OR^2$,
  —$SR^2$,
  —$NR^2R^3$,
  —C(O)$R^2$,
  —C(O)$NR^2R^3$,
  —$NR^3$C(O)$R^2$,
  —C(O)$OR^2$,
  —OC(O)$R^2$,
  —CH(=$NR^4$)$NR^2R^3$,
  —NHC(=$NR^4$)$NR^2R^3$,
  —S(O)$R^2$,
  —S(O)$_2R^2$,
  —S(O)$_2NR^2R^3$, and —$NR^3$S(O)$_2R^2$;
$R^2$, at each occurrence, is independently selected from
  $C_{1-4}$ alkyl,
  $C_{2-4}$ alkenyl,
  $C_{2-4}$ alkynyl,
  $C_{3-6}$ cycloalkyl,
  aryl substituted with 0–5 $R^{42}$;
  $C_{3-10}$ carbocyclic group substituted with 0–3 $R^{41}$, and
  5–10 membered heterocyclic ring system containing from 1–4 heteroatoms selected from the group consisting of N, O, and S substituted with 0–3 $R^{41}$;
$R^3$, at each occurrence, is independently selected from
  H, $C_{1-4}$ alkyl, $C_{2-4}$ alkenyl, $C_{2-4}$ alkynyl, and $C_{1-4}$ alkoxy;
alternatively, $R^2$ and $R^3$ join to form a 5- or 6-membered ring optionally substituted with —O— or —N($R^4$)—;
$R^4$, at each occurrence, is independently selected from H, methyl, ethyl, propyl, and butyl;
$R^5$ is H, methyl, or ethyl;
$R^{6a}$ is selected from
  H, —OH, —$NR^{46}R^{47}$, —$CF_3$,
  $C_{1-4}$ alkyl, $C_{2-4}$ alkenyl, $C_{2-4}$ alkynyl, $C_{1-4}$ alkoxy, $C_{1-4}$ haloalkyl, and $C_{3-6}$ cycloalkyl;
$R^{6b}$ is H;
$R^7$, $R^8$, and $R^9$, at each occurrence, are independently selected from
  H, halo, —$CF_3$, —$OCF_3$, —OH, —$OCH_3$, —CN, —$NO_2$, —$NR^{46}R^{47}$,
  $C_{1-6}$ alkyl, $C_{2-6}$ alkenyl, $C_{2-6}$ alkynyl, $C_{1-4}$ haloalkyl, $C_{1-6}$ alkoxy, ($C_{1-4}$ haloalkyl)oxy,
  $C_{1-4}$ alkyl substituted with 0–2 $R^{11}$,
  $C_{3-10}$ carbocyclic group substituted with 0–3 $R^{33}$,
  aryl substituted with 0–5 $R^{33}$,
  5–10 membered heterocyclic ring system containing from 1–4 heteroatoms selected from the group consisting of N, O, and S substituted with 0–3 $R^{31}$;
  $OR^{12}$, $SR^{12}$, $NR^{12}R^{13}$, C(O)H, C(O)$R^{12}$, C(O)$NR^{12}R^{13}$, $NR^{14}$C(O)$R^{12}$, C(O)$OR^{12}$, OC(O)$R^{12}$, CH(=$NR^{14}$)$NR^{12}R^{13}$, NHC(=$NR^{14}$)$NR^{12}R^{13}$, S(O)$R^{12}$, S(O)$_2R^{12}$, S(O)$_2NR^{12}R^{13}$, $NR^{14}$S(O)$_2R^{12}$, $NR^{14}$S(O)$R^{12}$, $NR^{14}$S(O)$_2R^{12}$, $NR^{12}$C(O)$R^{15}$, $NR^{12}$C(O)$OR^{15}$, $NR^{12}$S(O)$_2R^{15}$, and $NR^{12}$C(O)$NHR^{15}$;
$R^{10}$ is selected from H, —OH, $C_{1-6}$ alkyl, $C_{1-4}$ alkoxy, and $C_{1-2}$ alkyl substituted with 0–1 $R^{10B}$;
$R^{10B}$ is $C_{3-6}$ cycloalkyl or
  phenyl substituted with 0–3 $R^{33}$;
$R^{11}$ is selected from
  H, halo, —$CF_3$, —$OCF_3$, —OH, —$OCH_3$, —CN, —$NO_2$, —$NR^{46}R^{47}$,
  $C_{1-6}$ alkyl, $C_{2-6}$ alkenyl, $C_{2-6}$ alkynyl, $C_{1-4}$ haloalkyl, $C_{1-6}$ alkoxy, ($C_{1-4}$ haloalkyl)oxy,
  $C_{3-10}$ carbocyclic group substituted with 0–3 $R^{33}$,
  aryl substituted with 0–5 $R^{33}$,
  5–10 membered heterocyclic ring system containing from 1–4 heteroatoms selected from the group consisting of N, O, and S substituted with 0–3 $R^{31}$;
  $OR^{12}$, $SR^{12}$, $NR^{12}R^{13}$, C(O)H, C(O)$R^{12}$, C(O)$NR^{12}R^{13}$, $NR^{14}$C(O)$R^{12}$, C(O)$OR^{12}$, OC(O)$R^{12}$, CH(=$NR^{14}$)

$NR^{12}R^{13}$, $NHC(=NR^{14})NR^{12}R^{13}$, $S(O)R^{12}$, $S(O)_2R^{12}$, $S(O)_2NR^{12}R^{13}$, and $NR^{14}S(O)_2R^{12}$;

$R^{12}$, at each occurrence, is independently selected from
- $C_{1-4}$ alkyl,
- $C_{2-4}$ alkenyl,
- $C_{2-4}$ alkynyl,
- $C_{3-6}$ cycloalkyl,
- phenyl substituted with 0–5 $R^{33}$;
- $C_{3-10}$ carbocyclic group substituted with 0–3 $R^{33}$, and
- 5–10 membered heterocyclic ring system containing from 1-4 heteroatoms selected from the group consisting of N, O, and S substituted with 0–3 $R^{31}$;

$R^{13}$, at each occurrence, is independently selected from H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —N($R^{14}$)—;

$R^{14}$, at each occurrence, is independently selected from H and $C_{1-4}$ alkyl;

$R^{31}$, at each occurrence, is independently selected from H, OH, halo, $CF_3$, methyl, and ethyl;

$R^{33}$, at each occurrence, is independently selected from H, OH, halo, CN, $NO_2$, $CF_3$, methyl, and ethyl;

$R^{41}$, at each occurrence, is independently selected from
- H, $CF_3$, halo, OH, $CO_2H$, $SO_2R^{45}$, $NR^{46}R^{47}$, $NO_2$, CN, =O,
- $C_{2-8}$ alkenyl, $C_{2-8}$ alkynyl, $C_{1-4}$ alkoxy, $C_{1-4}$ haloalkyl,
- $C_{1-4}$ alkyl substituted with 0–1 $R^{43}$,
- aryl substituted with 0–3 $R^{42}$, and
- 5–10 membered heterocyclic ring system containing from 1-4 heteroatoms selected from the group consisting of N, O, and S substituted with 0–3 $R^{44}$;

$R^{42}$, at each occurrence, is independently selected from
- H, $CF_3$, halo, OH, $CO_2H$, $SO_2R^{45}$, $SR^{45}$, $NR^{46}R^{47}$, $OR^{48}$, $NO_2$, CN, $CH(=NH)NH_2$, $NHC(=NH)NH_2$,
- $C_{2-6}$ alkenyl, $C_{2-6}$ alkynyl, $C_{1-4}$ alkoxy, $C_{1-4}$ haloalkyl, $C_{3-6}$ cycloalkyl,
- $C_{1-4}$ alkyl substituted with 0–1 $R^{43}$,
- aryl substituted with 0–3 $R^{44}$, and
- 5–10 membered heterocyclic ring system containing from 1-4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-3}$ alkyl;

$R^{47}$, at each occurrence, is independently selected from H, $C_{1-4}$ alkyl, —C(=O)NH($C_{1-4}$ alkyl), —$SO_2$($C_{1-4}$ alkyl), —$SO_2$(phenyl), —C(=O)O($C_{1-4}$ alkyl), —C(=O)($C_{1-4}$ alkyl), and —C(=O)H;

$R^{48}$, at each occurrence, is independently selected from H, $C_{1-4}$ alkyl, —C(=O)NH($C_{1-4}$ alkyl), —C(=O)O($C_{1-4}$ alkyl), —C(=O)($C_{1-4}$ alkyl), and —C(=O)H;

k is 1 or 2;

m is 0, 1, 2; and n is 0, 1 or 2.

In a more preferred embodiment, the present invention provides the method as defined in claim 9 where in the compound administered:

X is —$CH_2$—;

$R^1$ is selected from
- $C_{2-4}$ alkyl substituted with Z,
- $C_{2-4}$ alkenyl substituted with Z,
- $C_{2-4}$ alkynyl substituted with Z,
- $C_{3-6}$ cycloalkyl substituted with Z,
- aryl substituted with Z,
- 5–6 membered heterocyclic ring system containing at least one heteroatom selected from the group consisting of N, O, and S, said heterocyclic ring system substituted with Z;
- $C_{2-4}$ alkyl substituted with 0–2 $R^2$, and
- $C_{2-4}$ alkenyl substituted with 0–2 $R^2$;

Z is selected from H,
- —CH(OH)$R^2$,
- —C(ethylenedioxy)$R^2$,
- —$SR^2$,
- —$NR^2R^3$,
- —C(O)$R^2$,
- —C(O)$NR^2R^3$,
- —$NR^3$C(O)$R^2$,
- —C(O)O$R^2$,
- —S(O)$R^2$,
- —S(O)$_2R^2$,
- —S(O)$_2NR^2R^3$, and —$NR^3$S(O)$_2R^2$;

$R^2$, at each occurrence, is independently selected from
- phenyl substituted with 0–5 $R^{42}$;
- $C_{3-10}$ carbocyclic group substituted with 0–3 $R^{41}$, and
- 5–10 membered heterocyclic ring system containing from 1-4 heteroatoms selected from the group consisting of N, O, and S substituted with 0–3 $R^{41}$;

$R^3$, at each occurrence, is independently selected from H, $C_{1-4}$ alkyl, $C_{2-4}$ alkenyl, $C_{2-4}$ alkynyl, and $C_{1-4}$ alkoxy;

alternatively, $R^2$ and $R^3$ join to form a 5- or 6-membered ring optionally substituted with —O— or —N($R^4$)—;

$R^4$, at each occurrence, is independently selected from H, methyl, ethyl, propyl, and butyl;

$R^5$ is H;

$R^{6a}$ is selected from H, —OH, —$CF_3$, methyl, ethyl, propyl, butyl, methoxy, and, ethoxy;

$R^{6b}$ is H;

$R^7$, $R^8$, and $R^9$, at each occurrence, are independently selected from
- H, halo, —$CF_3$, —$OCF_3$, —OH, —$OCH_3$, —CN, —$NO_2$, $C_{1-4}$ alkyl, $C_{1-4}$ haloalkyl, $C_{1-4}$ alkoxy, ($C_{1-3}$ haloalkyl)oxy, and
- $C_{1-4}$ alkyl substituted with 0–2 $R^{11}$;

$R^{11}$ is selected from
- H, halo, —$CF_3$, —$OCF_3$, —OH, —$OCH_3$, —CN, —$NO_2$, $C_{1-4}$ alkyl, $C_{1-4}$ haloalkyl, $C_{1-4}$ alkoxy, and ($C_{1-3}$ haloalkyl)oxy;

$R^{33}$, at each occurrence, is independently selected from H, OH, halo, $CF_3$, and methyl;

$R^{41}$, at each occurrence, is independently selected from
- H, $CF_3$, halo, OH, $CO_2H$, $SO_2R^{45}$, $NR^{46}R^{47}$, $NO_2$, CN, =O,
- $C_{2-8}$ alkenyl, $C_{2-8}$ alkynyl, $C_{1-4}$ alkoxy, $C_{1-4}$ haloalkyl,
- $C_{1-4}$ alkyl substituted with 0–1 $R^{43}$,
- aryl substituted with 0–3 $R^{42}$, and
- 5–10 membered heterocyclic ring system containing from 1-4 heteroatoms selected from the group consisting of N, O, and S substituted with 0–3 $R^{44}$;

$R^{42}$, at each occurrence, is independently selected from
- H, $CF_3$, halo, OH, $CO_2H$, $SO_2R^{45}$, $SR^{45}$, $NR^{46}R^{47}$, $OR^{48}$, $NO_2$, CN, $CH(=NH)NH_2$, $NHC(=NH)NH_2$,
- $C_{2-6}$ alkenyl, $C_{2-6}$ alkynyl, $C_{1-4}$ alkoxy, $C_{1-4}$ haloalkyl, $C_{3-6}$ cycloalkyl,
- $C_{1-4}$ alkyl substituted with 0–1 $R^{43}$,
- aryl substituted with 0–3 $R^{44}$, and 5–10 membered heterocyclic ring system containing from 1–4 heteroatoms selected from the group consisting of N, O, and S substituted with 0–3 $R^{44}$;

$R^{43}$ is cyclopropyl, cyclobutyl, cyclopentyl, cyclohexyl, phenyl, or pyridyl, each substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, methyl, ethyl, propyl, butyl, methoxy, ethoxy, propoxy, and butoxy;

$R^{45}$ is methyl, ethyl, propyl, or butyl;

$R^{46}$, at each occurrence, is independently selected from H, methyl, ethyl, propyl, and butyl;

$R^{47}$, at each occurrence, is independently selected from H, methyl, ethyl, n-propyl, i-propyl, n-butyl, i-butyl, —C(=O)NH(methyl), —C(=O)NH(ethyl), —$SO_2$(methyl), —$SO_2$(ethyl), —$SO_2$(phenyl), —C(=O)O(methyl), —C(=O)O(ethyl), —C(=O)(methyl), —C(=O)(ethyl), and —C(=O)H;

$R^{48}$, at each occurrence, is independently selected from H, methyl, ethyl, n-propyl, i-propyl, —C(=O)NH(methyl), —C(=O)NH(ethyl), —C(=O)O(methyl), —C(=O)O(ethyl), —C(=O)(methyl), —C(=O)(ethyl), and —C(=O)H;

k is 1;
m is 0, 1, or 2; and
n is 0, 1 or 2.

In a more preferred embodiment, the present invention provides the method as defined in claim 9 where in the compound administered:

X is —$CH_2$—;
$R^1$ is selected from
 ethyl substituted with Z,
 propyl substituted with Z,
 butyl substituted with Z,
 propenyl substituted with Z,
 butenyl substituted with Z,
 ethyl substituted with $R^2$,
 propyl substituted with $R^2$,
 butyl substituted with $R^2$,
 propenyl substituted with $R^2$, and
 butenyl substituted with $R^2$;

Z is selected from H,
 —CH(OH)$R^2$,
 —$OR^2$,
 —$SR^2$,
 —$NR^2R^3$,
 —C(O)$R^2$,
 —C(O)$NR^2R^3$,
 —$NR^3$C(O)$R^2$,
 —C(O)$OR^2$,
 —S(O)$R^2$,
 —S(O)$_2R^2$,
 —S(O)$_2NR^2R^3$, and —$NR^3$S(O)$_2R^2$;

$R^2$, at each occurrence, is independently selected from
 phenyl substituted with 0–3 $R^{42}$;
 naphthyl substituted with 0–3 $R^{42}$;
 cyclopropyl substituted with 0–3 $R^{41}$;
 cyclobutyl substituted with 0–3 $R^{41}$;
 cyclopentyl substituted with 0–3 $R^{41}$;
 cyclohexyl substituted with 0–3 $R^{41}$;
 pyridyl substituted with 0–3 $R^{41}$;
 indolyl substituted with 0–3 $R^{41}$;
 indolinyl substituted with 0–3 $R^{41}$;
 benzimidazolyl substituted with 0–3 $R^{41}$;
 benzotriazolyl substituted with 0–3 $R^{41}$;
 benzothienyl substituted with 0–3 $R^{41}$;
 benzofuranyl substituted with 0–3 $R^{41}$;
 phthalimid-1-yl substituted with 0–3 $R^{41}$;
 inden-2-yl substituted with 0–3 $R^{41}$;
 2,3-dihydro-1H-inden-2-yl substituted with 0–3 $R^{41}$;
 indazolyl substituted with 0–3 $R^{41}$;
 tetrahydroquinolinyl substituted with 0–3 $R^{41}$; and
 tetrahydro-isoquinolinyl substituted with 0–3 $R^{41}$;

$R^3$, at each occurrence, is independently selected from H, methyl, and ethyl;

$R^5$ is H;
$R^{6a}$ is selected from H, —OH, methyl, and methoxy;
$R^{6b}$ is H;

$R^7$, $R^8$, and $R^9$, at each occurrence, are independently selected from H, F, Cl, methyl, ethyl, methoxy, —$CF_3$, and —$OCF_3$;

$R^{41}$, at each occurrence, is independently selected from H, F, Cl, Br, OH, $CF_3$, $NO_2$, CN, =O, methyl, ethyl, propyl, butyl, methoxy, and ethoxy;

$R^{42}$, at each occurrence, is independently selected from H, F, Cl, Br, OH, $CF_3$, $SO_2R^{45}$, $SR^{45}$, $NR^{46}R^{47}$, $OR^{48}$, $NO_2$, CN, =O, methyl, ethyl, propyl, butyl, methoxy, and ethoxy;

$R^{45}$ is methyl, ethyl, propyl, or butyl;

$R^{46}$, at each occurrence, is independently selected from H, methyl, ethyl, propyl, and butyl;

$R^{47}$, at each occurrence, is independently selected from H, methyl, ethyl, n-propyl, i-propyl, n-butyl, i-butyl, —C(=O)NH(methyl), —C(=O)NH(ethyl), —$SO_2$(methyl), —$SO_2$(ethyl), —$SO_2$(phenyl), —C(=O)O(methyl), —C(=O)O(ethyl), —C(=O)(methyl), —C(=O)(ethyl), and —C(=O)H;

$R^{48}$, at each occurrence, is independently selected from H, methyl, ethyl, n-propyl, i-propyl, —C(=O)NH(methyl), —C(=O)NH(ethyl), —C(=O)O(methyl), —C(=O)O(ethyl), —C(=O)(methyl), —C(=O)(ethyl), and —C(=O)H;

k is 1;
m is 0, 1, or 2; and
n is 0, 1 or 2.

In a more preferred embodiment, the present invention provides the method as defined in claim 9 where the compound administered is a compound of Formula (I-a):

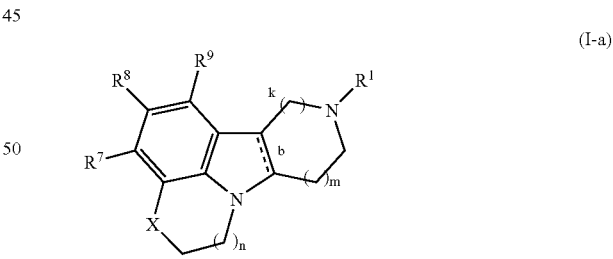

(I-a)

wherein:
b is a single bond;
X is —$CH_2$—, CH(OH)—, or —C(=O)—
$R^1$ is selected from
 —($CH_2$)$_3$C(=O)(4-fluoro-phenyl),
 —($CH_2$)$_3$C(=O)(4-bromo-phenyl),
 —($CH_2$)$_3$C(=O)(4-methyl-phenyl),
 —($CH_2$)$_3$C(=O)(4-methoxy-phenyl),
 —($CH_2$)$_3$C(=O)(4-(3,4-dichloro-phenyl)phenyl),
 —($CH_2$)$_3$C(=O)(3-methyl-4-fluoro-phenyl),
 —($CH_2$)$_3$C(=O)(2,3-dimethoxy-phenyl), —(CH$_2$)$_3$C(=O)(phenyl),
—(CH$_2$)$_3$C(=O)(4-chloro-phenyl),
—(CH$_2$)$_3$C(=O)(3-methyl-phenyl),
—(CH$_2$)$_3$C(=O)(4-t-butyl-phenyl),
—(CH$_2$)$_3$C(=O)(3,4-difluoro-phenyl),
—(CH$_2$)$_3$C(=O)(2-methoxy-5-fluoro-phenyl),
—(CH$_2$)$_3$C(=O)(4-fluoro-1-naphthyl),
—(CH$_2$)$_3$C(=O)(benzyl),
—(CH$_2$)$_3$C(=O)(4-pyridyl),
—(CH$_2$)$_3$C(=O)(3-pyridyl),
—(CH$_2$)$_3$CH(OH)(4-fluoro-phenyl),
—(CH$_2$)$_3$CH(OH)(4-pyridyl),
—(CH$_2$)$_3$CH(OH)(2,3-dimethoxy-phenyl),
—(CH$_2$)$_3$S(3-fluoro-phenyl),
—(CH$_2$)$_3$S(4-fluoro-phenyl),
—(CH$_2$)$_3$S(=O)(4-fluoro-phenyl),
—(CH$_2$)$_3$SO$_2$(3-fluoro-phenyl),
—(CH$_2$)$_3$SO$_2$(4-fluoro-phenyl),
—(CH$_2$)$_3$O(4-fluoro-phenyl),
—(CH$_2$)$_3$O(phenyl),
—(CH$_2$)$_3$O(3-pyridyl),
—(CH$_2$)$_3$O(4-pyridyl),
—(CH$_2$)$_3$O(2-NH$_2$-phenyl),
—(CH$_2$)$_3$O(2-NH$_2$-5-F-phenyl),
—(CH$_2$)$_3$O(2-NH$_2$-4-F-phenyl),
—(CH$_2$)$_3$O(2-NH$_2$-3-F-phenyl),
—(CH$_2$)$_3$O(2-NH$_2$-4-Cl-phenyl),
—(CH$_2$)$_3$O(2-NH$_2$-4-OH-phenyl),
—(CH$_2$)$_3$O(2-NH$_2$-4-Br-phenyl),
—(CH$_2$)$_3$O(2-NHC(=O)Me-4-F-phenyl),
—(CH$_2$)$_3$O(2-NHC(=O)Me-phenyl),
—(CH$_2$)$_3$NH(4-fluoro-phenyl),
—(CH$_2$)$_3$N(methyl)(4-fluoro-phenyl),
—(CH$_2$)$_3$CO$_2$(ethyl),
—(CH$_2$)$_3$C(=O)N(methyl)(methoxy),
—(CH$_2$)$_3$C(=O)NH(4-fluoro-phenyl),
—(CH$_2$)$_3$NHC(=O)(phenyl),
—(CH$_2$)$_3$NMeC(=O)(phenyl),
—(CH$_2$)$_3$NHC(=O)(2-fluoro-phenyl),
—(CH$_2$)$_3$NMeC(=O)(2-fluoro-phenyl),
—(CH$_2$)$_3$NHC(=O)(4-fluoro-phenyl),
—(CH$_2$)$_3$NMeC(=O)(4-fluoro-phenyl),
—(CH$_2$)$_2$NHC(=O)(2,4-difluoro-phenyl),
—(CH$_2$)$_2$NMeC(=O)(2,4-difluoro-phenyl),
—(CH$_2$)$_3$(3-indolyl),
—(CH$_2$)$_3$(1-methyl-3-indolyl),
—(CH$_2$)$_3$(1-indolyl),
—(CH$_2$)$_3$(1-indolinyl),
—(CH$_2$)$_3$(1-benzimidazolyl),
—(CH$_2$)$_3$(1H-1,2,3-benzotriazol-1-yl),
—(CH$_2$)$_3$(1H-1,2,3-benzotriazol-2-yl),
—(CH$_2$)$_2$(1H-1,2,3-benzotriazol-1-yl),
—(CH$_2$)$_2$(1H-1,2,3-benzotriazol-2-yl),
—(CH$_2$)$_3$(3,4 dihydro-1-(2H)-quinolinyl),
—(CH$_2$)$_2$C(=O)(4-fluoro-phenyl),
—(CH$_2$)$_2$C(=O)NH(4-fluoro-phenyl),
—CH$_2$CH$_2$(3-indolyl),
—CH$_2$CH$_2$(1-phthalimidyl),
—(CH$_2$)$_4$C(=O)N(methyl)(methoxy),
—(CH$_2$)$_4$CO$_2$(ethyl),
—(CH$_2$)$_4$C(=O)(phenyl),
—(CH$_2$)$_4$(cyclohexyl),
—(CH$_2$)$_3$CH(phenyl)$_2$,
—CH$_2$CH$_2$CH=C(phenyl)$_2$,
—CH$_2$CH$_2$CH=CMe(4-F-phenyl),
—(CH$_2$)$_3$CH(4-fluoro-phenyl)$_2$,
—CH$_2$CH$_2$CH=C(4-fluoro-phenyl)$_2$,
—(CH$_2$)$_2$(2,3-dihydro-1H-inden-2-yl),
—(CH$_2$)$_3$C(=O)(2-NH$_2$-phenyl),
—(CH$_2$)$_3$C(=O)(2-NH$_2$-5-F-phenyl),
—(CH$_2$)$_3$C(=O)(2-NH$_2$-4-F-phenyl),
—(CH$_2$)$_3$C(=O)(2-NH$_2$-3-F-phenyl),
—(CH$_2$)$_3$C(=O)(2-NH$_2$-4-Cl-phenyl),
—(CH$_2$)$_3$C(=O)(2-NH$_2$-4-OH-phenyl),
—(CH$_2$)$_3$C(=O)(2-NH$_2$-4-Br-phenyl),
—(CH$_2$)$_3$(1H-indazol-3-yl),
—(CH$_2$)$_3$(5-F-1H-indazol-3-yl),
—(CH$_2$)$_3$(7-F-1H-indazol-3-yl),
—(CH$_2$)$_3$(6-Cl-1-H-indazol-3-yl),
—(CH$_2$)$_3$(6-Br-1-H-indazol-3-yl),
—(CH$_2$)$_3$C(=O)(2-NHMe-phenyl),
—(CH$_2$)$_3$(1-benzothien-3-yl),
—(CH$_2$)$_3$(6-F-1H-indol-1-yl),
—(CH$_2$)$_3$(5-F-1H-indol-1-yl),
—(CH$_2$)$_3$(6-F-2,3-dihydro-1H-indol-1-yl),
—(CH$_2$)$_3$(5-F-2,3-dihydro-1H-indol-1-yl),
—(CH$_2$)$_3$(6-F-1H-indol-3-yl),
—(CH$_2$)$_3$(5-F-1H-indol-3-yl),
—(CH$_2$)$_3$(5-F-1H-indol-3-yl),
—(CH$_2$)$_3$(9H-purin-9-yl),
—(CH$_2$)$_3$(7H-purin-7-yl),
—(CH$_2$)$_3$(6-F-1H-indazol-3-yl),
—(CH$_2$)$_3$C(=O)(2-NHSO$_2$Me-4-F-phenyl),
—(CH$_2$)$_3$C(=O)(2-NHC(=O)Me-4-F-phenyl),
—(CH$_2$)$_3$C(=O)(2-NHC(=O)Me-phenyl),
—(CH$_2$)$_3$C(=O)(2-NHCO$_2$Et-4-F-phenyl),
—(CH$_2$)$_3$C(=O)(2-NHC(=O)NHEt-4-F-phenyl),
—(CH$_2$)$_3$C(=O)(2-NHCHO-4-F-phenyl),
—(CH$_2$)$_3$C(=O)(2-OH-4-F-phenyl),
—(CH$_2$)$_3$C(=O)(2-MeS-4-F-phenyl),
—(CH$_2$)$_3$C(=O)(2-NHSO$_2$Me-4-F-phenyl),
—(CH$_2$)$_2$C(Me)CO$_2$Me,
—(CH$_2$)$_2$C(Me)CH(OH)(4-F-phenyl)$_2$,
—(CH$_2$)$_2$C(Me)CH(OH)(4-Cl-phenyl)$_2$,
—(CH$_2$)$_2$C(Me)C(=O)(4-F-phenyl),
—(CH$_2$)$_2$C(Me)C(=O)(2-MeO-4-F-phenyl),
—(CH$_2$)$_2$C(Me)C(=O)(3-Me-4-F-phenyl),
—(CH$_2$)$_2$C(Me)C(=O)(2-Me-phenyl),
—(CH$_2$)$_2$C(Me)C(=O)phenyl,

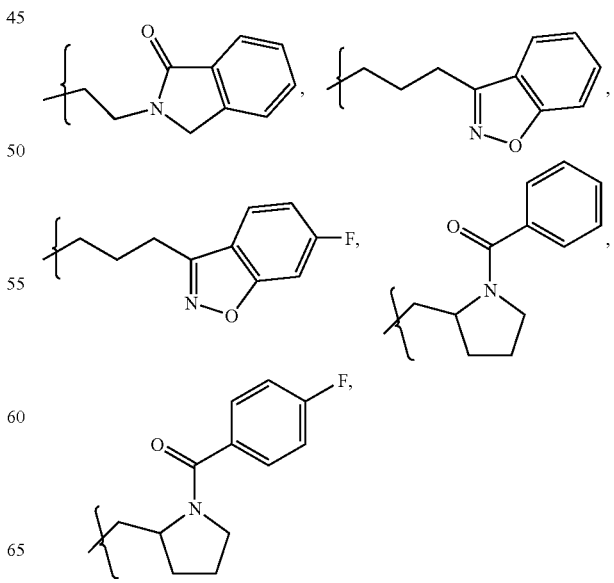

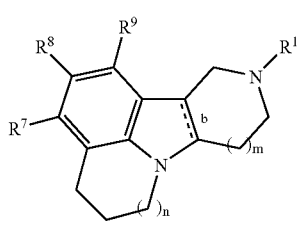

R[7], R[8], and R[9], at each occurrence, are independently selected from
hydrogen, fluoro, chloro, bromo, cyano, methyl, ethyl, propyl, isopropyl, butyl, t-butyl, nitro, trifluoromethyl, methoxy, ethoxy, isopropoxy, trifluoromethoxy, phenyl, benzyl,
HC(=O)—, methylC(=O)—, ethylC(=O)—, propylC(=O)—, isopropylC(=O)—, n-butylC(=O)—, isobutylC(=O)—, secbutylC(=O)—, tertbutylC(=O)—, phenylC(=O)—, methylC(=O)NH—, ethylC(=O)NH—, propylC(=O)NH—, isopropylC(=O)NH—, n-butylC(=O)NH—, isobutylC(=O)NH—, secbutylC(=O)NH—, tertbutylC(=O)NH—, phenylC(=O)NH—,
methylamino-, ethylamino-, propylamino-, isopropylamino-, n-butylamino-, isobutylamino-, secbutylamino-, tertbutylamino-, phenylamino-,
provided that two of substituents R[7], R[8], and R[9], are independently selected from hydrogen, fluoro, chloro, bromo, cyano, methyl, ethyl, propyl, isopropyl, butyl, t-butyl, nitro, trifluoromethyl, methoxy, ethoxy, isopropoxy, and trifluoromethoxy;
k is 1 or 2;
m is 1 or 2; and
n is 0, 1 or 2.

In a more preferred embodiment, the present invention provides the method as defined in claim 10 where the compound administered is a compound of Formula (V-a):

(V-a)

wherein:
b is a single bond, wherein the bridge hydrogens are in a cis position;
R[1] is selected from
—(CH$_2$)$_3$C(=O)(4-fluoro-phenyl),
—(CH$_2$)$_3$C(=O)(4-bromo-phenyl),
—(CH$_2$)$_3$C(=O)(4-methyl-phenyl),
—(CH$_2$)$_3$C(=O)(4-methoxy-phenyl),
—(CH$_2$)$_3$C(=O)(4-(3,4-dichloro-phenyl)phenyl),
—(CH$_2$)$_3$C(=O)(3-methyl-4-fluoro-phenyl),
—(CH$_2$)$_3$C(=O)(2,3-dimethoxy-phenyl),
—(CH$_2$)$_3$C(=O)(phenyl),
—(CH$_2$)$_3$C(=O)(4-chloro-phenyl),
—(CH$_2$)$_3$C(=O)(3-methyl-phenyl),
—(CH$_2$)$_3$C(=O)(4-t-butyl-phenyl),
—(CH$_2$)$_3$C(=O)(3,4-difluoro-phenyl),
—(CH$_2$)$_3$C(=O)(2-methoxy-5-fluoro-phenyl),
—(CH$_2$)$_3$C(=O)(4-fluoro-1-naphthyl),
—(CH$_2$)$_3$C(=O)(benzyl),
—(CH$_2$)$_3$C(=O)(4-pyridyl),
—(CH$_2$)$_3$C(=O)(3-pyridyl),
—(CH$_2$)$_3$CH(OH)(4-fluoro-phenyl),
—(CH$_2$)$_3$CH(OH)(4-pyridyl),
—(CH$_2$)$_3$CH(OH)(2,3-dimethoxy-phenyl),
—(CH$_2$)$_3$S(3-fluoro-phenyl),
—(CH$_2$)$_3$S(4-fluoro-phenyl),
—(CH$_2$)$_3$S(=O)(4-fluoro-phenyl),
—(CH$_2$)$_3$SO$_2$(3-fluoro-phenyl),
—(CH$_2$)$_3$SO$_2$(4-fluoro-phenyl),
—(CH$_2$)$_3$O(4-fluoro-phenyl),
—(CH$_2$)$_3$O(phenyl),
—(CH$_2$)$_3$NH(4-fluoro-phenyl),
—(CH$_2$)$_3$N(methyl)(4-fluoro-phenyl),
—(CH$_2$)$_3$CO$_2$(ethyl),
—(CH$_2$)$_3$C(=O)N(methyl)(methoxy),
—(CH$_2$)$_3$C(=O)NH(4-fluoro-phenyl),
—(CH$_2$)$_2$NHC(=O)(phenyl),
—(CH$_2$)$_2$NMeC(=O)(phenyl),
—(CH$_2$)$_2$NHC(=O)(2-fluoro-phenyl),
—(CH$_2$)$_2$NMeC(=O)(2-fluoro-phenyl),
—(CH$_2$)$_2$NHC(=O)(4-fluoro-phenyl),
—(CH$_2$)$_2$NMeC(=O)(4-fluoro-phenyl),
—(CH$_2$)$_2$NHC(=O)(2,4-difluoro-phenyl),
—(CH$_2$)$_2$NMeC(=O)(2,4-difluoro-phenyl),
—(CH$_2$)$_3$(3-indolyl),
—(CH$_2$)$_3$(1-methyl-3-indolyl),
—(CH$_2$)$_3$(1-indolyl),
—(CH$_2$)$_3$(1-indolinyl),
—(CH$_2$)$_3$(1-benzimidazolyl),
—(CH$_2$)$_3$(1H-1,2,3-benzotriazol-1-yl),
—(CH$_2$)$_3$(1H-1,2,3-benzotriazol-2-yl),
—(CH$_2$)$_2$(1H-1,2,3-benzotriazol-1-yl),
—(CH$_2$)$_2$(1H-1,2,3-benzotriazol-2-yl),
—(CH$_2$)$_3$(3,4 dihydro-1-(2H)-quinolinyl),
—(CH$_2$)$_2$C(=O)(4-fluoro-phenyl),
—(CH$_2$)$_2$C(=O)NH(4-fluoro-phenyl),
—CH$_2$CH$_2$(3-indolyl),
—CH$_2$CH$_2$(1-phthalimidyl),
—(CH$_2$)$_4$C(=O)N(methyl)(methoxy),
—(CH$_2$)$_4$CO$_2$(ethyl),
—(CH$_2$)$_4$C(=O)(phenyl),
—(CH$_2$)$_4$(cyclohexyl),
—(CH$_2$)$_3$CH(phenyl)$_2$,
—CH$_2$CH$_2$CH=C(phenyl)$_2$,
—CH$_2$CH$_2$CH=CMe(4-F-phenyl),
—(CH$_2$)$_3$CH(4-fluoro-phenyl)$_2$,
—CH$_2$CH$_2$CH=C(4-fluoro-phenyl)$_2$,
—(CH$_2$)$_2$(2,3-dihydro-1H-inden-2-yl),
—(CH$_2$)$_3$C(=O)(2-NH$_2$-phenyl),
—(CH$_2$)$_3$C(=O)(2-NH$_2$-5-F-phenyl),
—(CH$_2$)$_3$C(=O)(2-NH$_2$-4-F-phenyl),
—(CH$_2$)$_3$C(=O)(2-NH$_2$-3-F-phenyl),
—(CH$_2$)$_3$C(=O)(2-NH$_2$-4-Cl-phenyl),
—(CH$_2$)$_3$C(=O)(2-NH$_2$-4-OH-phenyl),
—(CH$_2$)$_3$C(=O)(2-NH$_2$-4-Br-phenyl),
—(CH$_2$)$_3$(1H-indazol-3-yl),
—(CH$_2$)$_3$(5-F-1H-indazol-3-yl),
—(CH$_2$)$_3$(7-F-1H-indazol-3-yl),
—(CH$_2$)$_3$(6-Cl-1-H-indazol-3-yl),
—(CH$_2$)$_3$(6-Br-1H-indazol-3-yl), —(CH$_2$)$_3$C(=O)(2-NHMe-phenyl),
—(CH$_2$)$_3$(1-benzothien-3-yl),
—(CH$_2$)$_3$(6-F-1H-indol-1-yl),
—(CH$_2$)$_3$(5-F-1H-indol-1-yl),
—(CH$_2$)$_3$(6-F-2,3-dihydro-1H-indol-1-yl),
—(CH$_2$)$_3$(5-F-2,3-dihydro-1H-indol-1-yl),
—(CH$_2$)$_3$(6-F-1H-indol-3-yl),
—(CH$_2$)$_3$(5-F-1H-indol-3-yl),
—(CH$_2$)$_3$(5-F-1H-indol-3-yl),
—(CH$_2$)$_3$(9H-purin-9-yl),
—(CH$_2$)$_3$(7H-purin-7-yl),
—(CH$_2$)$_3$(6-F-1H-indazol-3-yl),
—(CH$_2$)$_3$C(=O)(2-NHSO$_2$Me-4-F-phenyl),
—(CH$_2$)$_3$C(=O)(2-NHC(=O)Me-4-F-phenyl),
—(CH$_2$)$_3$C(=O)(2-NHC(=O)Me-4-F-phenyl),
—(CH$_2$)$_3$C(=O)(2-NHCO$_2$Et-4-F-phenyl),
—(CH$_2$)$_3$C(=O)(2-NHC(=O)NHEt-4-F-phenyl),
—(CH$_2$)$_3$C(=O)(2-NHCHO-4-F-phenyl),
—(CH$_2$)$_3$C(=O)(2-OH-4-F-phenyl),
—(CH$_2$)$_3$C(=O)(2-MeS-4-F-phenyl),
—(CH$_2$)$_3$C(=O)(2-NHSO$_2$Me-4-F-phenyl),
—(CH$_2$)$_2$C(Me)CO$_2$Me,
—(CH$_2$)$_2$C(Me)CH(OH)(4-F-phenyl)$_2$,
—(CH$_2$)$_2$C(Me)CH(OH)(4-Cl-phenyl)$_2$,
—(CH$_2$)$_2$C(Me)C(=O)(4-F-phenyl),
—(CH$_2$)$_2$C(Me)C(=O)(2-MeO-4-F-phenyl),
—(CH$_2$)$_2$C(Me)C(=O)(3-Me-4-F-phenyl),
—(CH$_2$)$_2$C(Me)C(=O)(2-Me-phenyl),
—(CH$_2$)$_2$C(Me)C(=O)phenyl,

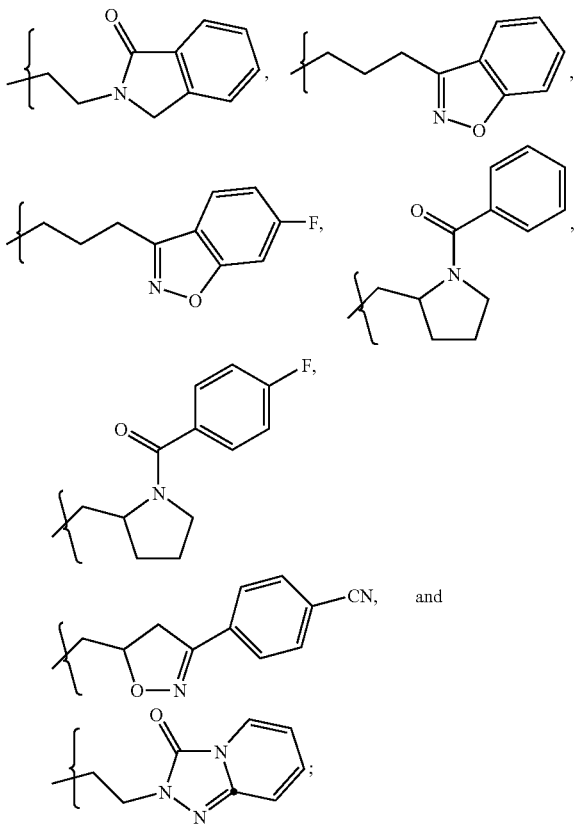

R$^7$, R$^8$, and R$^9$, at each occurrence, are independently selected from hydrogen, fluoro, chloro, bromo, cyano, methyl, ethyl, propyl, isopropyl, butyl, t-butyl, nitro, trifluoromethyl, methoxy, ethoxy, isopropoxy, trifluoromethoxy, methylC(=O)—, ethylC(=O)—, propylC(=O)—, isopropylC(=O)—, methylC(=O)NH—, ethylC(=O)NH—, propylC(=O)NH—, isopropylC(=O)NH, methylamino-, ethylamino-, propylamino-, and isopropylamino-, provided that two of substituents R$^7$, R$^8$, and R$^9$, are independently selected from hydrogen, fluoro, chloro, methyl, trifluoromethyl, methoxy, and trifluoromethoxy;

m is 1 or 2; and n is 0, 1 or 2.

In a more preferred embodiment, the present invention provides the method as defined in claim 1 where the compound administered is selected from the group:

(±)-cis-9-(cyclopropylcarbonyl)-4,5,6a,7,8,9,10,10a-octahydropyrido[4,3-b]pyrrolo[3,2,1-hi]indole;

(±)-cis-9-isobutyryl-4,5,6a,7,8,9,10,10a-octahydropyrido[4,3-b]pyrrolo[3,2,1-hi]indole;

tert-butyl(±)-cis-2-(2-chlorophenyl)-4,5,7,8,10,10a-hexahydropyrido[4,3-b]pyrrolo[3,2,1-hi]indole-9(6aH)-carboxylate;

tert-butyl(±)-cis-2-(2,4-dichlorophenyl)-4,5,7,8,10,10a-hexahydropyrido[4,3-b]pyrrolo[3,2,1-hi]indole-9(6aH)-carboxylate;

tert-butyl(±)-cis-2-(3,4-dichlorophenyl)-4,5,7,8,10,10a-hexahydropyrido[4,3-b]pyrrolo[3,2,1-hi]indole-9(6aH)-carboxylate;

tert-butyl(±)-cis-2-(2,3-dichlorophenyl)-4,5,7,8,10,10a-hexahydropyrido[4,3-b]pyrrolo[3,2,1-hi]indole-9(6aH)-carboxylate;

tert-butyl(±)-cis-2-[2-chloro-4-(trifluoromethyl)phenyl]-4,5,7,8,10,10a-hexahydropyrido[4,3-b]pyrrolo[3,2,1-hi]indole-9(6aH)-carboxylate;

tert-butyl(±)-cis-2-(2-chloro-4-methoxyphenyl)-4,5,7,8,10,10a-hexahydropyrido[4,3-b]pyrrolo[3,2,1-hi]indole-9(6aH)-carboxylate;

tert-butyl(±)-cis-2-(5-isopropyl-2-methoxyphenyl)-4,5,7,8,10,10a-hexahydropyrido[4,3-b]pyrrolo[3,2,1-hi]indole-9(6aH)-carboxylate;

tert-butyl(±)-cis-2-(3-fluorophenyl)-4,5,7,8,10,10a-hexahydropyrido[4,3-b]pyrrolo[3,2,1-hi]indole-9(6aH)-carboxylate;

tert-butyl(±)-cis-2-(2,4-dimethoxyphenyl)-4,5,7,8,10,10a-hexahydropyrido[4,3-b]pyrrolo[3,2,1-hi]indole-9(6aH)-carboxylate;

(±)-cis-2-(2-chlorophenyl)-4,5,6a,7,8,9,10,10a-octahydropyrido[4,3-b]pyrrolo[3,2,1-hi]indole;

(±)-cis-2-(2,4-dichlorophenyl)-4,5,6a,7,8,9,10,10a-octahydropyrido[4,3-b]pyrrolo[3,2,1-hi]indole;

(±)-cis-2-(3,4-dichlorophenyl)-4,5,6a,7,8,9,10,10a-octahydropyrido[4,3-b]pyrrolo[3,2,1-hi]indole;

(±)-cis-2-(2,3-dichlorophenyl)-4,5,6a,7,8,9,10,10a-octahydropyrido[4,3-b]pyrrolo[3,2,1-hi]indole;

(±)-cis-2-[2-chloro-4-(trifluoromethyl)phenyl]-4,5,6a,7,8,9,10,10a-octahydropyrido[4,3-b]pyrrolo[3,2,1-hi]indole;

(±)-cis-2-(2-chloro-4-methoxyphenyl)-4,5,6a,7,8,9,10,10a-octahydropyrido[4,3-b]pyrrolo[3,2,1-hi]indole;

(±)-cis-2-(4-isopropyl-2-methoxyphenyl)-4,5,6a,7,8,9,10,10a-octahydropyrido[4,3-b]pyrrolo[3,2,1-hi]indole;

(±)-cis-2-(3-fluorophenyl)-4,5,6a,7,8,9,10,10a-octahydropyrido[4,3-b]pyrrolo[3,2,1-hi]indole;

(±)-cis-2-(2,4-dimethoxyphenyl)-4,5,6a,7,8,9,10,10a-octahydropyrido[4,3-b]pyrrolo[3,2, 1-hi]indole;

tert-butyl(±)-cis-5,6,8,9,11,11a-hexahydro-4H-pyrido[3',4':4,5]pyrrolo[3,2,1-ij]quinoline-10(7aH)-carboxylate;

tert-butyl(±)-cis-2-bromo-5,6,8,9,11,11a-hexahydro-4H-py-rido[3',4':4,5]pyrrolo[3,2,1-ij]quinoline-10(7aH)-carboxylate;

tert-butyl(±)-cis-2-(2,3-dichlorophenyl)-5,6,8,9,11,11a-hexahydro-4H-pyrido[3',4':4,5]pyrrolo[3,2,1-ij]quinoline-10(7aH)-carboxylate;

tert-butyl(±)-cis-2-(3,4-dichlorophenyl)-5,6,8,9,11,11a-hexahydro-4H-pyrido[3',4':4,5]pyrrolo[3,2,1-ij]quinoline-10(7aH)-carboxylate;

tert-butyl(±)-cis-2-[2-chloro-4-(trifluoromethyl)phenyl]-5,6,8,9,11,11a-hexahydro-4H-pyrido[3',4':4,5]pyrrolo[3,2,1-ij]quinoline-10(7aH)-carboxylate;

(±)-cis-2-(2,3-dichlorophenyl)-5,6,6a,7,8,9,10,11,11a-octahydro-4H-pyrido[3',4':4,5]pyrrolo[3,2,1-ij]quinoline;

(±)-cis-2-(3,4-dichlorophenyl)-5,6,6a,7,8,9,10,11,11a-octahydro-4H-pyrido[3',4':4,5]pyrrolo[3,2,1-ij]quinoline;

(±)-cis-2-[2-chloro-4-(trifluoromethyl)phenyl]-5,6,6a,7,8,9,10,11,11a-octahydro-4H-pyrido[3',4':4,5]pyrrolo[3,2,1-ij]quinoline;

4-((±)-cis-2-(2-chlorophenyl)-4,5,7,8,10,10a-hexahydropyrido[4,3-b]pyrrolo[3,2,1-hi]indol-9(6aH)-yl)-1-(4-fluorophenyl)-1-butanone;

4-((±)-cis-2-(2,4-dichlorophenyl)-4,5,7,8,10,10a-hexahydropyrido[4,3-b]pyrrolo[3,2,1-hi]indol-9(6aH)-yl)-1-(4-fluorophenyl)-1-butanone;

4-((±)-cis-5,6,8,9,11,11a-hexahydro-4H-pyrido[3',4':4,5]pyrrolo[3,2,1-ij]qionolin-10(7aH)-yl)-1-(4-fluorophenyl)-1-butanone;

4-((±)-cis-4,5,7,8,10,10a-hexahydropyrido[4,3-b]pyrrolo[3,2,1-hi]indol-9(6aH)-yl)-1-(4-fluorophenyl)-1-butanone;

(6aS,10aR)-2-(2-fluoro-4-methoxyphenyl)-4,5,6a,7,8,9,10,10a-octahydropyrido[4,3-b]pyrrolo[3,2,1-hi]indole;

tert-butyl(6aS,10aR)-2-[4-ethoxy-2-(trifluoromethyl)phenyl]-4,5,7,8,10,10a-hexahydropyrido[4,3-b]pyrrolo[3,2,1-hi]indole-9(6aH)-carboxylate;

(6aS,10aR)-2-[4-ethoxy-2-(trifluoromethyl)phenyl]-4,5,6a,7,8,9,10,10a-octahydropyrido[4,3-b]pyrrolo[3,2,1-hi]indole;

tert-butyl(6aS,10aR)-2-(4-chloro-2-fluorophenyl)-4,5,7,8,10,10a-hexahydropyrido[4,3-b]pyrrolo[3,2,1-hi]indole-9(6aH)-carboxylate;

(6aS,10aR)-2-(4-chloro-2-fluorophenyl)-4,5,6a,7,8,9,10,10a-octahydropyrido[4,3-b]pyrrolo[3,2,1-hi]indole;

tert-butyl(6aS,10aR)-2-[4-isopropoxy-2-(trifluoromethyl)phenyl]-4,5,7,8,10,10a-hexahydropyrido[4,3-b]pyrrolo[3,2,1-hi]indole-9(6aH)-carboxylate;

(6aS,10aR)-2-[4-isopropoxy-2-(trifluoromethyl)phenyl]-4,5,6a,7,8,9,10,10a-octahydropyrido[4,3-b]pyrrolo[3,2,1-hi]indole;

tert-butyl(6aS,10aR)-2-[4-methoxy-2-(trifluoromethyl)phenyl]-4,5,7,8,10,10a-hexahydropyrido[4,3-b]pyrrolo[3,2,1-hi]indole-9(6aH)-carboxylate;

(6aS,10aR)-2-[4-methoxy-2-(trifluoromethyl)phenyl]-4,5,6a,7,8,9,10,10a-octahydropyrido[4,3-b]pyrrolo[3,2,1-hi]indole;

tert-butyl(6aS,10aR)-2-phenyl-4,5,7,8,10,10a-hexahydropyrido[4,3-b]pyrrolo[3,2,1-hi]indole-9(6aH)-carboxylate;

(6aS,10aR)-2-phenyl-4,5,6a,7,8,9,10,10a-octahydropyrido[4,3-b]pyrrolo[3,2,1-hi]indole;

tert-butyl(6aS,10aR)-2-(2-methylphenyl)-4,5,7,8,10,10a-hexahydropyrido[4,3-b]pyrrolo[3,2,1-hi]indole-9(6aH)-carboxylate;

(6aS,10aR)-2-(2-methylphenyl)-4,5,6a,7,8,9,10,10a-octahydropyrido[4,3-b]pyrrolo[3,2,1-hi]indole;

tert-butyl(6aS,10aR)-2-[2-(trifluoromethyl)phenyl]-4,5,7,8,10,10a-hexahydropyrido[4,3-b]pyrrolo[3,2,1-hi]indole-9(6aH)-carboxylate;

(6aS,10aR)-2-[2-(trifluoromethyl)phenyl]-4,5,6a,7,8,9,10,11α-octahydropyrido[4,3-b]pyrrolo[3,2,1-hi]indole;

tert-butyl(6aS,10aR)-2-(3,4-dimethoxyphenyl)-4,5,7,8,10,10a-hexahydropyrido[4,3-b]pyrrolo[3,2,1-hi]indole-9(6aH)-carboxylate;

(6aS,10aR)-2-(3,4-dimethoxyphenyl)-4,5,6a,7,8,9,10,10a-octahydropyrido[4,3-b]pyrrolo[3,2,1-hi]indole;

tert-butyl(6aS,10aR)-2-(2,5-dichlorophenyl)-4,5,7,8,10,10a-hexahydropyrido[4,3-b]pyrrolo[3,2,1-hi]indole-9(6aH)-carboxylate;

(6aS,10aR)-2-(2,5-dichlorophenyl)-4,5,6a,7,8,9,10,10a-octahydropyrido[4,3-b]pyrrolo[3,2,1-hi]indole;

tert-butyl(6aS,10aR)-2-(3,5-dichlorophenyl)-4,5,7,8,10,10a-hexahydropyrido[4,3-b]pyrrolo[3,2,1-hi]indole-9(6aH)-carboxylate;

(6aS,10aR)-2-(3,5-dichlorophenyl)-4,5,6a,7,8,9,10,10a-octahydropyrido[4,3-b]pyrrolo[3,2,1-hi]indole;

tert-butyl(6aS,10aR)-2-(2-isopropyl-4-methoxyphenyl)-4,5,7,8,10,10a-hexahydropyrido[4,3-b]pyrrolo[3,2,1-hi]indole-9(6aH)-carboxylate;

(6aS,10aR)-2-(2-isopropyl-4-methoxyphenyl)-4,5,6a,7,8,9,10,10a-octahydropyrido[4,3-b]pyrrolo[3,2,1-hi]indole;

tert-butyl(6aS,10aR)-2-(5-fluoro-4-methoxy-2-methylphenyl)-4,5,7,8,10,10a-hexahydropyrido[4,3-b]pyrrolo[3,2,1-hi]indole-9(6aH)-carboxylate;

(6aS,10aR)-2-(5-fluoro-4-methoxy-2-methylphenyl)-4,5,6a,7,8,9,10,10a-octahydropyrido[4,3-b]pyrrolo[3,2,1-hi]indole;

tert-butyl(6aS,10aR)-2-(4-methoxy-2-methylphenyl)-4,5,7,8,10,10a-hexahydropyrido[4,3-b]pyrrolo[3,2,1-hi]indole-9(6aH)-carboxylate;

(6aS,10aR)-2-(4-methoxy-2-methylphenyl)-4,5,6a,7,8,9,10,10a-octahydropyrido[4,3-b]pyrrolo[3,2,1-hi]indole;

tert-butyl(6aS,10aR)-2-(2-chloro-4-methoxyphenyl)-4,5,7,8,10,10a-hexahydropyrido[4,3-b]pyrrolo[3,2,1-hi]indole-9(6aH)-carboxylate;

(6aS,10aR)-2-(2-chloro-4-methoxyphenyl)-4,5,6a,7,8,9,10,10a-octahydropyrido[4,3-b]pyrrolo[3,2,1-hi]indole;

tert-butyl(6aS,10aR)-2-(3-chloro-2-methylphenyl)-4,5,7,8,10,10a-hexahydropyrido[4,3-b]pyrrolo[3,2,1-hi]indole-9(6aH)-carboxylate;

(6aS,10aR)-2-(3-chloro-2-methylphenyl)-4,5,6a,7,8,9,10,10a-octahydropyrido[4,3-b]pyrrolo[3,2,1-hi]indole;

2-[(6aS,10aR)-4,5,6a,7,8,9,10,10a-octahydropyrido[4,3-b]pyrrolo[3,2,1-hi]-2-yl]-5-methoxybenzaldehyde;

(6aS,10aR)-2-(2,6-dichlorophenyl)-4,5,6a,7,8,9,10,10a-octahydropyrido[4,3-b]pyrrolo[3,2,1-hi]indole;

N-[4-[(6aS,10aR)-4,5,6a,7,8,9,10,10a-octahydropyrido[4,3-b]pyrrolo[3,2,1-hi]indol-2-yl]-3-(trifluoromethyl)phenyl]-N-methylamine;

4-[(6aS,10aR)-4,5,6a,7,8,9,10,10a-octahydropyrido[4,3-b]pyrrolo[3,2,1-hi]indol-2-yl]-3-(trifluoromethyl)phenylamine;

1-(2-[(6aS,10aR)-4,5,6a,7,8,9,10,10a-octahydropyrido[4,3-b]pyrrolo[3,2,1-hi]indol-2-yl]-5-methoxyphenyl)ethanol;

tert-butyl(±)-cis-4,5,6,7,8a,9,10,11,12,12a-decahydroazepino[3,2,1-hi]pyrido[4,3-b]indole-11(8aH)-carboxylate;

tert-butyl(8aS,12aR)-2-bromo-4,5,6,7,8a,9,10,11,12,12a-decahydroazepino[3,2,1-hi]pyrido[4,3-b]indole-11(8aH)-carboxylate;

(8aS,12aR)-2-(2,4-dichlorophenyl)-4,5,6,7,8a,9,10,11,12,12a-decahydroazepino[3,2,1-hi]pyrido[4,3-b]indole;

(8aS,12aR)-2-(2,3-dichlorophenyl)-4,5,6,7,8a,9,10,11,12,12a-decahydroazepino[3,2,1-hi]pyrido[4,3-b]indole;

(8aS,12aR)-2-(3,4-dichlorophenyl)-4,5,6,7,8a,9,10,11,12,12a-decahydroazepino[3,2,1-hi]pyrido[4,3-b]indole;
(8aS,12aR)-2-(3,5-dichlorophenyl)-4,5,6,7,8a,9,10,11,12,12a-decahydroazepino[3,2,1-hi]pyrido[4,3-b]indole;
(8aS,12aR)-2-(2,5-dichlorophenyl)-4,5,6,7,8a,9,10,11,12,12a-decahydroazepino[3,2,1-hi]pyrido[4,3-b]indole;
(8aS,12aR)-2-(2,6-dichlorophenyl)-4,5,6,7,8a,9,10,11,12,12a-decahydroazepino[3,2,1-hi]pyrido[4,3-b]indole;
(8aS,12aR)-2-(2-chlorophenyl)-4,5,6,7,8a,9,10,11,12,12a-decahydroazepino[3,2,1-hi]pyrido[4,3-b]indole;
(8aS,12aR)-2-(3-chlorophenyl)-4,5,6,7,8a,9,10,11,12,12a-decahydroazepino[3,2,1-hi]pyrido[4,3-b]indole;
(8aS,12aR)-2-(4-chlorophenyl)-4,5,6,7,8a,9,10,11,12,12a-decahydroazepino[3,2,1-hi]pyrido[4,3-b]indole;
(±)-cis-2-(2,6-difluorophenyl)-4,5,6,7,8a,9,10,11,12,12a-decahydroazepino[3,2,1-hi]pyrido[4,3-b]indole;
(8aS,12aR)-2-(2,6-difluorophenyl)-4,5,6,7,8a,9,10,11,12,12a-decahydroazepino[3,2,1-hi]pyrido[4,3-b]indole;
(8aS,12aR)-2-(2,3-difluorophenyl)-4,5,6,7,8a,9,10,11,12,12a-decahydroazepino[3,2,1-hi]pyrido[4,3-b]indole;
(8aS,12aR)-2-(3,4-difluorophenyl)-4,5,6,7,8a,9,10,11,12,12a-decahydroazepino[3,2,1-hi]pyrido[4,3-b]indole;
(8aS,12aR)-2-(3-fluorophenyl)-4,5,6,7,8a,9,10,11,12,12a-decahydroazepino[3,2,1-hi]pyrido[4,3-b]indole;
(8aS,12aR)-2-[2-chloro-4-(trifluoromethyl)phenyl]-4,5,6,7,8a,9,10,11,12,12a-decahydroazepino[3,2,1-hi]pyrido[4,3-b]indole;
(8aS,12aR)-2-(2-chloro-4-methoxyphenyl)-4,5,6,7,8a,9,10,11,12,12a-decahydroazepino[3,2,1-hi]pyrido[4,3-b]indole;
(8aS,12aR)-2-(2-fluoro-4-methoxyphenyl)-4,5,6,7,8a,9,10,11,12,12a-decahydroazepino[3,2,1-hi]pyrido[4,3-b]indole;
(8aS,12aR)-2-(4-methoxy-2-methylphenyl)-4,5,6,7,8a,9,10,11,12,12a-decahydroazepino[3,2,1-hi]pyrido[4,3-b]indole;
(8aS,12aR)-2-[4-methoxy-2-(trifluoromethyl)phenyl]-4,5,6,7,8a,9,10,11,12,12a-decahydroazepino[3,2,1-hi]pyrido[4,3-b]indole;
(8aS,12aR)-2-[2-(trifluoromethyl)phenyl]-4,5,6,7,8a,9,10,11,12,12a-decahydroazepino[3,2,1-hi]pyrido[4,3-b]indole;
(8aS,12aR)-2-[4-isopropoxy-2-(trifluoromethyl)phenyl]-4,5,6,7,8a,9,10,11,12,12a-decahydroazepino[3,2,1-hi]pyrido[4,3-b]indole;
(8aS,12aR)-2-[2,4-bis(trifluoromethyl)phenyl]-4,5,6,7,8a,9,10,11,12,12a-decahydroazepino[3,2,1-hi]pyrido[4,3-b]indole;
(8aS,12aR)-2-[4-fluoro-2-(trifluoromethyl)phenyl]-4,5,6,7,8a,9,10,11,12,12a-decahydroazepino[3,2,1-hi]pyrido[4,3-b]indole;
4-[(8aS,12aR)-4,5,6,7,8a,9,10,11,12,12a-decahydroazepino[3,2,1-hi]pyrido[4,3-b]indol-2-yl]-3-(trifluoromethyl)aniline;
4-[(8aS,12aR)-4,5,6,7,8a,9,10,11,12,12a-decahydroazepino[3,2,1-hi]pyrido[4,3-b]indol-2-yl]-N-methyl-3-(trifluoromethyl)aniline;
2-[(8aS,12aR)-4,5,6,7,8a,9,10,11,12,12a-decahydroazepino[3,2,1-hi]pyrido[4,3-b]indol-2-yl]benzaldehyde;
{2-[(8aS,12aR)-4,5,6,7,8a,9,10,11,12,12a-decahydroazepino[3,2,1-hi]pyrido[4,3-b]indol-2-yl]phenyl}methanol;
2-[(8aS,12aR)-4,5,6,7,8a,9,10,11,12,12a-decahydroazepino[3,2,1-hi]pyrido[4,3-b]indol-2-yl]-5-methoxybenzaldehyde;
{2-[(8aS,12aR)-4,5,6,7,8a,9,10,11,12,12a-decahydroazepino[3,2,1-hi]pyrido[4,3-b]indol-2-yl]-5-methoxyphenyl}methanol;
4-[(8aS,12aR)-4,5,6,7,8a,9,10,11,12,12a-decahydroazepino[3,2,1-hi]pyrido[4,3-b]indol-2-yl]-3-methylbenzonitrile;
1-{2-[(8aS,12aR)-4,5,6,7,8a,9,10,11,12,12a-decahydroazepino[3,2,1-hi]pyrido[4,3-b]indol-2-yl]-5-methoxyphenyl}ethanol;
tert-butyl(7aS,11aR)-2-bromo-5,6,7a,8,9,10,11,11a-octahydro-4H-pyrido[3',4':4,5]pyrrolo[3,2,1-ij]quinoline-10(7aH)-carboxylate;
(7aS,11aR)-2-(2,4-dichlorophenyl)-5,6,7a,8,9,10,11,11a-octahydro-4H-pyrido[3',4':4,5]pyrrolo[3,2,1-ij]quinoline;
(7aS,11aR)-2-(3,4-dichlorophenyl)-5,6,7a,8,9,10,11,11a-octahydro-4H-pyrido[3',4':4,5]pyrrolo[3,2,1-ij]quinoline;
(7aS,11aR)-2-(3,5-dichlorophenyl)-5,6,7a,8,9,10,11,11a-octahydro-4H-pyrido[3',4':4,5]pyrrolo[3,2,1-ij]quinoline;
(7aS,11aR)-2-(2,5-dichlorophenyl)-5,6,7a,8,9,10,11,11a-octahydro-4H-pyrido[3',4':4,5]pyrrolo[3,2,1-ij]quinoline;
(7aS,11aR)-2-(2,6-dichlorophenyl)-5,6,7a,8,9,10,11,11a-octahydro-4H-pyrido[3',4':4,5]pyrrolo[3,2,1-ij]quinoline;
(7aS,11aR)-2-(2-chlorophenyl)-5,6,7a,8,9,10,11,11a-octahydro-4H-pyrido[3',4':4,5]pyrrolo[3,2,1-ij]quinoline;
(7aS,11aR)-2-(3-chlorophenyl)-5,6,7a,8,9,10,11,11a-octahydro-4H-pyrido[3',4':4,5]pyrrolo[3,2,1-ij]quinoline;
(7aS,11aR)-2-(4-chlorophenyl)-5,6,7a,8,9,10,11,11a-octahydro-4H-pyrido[3',4':4,5]pyrrolo[3,2,1-ij]quinoline;
(7aS,11aR)-2-(2,6-difluorophenyl)-5,6,7a,8,9,10,11,11a-octahydro-4H-pyrido[3',4':4,5]pyrrolo[3,2,1-ij]quinoline;
(7aS,11aR)-2-(2,6-difluorophenyl)-10-methyl-5,6,7a,8,9,10,11,11a-octahydro-4H-pyrido[3',4':4,5]pyrrolo[3,2,1-ij]quinoline;
(7aS,11aR)-2-(2,3-difluorophenyl)-5,6,7a,8,9,10,11,11a-octahydro-4H-pyrido[3',4':4,5]pyrrolo[3,2,1-ij]quinoline;
(7aS,11aR)-2-(3,4-difluorophenyl)-5,6,7a,8,9,10,11,11a-octahydro-4H-pyrido[3',4':4,5]pyrrolo[3,2,1-ij]quinoline;
(7aS,11aR)-2-(3-fluorophenyl)-5,6,7a,8,9,10,11,11a-octahydro-4H-pyrido[3',4':4,5]pyrrolo[3,2,1-ij]quinoline;
(7aS,11aR)-2-[2-chloro-4-methoxyphenyl)-5,6,7a,8,9,10,11,11a-octahydro-4H-pyrido[3',4':4,5]pyrrolo[3,2,1-ij]quinoline;
(7aS,11aR)-2-[2-fluoro-4-methoxyphenyl)-5,6,7a,8,9,10,11,11a-octahydro-4H-pyrido[3',4':4,5]pyrrolo[3,2,1-ij]quinoline;
(7aS,11aR)-2-(4-methoxy-2-methylphenyl)-5,6,7a,8,9,10,11,11a-octahydro-4H-pyrido[3',4':4,5]pyrrolo[3,2,1-yl]quinoline;
(7aS,11aR)-2-[4-methoxy-2-(trifluoromethyl)phenyl]-5,6,7a,8,9,10,11,11a-octahydro-4H-pyrido[3',4':4,5]pyrrolo[3,2,1-ij]quinoline;
4-[(7aS,11aR)-5,6,7a,8,9,10,11,11a-octahydro-4H-pyrido[3',4':4,5]pyrrolo[3,2,1-ij]quinolin-2-yl]-3-(trifluoromethyl)phenol;
(7aS,11aR)-2-[2-(trifluoromethyl)phenyl]-5,6,7a,8,9,10,11,11a-octahydro-4H-pyrido[3',4':4,5]pyrrolo[3,2,1-ij]quinoline;
(7aS,11aR)-2-[4-isopropoxy-2-(trifluoromethyl)phenyl]-5,6,7a,8,9,10,11,11a-octahydro-4H-pyrido[3',4':4,5]pyrrolo[3,2,1-ij]quinoline;
(7aS,11aR)-2-[2,4-bis(trifluoromethyl)phenyl]-5,6,7a,8,9,10,11,11a-octahydro-4H-pyrido[3',4':4,5]pyrrolo[3,2,1-ij]quinoline;
(7aS,11aR)-2-[4-fluoro-2-(trifluoromethyl)phenyl]-5,6,7a,8,9,10,11,11a-octahydro-4H-pyrido[3',2,1-ij]quinoline;
4-[(7aS,11aR)-5,6,7a,8,9,10,11,11a-octahydro-4H-pyrido[3',4':4,5]pyrrolo[3,2,1-ij]quinolin-2-yl]-3-(trifluoromethyl)aniline;

4-[(7aS,11aR)-5,6,7a,8,9,10,11,11a-octahydro-4H-pyrido[3',4':4,5]pyrrolo[3,2,1-ij]quinolin-2-yl]-N-methyl-3-(trifluoromethyl)aniline;

4-[(7aS,11aR)-5,6,7a,8,9,10,11,11a-octahydro-4H-pyrido[3',4':4,5]pyrrolo[3,2,1-ij]quinolin-2-yl]-3-methylbenzonitrile;

2-[(7aS,11aR)-5,6,7a,8,9,10,11,11a-octahydro-4H-pyrido[3',4':4,5]pyrrolo[3,2,1-ij]quinolin-2-yl]benzaldehyde;

{2-[(7aS,11aR)-5,6,7a,8,9,10,11,11a-octahydro-4H-pyrido[3',4':4,5]pyrrolo[3,2,1-ij]quinolin-2-yl]phenyl}methanol;

2-[(7aS,11aR)-5,6,7a,8,9,10,11,11a-octahydro-4H-pyrido[3',4':4,5]pyrrolo[3,2,1-ij]quinolin-2-yl]-5-methoxybenzaldehyde;

{2-[(7aS,11aR)-5,6,7a,8,9,10,11,11a-octahydro-4H-pyrido[3',4':4,5]pyrrolo[3,2,1-ij]quinolin-2-yl]-5-methoxyphenyl}methanol;

(8aS,12aR)-2-[4-ethoxy-2-(trifluoromethyl)phenyl]-4,5,6,7,8a,9,10,11,12,12a-decahydroazepino[3,2,1-hi]pyrido[4,3b]indole;

(7aS,11aR)-2-[4-ethoxy-2-(trifluoromethyl)phenyl]-5,6,7a,8,9,10,11,11a-octahydro-4H-pyrido[3',4':4,5]pyrrolo[3,2,1-ij]quinoline;

(8aS,12aR)-2-[3-chloro-2-methylphenyl]-4,5,6,7,8a,9,10,11,12,12a-decahydroazepino[3,2,1-hi]pyrido[4,3b]indole;

(7aS,11aR)-2-[3-chloro-2-methylphenyl]-5,6,7a,8,9,10,11,11a-octahydro-4H-pyrido[3',4':4,5]pyrrolo[3,2,1-ij]quinoline;

(7aS,11aR)-2-[5-fluoro-2-methylphenyl]-5,6,7a,8,9,10,11,11a-octahydro-4H-pyrido[3',4':4,5]pyrrolo[3,2,1-ij]quinoline;

(±)-cis-2-(2,3-dichlorophenyl)-10-propyl-5,6,7a,8,9,10,11,11a-octahydro-4H-pyrido[3',4':4,5]pyrrolo[3,2,1-ij]quinoline;

(7aS,11aR)-2-(2,3-dichlorophenyl)-10-propyl-5,6,7a,8,9,10,11,11a-octahydro-4H-pyrido[3',4':4,5]pyrrolo[3,2,1-ij]quinoline (±)-cis-10-butyl-2-(2,3-dichlorophenyl)-5,6,7a,8,9,10,11,11a-octahydro-4H-pyrido[3',4':4,5]pyrrolo[3,2,1-ij]quinoline;

(7aS,11aR)-10-butyl-2-(2,3-dichlorophenyl)-5,6,7a,8,9,10,11,11a-octahydro-4H-pyrido[3',4':4,5]pyrrolo[3,2,1-ij]quinoline;

(7aS,11aR)-2-(2,3-dichlorophenyl)-10-(4-pentenyl)-5,6,7a,8,9,10,11,11a-octahydro-4H-pyrido[3',4':4,5]pyrrolo[3,2,1-ij]quinoline;

(7aS,11aR)-2-(2,3-dichlorophenyl)-10-(3-methyl-2-butenyl)-5,6,7a,8,9,10,11,11a-octahydro-4H-pyrido[3',4':4,5]pyrrolo[3,2,1-ij]quinoline;

(7aS,11aR)-2-(2,4-dichlorophenyl)-10-propyl-5,6,7a,8,9,10,11,11a-octahydro-4H-pyrido[3',4':4,5]pyrrolo[3,2,1-ij]quinoline;

(7aS,11aR)-10-butyl-2-(2,4-dichlorophenyl)-5,6,7a,8,9,10,11,11a-octahydro-4H-pyrido[3',4':4,5]pyrrolo[3,2,1-ij]quinoline;

(7aS,11aR)-2-(2,4-dichlorophenyl)-10-(4-pentenyl)-5,6,7a,8,9,10,11,11a-octahydro-4H-pyrido[3',4':4,5]pyrrolo[3,2,1-ij]quinoline (7aS,11aR)-2-(2,4-dichlorophenyl)-10-(3-methyl-2-butenyl)-5,6,7a,8,9,10,11,11a-octahydro-4H-pyrido[3',4':4,5]pyrrolo[3,2,1-ij]quinoline;

(7aS,11aR)-10-(cyclobutylmethyl)-2-(2,3-dichlorophenyl)-5,6,7a,8,9,10,11,11a-octahydro-4H-pyrido[3',4':4,5]pyrrolo[3,2,1-ij]quinoline;

(7aS,11aR)-2-[4-methoxy-2-(trifluoromethyl)phenyl]-10-methyl-5,6,7a,8,9,10,11,11a-octahydro-4H-pyrido[3',4':4,5]pyrrolo[3,2,1-ij]quinoline;

(7aS,11aR)-10-ethyl-2-[4-methoxy-2-(trifluoromethyl)phenyl]-5,6,7a,8,9,10,11,11a-octahydro-4H-pyrido[3',4':4,5]pyrrolo[3,2,1-ij]quinoline;

(7aS,11aR)-2-[4-methoxy-2-(trifluoromethyl)phenyl]-10-propyl-5,6,7a,8,9,10,11,11a-octahydro-4H-pyrido[3',4':4,5]pyrrolo[3,2,1-ij]quinoline;

(7aS,11aR)-10-butyl-2-[4-methoxy-2-(trifluoromethyl)phenyl]-10-methyl-5,6,7a,8,9,10,11,11a-octahydro-4H-pyrido[3',4':4,5]pyrrolo[3,2,1-ij]quinoline;

(7aS,11aR)-2-[4-methoxy-2-(trifluoromethyl)phenyl]-10-(4-pentenyl)-5,6,7a,8,9,10,11,11a-octahydro-4H-pyrido[3',4':4,5]pyrrolo[3,2,1-ij]quinoline;

(7aS,11aR)-2-[4-methoxy-2-(trifluoromethyl)phenyl]-10-(3-methyl-2-butenyl)-5,6,7a,8,9,10,11,11a-octahydro-4H-pyrido[3',4':4,5]pyrrolo[3,2,1-ij]quinoline;

(7aS,11aR)-10-(2-fluoroethyl)-2-[4-methoxy-2-(trifluoromethyl)phenyl]-5,6,7a,8,9,10,11,11a-octahydro-4H-pyrido[3',4':4,5]pyrrolo[3,2,1-ij]quinoline;

(7aS,11aR)-10-(2,2-difluoroethyl)-2-[4-methoxy-2-(trifluoromethyl)phenyl]-5,6,7a,8,9,10,11,11a-octahydro-4H-pyrido[3',4':4,5]pyrrolo[3,2,1-ij]quinoline;

(7aS,11aR)-10-(cyclobutylmethyl)-2-[4-methoxy-2-(trifluoromethyl)phenyl]-5,6,7a,8,9,10,11,11a-octahydro-4H-pyrido[3',4':4,5]pyrrolo[3,2,1-ij]quinoline;

4-((7aS,11aR)-5,6,8,9,11,11a-hexahydro-4H-pyrido[3',4':4,5]pyrrolo[3,2,1-ij]quinolin-10(7aH)-yl)-1-(4-fluorophenyl)-1-butanone;

4-((7aR,11aS)-5,6,8,9,11,11a-hexahydro-4H-pyrido[3',4':4,5]pyrrolo[3,2,1-ij]quinolin-10(7aH)-yl)-1-(4-fluorophenyl)-1-butanone;

4-((7aS,11aR)-5,6,8,9,11,11a-hexahydro-4H-pyrido[3',4':4,5]pyrrolo[3,2,1-ij]quinolin-10(7aH)-yl)-1-(2-aminophenyl)-1-butanone;

4-((7aR,11aS)-5,6,8,9,11,11a-hexahydro-4H-pyrido[3',4':4,5]pyrrolo[3,2,1-ij]quinolin-10(7aH)-yl)-1-(2-aminophenyl)-1-butanone;

(±)-cis-3-(5,6,8,9,11,11a-hexahydro-4H-pyrido[3',4':4,5]pyrrolo[3,2,1-ij]quinolin-10(7aH)-yl)propyl 4-fluorophenyl ether;

4-((±)-cis-5,6,8,9,11,11a-hexahydro-4H-pyrido[3',4':4,5]pyrrolo[3,2,1-ij]quinolin-10(7aH)-yl)-1-(4-pyridinyl)-1-butanone;

(±)-cis-10-[3-(6-fluoro-1,2-benzisoxazol-3-yl)propyl]-5,6,7a,8,9,10,11-octahydro-4H-pyrido[3',4':4,5]pyrrolo[3,2,1-ij]quinoline;

(7aS,11aR)-10-[3-(6-fluoro-1,2-benzisoxazol-3-yl)propyl]-5,6,7a,8,9,10,11,11a-octahydro-4H-pyrido[3',4':4,5]pyrrolo[3,2,1-ij]quinoline;

(±)-cis-4-(4,5,6,7,9,10,12,12a-octahydroazepino[3,2,1-hi]pyrido[4,3-b]indol-11(8aH)-yl)-1-(4-fluorophenyl)-1-butanone;

4-((8aS,12aR)4,5,6,7,9,10,12,12a-octahydroazepino[3,2,1-hi]pyrido[4,3-b]indol-11(8aH)-yl)-1-(4-fluorophenyl)-1-butanone;

4-((8aR,12aS-4, 5,6,7,9,10,12,12a-octahydroazepino[3,2,1-hi]pyrido[4,3-b]indol-11(8aH)-yl)-1-(4-fluorophenyl)-1-butanone;

4-((±)-4,5,6,7,9,10,12,12a-octahydroazepino[3,2,1-hi]pyrido[4,3-b]indol-11(8aH)-yl)-1-(2-amino-4-fluorophenyl)-1-butanone;

4-((±)-cis-5,6,8,9,11,11a-hexahydro-4H-pyrido[3',4':4,5]pyrrolo[3,2,1-ij]quinolin-10(7aH)-yl)-1-(2-amino-4-fluorophenyl)-1-butanone;

4-((7aS,11aR)-5,6,8,9,11,11a-hexahydro-4H-pyrido[3',4':4,5]pyrrolo[3,2,1-ij]quinolin-10(7aH)-yl)-1-(2-amino-4-fluorophenyl)-1-butanone; and
4-((7aR,11aS)-5,6,8,9,11,11a-hexahydro-4H-pyrido[3',4':4,5]pyrrolo[3,2,1-ij]quinolin-10(7aH)-yl)-1-(2-amino-4-fluorophenyl)-1-butanone.

In a more preferred embodiment, the present invention provides the method as defined in claim 1 where the compound administered is selected from the group:
4-[(±)-5,6,8,9,10,11,12,12a-octahydro-4H,7aH-azepino[4',5':4,5]pyrrolo[3,2,1-ij]quinolin-10-yl]-1-(4-fluorophenyl)-1-butanone;
4-[(±)-5,6,8,9,10,11,12,12a-octahydro-4H,7aH-azepino[4',5':4,5]pyrrolo[3,2,1-ij]quinolin-10-yl]-1-(2-amino-4-fluorophenyl)-1-butanone;
4-[(±)-4,5,6,7,9,10,11,12,13,13a-decahydro-11H-diazepino[4,5-b:3,2,1-hi]indol-11-yl]-1-(4-fluorophenyl)-1-butanone;
4-[(±)-4,5,6,7,9,10,11,12,13,13a-decahydro-1H-diazepino[4,5-b:3,2,1-hi]indol-11-yl]-1-(2-amino-4-fluorophenyl)-1-butanone;
tert-butyl(±)-cis-5,6,8,9,10,11,12,12a-octahydro-4H,7aH-azepino[3',4':4,5]pyrrolo[3,2,1-ij]quinoline-11-carboxylate;
tert-butyl(±)-cis-2-bromo-5,6,8,9,10,11,12,12a-octahydro-4H,7aH-azepino[3',4':4,5]pyrrolo[3,2,1-ij]quinoline-11-carboxylate; and
(±)-cis-2-[4-methoxy-2-(trifluoromethyl)phenyl]-5,6,8,9,10,11,12,12a-octahydro-4H,7aH-azepino[3',4':4,5]pyrrolo[3,2,1-ij]quinoline.

In a more preferred embodiment, the present invention provides the method as defined in claim 1 where the compound administered is selected from the group:
tert-butyl(±)-cis-2-bromo-4-oxo-4,5,6,7,9,10,12,12a-octahydroazepino[3,2,1-hi]pyrido[4,3-b]indole-11(8aH)-carboxylate;
tert-butyl(±)-cis-2-(2,4-dichlorophenyl)-4-oxo-4,5,6,7,9,10,12,12a-octahydroazepino[3,2,1-hi]pyrido[4,3-b]indole-11(8aH)-carboxylate;
(±)-cis-2-(2,4-dichlorophenyl)-6,7,8a,9,10,11,12,12a-octahydroazepino[3,2,1-hi]pyrido[4,3-b]indol-4(5H)-one;
(8aS,12aR)-2-(2,4-dichlorophenyl)-6,7,8a,9,10,11,12,12a-octahydroazepino[3,2,1-hi]pyrido[4,3-b]indol-4(5H)-one;
(8aR,12aS)-2-(2,4-dichlorophenyl)-6,7,8a,9,10,11,12,12a-octahydroazepino[3,2,1-hi]pyrido[4,3-b]indol-4(5H)-one;
(8aS,12aR)-2-(2,4-dichlorophenyl)-6,7,8a,9,10,11,12,12a-decahydroazepino[3,2,1-hi]pyrido[4,3-b]indol-4-ol; and
(8aR,12aS)-2-(2,4-dichlorophenyl)-6,7,8a,9,10,11,12,12a-decahydroazepino[3,2,1-hi]pyrido[4,3-b]indol-4-ol.

DEFINITIONS

As used herein, the term "addictive behavior" includes behaviors associated with and/or caused by physical and/or psychological dependence on narcotics, opiates, analgesics, painkillers, amphetamines, cocaine, heroin, opium, marijuana, alcohol, smoking, nicotine, gambling and eating.

The term "sleep disorders," as used herein, includes insomnia, narcolepsy and sleep apnea.

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. C is and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The numbering of the tetracyclic ring-system present in the compounds of Formula (I), as defined by nomenclature known to one skilled in the art, is shown for two examples in Formula (I'), when k is 1, m is 1, and n is 1; and in Formula (I"), when k is 1, m is 1, and n is 2:

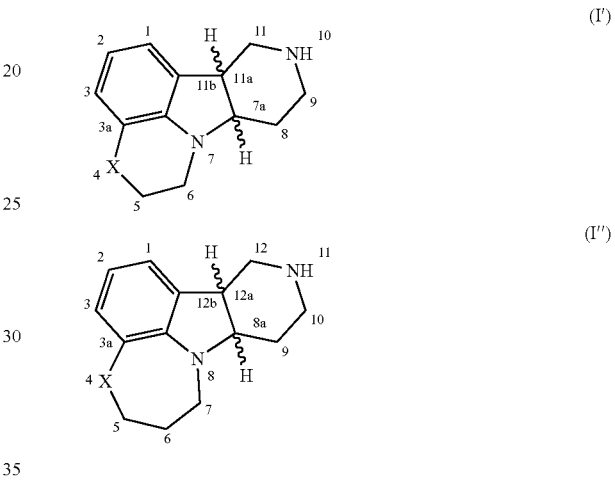

The tetracyclic ring-system present in compounds of Formula (I) occur as "cis" or "trans" isomers when the carbon-carbon bond b in Formula (I) is a single bond. As such, the terms "cis" and "trans", in conjunction with the tetracyclic ring structure, refer to the configuration of hydrogen atoms on carbon atoms 7a and 11 a in Formula (I') or, for example, on carbon atoms 8a and 12a in Formula (I"), above. When both hydrogens are on the same side of the mean plane determined by the octahydro tetracyclic moiety then the configuration is designated "cis", if not, the configuration is designated "trans". It is understood that the above example is for demonstrative puproses only and not intended to limit the scope of the tetracyclic ring-system present in compounds of Formula (I). As such, it is understood that one skilled in the art of organic chemistry can apply the above numbering system to other values of k, m, and n in the scope of compounds of Formula (I) to deterine the appropriate numbering. Additional Examples of the numbering of the tetracyclic ring-system are further provided below in the synthetic Examples. Lastly, it is understood that the use of "cis" or "trans" in the identification of the tetracyclic ring-system is not meant to construe the configuration of any other cis or trans geometric isomer in the molecule, for example, cis or trans butene.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced.

When any variable (e.g., $R^2$) occurs more than one time in any constituent or formula for a compound, its definition at each occurrence is independent of its definition at every other occurrence. Thus, for example, if a group is shown to be substituted with 0–2 $R^2$, then said group may optionally be substituted with up to two $R^2$ groups and $R^2$ at each occurrence is selected independently from the definition of $R^2$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms; for example, "$C_1$–$C_6$ alkyl" denotes alkyl having 1 to 6 carbon atoms. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

"Alkenyl" or "alkenylene" is intended to include hydrocarbon chains of either a straight or branched configuration having the specified number of carbon atoms and one or more unsaturated carbon-carbon bonds which may occur in any stable point along the chain. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either a straight or branched configuration and one or more carbon-carbon triple bonds which may occur in any stable point along the chain, such as ethynyl, propynyl, butynyl, pentynyl, hexynyl and the like.

"Cycloalkyl" is intended to include saturated ring groups, having the specified number of carbon atoms. For example, "$C_3$–$C_6$ cycloalkyl" denotes such as cyclopropyl, cyclobutyl, cyclopentyl, or cyclohexyl.

"Alkoxy" or "alkyloxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Similarly, "alkylthio" is represents an alkyl group as defined above with the indicated number of carbon atoms attached through a sulpher bridge.

"Halo" or "halogen" as used herein refers to fluoro, chloro, bromo, and iodo; and "counterion" is used to represent a small, negatively charged species such as chloride, bromide, hydroxide, acetate, sulfate, and the like.

"Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, pentachloroethyl, 2,2,2-trifluoroethyl, heptafluoropropyl, and heptachloropropyl.

As used herein, "carbocycle" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic ring" is intended to mean a stable 5- to 7-membered monocyclic or bicyclic or 7- to 14-membered bicyclic heterocyclic ring which is saturated partially unsaturated or unsaturated (aromatic), and which consists of carbon atoms and 1, 2, 3 or 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, imidazolopyridinyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolopyridinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thiazolopyridinyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Preferred heterocycles include, but are not limited to, pyridinyl, furanyl, thienyl, pyrrolyl, pyrazolyl, pyrazinyl, piperazinyl, imidazolyl, indolyl, benzimidazolyl, 1H-indazolyl, oxazolidinyl, benzotriazolyl, benzisoxazolyl, benzoxazolyl, oxindolyl, benzoxazolinyl, benzthiazolyl, benzisothiazolyl, isatinoyl, isoxazolopyridinyl, isothiazolopyridinyl, thiazolopyridinyl, oxazolopyridinyl, imidazolopyridinyl, and pyrazolopyridinyl. Preferred 5 to 6 membered heterocycles include, but are not limited to, pyridinyl, furanyl, thienyl, pyrrolyl, pyrazolyl, pyrazinyl, piperazinyl, imidazolyl, and oxazolidinyl. Also included are fused ring and spiro compounds containing, for example, the above heterocycles.

As used herein, the term "bicyclic heterocyclic ring system" is intended to mean a stable 9- to 10-membered bicyclic heterocyclic ring formed from the substituent $NR^{12}R^{13}$, which is partially unsaturated or unsaturated (aromatic), and which consists of carbon atoms, a nitrogen atom, and 1 or 2 additional heteroatoms independently selected from the group consisting of N, O and S. The additional nitrogen or sulfur heteroatoms may optionally be oxidized. The heterocyclic ring is attached to its pendant group by the nitrogen atom of the group $NR^{12}R^{13}$ and for which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. The term "bicyclic heterocyclic ring system" is intended to be a subset of the term "heterocyclic ring system". Preferred examples of a 9- to 10-membered bicyclic heterocyclic ring system are benzimidazolyl, benzimidazolinyl, benzoxazolinyl, dihydrobenzthiazolyl, dihydrodioxobenzthiazolyl, benzisoxazolinyl, 1H-indazolyl, indolyl, indolinyl, isoindolinyl, tetrahydro-isoquinolinyl, tetrahydro-quinolinyl, and benzotriazolyl.

Additionally, a subclass of preferred heterocycles are heterocycles which function as an isostere of a cyclic but non-heterocyclic substituent such as —$CH_2$—C(=O)-phenyl. Preferred examples of such heterocycles include, but are not limited to, benzimidazolyl, benzofuranyl, benzothiophenyl, benzoxazolyl, benzthiazolyl, benzisoxazolyl, furanyl, imidazolinyl, 1H-indazolyl, indolinyl, isoindolinyl, isoquinolinyl, oxazolyl, piperidinyl, pyrazinyl, pyridinyl, pyrimidinyl, quinolinyl, thiazolyl, thiophenyl, and 1,2,3-triazolyl.

As used herein, the term "aryl", or aromatic residue, is intended to mean an aromatic moiety containing the specified number of carbon atoms, such as phenyl, pyridinyl and naphthyl.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base formns of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

"Prodrugs" are intended to include any covalently bonded carriers which release the active parent drug according to formula (I) in vivo when such prodrug is administered to a mammalian subject. Prodrugs of a compound of formula (I) are prepared by modifying functional groups present in the compound in such a way that the modifications are cleaved, either in routine manipulation or in vivo, to the parent compound. Prodrugs include compounds of formula (I) wherein a hydroxy, amino, or sulfhydryl group is bonded to any group that, when the prodrug or compound of formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of Formula (I), and the like.

"Stable compound" and "stable structure" are meant to indicate a compound that is sufficiently robust to survive isolation to a useful degree of purity from a reaction mixture, and formulation into an efficacious therapeutic agent.

Synthesis

Throughout the details of the invention, the following abbreviations are used with the following meanings:

Reagents:

| | |
|---|---|
| MCPBA | m-chcloroperoxybenzoic acid |
| DIBAL | diisobutyl aluminum hydride |
| $Et_3N$ | triethylamine |
| TFA | trifluoroacetic acid |
| LAH | lithium aluminum hydride |
| NBS | N-bromo succinimide |
| Red-Al | Sodium bis(2-methoxyethoxy)aluminum hydride |
| $Pd_2dba_3$ | Tris(dibenzylideneacetone)dipalladium(0) |
| ACE-Cl | 2-chloroethylchloroformate |

Solvents:

| | |
|---|---|
| THF | tetrahydrofuran |
| MeOH | methanol |
| EtOH | ethanol |
| EtOAc | ethyl acetate |
| HOAc | acetic acid |
| DMF | dimethyl formamide |
| DMSO | dimethyl sulfoxide |

-continued

| | |
|---|---|
| DME | dimethoxyethane |
| Et₂O | diethylether |
| iPrOH | isopropanol |
| MEK | methyl ethyl ketone |
| Others: | |
| | |
| Ar | aryl |
| Ph | phenyl |
| Me | methyl |
| Et | ethyl |
| NMR | nuclear magnetic resonance |
| MHz | megahertz |
| BOC | tert-butoxycarbonyl |
| CBZ | benzyloxycarbonyl |
| Bn | benzyl |
| Bu | butyl |
| Pr | propyl |
| cat. | catalytic |
| mL | milliliter |
| nM | nanometer |
| ppm | part per million |
| mmol | millimole |
| mg | milligram |
| g | gram |
| kg | kilogram |
| TLC | thin layer chromatography |
| HPLC | high pressure liquid chromatography |
| RPM | revolutions per minute |
| rt | room temperature |
| aq. | aqueous |
| sat. | saturated |

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

The preparation of compounds of Formula (I) of the present invention may be carried out in a convergent or sequential synthetic manner. Detailed synthetic preparations of the compounds of Formula (I) are shown in the following reaction schemes. The skills required in preparation and purification of the compounds of Formula (I) and the intermediates leading to these compounds are known to those in the art. Purification procedures include, but are not limited to, normal or reverse phase chromatography, crystallization, and distillation.

Several methods for the preparation of the compounds of the present invention are illustrated in the schemes and examples shown below. The substitutions are as described and defined above.

Compounds of Formula (I) of this invention may be prepared as shown in Scheme 1. Thus, preparation of an aryl hydrazine (III) is accomplished, for example, by treatment of a corresponding substituted aniline (II) with $NaNO_2$ followed by reduction of the N-nitroso intermediate with a reducing agent such as LAH or zinc and an organic acid, such as acetic acid or trifluoroacetic acid at low temperature. Assembly of the core tetracyclic intermediate indole (V) is accomplished by Fischer indole cyclization of the aryl hydrazine and a suitably substituted ketone (i.e. (IV)) by methods described by, but not limited to, R. J. Sundberg, "Indoles, Best Synthetic Methods" 1996, Academic Press, San Diego, Calif. For example, treatment of the aryl hydrazine (III) as the free base or the corresponding mineral acid salt with the ketone (IV) ($R^1$=H, Bn, CBZ, $CO_2Et$, etc) in an alcoholic solvent in the presence of mineral acid affords the indoles (V) as the free bases (after treatment with aq. NaOH). Reduction of the indoles to the corresponding cis or trans substituted dihydroindoles is accomplished by, for example, treatment with hydrogen in the presence of a catalyst such as platinum oxide or palladium on carbon, or with a metal such as zinc and a mineral acid such as hydrochloric acid, or with sodium and liquid ammonia, or with borane-amine complex such as borane-triethylamine in tetrahydofuran, or preferably by treatment with $NaCNBH_3$ in an acid such as acetic or trifluoroacetic acid.

The corresponding enantiomers can be isolated by separation of the racemic mixture of (I) on a chiral stationary phase column utilizing normal or reverse phase HPLC techniques, the details of which are described in the examples. Alternatively, a diastereomeric mixture of (I) can be prepared by treatment of (I, $R^1$=H) with an appropriate chiral acid (or suitably activated derivative), for example dibenzoyl tartrate or the like (see, for example, Kinbara, K., et. al., *J. Chem. Soc., Perkin Trans.* 2, 1996, 2615; and Tomori, H., et. al., *Bull. Chem. Soc. Jpn.,* 1996, 3581). The diastereomers would then be separated by traditional techniques (i.e. silica chromatography, crystallization, HPLC, etc) followed by removal of the chiral auxiliary to afford enantiomerically pure (I).

In the cases where the carboline nitrogen has been protected (VI) (i.e. $R^1$=Boc, Bn, CBZ, $CO_2R$), it may be removed under a variety of conditions as described in Greene, T. W., Wuts, P. G. W., "Protective Groups in Organic Synthesis, 2nd Edition", John Wiley and Sons, Inc., New York, pages 309–405, 1991. The free secondary amine could then be alkylated, for example, by treatment with a suitably substituted alkyl halide ($R^1Cl$, or $R^1I$) and a base to afford additional compounds of type (I), as described, for example, by Glennon, R. A., et. al., *Med. Chem. Res.,* 1996, 197.

SCHEME 1

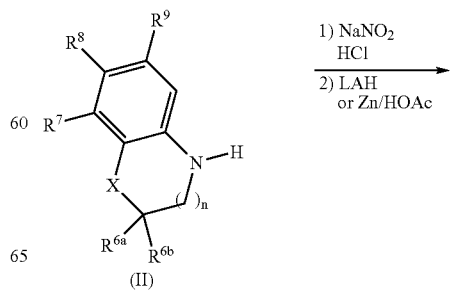

(II)

-continued

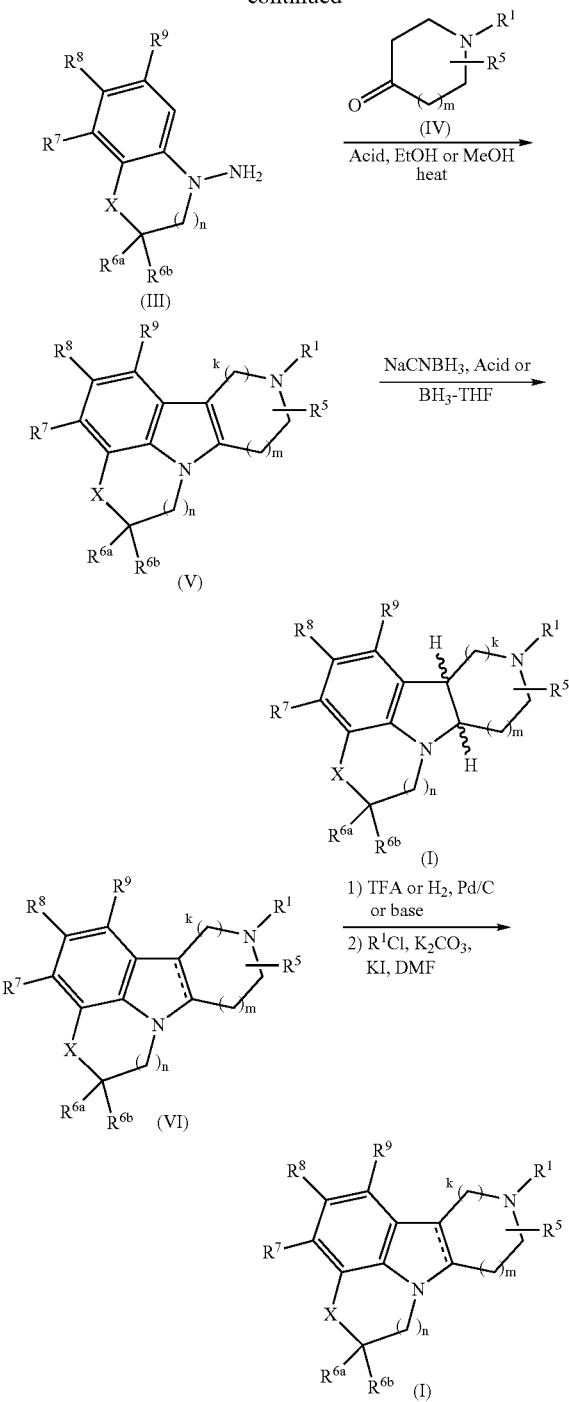

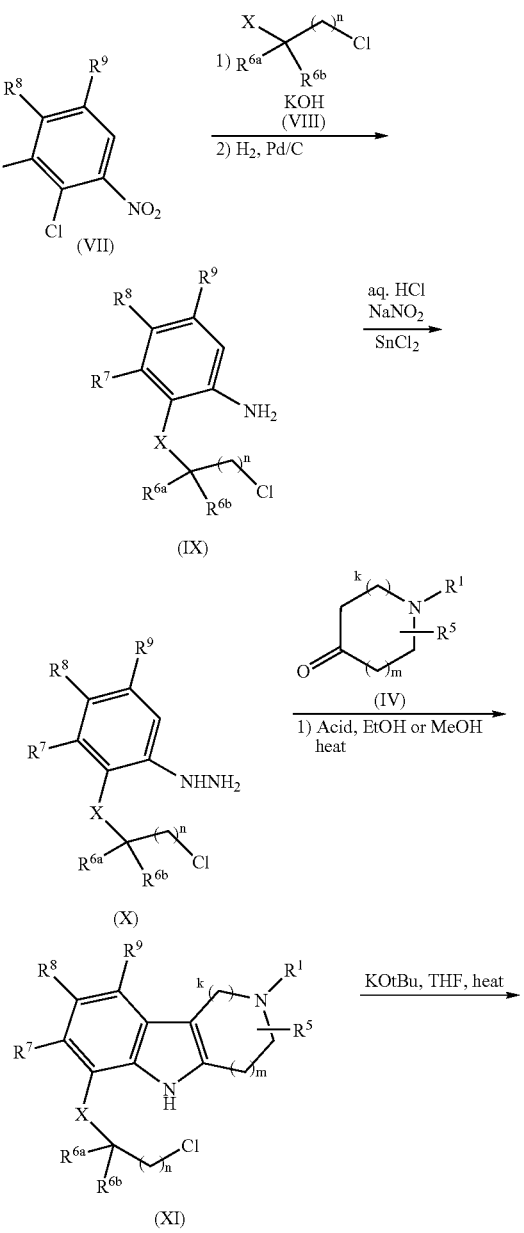

tions in Organic Chemistry", Ellis Horwood, Ltd., Chichester, UK, 1984). Formation of the aryl hydrazine (X) may be accomplished as described previously in Scheme 1 or more directly by treatment of the aniline (IX) with aq. hydrochloric acid, stannous chloride and $NaNO_2$ at room temperature (see, Buck, J. S., Ide, W. S., *Org. Syn., Coll. Vol.*, 2, 1943, 130). This primary aryl hydrazine (X) can then be cyclized under Fischer indole cyclization conditions as detailed above for compound (V), to afford the indole (XI) as the corresponding salt. Upon treatment of the indole (XI) with a base such potassium hydroxide or potassium t-butoxide in a solvent such as DME or THF affords the tetracyclic indole intermediates (V). These indoles can also be reduced to the corresponding cis or trans indolines (I) as described previously in Scheme 1.

Alternatively, compounds of Formula (I) can be prepared as described in Scheme 2. Treatment of an ortho halonitrobenzene compound (VII) with a nucleophilic alkyl halide (X=OH, SH, NHR, (VIII)) (as described by Kharasch, N., Langford, R. B., *J. Org. Chem.*, 1963, 1903) and a suitable base followed by subsequent reduction of the corresponding nitroaryl derivative to the aniline (IX). The reduction may be accomplished with a variety of reducing agents, for example, LAH, $SnCl_2$, $NaBH_4$, $N_2H_4$, etc. or with hydrogen in the presence of a suitable catalyst, such as palladium on carbon, or platinum oxide, etc., (see Hudlicky, M., "Reduc- -continued

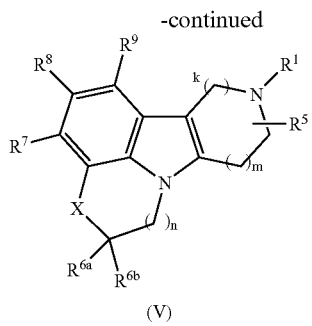

(V)

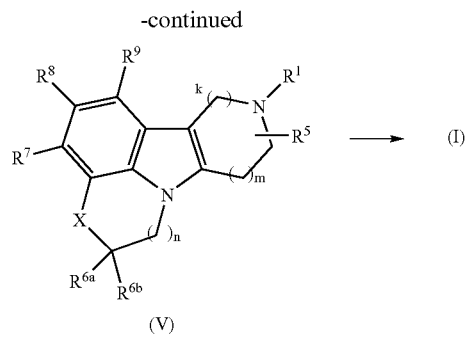

(V)

Still another related route to compounds of Formula (I) is shown in Scheme 3. Initiating the synthesis with a nitrobenzene derivative such as (XII), this approach allows for a variety of derivatization. More highly substituted nitrobenzenes can be obtained by traditional synthetic manipulation (i.e. aromatic substitution) and are known by those in the art (see Larock, R. C., *Comprehensive Organic Transformations*, VCH Publishers, New York, 1989). Treatment of nitrobenzene derivative with a reducing agent such as LAH, etc., as described previously (see Hudlicky, et. al.), affords the corresponding aniline intermediate. Subsequent formation of the hydrazine followed by Fischer indole cyclization with a suitably functionalized ketone as described above (i.e. Scheme 1, (III) to (V)) affords the g-carboline indole (XIII). At this point the fused ring may be appended by condensation of a haloalkyl carboxylic acid or a related activated carboxylic acid (i.e. acid chloride, mixed anhydride, etc.) such as (XIV). Reduction of the resultant heterocyclic carbonyl may be effected with various reducing agents, for example, sodium borohydride, diisobutyl aluminum hydride and the like (see Larock, R. C., *Comprehensive Organic Transformations*, VCH Publishers, New York, 1989 and/or Hudlicky, M., "Reductions in Organic Chemistry", Ellis Horwood, Ltd., Chichester, UK, 1984) to afford the tetracyclic indoles (V). Further reduction of the indole (V) to the indolines (I) is as described previously in Scheme 1.

Preparation of the aniline precursors (II) to the Fischer indole cyclizations is shown in Scheme 4. Treatment of a suitably ortho-functionalized aniline (XVI) with a chloroalkyl carboxylic acid or ester (or equivalent substrate, i.e. acrylic acid, acryloyl chloride, etc.) and concomitant condensation, followed by reduction of the resultant heterocyclic carbonyl with a reducing agent such as LAH, DIBAL, or Red-Al affords the fused heterocyclic benzene derivatives (II). More diverse intermediates of (II) may be obtained by formation of the ortho substitiuted aniline from the corresponding ortho substituted nitobenzenes and concomitant reduction of the nitro moiety as described above. Furthermore, aromatic substitution of the fluoro (or other halo derived nitrobenzene) functionality of (XV) for an oxygen, or sulphur moiety is accomplished, for example, by treatment of (XV) with a nucleophile, such as sodium sulfide or an alcohol, followed by formation of the requisite thiophenol or phenol, respectively, using standard techniques known by those in the art (see Larock, R. C., *Comprehensive Organic Transformations*, VCH Publishers, New York, 1989, page 481). Reduction of the nitro as before affords the substituted anilines (XVI).

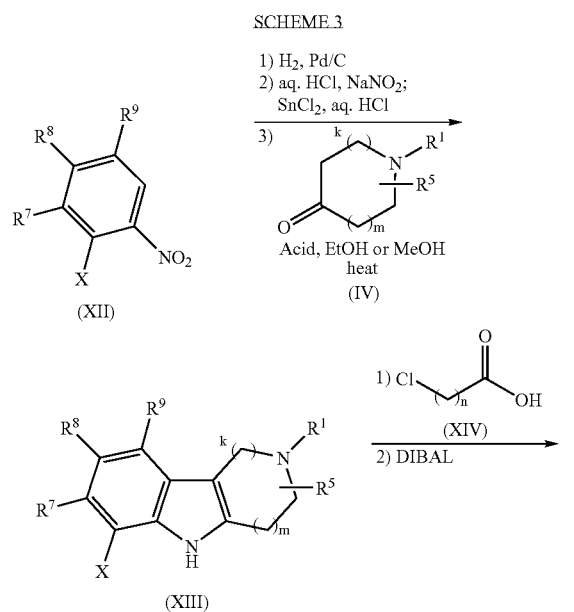

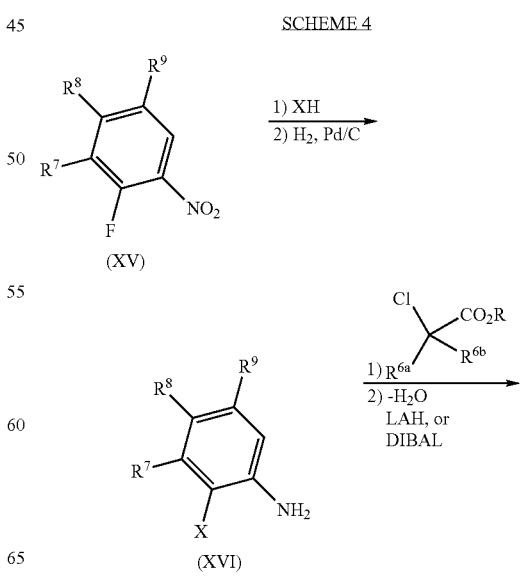

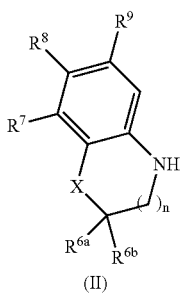

An alternate approach to the substituted fused anilines (II) is shown in Scheme 5. Treatment of the phenol (X=OH), thiophenol (X=SH), or other nucleophilically aromatic substituted derivative (XVII) with, for example, a haloalkyl carboxylic acid (or equivalent activated haloalkylcarboxylic acid, (i.e. acid halide, mixed anhydride, acrylic acid, acryloyl chloride, etc.), affords the derivative (XVIII) which when treated under Friedel-Crafts acylation conditions (see Ed. G. A. Olah, "Friedel-Crafts and Related Reactions", J. Wiley and Sons, New York, 1964, Vol 3, Pts 1 and 2 or Chem. Rev., 1955, 229, or Olah, G. A., "Friedel-Crafts Chemistry", Wiley Interscience, New York, 1973, for varying conditions and protocols), i.e. strong Lewis acids ($AlCl_3$, $FeCl_3$, etc.), affords the cyclic alkylphenones (XIX). Incorporation of the nitrogen functionality can be accomplished in several ways. For example, Schmidt rearrangement (as described by Smith, P. A. S., *J. Am. Chem. Soc.*, 1948, 320) is effected by treatment of the carbonyl derivative (XIX) with $NaN_3$ and methanesulfonic acid to afford the bicyclic lactam (XX). Alternatively, this transformation may be carried out under Hoffmann rearrangement protocol (see, for example, Dike, S. Y., et. al., *Bioorg. Med. Chem. Lett.*, 1991, 383), by initial formation of the oxime derivative of (XXI) by treatment with hydroxylamine hydrochloride. Subsequent rearrangement to the lactam is efficiently accomplished by heating in polyphosphoric acid to afford the lactam (XX). Reduction of the lactam (XX) can be accomplished with a variety of reducing agents, for example, DIBAL, Red-Al and the like to afford the aniline (II).

SCHEME 5

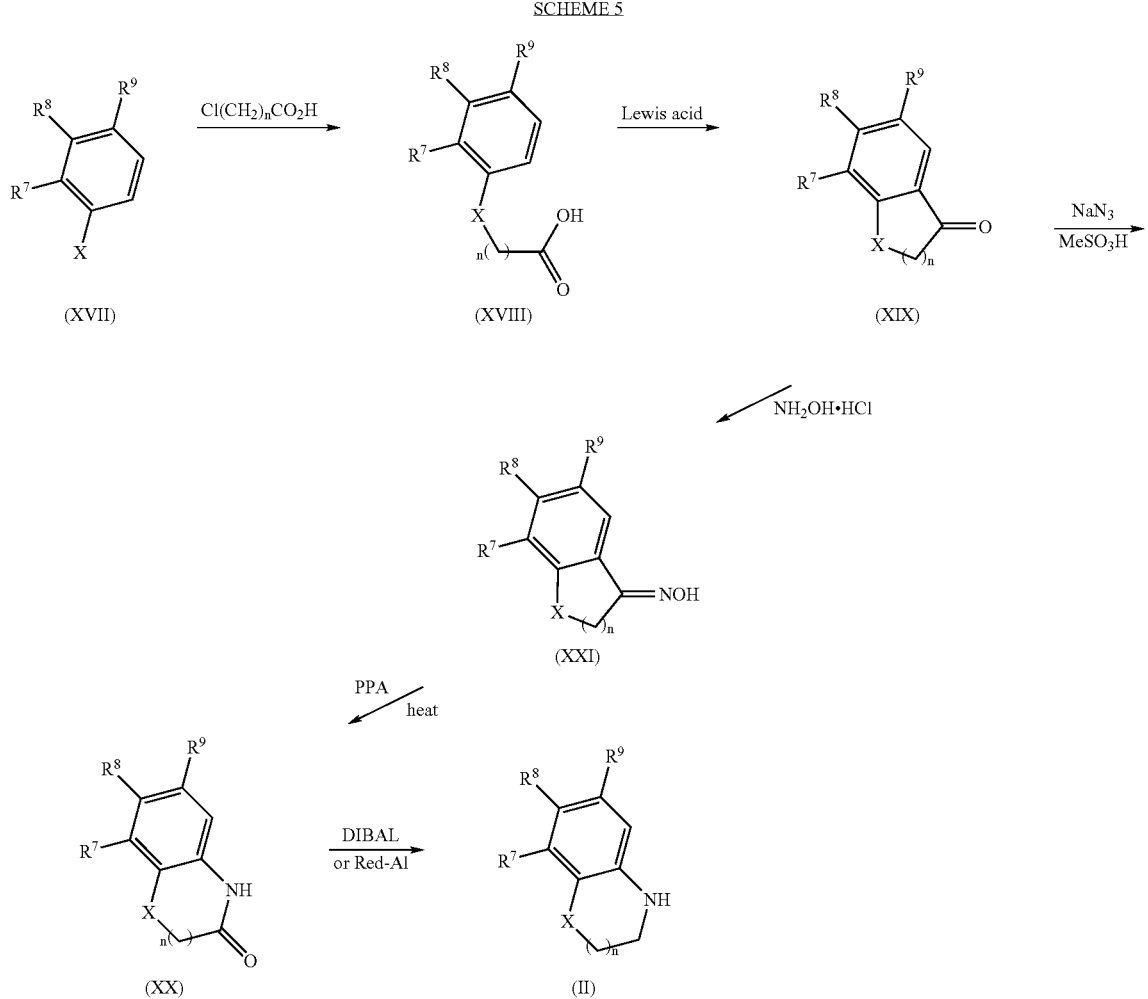

The preparation of compounds of Formula (I) with additional diversity of functionalization of the aromatic A ring of the tetracycle is shown in Scheme 6 and Scheme 7 and described here. Due to the nature of the synthetic route of Scheme 1 to derivatives of Formula (I), compounds with halogen substituents on the A-ring are difficult to prepare. However, bromination of the indolines (I, $R^8$=H) when the amine is protected, for example, with the Boc or CBZ protecting groups, with, for example, NBS in DMF affords the $R^8$ brominated derivatives (XXII). These activated aryl derivatives (XXII) act as excellent counterparts for a number of important synthetic transformations.

For example, biaryl coupling is accomplished under Suzuki coupling protocol. For a review and leading references of palladium catalyzed cross coupling reactions, see Miyaura, N., Suzuki, A., Chem. Rev., 1995, 2457. One such procedure entails treatment of the aryl bromide (XXII) with a functionalized aryl boronic acid (XXIII) in the presence of a catalytic Pd(0) species, such as Pd(PPh$_3$)$_4$, Pd(PPh$_3$)$_2$Cl$_2$, Pd(OAc)$_2$, Pd$_2$(dba)$_3$ and a suitable ligand such as PPh$_3$, AsPh$_3$, etc., or other such Pd(0) catalyst, and a base such as Na$_2$CO$_3$ or Et$_3$N in a suitable solvent such as DMF, toluene, THF, DME or the like, to afford the indolines (XXIV). Alternatively formation of the indole boronic acid from the bromine derivative (XXII) (i.e. (I, $R^8$=B(OH)$_2$)) would allow for greater diversity in the subsequent coupling of this indole boronic acid with commercially available haloaromatic derivatives in a similar Suzuki coupling strategy as described above to afford the indolines (XXIV).

Similarly biaryl coupling of the bromine derivatives (XXV), readily obtained by the synthetic sequence exemplified in Scheme 2, (starting with the suitably functionalized bromo nitrobenzenes (II)), is shown in Scheme 7. This approach allows for the preparation of biaryl indoles as well as the corresponding indoline derivatives. Protection of the amine functionality must be carried out if $R^1$=H (see Greene et. al for protections of amines). This is readily accomplished, for example, by treatment of bromo derivatives (XXV) with (Boc)$_2$O in aqueous sodium hydroxide and dioxane. Subsequent Suzuki coupling with a variety of aryl boronic acids is carried out as described above in Scheme 6, to afford the biaryl adducts (XXVI). This protocol is amenable to $R^7$, $R^8$, and $R^9$ bromide, iodide, triflates, and/or diazo derivatives (see Miyaura, N., Suzuki, A., Chem. Rev., 1995, 2457, for a review of aryl couplings).

SCHEME 6

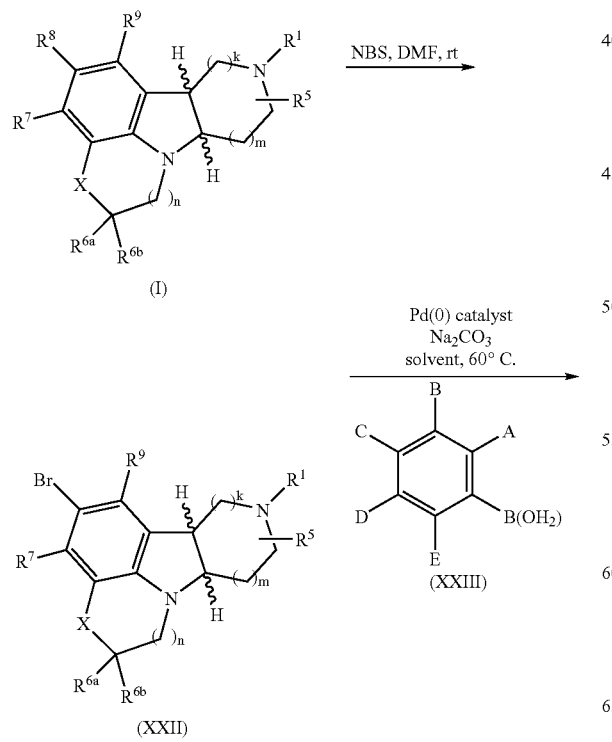

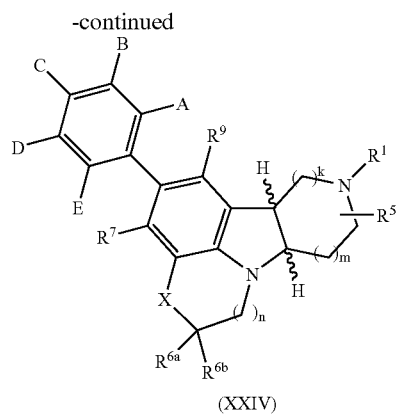

(XXIV)

SCHEME 7

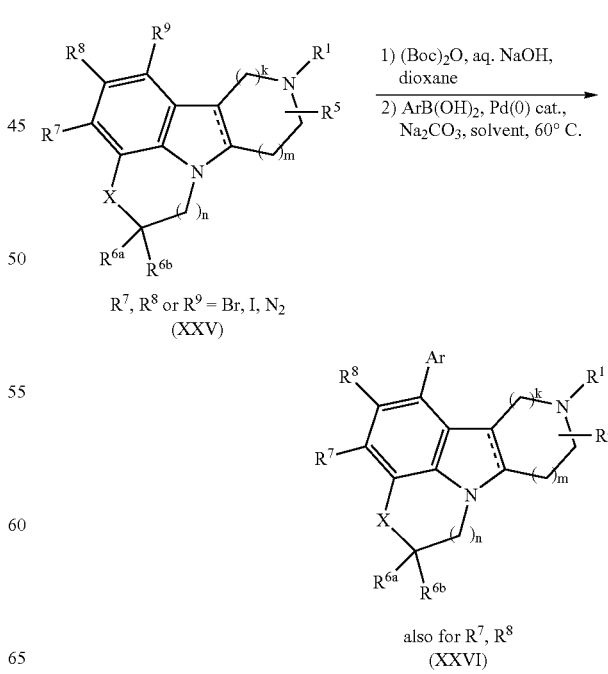

Furthermore and as an extension of this approach to a rapid preparation of a large array of biaryl indole and indoline derivatives, these bromide derivatives (XXV) can be bound to a solid support and the Suzuki couplings can be carried out on solid support (see XXVIII) as illustrated in Scheme 8. Towards that end treatment of indoline (XXV) with TFA in $CH_2Cl_2$, to remove the Boc protecting group, followed extraction from aqueous base provides the free amine (XXXVII). The free amine can be loaded onto a suitable solid support such as (XXVIII) using conditions well known to those skilled in the art. Thus, p-nitrophenylchloroformate Wang resin (XXVIII) which can be obtained commercially from sources such as Novabiochem, Inc. is swollen in a suitable solvent such as N-methylpyrrolidinone and treated with 1.5 equiv. of amine to afford the functionalized resin (XXIX). Suzuki couplings are then carried out in array format by treatment of resins (XXIX) with a suitable palladium source such as $Pd(PPh_3)_4$ or $Pd(dppf)Cl_2$ and a suitable base such as 2M aqueous $K_2CO_3$ or $Na_2CO_3$ or triethylamine with an excess (typically 5 equivalents) of an aryl boronic acid (procedures for solid-phase Suzuki and other palladium couplings are well-known by those in the art, see for instance L. A. Thompson and J. A. Ellman, *Chem. Rev.* 1996, 96, (1), 555–600). The coupling may be repeated to ensure complete conversion to the desired coupled product. Cleavage from the solid support by treatment with TFA affords the corresponding indoles and indolines (XXX) as their TFA salts.

In addition, there exists a wide range of procedures and protocols for functionalizing haloaromatics, aryldiazonium and aryltriflate compounds. These procedures are well known by those in the art and described, for example, by Stanforth, S. P., *Tetrahedron,* 1998, 263; Buchwald, S. L., et. al., *J. Am. Chem. Soc.,* 1998, 9722; Stille, J. K., et. al., *J. Am. Chem. Soc.,* 1984, 7500. Among these procedures are biaryl couplings, alkylations, acylations, aminations, and amidations. The power of palladium catalyzed functionalization of aromatic cores has been explored in depth in the last decade. An excellent review of this field can be found in J. Tsuji, "Palladium Reagents and Catalysts, Innovations in Organic Synthesis", J. Wiley and Sons, New York, 1995.

One such method to prepare compounds of Formula (I) with substituted $R^1$ sidechains in a more direct manner is shown in Scheme 9. Alkylation of the indole or indoline derivatives (I, $R^1$=H) with a haloalkyl ester, such as $ClCH_2(CH_2)_pCO_2Me$, in the presence of NaI or KI and a base such as $K_2CO_3$, $Na_2CO_3$ or the like, in dioxane or THF or other such solvent while heating (see Glennon, R. A., et. al., *Med. Chem. Res.,* 1996, 197) affords the $R^1$ alkylated esters. Subsequent formation of the activated amides (XXXI) is accomplished by treatment of the ester with N,O-dimethylhydroxylamine hydrochloride and a Lewis acid such as trimethylaluminum or triethylaluminum in toluene (see, for example, Golec, J. M. C., et. al., *Tetrahedron,* 1994, 809) at 0° C. Treatment of the amide (XXXI) with a variety of organometallic agents, such as Grignard reagents $R^{1a}MgBr$,

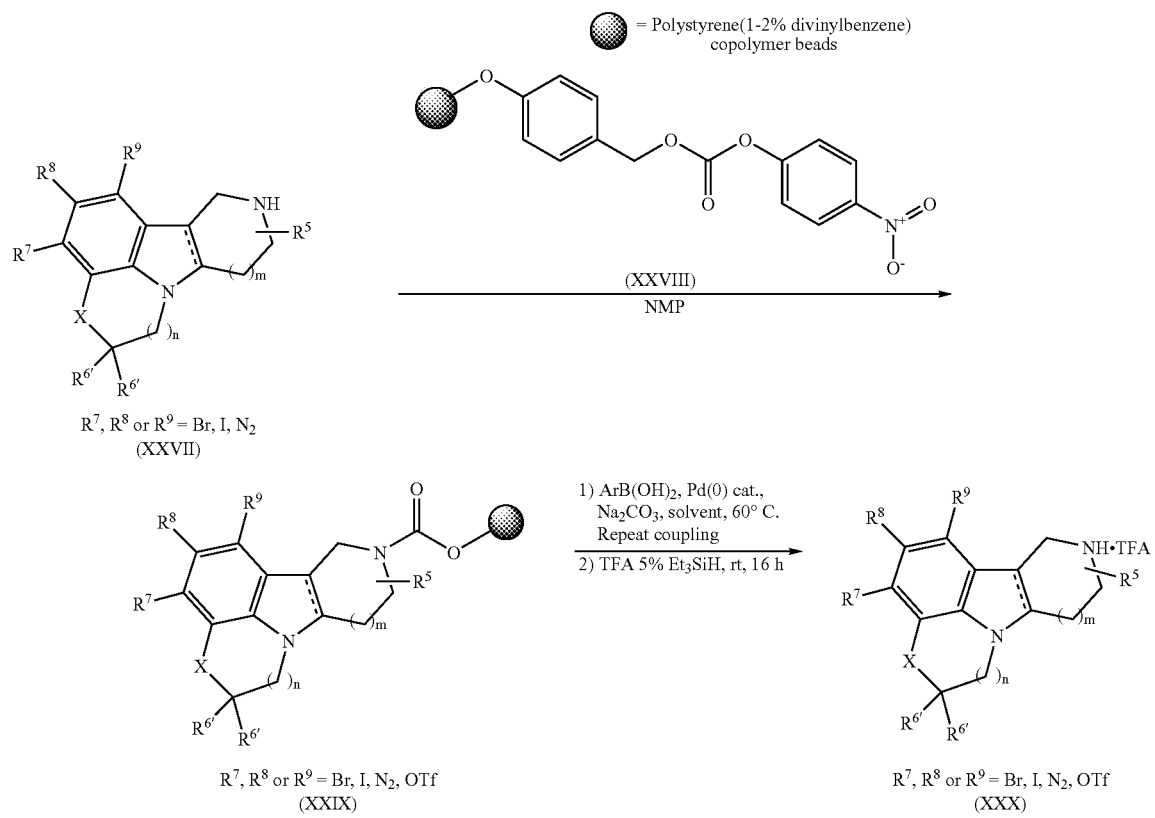

alkyl and aryl lithium reagents etc. (see Sibi, M. P., et. al., *Tetrahedron Lett.*, 1992, 1941; and more generally House, H. O., *Modern Synthetic Reactions*, W. A. Benjamin, Inc., Menlo Park, Calif., 1972), in a suitable solvent such as THF, ether, etc. at low temperatures affords the substituted ketones (XXXII).

SCHEME 9

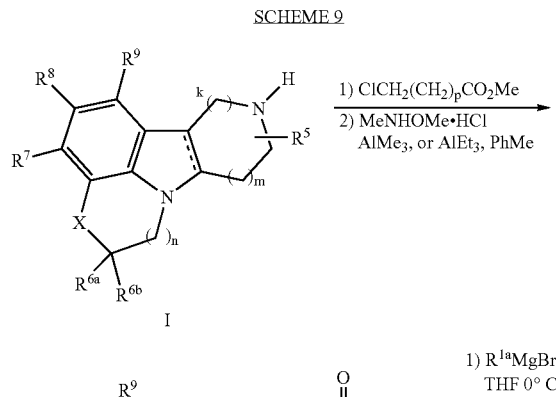

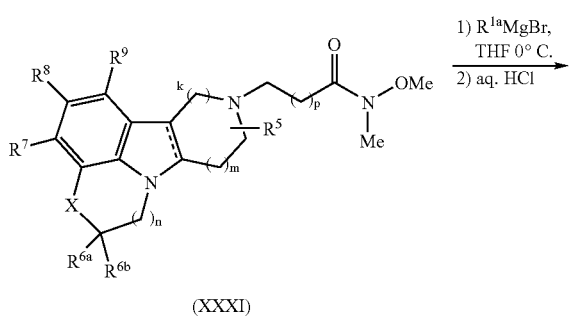

(XXXI)

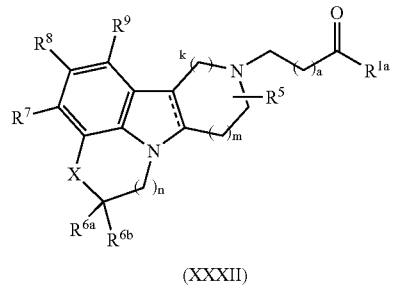

(XXXII)

Preparation of compounds of Formula (I) where m=0, k=1 is outlined in Scheme 10 and described here. Fischer indole cyclization of the previously described hydrazine (III) with a known protected 2,3-dioxopyrolidine (Carlson, E. H., et. al., *J. Org. Chem.*, 1956, 1087) under a variety of typical cyclization conditions affords the tetracyclic indole (XXXII). The reduction may be accomplished with a variety of reducing agents, for example, LAH, DIBAL, etc., to yield the pyrole fused indole (XXXIV). This derivative can then be deprotected and subsequently alkylated as described previously (see Greene, T. W., Wuts, P. G. W., "Protective Groups in Organic Synthesis, 2nd Edition", John Wiley and Sons, Inc., New York, 1991, and Scheme 1), to give the $R^1$ alkylated indole analogs (XXXV). Alternatively, reduction of the indole to the indoline, as described previously (see Scheme 1), followed by deprotection of the benzyl group to give (XXXVI) and alkylation gives access to the corresponding $R^1$ alkylated indoline derivatives (XXXVII). All the previously described methods to functionalize the aromatic ring, and to afford derivatives of varying $R^1$ sidecahins are applicable to these cores.

SCHEME 10

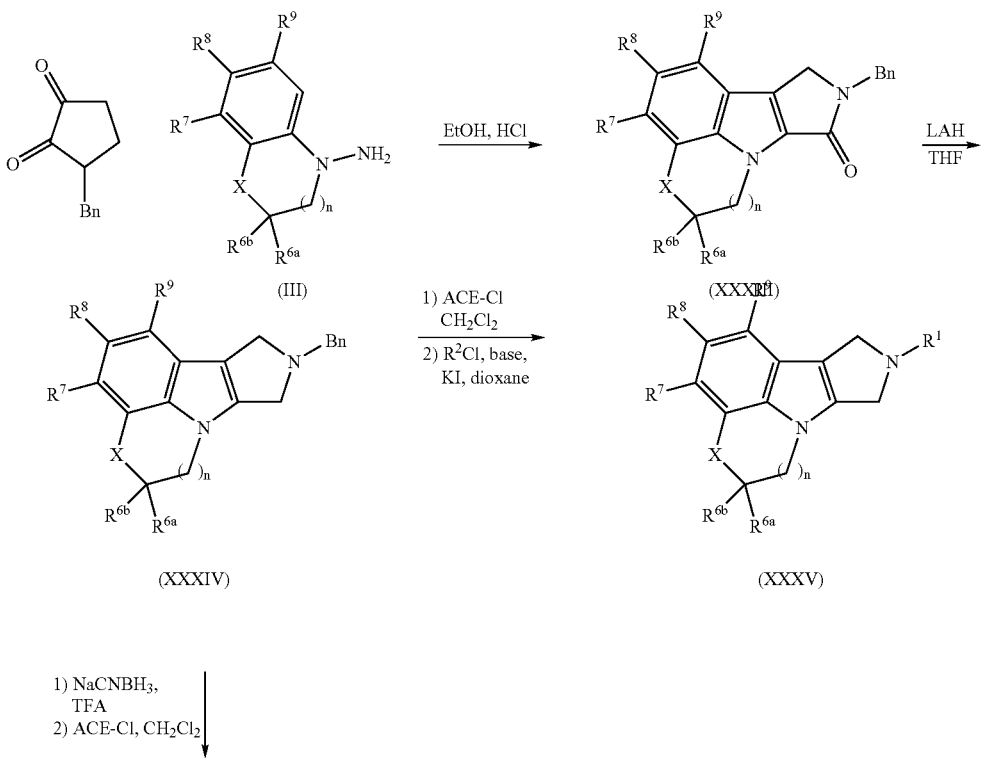

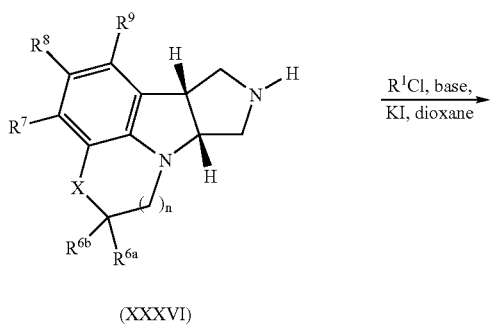 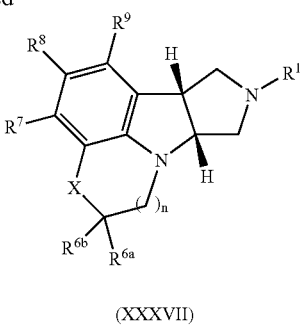

(XXXVI) → (XXXVII)

R¹Cl, base, KI, dioxane

EXAMPLES

Chemical abbreviations used in the Examples are defined above. The detailed processes for preparing the compounds of Formula (I) are illustrated by the following Examples. It is, however, understood that this invention is not limited to the specific details of these examples. The Examples as set forth below are intended to demonstrate the scope of the invention but are not intended to limit the scope of the invention. Proton nuclear magnetic resonance spectra ($^1$H NMR) were measured in chloroform-d (CDCl$_3$) unless otherwise specified and the peaks are reported in parts per million (ppm) downfield from tetramethylsilane (TMS). The coupling patterns are reported as follows: s, singlet; d, doublet; dd, doublet of doublets; t, triplet; q, quartet; m, multiplet; bs, broad singlet; bm, broad multiplet.

Example 1

4,5,7,8,9,10-hexahydropyrido[4,3-b]pyrrolo[3,2,1-hi]indole hydrochloride

A mixture of 1-amino-2,3-dihydroindole (1.0 g, 5.9 mmol), piperidone hydrochloride monohydrate (0.91 g, 5.9 mmol) and isopropanol (29 mL) was brought to reflux for 4 hours. The resulting brown solid was filtered and washed with cold diethylether (20 mL) and dried under vacuum, affording the title compound (1.01 g, 74%). $^1$H NMR (CD$_3$OD, 300 MHz) δ 7.15 (d, 1H, J=7.7 Hz), 6.85–6.96 (m, 2H), 4.39–4.50 (m, 4H), 3.75 (t, 2H, J=7.3 Hz), 3.57 (t, 2H, J=6.2 Hz), 3.15 (t, 2H, J=6.2 Hz) ppm.

Example 2

9-cyclopropyl-4,5,7,8,9,10-hexahydropyrido[4,3-b]pyrrolo[3,2,1-hi]indole hydrochloride The title compound was prepared by substituting cyclopropylpiperidone for the monohydrate piperidone hydrochloride by the procedure of Example 1 in 64% $^1$H NMR (DMSO, 300 MHz) δ 7.16 (d, 1H, J=7.3), 7.85–7.93 (m, 2H), 4.6 (d, 1H, J=6.6), 4.38–4.48 (m, 3H), 3.72–3.85 (m, 1H), 3.7 (t, 2H, J=7 Hz), 3.58–3.62 (m, 1H), 3.0–3.18 (m, 3H), 1.07–1.12 (m, 2H), 0.83–0.9 (m, 2H) ppm.

Example 3

(±)-cis-4,5,6a,7,8,9,10,10a-octahydropyrido[4,3-b]pyrrolo[3,2,1-hi]indole 4,5,7,8,9,10-Hexahydropyrido[4,3-b]pyrrolo[3,2,1-hi]indole from Example 1 (0.50 g, 2.14 mmol) was stirred under N$_2$ in TFA (15.5 mL) at 0° C. for 10 minutes. NaBH$_4$ (0.44 g, 6.4 mmol) was added slowly keeping the temperature below 2° C. The reaction was allowed to warm to room temperature and stirred overnight. Ice chips were then added and the reaction basified to pH 12 with 50% aqueous NaOH. The aqueous layer was then extracted with CHCl$_3$(3×20 mL). The combined extracts were washed with brine, H$_2$O and dried (Na$_2$SO$_4$) and evaporated affording the title compound (0.42 g, 100%). $^1$H NMR (CDCl$_3$, 300 MHz) δ 6.94 (d, 1H, J=7.7 Hz), 6.88 (d, 1H, J=6.9 Hz), 6.63 (t, 7.3, 1H, J=7.3 Hz), 3.64 (dt, 1H, J=8.0, 1.5 Hz), 3.29–3.5 (m, 2H), 3.05–3.29 (m, 3H), 3.03 (dd, 1H, J=11.7, 3.6 Hz), 2.72–3.02 (m, 2H), 1.66–1.90 (m, 2H) ppm.

Example 16

5,6,8,9,10,11-hexahydro-4H-pyrido[3',4':4,5]pyrrolo[3,2,1-ij]quinoline

Step A:

1,2,3,4-Tetrahydroquinoline (2.12 g, 15.9 mmol) was dissolved in AcOH (30 mL) and water (10 mL). The solution was cooled to 0° C. An aqueous solution of NaNO$_2$ (1.20 g, 17.5 mmol in 3 mL water) was added dropwise. The reaction was warmed to RT and stirred 2 hrs. Water (20 mL) and EtOAc (20 mL) were added. The layers were separated and the aqueous phase was extracted (2×20 mL) with EtOAc. The combined organic layers were washed with brine, dried, and concentrated to afford a crude orange oil (2.62 g). The product was purified by column chromatography (20–40% EtOAc/hexane) to afford 1-nitroso-1,2,3,4-tetrahydroquinoline (2.48 g, 96%) as a yellow oil. $^1$H NMR (CDCl$_3$, 300 MHz) δ 8.07 (d, 1H, J=8.1 Hz), 7.21–7.34 (m, 3H), 3.91 (t, 2H, J=6.2 Hz), 3.81 (t, 2H, J=6.2 Hz), 1.97–2.05 (m, 2H) ppm.

Step B:

1-Nitroso-1,2,3,4-tetrahydroquinoline (1.51 g, 9.0 mmol) was dissolved in THF. The solution was cooled to 0° C. 1M LAH in THF (9 ML, 9.0 mmol) was added dropwise. The reaction was allowed to warm to RT and was stirred over night. The reaction was cooled to 0° C. and was quenched with 20 mL a saturated aqueous Rochelle salt solution (20 mL). The suspension was stirred for 2 h and the layers were separated. The aqueous phase was extracted with EtOAc (3×20 mL). The combined organic layers were washed with brine, dried, and concentrated to afford an orange solid (1.26 g). The crude product was purified by column chromatography (20–0% hexane/CH$_2$Cl$_2$) to afford 1,2,3,4-tetrahydroquinoylamine (1.02 g, 76%) as a yellow solid. $^1$H NMR (CDCl$_3$, 300 MHz) δ 7.09–7.18 (m, 2H), 6.97 (dd, 1H, J=0.7 Hz, 7.3 Hz), 6.68–6.74 (m, 1H), 3.64 (m, 2H), 3.31 (t, 2H, J=6.0 Hz), 2.77 (t, 2H, J=6.6 Hz), 2.02–2.11(m, 2H) ppm.

Step C:

1,2,3,4-Tetrahydroquinoylamine (0.925 g, 6.25 mmol) and 4-piperidone monohydrate hydrochloride (0.960 g, 6.25 mmol) were dissolved in EtOH (15 mL). Conc. HCl (0.52 mL, 6.25 mmol) was added. The reaction was refluxed for 3 hrs and then cooled to RT. The precipitate was collected by vacuum filtration. The residue was washed with 5 mL of EtOH, to afford the title compound (1.32 g, 85%) as a pure, white powder. $^1$H NMR (CD$_3$OD, 300 MHz) δ 7.22 (d, 1H, J=8.1 Hz), 6.92–6.97 (m, 1H), 6.86 (d, 1H, J=7.2 Hz), 4.87 (s, 2H), 4.05 (t, 2H, J=6.0 Hz), 3.61 (t, 2H, J=6.0 Hz), 3.14 (t, 2H, J=6.0 Hz), 2.94 (t, 2H, J=6.3 Hz), 2.16–2.24 (m, 2H) ppm.

Example 17

(±)-cis-5,6,7a,8,9,10,11,11a-octahydro-4H-pyrido[3',4':4,5]pyrrolo[3,2,1-ij]quinoline 5,6,8,9,10,11-Hexahydro-4H-pyrido[3',4':4,5]pyrrolo[3,2,1-ij]quinoline (2.84 g, 11.4 mmol) was dissolved in TFA (35 mL). The reaction was cooled to 0° C. NaCNBH$_3$(2.15 g, 34.27 mmol) was added in small portions over 30 min, keeping the temperature less than 5° C. The reaction was stirred at 0° C. for 2 h. Ice was added to the reaction flask, and the reaction was basified with 50% NaOH until pH=14. Water (20 mL) was added to dissolve the precipitate. The reaction was extracted with CHCl$_3$(3×20 mL). The combined organic layers were washed with brine, dried, and concentrated to afford the title compound (1.67 g, 68%) as a pale-brown, amorphous solid. $^1$H NMR (CDCl$_3$, 300 MHz) δ 6.80–7.00 (m, 2H), 6.55–6.6.70 (m, 1H), 3.20–3.40 (m, 2H), 2.95–3.20 (m, 2H), 2.75–2.95 (m, 2H), 2.50–2.75 (m, 4H), 2.00–2.20 (m, 2H), 1.85–2.00 (m, 1H), 1.70–1.85 (m, 1H) ppm.

Example 37

(±)-cis-9-(cyclopropylcarbonyl)-4,5,6a,7,8,9,10,10a-octahydropyrido[4,3-b]pyrrolo[3,2,1-hi]indole (±)-cis-4,5,6a,7,8,9,10,10a-octahydropyrido[4,3-b]pyrrolo[3,2,1-hi]indole from Example 3 (0.050 g, 0.25 mmol) was dissolved in CH$_2$Cl$_2$ (5 mL) with Et$_3$N (0.75 mL) and cooled to 0° C. The cyclopropanecarbonyl chloride (0.026 g, 0.26 mmol) was then added dropwise. The solution was stirred at 0° C. for 1 h and then warmed to room temperature and stirred for 1 h. The reaction mixture was partitioned between water and CHCl$_3$(3×15 mL) and the layers separated. The aqueous layer was extracted with CHCl$_3$. The combined organics were washed with brine, H$_2$O and dried (Na$_2$SO$_4$) and evaporated affording a light yellow liquid which was further purified by preparatory silica gel TLC (5% MeOH/CH$_2$Cl$_2$). The title compound was isolated as a clear colorless liquid (0.042 g, 65%). $^1$H NMR (CD$_3$OD, 300 MHz) δ 7.22–7.58 (m, 3H), 4.62–4.75 (m, 1H), 3.85–4.30 (m, 5H), 3.55–3.62 (m, 2H), 1.9–2.18 (m, 3H), 0.75–0.9 (m, 4H) ppm.

Example 38

(±)-cis-9-isobutyryl-4,5,6a,7,8,9,10,10a-octahydropyrido[4,3-b]pyrrolo[3,2,1-hi]indole The title compound was prepared by substituting isobutyrlchloride for cyclopropanecarbonyl chloride by the procedure of Example 37 in 53% yield. $^1$H NMR (CD$_3$OD, 300 MHz) δ 6.85–6.95 (m, 2H), 6.6 (t, 1H, J=7.3), 4.48 (dd, 0.5H, J=8.4, 4.0 Hz), 4.21 (br d, 0.5H, J=13.2 Hz), 4.05 (dd, 0.5H, J=11.7, 4 Hz), 3.85 (br d, 0.5H, J=13.9 Hz), 3.47–3.7 (m, 2H), 3.18–3.45 (m, 4H), 2.85–3.18 (m, 3H), 2.72–2.85 (m, 1H), 1.75–2.05 (m, 2H), 1.15 (t, 3H, J=6.5 Hz), 1.05 (t, 3H, J=6.9 Hz) ppm.

Example 89 tert-butyl(±)-cis-2-(2-chlorophenyl)-4,5,7,8,10,10a-hexahydropyrido[4,3-b]pyrrolo[3,2,1-hi]indole-9(6aH)-carboxylate Step A:

(±)-cis-4,5,6a,7,8,9,10,10a-octahydropyrido[4,3-b]pyrrolo[3,2,1-hi]indole (387 mg, 1.93 mmol) was dissolved in CHCl$_3$(8 mL). BOC$_2$O(464 mg, 2.13 mmol) was added. The reaction was stirred at R$_T$ 18 h. 1M aqueous NaOH (10 mL) was added. The biphasic mixture was stirred 10 min, and the layers were separated. The aqueous phase was extracted with CH$_2$Cl$_2$ (3×10 mL). The combined organic layers were washed with brine, dried, and concentrated to afford an amorphous white solid (820 mg). The crude product was purified by column chromatography (0–10% MeOH/CH$_2$Cl$_2$) to afford tert-butyl(±)-cis-4,5,7,8,10,10a-hexahydropyrido[4,3-b]pyrrolo[3,2,1-hi]indole-9(6aH)-carboxylate (596 mg, 100%) as an amorphous white solid. $^1$H NMR (CDCl$_3$, 300 MHz) δ 6.97 (d, 1H, J=7.3 Hz), 6.93 (d, 1H, J=7.3 Hz), 6.60–6.75 (m, 1H), 3.75–3.90 (m, 1H), 3.50–3.72 (m, 1H), 3.05–3.48 (m, 5H), 2.70–2.90 (m, 1H), 1.70–1.90 (m, 2H) ppm. MS (CI, NH3): 301 (base, M+H)

Step B:

To a solution of tert-butyl(±)-cis-4,5,7,8,10,10a-hexahydropyrido[4,3-b]pyrrolo[3,2,1-hi]indole-9(6aH)-carboxylate (0.576 g, 1.92 mmol) in DMF (4 mL) at 0° C., freshly recrystalized NBS (0.375 g, 2.1 mmol) was added as a solution in DMF (4 mL). The reaction was stirred at 0° C. for 20 min, after which it was warmed to RT. The reaction was stirred at RT for 0.5 h. Water (10 mL) and EtOAc (10 mL) were added. The layers were separated, and the aqueous phase was extracted with EtOAc (2×20 mL). The combined organic layers were washed with brine (2×20 mL) and dried. Concentration afforded a crude brown oil. The crude product was purified by column chromatography (MeOH/CH$_2$Cl$_2$). Tert-butyl(±)-cis-2-bromo-4,5,7,8,10,10a-hexahydropyrido[4,3-b]pyrrolo[3,2,1-hi]indole-9(6aH)-carboxylate (550 mg, 75%) was isolated as a brown amorphous solid. $^1$H NMR (CDCl$_3$, 300 MHz) δ 7.06 (s, 1H), 7.02 (s, 1H), 3.70–3.90 (m, 1H), 3.50–3.70 (m, 1H), 3.00–3.45 (m, 6H), 2.70–2.90 (m, 2H), 1.70–1.90 (m, 2H), 1.48 (s, 9H) ppm.

Step C:

Tert-butyl(±)-cis-2-bromo-4,5,7,8,10,10a-hexahydropyrido[4,3-b]pyrrolo[3,2,1-hi]indole-9(6aH)-carboxylate (87.5 mg, 0.23 mmol) was dissolved benzene (4 mL). 2M sodium carbonate (0.4 mL) added. 2-Chlorophenylboronic acid (71.9 mg, 0.46 mmol) was added, followed by Pd(PPh$_3$)$_2$Cl$_2$ (8.1 mg, 0.0115 mmol). The reaction was evacuated and kept under a nitrogen atmosphere. The suspension was refluxed for 18 h and then cooled to RT. The reaction was concentrated in vacuo, after which water (10 mL) and EtOAc (10 mL) were added. The layers were separated and the aqueous phase was extracted with EtOAc (2×10 mL). The organic layers were washed with brine (2×10 mL), dried, and concentrated to afford a crude brown amorphous solid (110.9 mg). The residue was purified by column chromatography (20–40% EtOAc/Hexane) to afford the title compound (62 mg, 66%) as a white amorphous solid. MS (CI, NH3): 411(base, M+H).

Example 90 tert-butyl(±)-cis-2-(2,4-dichlorophenyl)-4,5,7,8,10, 10a-hexahydropyrido[4,3-b]pyrrolo[3,2,1-hi]indole-9(6aH)-carboxylate The title compound (55.9 mg, 50%) was prepared by the method of Example 89 Step C from tert-butyl(±)-cis-2-bromo-4,5,7,8,10,10a-hexahydropyrido[4,3-b]pyrrolo[3,2,1-hi]indole-9(6aH)-carboxylate (94 mg, 0.25 mmol) and 2,4-dichlorophenylboronic acid (95 mg, 0.5 mmol) as a white amorphous solid. MS (CI, NH3): 445 (base, M+H).

Example 91 tert-butyl(±)-cis-2-(3,4-dichlorophenyl)-4,5,7,8,10, 10a-hexahydropyrido[4,3-b]pyrrolo[3,2,1-hi]indole-9(6aH)-carboxylate Tert-butyl(±)-cis-2-bromo-4,5,7,8,10,10a-hexahydropyrido[4,3-b]pyrrolo[3,2,1-hi]indole-9(6aH)-carboxylate (135 mg, 0.30 mmol) was dissolved in DME (4 mL). 2M sodium carbonate (0.75 mL)was added. 3,4-Dichlorophenylboronic acid (114 mg, 0.60 mmol) was added, followed by $Pd_2(dba)_3$ (15 mg, 0.015 mmol). $PPh_3$(16 mg, 0.06 mmol) was added. The reaction flask was degassed and kept under a nitrogen atmosphere. The suspension was refluxed for 18 h cooled to RT. The reaction was concentrated in vacuo, after which water (10 mL) and EtOAc (10 mL) were added. The layers were separated and the aqueous phase was extracted with EtOAc (2×10 mL). The combined organic layers were washed with brine (2×10 mL), dried, and concentrated to afford a crude brown amorphous solid (214 mg). The residue was purified by column chromatography (20–40% EtOAc/Hexane) to afford the title compound (120 mg, 90%) as a white amorphous solid. $^1$H NMR (CDCl$_3$, 300 MHz) δ 7.55 (d, 1H, J=1.5 Hz), 7.41 (d, 1H, J=8.4 Hz), 7.30 (dd, 1H, J=1.8 Hz, 8.4 Hz), 7.26 (s, 1H), 7.13 (s, 1H), 3.75–3.90 (m, 1H), 3.60–3.70 (m, 1H), 3.10–3.50 (m, 7H), 2.80–3.00 (m, 1H), 1.70–1.90 (m, 2H), 1.48 (s, 9H) ppm. MS (CI, NH3): 445 (base, M+H).

Example 92 tert-butyl(±)-cis-2-(2,3-dichlorophenyl)-4,5,7,8,10, 10a-hexahydropyrido[4,3-b]pyrrolo[3,2,1-hi]indole-9(6aH)-carboxylate The title compound was prepared by the method of Example 90 from tert-butyl(±)-cis-2-bromo-4,5,7,8,10,10a-hexahydropyrido[4,3-b]pyrrolo[3,2,1-hi]indole-9(6aH)-carboxylate (124 mg, 0.27 mmol) and corresponding 2,3-dichlorophenylboronic acid (104 mg, 0.54 mmol), to afford after chromatographic purification the title compound (157 mg, 99%) as a white amorphous solid. $^1$H NMR (CDCl$_3$, 300 MHz) δ 7.30–7.40 (m, 1H), 7.20 (s, 1H), 7.18 (d, 1H, J=3.6 Hz), 6.99 (s, 1H), 6.94 (s, 1H), 3.80–3.90 (m, 1H), 3.60–3.80 (m, 1H), 3.10–3.50 (m, 7H), 2.80–3.00 (m, 1H), 1.70–1.90 (m, 2H), 1.47 (s, 9H) ppm. MS (CI, NH3): 445 (base, M+H).

Example 93 tert-butyl(±)-cis-2-[2-chloro-4-(trifluoromethyl)phenyl]-4,5,7,8,10,10a-hexahydropyrido[4,3-b]pyrrolo[3,2,1-hi]indole-9(6aH)-carboxylate The title compound was prepared by the method of Example 90 from tert-butyl(±)-cis-2-bromo-4,5,7,8,10,10a-hexahydropyrido[4,3-b]pyrrolo[3,2,1-hi]indole-9(6aH)-carboxylate (136 mg, 0.30 mmol) and corresponding 2-chloro-4-trifluoromethylphenylboronic acid (128 mg, 0.60 mmol), to afford after chromatographic purification the title compound (160 mg, 99%) as a white amorphous solid. $^1$H NMR (CDCl$_3$, 300 MHz) δ 7.70 (br, 1H), 7.51 (dd, 1H, J=1.1 Hz, 8.0 Hz), 7.42 (d, 1H, J=8.0 Hz), 7.03 (s, 1H), 6.99 (s, 1H), 3.80–3.90 (m, 1H), 3.60–3.80 (m, 1H), 3.10–3.50 (m, 7H), 2.80–3.00 (m, 1H), 1.70–1.90 (m, 2H), 1.48 (s, 9H) ppm. MS (CI, NH3): 479 (base, M+H).

Example 94 tert-butyl(±)-cis-2-(2-chloro-4-methoxyphenyl)-4,5, 7,8,10,10a-hexahydropyrido[4,3-b]pyrrolo[3,2,1-hi]indole-9(6aH)-carboxylate The title compound was prepared by the method of Example 90 from tert-butyl(±)-cis-2-bromo-4,5,7,8,10,10a-hexahydropyrido[4,3-b]pyrrolo[3,2,1-hi]indole-9(6aH)-carboxylate (121 mg, 0.27 mmol) and corresponding 2-chloro-4-methoxyphenylboronic acid (100 mg, 0.54 mmol), to afford after chromatographic purification the title compound (141 mg, 68%) as a white amorphous solid. $^1$H NMR (CDCl$_3$, 300 MHz) δ 7.21 (d, 1H, J=8.4 Hz), 6.94–6.99 (m, 3H), 6.82 (dd, 1H, J=2.9 Hz, 8.8 Hz), 3.75–4.00 (m, 7H), 3.60–3.70 (m, 1H), 3.10–3.50 (m, 7H), 2.80–3.00 (m, 1H), 1.70–1.90 (m, 2H), 1.48 (s, 9H) ppm. MS (CI, NH3): 441 (base, M+H).

Example 95 tert-butyl(±)-cis-2-(5-isopropyl-2-methoxyphenyl)-4, 5,7,8,10,10a-hexahydropyrido[4,3-b]pyrrolo[3,2,1-hi]indole-9(6aH)-carboxylate The title compound was prepared by the method of Example 90 from tert-butyl(±)-cis-2-bromo-4,5,7,8,10,10a-hexahydropyrido[4,3-b]pyrrolo[3,2,1-hi]indole-9(6aH)-carboxylate (127 mg, 0.28 mmol) and corresponding 4-isopropyl-2-methoxyphenylboronic acid (109 mg, 0.56 mmol), to afford after chromatographic purification the title compound (58.4 mg, 46%) as a white amorphous solid. $^1$H NMR (CDCl$_3$, 300 MHz) δ 7.00–7.20 (m, 4H), 6.87 (d, 1H, J=8.4 Hz), 3.85–4.0 (m, 1H), 3.79 (s, 3H), 3.60–3.75 (m, 1H), 3.10–3.50 (m, 6H), 2.70–3.00 (m, 2H), 1.70–1.90 (m, 2H), 1.48 (s, 9H), 1.25 (d, 6H, J=7.0 Hz) ppm. MS (CI, NH3): 449 (base, M+H).

Example 96 tert-butyl(±)-cis-2-(3-fluorophenyl)-4,5,7,8,10,10a-hexahydropyrido[4,3-b]pyrrolo[3,2,1-hi]indole-9 (6aH)-carboxylate The title compound was prepared by the method of Example 90 tert-butyl(±)-cis-2-bromo-4,5,7,8,10,10a-hexahydropyrido[4,3-b]pyrrolo[3,2,1-hi]indole-9(6aH)-carboxylate (125 mg, 0.28 mmol) and corresponding 3-fluorophenylboronic acid (77 mg, 0.56 mmol), to afford after chromatographic purification the title compound (48 mg, 44%) as a white amorphous solid. $^1$H NMR (CDCl$_3$, 300 MHz) δ 7.20–7.40 (m, 2H), 7.10–7.20 (m, 3H), 6.80–7.00 (m, 1H), 3.80–3.90 (m, 1H), 3.60–3.80 (m, 1H), 3.10–3.50 (m, 7H), 2.80–3.00 (m, 1H), 1.70–1.90 (m, 2H), 1.48 (s, 9H) ppm. MS (CI, NH3): 395 (base, M+H).

Example 97 tert-butyl(±)-cis-2-(2,4-dimethoxyphenyl)-4,5,7,8,10,10a-hexahydropyrido[4,3-b]pyrrolo[3,2,1-hi]indole-9(6aH)-carboxylate The title compound was prepared by the method of Example 90 from tert-butyl(±)-cis-2-bromo-4,5,7,8,10,10a-hexahydropyrido[4,3-b]pyrrolo[3,2,1-hi]indole-9(6aH)-carboxylate (143 mg, 0.32 mmol) and corresponding 2,4-dimethoxyphenylboronic acid (115 mg, 0.63 mmol), to afford after chromatographic purification the title compound (92 mg, 66%) as a white amorphous solid. $^1$H NMR (CDCl$_3$, 300 MHz) δ 7.15–7.18 (m, 1H), 7.08 (s, 1H), 7.04 (s, 1H), 6.40–6.60 (m, 2H), 3.75–4.00 (m, 7H), 3.60–3.70 (m, 1H), 3.00–3.50 (m, 7H), 2.70–2.90 (m, 1H), 1.70–1.90 (m, 2H), 1.48 (s, 9H) ppm. MS (CI, NH3): 437 (base, M+H).

Example 98

(±)-cis-2-(2-chlorophenyl)-4,5,6a,7,8,9,10,10a-octahydropyrido[4,3-b]pyrrolo[3,2,1-hi]indole Tert-butyl(±)-cis-2-(2-chlorophenyl)-4,5,7,8,10,10a-hexahydropyrido[4,3-b]pyrrolo[3,2,1-hi]indole-9(6aH)-carboxylate (45.1 mg, 0.11 mmol) was dissolved in 20% TFA in methylene chloride (4 mL) and was stirred at RT for 2 h. The reaction was solution was cooled to 0° C. and basified with 1M NaOH until pH>14. The layers were separated. The aqueous phase was extracted the methylene chloride (2×10 ml). The organic layers were washed with brine and dried. Concentration afforded the title compound (29.3 mg, 86%) as a pale yellow amorphous solid. $^1$H NMR (CDCl$_3$, 300 MHz) δ 7.42 (dd, 1H, J=1.4, 7.3 Hz), 7.16–7.33 (m, 3H), 7.02 (s, 1H), 6.96 (s, 1H), 3.69 (dt, 1H, J=1.4, 8.1 Hz), 3.15–3.50 (m, 5H), 3.06 (dt, 1H, J=3.2, 12.3 Hz), 2.82–2.97 (m, 3H), 1.78–1.93 (m, 2H) ppm. MS (CI, NH3): 311 (base, M+H).

Example 99

(±)-cis-2-(2,4-dichlorophenyl)-4,5,6a,7,8,9,10,10a-octahydropyrido[4,3-b]pyrrolo[3,2,1-hi]indole The title compound was prepared by the method of Example 98 from tert-butyl(±)-cis-2-(2,4-dichlorophenyl)-4,5,7,8,10,10a-hexahydropyrido[4,3-b]pyrrolo[3,2,1-hi]indole-9(6aH)-carboxylate (44.3 mg, 0.99 mmol) to afford the title compound (35 mg, 100%) as a pale yellow amorphous solid. The enatiomers of (±)-cis-2-(2,4-dichlorophenyl)-4,5,6a,7,8,9,10,10a-octahydropyrido[4,3-b]pyrrolo[3,2,1-hi]indole were separated by preparative HPLC on a chiracel OD column using isocratic 6% IPA/hexane as the eluent. $^1$H NMR (CDCl$_3$, 300 MHz) δ 7.44 (s, 1H), 7.23–7.26 (m, 2H), 6.97 (s, 1H), 6.92 (s, 1H), 3.70 (dt, 1H, J=1.4, 8.0 Hz), 3.15–3.50 (m, 5H), 3.06 (dt, 1H, J=3.3, 11.3 Hz), 2.77–2.96 (m, 3H), 1.76–1.93 (m, 2H) ppm. MS (CI, NH3): 345 (base, M+H).

Example 100

(±)-cis-2-(3,4-dichlorophenyl)-4,5,6a,7,8,9,10,10a-octahydropyrido[4,3-b]pyrrolo[3,2,1-hi]indole The title compound was prepared by the method of Example 98 from tert-butyl(±)-cis-2-(3,4-dichlorophenyl)-4,5,7,8,10,10a-hexahydropyrido[4,3-b]pyrrolo[3,2,1-hi]indole-9(6aH)-carboxylate (110 mg, 0.25 mmol) to afford the title compound (71 mg, 82%) as a pale yellow amorphous solid. $^1$H NMR (CDCl$_3$, 300 MHz) δ 7.57 (d, 1H, J=2.2 Hz), 7.41 (d, 1H, J=8.4 Hz), 7.30 (dd, 1H, J=1.8, 8.1 Hz), 7.13 (s, 1H), 7.07 (s, 1H), 3.70 (dt, 1H, J=1.8, 7.6 Hz), 3.15–3.50 (m, 5H), 3.04 (dt, 1H, J=3.6, 12.4 Hz), 2.83–2.95 (m, 3H), 1.76–1.92 (m, 2H) ppm. MS (CI, NH3): 345 (base, M+H).

Example 101

(±)-cis-2-(2,3-dichlorophenyl)-4,5,6a,7,8,9,10,10a-octahydropyrido[4,3-b]pyrrolo[3,2,1-hi]indole The title compound was prepared by the method of Example 98 from tert-butyl(±)-cis-2-(2,3-dichlorophenyl)-4,5,7,8,10,10a-hexahydropyrido[4,3-b]pyrrolo[3,2,1-hi]indole-9(6aH)-carboxylate (128 mg, 0.29 mmol) to afford the title compound (99 mg, 100%) as a pale yellow amorphous solid. The enatiomers were separated by preparative HPLC on a chiracel OD column using isocratic 6% IPA/hexane as the eluent. $^1$H NMR (CDCl$_3$, 300 MHz) δ 7.38 (dd, 1H, J=2.6, 7.3 Hz), 7.14–7.23 (m, 2H), 7.02 (s, 1H), 6.98 (s, 1H), 6.92 (s, 1H), 3.70 (dt, 1H, J=1.8, 8.1 Hz), 3.15–3.50 (m, 5H), 3.05 (dt, 1H, J=3.3, 12.2 Hz), 2.85–2.95 (m, 3H), 1.73–1.93 (m, 2H) ppm. MS (CI, NH3): 345 (base, M+H).

Example 102

(±)-cis-2-[2-chloro-4-(trifluoromethyl)phenyl]-4,5,6a,7,8,9,10,10a-octahydropyrido[4,3-b]pyrrolo[3,2,1-hi]indole The title compound was prepared by the method of Example 98 tert-butyl(±)-cis-2-[2,-chloro-4-(trifluoromethyl)phenyl]-4,5,7,8,10,10a-hexahydropyrido[4,3-b]pyrrolo[3,2,1-hi]indole-9(6aH)-carboxylate (80 mg, 0.17 mmol) to afford the title compound (65.3 mg, 100%) as a pale yellow amorphous solid. The enantiomers were separated by preparative HPLC on a chiracel OD column using isocratic 3% IPA/hexane as the eluent. $^1$H NMR (CDCl$_3$, 300 MHz) δ 7.69 (s, 1H), 7.51 (d, 1H, J=8.1 Hz), 7.42 (d, 1H, J=8.0 Hz), 7.02 (s, 1H), 6.96 (s, 1H), 3.68–3.73 (m, 1H), 3.16–3.50 (m, 5H), 2.85–3.09 (m, 4H), 1.75–1.93 (m, 2H) ppm. MS (CI, NH3): 379 (base, M+H).

Example 103

(±)-cis-2-(2-chloro-4-methoxyphenyl)-4,5,6a,7,8,9,10,10a-octahydropyrido[4,3-b]pyrrolo[3,2,1-hi]indole The title compound was prepared by the method of Example 98 from tert-butyl(±)-cis-2-(2-chloro-4-methoxyphenyl)-4,5,7,8,10,10a-hexahydropyrido[4,3-b]pyrrolo[3,2,1-hi]indole-9(6aH)-carboxylate (60 mg, 0.14 mmol) to afford the title compound (50.4 mg, 100%) as a pale yellow amorphous solid. $^1$H NMR (CDCl$_3$, 300 MHz) δ 7.22 (d, 1H, J=8.8 Hz), 6.95–7.00 (m, 2H), 7.02 (s, 1H), 6.92 (s, 1H), 6.81 (dd, 1H, J=2.7, 8.5 Hz), 3.82 (s, 3H), 3.69 (dt, 1H, J=1.4, 7.7 Hz), 3.13–3.50 (m, 5H), 3.00–3.10 (dt, 1H, J=3.3, 11.7 Hz), 2.84–2.94 (m, 3H), 1.74–1.92 (m, 2H) ppm. MS (CI, NH3): 341 (base, M+H).

Example 104

(±)-cis-2-(4-isopropyl-2-methoxyphenyl)-4,5,6a,7,8,9,10,10a-octahydropyrido[4,3-b]pyrrolo[3,2,1-hi]indole The title compound was prepared by the method of Example 98 from tert-butyl(±)-cis-2-(4-isopropyl-2-methoxyphenyl)-4,5,7,8,10,10a-hexahydropyrido[4,3-b]pyrrolo[3,2,1-hi]indole-9(6aH)-carboxylate (52 mg, 0.12 mmol) to afford the title compound (42 mg, 100%) as a pale yellow amorphous solid. $^1$H NMR (CDCl$_3$, 300 MHz) δ 7.07–7.14 (m, 4H), 6.88 (d, 1H, J=8.4 Hz), 3.79 (s, 3H), 3.68 (dt, 1H, J=1.4, 8.0 Hz), 3.14–3.50 (m, 5H), 3.05 (dt, 1H, J=3.3, 12.1 Hz), 2.79–2.94 (m, 3H), 1.60–1.93 (m, 3H), 1.25 (d, 6H, J=6.9 Hz) ppm. MS (CI, NH3): 349 (base, M+H).

Example 105

(±)-cis-2-(3-fluorophenyl)-4,5,6a,7,8,9,10,10a-octahydropyrido[4,3-b]pyrrolo[3,2,1-hi]indole The title compound was prepared by the method of Example 98 from tert-butyl(±)-cis-2-(3-fluorophenyl)-4,5,7,8,10,10a-hexahydropyrido[4,3-b]pyrrolo[3,2,1-hi]indole-9(6aH)-carboxylate (39.5 mg, 0.10 mmol) to afford the title compound (35.4 mg, 90%) as a pale yellow amorphous solid. The enatiomers were separated by preparative HPLC on a chiracel OD column using isocratic 5% IPA/hexane as the eluent. $^1$H NMR (CDCl$_3$, 300 MHz) 67.19–7.35 (m, 3H), 7.16 (s, 1H), 7.11(s, 1H), 6.89–6.96 (m, 1H), 3.69 (dt, 1H, J=1.8, 8.0 Hz), 3.15–3.50 (m, 5H), 3.04 (dt, 1H, J=3.3, 12.1 Hz), 2.83–2.95 (m, 3H), 1.76–1.92 (m, 2H) ppm. MS (CI, NH3): 295 (base, M+H).

Example 106

(±)-cis-2-(2,4-dimethoxyphenyl)-4,5,6a,7,8,9,10,10a-octahydropyrido[4,3-b]pyrrolo[3,2,1-hi]indole The title compound was prepared by the method of Example 98 from tert-butyl(±)-cis-2-(2,4-dimethoxyphenyl)-4,5,7,8,10,10a-hexahydropyrido[4,3-b]pyrrolo[3,2,1-hi]indole-9(6aH)-carboxylate (85.0 mg, 0.19 mmol) to afford the title compound (55.0 mg, 86%) as a pale yellow amorphous solid. The enatiomers were separated by preparative HPLC on a chiracel OD column using isocratic 8% IPA/hexane as the eluent. $^1$H NMR (CDCl$_3$, 300 MHz) 67.17 (dd, 1H, J=1.4, 6.9 Hz), 7.06 (s, 1H), 7.01 (s, 1H), 6.50–6.60 (m, 2H), 3.84 (s, 3H), 3.79 (s, 3H), 3.67 (dt, 1H, J=1.5, 7.7 Hz), 3.12–3.49 (m, 5H), 3.05 (dt, 1H, J=3.3, 12.1 Hz), 2.78–2.98 (m, 3H), 1.73–1.91 (m, 2H) ppm. MS (CI, NH3): 337 (base, M+H).

Example 107 tert-butyl(±)-cis-5,6,8,9,11,11a-hexahydro-4H-pyrido[3',4':4,5]pyrrolo[3,2,1-ij]quinoline-10(7aH)-carboxylate (±)-Cis-5,6,7a,8,9,10,11,11a-octahydro-4H-pyrido[3',4':4,5]pyrrolo[3,2,1-ij]quinoline, from Example 17 (1.67 g, 7.79 mmol) was dissolved in dioxane (16 mL) and 1M NaOH (8 mL). The reaction was cooled to 0° C. BOC$_2$O (1.87 g, 8.57 mmol) was added. The reaction was stirred at RT 18 hrs. EtOAc (10 mL) was added and the biphasic mixture was stirred for 10 min. the layers were separated. The aqueous phase was extracted with EtOAc (3×10 mL). The combined organic layers were washed with brine, dried, and concentrated to afford an amorphous white solid (2.30 g). The crude product was purified by column chromatography (20–40% EtOAc/hexane) to afford the title compound (2.17 g, 69%) as an amorphous white solid. $^1$H NMR (CDCl$_3$, 300 MHz) δ 6.93 (d, 1H, J=7.3 Hz), 6.86 (d, 1H, J=7.3 Hz), 6.61–6.66 (m, 1H), 3.65–3.80 (m, 1H), 3.30–3.50 (m, 1H), 3.10–3.31 (m, 3H), 2.70 (t, 2H, J=6.6 Hz), 2.50–2.65 (m, 1H), 2.00–2.20 (m, 2H), 1.75–1.90 (m, 2H) ppm. MS (CI, NH3): 315 (base, M+H)

Example 108 tert-butyl(±)-cis-2-bromo-5,6,8,9,11,11a-hexahydro-4H-pyrido3',4':4,5]pyrrolo[3,2,1-ij]quinoline-10(7aH)-carboxylate The title compound (0.81 g, 35%) was prepared by the method of Example 89 Step B using tert-butyl(±)-cis-5,6,8,9,11,11a-hexahydro-4H-pyrido[3',4':4,5]pyrrolo[3,2,1-ij]quinoline-10(7aH)-carboxylate (1.85 g) as an amorphous white solid. $^1$H NMR (CDCl$_3$, 300 MHz) δ 7.01 (s, 1H), 6.98 (s, 1H), 3.50–3.70 (m, 1H), 3.30–3.50 (m, 1H), 3.00–3.30 (m, 5H), 2.50–2.70 (m, 3H), 2.00–2.30 (m, 2H), 1.70–1.90 (m, 2H), 1.48 (s, 9H) ppm.

Example 109 tert-butyl(±)-cis-2-(2,3-dichlorophenyl)-5,6,8,9,11,11a-hexahydro-4H-pyrido[3',4':4,5]pyrrolo[3,2,1-ij]quinoline-10(7aH)-carboxylate Tert-butyl(±)-cis-2-bromo-5,6,8,9,11,11a-hexahydro-4H-pyrido[3',4':4,5]pyrrolo[3,2,1-ij]quinoline-10(7aH)-carboxylate (110 mg, 0.28 mmol) was dissolved in DME (4 mL). 2M aqueous sodium carbonate (0.75 ml) was added. 2,3-Dichlorophenylboronic acid (107 mg, 0.56 mmol) was added, followed by Pd$_2$(dba)$_3$(14.5 mg, 0.014 mmol). P(Ph)$_3$ (14.7 mg, 0.056 mmol) was added. The reaction flask was degassed and kept under a nitrogen atmosphere. The suspension was refluxed for 18 h cooled to rt. The reaction was concentrated in vacuo, after which water (10 mL) and EtOAc (10 mL) were added. The layers were separated and the aqueous phase was extracted with EtOAc (2×10 mL). The combined organic layers were washed with brine (2×10 mL), dried, and concentrated to afford a crude brown amorphous solid (162 mg). The residue was purified by column chromatography (20–0% hexane/CH$_2$Cl$_2$) to afford the title compound (96.8 mg, 75%) as a white amorphous solid. $^1$H NMR (CDCl$_3$, 300 MHz) δ 7.61–7.94 (m, 1H), 7.20 (s, 1H), 7.18 (d, 1H, 3.3 Hz), 7.00 (s, 1H), 6.93 (s, 1H), 3.70–3.74 (m, 1H), 3.45–60 (m, 1H), 3.15–3.35 (m, 4H), 2.65–2.80 (m, 4H), 2.10–2.20 (m, 2H), 1.80–2.00 (m, 2H), 1.46 (s, 9H) ppm.

Example 110 tert-butyl(±)-cis-2-(3,4-dichlorophenyl)-5,6,8,9,11,11a-hexahydro-4H-pyrido[3',4':4,5]pyrrolo[3,2,1-ij]quinoline-10(7aH)-carboxylate The title compound was prepared by the method of Example 109 from tert-butyl(±)-cis-2-bromo-5,6,8,9,11, 11a-hexahydro-4H-pyrido[3',4':4,5]pyrrolo[3,2,1-ij]quinoline-10(7aH)-carboxylate (101.7 mg, 0.26 mmol) and 3,4-dichlorophenylboronic acid (97 mg, 0.52 mmol), after chromatographic purification (91.6 mg, 77%) as a white amorphous solid. $^1$H NMR (CDCl$_3$, 300 MHz) δ 7.57 (d, 1H, J=1.8 Hz), 7.42 (d, 1H, J=8.4 Hz), 7.31 (dd, 1H, J=2.2, 8.4 Hz), 7.12 (bs, 1H), 7.07 (bs, 1H), 3.62–3.75 (m, 1H), 3.48–60 (m, 1H), 3.15–3.35 (m, 4H), 2.65–2.80 (m, 4H), 2.10–2.20 (m, 2H), 1.85–2.00 (m, 2H), 1.46 (s, 9H) ppm.

Example 111 tert-butyl(±)-cis-2-[2-chloro-4-(trifluoromethyl)phenyl]-5,6,8,9,11,11a-hexahydro-4H-pyrido[3',4':4,5]pyrrolo[3,2,1-ij]quinoline-10(7aH)-carboxylate The title compound was prepared by the method of Example 109 from tert-butyl(±)-cis-2-bromo-5,6,8,9,11,11a-hexahydro-4H-pyrido[3',4':4,5]pyrrolo[3,2,1-ij]quinoline-10(7aH)-carboxylate (63 mg, 0.16 mmol) and 2-chloro-4-(trifluoromethyl)phenylboronic acid (69 mg, 0.32 mmol), after chromatographic purification (35.9 mg, 46%) as a white amorphous solid. $^1$H NMR (CDCl$_3$, 300 MHz) δ 7.69 (s, 1H), 7.51 (bd, 1H, J=8.0 Hz), 7.42 (d, 1H, J=8.1 Hz), 7.04 (s, 1H), 6.97 (s, 1H), 3.60–3.75 (m, 1H), 3.48–60 (m, 1H), 3.15–3.35 (m, 4H), 2.65–2.80 (m, 4H), 2.10–2.20 (m, 2H), 1.85–2.00 (m, 2H), 1.46 (s, 9H) ppm. MS (CI, NH3): 493 (base, M+H).

Example 112

(±)-cis-2-(2,3-dichlorophenyl)-5,6,7a,8,9,10,11,11a-octahydro-4H-pyrido[3',4':4,5]pyrrolo[3,2,1-ij]quinoline Tert-butyl(±)-cis-2-(2,3-dichlorophenyl)-5,6,8,9,11,11a-hexahydro-4H-pyrido[3',4':4,5]pyrrolo[3,2,1-ij]quinoline-10(7aH)-carboxylate (55 mg, 0.12 mmol) was dissolved in 20% TFA in methylene chloride (4 mL) and was stirred at RT for 2 h. The reaction was solution was cooled to 0° C. and basified with 1 M NaOH until pH >14. The layers were separated. The aqueous phase was extracted the methylene chloride (2×10 ml). The organic layers were washed with brine and dried. Concentration afforded the title compound (43 mg, 100%) as a pale yellow amorphous solid. $^1$H NMR (CDCl$_3$, 300 MHz) δ 7.37 (dd, 1H, J=2.6, 7.3 Hz), 7.15–7.23 (m, 2H), 6.97 (s, 1H), 6.92 (s, 1H), 3.43–3.46 (m, 1H), 3.31 (dt, 1H, J=4.4, 10.2), 3.03–3.11(m, 2H), 2.81–2.94 (m, 2H), 2.60–2.80 (m, 4H), 2.11–2.20 (m, 2H), 1.89–1.98 (m, 1H), 1.74–1.85 (m, 1H) ppm. MS (CI, NH$_3$): 359 (base, M+H).

Example 113

(±)-cis-2-(3,4-dichlorophenyl)-5,6,7a,8,9,10,11,11a-octahydro-4H-pyrido[3',4':4,5]pyrrolo[3,2,1-ij]quinoline The title compound (72.6 mg, 100%) was prepared by the method of Example 112 from tert-butyl(±)-cis-2-(3,4-dichlorophenyl)-5,6,8,9,11,11a-hexahydro-4H-pyrido[3',4':4,5]pyrrolo[3,2,1-ij]quinoline-10(7aH)-carboxylate (90 mg, 0.20 mmol) as pale yellow amorphous solid. $^1$H NMR (CDCl$_3$, 300 MHz) δ 7.58 (d, 1H, J=2.2 Hz), 7.41 (d, 1H, J=8.4 Hz), 7.32 (dd, 1H, J=2.2, 8.4 Hz), 7.09 (s, 1H), 7.07 (s, 1H), 3.34–3.46 (m, 1H), 3.31 (dt, 1H, J=4.4, 10.7 Hz), 3.03–3.13 (m, 2H), 2.83–2.92 (m, 2H), 2.61–2.78 (m, 4H), 2.10–2.19 (m, 2H), 1.74–1.91 (m, 2H) ppm. MS (CI, NH$_3$): 359 (base, M+H).

Example 114

(±)-cis-2-[2-chloro-4-(trifluoromethyl)phenyl]-5,6,7a,8,9,10,11,11a-octahydro-4H-pyrido[3',4':4,5]pyrrolo[3,2,1-ij]quinoline The title compound (21 mg, 90%) was prepared by the method of Example 112 from tert-butyl(±)-cis-2-(3,4-dichlorophenyl)-5,6,8,9,11,11a-hexahydro-4H-pyrido[3',4':4,5]pyrrolo[3,2,1-ij]quinoline-10(7aH)-carboxylate (28.5 mg, 0.06 mmol) as a pale yellow amorphous solid. The enantiomers of the title compound were separated by preparative HPLC on a Chiracel OD column using isocratic 6% IPA/hexane as the eluent. $^1$H NMR (CDCl$_3$, 300 MHz) δ 7.46 (s, 1H), 7.69 (s, 1H), 7.49 (d, 1H, J=8.0 Hz), 7.43 (d, 1H, J=8.08 Hz), 7.02 (s, 1H), 6.96 (s, 1H), 3.45–3.50 (m, 1H), 3.32 (dt, 1H, J=4.4, 10.3 Hz), 3.01–3.12 (m, 2H), 2.84–2.89 (m, 2H), 2.64–2.81 (m, 4H), 2.11–2.23 (m, 2H), 1.90–1.98 (m, 1H), 175–1.86 (m, 1H) ppm. MS (CI, NH3): 393 (base, M+H).

Example 189

4-((±)-cis-2-(2-chlorophenyl)-4,5,7,8,10,10a-hexahydropyrido[4,3-b]pyrrolo[3,2,1-hi]indol-9(6aH)-yl)-1-(4-fluorophenyl)-1-butanone (±)-Cis-2-(2-chlorophenyl)-4,5,6a,7,8,9,10,10a-octahydropyrido[4,3-b]pyrrolo[3,2,1-hi]indole (26.4 mg, 0.085 mmol) 0.7 ml of MEK. KI (14 mg, 0.085 mmol) and K$_2$CO$_3$ (22 mg, 0.26 mmol), and 4-chloro-4'-fluorobutyrophenone (22.2 mg, 0.11 mmol) were added. The suspension was refluxed for 48 h and then cooled to rt. The suspension was filtered and the residue was washed with CH$_2$Cl$_2$ (5 ml). The solution was concentrated in vacuo. The residue was purified by column chromatography (10% MeOH—CH$_2$Cl$_2$) to afford the title compound (18.8 mg, 47%) as a white amorphous solid. $^1$H NMR (CDCl$_3$, 300 MHz) δ 8.00–8.04 (m, 2H), 7.41 (dd, 1H, J=1.5, 7.3 Hz), 7.30 (dd, 1H, J=1.8, 7.3 Hz), 7.10–7.20 (m, 4H), 7.01 (s, 1H), 6.96 (s, 1H), 3.68 (bt, 1H, J=6.6 Hz), 3.30–3.50 (m, 2H), 3.10–3.30 (m, 2H), 2.92–3.08 (m, 3H), 2.60–2.92 (m, 2H), 2.38–2.58 (m, 3H), 2.27 (t, 1H, J=11.3 Hz), 1.70–2.05 (m, 4H) ppm. MS (CI, NH$_3$): 475 (base, M+H).

Example 190

4-((±)-cis-2-(2,4-dichlorophenyl)-4,5,7,8,10,10a-hexahydropyrido[4,3-b]pyrrolo[3,2,1-hi]indol-9(6aH)-yl)-1-(4-fluorophenyl)-1-butanone The title compound (36 mg, 37%) was prepared by the method of Example 189 from (±)-cis-2-(2,4-dichlorophenyl)-4,5,6a,7,8,9,10,10a-octahydropyrido[4,3-b]pyrrolo[3,2,1-hi]indole (65.8 mg, 0.19 mmol), 4-chloro-4'-fluorobutyrophenone (50.0 mg, 0.25 mmol), KI (31.5 mg, 0.19 mmol), and K$_2$CO$_3$ (50.0 mg, 0.57 mmol) after chromatographic purification as a white amorphous solid. $^1$H NMR (CDCl$_3$, 300 MHz) δ 7.90–7.95 (m, 2H), 7.37 (s, 1H), 7.16 (s, 2H), 7.03 (t, 2H, J=8.8 Hz), 6.91 (s, 1H), 6.85 (s, 1H), 3.49 (bt, 1H, J=8.0 Hz), 3.25–3.45 (m, 2H), 3.02–3.22 (m, 2H), 2.90–3.02 (m, 3H), 2.50–2.88 (m, 2H), 2.10–2.45 (m, 4H), 1.70–2.00 (m, 4H) ppm. MS (CI, NH$_3$): 509 (base, M+H).

Example 191

4-((±)-cis-5,6,8,9,11,11a-hexahydro-4H-pyrido[3',4': 4,5]pyrrolo[3,2,1-ij]qionolin-10(7aH)-yl)-1-(4-fluorophenyl)-1-butanone The title compound (19.1 mg, 56%) was prepared by the method of Example 189 from (±)-cis-5,6,7a,8,9,10,11,11a-octahydro-4H-pyrido[3',4':4,5]pyrrolo[3,2,1-ij]qionoline (30.0 mg, 0.0.09 mmol), 4-chloro-4'-fluorobutyrophenone (23.0 mg, 0.12 mmol), KI (15.0 mg, 0.09 mmol), and $K_2CO_3$ (37.0 mg, 0.27 mmol) after chromatographic purification as a white amorphous solid. $^1H$ NMR (CDCl$_3$, 300 MHz) δ 7.91–7.96 (m, 2H), 7.01–7.19 (m, 2H), 6.82 (d, 1H, J=12.1 Hz), 6.80 (d, 1H, J=11.7 Hz), 2.98–3.25 (m, 3H), 2.94 (t, 2H, J=6.9 Hz), 2.80–2.85 (m, 1H), 2.55–2.75 (m, 3H), 2.20–2.55 (m, 4H), 1.80–2.18 (m, 7H) ppm. MS (ESI): 379 (base, M+H).

Example 265

4-((±)-cis-4,5,7,8,10,10a-hexahydropyrido[4.3-b]pyrrolo[3,2,1-hi]indol-9(6aH)-yl)-1-(4-fluorophenyl)-1-butanone A mixture of (±)-cis-4,5,6a,7,8,9,10,10a-octahydropyrido[4.3-b]pyrrolo[3,2,1-hi]indole (2.8 g, 14 mmol), 4-chloro-4'-fluorobutyrophenone (4.21 g, 21 mmol), triethylamine (3 mL), KI (3.48 g, 21 mmol), dioxane (25 mL), and toluene (25 mL) was stirred and refluxed for 15 h under an atmosphere of nitrogen and then evaporated under reduced pressure to remove the volatiles. The residue was triturated with a small volume of dichloromethane and decanted from the insoluble material. The process was repeated two more times and the combined dichloromethane solution was added to 0.5N solution of hydrogen chloride in ether(200 mL). The salt that separated was filtered off, washed with ether, dissolved immediately in a minimum quantity of water and the solution extracted with ether. The ether extract was discarded and aqueous layer basified with 10% aqueous sodium hydroxide. The resulting mixture was extracted with dichloro-methane (2×) and the extract dried over magnesium sulfate and stripped of the solvent under reduced pressure to yield the title compound (3.3 g, 65%) as a highly viscous light brown liquid. $^1H$ NMR (CDCl$_3$, 300 MHz) δ 1.70–1.80 (m, 2H), 1.80–2.02 (m, 2H), 2.19 (t, J=10.9 Hz, 1H), 2.30–2.52 (m, 3H), 2.62–2.72 (m, 1H), 2.72–2.85 (m, 1H), 2.99 (t, J=7.0 Hz, 2H), 3.02–3.20 (m, 2H), 3.25–3.42 (m, 2H), 3.59–3.65 (m, 1H), 6.85 (s, 1H), 6.90 (s, 1H0, 7.01 (t, J=7.0 Hz, 2H), 7.98–8.03 (m, 2H) ppm. MS (CI): 365 (M+H$^+$).

Example 274

(6aS,10aR)-2-(2-fluoro-4-methoxyphenyl)-4,5,6a,7,8,9,10,10a-octahydropyrido[4,3-b]pyrrolo[3,2,1-hi]indole Step A:
Tert-butyl(6aS,10aR)-2-(2-fluoro-4-methoxyphenyl)-4,5,7,8,10,10a-hexahydropyrido[4,3-b]pyrrolo[3,2,1-hi]indole-9(6aH)-carboxylate (116 mg, 55%) was prepared by the method of Example 89 step C from tert-butyl(6aS,10aR)-2-bromo-4,5,7,8,10,10a-hexahydropyrido[4,3-b]pyrrolo[3,2,1-hi]indole-9(6aH)-carboxylate (189 mg, 0.5 mmol) and 2-fluoro-4-methoxyphenylboronic acid (158 mg, 1.0 mmol).

Step B:
The title compound was prepared by the method of Example 98 from tert-butyl(6aS,10aR)-2-(2-fluoro-4-methoxyphenyl)-4,5,7,8,10,10a-hexahydropyrido[4,3-b]pyrrolo[3,2,1-hi]indole-9(6aH)-carboxylate to afford the title compound (82 mg, 93%). $^1H$ NMR (CDCl$_3$, 300 MHz) δ 7.24–7.30 (m, 1H), 7.08 (s, 1H), 7.02 (s, 1H), 6.65–6.73 (m, 2H), 3.81 (s, 3H), 3.66–3.71 (m, 1H), 3.32–3.49 (m, 3H), 3.01–3.30 (m, 4H), 2.82–2.97 (m, 2H), 2.25 (bs, 1H), 1.79–1.93 (m, 2H) ppm. MS-ESI: 325 [MH]$^+$.

Example 275 tert-butyl(6aS,10aR)-2-[4-ethoxy-2-(trifluoromethyl)phenyl]-4,5,7,8,10,10a-hexahydropyrido[4,3-b]pyrrolo[3,2,1-hi]indole-9(6aH)-carboxylate Tert-butyl(6aS,10aR)-2-bromo-4,5,7,8,10,10a-hexahydropyrido[4,3-b]pyrrolo[3,2,1-hi]indole-9(6aH)carboxylate (189 mg, 0.5 mmol) was dissolved in DME (7.8 mL). Ba(OH)$_2$ 8H$_2$O (236.6 mg, 0.75 mmol) in H$_2$O (2.6 mL) was added. 4-ethoxy-2-trifluoromethylphenyl boronic acid (140 mg, 0.6 mmol) was added followed by Pd(PPh$_3$)$_4$ (12 mg, 0.01 mmol). The reaction flask was degassed and refluxed under a nitrogen atmosphere for 18 hrs. After cooling to RT, the reaction was concentrated in vacuo. Water (10 mL) and EtOAc (10 mL) were added. The layers were separated and the aqueous phase was extracted with EtOAc (2×10 mL). The combined organic layer was washed with brine (2×10 mL), dried over MgSO$_4$ and concentrated in vacuo and after chromatographic purification (30% EtOAc/Hexane) to afford the title compound (140 mg, 57%). $^1H$ NMR (CDCl$_3$, 300 MHz) δ 7.20 (d, 2H, J=5.9 Hz), 7.19 (s, 1H), 7.01 (dd, 1H, J=6.2, 2.2 Hz), 6.85 (s, 1H), 6.81 (s, 1H), 4.05–4.10 (m, 3H), 3.82–3.94 (m, 1H), 3.64–3.68 (m, 1H), 3.22–3.44 (m, 4H), 2.84–3.10 (m, 3H), 1.80–1.90 (m, 2H), 1.42–1.47 (m, 12H) ppm. MS-ApCI: 489 [M+H$^+$].

Example 276

(6aS,10aR)-2-[4-ethoxy-2-(trifluoromethyl)phenyl]-4,5,6a,7,8,9,10,10a-octahydropyrido[4,3-b]pyrrolo[3,2,1-hi]indole The title compound was prepared by the method of Example 98 from tert-butyl(6aS,10aR)-2-[4-ethoxy-2-(trifluoromethyl)phenyl]-4,5,7,8,10,10a-hexahydropyrido[4,3-b]pyrrolo[3,2,1-hi]indole-9(6aH)-carboxylate to afford the title compound (97 mg, 87%). $^1H$ NMR (CDCl$_3$, 300 MHz) δ 7.17 (d, 1H, J=8.1 Hz), 7.12 (d, 1H, J=2.9 Hz), 6.93 (dd, 1H, J=8.4, 2.6 Hz), 6.77 (s, 1H), 6.71 (s, 1H), 4.00 (q, 2H, J=6.9 Hz), 3.61 (t, 1H, J=8.0 Hz), 2.93–3.41 (m, 6H), 2.75–2.86 (m, 3H), 1.62–1.97 (m, 3H), 1.37 (t, 3H, J=6.9 Hz) ppm. MS-ApCI: 389 [M+H$^+$].

Example 277 tert-butyl(6aS,10aR)-2-(4-chloro-2-fluorophenyl)-4,5,7,8,10,10a-hexahydropyrido[4,3-b]pyrrolo[3,2,1-hi]indole-9(6aH)-carboxylate The title compound was prepared by the method of Example 89 step C from tert-butyl(6aS,10aR)-2-bromo-4,5,7,8,10,10a-hexahydropyrido[4,3-b]pyrrolo[3,2,1-hi]indole-9(6aH)carboxylate (189 mg, 0.5 mmol) and corresponding 4-chloro-2-fluorophenyl boronic acid (175 mg, 1.0 mmol) to afford after chromatographic purification the title compound (128 mg, 60%). ¹H NMR (CDCl₃, 300 MHz) δ 7.28–7.29 (m,1H), 7.05–7.15 (m, 4H), 3.6–4.2 (m, 3H), 2.80–3.50 (m, 7H), 1.80–1.90 (m, 2H), 1.48 (s, 9H) ppm. MS-ApCI: 429 [M+H⁺].

Example 278

(6aS,10aR)-2-(4-chloro-2-fluorophenyl)-4,5,6a,7,8,9,10,10a-octahydropyrido[4,3-b]pyrrolo[3,2,1-hi]indole The title compound was prepared by the method of Example 98 from tert-butyl(6aS,10aR)-2-(4-chloro-2-fluorophenyl)-4,5,7,8,10,10a-hexahydropyrido[4,3-b]pyrrolo[3,2,1-hi]indole-9(6aH)-carboxylate to afford the title compound (66 mg, 67%). ¹H NMR (CDCl₃, 300 MHz) δ 7.29–7.35 (m, 1H), 6.99–7.15 (m, 4H), 3.60–3.80 (m, 1H), 2.80–3.50 (m, 9H), 1.70–1.95 (m, 2H), 1.62 (bs, 1H) ppm. MS-ApCI: 329 [M+H⁺].

Example 279 tert-butyl(6aS,10aR)-2-[4-isopropoxy-2-(trifluoromethyl)phenyl]-4,5,7,8,10,10a-hexahydropyrido[4,3-b]pyrrolo[3,2,1-hi]indole-9(6aH)-carboxylate The title compound was prepared by the method of Example 89 step C from tert-butyl(6aS,10aR)-2-bromo-4,5,7,8,10,10a-hexahydropyrido[4,3-b]pyrrolo[3,2,1-hi]indole-9(6aH)carboxylate (189 mg, 0.5 mmol) and 4-isopropoxy-2-(trifluoromethyl)phenylboronic acid (248 mg, 1.0 mmol) to afford after chromatographic purification the title compound (186 mg, 74%). ¹H NMR (CDCl₃, 300 MHz) δ 7.11–7.18 (m,2H), 6.90–6.94 (m, 1H), 6.78 (s, 1H), 6.74 (s, 1H), 4.50–4.54 (m, 1H), 3.75–3.85 (m, 1H), 3.59–3.70 (m, 1H), 2.79–3.40 (m, 8H), 1.74–1.84 (m, 2H), 1.40 (s, 9H), 1.21 (d, 6H, J=5.9 Hz) ppm. MS-ApCI: 503 [M+H⁺].

Example 280

(6aS,10aR)-2-[4-isopropoxy-2-(trifluoromethyl)phenyl]-4,5,6a,7,8,9,10,10a-octahydropyrido[4,3-b]pyrrolo[3,2,1-hi]indole The title compound was prepared by the method of Example 98 from tert-butyl(6aS,10aR)-2-[4-isopropoxy-2-(trifluoromethyl)phenyl]-4,5,7,8,10,10a-hexahydropyrido[4,3-b]pyrrolo[3,2,1-hi]indole-9(6aH)-carboxylate to afford the title compound (96 mg, 65%). ¹H NMR (CDCl₃, 300 MHz) δ 7.14 (d, 1H, J=8.4 Hz), 7.10 (d, 1H, J=2.5 Hz), 6.90 (dd, 1H, J=2.6, 8.4 Hz), 6.75 (s, 1H), 6.69 (s, 1H), 4.46–4.54 (m, 1H), 3.56–3.62 (m, 1H), 2.91–3.39 (m, 6H), 2.73–2.83 (m, 3H), 1.64–1.82 (m, 3H), 1.46 (d, 6H, J=5.8 Hz) ppm. MS-ApCI: 403 [M+H⁺].

Example 281 tert-butyl(6aS,10aR)-2-[4-methoxy-2-(trifluoromethyl)phenyl]-4,5,7,8,10,10a-hexahydropyrido[4,3-b]pyrrolo[3,2,1-hi]indole-9(6aH)-carboxylate The title compound was prepared by the method of Example 89 step C from tert-butyl(6aS,10aR)-2-bromo-4,5,7,8,10,10a-hexahydropyrido[4,3-b]pyrrolo[3,2,1-hi]indole-9(6aH)carboxylate (189 mg, 0.5 mmol) and 4-methoxy-2-(trifluoromethyl)phenylboronic acid (248 mg, 1.0 mmol) to afford after chromatographic purification the title compound (196 mg, 83%). ¹H NMR (CDCl₃, 300 MHz) δ 7.21–7.26 (m,2H), 7.01–7.05 (m, 1H), 6.86 (s, 1H), 6.82 (s, 1H), 3.90–4.30 (m, 3H), 3.86 (s, 3H), 3.3.64–3.75 (m, 1H), 3.25–3.50 (m, 4H), 3.05–3.12 (m, 1H), 2.85–2.95 (m, 1H), 1.80–1.90 (m, 2H), 1.47 (s, 9H) ppm. MS-ApCI: 475 [M+H⁺].

Example 282

(6aS,10aR)-2-[4-methoxy-2-(trifluoromethyl)phenyl]-4,5,6a,7,8,9,10,10a-octahydropyrido[4,3-b]pyrrolo[3,2,1-hi]indole The title compound was prepared by the method of Example 98 from tert-butyl(6aS,10aR)-2-[4-methoxy-2-(trifluoromethyl)phenyl]-4,5,7,8,10,10a-hexahydropyrido[4,3-b]pyrrolo[3,2,1-hi]indole-9(6aH)-carboxylate to afford the title compound (94 mg, 61%). ¹H NMR (CDCl₃, 300 MHz) δ 7.20–7.25 (m, 2H), 7.02 (dd, 1H, J=8.6, 2.5 Hz), 6.85 (s, 1H), 6.77 (m, 1H), 3.86 (s, 1H), 3.64–3.74 (m, 1H), 3.26–3.48 (m, 3H), 3.02–3.24 (m, 3H), 2.82–2.98 (m, 3H), 1.74–1.96 (m, 3H) ppm. MS-ApCI: 375 [M+H⁺].

Example 283 tert-butyl(6aS,10aR)-2-phenyl-4,5,7,8,10,10a-hexahydropyrido[4,3-b]pyrrolo[3,2,1-hi]indole-9(6aH)-carboxylate The title compound was prepared by the method of Example 89 step C from tert-butyl(6aS,10aR)-2-bromo-4,5,7,8,10,10a-hexahydropyrido[4,3-b]pyrrolo[3,2,1-hi]indole-9(6aH)carboxylate (189 mg, 0.5 mmol) and phenylboronic acid (122 mg, 1.0 mmol) to afford after chromatographic purification the title compound (74 mg, 20%).
¹H NMR (CDCl₃, 300 MHz) δ 7.49 (d, 2H, J=7.7 Hz), 7.34–7.40 (m, 2H), 7.25–7.30 (m, 1H), 7.20 (s, 1H), 7.15 (s, 1H), 3.85–3.95 (m, 1H), 3.68–3.70 (m, 1H), 3.24–3.52 (m, 4H), 2.84–3.22 (m, 4H), 1.82–1.94 (m, 2H), 1.49 (s, 9H) ppm. MS-ApCI: 377 [M+H⁺].

Example 284

(6aS,10aR)-2-phenyl-4,5,6a,7,8,9,10,10a-octahydropyrido[4,3-b]pyrrolo[3,2,1-hi]indole The title compound was prepared by the method of Example 98 from tert-butyl(6aS,10aR)-2-phenyl-4,5,7,8,10,10a-hexahydropyrido[4,3-b]pyrrolo[3,2,1-hi]indole-9(6aH)-carboxylate to afford the title compound (35 mg, 64%). ¹H NMR (CDCl₃, 300 MHz) δ 7.49 (d, 2H, J=7.7 Hz), 7.34–7.40 (m, 2H), 7.22–7.27 (m, 1H), 7.19 (s, 1H), 7.13 (s, 1H), 3.68–3.73 (m, 1H), 2.98–3.56 (m, 6H), 2.82–2.96 (m, 3H), 1.70–1.96 (m, 2H), 1.63 (bs, 1H) ppm. MS-ApCI: 277 [M+H⁺].

Example 285 tert-butyl(6aS,10aR)-2-(2-methylphenyl)-4,5,7,8,10,10a-hexahydropyrido[4,3-b]pyrrolo[3,2,1-hi]indole-9(6aH)-carboxylate The title compound was prepared by the method of Example 89 step C from tert-butyl(6aS,10aR)-2-bromo-4,5,7,8,10,10a-hexahydropyrido[4,3-b]pyrrolo[3,2,1-hi]indole-9(6aH)carboxylate (189 mg, 0.5 mmol) and 2-methylphenylboronic acid (136 mg, 1.0 mmol) to afford after chromatographic purification the title compound (90 mg, 46%). $^1$H NMR (CDCl$_3$, 300 MHz) δ 7.11–7.18 (m,4H), 6.82 (s, 1H), 6.77 (s, 1H), 3.86–4.30 (m, 2H), 3.58–3.64 (m, 1H), 2.76–3.42 (m, 7H), 2.20 (s, 3H), 1.70–1.85 (m, 2H), 1.40 (s, 9H) ppm. MS-ApCI: 391 [M+H$^+$].

Example 286

(6aS,10aR)-2-(2-methylphenyl)-4,5,6a,7,8,9,10,10a-octahydropyrido[4,3-b]pyrrolo[3,2,1-hi]indole The title compound was prepared by the method of Example 98 from tert-butyl(6aS,10aR)-2-(2-methylphenyl)-4,5,7,8,10,10a-hexahydropyrido[4,3-b]pyrrolo[3,2,1-hi]indole-9(6aH)-carboxylate to afford the title compound (52 mg, 78%). $^1$H NMR (CDCl$_3$, 300 MHz) δ 7.09–7.18 (m, 4H), 6.80 (s, 1H), 6.74 (s, 1H), 3.59–3.65 (m, 1H), 2.93–3.42 (m, 6H), 2.74–2.87 (m, 3H), 2.20 (s, 3H), 1.66–1.85 (m, 2H), 1.51 (bs, 1H) ppm. MS-ApCI: 291 [M+H$^+$].

Example 287 tert-butyl(6aS,10aR)-2-[2-(trifluoromethyl)phenyl]-4,5,7,8,10,10a-hexahydropyrido[4,3-b]pyrrolo[3,2,1-hi]indole-9(6aH)-carboxylate The title compound was prepared by the method of Example 89 step C from tert-butyl(6aS,10aR)-2-bromo-4,5,7,8,10,10a-hexahydropyrido[4,3-b]pyrrolo[3,2,1-hi]indole-9(6aH)carboxylate (189 mg, 0.5 mmol) and 2-(trifluoromethyl)phenylboronic acid (190 mg, 1.0 mmol) to afford after chromatographic purification the title compound (175 mg, 79%). $^1$H NMR (CDCl$_3$, 300 MHz) δ 7.69 (d, 1H, J=7.7 Hz), 7.50 (dd, 1H, J=7.3, 7.7 Hz), 7.40 (dd, 1 H, J=7.7, 7.3 Hz), 7.31 (d, 1H, J=7.3 Hz), 6.89 (s, 1H), 6.85 (s, 1H), 3.82–4.30 (m, 2H), 3.66–3.71 (m, 1H), 2.88–3.50 (m, 7H), 1.80–1.90 (m, 2H), 1.47 (s, 9H) ppm. MS-ApCI: 445 [M+H$^+$].

Example 288

(6aS,10aR)-2-[2-(trifluoromethyl)phenyl]-4,5,6a,7,8,9,10,10a-octahydropyrido [4,3-b]pyrrolo[3,2,1-hi]indole The title compound was prepared by the method of Example 98 from tert-butyl(6aS,10aR)-2-[2-(trifluoromethyl)phenyl]-4,5,7,8,10,10a-hexahydropyrido[4,3-b]pyrrolo[3,2,1-hi]indole-9(6aH)-carboxylate to afford the title compound (92 mg, 68%). $^1$H NMR (CDCl$_3$, 300 MHz) δ 7.71 (d, 1H, J=7.6 Hz), 7.51 (dd, 1H, J=6.9, 7.4 Hz), 7.33–7.42 (m, 2H), 6.89 (s, 1H), 6.83 (s, 1H), 3.68–3.73 (m, 1H), 3.03–3.48 (m, 7H), 2.83–2.99 (m, 3H), 1.74–1.94 (m, 2H), 1.59 (bs, 1H) ppm. MS-ApCI: 345 [M+H$^+$].

Example 289 tert-butyl(6aS,10aR)-2-(3,4-dimethoxyphenyl)-4,5,7,8,10,10a-hexahydropyrido[4,3-b]pyrrolo[3,2,1-hi]indole-9(6aH)-carboxylate The title compound was prepared by the method of Example 89 step C from tert-butyl(6aS,10aR)-2-bromo-4,5,7,8,10,10a-hexahydropyrido[4,3-b]pyrrolo[3,2,1-hi]indole-9(6aH)carboxylate (189 mg, 0.5 mmol) and corresponding 3,4-dimethoxyphenyl boronic acid (182 mg, 1.0 mmol) to afford after chromatographic purification the title compound (92 mg, 42%). $^1$H NMR (CDCl$_3$, 300 MHz) δ 7.15 (s, 1H), 7.11(s, 1H), 7.01–7.04 (m, 2H), 6.89 (d, 1H, J=8.0 Hz), 4.02–4.10 (m, 1H), 3.92 (d, 6H, J=8.1 Hz), 3.64–3.78 (m, 1H), 2.82–3.52 (m, 8H), 1.82–1.90 (m, 2H), 1.49 (s, 9H) ppm. MS-ApCI: 437 [M+H$^+$].

Example 290

(6aS,10aR)-2-(3,4-dimethoxyphenyl)-4,5,6a,7,8,9,10,10a-octahydropyrido[4,3-b]pyrrolo[3,2,1-hi]indole The title compound was prepared by the method of Example 98 from tert-butyl(6aS,10aR)-2-(3,4-dimethoxyphenyl)-4,5,7,8,10,10a-hexahydropyrido[4,3-b]pyrrolo[3,2,1-hi]indole-9(6aH)-carboxylate to afford the title compound (52 mg, 73%). $^1$H NMR (CDCl$_3$, 300 MHz) δ 7.16 (s, 1H), 7.10 (s, 1H), 7.03–7.06 (m, 2H), 6.91(d, 1H, J=8.8 Hz), 3.93 (d, 6H, J=8.1 Hz), 3.69–3.75 (m, 1H), 2.83–3.52 (m, 9H), 1.74–1.94 (m, 3H) ppm. MS-ApCI: 337 [M+H$^+$].

Example 291 tert-butyl(6aS,10aR)-2-(2,5-dichlorophenyl)-4,5,7,8,10,10a-hexahydropyrido[4,3-b]pyrrolo[3,2,1-hi]indole-9(6aH)-carboxylate The title compound was prepared by the method of Example 89 step C from tert-butyl(6aS,10aR)-2-bromo-4,5,7,8,10,10a-hexahydropyrido[4,3-b]pyrrolo[3,2,1-hi]indole-9(6aH)carboxylate (189 mg, 0.5 mmol) and 2,5-dichlorophenylboronic acid (191 mg, 1.0 mmol) to afford after chromatographic purification the title compound (105 mg, 47%). $^1$H NMR (CDCl$_3$, 300 MHz) δ 7.30–7.36 (m, 2H), 7.15–7.19 (m, 1H), 7.01 (s, 1H), 3.82–4.22 (m, 2H), 3.82–3.96 (m, 1H), 2.82–3.52 (m, 7H), 1.82–1.90 (m, 2H), 1.48 (s, 9H) ppm. MS-ApCI: 445 [M+H$^+$].

Example 292

(6aS,10aR)-2-(2,5-dichlorophenyl)-4,5,6a,7,8,9,10,10a-octahydropyrido[4,3-b]pyrrolo[3,2,1-hi]indole The title compound was prepared by the method of Example 98 from tert-butyl(6aS,10aR)-2-(2,5-dichlorophenyl)-4,5,7,8,10,10a-hexahydropyrido[4,3-b]pyrrolo[3,2,1-hi]indole-9(6aH)-carboxylate to afford the title compound (60 mg, 74%). $^1$H NMR (CDCl$_3$, 300 MHz) δ 7.18–7.28 (m, 2H), 7.08 (dd, 1H, J=2.6, 8.4 Hz), 6.92 (s, 1H), 6.86 (s, 1H), 3.59–3.64 (m, 1H), 3.06–3.41 (m, 6H), 2.74–3.01 (m, 3H), 1.64–1.83 (m, 2H), 1.48 (bs, 1H) ppm. MS-ApCI: 345 [M+H$^+$].

Example 293 tert-butyl(6aS,10aR)-2-(3,5-dichlorophenyl)-4,5,7,8,10,10a-hexahydropyrido[4,3-b]pyrrolo[3,2,1-hi]indole-9(6aH)-carboxylate The title compound was prepared by the method of Example 89 step C from tert-butyl(6aS,10aR)-2-bromo-4,5,7,8,10,10a-hexahydropyrido[4,3-b]pyrrolo[3,2,1-hi]indole-9(6aH)carboxylate (189 mg, 0.5 mmol) and 3,5-dichlorophenylboronic acid (191 mg, 1.0 mmol) to afford after chromatographic purification the title compound (85 mg, 38%). $^1$H NMR (CDCl$_3$, 300 MHz) δ 7.35 (s, 2H), 7.21–7.23 (m, 1H), 7.13 (s, 1H), 7.10 (s, 1H), 3.82–4.22 (m, 2H), 3.65–3.75 (m, 1H), 2.84–3.52 (m, 7H), 1.80–1.90 (m, 2H), 1.49 (s, 9H) ppm. MS-ApCI: 445 [M+H$^+$].

Example 294

(6aS,10aR)-2-(3,5-dichlorophenyl)-4,5,6a,7,8,9,10,10a-octahydropyrido[4,3-b]pyrrolo[3,2,1-hi]indole The title compound was prepared by the method of Example 98 from tert-butyl(6aS,10aR)-2-(3,5-dichlorophenyl)-4,5,7,8,10,10a-hexahydropyrido[4,3-b]pyrrolo[3,2,1-hi]indole-9(6aH)-carboxylate to afford the title compound (60 mg, 74%). $^1$H NMR (CDCl$_3$, 300 MHz) δ 7.27 (d, 2H, J=1.9 Hz), 7.12–7.14 (m, 1H), 7.05 (s, 1H), 6.99 (s, 1H), 3.59–3.65 (m, 1H), 3.00–3.41 (m, 5H), 2.91–2.99 (m, 1H), 2.74–2.89 (m, 3H), 1.65–1.83 (m, 2H), 1.49 (bs, 1H) ppm. MS-ApCI: 345 [M+H$^+$].

Example 295 tert-butyl(6aS,10aR)-2-(2-isopropyl-4-methoxyphenyl)-4,5,7,8,10,10a-hexahydropyrido[4,3-b]pyrrolo[3,2,1-hi]indole-9(6aH)-carboxylate The title compound was prepared by the method of Example 89 step C from tert-butyl(6aS,10aR)-2-bromo-4,5,7,8,10,10a-hexahydropyrido[4,3-b]pyrrolo[3,2,1-hi]indole-9(6aH)carboxylate (189 mg, 0.5 mmol) and corresponding 2-isopropyl-4-methoxyphenyl boronic acid (178 mg, 1.0 mmol) to afford after chromatographic purification the title compound (152 mg, 68%). $^1$H NMR (CDCl$_3$, 300 MHz) δ 7.09 (d, 1H, J=8.4 Hz), 6.88 (d, 1H, J=2.5 Hz), 6.83 (s, 1H), 6.78 (s, 1H), 6.72 (dd, 1H, J=8.4, 2.9 Hz), 3.80–4.20 (m, 2H), 3.84 (s, 3H), 3.74–3.78 (m, 1H), 3.05–3.50 (m, 7H), 2.84–2.98 (m, 1H), 1.82–1.94 (m, 2H), 1.48 (s, 9H), 1.12–1.17 (m, 6H) ppm. MS-ApCI: 449. [M+H$^+$].

Example 296

(6aS,10aR)-2-(2-isopropyl-4-methoxyphenyl)-4,5,6a,7,8,9,10,10a-octahydropyrido[4,3-b]pyrrolo[3,2,1-hi]indole The title compound was prepared by the method of Example 98 from tert-butyl(6aS,10aR)-2-(2-isopropyl-4-methoxyphenyl)-4,5,7,8,10,10a-hexahydropyrido[4,3-b]pyrrolo[3,2,1-hi]indole-9(6aH)-carboxylate to afford the title compound (88 mg, 75%). $^1$H NMR (CDCl$_3$, 300 MHz) δ 7.10 (d, 1H, J=8.0 Hz), 6.87 (d, 1H, J=3.0 Hz), 6.81 (s, 1H), 6.70–6.75 (m, 2H), 3.84 (s, 3H), 3.67–3.73 (m, 1H), 3.01–3.50 (m, 7H), 2.82–2.94 (m, 3H), 1.73–1.93 (m, 2H), 1.67 (bs, 1H), 1.14 (m, 6H) ppm. MS-ApCI: 349 [M+H$^+$].

Example 297 tert-butyl(6aS,10aR)-2-(5-fluoro-4-methoxy-2-methylphenyl)-4,5,7,8,10,10a-hexahydropyrido[4,3-b]pyrrolo[3,2,1-hi]indole-9(6aH)-carboxylate The title compound was prepared by the method of Example 89 step C from tert-butyl(6aS,10aR)-2-bromo-4,5,7,8,10,10a-hexahydropyrido[4,3-b]pyrrolo[3,2,1-hi]indole-9(6aH)carboxylate (189 mg, 0.5 mmol) and corresponding 5-fluoro-4-methoxy-2-methylphenyl boronic acid (184 mg, 1.0 mmol) to afford after chromatographic purification the title compound (130 mg, 60%). $^1$H NMR (CDCl$_3$, 300 MHz) δ 6.94 (d, 1H, J=12.5 Hz), 6.84 (s, 1H), 6.79–6.82 (m, 2H), 4.02–4.22 (m, 1H), 3.90 (s, 3H), 3.82–3.92 (m, 1H), 3.64–3.74 (m, 1H), 3.24–3.54 (m, 4H), 2.86–3.22 (m, 3H), 2.22 (s, 3H), 1.82–1.94 (m, 2H), 1.48 (s, 9H) ppm. MS-ApCI: 439 [M+H$^+$].

Example 298

(6aS,10aR)-2-(5-fluoro-4-methoxy-2-methylphenyl)-4,5,6a,7,8,9,10,10a-octahydropyrido[4,3-b]pyrrolo[3,2,1-hi]indole The title compound was prepared by the method of Example 98 from tert-butyl(6aS,10aR)-2-(5-fluoro-4-methoxy-2-methylphenyl)-4,5,7,8,10,10a-hexahydropyrido[4,3-b]pyrrolo[3,2,1-hi]indole-9(6aH)-carboxylate to afford the title compound (85 mg, 85%). $^1$H NMR (CDCl$_3$, 300 MHz) δ 6.93 (d, 1H, J=13.1 Hz), 6.77–6.82 (m, 3H), 3.90 (s, 3H), 3.66–3.72 (m, 1H), 3.01–3.49 (m, 6H), 2.81–2.94 (m, 3H), 2.23 (s, 3H), 1.69–1.93 (m, 3H) ppm. MS-ApCI: 339 [M+H$^+$].

Example 299 tert-butyl(6aS,10aR)-2-(4-methoxy-2-methylphenyl)-4,5,7,8,10,10a-hexahydropyrido[4,3-b]pyrrolo[3,2,1-hi]indole-9(6aH)-carboxylate The title compound was prepared by the method of Example 89 step C from tert-butyl(6aS,10aR)-2-bromo-4,5,7,8,10,10a-hexahydropyrido[4,3-b]pyrrolo[3,2,1-hi]indole-9(6aH)carboxylate (189 mg, 0.5 mmol) and 4-methoxy-2-methylphenylboronic acid (166 mg, 1.0 mmol) to afford after chromatographic purification the title compound (105 mg, 50%). $^1$H NMR (CDCl$_3$, 300 MHz) δ 7.04 (d, 1H, J=8.5 Hz), 6.65–6.79 (m, 4H), 3.75–4.22 (m, 2H), 3.74 (s, 3H), 3.58–3.68 (m, 1H), 3.18–3.42 (m, 4H), 2.76–3.16 (m, 3H), 2.17 (s, 3H), 1.70–1.84 (m, 2H), 1.40 (s, 9H) ppm. MS-ApCI: 421 [M+H$^+$].

Example 300

(6aS,10aR)-2-(4-methoxy-2-methylphenyl)-4,5,6a,7,8,9,10,10a-octahydropyrido[4,3-b]pyrrolo[3,2,1-hi]indole The title compound was prepared by the method of Example 98 from tert-butyl(6aS,10aR)-2-(4-methoxy-2-methylphenyl)-4,5,7,8,10,10a-hexahydropyrido[4,3-b]pyrrolo[3,2,1-hi]indole-9(6aH)-carboxylate to afford the title compound (50 mg, 63%). $^1$H NMR (CDCl$_3$, 300 MHz) δ 7.14 (d, 1H, J=8.5 Hz), 6.85 (s, 1H), 6.73–6.79 (m, 3H), 3.82 (s, 3H), 3.67–3.69 (m, 1H), 3.02–3.50 (m, 6H), 2.82–2.94 (m, 3H), 2.26 (s, 3H), 1.73–1.93 (m, 2H), 1.63 (bs, 1H) ppm. MS-ApCI: 321 [M+H$^+$].

Example 301 tert-butyl(6aS,10aR)-2-(2-chloro-4-methoxyphenyl)-4,5,7,8,10,10a-hexahydropyrido[4,3-b]pyrrolo[3,2,1-hi]indole-9(6aH)-carboxylate The title compound was prepared by the method of Example 89 step C from tert-butyl(6aS,10aR)-2-bromo-4,5,7,8,10,10a-hexahydropyrido[4,3-b]pyrrolo[3,2,1-hi]indole-9(6aH)carboxylate (189 mg, 0.5 mmol) and 2-chloro-4-methoxyphenylboronic acid (187 mg, 1.0 mmol) to afford after chromatographic purification the title compound (133 mg, 60%). ¹H NMR (CDCl₃, 300 MHz) δ 7.23 (d, 1H, J=8.8 Hz), 7.01 (s, 2H), 6.97 (s, 1H), 6.84 (dd, 1H, J=8.5, 2.6 Hz), 3.84–4.24 (m, 2H), 3.84 (s, 3H), 3.68–3.74 (m, 1H), 3.24–3.54 (m, 4H), 2.86–3.26 (m, 3H), 1.84–1.8 (m, 2H), 1.49 (s, 9H) ppm. MS-ApCI: 441 [M+H⁺].

Example 302

(6aS10aR)-2-(2-chloro-4-methoxyphenyl)-4,5,6a,7,8,9,10,10a-octahydropyrido[4,3-b]pyrrolo[3,2,1-hi]indole The title compound was prepared by the method of Example 98 from tert-butyl(6aS,10aR)-2-(2-chloro-4-methoxyphenyl)-4,5,7,8,10,10a-hexahydropyrido[4,3-b]pyrrolo[3,2,1-hi]indole-9(6aH)-carboxylate to afford the title compound (66 mg, 64%). ¹H NMR (CDCl₃, 300 MHz) δ 7.24 (d, 1H, J=8.4 Hz), 7.00–7.01 (m, 2H), 6.94 (s, 1H), 6.83 (dd, 1H, J=8.7, 2.6 Hz), 3.84 (s, 3H), 3.68–3.74 (m, 1H), 3.02–3.51 (m, 6H), 2.85–2.95 (m, 3H), 1.76–1.93 (m, 2H), 1.63 (bs, 1H) ppm. MS-ApCI: 341 [M+H⁺].

Example 303 tert-butyl(6aS,10aR)-2-(3-chloro-2-methylphenyl)-4,5,7,8,10,10a-hexahydropyrido[4,3-b]pyrrolo[3,2,1-hi]indole-9(6aH)-carboxylate The title compound was prepared by the method of Example 89 step C from tert-butyl(6aS,10aR)-2-bromo-4,5,7,8,10,10a-hexahydropyrido[4,3-b]pyrrolo[3,2,1-hi]indole-9(6aH)carboxylate (189 mg, 0.5 mmol) and 3-chloro-2-methylphenylboronic acid (140 mg, 1.0 mmol) to afford after chromatographic purification the title compound (99 mg, 47%). ¹H NMR (CDCl₃, 300 MHz) δ 7.28–7.31 (m, 1H), 7.10 (d, 2H, J=4.4 Hz), 6.85 (s, 1H), 6.81 (s, 1H), 3.82–4.24 (m, 2H), 3.64–3.74 (m, 1H), 3.24–3.54 (m, 4H), 2.86–3.26 (m, 3H), 1.86 (s, 3H),1.84–1.89 (m, 2H), 1.48 (s, 9H) ppm. MS-ApCI: 425 [M+H⁺].

Example 304

(6aS,10aR)-2-(3-chloro-2-methylphenyl)-4,5,6a,7,8,9,10,10a-octahydropyrido[4,3-b]pyrrolo[3,2,1-hi]indole The title compound was prepared by the method of Example 98 from tert-butyl(6aS,10aR)-2-(3-chloro-2-methylphenyl)-4,5,7,8,10,10a-hexahydropyrido[4,3-b]pyrrolo[3,2,1-hi]indole-9(6aH)-carboxylate to afford the title compound (48 mg, 63%). ¹H NMR (CDCl₃, 300 MHz) δ 7.27–7.30 (m, 1H), 7.07–7.13 (m, 2H), 6.83 (s, 1H), 6.78 (s,1H), 3.67–3.73 (m, 1H), 3.01–3.50 (m, 6H), 2.83–2.94 (m, 3H), 2.29 (s, 3H), 1.75–1.93 (m, 2H), 1.62 (bs, 1H) ppm. MS-ApCI: 325 [M+H⁺].

Example 305

2-[(6aS,10aR)-4,5,6a,7,8,9,10,10a-octahydropyrido[4,3-b]pyrrolo[3,2,1-hi]-2-yl]-5-methoxybenzaldehyde Step A:

To a solution of tert-butyl(6aS,10aR)-2-bromo-4,5,7,8,10,10a-hexahydropyrido[4,3-b]pyrrolo[3,2,1-hi]indole-9(6aH)-carboxylate (0.600 g, 1.59 mmol) in DME (35 mL) was added 2-formyl-4-methoxybenzeneboronic acid (0.344 g, 1.91 mmol), tetrakis(triphenylphosphine)palladium(0) (0.110 g), barium hydroxide octahydrate (0.753 g, 2.39 mmol), and H₂O (10 mL). The combined mixture was refluxed for 20 h. Once at room temperature, the mixture was taken up in H₂O (300 mL) and extracted with EtOAc (3×100 mL). The combined extracts were dried over MgSO₄ and stripped of solvent under reduced pressure. Purification by normal phase HPLC using 25% EtOAc in hexanes afforded 0.280 g (41%) of tert-butyl(6aS,10aR)-2-(2-formyl-4-methoxyphenyl)-4,5,7,8,10,10a-hexahydropyrido[4,3-b]pyrrolo[3,2,1-hi]indole-9(6aH)-carboxylate.

Step B:

A solution of tert-butyl(6aS,10aR)-2-(2-formyl-4-methoxyphenyl)-4,5,7,8,10,10a-hexahydropyrido[4,3-b]pyrrolo[3,2,1-hi]indole-9(6aH)-carboxylate (0.066 g, 0.15 mmol) in CH₂Cl₂ (5 mL) was treated with TFA (2 mL) and stirred at room temperature for 18 h in a closed vial. The solution was basified with 1N NaOH (50 mL) and extracted with CH₂Cl₂ (3×25 mL). The combined extracts were dried over Na₂SO₄, and stripped of the solvent under reduced pressure to yield 0.042 g (82%) of 2-[(6aS,10aR)-4,5,6a,7,8,9,10,10a-octahydropyrido[4,3-b]pyrrolo[3,2,1-hi]-2-yl]-5-methoxybenzaldehyde as a foam. ¹H NMR (CDCl₃, 300 MHz) δ 7.45 (d, 1H), 7.35 (d, 1H), 7.16 (dd, 1H), 6.92 (d, 1H), 6.86 (d, 1H), 3.88 (s, 1H), 3.74 (td, 1H), 3.51–3.24 (m, 3H), 3.23–3.00 (m, 2H), 2.98–2.83 (m, 1H), 2.00–1.92 (m, 2H). MS (CI): 337 (M+H⁺).

Example 306

(6aS,10aR)-2-(2,6-dichlorophenyl)-4,5,6a,7,8,9,10,10a-octahydropyrido[4,3-b]pyrrolo[3,2,1-hi]indole The title compound was prepared by Example 305, Step A, from tert-butyl(6aS,10aR)-2-bromo-4,5,7,8,10,10a-hexahydropyrido[4,3-b]pyrrolo[3,2,1-hi]indole-9(6aH)-carboxylate and the corresponding 2,6-dichlorobenzeneboronic acid followed by hydrolysis of the resultant BOC protected amine adduct by the procedure of Example 305, Step B. ¹H NMR (CDCl₃, 300 MHz) δ 7.38 (dd, 2H), 7.15 (t, 1H), 6.80 (d, 1H), 6.73 (d, 1H), 3.69 (td, 1H), 3.57–3.30(m, 3H), 3.28–3.00 (m, 3H), 3.00–2.83 (m, 3H), 2.20 (bs, 2H), 2.00–1.81 (m, 2H). MS (CI): 346 (M+H⁺).

Example 307

N-[4-[(6aS,10aR)-4,5,6a,7,8,9,10,10a-octahydropyrido[4,3-b]pyrrolo[3,2,1-hi]indol-2-yl]-3-(trifluoromethyl)phenyl]-N-methylamine The title compound was prepared by Example 305, Step A, from tert-butyl(6aS,10aR)-2-bromo-4,5,7,8,10,10a-hexahydropyrido[4,3-b]pyrrolo[3,2,1-hi]indole-9(6aH)-carboxylate and the corresponding 2-(trifluoromethyl)benzeneboronic acid followed by hydrolysis of the resultant BOC protected amine adduct by the procedure of Example 305, Step B. ¹H NMR (CDCl₃, 300 MHz) δ 7.09 (d, 1H), 6.76 (dd, 21'), 6.70 (dd, 1H), 6.63 (dd, 2H), 3.80 (bs, 1H), 3.60 (t, 1H), 3.41–2.96 (m, 5H), 2.95–2.73 (m, 4H), 2.10 (bs, 2H), 1.98–1.75 (m, 2H). MS (CI): 374 (M+H⁺).

Example 308

4-[(6aS,10aR)-4,5,6a,7,8,9,10,10a-octahydropyrido[4,3-b]pyrrolo[3,2,1-h]indol-2-yl]-3-(trifluoromethyl)phenylamine The title compound was prepared by Example 305, Step A, from tert-butyl(6aS,10aR)-2-bromo-4,5,7,8,10,10a-hexahydropyrido[4,3-b]pyrrolo[3,2,1-hi]indole-9(6aH)-carboxylate and the corresponding 2-(trifluoromethyl)benzeneboronic acid followed by hydrolysis of the resultant BOC protected amine adduct by the procedure of Example 305, Step B. $^1$H NMR (CDCl$_3$, 300 MHz) δ 7.03 (d, 1H), 6.90 (d, 1H), 6.79–6.70 (m, 3H), 3.78 (bs, 1H), 3.60 (t, 1H), 3.41–3.18 (m, 2H), 3.17–2.79 (m, 5H), 2.27 (bs, 2H), 1.90–1.80 (m, 2H). MS (CI): 360 (M+H$^+$).

Example 309

1-(2-[(6aS,10aR)-4,5,6a,7,8,9,10,10a-octahydropyrido[4,3-b]pyrrolo[3,2,1-hi]indol-2-yl]-5-methoxyphenyl)ethanol To a solution of 2-[(6aS,10aR)-4,5,6a,7,8,9,10,10a-octahydropyrido[4,3-b]pyrrolo[3,2,1-hi]-2-yl]-5-methoxybenzaldehyde (0.156 g, 0.47 mmol) from Example 305 in freshly distilled THF (8 mL) at −78° C. was added 3.0 M methylmagnesiumbromide in diethylether (0.88 mL, 2.65 mmol). The reaction was stirred at room temperature for 18 h under a nitrogen atmosphere. The reaction mixture was quenched with aqueous ammonium chloride (20 mL) and extracted with EtOAc (3×10 mL). The combined extracts were dried over Na$_2$SO$_4$ and evaporated to dryness under reduced pressure to yield a 60% mixture of product and 40% starting material. Purification by reverse phase HPLC using a gradient of 0–100% water, acetonitrile with 0.1% TFA afforded 0.024 g (15%) of 1-(2-[(6aS,10aR)-4,5,6a,7,8,9,10,10a-octahydropyrido[4,3-b]pyrrolo[3,2,1-hi]indol-2-yl]-5-methoxyphenyl)ethanol after generation of the free base. $^1$H NMR (CDCl$_3$, 300 MHz) δ 7.18 (d, 1H), 7.13 (dd, 1H), 6.80 (dd, 2H), 6.77 (d, 1H), 5.03–4.96 (m, 1H), 3.85 (s, 3H), 3.68 (dt, 1H), 3.51–3.39 (m, 1H), 3.36–3.28 (m, 2H), 3.21–3.00 (m, 3H), 2.98–2.80 (m, 3H), 2.00–1.78 (m, 2H), 1.19 (q, 3H). MS (CI): 351 (M+H$^+$).

Example 310

(±)-cis-4,5,6,7,8a,9,10,11,12,12a-decahydroazepino[3,2,1-hi]pyrido[4,3-b]indole

Step A:

Sodium azide (1.95 g, 30 mmol) was added in small portions to a solution of 3,4-dihydro-[(2H)-naphthalenone (2.92 g, 20 mmol) in CH$_3$SO$_3$H (50 mL) at 0° C. The mixture was stirred at 0° C. for 15 min, 1 hr at room temperature, poured into ice (400 mL), basified until pH>8 with 1N NaOH at 0° C. and extracted with ether (3×100 mL). The combined organic layer was dried (MgSO$_4$), concentrated in vacuo and flash column chromatography (EtOAc:hexane/1:1) gave 1,3,4,5-tetrahydro-2H-1-benzazepin-2-one (2.71 g, 85%) as a white solid.]H NMR (CDCl$_3$, 300 MHz) δ 2.18–2.32 (m, 2H), 2.36 (t, J=7.1 Hz, 2H), 2.80 (t, J=7.6 Hz, 2H), 6.99 (d, J=8.1 Hz, 1H), 7.13 (td, J=7.6, 1.5 Hz, 1H), 7.22 (d, J=7.0 Hz, 2H), 8.10 (br, 1H) ppm.

Step B:

A solution of 1,3,4,5-tetrahydro-2H-1-benzazepin-2-one (2.71 g, 16.7 mmol) in THF (40 mL) was added dropwise to a suspension of LAH (1.27 g, 33.4 mmol) in ether (150 mL) at room temperature. The mixture was refluxed for 16 h. Saturated Rochelle's salt solution (15 mL) was added to the mixture cooled with an ice-water bath. The mixture was stirred for 2 hrs and the two layers were separated. The aqueous layer was extracted with ether (2×25 mL). The combined organic layer was dried (Na$_2$SO$_4$), concentrated in vacuo and flash column chromatography (EtOAc:hexane/3:7) gave 2,3,4,5-tetrahydro-1H-1-benzazepine (2.40 g, 98%) as a yellow liquid. $^1$H NMR (CDCl$_3$, 300 MHz) δ 1.58–1.70 (m, 2H), 1.72–1.86 (m, 2H), 2.72–2.82 (m, 2H), 3.00–3.10 (m, 2H), 3.78 (br, 1H), 6.74 (dd, J=1.1, 7.7 Hz, 1H), 6.82 (td, J=7.3, 1.1 Hz, 1H), 7.04 (td, J=7.5, 1.5 Hz, 1H), 7.11(d, J=7.4 Hz, 1H) ppm.

Step C:

A solution of sodium nitrite (1.35 g, 19.6 mmol) in water (4.0 mL) was added dropwise to a solution of 2,3,4,5-tetrahydro-1H-1-benzazepine (2.40 g, 16.3 mmol) in AcOH (10 mL) at 0–10° C. The mixture was stirred at 5° C. for 10 min, room temperature for 1 h and extracted with CH$_2$Cl$_2$ (3×20 mL). The organic layer was dried (MgSO$_4$), concentrated in vacuo and flash column chromatography (EtOAc:hexane/1:9) gave 1-nitroso-2,3,4,5-tetrahydro-1H-1-benzazepine (2.60 g, 91%) as a brown liquid. $^1$H NMR (CDCl$_3$, 300 MHz) δ 1.70–1.85 (m, 4H), 2.70–2.82 (m, 2H), 3.92 (br, 2H), 7.25–7.32 (m, 1H), 7.32–7.40 (m, 2H), 7.40–7.48 (m, 1H) ppm.

Step D:

A solution of 1-nitroso-2,3,4,5-tetrahydro-1H-1-benzazepine (2.60 g, 14.7 mmol) in THF (40 mL) was added dropwise under N$_2$ to a suspension of LAH (0.56 g, 14.7 mmol) in THF (10 mL) cooled with an ice-bath such that the temperature did not rise above 15° C. The mixture was stirred at room temperature for 1 h, quenched with saturated Rochelle's salt solution (15 mL) and extracted with ether (3×20 mL). The organic layer was dried (Na$_2$SO$_4$), concentrated in vacuo and flash column chromatography (EtOAc:hexane/1:4) gave 2,3,4,5-tetrahydro-1H-1-benzazepinamine (1.63 g, 68%) as a light yellow solid. $^1$H NMR (CDCl$_3$, 300 MHz) δ 1.50–1.72 (m, 2H), 1.78–1.92 (m, 2H), 2.70–2.82 (m, 2H), 3.180–3.22 (m, 2H), 3.78 (br, 2H), 6.91 (td, J=7.3, 1.5 Hz, 1H), 7.10 (dd, J=1.1, 7.4 Hz, 1H), 7.21 (td, J=8.0, 1.4 Hz, 1H), 7.28 (dd, J=1.4, 8.0 Hz, 1H) ppm.

Step E:

A mixture of 4-piperidone monohydrate HCl (1.54 g, 10 mmol) and 2,3,4,5-tetrahydro-1H-1-benzazepin-amine (1.62 g, 10 mmol) in IPA (50 mL) was refluxed for 2 h and cooled to room temperature. Concentrated HCl (0.82 mL, 10 mmol) was added and the resultant mixture was refluxed for 3 hrs before being cooled to room temperature. The solid was filtered, rinsed with cold IPA (2×20 mL) and concentrated in vacuo. 4,5,6,7,9,10,11,12-Octahydroazepino[3,2,1-hi]pyrido[4,3-b]indole hydrochloride (1.88 g, 71%) was obtained as a pink solid. 4,5,6,7,9,10,11,12-Octahydroazepino[3,2,1-hi]pyrido[4,3-b]indole hydrochloride (20 mg, 0.076 mmol) in water (1.0 mL) was basified with 1N NaOH until pH>14 and extracted with CHCl$_3$ (3×10 mL). The combined organic layer was washed with brine (10 mL), dried (MgSO$_4$) and concentrated in vacuo. 4,5,6,7,9,10,11,12-Octahydroazepino[3,2,1-hi]pyrido[4,3-b]indole (16 mg, 95%) was obtained as a white foam. $^1$H NMR (CDCl$_3$, 300 MHz) δ 1.83 (br, 1H), 2.00–2.20 (m, 4H), 2.72 (t, J=5.7 Hz, 2H), 3.05–3.20 (m, 2H), 3.25 (t, J=5.6 Hz, 2H), 3.92–4.02 (m, 2H), 4.05 (t, J=1.6 Hz, 2H), 6.92 (d, J=6.3 Hz, 1H), 6.98 (t, J=7.4 Hz, 1H), 7.25 (dd, J=1.0, 7.4 Hz, 1H) ppm.

Step F:

NaCNBH$_3$ (0.94 g, 15 mmol) was added in small portions to a solution of 4,5,6,7,9,10,11,12-octahydroazepino[3,2,1-hi]pyrido[4,3-b]indole hydrochloride (1.32 g, 5.0 mmol) in TFA (15 mL) at 0° C. After stirring at room temperature for 2 h, the mixture was carefully treated with 6 N HCl (10 mL) and refluxed for 1 h. The mixture was basified with 50% NaOH and extacted with CH$_2$Cl$_2$ (3×20 mL). The organic layer was dried (MgSO$_4$) and concentrated in vacuo. The title compound (1.0 g, 89%) was obtained as a yellow oil. $^1$H NMR (CDCl$_3$, 300 MHz) δ 1.48–1.68 (m, 1H), 1.68–2.10 (m, 7H), 2.42–2.72 (m, 3H), 2.80–3.00 (m, 3H), 3.05 (dd, J=6.3, 12.4 Hz, 1H), 3.12–3.55 (m, 2H), 6.69 (t, J=7.4 Hz, 1H), 6.92 (dd, J=2.5, 7.4 Hz, 2H) ppm.

Example 311 tert-butyl(±)-cis-4,5,6,7,8a,9,10,11,12,12a-decahydroazepino[3,2,1-hi]pyrido[4,3-b]indole-11(8aH)-carboxylate 1 N NaOH (10 mL) was added to a solution of (±)-cis-4,5,6,7,8a,9,10,11,12,12a-decahydroazepino[3,2,1-hi]pyrido[4,3-b]indole (1.00 g, 4.37 mmol) and di-tert-butyl dicarbonate (1.05 g, 4.8 mmol) in 1,4-dioxane (20 mL) and the mixture was stirred for 2 h at room temperature. The solvent was concentrated in vacuo and EtOAc (30 mL) was added. The solution was washed with brine (30 mL), dried (MgSO$_4$), concentrated in vacuo and flash column chromatography (EtOAc:hexane/1:4) gave the title compound (1.2 g, 83%) as a white solid.

Example 312

(8aS,12aR)-4,5,6,7,8a,9,10,11,12,12a-decahydroazepino[3,2,1-hi]pyrido[4,3-b]indole Step A:

Tert-Butyl (8aS,12aR)-4,5,6,7,9,10,12,12a-octahydroazepino[3,2,1-hi]pyrido[4,3-b]indole-11(8aH)-carboxylate was obtained from (±)-tert-butyl cis-4,5,6,7,9,10,12,12a-octahydroazepino[3,2,1-hi]pyrido[4,3-b]indole-11(8aH)-carboxylate by using preparative HPLC on a Chiracel® OD column (2% IPA in hexane).

Step B:

Tert-Butyl (8aS,12aR)-4,5,6,7,9,10,12,12a-octahydroazepino[3,2,1-hi]pyrido[4,3-b]indole-11(8aH)-carboxylate (0.24 g, 0.73 mmol) was stirred in 20% TFA in CH$_2$Cl$_2$ (10 mL) at room temperature for 2 h before the solution was basified with saturated NH$_4$OH until pH>10. The layers were separated and the aqueous layer was extracted with CH$_2$Cl$_2$ (3×20 mL). The combined organic layer was washed with brine (20 mL), dried (MgSO$_4$) and concentrated in vacuo. The title compound (0.16 g, 94%) was obtained as a white foam. $^1$H NMR was identical to (±)-cis-4,5,6,7,8a,9,10,11,12,12a-decahydroazepino[3,2,1-hi]pyrido[4,3-b]indole of Example 310.

Example 313

(8aR,12aS)-4,5,6,7,8a,9,10,11,12,12a-decahydroazepino[3,2,1-hi]pyrido[4,3-b]indole Step A:

Tert-butyl(8aR,12aS)-4,5,6,7,9,10,12,12a-octahydroazepino[3,2,1-hi]pyrido[4,3-b]indole-11(8aH)-carboxylate was obtained from (±)-tert-butyl cis-4,5,6,7,9,10,12,12a-octahydroazepino[3,2,1-hi]pyrido[4,3-b]indole-11(8aH)-carboxylate by using preparative HPLC on a Chiracel® OD column (2% IPA in hexane).

Step B:

The title compound (0.063 g, 98%) was prepared by the general method of Example 312, step B from tert-butyl(8aR,12aS)-4,5,6,7,9,10,12,12a-octahydroazepino[3,2,1-hi]pyrido[4,3-b]indole-11(8aH)-carboxylate (0.092 g, 0.28 mmol) as a white foam. $^1$H NMR was identical to (±)-cis-4,5,6,7,8a,9,10,11,12,12a-decahydroazepino[3,2,1-hi]pyrido[4,3-b]indole of Example 310.

Example 314 tert-butyl(8aS,12aR)-2-bromo-4,5,6,7,8a,9,10,11,12,12a-decahydroazepino[3,2,1-hi]pyrido[4,3-b]indole-11(8aH)-carboxylate A solution of NBS (0.29 g, 1.6 mmol) in DMF (2.0 mL) was added dropwise to a solution of tert-butyl(8aS,12aR)-4,5,6,7,9,10,12,12a-octahydroazepino[3,2,1-hi]pyrido[4,3-b]-indole-11(8aH)-carboxylate (0.53 g, 1.6 mmol) in DMF (3.0 mL) at 0° C. The mixture was stirred at 0° C. for 15 min and room temperature for 0.5 h before poured into water (10 mL). The milky mixture was extracted with EtOAc (3×10 mL) and the extract was dried (MgSO$_4$), concentrated in vacuo and flash column chromatography (EtOAc:hexane/1:4) gave the title compound (0.58 g, 89%) as a white solid.

Example 315

(8aS,12aR)-2-(2,4-dichlorophenyl)-4,5,6,7,8a,9,10,11,12,12a-decahydroazepino[3,2,1-hi]pyrido[4,3-b]indole Step A:

A mixture of tert-butyl(8aS,12aR)-2-bromo-4,5,6,7,9,10,12,12a-octahydroazepino[3,2,1-hi]pyrido[4,3-b]indole-11(8aH)-carboxylate (0.20 g, 0.50 mmol), 2,4-dichlorophenylboronic acid (0.19 g, 1.0 mmol), Ba(OH)$_2$·8H$_2$O (0.32 g, 1.0 mmol), Pd$_2$(dba)$_3$ (7.5 mg, 0.0075 mmol) and PPh$_3$ (5.24 mg, 0.02 mmol) in DME (10 mL) and water (2.5 mL) was degassed and refluxed for 18 h and cooled to room temperature. The mixture was concentrated in vacuo and EtOAc (20 mL) was added. The solution was washed with saturated Na$_2$CO$_3$ (2×10 mL), dried (Na$_2$SO$_4$), concentrated in vacuo and flash column chromatography (EtOAc:hexane/1:9) gave tert-butyl(8aS,12aR)-2-(2,4-dichlorophenyl)-4,5,6,7,8a,9,10,11,12,12a-decahydroazepino[3,2,1-hi]pyrido[4,3-b]indole-11(8aH)-carboxylate (0.16 g, 66%) as a white foam.

Step B:

The title compound (0.087 g, 77%) was prepared by the general method of Example 312, step B from tert-butyl(8aS,12aR)-2-(2,4-dichlorophenyl)-4,5,6,7,8a,9,10,11,12,12a-decahydroazepino[3,2,1-hi]pyrido[4,3-b]indole-11(8aH)-carboxylate (0.14 g, 0.30 mmol) as a white foam. $^1$H NMR (CDCl$_3$, 300 MHz) δ 1.50–1.70 (m, 1H), 1.70–1.90 (m, 2H), 1.90–2.10 (m, 4H), 2.48–2.80 (m, 3H), 2.80–3.00 (m, 3H), 3.04 (dd, J=6.3, 12.4 Hz, 1H), 3.10–3.25 (m, 1H), 3.25–3.42 (m, 2H), 6.96 (s, 1H), 7.00 (s, 1H), 7.20–7.30 (m, 2H), 7.44 (d, J=1.1 Hz, 1H) ppm.

Example 316

(8aS,12aR)-2-(2,3-dichlorophenyl)-4,5,6,7,8a,9,10,11,12,12a-decahydroazepino[3,2,1-hi]pyrido[4,3-b]indole Step A:

Tert-butyl(8aS,12aR)-2-(2,3-dichlorophenyl)-4,5,6,7,8a,9,10,11,12,12a-decahydroazepino[3,2,1-hi]pyrido[4,3-b]indole-11(8aH)-carboxylate (0.14 g, 59%) was prepared by the general method of Example 89, step C from tert-butyl (8aS,12aR)-2-bromo-4,5,6,7,9,10,12,12a-octahydroazepino[3,2,1-hi]pyrido[4,3-b]indole-11(8aH)-carboxylate (0.20 g, 0.50 mmol), 2,3-dichlorophenyl boronic acid (0.19 g, 1.0 mmol), Pd(PPh$_3$)$_2$Cl$_2$ (17 mg, 0.025 mmol), Na$_2$CO$_3$(2.0 M, 1.0 mL, 2.0 mmol) as a white foam.

Step B:

The title compound (0.10 g, 92%) was prepared by the general method of Example 312, step B from tert-butyl(8aS,12aR)-2-(2,3-dichlorophenyl)-4,5,6,7,8a,9,10,11,12,12a-decahydroazepino[3,2,1-hi]pyrido[4,3-b]indole-11(8aH)-carboxylate (0.14 g, 0.30 mmol) as a white foam. $^1$H NMR (CDCl$_3$, 300 MHz) δ 1.50–1.70 (m, 1H), 1.70–1.92 (m, 21H), 1.92–2.08 (m, 3H), 2.15–2.80 (m, 4H), 2.80–3.00 (m, 3H), 3.05 (dd, J=6.3, 12.4 Hz, 1H), 3.10–3.34 (m, 2H), 3.34–3.42 (m, 1H), 6.96 (d, J=1.6 Hz, 1H), 7.00 (d, J=1.6 Hz, 1H), 7.12–7.25 (m, 2H), 7.38 (dd, J=2.4, 7.2 Hz, 1H) ppm. MS (ESI): 373 (base, M+H).

Example 317

(8aS,12aR)-2-(3,4-dichlorophenyl)-4,5,6,7,8a,9,10,11,12,12a-decahydroazepino[3,2,1-hi]pyrido[4,3-b]indole Step A:

Tert-butyl(8aS,12aR)-2-(3,4-dichlorophenyl)-4,5,6,7,8a,9,10,11,12,12a-decahydroazepino[3,2,1-hi]pyrido[4,3-b]indole-11(8aH)-carboxylate (0.070 g, 30%) was prepared by the general method of Example 89, step C from tert-butyl (8aS,12aR)-2-bromo-4,5,6,7,9,10,12,12a-octahydroazepino[3,2,1-hi]pyrido[4,3-b]indole-11(8aH)-carboxylate (0.20 g, 0.50 mmol), 3,4-dichlorophenyl boronic acid (0.19 g, 1.0 mmol), Pd(PPh$_3$)$_2$Cl$_2$ (17 mg, 0.025 mmol), Na$_2$CO$_3$(2.0 M, 1.0 mL, 2.0 mmol) as a white foam.

Step B:

The title compound (0.040 g, 72%) was prepared by the general method of Example 312, step B from tert-butyl(8aS,12aR)-2-(3,4-dichlorophenyl)-4,5,6,7,8a,9,10,11,12,12a-decahydroazepino[3,2,1-hi]pyrido[4,3-b]indole-11(8aH)-carboxylate (0.070 g, 0.15 mmol) as a white foam. $^1$H NMR (CDCl$_3$, 300 MHz) δ 1.50–1.70 (m, 1H), 1.70–1.92 (m, 2H), 1.92–2.10 (m, 3H), 2.23 (br, 1H), 2.48–2.80 (m, 3H), 2.80–3.00 (m, 3H), 3.06 (dd, J=6.3, 12.4 Hz, 1H), 3.14–3.25 (m, 1H), 3.25–3.40 (m, 2H), 7.11(s, 2H), 7.35 (dd, J=2.2, 8.4 Hz, 1H), 7.42 (d, J=8.4 Hz, 1H), 7.61 (d, J=2.2 Hz, 1H) ppm.

Example 318

(8aS,12aR)-2-(3,5-dichlorophenyl)-4,5,6,7,8a,9,10,11,12,12a-decahydroazepino[3,2,1-hi]pyrido[4,3-b]indole Step A:

Tert-butyl(8aS,12aR)-2-(3,5-dichlorophenyl)-4,5,6,7,8a,9,10,11,12,12a-decahydroazepino[3,2,1-hi]pyrido[4,3-b]indole-11(8aH)-carboxylate (0.13 g, 55%) was prepared by the general method of Example 89, step C from tert-butyl (8aS,12aR)-2-bromo-4,5,6,7,9,10,12,12a-octahydroazepino[3,2,1-hi]pyrido[4,3-b]indole-11(8aH)-carboxylate (0.20 g, 0.50 mmol), 3,5-dichlorophenyl boronic acid (0.19 g, 1.0 mmol), Pd(PPh$_3$)$_2$Cl$_2$ (17 mg, 0.025 mmol), Na$_2$CO$_3$(2.0 M, 1.0 mL, 2.0 mmol) as a white foam. MS (ESI): 473 (base, M+H).

Step B:

The title compound (0.10 g, 92%) was prepared by the general method of Example 312, step B from tert-butyl(8aS,12aR)-2-(3,5-dichlorophenyl)-4,5,6,7,8a,9,10,11,12,12a-decahydroazepino[3,2,1-hi]pyrido[4,3-b]indole-11(8aH)-carboxylate (0.14 g, 0.30 mmol) as a white foam. $^1$H NMR (CDCl$_3$, 300 MHz) δ 1.50–1.70 (m, 1H), 1.70–1.90 (m, 2H), 1.90–2.15 (m, 5H), 2.48–65 (m, 2H), 2.65–2.80 (m, 1H), 2.82–2.90 (m, 2H), 3.07 (dd, J=6.3, 12.4 Hz, 1H), 3.12–3.26 (m, 1H), 3.26–3.40 (m, 2H), 7.10 (s, 2H), 7.22 (t, J=1.8 Hz, 2H), 7.39 (d, J=1.8 Hz, 2H) ppm. MS (ESI): 373 (base, M+H).

Example 319

(8aS,12aR)-2-(2,5-dichlorophenyl)-4,5,6,7,8a,9,10,11,12,12a-decahydroazepino[3,2,1-hi]pyrido[4,3-b]indole Step A:

A mixture of tert-butyl(8aS,12aR)-2-bromo-4,5,6,7,9,10,12,12a-octahydroazepino[3,2,1-hi]pyrido[4,3-b]indole-11(8aH)-carboxylate (0.10 g, 0.25 mmol), 2,5-dichlorophenyl boronic acid (0.10 g, 0.50 mmol) and Ba(OH)$_2$ (0.17 M, 3.0 mL, 0.51 mmol) in DME (15 mL) was degassed at 40–50° C. before Pd(PPh$_3$)$_4$ (12 mg, 0.010 mmol) was added. The mixture was degassed again as described before and refluxed for 16 h. The mixture was concentrated in vacuo and EtOAc (20 mL) was added. The solution was washed with saturated Na$_2$CO$_3$(2×10 mL), dried (Na$_2$SO$_4$), concentrated in vacuo and flash column chromatography (EtOAc:hexane/1:9) gave tert-butyl(8aS,12aR)-2-(2,5-dichlorophenyl)-4,5,6,7,8a,9,10,11,12,12a-decahydroazepino[3,2,1-hi]pyrido[4,3-b]indole-11(8aH)-carboxylate (0.098 g, 83%) as a white foam. MS (ESI): 473 (base, M+H).

Step B:

The title compound (0.077 g, 100%) was prepared by the general method of Example 312, step B from tert-butyl(8aS,12aR)-2-(2,5-dichlorophenyl)-4,5,6,7,8a,9,10,11,12,12a-decahydroazepino[3,2,1-hi]pyrido[4,3-b]indole-11(8aH)-carboxylate (0.098 g, 0.21 mmol) as a white foam. $^1$H NMR (CDCl$_3$, 300 MHz) δ 1.50–1.70 (m, 2H), 1.70–1.90 (m, 2H), 1.90–2.10 (m, 3H), 2.48–2.80 (m, 3H), 2.85–3.00 (m, 3H), 3.08 (dd, J=6.3, 12.4 Hz, 1H), 3.15–3.35 (m, 2H), 3.35–3.44 (m, 1H), 6.98 (s, 1H), 7.02 (s, 1H), 7.18 (dd, J=2.6, 8.6 Hz, 1H), 7.32 (d, J=2.6 Hz, 1H), 7.35 (d, J=8.6 Hz, 1H) ppm. MS (ESI): 373 (base, M+H).

Example 320

(8aS,12aR)-2-(2,6-dichlorophenyl)-4,5,6,7,8a,9,10, 11,12,12a-decahydroazepino[3,2,1-hi]pyrido[4,3-b] indole Step A:

A mixture of tert-butyl(8aS,12aR)-2-bromo-4,5,6,7,9,10, 12,12a-octahydroazepino[3,2,1-hi]pyrido[4,3-b]indole-11 (8aH)-carboxylate (0.10 g, 0.25 mmol), 2,6-dichlorophenylboronic acid (0.10 g, 0.50 mmol), Pd(dppf)$_2$Cl$_2$ (10 mg, 0.012 mmol) and TEA (1.0 mL, 7.2 mmol) in DME (15 mL) was degassed at 40–50° C. and refluxed for 32 h. The mixture was concentrated in vacuo and EtOAc (20 mL) was added. The solution was washed with saturated Na$_2$CO$_3$(2× 10 mL), dried (Na$_2$SO$_4$) and concentrated in vacuo. Normal phase HPLC (5% EtOAc in hexane) gave tert-butyl(8aS, 12aR)-2-(2,6-dichlorophenyl)-4,5,6,7,8a,9,10,11,12,12a-decahydroazepino[3,2,1-hi]pyrido[4,3-b]indole-11(8aH)-carboxylate (0.030 g, 26%) as a white foam. MS (ESI): 473 (base, M+H).

Step B:

The title compound (0.025 g, 100%) was prepared by the general method of Example 312, step B from tert-butyl(8aS, 12aR)-2-(2,6-dichlorophenyl)-4,5,6,7,8a,9,10,11,12,12a-decahydroazepino[3,2,1-hi]pyrido[4,3-b]indole-11(8aH)-carboxylate (0.030 g, 0.060 mmol) as a white foam. $^1$H NMR (CDCl$_3$, 300 MHz) δ 1.50–1.70 (m, 1H), 1.70–1.88 (m, 2H), 1.88–2.10 (m, 3H), 2.48–2.80 (m, 4H), 2.82–3.00 (m, 3H), 3.06 (dd, J=6.3, 12.4 Hz, 1H), 3.15–3.38 (m, 2H), 3.38–3.44 (m, 1H), 6.79 (s, 2H), 7.14 (t, J=8.0 Hz, 1H), 7.35 (d, J=8.0 Hz, 2H) ppm. MS (ESI): 373 (base, M+H).

Example 321

(8aS,12aR)-2-(2-chlorophenyl)-4,5,6,7,8a,9,10,11, 12,12a-decahydroazepino[3,2,1-hi]pyrido[4,3-b] indole Step A:

Tert-butyl(8aS,12aR)-2-(2-chlorophenyl)-4,5,6,7,8a,9,10, 11,12,12a-decahydroazepino[3,2,1-hi]pyrido[4,3-b]indole-11(8aH)-carboxylate (0.15 g, 67%) was prepared by the general method of Example 89, step C from tert-butyl(8aS, 12aR)-2-bromo-4,5,6,7,9,10,12,12a-octahydroazepino[3,2, 1-hi]pyrido[4,3-b]indole-11(8aH)-carboxylate (0.20 g, 0.50 mmol), 2-chlorophenylboronic acid (0.16 g, 1.0 mmol), Pd(PPh$_3$)$_2$Cl$_2$ (17 mg, 0.025 mmol), Na$_2$CO$_3$(2.0 M, 1.0 mL, 2.0 mmol) as a white foam. MS (ESI): 439 (base, M+H).

Step B:

The title compound (0.087 g, 77%) was prepared by the general method of Example 312, step B from tert-butyl(8aS, 12aR)-2-(2-chlorophenyl)-4,5,6,7,8a,9,10,11,12,12a-decahydroazepino[3,2,1-hi]pyrido[4,3-b]indole-11(8aH)-carboxylate (0.15 g, 0.33 mmol) as a white foam. $^1$H NMR (CDCl$_3$, 300 MHz) δ 1.50–1.70 (m, 1H), 1.70–2.10 (m, 5H), 2.48–2.78 (m, 3H), 2.88–3.02 (m, 3H), 3.10 (dd, J=6.3, 12.4 Hz, 1H), 3.20–3.35 (m, 2H), 3.35–3.42 (m, 1H), 3.63 (br, 1H), 7.01 (s, 1H), 7.05 (s, 1H), 7.15–7.35 (m, 3H), 7.43 (dd, J=1.7, 7.5 Hz, 1H) ppm. MS (ESI): 339 (base, M+H).

Example 322

(8aS,12aR)-2-(3-chlorophenyl)-4,5,6,7,8a,9,10,11, 12,12a-decahydroazepino[3,2,1-hi]pyrido[4,3-b] indole Step A:

Tert-butyl(8aS,12aR)-2-(3-chlorophenyl)-4,5,6,7,8a,9,10, 11,12,12a-decahydroazepino[3,2,1-hi]pyrido[4,3-b]indole-11(8aH)-carboxylate (0.12 g, 55%) was prepared by the general method of Example 89, step C from tert-butyl(8aS, 12aR)-2-bromo-4,5,6,7,9,10,12,12a-octahydroazepino[3,2, 1-hi]pyrido[4,3-b]indole-11(8aH)-carboxylate (0.20 g, 0.50 mmol), 3-chlorophenylboronic acid (0.16 g, 1.0 mmol), Pd(PPh$_3$)$_2$Cl$_2$ (17 mg, 0.025 mmol), Na$_2$CO$_3$(2.0 M, 1.0 mL, 2.0 mmol) as a white foam. MS (ESI): 439 (base, M+H).

Step B:

The title compound (0.045 g, 100%) was prepared by the general method of Example 312, step B from tert-butyl(8aS, 12aR)-2-(3-chlorophenyl)-4,5,6,7,8a,9,10,11,12,12a-decahydroazepino[3,2,1-hi]pyrido[4,3-b]indole-11(8aH)-carboxylate (0.058 g, 0.13 mmol) as a white foam. $^1$H NMR (CDCl$_3$, 300 MHz) δ 1.43 (br, 1H), 1.50–1.70 (m, 1H), 1.70–2.10 (m, 5H), 2.40–2.80 (m, 3H), 2.80–3.00 (m, 3H), 3.08 (dd, J=6.3, 12.4 Hz, 1H), 3.10–3.42 (m, 3H), 7.14 (s, 2H), 7.21 (d, J=7.5 Hz, 1H), 7.30 (t, J=7.8 Hz, 1H), 7.41 (d, J=7.8 Hz, 1H), 7.52 (s, 1H) ppm. MS (ESI): 339 (base, M+H).

Example 323

(8aS,12aR)-2-(4-chlorophenyl)-4,5,6,7,8a,9,10,11, 12,12a-decahydroazepino[3,2,1-hi]pyrido[4,3-b] indole Step A:

Tert-butyl(8aS,12aR)-2-(4-chlorophenyl)-4,5,6,7,8a,9,10, 11,12,12a-decahydroazepino[3,2,1-hi]pyrido[4,3-b]indole-11(8aH)-carboxylate (0.11 g, 50%) was prepared by the general method of Example 89, step C from tert-butyl(8aS, 12aR)-2-bromo-4,5,6,7,9,10,12,12a-octahydroazepino[3,2, 1-hi]pyrido[4,3-b]indole-11(8aH)-carboxylate (0.20 g, 0.50 mmol), 4-chlorophenylboronic acid (0.16 g, 1.0 mmol), Pd(PPh$_3$)$_2$Cl$_2$ (17 mg, 0.025 mmol), Na$_2$CO$_3$(2.0 M, 1.0 mL, 2.0 mmol) as a white foam. MS (ESI): 439 (base, M+H).

Step B:

The title compound (0.084 g, 99%) was prepared by the general method of Example 312, step B from tert-butyl(8aS, 12aR)-2-(4-chlorophenyl)-4,5,6,7,8a,9,10,11,12,12a-decahydroazepino[3,2,1-hi]pyrido[4,3-b]indole-11(8aH)-carboxylate (0.11 g, 0.25 mmol) as a white foam. $^1$H NMR (CDCl$_3$, 300 MHz) δ 1.50–1.70 (m, 1H), 1.70–2.10 (m, 5H), 2.48–2.80 (m, 3H), 2.80–3.05 (m, 4H), 3.12 (dd, J=6.3, 12.4 Hz, 1H), 3.20–3.42 (m, 3H), 7.14 (s, 2H), 7.36 (d, J=8.4 Hz, 2H), 7.46 (d, J=8.4 Hz, 2H) ppm. MS (ESI): 339 (base, M+H).

Example 324

(±)-cis-2-(2,6-difluorophenyl)-4,5,6,7,8a,9,10,11,12, 12a-decahydroazepino[3,2,1-hi]pyrido[4,3-b]indole Step A:

Tert-butyl(±)-2-(2,6-difluorophenyl)-4,5,6,7,8a,9,10,11, 12,12a-decahydroazepino[3,2,1-hi]pyrido[4,3-b]indole-11 (8aH)-carboxylate (0.045 g, 21%) was prepared by the general method of Example 320, step A from tert-butyl(±)-2-bromo-4,5,6,7,9,10,12,12a-octahydroazepino[3,2,1-hi]pyrido[4,3-b]indole-11(8aH)-carboxylate (0.20 g, 0.50 mmol), 2,6-difluorophenylboronic acid (0.32 g, 2.0 mmol), Pd(dppf)$_2$Cl$_2$ (24 mg, 0.030 mmol), TEA (1.6 mL, 11 mmol) as a white foam.

Step B:

The title compound (0.017 g, 49%) was prepared by the general method of Example 312, step B from tert-butyl(8aS,12aR)-2-(2,6-difluorophenyl)-4,5,6,7,8a,9,10,11,12,12a-decahydroazepino[3,2,1-hi]pyrido[4,3-b]indole-11(8aH)-carboxylate (0.045 g, 0.10 mmol) as a white foam. $^1$H NMR (CDCl$_3$, 300 MHz) δ 1.50–1.70 (m, 1H), 1.70–2.10 (m, 5H), 2.50–2.80 (m, 3H), 2.80–3.05 (m, 3H), 3.05–3.20 (m, 2H), 3.20–3.35 (m, 2H), 3.35–3.42 (m, 1H), 6.94 (t, J=8.1 Hz, 2H), 7.04 (s, 2H), 7.15–7.22 (m, 1H) ppm.

Example 325

(8aS,12aR)-2-(2,6-difluorophenyl)-4,5,6,7,8a,9,10,11,12,12a-decahydroazepino[3,2,1-hi]pyrido[4,3-b]indole Step A:

Tert-butyl(8aS,12aR)-2-(2,6-difluorophenyl)-4,5,6,7,8a,9,10,11,12,12a-decahydroazepino[3,2,1-hi]pyrido[4,3-b]indole-11(8aH)-carboxylate (0.040 g, 18%) was prepared by the general method of Example 320, step A from tert-butyl (8aS,11aR)-2-bromo-4,5,6,7,9,10,12,12a-octahydroazepino[3,2,1-hi]pyrido[4,3-b]indole-11(8aH)-carboxylate (0.20 g, 0.50 mmol), 2,6-difluorophenylboronic acid (0.32 g, 2.0 mmol), Pd(dppf)$_2$Cl$_2$ (24 mg, 0.030 mmol), TEA (1.6 mL, 11 mmol) as a white foam.

Step B:

The title compound (9.0 mg, 29%) was prepared by the general method of Example 312, step B from tert-butyl(8aS,12aR)-2-(2,6-difluorophenyl)-4,5,6,7,8a,9,10,11,12,12a-decahydroazepino[3,2,1-hi]pyrido[4,3-b]indole-11(8aH)-carboxylate (0.040 g, 0.091 mmol) as a white foam. $^1$H NMR was identical to that of (±)-cis-2-(2,6-difluorophenyl)-4,5,6,7,8a,9,10,11,12,12a-decahydroazepino[3,2,1-hi]pyrido[4,3-b]indole Example 326

(8aS,12aR)-2-(2,3-difluorophenyl)-4,5,6,7,8a,9,10,11,12,12a-decahydroazepino[3,2,1-hi]pyrido[4,3-b]indole Step A:

Tert-butyl(8aS,12aR)-2-(2,3-difluorophenyl)-4,5,6,7,8a,9,10,11,12,12a-decahydroazepino[3,2,1-hi]pyrido[4,3-b]indole-11(8aH)-carboxylate (0.069 g, 63%) was prepared by the general method of Example 319, step A from tert-butyl (8aS,12aR)-2-bromo-4,5,6,7,9,10,12,12a-octahydroazepino[3,2,1-hi]pyrido[4,3-b]indole-11(8aH)-carboxylate (0.10 g, 0.25 mmol), 2,3-difluorophenylboronic acid (0.080 g, 0.5 mmol), Pd(PPh$_3$)$_4$ (12 mg, 0.010 mmol), and Ba(OH)$_2$ (0.17 M, 3.0 mL, 0.51 mmol) as a white foam. MS (ESI): 441 (base, M+H).

Step B:

The title compound (0.053 g, 100%) was prepared by the general method of Example 312, step B from tert-butyl(8 as,12aR)-2-(2,3-difluorophenyl)-4,5,6,7,8a,9,10,11,12,12a-decahydroazepino[3,2,1-hi]pyrido[4,3-b]indole-11(8aH)-carboxylate (0.069 g, 0.16 mmol) as a white foam. $^1$H NMR (CDCl$_3$, 300 MHz) δ 1.50–1.70 (m, 1H), 1.70–2.10 (m, 5H), 2.48–2.80 (m, 3H), 2.85–3.02 (m, 3H), 3.12 (dd, J=6.3, 12.4 Hz, 1H), 3.20–3.60 (m, 4H), 7.00–7.22 (m, 5H) ppm. MS (ESI): 341 (base, M+H).

Example 327

(8aS,12aR)-2-(3,4-difluorophenyl)-4,5,6,7,8a,9,10,11,12,12a-decahydroazepino[3,2,1-hi]pyrido[4,3-b]indole Step A:

Tert-butyl(8aS,12aR)-2-(3,4-difluorophenyl)-4,5,6,7,8a,9,10,11,12,12a-decahydroazepino[3,2,1-hi]pyrido[4,3-b]indole-11(8aH)-carboxylate (0.078 g, 71%) was prepared by the general method of Example 319, step A from tert-butyl (8aS,12aR)-2-bromo-4,5,6,7,9,10,12,12a-octahydroazepino[3,2,1-hi]pyrido[4,3-b]indole-11(8aH)-carboxylate (0.10 g, 0.25 mmol), 3,4-difluorophenylboronic acid (0.080 g, 0.50 mmol), Pd(PPh$_3$)$_4$ (12 mg, 0.010 mmol), and Ba(OH)$_2$ (0.17 M, 3.0 mL, 0.51 mmol) as a white foam. MS (ESI): 441 (base, M+H).

Step B:

The title compound (0.055 g, 92%) was prepared by the general method of Example 312, step B from tert-butyl(8aS,12aR)-2-(3,4-difluorophenyl)-4,5,6,7,8a,9,10,11,12,12a-decahydroazepino[3,2,1-hi]pyrido[4,3-b]indole-11(8aH)-carboxylate (0.078 g, 0.18 mmol) as a white foam. $^1$H NMR (CDCl$_3$, 300 MHz) δ 1.50–1.70 (m, 1H), 1.70–2.12 (m, 5H), 2.50–2.80 (m, 3H), 2.92–3.05 (m, 3H), 3.14 (dd, J=6.3, 12.4 Hz, 1H), 3.22–3.42 (m, 3H), 3.49 (s, 1H), 7.05–7.40 (m, 5H) ppm. MS (ESI): 341 (base, M+H).

Example 328

(8aS,12aR)-2-(3-fluorophenyl)-4,5,6,7,8a,9,10,11,12,12a-decahydroazepinot3,2,1-hlipyrido[4,3-b]indole Step A:

Tert-butyl(8aS,12aR)-2-(3-fluorophenyl)-4,5,6,7,8a,9,10,11,12,12a-decahydroazepino[3,2,1-hi]pyrido[4,3-b]indole-11(8aH)-carboxylate (0.13 g, 62%) was prepared by the general method of Example 89, step C from tert-butyl(8aS,12aR)-2-bromo-4,5,6,7,9,10,12,12a-octahydroazepino[3,2,1-hi]pyrido[4,3-b]indole-11(8ah7)-carboxylate (0.20 g, 0.50 mmol), 3-fluorophenylboronic acid (0.14 g, 1.0 mmol), Pd(PPh$_3$)$_2$Cl$_2$ (17 mg, 0.025 mmol), Na$_2$CO$_3$(2.0 M, 1.0 mL, 2.0 mmol) as a white foam. MS (ESI): 423 (base, M+H).

Step B:

The title compound (0.025 g, 93%) was prepared by the general method of Example 312, step B from tert-butyl(8aS,12aR)-2-(3-fluorophenyl)-4,5,6,7,8a,9,10,11,12,12a-decahydroazepino[3,2,1-hi]pyrido[4,3-b]indole-11(8aH)-carboxylate (0.035 g, 0.083 mmol) as a white foam. $^1$H NMR (CDCl$_3$, 300 MHz) δ 1.50–1.70 (m, 1H), 1.70–2.17 (m, 6H), 2.48–2.82 (m, 3H), 2.82–3.05 (m, 3H), 3.08 (dd, J=6.3, 12.4 Hz, 1H), 3.15–3.40 (m, 3H), 6.88–6.96 (m, 1H), 7.15 (s, 2H), 7.18–7.26 (m, 1H), 7.28–7.35 (m, 2H) ppm. MS (ESI): 323 (base, M+H).

Example 329

(8aS,12aR)-2-[2-chloro-4-(trifluoromethyl)phenyl]-4,5,6,7,8a,9,10,11,12,12a-decahydroazepino[3,2,1-hi]pyrido[4,3-b]indole

Step A:

Tert-butyl(8aS,12aR)-2-[2-chloro-4-(trifluoromethyl)phenyl]-4,5,6,7,8a,9,10,11,12,12a-decahydroazepino[3,2,1-hi]pyrido[4,3-b]indole-11(8aH)-carboxylate (0.21 g, 82%) was prepared by the general method of Example 89, step C from tert-butyl(8aS,12aR)-2-bromo-4,5,6,7,9,10,12,12a-octahydroazepino[3,2,1-hi]pyrido[4,3-b]indole-11(8aH)-carboxylate (0.20 g, 0.50 mmol), 2-chloro-4-(trifluoromethyl)phenylboronic acid (0.22 g, 1.0 mmol), Pd(PPh$_3$)$_2$Cl$_2$ (17 mg, 0.025 mmol), Na$_2$CO$_3$(2.0 M, 1.0 mL, 2.0 mmol) as a white foam.

Step B:

The title compound (0.15 g, 87%) was prepared by the general method of Example 312, step B from tert-butyl(8aS,12aR)-2-[2-chloro-4-(trifluoromethyl)phenyl]-4,5,6,7,8a,9,10,11,12,12a-decahydroazepino[3,2,1-hi]pyrido[4,3-b]indole-11(8aH)-carboxylate (0.21 g, 0.41 mmol) as a white foam. $^1$H NMR (CDCl$_3$, 300 MHz) δ 1.50–1.70 (m, 1H), 1.70–1.90 (m, 2H), 1.90–2.20 (m, 4H), 2.48–2.80 (m, 3H), 2.80–3.00 (m, 3H), 3.05 (dd, J=6.3, 12.4 Hz, 1H), 3.10–3.25 (m, 1H), 3.25–3.36 (m, 1H), 3.36–3.45 (m, 1H), 7.00 (d, J=1.5 Hz, 1H), 7.05 (d, J=1.5 Hz, 1H), 7.44 (d, J=8.1 Hz, 1H), 7.51 (dd, J=1.1, 8.1 Hz, 1H), 7.70 (s, 1H) ppm.

Example 330

(8aS,12aR)-2-(2-chloro-4-methoxyphenyl)-4,5,6,7,8a,9,10,11,12,12a-decahydroazepino[3,2,1-hi]pyrido[4,3-b]indole

Step A:

Tert-butyl(8aS,12aR)-2-(2-chloro-4-methoxyphenyl)-4,5,6,7,8a,9,10,11,12,12a-decahydroazepino[3,2,1-hi]pyrido[4,3-b]indole-11(8aH)-carboxylate (0.15 g, 64%) was prepared by the general method of Example 89, step C from tert-butyl(8aS,12aR)-2-bromo-4,5,6,7,9,10,12,12a-octahydroazepino[3,2,1-hi]pyrido[4,3-b]indole-11(8aH)-carboxylate (0.20 g, 0.50 mmol), 2-chloro-4-methoxyphenylboronic acid (0.19 g, 1.0 mmol), Pd(PPh$_3$)$_2$Cl$_2$ (17 mg, 0.025 mmol), Na$_2$CO$_3$(2.0 M, 1.0 mL, 2.0 mmol) as a white foam.

Step B:

The title compound (0.12 g, 97%) was prepared by the general method of Example 312, step B from tert-butyl(8aS,12aR)-2-(2-chloro-4-methoxyphenyl)-4,5,6,7,8a,9,10,11,12,12a-decahydroazepino[3,2,1-hi]pyrido[4,3-b]indole-11(8aH)-carboxylate (0.15 g, 0.32 mmol) as a white foam. $^1$H NMR (CDCl$_3$, 300 MHz) δ 1.50–1.70 (m, 1H), 1.70–1.85 (m, 2H), 1.90–2.10 (m, 3H), 2.10–2.30 (m, 2H), 2.48–2.72 (m, 3H), 2.88–3.00 (m, 1H), 3.08–3.40 (m, 4H), 3.48–3.58 (m, 1H), 3.81 (s, 3H), 6.82 (dd, J=2.4, 8.4 Hz, 1H), 6.92–7.05 (m, 3H), 7.19 (d, J=8.4 Hz, 1H) ppm.

Example 331

(8aS,12aR)-2-(2-fluoro-4-methoxyphenyl)-4,5,6,7,8a,9,10,11,12,12a-decahydroazepino[3,2,1-hi]pyrido[4,3-b]indole

Step A:

Tert-butyl(8aS,12aR)-2-(2-fluoro-4-methoxyphenyl)-4,5,6,7,8a,9,10,11,12,12a-decahydroazepino[3,2,1-hi]pyrido[4,3-b]indole-11(8aH)-carboxylate (0.16 g, 69%) was prepared by the general method of Example 89, step C from tert-butyl(8aS,12aR)-2-bromo-4,5,6,7,9,10,12,12a-octahydroazepino[3,2,1-hi]pyrido[4,3-b]indole-11(8aH)-carboxylate (0.20 g, 0.50 mmol), 2-fluoro-4-methoxyphenylboronic acid (0.17 g, 1.0 mmol), Pd(PPh$_3$)$_2$Cl$_2$ (17 mg, 0.025 mmol), Na$_2$CO$_3$(2.0 M, 1.0 mL, 2.0 mmol) as a white foam. MS (ESI): 453 (base, M+H).

Step B:

The title compound (0.11 g, 94%) was prepared by the general method of Example 312, step B from tert-butyl(8aS,12aR)-2-(2-fluoro-4-methoxyphenyl)-4,5,6,7,8a,9,10,11,12,12a-decahydroazepino[3,2,1-hi]pyrido[4,3-b]indole-11(8aH)-carboxylate (0.15 g, 0.34 mmol) as a white foam. $^1$H NMR (CDCl$_3$, 300 MHz) δ 1.50–1.70 (m, 1H), 1.70–1.90 (m, 2H), 1.90–2.10 (m, 3H), 2.50–2.80 (m, 3H), 2.80–3.00 (m, 3H), 3.05 (dd, J=6.3, 12.4 Hz, 1H), 3.10–3.25 (m, 1H), 3.25–3.40 (m, 2H), 3.82 (s, 3H), 6.64–6.76 (m, 2H), 7.07 (s, 1H), 7.08 (s, 1H), 7.31 (t, J=8.8 Hz, 1H) ppm. MS (ESI): 353 (base, M+H).

Example 332

(8aS,12aR)-2-(4-methoxy-2-methylphenyl)-4,5,6,7,8a,9,10,11,12,12a-decahydroazepino[3,2,14-hi]pyrido[4,3-b]indole

Step A:

Tert-butyl(8aS,12aR)-2-(4-methoxy-2-methylphenyl)-4,5,6,7,8a,9,10,11,12,12a-decahydroazepino[3,2,1-hi]pyrido[4,3-b]indole-11(8aH)-carboxylate (0.095 g, 42%) was prepared by the general method of Example 89, step C from tert-butyl(8aS,12aR)-2-bromo-4,5,6,7,9,10,12,12a-octahydroazepino[3,2,1-hi]pyrido[4,3-b]indole-11(8aH)-carboxylate (0.20 g, 0.50 mmol), 4-methoxy-2-methylphenyl boronic acid (0.17 g, 1.0 mmol), Pd(PPh$_3$)$_2$Cl$_2$ (17 mg, 0.025 mmol), Na$_2$CO$_3$(2.0 M, 1.0 mL, 2.0 mmol) as a white foam. MS (ESI): 449 (base, M+H).

Step B:

The title compound (0.071 g, 96%) was prepared by the general method of Example 312, step B from tert-butyl(8aS,12aR)-2-(4-methoxy-2-methylphenyl)-4,5,6,7,8a,9,10,11,12,12a-decahydroazepino[3,2,1-hi]pyrido[4,3-b]indole-11(8aH)-carboxylate (0.095 g, 0.21 mmol) as a white foam. $^1$H NMR (CDCl$_3$, 300 MHz) δ 1.50–1.70 (m, 1H), 1.70–1.92 (m, 2H), 1.92–2.10 (m, 3H), 2.28 (s, 3H), 2.45–2.60 (m, 3H), 2.62–2.78 (m, 1H), 2.85–2.98 (m, 3H), 3.08 (dd, J=6.3, 12.4 Hz, 1H), 3.12–3.40 (m, 3H), 3.82 (s, 3H), 6.70–6.80 (m, 3H), 6.84 (s, 1H), 6.85 (s, 1H), 7.14 (d, J=8.4 Hz, 1H) ppm. MS (ESI): 349 (base, M+H).

Example 333

(8aS,12aR)-2-[4-methoxy-2-(trifluoromethyl)phenyl]-4,5,6,7,8a,9,10,11,12,12a-decahydroazepino[3,2,1-hi]pyrido[4,3-b]indole

Step A:

Tert-butyl(8aS,12aR)-2-[4-methoxy-2-(trifluoromethyl)phenyl]-4,5,6,7,8a,9,10,11,12,12a-decahydroazepino[3,2,1-hi]pyrido[4,3-b]indole-11(8aH)-carboxylate (0.20 g, 78%) was prepared by the general method of Example 89, step C from tert-butyl(8aS,12aR)-2-bromo-4,5,6,7,9,10,12,12a-octahydroazepino[3,2,1-hi]pyrido[4,3-b]indole-11(8aH)-carboxylate (0.20 g, 0.50 mmol), 4-methoxy-2-(trifluoromethyl)phenylboronic acid (0.22 g, 1.0 mmol), Pd(PPh$_3$)$_2$Cl$_2$ (17 mg, 0.025 mmol), Na₂CO₃(2.0 M, 1.0 mL, 2.0 mmol) as a white foam. MS (ESI): 503 (base, M+H).

Step B:

The title compound (0.13 g, 84%) was prepared by the general method of Example 312, step B from tert-butyl(8aS,12aR)-2-[4-methoxy-2-(trifluoromethyl)phenyl]-4,5,6,7,8a,9,10,11,12,12a-decahydroazepino[3,2,1-hi]pyrido[4,3-b]indole-11(8aH)-carboxylate (0.20 g, 0.39 mmol) as a white foam. ¹H NMR (CDCl₃, 300 MHz) δ 1.50–1.70 (m, 1H), 1.70–1.90 (m, 2H), 1.90–2.10 (m, 4H), 2.45–2.62 (m, 2H), 2.62–2.75 (m, 1H), 2.80–2.95 (m, 3H), 3.08 (dd, J=6.3, 12.4 Hz, 1H), 3.08–3.20 (m, 1H), 3.25–3.40 (m, 2H), 3.86 (s, 3H), 6.83 (s, 1H), 6.85 (s, 1H), 7.03 (dd, J=2.2, 8.4 Hz, 1H), 7.18–7.25 (m, 2H) ppm. MS (ESI): 403 (base, M+H).

Example 334

(8aS,12aR)-2-[2-(trifluoromethyl)phenyl]-4,5,6,7,8a,9,10,11,12,12a-decahydroazepino[3,2,1-hi]pyrido[4,3-b]indole Step A:

Tert-butyl(8aS,12aR)-2-[2-(trifluoromethyl)phenyl]-4,5,6,7,8a,9,10,11,12,12a-decahydroazepino[3,2,1-hi]pyrido[4,3-b]indole-11(8aH)-carboxylate (0.15 g, 61%) was prepared by the general method of Example 89, step C from tert-butyl(8aS,12aR)-2-bromo-4,5,6,7,9,10,12,12a-octahydroazepino[3,2,1-hi]pyrido[4,3-b]indole-11(8aH)-carboxylate (0.20 g, 0.50 mmol), 2-(trifluoromethyl)phenylboronic acid (0.19 g, 1.0 mmol), Pd(PPh₃)₂Cl₂ (17 mg, 0.025 mmol), Na₂CO₃(2.0 M, 1.0 mL, 2.0 mmol) as a white foam. MS (ESI): 473 (base, M+H).

Step B:

The title compound (0.11 g, 96%) was prepared by the general method of Example 312, step B from tert-butyl(8aS,12aR)-2-[2-(trifluoromethyl)phenyl]-4,5,6,7,8a,9,10,11,12,12a-decahydroazepino[3,2,1-hi]pyrido[4,3-b]indole-11(8aH)-carboxylate (0.15 g, 0.31 mmol) as a white foam. ¹H NMR (CDCl₃, 300 MHz) δ 1.50–1.70 (m, 1H), 1.70–1.92 (m, 2H), 1.92–2.25 (m, 3H), 2.45–2.65 (m, 2H), 2.65–2.80 (m, 1H), 2.80–3.00 (m, 4H), 3.08 (dd, J=6.3, 12.4 Hz, 1H), 3.12–3.25 (m, 1H), 3.25–3.42 (m, 2H), 6.88 (s, 1H), 6.90 (s, 1H), 7.30–7.45 (m, 2H), 7.52 (t, J=7.3 Hz, 1H), 7.72 (d, J=8.0 Hz, 1H) ppm. MS (ESI): 373 (base, M+H).

Example 335

(8aS,12aR)-2-[4-isopropoxy-2-(trifluoromethyl)phenyl]-4,5,6,7,8a,9,10,11,12,12a-decahydroazepino[3,2,1-hi]pyrido[4,3-b]indole Step A:

Tert-butyl(8aS,12aR)-2-[4-isopropoxy-2-(trifluoromethyl)phenyl]-4,5,6,7,8a,9,10,11,12,12a-decahydroazepino[3,2,1-hi]pyrido[4,3-b]indole-11(8aH)-carboxylate (0.17 g, 63%) was prepared by the general method of Example 89, step C from tert-butyl(8aS,12aR)-2-bromo-4,5,6,7,9,10,12,12a-octahydroazepino[3,2,1-hi]pyrido[4,3-b]indole-11(8aH)-carboxylate (0.20 g, 0.50 mmol), 4-isopropoxy-2-(trifluoromethyl)phenylboronic acid (0.18 g, 1.0 mmol), Pd(PPh₃)₂Cl₂ (17 mg, 0.025 mmol), Na₂CO₃(2.0 M, 1.0 mL, 2.0 mmol) as a white foam. MS (ESI): 531 (base, M+H).

Step B:

The title compound (0.14 g, 100%) was prepared by the general method of Example 312, step B from tert-butyl(8aS,12aR)-2-[4-isopropoxy-2-(trifluoromethyl)phenyl]-4,5,6,7,8a,9,10,11,12,12a-decahydroazepino[3,2,1-hi]pyrido[4,3-b]indole-11(8aH)-carboxylate (0.17 g, 0.32 mmol) as a white foam. ¹H NMR (CDCl₃, 300 MHz) δ 1.50–1.70 (m, 1H), 1.39 (d, J=6.0 Hz, 6H), 1.70–2.10 (m, 5H), 2.45–2.78 (m, 3H), 2.85–3.00 (m, 3H), 3.00–3.10 (m, 1H), 3.12–3.32 (m, 4H), 4.62 (p, J=6.0 Hz, 1H), 6.86 (s, 1H), 6.87 (s, 1H), 6.98–7.08 (m, 1H), 7.18–7.26 (m, 2H) ppm. MS (ESI): 431 (base, M+H).

Example 336

(8aS,12aR)-2-[2,4-bis(trifluoromethyl)phenyl]-4,5,6,7,8a,9,10,11,12,12a-decahydroazepino[3,2,1-hi]pyrido[4,3-b]indole Step A:

Tert-butyl(8aS,12aR)-2-[2,4-bis(trifluoromethyl)phenyl]-4,5,6,7,8a,9,10,11,12,12a-decahydroazepino[3,2,1-hi]pyrido[4,3-b]indole-11(8aH)-carboxylate (0.047 g, 17%) was prepared by the general method of Example 319, step A from tert-butyl(8aS,12aR)-2-bromo-4,5,6,7,9,10,12,12a-octahydroazepino[3,2,1-hi]pyrido[4,3-b]indole-11(8aH)-carboxylate (0.20 g, 0.50 mmol), 2,4-bis(trifluoromethyl)phenylboronic acid (0.26 g, 1.0 mmol), Pd(PPh₃)₄ (12 mg, 0.010 mmol), and Ba(OH)₂ (2 M, 1.0 mL, 2.0 mmol) as a white foam. MS (ESI): 541 (base, M+H).

Step B:

The title compound (0.038 g, 100%) was prepared by the general method of Example 312, step B from tert-butyl(8aS,12aR)-2-[2,4-bis(trifluoromethyl)phenyl]-4,5,6,7,8a,9,10,11,12,12a-decahydroazepino[3,2,1-hi]pyrido[4,3-b]indole-11(8aH)-carboxylate (0.047 g, 0.087 mmol) as a white foam. ¹H NMR (CDCl₃, 300 MHz) δ 1.40–1.80 (m, 3H), 1.80–2.30 (m, 5H), 2.30–2.72 (m, 3H), 2.72–3.00 (m, 1H), 3.00–3.50 (m, 5H), 6.83 (s, 1H), 6.84 (s, 1H), 7.36 (d, J=8.3 Hz, 1H), 7.69 (d, J=8.3 Hz, 1H), 7.87 (s, 1H) ppm. MS (ESI): 441 (base, M+H).

Example 337

(8aS,12aR)-2-14-fluoro-2-(trifluoromethyl)phenyl]-4,5,6,7,8a,9,10,11,12,12a-decahydroazepino[3,2,1-hi]pyrido[4,3-b]indole Step A:

Tert-butyl(8aS,12aR)-2-[4-fluoro-2-(trifluoromethyl)phenyl]-4,5,6,7,8a,9,10,11,12,12a-decahydroazepino[3,2,1-hi]pyrido[4,3-b]indole-11(8aH)-carboxylate (0.10 g, 84%) was prepared by the general method of Example 319, step A from tert-butyl(8aS,12aR)-2-bromo-4,5,6,7,9,10,12,12a-octahydroazepino[3,2,1-hi]pyrido[4,3-b]indole-11(8aH)-carboxylate (0.10 g, 0.25 mmol), 4-fluoro-2-(trifluoromethyl)phenylboronic acid (0.10 g, 0.50 mmol), Pd(PPh₃)₄ (12 mg, 0.010 mmol), and Ba(OH)₂ (0.17 M, 3.0 mL, 0.51 mmol) as a white foam. MS (ESI): 491 (base, M+H).

Step B:

The title compound (0.042 g, 52%) was prepared by the general method of Example 312, step B from tert-butyl(8aS,12aR)-2-[4-fluoro-2-(trifluoromethyl)phenyl]-4,5,6,7,8a,9,10,11,12,12a-decahydroazepino[3,2,1-hi]pyrido[4,3-b]indole-11(8aH)-carboxylate (0.10 g, 0.21 mmol) as a white foam. ¹H NMR (CDCl₃, 300 MHz) δ 1.50–1.70 (m, 1H), 1.70–2.10 (m, 5H), 2.48–2.65 (m, 2H), 2.65–2.80 (m, 1H), 2.85–3.20 (m, 4H), 3.20–3.42 (m, 4H), 7.10 (s, 2H), 7.20 (t, J=9.3 Hz, 1H), 6.60–7.70 (m, 1H), 7.70–7.72 (m, 1H) ppm. MS (ESI): 391 (base, M+H).

Example 338

4-[(8aS,12aR)-4,5,6,7,8a,9,10,11,12,12a-decahydroazepino[3,2,1-hi]pyrido[4,3-b]indol-2-yl]-3-(trifluoromethyl)aniline Step A:
Tert-butyl(8aS,12aR)-2-[4-[(tert-butoxycarbonyl)amino]-2-(trifluoromethyl)phenyl]-4,5,6,7,8a,9,10,11,12,12a-decahydroazepino[3,2,1-hi]pyrido[4,3-b]indole-11(8aH)-carboxylate (0.12 g, 84%) was prepared by the general method of Example 319, step A from tert-butyl(8aS,12aR)-2-bromo-4,5,6,7,9,10,12,12a-octahydroazepino[3,2,1-hi]pyrido[4,3-b]indole-11(8aH)-carboxylate (0.10 g, 0.25 mmol), 4-[(tert-butoxycarbonyl)amino]-2-(trifluoromethyl)phenylboronic acid (0.15 g, 0.50 mmol), Pd(PPh₃)₄ (12 mg, 0.010 mmol), and Ba(OH)₂ (0.17 M, 3.0 mL, 0.51 mmol) as a white foam. MS (ESI): 588 (base, M+H).

Step B:
The title compound (0.079 g, 98%) was prepared by the general method of Example 312, step B from tert-butyl(8aS,12aR)-2-[4-[(tert-butoxycarbonyl)amino]-2-(trifluoromethyl)phenyl]-4,5,6,7,8a,9,10,11,12,12a-decahydroazepino[3,2,1-hi]pyrido[4,3-b]indole-11(8aH)-carboxylate (0.12 g, 0.21 mmol) as a white foam. ¹H NMR (CDCl₃, 300 MHz) δ 1.50–1.70 (m, 2H), 1.70–1.95 (m, 2H), 1.95–2.10 (m, 3H), 2.28–2.76 (m, 3H), 2.80–3.00 (m, 3H), 3.08 (dd, J=6.3, 12.4 Hz, 1H), 3.10–3.40 (m, 3H), 3.84 (br, 2H), 6.77–6.90 (m, 3H), 7.01 (d, J=2.6 Hz, 1H), 7.12 (d, J=8.4 Hz, 1H) ppm. MS (ESI): 388 (lost two BOC groups)(base, M+H).

Example 339

4-[(8aS,12aR)-4,5,6,7,8a,9,10,11,12,12a-decahydroazepino[3,2,1-hi]pyrido[4,3-b]indol-2-yl]-N-methyl-3-(trifluoromethyl)aniline Step A:
Tert-butyl(8aS,12aR)-2-[4-[(tert-butoxycarbonyl)(methyl)amino]-2-(trifluoromethyl)phenyl]-4,5,6,7,8a,9,10,11,12,12a-decahydroazepino[3,2,1-hi]pyrido[4,3-b]indole-11(8aH)-carboxylate (0.12 g, 81%) was prepared by the general method of Example 319, step A from tert-butyl(8aS,12aR)-2-bromo-4,5,6,7,9,10,12,12a-octahydroazepino[3,2,1-hi]pyrido[4,3-b]indole-11(8aH)-carboxylate (0.10 g, 0.25 mmol), 4-[(tert-butoxycarbonyl)(methyl)amino]-2-(trifluoromethyl)phenylboronic acid (0.16 g, 0.50 mmol), Pd(PPh₃)₄ (12 mg, 0.010 mmol), and Ba(OH)₂ (0.17 M, 3.0 mL, 0.51 mmol) as a white foam. MS (ESI): 602 (base, M+H).

Step B:
The title compound (0.081 g, 100%) was prepared by the general method of Example 312, step B from tert-butyl(8aS,12aR)-2-[4-[(tert-butoxycarbonyl)(methyl)amino]-2-(trifluoromethyl)phenyl]-4,5,6,7,8a,9,10,11,12,12a-decahydroazepino[3,2,1-hi]pyrido[4,3-b]indole-11(8aH)-carboxylate (0.12 g, 0.20 mmol) as a white foam. ¹H NMR (CDCl₃, 300 MHz) δ 1.50–1.70 (m, 1H), 1.70–2.10 (m, 5H), 2.48–2.78 (m, 3H), 2.80–3.00 (m, 4H), 3.08 (dd, J=6.3, 12.4 Hz, 1H), 3.10–3.40 (m, 3H), 3.91 (br, 1H), 6.74 (dd, J=2,6, 8.2 Hz, 1H), 6.86 (s, 1H), 6.87 (s, 1H), 6.91 (d, J=2.6 Hz, 1H), 7.15 (d, J=8.2 Hz, 1H) ppm. MS (ESI): 402 (lost two BOC groups)(base, M+H).

Example 340

2-[(8aS,12aR)-4,5,6,7,8a,9,10,11,12,12a-decahydroazepino[3,2,1-hi]pyrido[4,3-b]indol-2-yl]benzaldehyde Step A:
Tert-butyl(8aS,12aR)-2-(2-formylphenyl)-4,5,6,7,8a,9,10,11,12,12a-decahydroazepino[3,2,1-hi]pyrido[4,3-b]indole-11(8aH)-carboxylate (0.081 g, 38%) was prepared by the general method of Example 89, step C from tert-butyl(8aS,12aR)-2-bromo-4,5,6,7,9,10,12,12a-octahydroazepino[3,2,1-hi]pyrido[4,3-b]indole-11(8aH)-carboxylate (0.20 g, 0.50 mmol), 2-formylphenylboronic acid (0.15 g, 1.0 mmol), Pd(PPh₃)₂Cl₂ (17 mg, 0.025 mmol), Na₂CO₃(2.0 M, 1.0 mL, 2.0 mmol) as a white foam. MS (ESI): 433 (base, M+H).

Step B:
The title compound (0.021 g, 91%) was prepared by the general method of Example 312, step B from tert-butyl(8aS,12aR)-2-(2-formylphenyl)-4,5,6,7,8a,9,10,11,12,12a-decahydroazepino[3,2,1-hi]pyrido[4,3-b]indole-11(8aH)-carboxylate (0.030 g, 0.070 mmol) as a white foam. ¹H NMR (CDCl₃, 300 MHz) δ 1.50–1.88 (m, 3H), 1.90–2.12 (m, 4H), 2.52–2.80 (m, 3H), 2.87–3.04 (m, 3H), 3.08–3.20 (m, 1H), 3.24–3.38 (m, 2H), 3.38–3.44 (m, 1H), 6.93 (s, 1H), 6.97 (s, 1H), 7.38–7.46 (m, 2H), 7.66 (td, J=7.5, 1.4 Hz, 1H), 7.99 (dd, J=1.4, 8.0 Hz, 1H), 10.02 (s, 1H) ppm. MS (ESI): 333 (base, M+H).

Example 341

{2-[(8aS,12aR)-4,5,6,7,8a,9,10,11,12,12a-decahydroazepino[3,2,1-hi]pyrido[4,3-b]indol-2-yl]phenyl}methanol Step A:
NaBH₄ (0.050 g, 1.3 mmol) was added in one portion to a solution of tert-butyl(8aS,12aR)-2-(2-formylphenyl)-4,5,6,7,8a,9,10,11,12,12a-decahydroazepino[3,2,1-hi]pyrido[4,3-b]indole-11(8aH)-carboxylate (0.051 g, 0.12 mmol) in MeOH (12 mL) at room temperature. The mixture was stirred at room temperature for 1 h, quenched with acetone (5.0 mL) and concentrated in vacuo. Water (10 mL) was added to the residue and extracted with EtOAc (3×10 mL). The combined organic layer was dried, concentrated in vacuo and flash column chromatography (EtOAc:hexane/1:4) gave tert-butyl(8aS,12aR)-2-[2-(hydroxymethyl)phenyl]-4,5,6,7,8a,9,10,11,12,12a-decahydroazepino[3,2,1-hi]pyrido[4,3-b]indole-11(8aH)-carboxylate (0.043, 84%) as a white solid. MS (ESI): 435 (base, M+H).

Step B:
The title compound (0.033 g, 100%) was prepared by the general method of Example 312, step B from tert-butyl(8aS,12aR)-2-[2-(hydroxymethyl)phenyl]-4,5,6,7,8a,9,10,11,12,12a-decahydroazepino[3,2,1-hi]pyrido[4,3-b]indole-11(8aH)-carboxylate (0.043, 0.10 mmol) as a white foam. ¹H NMR (CDCl₃, 300 MHz) δ 1.50–1.95 (m, 3H), 1.95–2.10 (m, 3H), 2.44–2.80 (m, 3H), 2.80–3.00 (m, 3H), 3.00–3.10

(m, 1H), 3.10–3.40 (m, 3H), 4.65 (br, 2H), 6.92 (s, 1H), 6.95 (s, 1H), 7.22–7.38 (m, 3H), 7.50–7.57 (m, 1H) ppm. MS (ESI): 335 (base, M+H).

Example 342

2-[(8aS,12aR)-4,5,6,7,8a,9,10,11,12,12a-decahydroazepino[3,2,1-hi]pyrido[4,3-b]indol-2-yl]-5-methoxybenzaldehyde Step A:

Tert-butyl(8aS,12aR)-2-(2-formyl-4-methoxyphenyl)-4,5,6,7,8a,9,10,11,12,12a-decahydroazepino[3,2,1-hi]pyrido[4,3-b]indole-11(8aH)-carboxylate (0.094 g, 41%) was prepared by the general method of Example 89, step C from tert-butyl(8aS,12aR)-2-bromo-4,5,6,7,9,10,12,12a-octahydroazepino[3,2,1-hi]pyrido[4,3-b]indole-11(8aH)-carboxylate (0.20 g, 0.50 mmol), 2-formyl-4-methoxyphenylboronic acid (0.18 g, 1.0 mmol), Pd(PPh$_3$)$_2$Cl$_2$ (17 mg, 0.025 mmol), Na$_2$CO$_3$(2.0 M, 1.0 mL, 2.0 mmol) as a white foam. MS (ESI): 463 (base, M+H).

Step B:

The title compound (0.060 g, 81%) was prepared by the general method of Example 312, step B from tert-butyl(8aS,12aR)-2-(2-formyl-4-methoxyphenyl)-4,5,6,7,8a,9,10,11,12,12a-decahydroazepino[3,2,1-hi]pyrido[4,3-b]indole-11(8aH)-carboxylate (0.094 g, 0.20 mmol) as a white foam. $^1$H NMR (CDCl$_3$, 300 MHz) δ 1.50–1.70 (m, 1H), 1.70–1.90 (m, 211), 1.90–2.10 (m, 4H), 2.50–2.76 (m, 3H), 2.85–3.08 (m, 3H), 3.08–3.20 (m, 1H), 3.25–3.42 (m, 3H), 3.47 (s, 1H), 3.88 (s, 3H), 6.88 (s, 1H), 6.91 (s, 1H), 7.16 (dd, J=2.6, 8.4 Hz, 1H), 7.35 (d, J=8.4 Hz, 1H), 7.46 (d, J=2.6 Hz, 1H), 9.95 (s, 1H) ppm. MS (ESI): 363 (base, M+H).

Example 343

{2-[(8aS,12aR)-4,5,6,7,8a,9,10,11,12,12a-decahydroazepino[3,2,1-hi]pyrido[4,3-b]indol-2-yl]-5-methoxyphenyl}methanol Step A:

Tert-butyl(8aS,12aR)-2-[2-(hydroxymethyl)-4-methoxyphenyl]-4,5,6,7,8a,9,10,11,12,12a-decahydroazepino[3,2,1-hi]pyrido[4,3-b]indole-11(8aH)-carboxylate (0.54 g) was obtained as a byproduct of Example 342 as a white foam. MS (ESI): 465 (base, M+H).

Step B:

The title compound (0.42 g, 100%) was prepared by the general method of Example 312, step B from tert-butyl(8aS,12aR)-2-[2-(hydroxymethyl)-4-methoxyphenyl]-4,5,6,7,8a,9,10,11,12,12a-decahydroazepino[3,2,1-hi]pyrido[4,3-b]indole-11(8aH)-carboxylate (0.054 g, 0.12 mmol) as a white foam. $^1$H NMR (CDCl$_3$, 300 MHz) δ 1.50–1.68 (m, 1H), 1.68–2.10 (m, 5H), 2.40–2.80 (m, 3H), 2.80–3.00 (m, 3H), 3.00–3.10 (m, 1H), 3.10–3.40 (m, 3H), 3.86 (s, 3H), 4.62 (br, 2H), 6.78–6.92 (m, 3H), 7.10 (d, J=3.0 Hz, 1H), 7.19 (d, J=8.4 Hz, 1H), ppm. MS (ESI): 365 (base, M+H).

Example 344

4-[(8aS,12aR)-4,5,6,7,8a,9,10,11,12,12a-decahydroazepino[3,2,1-hi]pyrido[4,3-b]indol-2-yl]-3-methylbenzonitrile Step A:

Tert-butyl(8aS,12aR)-2-(4-cyano-2-methylphenyl)-4,5,6,7,8a,9,10,11,12,12a-decahydroazepino[3,2,1-hi]pyrido[4,3-b]indole-11(8aH)-carboxylate (0.095 g, 86%) was prepared by the general method of Example 319, step A from tert-butyl(8aS,12aR)-2-bromo-4,5,6,7,9,10,12,12a-octahydroazepino[3,2,1-hi]pyrido[4,3-b]indole-11(8aH)-carboxylate (0.10 g, 0.25 mmol), 4-cyano-2-methylphenylboronic acid (0.080 g, 0.50 mmol), Pd(PPh$_3$)$_4$ (12 mg, 0.010 mmol), and Ba(OH)$_2$ (0.17 M, 3.0 mL, 0.51 mmol) as a white foam. MS (ESI): 444 (base, M+H).

Step B:

The title compound (0.074 g, 100%) was prepared by the general method of Example 312, step B from tert-butyl(8aS,12aR)-2-(4-cyano-2-methylphenyl)-4,5,6,7,8a,9,10,11,12,12a-decahydroazepino[3,2,1-hi]pyrido[4,3-b]indole-11(8aH)-carboxylate (0.095 g, 0.21 mmol) as a white foam. $^1$H NMR (CDCl$_3$, 300 MHz) δ 1.50–1.70 (m, 1H), 1.70–2.10 (m, 5H), 2.32 (s, 3H), 2.85–3.00 (m, 3H), 3.08 (dd, J=6.3, 12.4 Hz, 1H), 3.20–3.50 (m, 4H), 6.85 (s, 2H), 7.29 (d, J=7.9 Hz, 1H),7.47 (d, J=7.9 Hz, 1H), 7.51 (s, 1H) ppm. MS (ESI): 344 (base, M+H).

Example 345

1-{2-[(8aS,12aR)-4,5,6,7,8a,9,10,11,12,12a-decahydroazepino[3,2,1-hi]pyrido[4,3-b]indol-2-yl]-5-methoxyphenyl}ethanol CH$_3$MgBr (1 M, 2.3 mL, 2.3 mmol) was added to a solution of 2-[(8aS,12aR)-4,5,6,7,8a,9,10,11,12,12a-decahydroazepino[3,2,1-hi]pyrido[4,3-b]indol-2-yl]-5-methoxybenzaldehyde (0.080 g, 0.23 mmol) in THF (5 mL) at 0° C. The mixture was stirred at room temperature for 18 h and quenched with water (5.0 mL). The mixture was extracted with CH$_2$Cl$_2$ (3×10 mL) and the organic layer was dried (Na$_2$SO$_4$) and concentrated in vacuo. Reverse phase HPLC (H$_2$O—CH$_3$CN-TFA (0.05%)) gave the title compound (2.0 mg, 4%). MS (ESI): 379 (base, M+H)

Example 346 tert-butyl(7aS,11aR)-2-bromo-5,6,7a,8,9,10,11,11a-octahydro-4H-pyrido[3',4':4,5]pyrrolo[3,2,1-i)]quinoline-10(7aH)-carboxylate The title compound (7.73 g, 97%) was prepared by the method of Example 314 from tert-butyl(7aS,11aR)-5,6,7a,8,9,10,11,11a-octahydro-4H-pyrido[3',4':4,5]pyrrolo[3,2,1-ij]quinoline-10(7aH)-carboxylate (6.40 g, 20 mmol) and NBS (3.63 g, 20 mmol) as a white solid.

Example 347

(7aS,11aR)-2-(2,4-dichlorophenyl)-5,6,7a,8,9,10,11,11a-octahydro-4H-pyrido[3',4':4,5]pyrrolo[3,2,1-ij]quinoline Step A:

Tert-butyl(7aS,11aR)-2-(2,4-dichlorophenyl)-5,6,7a,8,9,10,11,11a-octahydro-4H-pyrido[3',4':4,5]pyrrolo[3,2,1-ij]quinoline-10(7aH)-carboxylate (0.15 g, 63%) was prepared by the method of Example 315 from tert-butyl(7aS,11aR)-2-bromo-5,6,7a,8,9,10,11,11a-octahydro-4H-pyrido[3',4':4,5]pyrrolo[3,2,1-ij]quinoline-10(7aH)-carboxylate (0.20 g, 0.50 mmol), 2,4-dichlorophenylboronic acid (0.19 g, 1.0 mmol), Ba(OH)$_2$–$_8$H$_2$O (0.32 g, 1.0 mmol), Pd$_2$(dba)$_3$(7.5 mg, 0.0075 mmol) and PPh$_3$(5.24 mg, 0.02 mmol) as a white foam.

Step B:

The title compound (0.087 g, 77%) was prepared by the general method of Example 312, step B from tert-butyl(7aS,11aR)-2-(2,4-dichlorophenyl)-5,6,7a,8,9,10,11,11a-octahydro-4H-pyrido[3',4':4,5]pyrrolo[3,2,1-ij]quinoline-10(7aH)-carboxylate (0.15 g, 0.32 mmol) as a white foam. $^1$H NMR (CDCl$_3$, 300 MHz) δ 1.75–2.00 (m, 2H), 2.08–2.30 (m, 3H), 2.60–2.80 (m, 4H), 2.80–2.92 (m, 2H), 3.07–3.15 (m, 2H), 3.28–3.35 (m, 1H), 3.38–3.48 (m, 1H), (s, 1H), 6.98 (s, 1H), 7.23 (d, J=1.9 Hz, 2H), 7.44 (t, J=1.3 Hz, 1H) ppm.

Example 348

(7aS,11aR)-2-(3,4-dichlorophenyl)-5,6,7a,8,9,10,11,11a-octahydro-4H-pyrido[3',4':4,5]pyrrolo[3,2,1-ij]quinoline Step A:

Tert-butyl(7aS,11aR)-2-(3,4-dichlorophenyl)-5,6,7a,8,9,10,11,11a-octahydro-4H-pyrido[3',4':4,5]pyrrolo[3,2,1-ij]quinoline-10(7aH)-carboxylate (0.085 g, 37%) was prepared by the general method of Example 89, step C from tert-butyl(7aS,11aR)-2-bromo-5,6,7a,8,9,10,11,11a-octahydro-4H-pyrido[3',4':4,5]pyrrolo[3,2,1-ij]quinoline-10(7aH)-carboxylate (0.20 g, 0.50 mmol), 3,4-dichlorophenylboronic acid (0.19 g, 1.0 mmol), Pd(PPh$_3$)$_2$Cl$_2$ (17 mg, 0.025 mmol), Na$_2$CO$_3$(2.0 M, 1.0 mL, 2.0 mmol) as a white foam. MS (ESI): 459 (base, M+H).

Step B:

The title compound (0.066 g, 100%) was prepared by the general method of Example 312, step B from tert-butyl(7aS,11aR)-2-(3,4-dichlorophenyl)-5,6,7a,8,9,10,11,11a-octahydro-4H-pyrido[3',4':4,5]pyrrolo[3,2,1-ij]quinoline-10(7aH)-carboxylate (0.085 g, 0.19 mmol) as a white foam. $^1$H NMR (CDCl$_3$, 300 MHz) δ 1.80–2.05 (m, 2H), 2.05–2.20 (m, 2H), 2.55–2.80 (m, 4H), 2.82–2.98 (m, 2H), 3.07–3.20 (m, 2H), 3.20–3.38 (m, 1H), 3.38–3.48 (m, 1H), 3.64 (br, 1H), 7.01 (s, 1H), 7.11(s, 1H), 7.34 (dd, J=1.8, 8.4 Hz, 1H), 7.43 (d, J=8.4 Hz, 2H), 7.59 (d, J=1.8 Hz, 1H) ppm. MS (ESI): 359 (base, M+H).

Example 349

(7aS,11aR)-2-(3,5-dichlorophenyl)-5,6,7a,8,9,10,11,11a-octahydro-4H-pyrido[3',4':4,5]pyrrolo[3,2,1-ij]quinoline Step A:

Tert-butyl(7aS,11aR)-2-(3,5-dichlorophenyl)-5,6,7a,8,9,10,11,11a-octahydro-4H-pyrido[3',4':4,5]pyrrolo[3,2,1-ij]quinoline-10(7aH)-carboxylate (0.045 g, 40%) was prepared by the general method of Example 89, step C from tert-butyl(7aS,11aR)-2-bromo-5,6,7a,8,9,10,11,11a-octahydro-4H-pyrido[3',4':4,5]pyrrolo[3,2,1-ij]quinoline-10(7aH)-carboxylate (0.098 g, 0.25 mmol), 3,5-dichlorophenylboronic acid (0.10 g, 0.5 mmol), Pd(PPh$_3$)$_2$Cl$_2$ (8.8 mg, 0.013 mmol), Na$_2$CO$_3$(2.0 M, 0.5 mL, 1.0 mmol) as a white foam. MS (ESI): 459 (base, M+H).

Step B:

The title compound (0.035 g, 100%) was prepared by the general method of Example 312, step B from tert-butyl(7aS,11aR)-2-(3,5-dichlorophenyl)-5,6,7a,8,9,10,11,11a-octahydro-4H-pyrido[3',4':4,5]pyrrolo[3,2,1-ij]quinoline-10(7aH)-carboxylate (0.045 g, 0.10 mmol) as a white foam. $^1$H NMR (CDCl$_3$, 300 MHz) δ 1.80–2.05 (m, 2H), 2.05–2.20 (m, 2H), 2.55–2.80 (m, 4H), 2.88–2.96 (m, 3H), 3.07–3.20 (m, 2H), 3.23–3.36 (m, 1H), 3.38–3.48 (m, 1H), 7.08 (s, 1H), 7.10 (s, 1H), 7.21 (t, J=1.9 Hz, 1H), 7.37 (d, J=1.9 Hz, 2H) ppm. MS (ESI): 359 (base, M+H).

Example 350

(7aS,11aR)-2-(2,5-dichlorophenyl)-5,6,7a,8,9,10,11,11a-octahydro-4H-pyrido[3',4':4,5]pyrrolo[3,2,1-ij]quinoline Step A:

Tert-butyl(7aS,11aR)-2-(2,5-dichlorophenyl)-5,6,7a,8,9,10,11,11a-octahydro-4H-pyrido[3',4':4,5]pyrrolo[3,2,1-ij]quinoline-10(7aH)-carboxylate (0.080 g, 55%) was prepared by the general method of Example 319, step A from tert-butyl (7aS,11aR)-2-bromo-5,6,7a,8,9,10,11,11a-octahydro-4H-pyrido[3',4':4,5]pyrrolo[3,2,1-ij]quinoline-10(7aH)-carboxylate (0.13 g, 0.32 mmol), 2,5-dichlorophenylboronic acid (0.12 g, 0.64 mmol), Pd(PPh$_3$)$_4$ (14 mg, 0.012 mmol), and Ba(OH)$_2$ (0.17 M, 3.0 mL, 0.51 mmol) as a white foam. MS (ESI): 459 (base, M+H).

Step B:

The title compound (0.063 g, 100%) was prepared by the general method of Example 312, step B from tert-butyl(7aS,11aR)-2-(2,5-dichlorophenyl)-5,6,7a,8,9,10,11,11a-octahydro-4H-pyrido[3',4':4,5]pyrrolo[3,2,1-ij]quinoline-10(7aH)-carboxylate (0.080 g, 0.17 mmol) as a white foam. $^1$H NMR (CDCl$_3$, 300 MHz) δ 1.80–2.05 (m, 2H), 2.05–2.20 (m, 2H), 2.55–2.80 (m, 4H), 2.88–2.96 (m, 3H), 3.07–3.20 (m, 2H), 3.23–3.36 (m, 1H), 3.38–3.48 (m, 1H), 6.95 (s, 1H), 6.99 (s, 1H), 7.16 (dd, J=2.7, 8.4 Hz, 1H), 7.30 (d, J=2.7 Hz, 1H), 7.34 (d, J=8.4 Hz) ppm. MS (ESI): 359 (base, M+H).

Example 351

(7aS,11aR)-2-(2,6-dichlorophenyl)-5,6,7a,8,9,10,11,11a-octahydro-4H-pyrido[3',4':4,5]pyrrolo[3,2,1-ij]quinoline Step A:

Tert-butyl(7aS,11aR)-2-(2,6-dichlorophenyl)-5,6,7a, 8,9,10,11,11a-octahydro-4H-pyrido[3',4':4,5]pyrrolo[3,2,1-ij]quinoline-10(7aH)-carboxylate (0.023 g, 19%) was prepared by the general method of Example 320, step A from tert-butyl(8aS,11aR)-2-bromo-4,5,6,7,9,10,12,12a-octahydroazepino[3,2,1-hi]pyrido[4,3-b]indole-11(8aH)-carboxylate (0.10 g, 0.26 mmol), 2,6-dichlorophenyl boronic acid (0.10 g, 0.52 mmol), Pd(dppf)$_2$Cl$_2$ (10 mg, 0.012 mmol), TEA (1.0 mL, 7.2 mmol) as a white foam.

Step B:

The title compound (0.018 g, 100%) was prepared by the general method of Example 312, step B from tert-butyl(7aS,11aR)-2-(2,6-dichlorophenyl)-5,6,7a,8,9,10,11,11a-octahydro-4H-pyrido[3',4':4,5]pyrrolo[3,2,1-ij]quinoline-10(7aH)-carboxylate (0.023 g, 0.050 mmol) as a white foam. $^1$H NMR (CDCl$_3$, 300 MHz) δ 1.80–2.05 (m, 2H), 2.05–2.20 (m, 2H), 2.55–2.80 (m, 4H), 2.88–2.96 (m, 3H), 3.07–3.20 (m, 2H), 3.23–3.36 (m, 1H), 3.38–3.48 (m, 1H), 6.73 (s, 1H), 6.79 (s, 1H), 7.16 (t, J=8.0 Hz, 1H), 7.38 (d, J=8.0 Hz) ppm. MS (ESI): 359 (base, M+H).

Example 352

(7aS,11aR)-2-(2-chlorophenyl)-5,6,7a,8,9,10,11,11a-octahydro-4H-pyrido[3',4':4,5]pyrrolo[3,2,1-ij]quinoline Step A:
Tert-butyl(7aS,11aR)-2-(2-chlorophenyl)-5,6,7a,8,9,10,11,11a-octahydro-4H-pyrido[3',4':4,5]pyrrolo[3,2,1-ij]quinoline-10(7aH)-carboxylate (0.054 g, 51%) was prepared by the general method of Example 89, step C from tert-butyl(7aS,11aR)-2-bromo-5,6,7a,8,9,10,11,11a-octahydro-4H-pyrido[3',4':4,5]pyrrolo[3,2,1-ij]quinoline-10(7aH)-carboxylate (0.098 g, 0.25 mmol), 2-chlorophenylboronic acid (0.078 g, 0.5 mmol), Pd(PPh$_3$)$_2$Cl$_2$ (8.8 mg, 0.013 mmol), Na$_2$CO$_3$(2.0 M, 0.5 mL, 1.0 mmol) as a white foam. MS (ESI): 425 (base, M+H).

Step B:
The title compound (0.040 g, 99%) was prepared by the general method of Example 312, step B from tert-butyl(7aS,11aR)-2-(2-chlorophenyl)-5,6,7a,8,9,10,11,11a-octahydro-4H-pyrido[3',4':4,5]pyrrolo[3,2,1-ij]quinoline-10(7aH)-carboxylate (0.054 g, 0.13 mmol) as a white foam. $^1$H NMR (CDCl$_3$, 300 MHz)-δ 1.80–2.05 (m, 2H), 2.05–2.20 (m, 2H), 2.55–2.80 (m, 4H), 2.88–2.96 (m, 3H), 3.07–3.20 (m, 2H), 3.23–3.36 (m, 1H), 3.38–3.48 (m, 1H), 6.97 (s, 1H), 7.02 (s, 1H), 7.12–7.35 (m, 3H), 7.35–7.46 (m, 2H) ppm. MS (ESI): 325 (base, M+H).

Example 353

(7aS,11aR)-2-(3-chlorophenyl)-5,6,7a,8,9,10,11,11a-octahydro-4H-pyrido[3',4':4,5]pyrrolo[3,2,1-ij]quinoline Step A:
Tert-butyl(7aS,11aR)-2-(3-chlorophenyl)-5,6,7a,8,9,10,11,11a-octahydro-4H-pyrido[3',4':4,5]pyrrolo[3,2,1-ij]quinoline-10(7aH)-carboxylate (0.060 g, 57%) was prepared by the general method of Example 89, step C from tert-butyl(7aS,11aR)-2-bromo-5,6,7a,8,9,10,11,11a-octahydro-4H-pyrido[3',4':4,5]pyrrolo[3,2,1-ij]quinoline-10(7aH)-carboxylate (0.098 g, 0.25 mmol), 3-chlorophenylboronic acid (0.078 g, 0.5 mmol), Pd(PPh$_3$)$_2$Cl$_2$ (8.8 mg, 0.013 mmol), Na$_2$CO$_3$(2.0 M, 0.5 mL, 1.0 mmol) as a white foam. MS (ESI): 425 (base, M+H).

Step B:
The title compound (0.046 g, 100%) was prepared by the general method of Example 312, step B from tert-butyl(7aS,11aR)-2-(3-chlorophenyl)-5,6,7a,8,9,10,11,11a-octahydro-4H-pyrido[3',4':4,5]pyrrolo[3,2,1-ij]quinoline-10(7aH)-carboxylate (0.060 g, 0.14 mmol) as a white foam. $^1$H NMR (CDCl$_3$, 300 MHz) δ 1.80–2.05 (m, 2H), 2.05–2.20 (m, 2H), 2.55–2.80 (m, 4H), 2.88–2.96 (m, 3H), 3.07–3.20 (m, 2H), 3.23–3.36 (m, 1H), 3.38–3.48 (m, 1H), 7.11(s, 1H), 7.12 (s, 1H), 7.20–7.40 (m, 3H), 7.48 (t, J=1.7 Hz, 1H) ppm. MS (ESI): 325 (base, M+H).

Example 354

(7aS,11aR)-2-(4-chlorophenyl)-5,6,7a,8,9,10,11,11a-octahydro-4H-pyrido[3',4':4,5]pyrrolo[3,2,1-ij]quinoline Step A:
Tert-butyl(7aS,11aR)-2-(4-chlorophenyl)-5,6,7a,8,9,10,11,11a-octahydro-4H-pyrido[3',4':4,5]pyrrolo[3,2,1-ij]quinoline-10(7aH)-carboxylate (0.045 g, 21%) was prepared by the general method of Example 89, step C from tert-butyl(7aS,11aR)-2-bromo-5,6,7a,8,9,10,11,11a-octahydro-4H-pyrido[3',4':4,5]pyrrolo[3,2,1-ij]quinoline-10(7aH)-carboxylate (0.20 g, 0.50 mmol), 4-chlorophenylboronic acid (0.16 g, 1.0 mmol), Pd(PPh$_3$)$_2$Cl$_2$ (17 mg, 0.025 mmol), Na$_2$CO$_3$(2.0 M, 1.0 mL, 2.0 mmol) as a white foam. MS (ESI): 425 (base, M+H).

Step B:
The title compound (0.033 g, 99%) was prepared by the general method of Example 312, step B from tert-butyl(7aS,11aR)-2-(4-chlorophenyl)-5,6,7a,8,9,10,11,11a-octahydro-4H-pyrido[3',4':4,5]pyrrolo[3,2,1-ij]quinoline-10(7aH)-carboxylate (0.045 g, 0.11 mmol) as a white foam. $^1$H NMR (CDCl$_3$, 300 MHz) δ 1.80–2.05 (m, 2H), 2.05–2.20 (m, 2H), 2.58–2.82 (m, 4H), 2.82–3.06 (m, 3H), 3.07–3.20 (m, 2H), 3.23–3.40 (m, 1H), 3.40–3.48 (m, 1H), 7.11(s, 1H), 7.13 (s, 1H), 7.34 (d, J=8.4 Hz, 2H), 7.45 (d, J=8.4 Hz) ppm. MS (ESI): 325 (base, M+H).

Example 355

(7aS,11aR)-2-(2,6-difluorophenyl)-5,6,7a,8,9,10,11,11a-octahydro-4H-pyrido[3',4':4,5]pyrrolo[3,2,1-ij]quinoline Step A:
Tert-butyl(7aS,11aR)-2-(2,6-difluorophenyl)-5,6,7a,8,9,10,11,11a-octahydro-4H-pyrido[3',4':4,5]pyrrolo[3,2,1-ij]quinoline-10(7aH)-carboxylate (0.064 g, 15%) was prepared by the general method of Example 320, step A from tert-butyl(8aS,11aR)-2-bromo-4,5,6,7,9,10,12,12a-octahydroazepino[3,2,1-hi]pyrido[4,3-b]indole-11(8aH)-carboxylate (0.39 g, 1.0 mmol), 2,6-difluorophenylboronic acid (0.63 g, 4.0 mmol), Pd(dppf)$_2$Cl$_2$ (48 mg, 0.06 mmol), TEA (3.0 mL, 22 mmol) as a white foam.

Step B:
The title compound (0.029 g, 59%) was prepared by the general method of Example 312, step B from tert-butyl(7aS,11aR)-2-(2,6-difluorophenyl)-5,6,7a,8,9,10,11,11a-octahydro-4H-pyrido[3',4':4,5]pyrrolo[3,2,1-ij]quinoline-10(7aH)-carboxylate (0.064 g, 0.15 mmol) as a white foam. $^1$H NMR (CDCl$_3$, 300 MHz) δ 1.80–2.05 (m, 2H), 2.05–2.25 (m, 2H), 2.58–2.83 (m, 4H), 2.83–3.08 (m, 2H), 3.08–3.60 (m, 5H), 6.85–7.08 (m, 4H), 7.08–7.22 (m, 1H) ppm.

Example 356

(7aS,11aR)-2-(2,6-difluorophenyl)-10-methyl-5,6,7a,8,9,10,11,11a-octahydro-4H-pyrido[3',4':4,5]pyrrolo[3,2,1-ij]quinoline A mixture of (7aS,11aR)-2-(2,6-difluorophenyl)-5,6,7a,8,9,10,11,11a-octahydro-4H-pyrido[3',4':4,5]pyrrolo[3,2,1-ij]quinoline (0.050, 0.15 mmol), HCHO (0.20 mL, 2.9 mmol) and formic acid (1.0 mL, 2.9 mmol) was heated at 80° C. for 4 h and cooled to room temperature. Water (5.0 mL) was added and the solution was basified with saturated Na$_2$CO$_3$ until pH>8. The mixture was extracted with CH$_2$Cl$_2$ (3×10 mL), dried (Na$_2$SO$_4$) and flash column chromatography (1–5% MeOH in CHCl$_3$) gave the title compound (0.032 g, 62%) as a white foam. $^1$H NMR (CDCl$_3$, 300 MHz) δ 2.00–2.20 (m, 5H), 2.20–2.50 (m, 4H), 2.55–2.68 (m, 1H), 2.68–2.82 (m, 3H), 2.86–2.98 (m, 1H), 3.28–3.42 (m, 3H), 6.90–7.08 (m, 4H), 7.14–7.25 (m, 1H) ppm. MS (ESI): 341 (base, M+H).

Example 357

(7aS,11aR)-2-(2,3-difluorophenyl)-5,6,7a,8,9,10,11,
11a-octahydro-4H-pyrido[3',4':4,5]pyrrolo[3,2,1-ij]
quinoline Step A:
Tert-butyl(7aS,11aR)-2-(2,3-difluorophenyl)-5,6,7a,8,9,
10,11,11a-octahydro-4H-pyrido[3',4':4,5]pyrrolo[3,2,1-ij]
quinoline-10(7aH)-carboxylate (0.15 g, 70%) was prepared by the general method of Example 89, step C from tert-butyl(7aS,11aR)-2-bromo-5,6,7a,8,9,10,11,11a-octahydro-4H-pyrido[3',4':4,5]pyrrolo[3,2,1-ij]quinoline-10(7aH)-carboxylate (0.20 g, 0.50 mmol), 2,3-difluorophenyl boronic acid (0.16 g, 1.0 mmol), Pd(PPh₃)₂Cl₂ (17 mg, 0.025 mmol), Na₂CO₃(2.0 M, 1.0 mL, 2.0 mmol) as a white foam. MS (ESI): 427 (base, M+H).

Step B:
The title compound (0.10 g, 88%) was prepared by the general method of Example 312, step B from tert-butyl(7aS,11aR)-2-(2,3-difluorophenyl)-5,6,7a,8,9,10,11,11a-octahydro-4H-pyrido[3',4':4,5]pyrrolo[3,2,1-ij]quinoline-10(7aH)-carboxylate (0.15 g, 0.35 mmol) as a white foam. $^1$H NMR (CDCl₃, 300 MHz) δ 1.75–2.00 (m, 2H), 2.05–2.30 (m, 3H), 2.60–2.80 (m, 4H), 2.80–2.90 (m, 21H), 3.02–3.16 (m, 2H), 3.24–3.38 (m, 1H), 3.38–3.48 (m, 1H), 6.94–7.20 (m, 5H) ppm. MS (ESI): 327 (base, M+H).

Example 358

(7aS,11aR)-2-(3,4-difluorophenyl)-5,6,7a,8,9,10,11,
11a-octahydro-4H-pyrido[3',4':4,5]pyrrolo[3,2,1-ij]
quinoline Step A:
Tert-butyl(7aS,11aR)-2-(3,4-difluorophenyl)-5,6,7a,8,9,
10,11,11a-octahydro-4H-pyrido[3',4':4,5]pyrrolo[3,2,1-ij]
quinoline-10(7aH)-carboxylate (0.077 g, 72%) was prepared by the general method of Example 319, step A from tert-butyl(7aS,11aR)-2-bromo-5,6,7a,8,9,10,11,11a-octahydro-4H-pyrido[3',4':4,5]pyrrolo[3,2,1-ij]quinoline-10(7aH)-carboxylate (0.10 g, 0.25 mmol), 3,4-difluorophenyl boronic acid (0.080 g, 0.50 mmol), Pd(PPh₃)₄ (12 mg, 0.010 mmol), and Ba(OH)₂ (0.17 M, 3.0 mL, 0.51 mmol) as a white foam. MS (ESI): 427 (base, M+H).

Step B:
The title compound (0.054 g, 90%) was prepared by the general method of Example 312, step B from tert-butyl(7aS,11aR)-2-(3,4-difluorophenyl)-5,6,7a,8,9,10,11,11a-octahydro-4H-pyrido[3',4':4,5]pyrrolo[3,2,1-ij]quinoline-10(7aH)-carboxylate (0.077 g, 0.18 mmol) as a white foam. $^1$H NMR (CDCl₃, 300 MHz) δ 1.70–2.00 (m, 4H), 2.10–2.50 (m, 3H), 2.50–2.70 (m, 1H), 2.79–2.85 (m, 2H), 3.10–3.60 (m, 5H), 7.06–7.35(m, 5H) ppm. MS (ESI): 327 (base, M+H).

Example 359

(7aS,11aR)-2-(3-fluorophenyl)-5,6,7a,8,9,10,11,11a-
octahydro-4H-pyrido[3',4':4,5]pyrrolo[3,2,1-ij]
quinoline Step A:
Tert-butyl(7aS,11aR)-2-(3-fluorophenyl)-5,6,7a,8,9,10,
11,11a-octahydro-4H-pyrido[3',4':4,5]pyrrolo[3,2,1-ij]
quinoline-10(7aH)-carboxylate (0.055 g, 52%) was prepared by the general method of Example 319, step A from tert-butyl(7aS,11aR)-2-bromo-5,6,7a,8,9,10,11,11a-octahydro-4H-pyrido[3',4':4,5]pyrrolo[3,2,1-ij]quinoline-10(7aH)-carboxylate (0.10 g, 0.25 mmol), 3-fluorophenyl boronic acid (0.070 g, 0.50 mmol), Pd(PPh₃)₄ (12 mg, 0.010 mmol), and Ba(OH)₂ (0.17 M, 3.0 mL, 0.51 mmol) as a white foam. MS (ESI): 409 (base, M+H).

Step B:
The title compound (0.042 g, 100%) was prepared by the general method of Example 312, step B from tert-butyl(7aS,11aR)-2-(3-fluorophenyl)-5,6,7a,8,9,10,11,11a-octahydro-4H-pyrido[3',4':4,5]pyrrolo[3,2,1-ij]quinoline-10(7aH)-carboxylate (0.055 g, 0.13 mmol) as a white foam. $^1$H NMR (CDCl₃, 300 MHz) δ 2.05–2.22 (m, 4H), 2.55–2.68 (m, 1H), 2.68–2.80 (m, 3H), 3.00–3.20 (m, 2H), 3.2–3.48 (m, 4H), 5.00–5.50 (br, 1H), 6.85–7.00 (m, 1H), 7.08–7.40 (m, 5H) ppm. MS (ESI): 309 (base, M+H).

Example 360

(7aS,11aR)-2-[2-chloro-4-methoxyphenyl)-5,6,7a,8,
9,10,11,11a-octahydro-4H-pyrido[3',4':4,5]pyrrolo[3,
2,1-ij]quinoline Step A:
Tert-butyl(7aS,11aR)-2-[2-chloro-4-methoxyphenyl)-5,6,
7a,8,9,10,11,11a-octahydro-4H-pyrido[3',4':4,5]pyrrolo[3,2,
1-ij]quinoline-10(7aH)-carboxylate (0.053 g, 23%) was prepared by the general method of Example 89, step C from tert-butyl (7aS,11aR)-2-bromo-5,6,7a,8,9,10,11,11a-octahydro-4H-pyrido[3',4':4,5]pyrrolo[3,2,1-ij]quinoline-10(7aH)-carboxylate (0.20 g, 0.50 mmol), 2-chloro-4-methoxyphenyl boronic acid (0.19 g, 1.0 mmol), Pd(PPh₃)₂Cl₂ (17 mg, 0.025 mmol), Na₂CO₃(2.0 M, 1.0 mL, 2.0 mmol) as a white foam.

Step B:
The title compound (0.035 g, 85%) was prepared by the general method of Example 312, step B from tert-butyl(7aS,11aR)-2-[2-chloro-4-methoxyphenyl)-5,6,7a,8,9,10,11,11a-octahydro-4H-pyrido[3',4':4,5]pyrrolo[3,2,1-ij]quinoline-10(7aH)-carboxylate (0.053 g, 0.12 mmol) as a white foam. $^1$H NMR (CDCl₃, 300 MHz) δ 1.80–2.05 (m, 2H), 2.05–2.20 (m, 3H), 2.58–2.68 (m, 1H), 2.68–2.80 (m, 2H), 2.85–3.05 (m, 3H), 3.07–3.20 (m, 2H), 3.23–3.36 (m, 1H), 3.38–3.48 (m, 1H), 6.95 (s, 1H), 6.99 (s, 1H), 7.16 (dd, J=2.7, 8.4 Hz, 1H), 7.30 (d, J=2.7 Hz, 1H), 7.34 (d, J=8.4 Hz, 1H) ppm.

Example 361

(7aS,11aR)-2-[2-fluoro-4-methoxyphenyl)-5,6,7a,8,
9,10,11,11a-octahydro-4H-pyrido[3',4':4,5]pyrrolo[3,
2,1-ij]quinoline Step A:
Tert-butyl(7aS,11a)-2-[2-fluoro-4-methoxyphenyl)-5,6,
7a,8,9,10,11,11a-octahydro-4H-pyrido[3',4':4,5]pyrrolo[3,2,
1-ij]quinoline-10(7aH)-carboxylate (0.15 g, 68%) was prepared by the general method of Example 89, step C from tert-butyl(7aS,1 aR)-2-bromo-5,6,7a,8,9,10,11,11a-octahydro-4H-pyrido[3',4':4,5]pyrrolo[3,2,1-ij]quinoline-10(7aH)-carboxylate (0.20 g, 0.50 mmol), 2-fluoro-4-methoxyphenylboronic acid (0.17 g, 1.0 mmol), Pd(PPh₃)₂Cl₂ (17 mg, 0.025 mmol), Na₂CO₃(2.0 M, 1.0 mL, 2.0 mmol) as a white foam. MS (ESI): 339 (base, M+H).

Step B:
The title compound (0.11 g, 94%) was prepared by the general method of Example 312, step B from tert-butyl(7aS, 11aR)-2-[2-fluoro-4-methoxyphenyl)-5,6,7a,8,9,10,11,11a-octahydro-4H-pyrido[3',4':4,5]pyrrolo[3,2,1-ij]quinoline-10 (7aH)-carboxylate (0.15 g, 0.34 mmol) as a white foam. $^1$H NMR (CDCl$_3$, 300 MHz) δ 1.70–1.88 (m, 1H), 1.88–2.00 (m, 1H), 2.00–2.20 (m, 3H), 2.55–2.80 (m, 4H), 2.80–2.96 (m, 2H), 3.02–3.12 (m, 2H), 3.28–3.37 (m, 1H), 3.38–3.48 (m, 1H), 3.81 (s, 3H), 6.64–6.75 (m, 2H), 7.03 (s, 1H), 7.07 (s, 1H), 7.29 (t, J=8.8 Hz, 1H) ppm. MS (ESI): 339 (base, M+H).

Example 362

(7aS,11aR)-2-(4-methoxy-2-methylphenyl)-5,6,7a,8,9,10,11,11a-octahydro-4H-pyrido[3',4':4,5]pyrrolo[3,2,1-ij]quinoline Step A:
Tert-butyl(7aS,11aR)-2-(4-methoxy-2-methylphenyl)-5,6,7a,8,9,10,11,11a-octahydro-4H-pyrido[3',4':4,5]pyrrolo[3,2,1-ij]quinoline-10(7aH)-carboxylate (0.15 g, 68%) was prepared by the general method of Example 89, step C from tert-butyl(7aS,11aR)-2-bromo-5,6,7a,8,9,10,11,11a-octahydro-4H-pyrido[3',4':4,5]pyrrolo[3,2,1-ij]quinoline-10(7aH)-carboxylate (0.20 g, 0.50 mmol), 4-methoxy-2-methylphenylboronic acid (0.17 g, 1.0 mmol), Pd(PPh$_3$)$_2$Cl$_2$ (17 mg, 0.025 mmol), Na$_2$CO$_3$(2.0 M, 1.0 mL, 2.0 mmol) as a white foam. MS (ESI): 449 (base, M+H).

Step B:
The title compound (0.095 g, 97%) was prepared by the general method of Example 312, step B from tert-butyl(7aS,11aR)-2-(4-methoxy-2-methylphenyl)-5,6,7a,8,9,10,11,11a-octahydro-4H-pyrido[3',4':4,5]pyrrolo[3,2,1-ij]quinoline-10 (7aH)-carboxylate (0.13 g, 0.29 mmol) as a white foam. $^1$H NMR (CDCl$_3$, 300 MHz) δ 1.74–1.88 (m, 1H), 1.88–2.00 (m, 1H), 2.05–2.28 (m, 3H), 2.28 (s, 3H), 2.55–2.80 (m, 4H), 2.80–2.92 (m, 2H), 3.00–3.12 (m, 2H), 3.28–3.36 (m, 1H), 3.36–3.45 (m, 1H), 3.82 (s, 3H), 6.70–6.82 (m, 3H), 6.84 (s, 1H), 7.14 (d, J=8.4 Hz, 1H) ppm. MS (ESI): 349 (base, M+H).

Example 363

(7aS,11aR)-2-[4-methoxy-2-(trifluoromethyl)phenyl]-5,6,7a,8,9,10,11,11a-octahydro-4H-pyrido[3',4':4,5]pyrrolo[3,2,1-ij]quinoline Step A:
Tert-butyl(7aS,11aR)-2-[4-methoxy-2-(trifluoromethyl)phenyl]-5,6,7a,8,9,0,11,11a-octahydro-4H-pyrido[3',4':4,5]pyrrolo[3,2,1-ij]quinoline-10(7aH)-carboxylate (3.02 g, 61%) was prepared by the general method of Example 89, step C from tert-butyl(7aS,11aR)-2-bromo-5,6,7a,8,9,10,11,11a-octahydro-4H-pyrido[3',4':4,5]pyrrolo[3,2,1-ij]quinoline-10(7aH)-carboxylate (3.93 g, 10 mmol), 4-methoxy-2-(trifluoromethyl)phenylboronic acid (4.40 g, 20 mmol), Pd(PPh$_3$)$_2$Cl$_2$ (0.35 g, 0.50 mmol), Na$_2$CO$_3$(2.0 M, 20 mL, 40 mmol) as a white solid. MS (ESI): 489 (base, M+H).

Step B:
The title compound (2.38 g, 99%) was prepared by the general method of Example 312, step B from tert-butyl(7aS,11aR)-2-[4-methoxy-2-(trifluoromethyl)phenyl]-5,6,7a,8,9,10,11,11a-octahydro-4H-pyrido[3',4':4,5]pyrrolo[3,2,1-ij]quinoline-10(7aH)-carboxylate (3.02 g, 6.1 mmol) as a white foam. $^1$H NMR (CDCl$_3$, 300 MHz) δ 1.80–2.05 (m, 2H), 2.08–2.10 (m, 3H), 2.60–2.80 (m, 4H), 2.80–2.96 (m, 2H), 3.04–3.15 (m, 2H), 3.32 (td, J=4.0, 10.0 Hz, 1H), 3.40–3.48 (m, 1H), 3.88 (s, 3H), 6.81 (s, 1H), 6.85 (s, 1H), 7.04 (dd, J=2.7, 8.4 Hz, 1H), 7.20–7.28 (m, 2H) ppm. MS (ESI): 389 (base, M+H).

Example 364

2-[4-methoxy-2-(trifluoromethyl)phenyl]-5,6,8,9,10,11-hexahydro-4H-pyrido[3',4':4,5]pyrrolo[3,2,1-ij] quinoline Step A:
Tert-butyl 2-[4-methoxy-2-(trifluoromethyl)phenyl]-5,6,8,9,10,11-hexahydro-4H-pyrido[3',4':4,5]pyrrolo[3,2,1-ij]quinoline-10 (7aH)-carboxylate (0.78 g) was obtained as a byproduct of Example 363 as a white solid.

Step B:
The title compound (0.60 g, 98%) was prepared by the general method of Example 312, step B from tert-butyl 2-[4-methoxy-2-(trifluoromethyl)phenyl]-5,6,8,9,10,11-hexahydro-4H-pyrido[3',4':4,5]pyrrolo[3,2,1-ij]quinoline-10(7aH)-carboxylate (0.78 g, 1.6 mmol) as a white foam. $^1$H NMR (CDCl$_3$, 300 MHz) δ 2.20–2.30 (m, 2H), 2.79 (t, J=5.4 Hz, 2H), 2.90–3.20 (m, 3H), 3.30 (t, J=5.8 Hz, 2H), 3.91 (s, 3H), 3.98 (t, J=5.8 Hz, 2H), 4,12 (s, 2H), 6.84 (s, 1H), 7.07 (dd, J=2.5, 8.4 Hz, 1H), 7.18 (s, 1H), 7.25–7.35 (m, 2H) ppm. MS (ESI): 428 (base, M+CH$_3$CN).

Example 365

4-[(7aS,11aR)-5,6,7a,8,9,10,11,11a-octahydro-4H-pyrido[3',4':4,5]pyrrolo[3,2,1-ij]quinolin-2-yl]-3-(trifluoromethyl)phenol BBr$_3$ in CH$_2$Cl$_2$ (0.91 M, 0.66 mL, 0.60 mmol) was added dropwise to a solution of tert-butyl(7aS,11aR)-2-[4-methoxy-2-(trifluoromethyl)phenyl]-5,6,7a,8,9,10,11 a-octahydro-4H-pyrido[3',4':4,5]pyrrolo[3,2,1-ij]quinoline-10 (7aH)-carboxylate (0.049 g, 0.10 mmol) in CH$_2$Cl$_2$ (5.0 mL) at room temperature under N$_2$. The mixture was stirred for 18 h before quenched with water (5.0 mL). The mixture was basified with saturated NaHCO$_3$ until pH ~8 and extracted with CH$_2$Cl$_2$ (3×10 mL). The combined organic layer was dried (Na$_2$SO$_4$) and concentrated in vacuo. Reverse phase HPLC (H$_2$O—CH$_3$CN-TFA (0.05%)) gave the title compound (0.012 g, 32%) as a white solid. $^1$H NMR (CDCl$_3$, 300 MHz) δ 2.00–2.22 (m, 2H), 2.05–2.20 (m, 2H), 2.55–2.80 (m, 4H), 2.88–2.96 (m, 2H), 3.07–3.20 (m, 2H), 3.23–3.36 (m, 1H), 3.38–3.48 (m, 1H), 6.95 (s, 1H), 6.99 (s, 1H), 7.16 (dd, J=2.7, 8.4 Hz, 1H), 7.30 (d, J=2.7 Hz, 1H), 7.34 (d, J=8.4 Hz) ppm. MS (ESI): 375 (base, M+H).

Example 366

(7aS,11aR)-2-[2-(trifluoromethyl)phenyl]-5,6,7a,8,9,10,11,11a-octahydro-4H-pyrido[3',4':4,5]pyrrolo[3,2,1-ij]quinoline Step A:
Tert-butyl(7aS,11aR)-2-[2-(trifluoromethyl)phenyl]-5,6,7a,8,9,10,11,11a-octahydro-4H-pyrido[3',4':4,5]pyrrolo[3,2,1-yl]quinoline-10(7aH)-carboxylate (0.041 g, 18%) was prepared by the general method of Example 89, step C from tert-butyl(7aS,11aR)-2-bromo-5,6,7a,8,9,10,11,11a-octahydro-4H-pyrido[3',4':4,5]pyrrolo[3,2,1-ij]quinoline-10(7aH)- carboxylate (0.20 g, 0.50 mmol), 2-(trifluoromethyl)phenyl boronic acid (0.19 g, 1.0 mmol), Pd(PPh$_3$)$_2$Cl$_2$ (17 mg, 0.025 mmol), Na$_2$CO$_3$(2.0 M, 1.0 mL, 2.0 mmol) as a white foam. MS (ESI): 459 (base, M+H).

Step B:

The title compound (0.030 g, 94%) was prepared by the general method of Example 312, step B from tert-butyl(7aS,11aR)-2-[2-(trifluoromethyl)phenyl]-5,6,7a,8,9,10,11,11a-octahydro-4H-pyrido[3',4':4,5]pyrrolo[3,2,1-ij]quinoline-10(7aH)-carboxylate (0.041 g, 0.090 mmol) as a white foam. $^1$H NMR (CDCl$_3$, 300 MHz) δ 1.80–2.08 (m, 2H), 2.08–2.28 (m, 2H), 2.43 (br, 1H), 2.60–2.80 (m, 4H), 2.85–2.98 (m, 2H), 3.07–3.20 (m, 2H), 3.25–3.40 (m, 1H), 3.40–3.48 (m, 1H), 6.84 (s, 1H), 6.88 (s, 1H), 7.34 (d, J=7.7 Hz, 1H), 7.40 (t, J=7.6 Hz, 1H), 7.51 (t, J=7.4 Hz, 1H), 7.71 (d, J=8.1 Hz, 1H) ppm. MS (ESI): 359 (base, M+H).

Example 367

(7aS,11aR)-2-[4-isopropoxy-2-(trifluoromethyl)phenyl]-5,6,7a,8,9,10,11,11a-octahydro-4H-pyrido[3',4':4,5]pyrrolo[3,2,1-ij]quinoline Step A:

Tert-butyl(7aS,11aR)-2-[4-isopropoxy-2-(trifluoromethyl)phenyl]-5,6,7a,8,9,10,11,11a-octahydro-4H-pyrido[3',4':4,5]pyrrolo[3,2,1-ij]quinoline-10(7aH)-carboxylate (0.16 g, 61%) was prepared by the general method of Example 89, step C from tert-butyl(7aS,11aR)-2-bromo-5,6,7a,8,9,10,11,11a-octahydro-4H-pyrido[3',4':4,5]pyrrolo[3,2,1-ij]quinoline-10(7aH)-carboxylate (0.20 g, 0.50 mmol), 4-isopropoxy-2-(trifluoromethyl)phenylboronic acid (0.18 g, 0.73 mmol), Pd(PPh$_3$)$_2$Cl$_2$ (17 mg, 0.025 mmol), Na$_2$CO$_3$(2.0 M, 1.0 mL, 2.0 mmol) as a white foam. MS (ESI): 517 (base, M+H).

Step B:

The title compound (0.13 g, 100%) was prepared by the general method of Example 312, step B from tert-butyl(7aS,11aR)-2-[4-isopropoxy-2-(trifluoromethyl)phenyl]-5,6,7a,8,9,10,11,11a-octahydro-4H-pyrido[3',4':4,5]pyrrolo[3,2,1-ij]quinoline-10(7aH)-carboxylate (0.16 g, 0.31 mmol) as a white foam. $^1$H NMR (CDCl$_3$, 300 MHz) δ 1.38 (d, J=6.0 Hz, 6H), 1.70–1.88 (m, 1H), 1.88–2.00 (m, 1H), 2.02–2.18 (m, 3H), 2.55–2.80 (m, 4H), 2.80–2.98 (m, 2H), 3.00–3.13 (m, 2H), 3.25–3.37 (m, 1H), 3.38–3.55 (m, 1H), 4.61, (p, J=6.0 Hz, 1H), 6.81 (s, 1H), 6.85 (s, 1H), 7.01 (dd, J=1.2, 8.6 Hz, 1H), 7.18–7.26 (m, 2H) ppm. MS (ESI): 417 (base, M+H).

Example 368

(7aS,11aR)-2-[2,4-bis(trifluoromethyl)phenyl]-5,6,7a,8,9,10,11,11a-octahydro-4H-pyrido[3',4':4,5]pyrrolo[3,2,1-ij]quinoline Step A:

Tert-butyl(7aS,11aR)-2-[2,4-bis(trifluoromethyl)phenyl]-5,6,7a,8,9,10,11,11a-octahydro-4H-pyrido[3',4':4,5]pyrrolo[3,2,1-ij]quinoline-10(7aH)-carboxylate (0.029 g, 11%) was prepared by the general method of Example 89, step C from tert-butyl(7aS,11aR)-2-bromo-5,6,7a,8,9,10,11,11a-octahydro-4H-pyrido[3',4':4,5]pyrrolo[3,2,1-ij]quinoline-10(7aH)-carboxylate (0.20 g, 0.50 mmol), 2,4-bis(trifluoromethyl)phenylboronic acid (0.26 g, 1.0 mmol), Pd(PPh$_3$)$_2$Cl$_2$ (17 mg, 0.025 mmol), Na$_2$CO$_3$(2.0 M, 1.0 mL, 2.0 mmol) as a white foam. MS (ESI): 527 (base, M+H).

Step B:

The title compound (0.023 g, 100%) was prepared by the general method of Example 312, step B from tert-butyl(7aS,11aR)-2-[2,4-bis(trifluoromethyl)phenyl]-5,6,7a,8,9,10,11,11a-octahydro-4H-pyrido[3',4':4,5]pyrrolo[3,2,1-ij]quinoline-10(7aH)-carboxylate (0.029 g, 0.055 mmol) as a white foam. $^1$H NMR (CDCl$_3$, 300 MHz) δ 2.10–2.30 (m, 4H), 2.50–2.70 (m, 3H), 2.70–2.86 (m, 3H), 3.10–3.55 (m, 5H), 6.90 (s, 2H), 7.45 (d, J=7.8 Hz, 1H), 7.78 (d, J=7.8 Hz, 1H), 7.97 (s, 1H) ppm. MS (ESI): 427 (base, M+H).

Example 369

(7aS,11aR)-2-[4-fluoro-2-(trifluoromethyl)phenyl]-5,6,7a,8,9,10,11,11a-octahydro-4H-pyrido[3',4':4,5]pyrrolo[3,2,1-ij]quinoline Step A:

Tert-butyl(7aS,11aR)-2-[4-fluoro-2-(trifluoromethyl)phenyl]-5,6,7a,8,9,10,11,11a-octahydro-4H-pyrido[3',4':4,5]pyrrolo[3,2,1-ij]quinoline-10(7aH)-carboxylate (0.093 g, 75%) was prepared by the general method of Example 319, step A from tert-butyl(7aS,11aR)-2-bromo-5,6,7a,8,9,10,11,11a-octahydro-4H-pyrido[3',4':4,5]pyrrolo[3,2,1-ij]quinoline-10(7aH)-carboxylate (0.10 g, 0.26 mmol), 4-fluoro-2-(trifluoromethyl)phenylboronic acid (0.11 g, 0.51 mmol), Pd(PPh$_3$)$_4$ (12 mg, 0.010 mmol), and Ba(OH)$_2$ (0.17 M, 3.0 mL, 0.51 mmol) as a white foam. MS (ESI): 477 (base, M+H).

Step B:

The title compound (0.071 g, 97%) was prepared by the general method of Example 312, step B from tert-butyl(7aS,11aR)-2-[4-fluoro-2-(trifluoromethyl)phenyl]-5,6,7a,8,9,10,11,11a-octahydro-4H-pyrido[3',4':4,5]pyrrolo[3,2,1-ij]quinoline-10(7aH)-carboxylate (0.093 g, 0.19 mmol) as a white foam. $^1$H NMR (CDCl$_3$, 300 MHz) δ 2.08–2.12 (m, 4H), 2.58–2.85 (m, 4H), 3.02–3.24 (m, 2H), 3.28–3.50 (m, 5H), 7.11(s, 1H), 7.12 (s, 1H), 7.21 (t, J=9.4 Hz, 1H), 7.58–7.68 (m, 1H), 7.68–7.75 (m, 1H) ppm. MS (ESI): 377 (base, M+H).

Example 370

4-[(7aS,11aR)-5,6,7a,8,9,10,11,11a-octahydro-4H-pyrido[3',4':4,5]pyrrolo[3,2,1-ij]quinolin-2-yl]-3-(trifluoromethyl)aniline Step A:

Tert-butyl(7aS,11aR)-2-[4-[(tert-butoxycarbonyl)amino]-2-(trifluoromethyl)phenyl]-5,6,7a,8,9,10,11,11a-octahydro-4H-pyrido[3',4':4,5]pyrrolo[3,2,1-ij]quinoline-10(7aH)-carboxylate (0.13 g, 93%) was prepared by the general method of Example 319, step A from tert-butyl(7aS,11aR)-2-bromo-5,6,7a,8,9,10,11,11a-octahydro-4H-pyrido[3',4':4,5]pyrrolo[3,2,1-ij]quinoline-10(7aH)-carboxylate (0.10 g, 0.25 mmol), 4-[(tert-butoxycarbonyl)amino]-2-(trifluoromethyl)phenylboronic acid (0.15 g, 0.50 mmol), Pd(PPh$_3$)$_4$ (12 mg, 0.010 mmol), and Ba(OH)$_2$ (0.17 M, 3.0 mL, 0.51 mmol) as a white foam. MS (ESI): 574 (base, M+H).

Step B:

The title compound (0.079 g, 72%) was prepared by the general method of Example 312, step B from tert-butyl(7aS, 11aR)-2-[4-[(tert-butoxycarbonyl)amino]-2-(trifluoromethyl)phenyl]-5,6,7a,8,9,10,11,11a-octahydro-4H-pyrido[3',4':4,5]pyrrolo[3,2,1-ij]quinoline-10(7aH)-carboxylate (0.13 g, 0.23 mmol) as a white foam. $^1$H NMR (CDCl$_3$, 300 MHz) δ 1.78–2.00 (m, 2H), 2.05–2.22 (m, 2H), 2.58–2.80 (m, 4H), 2.80–2.98 (m, 2H), 3.04–3.16 (m, 2H), 3.28–3.38 (m, 1H), 3.38–3.48 (m, 1H), 3.82 (br, 3H), 6.72–6.88 (m, 3H), 7.00 (d, J=2.6 Hz, 1H), 7.11(d, J=8.1 Hz, 1H) ppm. MS (ESI): 374 (base, M+H).

Example 371

4-[(7aS,11aR)-5,6,7a,8,9,10,11,11a-octahydro-4H-pyrido[3',4':4,5]pyrrolo[3,2,1-ij]quinolin-2-yl]-N-methyl-3-(trifluoromethyl)aniline Step A:

Tert-butyl(7aS,11aR)-2-[4-[(tert-butoxycarbonyl)(methyl)amino]-2-(trifluoromethyl)phenyl]-5,6,7a,8,9,10,11,11a-octahydro-4H-pyrido[3',4':4,5]pyrrolo[3,2,1-ij]quinoline-10(7aH)-carboxylate (0.12 g, 82%) was prepared by the general method of Example 319, step A from tert-butyl(7as,11aR)-2-bromo-5,6,7a,8,9,10,11,11a-octahydro-4H-pyrido[3',4':4,5]pyrrolo[3,2,1-ij]quinoline-10(7aH)-carboxylate (0.10 g, 0.25 mmol), 4-[(tert-butoxycarbonyl)(methyl)amino]-2-(trifluoromethyl)phenylboronic acid (0.16 g, 0.50 mmol), Pd(PPh$_3$)$_4$ (12 mg, 0.010 mmol), and Ba(OH)$_2$ (0.17 M, 3.0 mL, 0.51 mmol) as a white foam. MS (ESI): 588 (base, M+H).

Step B:

The title compound (0.071 g, 71%) was prepared by the general method of Example 312, step B from tert-butyl(7aS,11aR)-2-[4-[(tert-butoxycarbonyl)(methyl)amino]-2-(trifluoromethyl)phenyl]-5,6,7a,8,9,10,11,11a-octahydro-4H-pyrido[3',4':4,5]pyrrolo[3,2,1-ij]quinoline-10(7aH)-carboxylate (0.12 g, 0.20 mmol) as a white foam. $^1$H NMR (CDCl$_3$, 300 MHz) δ 1.78–2.00 (m, 2H), 2.05–2.25 (m, 2H), 2.60–2.80 (m, 4H), 2.80–3.00 (m, 5H), 3.00–3.20 (m, 2H), 3.28–3.40 (m, 1H), 3.40–3.50 (m, 1H), 3.91 (br, 2H), 6.73 (dd, J=2.6, 8.3 Hz, 1H), 6.81 (s, 1H), 6.85 (s, 1H), 6.91 (d, J=2.6 Hz, 1H), 7.15 (d, J=8.3 Hz, 1H) ppm. MS (ESI): 388 (base, M+H).

Example 372

4-[(7aS,11aR)-5,6,7a,8,9,10,11,11a-octahydro-4H-pyrido[3',4':4,5]pyrrolo[3,2,1-ij]quinolin-2-yl]-3-methylbenzonitrile Step A:

Tert-butyl(7aS,11aR)-2-(4-cyano-2-methylphenyl)-5,6,7a,8,9,10,11,11a-octahydro-4H-pyrido[3',4':4,5]pyrrolo[3,2,1-ij]quinoline-10(7aH)-carboxylate (0.073 g, 65%) was prepared by the general method of Example 319, step A from tert-butyl(7aS,11aR)-2-bromo-5,6,7a,8,9,10,11,11a-octahydro-4H-pyrido[3',4':4,5]pyrrolo[3,2,1-ij]quinoline-10(7aH)-carboxylate (0.10 g, 0.26 mmol), 4-cyano-2-methylphenylboronic acid (0.088 g, 0.52 mmol), Pd(PPh$_3$)$_4$ (12 mg, 0.010 mmol), and Ba(OH)$_2$ (0.17 M, 3.0 mL, 0.51 mmol) as a white foam. MS (ESI): 430 (base, M+H).

Step B:

The title compound (0.050 g, 89%) was prepared by the general method of Example 312, step B from tert-butyl (7aS,1 aR)-2-(4-cyano-2-methylphenyl)-5,6,7a,8,9,10,11,11a-octahydro-4H-pyrido[3',4':4,5]pyrrolo[3,2,1-ij]quinoline-10(7aH)-carboxylate (0.073 g, 0.17 mmol) as a white foam. $^1$H NMR (CDCl$_3$, 300 MHz) δ 2.10–2.20 (m, 4H), 2.30 (s, 3H), 2.55–2.70 (m, 1H), 2.70–2.80 (m, 3H), 3.07–3.26 (m, 2H), 3.26–3.48 (m, 5H), 6.84 (s, 2H), 7.25 (d, J=7.7 Hz, 1H), 7.47 (d, J=7.7 Hz, 1H), 7.51 (s, 1H) ppm. MS (ESI): 330 (base, M+H).

Example 373

2-[(7aS,11aR)-5,6,7a,8,9,10,11,11a-octahydro-4H-pyrido[3',4':4,5]pyrrolo[3,2,1-ij]quinolin-2-yl]benzaldehyde Step A:

Tert-butyl(7aS,11aR)-2-(2-formylphenyl)-5,6,7a,8,9,10,11,11a-octahydro-4H-pyrido[3',4':4,5]pyrrolo[3,2,1-ij]quinoline-10(7aH)-carboxylate (0.091 g, 44%) was prepared by the general method of Example 89, step C from tert-butyl(7 aS,11aR)-2-bromo-5,6,7a,8,9,10,11,11a-octahydro-4H-pyrido[3',4':4,5]pyrrolo[3,2,1-ij]quinoline-10(7aH)-carboxylate (0.20 g, 0.50 mmol), 2-formylphenylboronic acid (0.15 g, 1.0 mmol), Pd(PPh$_3$)$_2$Cl$_2$ (17 mg, 0.025 mmol), Na$_2$CO$_3$(2.0 M, 1.0 mL, 2.0 mmol) as a white foam. MS (ESI): 419 (base, M+H).

Step B:

The title compound (0.021 g, 91%) was prepared by the general method of Example 312, step B from tert-butyl(7aS,11aR)-2-(2-formylphenyl)-5,6,7a,8,9,10,11,11a-octahydro-4H-pyrido[3',4':4,5]pyrrolo[3,2,1-ij]quinoline-10(7aH)-carboxylate (0.030 g, 0.070 mmol) as a white foam. $^1$H NMR (CDCl$_3$, 300 MHz) δ 1.94–2.24 (m, 4H), 2.59–2.82 (m, 5H), 3.00–3.24 (m, 2H), 3.28–3.42 (m, 3H), 3.44–3.52 (m, 1H), 6.90 (s, 1H), 6.97 (s, 1H), 7.38–7.46 (m, 2H), 7.66 (td, J=7.5, 1.4 Hz, 1H), 7.99 (dd, J=1.4, 8.0 Hz, 1H), 10.01 (s, 1H) ppm. MS (ESI): 319 (base, M+H).

Example 374

{2-[(7aS,11aR)-5,6,7a,8,9,10,11,11a-octahydro-4H-pyrido[3',4':4,5]pyrrolo[3,2,1-ij]quinolin-2-yl]phenyl}methanol Step A:

Tert-butyl(7aS,11aR)-2-[2-(hydroxymethyl)phenyl]-5,6,7a,8,9,10,11,11a-octahydro-4H-pyrido[3',4':4,5]pyrrolo[3,2,1-ij]quinoline-10(7aH)-carboxylate (0.42 g, 69%) was prepared by the method of Example 341 from tert-butyl(7aS,11aR)-2-(2-formylphenyl)-5,6,7a,8,9,10,11,11a-octahydro-4H-pyrido[3',4':4,5]pyrrolo[3,2,1-ij]quinoline-10(7aH)-carboxylate (0.061 g, 0.15 mmol) and NaBH$_4$ (0.060 g, 1.6 mmol) as a white solid. MS (ESI): 421 (base, M+H).

Step B:

The title compound (0.032 g, 100%) was prepared by the general method of Example 312, step B from tert-butyl(7aS,11aR)-2-[2-(hydroxymethyl)phenyl]-5,6,7a,8,9,10,11,11a-octahydro-4H-pyrido[3',4':4,5]pyrrolo[3,2,1-ij]quinoline-10(7aH)-carboxylate (0.042 g, 0.10 mmol) as a white foam. $^1$H NMR (CDCl$_3$, 300 MHz) δ 1.80–2.04 (m, 2H), 2.08–2.20 (m, 2H), 2.50–2.80 (m, 4H), 2.82–2.97 (m, 2H), 3.04–3.20 (m, 2H), 3.20–3.38 (m, 1H), 3.38–3.42 (m, 1H), 4.65 (s, 2H), 6.89 (s, 1H), 6.93 (s, 1H), 7.22–7.38 (m, 3H), 7.50–7.57 (m, 1H) ppm. MS (ESI): 321 (base, M+H).

Example 375

2-[(7aS,11aR)-5,6,7a,8,9,10,11,11a-octahydro-4H-pyrido[3',4':4,5]pyrrolo[3,2,1-ij]quinolin-2-yl]-5-methoxybenzaldehyde Step A:

Tert-butyl(7aS,11aR)-2-(2-formyl-4-methoxyphenyl)-5,6,7a,8,9,10,11,11a-octahydro-4H-pyrido[3',4':4,5]pyrrolo[3,2,1-ij]quinoline-10(7aH)-carboxylate (0.084 g, 38%) was prepared by the general method of Example 89, step C from tert-butyl(7aS,11aR)-2-bromo-5,6,7a,8,9,10,11,11a-octahydro-4H-pyrido[3',4':4,5]pyrrolo[3,2,1-ij]quinoline-10(7aH)-carboxylate (0.20 g, 0.50 mmol), 2-formyl-4-methoxyphenylboronic acid (0.18 g, 1.0 mmol), Pd(PPh$_3$)$_2$Cl$_2$ (17 mg, 0.025 mmol), Na$_2$CO$_3$(2.0 M, 1.0 mL, 2.0 mmol) as a white foam. MS (ESI): 449 (base, M+H).

Step B:

The title compound (0.056 g, 86%) was prepared by the general method of Example 312, step B from tert-butyl(7aS,11aR)-2-(2-formyl-4-methoxyphenyl)-5,6,7a,8,9,10,11,11a-octahydro-4H-pyrido[3',4':4,5]pyrrolo[3,2,1-ij]quinoline-10(7aH)-carboxylate (0.084 g, 0.19 mmol) as a white foam. $^1$H NMR (CDCl$_3$, 300 MHz) δ 2.00–2.10 (m, 2H), 2.10–2.25 (m, 2H), 2.59–2.82 (m, 4H), 2.98–3.20 (m, 2H), 3.20–3.40 (m, 3H), 3.42–3.52 (m, 2H), 3.92 (s, 3H), 6.86 (s, 1H), 6.92 (s, 1H), 7.18 (dd, J=8.4, 2.6 Hz, 1H), 7.35 (d, J=8.4 Hz, 1H), 7.47 (d, J=2.6 Hz, 1H), 9.97 (s, 1H) ppm. MS (ESI): 349 (base, M+H).

Example 376

{2-[(7aS,11aR)-5,6,7a,8,9,10,11,11a-octahydro-4H-pyrido[3',4':4,5]pyrrolo[3,2,1-ij]quinolin-2-yl]-5-methoxyphenyl}methanol Step A:

Tert-butyl(7aS,11aR)-2-[2-(hydroxymethyl)-4-methoxyphenyl]-5,6,7a,8,9,10,11,11a-octahydro-4H-pyrido[3',4':4,5]pyrrolo[3,2,1-ij]quinoline-10(7aH)-carboxylate (0.016 g) was obtained as a byproduct of Example 375. MS (ESI): 451 (base, M+H).

Step B:

The title compound (0.010 g, 83%) was prepared by the general method of Example 312, step B from tert-butyl(7aS,11aR)-2-[2-(hydroxymethyl)-4-methoxyphenyl]-5,6,7a,8,9,10,11,11a-octahydro-4H-pyrido[3',4':4,5]pyrrolo[3,2,1-ij]quinoline-10(7aH)-carboxylate (0.016 g, 0.036 mmol) as a white foam. $^1$H NMR (CDCl$_3$, 300 MHz) δ 1.70–2.02 (m, 2H), 2.08–2.20 (m, 2H), 2.50–2.80 (m, 4H), 2.80–2.95 (m, 2H), 3.00–3.14 (m, 2H), 3.28–3.38 (m, 1H), 3.38–3.46 (m, 1H), 3.87 (s, 3H), 4.65 (s, 2H), 6.80–6.90 (m, 3H), 7.10 (d, J=3.0 Hz, 1H), 7.19 (d, J=8.4 Hz, 1H) ppm. MS (ESI): 351 (base, M+H).

Example 377

(8aS,12aR)-2-[4-ethoxy-2-(trifluoromethyl)phenyl]-4,5,6,7,8a,9,10,11,12,12a-decahydroazepino[3,2,1-hi]pyrido[4,3b]indole The title compound was afforded as a yellow oil (81 mg, 79%) according to the method of Example 319, step A followed by Example 312, step B from tert-butyl(8aS,12aR)-2-bromo-4,5,6,7,9,10,12,12a-octahydroazepino[3,2,1-ij]pyrido[4,3b]indole-11(8H)-carboxylate (100 mg, 0.25 mmol) and 4-ethoxy-2-(trifluoromethyl)phenylboronic acid (83 mg, 0.5 mmol). $^1$H NMR (CDCl$_3$) δ 1.37 (t, 3H, J=7.0 Hz), 1.44–1.58 (m, 1H), 1.66–1.84 (m, 2H), 1.89–2.00 (m, 3H), 2.42–2.73 (m, 3H), 2.80–3.04 (m, 5H), 3.10–3.36 (m, 3H), 4.01 (q, 2H, J=7.00 Hz), 6.77 (d, 2H, J=5.2 Hz), 6.94 (dd, 1H, J=2.5, 8.5 Hz), 7.13–7.19 (m, 2H) ppm. MS (ESI): 417 (base, M+H).

Example 378

(7aS,11aR)-2-[4-ethoxy-2-(trifluoromethyl)phenyl]-5,6,7a,8,9,10,11,11a-octahydro-4H-pyrido[3',4':4,5]pyrrolo[3,2,1-ij]quinoline The title compound was afforded as a yellow oil (56 mg, 56%) according to the method of Example 319, step A followed by Example 312, step B from tert-butyl(7aS,11aR)-2-bromo-5,6,8,9,11,11a-hexahydro-4H-pyrido[3',4':4,5]pyrrolo[3,2,1-ij]quinoline-10(7aH)-carboxylate (100 mg, 0.25 mmol) and 4-methoxy-2-(trifluoromethyl)phenylboronic acid (76 mg, 0.5 mmol). $^1$H NMR (CDCl$_3$) δ 1.46 (t, 3H, J=7.0 Hz), 1.86–2.03 (m, 2H), 2.10–2.21 (m, 2H), 2.62–2.80 (m, 5H), 2.84–2.96 (m, 2H), 3.09–3.19 (m, 2H), 3.33–3.39 (m, 1H), 3.42–3.47 (m, 1H), 4.10 (q, 2H, J=7.0 Hz), 6.83 (d, 2H, J=11.0 Hz), 7.02 (dd, 1H, J=2.7, 8.3 Hz), 7.16–7.28 (m, 2H) ppm. MS (ESI): 403 (base, M+H).

Example 379

(8aS,12aR)-2-[3-chloro-2-methylphenyl]-4,5,6,7,8a,9,10,11,12,12a-decahydroazepino[3,2,1-hi]pyrido[4,3b]indole The title compound was afforded as a yellow oil (49 mg, 53%) according to the method of Example 319, step A followed by Example 312, step B from tert-butyl(8aS,12aR)-2-bromo-4,5,6,7,9,10,12,12a-octahydroazepino[3,2,1-hi]pyrido[4,3b]indole-11(8H)-carboxylate (100 mg, 0.24 mmol) and 3-chloro-2-methylphenylboronic acid (84 mg, 0.48 mmol). MS (ESI): 353 (base, M+H).

Example 380

(7aS,11aR)-2-[3-chloro-2-methylphenyl]-5,6,7a,8,9,10,11,11a-octahydro-4H-pyrido[3',4':4,5]pyrrolo[3,2,1-ij]quinoline The title compound was afforded as a yellow oil (55 mg, 65%) according to the method of Example 319, step A followed by Example 312, step B from tert-butyl(7aS,11aR)-2-bromo-5,6,8,9,11,11a-hexahydro-4H-pyrido[3',4': 4,5]pyrrolo[3,2,1-ij]quinoline-10(7aH)-carboxylate (100 mg, 0.24 mmol) and 3-chloro-2-methylphenylboronic acid (80 mg, 0.48 mmol). MS (ESI): 339 (base, M+H).

Example 381

(7aS,11aR)-2-[5-fluoro-2-methylphenyl]-5,6,7a,8,9,10,11,11a-octahydro-4H-pyrido[3',4':4,5]pyrrolo[3,2,1-ij]quinoline The title compound was afforded as a yellow oil (29 mg, 91%) according to the method of Example 319, step A followed by Example 312, step B from tert-butyl(7aS,11aR)-2-bromo-5,6,8,9,11,11a-hexahydro-4H-pyrido[3',4': 4,5]pyrrolo[3,2,1-ij]quinoline-10(7aH)-carboxylate (50 mg, 0.13 mmol) and 5-fluoro-2-methylphenylboronic acid (39 mg, 0.25 mmol). MS (ESI): 323 (base, M+H).

Example 382

(±)-cis-2-(2,3-dichlorophenyl)-10-propyl-5,6,7a,8,9,10,11,11a-octahydro-4H-pyrido[3',4':4,5]pyrrolo[3,2,1-ij]quinoline To a solution of (±)-cis-2-(2,3-dichlorophenyl)-5,6,7a,8,9,10,11,11a-octahydro-4H-pyrido[3',4':4,5]pyrrolo[3,2,1-ij]quinoline (30 mg, 0.083 mmol) in 1,4-dioxane (0.5 mL) and N,N-diisopropylethylamine (108 mg, 0.83 mmol) were added 1-bromopropane (21 mg, 0.17 mmol) and KI (catalytic amount). The reaction mixture was heated at 100° C. for 15 h. The reaction mixture was cooled to 20° C. then concentrated in vacuo and chromatographed on a silica gel column by elution with $CHCl_3$/MeOH (99/1) to give the title compound (27 mg, 82%) as a yellow oil. $^1$H NMR ($CDCl_3$, 300 MHz) δ 0.92(t, J=7.3 Hz, 3H), 1.58–1.75 (br, 2H), 2.03–2.23 (m, 5H), 2.42–2.55 (br, 2H), 2.58–2.67 (m, 1H), 2.75 (t, J=7.4 Hz, 2H), 2.85–2.95 (br, 1H), 2.98–3.12 (br, 1H), 3.31 (dt, J=10.3, 3.6 Hz, 1H), 3.37–3.45 (br, 2H), 6.94 (s, 1H), 6.97 (s, 1H), 7.15–7.20 (m, 2H), 7.36–7.42 (m, 1H) ppm.

Example 383

(7aS,11aR)-2-(2,3-dichlorophenyl)-10-propyl-5,6,7a,8,9,10,11,11a-octahydro-4H-pyrido[3',4':4,5]pyrrolo[3,2,1-ij]quinoline The title compound was prepared by the method of Example 382 as a yellow oil (22 mg, 66%) from (7aS,11aR)-2-(2,3-dichlorophenyl)-5,6,7a,8,9,10,11,11a-octahydro-4H-pyrido[3',4':4,5]pyrrolo[3,2,1-ij]quinoline (30 mg, 0.083 mmol). The title compound was spectroscopically identical to Example 382. MS (CI, $NH_3$): 401.1 (base, M+H).

Example 384

(±)-cis-10-butyl-2-(2,3-dichlorophenyl)-5,6,7a,8,9,10,11,11a-octahydro-4H-pyrido[3',4':4,5]pyrrolo[3,2,1-ij]quinoline The title compound was prepared by the method of Example 382 as a yellow oil (28 mg, 82%) from (±)-cis-2-(2,3-dichlorophenyl)-5,6,7a,8,9,10,11,11a-octahydro-4H-pyrido[3',4':4,5]pyrrolo[3,2,1-ij]quinoline (30 mg, 0.083 mmol) and 1-bromobutane (23 mg, 0.17 mmol). $^1$H NMR ($CDCl_3$, 300 MHz) δ 0.92(t, J=7.3 Hz, 3H), 1.32 (se, J=7.3 Hz, 2H), 1.53–1.65 (br, 2H), 2.02–2.25 (m, 5H), 2.38–2.53 (br, 2H), 2.58–2.68 (m, 1H), 2.75 (t, J=6.4 Hz, 2H), 2.80–2.92 (br, 1H), 2.95–3.07 (br, 1H), 3.31 (dt, J=10.3, 3.6 Hz, 1H), 3.37–3.45 (br, 2H), 6.94 (s, 1H), 6.99 (s, 1H), 7.15–7.21 (m, 2H), 7.35–7.40 (m, 1H) ppm.

Example 385

(7aS,11aR)-10-butyl-2-(2,3-dichlorophenyl)-5,6,7a,8,9,10,11,11a-octahydro-4H-pyrido[3',4':4,5]pyrrolo[3,2,1-ij]quinoline The title compound was prepared by the method of Example 382 as a yellow oil (23 mg, 62%) from (7aS,11aR)-2-(2,3-dichlorophenyl)-5,6,7a,8,9,10,11,11a-octahydro-4H-pyrido[3',4':4,5]pyrrolo[3,2,1-ij]quinoline (30 mg, 0.083 mmol). The title compound was spectroscopically identical to Example 384. MS (CI, $NH_3$): 415.1 (base, M+H).

Example 386

(7aS,11aR)-2-(2,3-dichlorophenyl)-10-(4-pentenyl)-5,6,7a,8,9,10,11,11a-octahydro-4H-pyrido[3',4':4,5]pyrrolo[3,2,1-ij) quinoline The title compound was prepared by the method of Example 382 as a yellow oil (22 mg, 62%) from (7aS,11aR)-2-(2,3-dichlorophenyl)-5,6,7a,8,9,10,11,11a-octahydro-4H-pyrido[3',4':4,5]pyrrolo[3,2,1-ij]quinoline (30 mg, 0.083 mmol) and 5-bromo-1-pentene (25 mg, 0.17 mmol). $^1$H NMR ($CDCl_3$, 300 MHz) δ 1.62–1.75 (br, 2H), 2.01–2.22 (m, 7H), 2.35–2.53 (br, 3H), 2.58–2.65 (m, 1H), 2.74 (t, J=6.6 Hz, 2H), 2.75–2.85 (br, 1H), 2.88–3.05 (br, 1H), 3.28–3.41 (m, 3H), 4.97 (d, J=13.5 Hz, 1H), 5.02 (dd, J=17.6, 1.5 Hz, 1H), 5.73–5.83 (m, 1H), 6.93 (s, 1H), 6.98 (s, 1H), 7.15–7.21 (m, 2H), 7.36–7.40 (m, 1H) ppm. MS (CI, $NH_3$): 427.1 (base, M+H).

Example 387

(7aS,11aR)-2-(2,3-dichlorophenyl)-10-(3-methyl-2-butenyl)-5,6,7a,8,9,10,11,11a-octahydro-4H-pyrido[3',4':4,5]pyrrolo[3,2,1-ij]quinoline The title compound was prepared by the method of Example 382 as a yellow oil (27 mg, 76%) from (7aS,11aR)-2-(2,3-dichlorophenyl)-5,6,7a,8,9,10,11,11a-octahydro-4H-pyrido[3',4':4,5]pyrrolo[3,2,1-ij]quinoline (30 mg, 0.083 mmol) and 4-bromo-2-methyl-2-butene (25 mg, 0.17 mmol). MS (CI, $NH_3$): 427.1 (base, M+H).

Example 388

(7aS,11aR)-2-(2,4-dichlorophenyl)-10-propyl-5,6,7a,8,9,10,11,11a-octahydro-4H-pyrido[3',4':4,5]pyrrolo[3,2,1-ij]quinoline The title compound was prepared by the method of Example 382 as a yellow oil (21 mg, 65%) from (7aS,11aR)-2-(2,4-dichlorophenyl)-5,6,7a,8,9,10,11,11a-octahydro-4H-pyrido[3',4':4,5]pyrrolo[3,2,1-ij]quinoline (30 mg, 0.083 mmol) and 1-bromopropane (30 mg, 0.24 mmol). $^1$H NMR ($CDCl_3$, 300 MHz) δ 0.92 (t, J=7.3 Hz, 3H), 1.61–1.75 (m, 2H), 2.02–2.35 (m, 6H), 2.45–2.63 (m, 3H), 2.75 (t, J=6.5 Hz, 2H), 2.87–2.98 (br, 1H), 3.00–3.08 (br, 1H), 3.30 (dt, J=10.6, 4.0 Hz, 1H), 3.35–3.48 (m, 2H), 6.94 (s, 1H), 6.99 (s, 1H), 7.21–7.25 (m, 1H), 7.44 (d, J=1.5 Hz, 1H) ppm. MS (CI, $NH_3$): 401.1 (base, M+H).

Example 389

(7aS,11aR)-10-butyl-2-(2,4-dichlorophenyl)-5,6,7a,8,9,10,11,11a-octahydro-4H-pyrido[3',4':4,5]pyrrolo[3,2,1-ij]quinoline The title compound was prepared by the method of Example 382 as a yellow oil (21 mg, 61%) from (7aS,11aR)-2-(2,4-dichlorophenyl)-5,6,7a,8,9,10,11,11a-octahydro-4H-pyrido[3',4':4,5]pyrrolo[3,2,1-ij]quinoline (30 mg, 0.083 mmol) and 1-bromobutane (23 mg, 0.17 mmol). MS (CI, $NH_3$): 415.1 (base, M+H).

Example 390

(7aS,11aR)-2-(2,4-dichlorophenyl)-10-(4-pentenyl)-5,6,7a,8,9,10,11,11a-octahydro-4H-pyrido[3',4':4,5]pyrrolo[3,2,1-ij]quinoline The title compound was prepared by the method of Example 382 as a yellow oil (23 mg, 67%) from (7aS,11aR)-2-(2,4-dichlorophenyl)-5,6,7a,8,9,10,11,11a-octahydro-4H-pyrido[3',4':4,5]pyrrolo[3,2,1-ij]quinoline (30 mg, 0.083 mmol) and 5-bromo-1-pentene (25 mg, 0.16 mmol). MS (CI, NH$_3$): 427.1 (base, M+H).

Example 391

(7aS,11aR)-2-(2,4-dichlorophenyl)-10-(3-methyl-2-butenyl)-5,6,7a,8,9,10,11,11a-octahydro-4H-pyrido[3',4':4,5]pyrrolo[3,2,1-ij]quinoline The title compound was prepared by the method of Example 382 as a yellow oil (26 mg, 76%) from (7aS,11aR)-2-(2,4-dichlorophenyl)-5,6,7a,8,9,10,11,11a-octahydro-4H-pyrido[3',4':4,5]pyrrolo[3,2,1-ij]quinoline (30 mg, 0.083 mmol) and 4-bromo-2-methyl-2-butene (25 mg, 0.16 mmol). $^1$H NMR (CDCl$_3$, 300 MHz) δ 1.68 (s, 3H), 1.81 (s, 3H), 2.12–2.23 (m, 3H), 2.26–2.42 (m, 1H), 2.55–2.70 (m, 2H), 2.78 (t, J=6.6 Hz, 2H), 3.10–3.45 (m, 6H), 3.63–3.77 (m, 2H), 5.42–5.55 (br, 1H), 6.99 (s, 1H), 7.03 (s, 1H), 7.24–7.217.29 (m, 2H), 7.47 (d, J=1.8 Hz, 1H) ppm. MS (CI, NH$_3$): 427.1 (base, M+H).

Example 392

(7aS,11aR)-10-(cyclobutylmethyl)-2-(2,3-dichlorophenyl)-5,6,7a,8,9,10,11,11a-octahydro-4H-pyrido[3',4':4,5]pyrrolo[3,2,1-ij]quinoline The title compound was prepared by the method of Example 382 as a yellow oil (22 mg, 58%) from (7aS,11aR)-2-(2,4-dichlorophenyl)-5,6,7a,8,9,10,11,11a-octahydro-4H-pyrido[3',4':4,5]pyrrolo[3,2,1-ij]quinoline (32 mg, 0.089 mmol) and (bromomethyl)cyclobutane (27 mg, 0.18 mmol). MS (CI, NH$_3$): 427.1 (base, M+H).

Example 393

(7aS,11aR)-2-[4-methoxy-2-(trifluoromethyl)phenyl]-10-methyl-5,6,7a,8,9,10,11,11a-octahydro-4H-pyrido[3',4':4,5]pyrrolo[3,2,1-ij]quinoline The solution of (7aS,11aR)-2-[4-methoxy-2-(trifluoromethyl)phenyl]-5,6,7a,8,9,10,11,11a-octahydro-4H-pyrido[3',4':4,5]pyrrolo[3,2,1-ij]quinoline (30 mg, 0.077 mmol) in formaldehyde (37 wt % aqueous solution, 97 mg, 1.16 mmol) and formic acid (54 mg, 1.16 mmol) was heated at 80° C. for 2 h. The reaction mixture was diluted with H$_2$O then basified with 1N NaOH to pH 12 and extract with CHCl$_3$. The combined organic solution was dried over MgSO$_4$, concentrated in vacuo, and the residue was chromatographed (silica gel; CHCl$_3$: MeOH 99:1–95:5) to give the title compound as a pale yellow oil (19 mg, 61%). MS (CI, NH$_3$): 403.1 (base, M+H).

Example 394

(7aS,11aR)-10-ethyl-2-[4-methoxy-2-(trifluoromethyl)phenyl]-5,6,7a,8,9,10,11,11a-octahydro-4H-pyrido[3',4':4,5]pyrrolo[3,2,1-ij]quinoline To a solution of (7aS,11aR)-2-[4-methoxy-2-(trifluoromethyl)phenyl]-5,6,7a,8,9,10,11,11a-octahydro-4H-pyrido[3',4':4,5]pyrrolo[3,2,1-ij]quinoline (30 mg, 0.077 mmol) in acetic acid (0.28 mL) was added NaBH (30 mg, 0.80 mmol) in 2 portion in 10 min interval at 55° C. The reaction mixture was stirred for 15 h at 55° C. then quenched by addition of H$_2$O. The aqueous solution was basified with 50% NaOH then extracted with CHCl$_3$. The combined organic solution was dried over MgSO$_4$, concentrated in vacuo. The residue was chromatographed (silica gel; CHCl$_3$: MeOH 99:1–98:2) to give the title compound as a yellow oil (26 mg, 81%). $^1$H NMR (CDCl$_3$, 300 MHz) δ 1.21–1.35 (m, 3H), 2.05–2.30 (m, 5H), 2.53–2.78 (m, 6H), 2.98–3.07 (br, 1H), 3.08–3.18 (br, 1H), 3.27–3.42 (m, 2H), 3.43–3.57 (br, 1H), 3.88 (s, 3H), 6.83 (s, 1H), 6.86 (s, 1H), 7.04 (dd, J=8.8, 2.9 Hz, 1H), 7.20–7.26 (m, 2H) ppm. MS (CI, NH$_3$): 417.1 (base, M+H).

Example 395

(7aS,11aR)-2-[4-methoxy-2-(trifluoromethyl)phenyl]-10-propyl-5,6,7a,8,9,10,11,11a-octahydro-4H-pyrido[3',4':4,5]pyrrolo[3,2,1-ij]quinoline The title compound was prepared by the method of Example 382 as a yellow oil (23 mg, 69%) from (7aS,11aR)-2-[4-methoxy-2-(trifluoromethyl)phenyl]-5,6,7a,8,9,10,11,11a-octahydro-4H-pyrido[3',4':4,5]pyrrolo[3,2,1-ij]quinoline (30 mg, 0.077 mmol) and 1-bromopropane (20 mg, 0.15 mmol). $^1$H NMR (CDCl$_3$, 300 MHz) δ 0.98 (t, J=7.3 Hz, 3H), 1.78–1.92 (br, 2H), 2.11–2.25 (m, 5H), 2.28–2.42 (m, 1H), 2.53–2.80 (m, 5H), 3.05–3.25 (br, 2H), 3.31 (dt, J=10.2, 3.6 Hz, 1H), 3.37–3.45 (br, 1H), 3.60–3.72 (br, 1H), 3.89 (s, 3H), 6.85 (s, 1H), 6.87 (s, 1H), 7.05 (dd, J=8.7, 2.6 Hz, 1H), 7.21–7.27 (m, 2H) ppm. MS (CI, NH$_3$): 431.2 (base, M+H).

Example 396

(7aS,11aR)-10-butyl-2-[4-methoxy-2-(trifluoromethyl)phenyl]-10-methyl-5,6,7a,8,9,10,11,11a-octahydro-4H-pyrido[3',4':4,5]pyrrolo[3,2,1-ij]quinoline The title compound was prepared by the method of Example 382 as a yellow oil (23 mg, 67%) from (7aS,11aR)-2-[4-methoxy-2-(trifluoromethyl)phenyl]-5,6,7a,8,9,10,11,11a-octahydro-4H-pyrido[3',4':4,5]pyrrolo[3,2,1-ij]quinoline (30 mg, 0.077 mmol) and 1-bromobutane (21 mg, 0.15 mmol). $^1$H NMR (CDCl$_3$, 300 MHz) δ 0.93 (t, J=7.3 Hz, 3H), 1.34 (se, J=7.3 Hz, 2H), 1.65–1.77 (br, 2H), 2.05–2.23 (m, 5H), 2.25–2.38 (br, 1H), 2.55–2.77 (m, 3H), 2.95–3.15 (br, 2H), 3.30 (dt, J=10.2, 3.7 Hz, 1H), 3.32–3.40 (br, 1H), 3.42–3.55 (br, 1H), 3.86 (s, 3H), 6.82 (s, 1H), 6.85 (s, 1H), 7.03 (dd, J=8.8, 2.6 Hz, 1H), 7.20–7.25 (m, 2H) ppm. MS (CI, NH$_3$): 445.2 (base, M+H).

Example 397

(7aS,11aR)-2-[4-methoxy-2-(trifluoromethyl)phenyl]-10-(4-pentenyl)-5,6,7a,8,9,10,11,11a-octahydro-4H-pyrido[3',4':4,5]pyrrolo[3,2,1-ij]quinoline The title compound was prepared by the method of Example 382 as a yellow oil (22 mg, 63%) from (7aS,11aR)-2-[4-methoxy-2-(trifluoromethyl)phenyl]-5,6,7a,8,9,10,11,11a-octahydro-4H-pyrido[3',4':4,5]pyrrolo[3,2,1-ij]quinoline (30 mg, 0.077 mmol) and 5-bromo-1-pentene (23 mg, 0.15 mmol). $^1$H NMR (CDCl$_3$, 300 MHz) δ 1.68–1.79 (m, 2H), 2.01–2.26 (m, 7H), 2.43–2.62 (m, 4H), 2.71 (t, J=6.3 Hz, 2H), 2.83–2.92 (br, 1H), 2.95–3.07 (br, 1H), 3.27–3.44 (m, 3H), 3.86 (s, 3H), 4.93–5.05 (m, 2H), 5.70–5.85 (m, 1H), 6.80 (s, 1H), 6.84 (s, 1H), 7.02 (dd, J=8.1, 2.6 Hz, 1H), 7.18–7.24 (m, 2H) ppm. MS (CI, NH$_3$): 457.2 (base, M+H).

Example 398

(7aS,11aR)-2-[4-methoxy-2-(trifluoromethyl)phenyl]-10-(3-methyl-2-butenyl)-5,6,7a,8,9,10,11,11a-octahydro-4H-pyrido[3',4':4,5]pyrrolo[3,2,1-ij]quinoline The title compound was prepared by the method of Example 382 as a yellow oil (25 mg, 71%) from (7aS,11aR)-2-[4-methoxy-2-(trifluoromethyl)phenyl]-5,6,7a,8,9,10,11,11a-octahydro-4H-pyrido[3',4':4,5]pyrrolo[3,2,1-ij]quinoline (30 mg, 0.077 mmol) and 4-bromo-2-methyl-2-butene (23 mg, 0.15 mmol). $^1$H NMR (CDCl$_3$, 300 MHz) δ 1.65 (s, 3H), 1.79 (s, 3H), 2.12–2.22 (m, 3H), 2.24–2.40 (m, 1H), 2.57 (se, J=7.7 Hz, 2H), 2.72 (t, J=6.6 Hz, 2H), 2.74–2.84 (br, 1H), 3.05–3.45 (m, 6H), 3.59–3.77 (m, 1H), 3.86 (s, 3H), 5.42–5.55 (br, 1H), 6.83 (s, 1H), 6.85 (s, 1H), 7.03 (d, J=8.8 Hz, 1H), 7.17–7.25 (m, 2H) ppm. MS (CI, NH$_3$): 457.2 (base, M+H).

Example 399

(7aS,11aR)-10-(2-fluoroethyl)-2-[4-methoxy-2-(trifluoromethyl)phenyl-5,6,7a,8,9,10,11,11a-octahydro-4H-pyrido[3',4':4,5]pyrrolo[3,2,1-ij]quinoline The title compound was prepared by the method of Example 382 as a yellow oil (32 mg, 96%) from (7aS,11aR)-2-[4-methoxy-2-(trifluoromethyl)phenyl]-5,6,7a,8,9,10,11,11a-octahydro-4H-pyrido[3',4':4,5]pyrrolo[3,2,1-ij]quinoline (30 mg, 0.077 mmol) and 1-bromo-2-fluoroethane (30 mg, 0.23 mmol). MS (CI, NH$_3$): 435.1 (base, M+H).

Example 400

(7aS,11aR)-10-(2,2-difluoroethyl)-2-[4-methoxy-2-(trifluoromethyl)phenyl]-5,6,7a,8,9,10,11,11a-octahydro-4H-pyrido[3',4':4,5]pyrrolo[3,2,1-ij]quinoline The title compound was prepared by the method of Example 382 as a yellow oil (27 mg, 77%) from (7aS,11aR)-2-[4-methoxy-2-(trifluoromethyl)phenyl]-5,6,7a,8,9,10,11,11a-octahydro-4H-pyrido[3',4':4,5]pyrrolo[3,2,1-ij]quinoline (30 mg, 0.077 mmol) and 2-bromo-1,1-difluoroethane (35 mg, 0.23 mmol). MS (C$_1$, NH$_3$): 453.1 (base, M+H).

Example 401

(7aS,11aR)-10-(cyclobutylmethyl)-2-[4-methoxy-2-(trifluoromethyl)phenyl]-5,6,7a,8,9,10,11,11a-octahydro-4H-pyrido[3',4':4,5]pyrrolo[3,2,1-ij]quinoline The title compound was prepared by the method of Example 382 as a yellow oil (32 mg, 96%) from (7aS,11aR)-2-[4-methoxy-2-(trifluoromethyl)phenyl]-5,6,7a,8,9,10,11,11a-octahydro-4H-pyrido[3',4':4,5]pyrrolo[3,2,1-ij]quinoline (30 mg, 0.077 mmol) and 1-bromo-2-fluoroethane (30 mg, 0.23 mmol). $^1$H NMR (CDCl$_3$, 300 MHz) δ 1.70–1.82 (m, 4H), 1.85–1.98 (m, 1H), 2.02–2.30 (m, 7H), 2.53–2.63 (m, 1H), 2.68–2.88 (m, 5H), 2.92–3.15 (br, 2H), 3.25–3.38 (m, 2H), 3.52–3.62 (br, 1H), 3.87 (s, 3H), 6.82 (s, 1H), 6.84 (s, 1H), 7.03 (dd, J=8.5, 2.5 Hz, 1H), 7.20–7.25 (m, 2H) ppm. MS (CI, NH3): 457.2 (base, M+H).MS (CI, NH$_3$): 457.2 (base, M+H).

Example 402

4-((7aS,11aR)-5,6,8,9,11,11a-hexahydro-4H-pyrido[3',4':4,5]pyrrolo[3,2,1-ij]quinolin-10(7aH)-yl)-1-(4-fluorophenyl)-1-butanone To a solution of (7aS,11aR)-5,6,7a,8,9,10,11,11a-octahydro-4H-pyrido[3',4':4,5]pyrrolo[3,2,1-ij]quinoline (0.21 g, 1.0 mmol)) in 1,4-dioxane (7.0 mL) were added 4-chloro-4'-fluorobutyrophenone (0.40 g, 2.0 mmol), KI (catalytic amount) and K$_2$CO$_3$ (0.28 g, 2.0 mmol). The reaction mixture was heated at 100° C. for 48 h. The reaction mixture was cooled to 20° C. then diluted with CHCl$_3$. The solution was filtered to remove excess K$_2$CO$_3$ and the filtrate was concentrated in vacuo and chromatographed (silica gel, CHCl$_3$:MeOH 98:2) to give the title compound (0.22 g, 58%) as a white amorphous solid. $^1$H NMR (CDCl$_3$, 300 MHz) δ 1.75–2.20 (m, 7H), 2.20–2.35 (m, 1H), 2.35–2.48 (m, 2H), 2.48–2.60 (m, 1H), 2.60–2.78 (m, 3H), 2.78–2.90 (m, 1H), 2.99 (t, J=7.2 Hz, 2H), 3.05–3.15 (m, 1H), 3.18–3.32 (m, 2H), 6.62 (t, J=7.3 Hz, 1H), 6.86 (d, J=7.3 Hz, 1H), 7.12 (t, J=8.6 Hz, 2H), 7.90–8.08 (m, 2H) ppm.

Example 403

4-((7aR,11aS)-5,6;8,9,11,11a-hexahydro-4H-pyrido[3',4':4,5]pyrrolo[3,2,1-ij]quinolin-10(7aH)-yl)-1-(4-fluorophenyl)-1-butanone The title compound (0.16 g, 42%) was prepared by the general method of Example 402 from (7aR,11aS)-5,6,7a,8,9,10,11,11a-octahydro-4H-pyrido[3',4':4,5]pyrrolo[3,2,1-ij]quinoline (0.21 g, 1.0-mmol), 4-chloro-4'-fluorobutyrophenone (0.40 g, 2.0 mmol), KI (catalytic) and K$_2$CO$_3$(0.28 g, 2.0 mmol) after chromatographic purification as a white amorphous solid. The $^1$H NMR was identical to that of Example 402, 4-((7aS,11aR)-5,6,8,9,11,11a-hexahydro-4H-pyrido[3',4':4,5]pyrrolo[3,2,1-ij]quinolin-10(7aH)-yl)-1-(4-fluorophenyl)-1-butanone Example 404

4-((7aS,11aR)-5,6,8,9,11,11a-hexahydro-4H-pyrido[3',4':4,5]pyrrolo[3,2,1-ij]quinolin-10(7aH)-yl)-1-(2-aminophenyl)-1-butanone The title compound (0.031 g, 16%) was prepared by the general method of Example 402 from (7aS,11aR)-5,6,7a,8,9,10,11,11a-octahydro-4H-pyrido[3',4':4,5]pyrrolo[3,2,1-ij]quinoline (0.11 g, 0.50 mmol), 4-chloro-2'-aminobutyrophenone (0.20 g, 1.0 mmol), KI (catalytic) and K$_2$CO$_3$(0.14 g, 1.0 mmol) after chromatographic purification as a white amorphous solid. $^1$H NMR (CDCl$_3$, 300 MHz) δ 1.80–2.20 (m, 7H), 2.20–2.60 (m, 3H), 2.82–2.95 (m, 1H), 2.98 (t, J=7.4 Hz, 2H), 3.05–3.20 (m, 2H), 3.20–3.38 (m, 2H), 3.64 (t, J=6.6 Hz, 1H), 3.68–3.80 (m, 1H), 3.81 (t, J=6.0 Hz, 1H), 6.26 (br, 2H), 6.58–6.68 (m, 2H), 6.80–6.92 (m, 2H), 7.10–7.30 (m, 2H), 7.52–7.72 (m, 1H), 7.77 (dd, J=1.3, 8.4 Hz, 1H), 8.09 (td, J=1.6, 8.4 Hz, 1H) ppm.

Example 405

4-((7aR,11aS)-5,6,8,9,11,11a-hexahydro-4H-pyrido[3',4':4,5]pyrrolo[3,2,1-ij]quinolin-10(7aH)-yl)-1-(2-aminophenyl)-1-butanone The title compound (0.080 g, 42%) was prepared by the general method of Example 402 from (7aR,11aS)-5,6,7a,8, 9,10,11,11a-octahydro-4H-pyrido[3',4':4,5]pyrrolo[3,2,1-ij]quinoline (0.11 g, 0.50 mmol), 4-chloro-2'-aminobutyrophenone (0.20 g, 1.0 mmol), KI (catalytic) and $K_2CO_3$ (0.14 g, 1.0 mmol) after chromatographic purification as a white amorphous solid. The $^1H$ NMR was identical to that of Example 404, 4-((7aS,11aR)-5,6,8,9,11,11a-hexahydro-4H-pyrido[3',4':4,5]pyrrolo[3,2,1-ij]quinolin-10(7aH)-yl)-1-(2-aminophenyl)-1-butanone

Example 406

(±)-cis-3-(5,6,8,9,11,11a-hexahydro-4H-pyrido[3',4':4,5]pyrrolo[3,2,1-ij]quinolin-10(7aH)-yl)propyl 4-fluorophenyl ether The title compound (0.14 g, 32%) was prepared by the general method of Example 402 from (±)-cis-5,6,7a,8,9,10,11,11a-octahydro-4H-pyrido[3',4':4,5]pyrrolo[3,2,1-ij]quinoline (0.25 g, 1.2 mmol), 1-(3-chloropropoxy)-4-fluorobezene (0.37 g, 2.0 mmol), KI (catalytic) and $K_2CO_3$ (0.28 g, 2.0 mmol) after chromatographic purification as a white amorphous solid. $^1H$ NMR ($CDCl_3$, 300 MHz) δ 1.78–2.08 (m, 7H), 2.10–2.30 (m, 1H), 2.32–2.50 (m, 3H), 2.51–2.72 (m, 3H), 2.75–2.82 (m, 1H), 3.00–3.12 (m, 1H), 3.12–3.25 (m, 2H), 3.89 (t, J=6.3 Hz, 2H), 6.55 (t, J=7.5 Hz, 1H), 6.70–6.92 (m, 6H) ppm.

Example 407

4-((±)-cis-5,6,8,9,11,11a-hexahydro-4H-pyrido[3',4':4,5]pyrrolo[3,2,1-ij quinolin-10(7aH)-yl)-1-(4-pyridinyl)-1-butanone The title compound (0.080 g, 18%) was prepared by the general method of Example 402 from (±)-cis-5,6,7a,8,9,10,11,11a-octahydro-4H-pyrido[3',4':4,5]pyrrolo[3,2,1-ij]quinoline (0.25 g, 1.2 mmol), 4-chloro-1-(4-pyridinyl)-1-butanone (0.36 g, 2.0 mmol), KI (catalytic) and $K_2CO_3$ (0.28 g, 2.0 mmol) after chromatographic purification as a white amorphous solid. $^1H$ NMR ($CDCl_3$, 300 MHz) δ 1.68–2.18 (m, 7H), 2.20–2.65 (m, 5H), 2.69 (t, J=6.4 Hz, 2H), 2.72–2.82 (m, 1H), 2.92–3.08 (m, 3H), 3.15–3.28 (m, 2H), 6.62 (t, J=7.5 Hz, 1H), 6.86 (d, J=7.6 Hz, 1H), 6.89 (d, J=7.4 Hz, 1H), 7.70–7.80 (m, 2H), 8.75–8.82 (m, 2H) ppm.

Example 408

(±)-cis-10-[3-(6-fluoro-1,2-benzisoxazol-3-yl)propyl]-5,6,7a,8,9,10,11,11a-octahydro-4H-pyrido[3',4':4,5]pyrrolo[3,2,1-ij]quinoline The title compound (0.15 g, 32%) was prepared by the general method of Example 402 from (±)-cis-5,6,7a,8,9,10,11,11a-octahydro-4H-pyrido[3',4':4,5]pyrrolo[3,2,1-ij]quinoline (0.25 g, 1.2 mmol), 3-(3-chloropropyl)-6-fluoro-1,2-benzisoxazole (0.43 g, 2.0 mmol), KI (catalytic) and $K_2CO_3$ (0.28 g, 2.0 mmol) after chromatographic purification as a white amorphous solid. $^1H$ NMR ($CDCl_3$, 300 MHz) δ 1.80–2.18 (m, 7H), 2.25 (td, J=11.5, 3.0 Hz, 1H), 2.35–2.68 (m, 4H), 2.70 (t, J=6.6 Hz, 2H), 2.75–2.88 (m, 1H), 3.01 (t, J=7.6 Hz, 2H), 3.05–3.15 (m, 1H), 3.20–3.30 (m, 2H), 6.62 (t, J=7.5 Hz, 1H), 6.86 (d, J=7.5 Hz, 1H), 6.92 (d, J=7.5 Hz, 1H), 7.06 (td, J=9.0, 2.1 Hz, 1H), 7.20–7.26 (m, 1H), 7.61 (dd, J=4.8, 8.7 Hz, 1H) ppm.

Example 409

(7aS,11aR)-10-[3-(6-fluoro-1,2-benzisoxazol-3-yl)propyl]-5,6,7a,8,9,10,11,11a-octahdro-4H-pyrido[3',4':4,5]pyrrolo[3,2,1-ij]quinoline The title compound (0.31 g, 75%) was prepared by the general method of Example 402 from (7aS,11aR)-5,6,7a,8,9,10,11,11a-octahydro-4H-pyrido[3',4':4,5]pyrrolo[3,2,1-ij]quinoline (0.21 g, 1.0 mmol), 3-(3-chloropropyl)-6-fluoro-1,2-benzisoxazole (0.43 g, 2.0 mmol), KI (catalytic) and $K_2CO_3$ (0.28 g, 2.0 mmol) after chromatographic purification as a white amorphous solid. The $^1H$ NMR was identical to that of Example 408, (±)-cis-10-[3-(6-fluoro-1,2-benzisoxazol-3-yl)propyl]-5,6,7a,8,9,10,11,11a-octahydro-4H-pyrido[3',4':4,5]pyrrolo[3,2,1-ij]quinoline

Example 410

1-(4-fluorophenyl)-4-(5,6,8,11-tetrahydro-4H-pyrido[3',4':4,5]pyrrolo[3,2,1-ij]quinolin-10(9H)-yl)-1-butanone The title compound (0.060 g, 28%) was prepared by the general method of Example 402 from 5,6,8,11-tetrahydro-4H-pyrido[3',4':4,5]pyrrolo[3,2,1-ij]quinoline (0.12 g, 0.57 mmol), 4-chloro-4'-fluorobutyrophenone (0.40 g, 2.0 mmol), KI (catalytic) and $K_2CO_3$ (0.28 g, 2.0 mmol) after chromatographic purification as a white amorphous solid. $^1H$ NMR ($CDCl_3$, 300 MHz) δ 1.80–2.15 (m, 2H), 2.15–2.30 (m, 2H), 2.71 (t, J=7.0 Hz, 2H), 2.82 (d, J=5.1 Hz, 2H), 2.90 (t, J=5.8 Hz, 2H), 2.97 (t, J=6.1 Hz, 2H), 3.02–3.20 (m, 2H), 3.73 (s, 2H), 3.98 (t, J=5.7 Hz, 2H), 6.84 (d, J=6.9 Hz, 1H), 6.97 (t, J=7.5 Hz, 1H), 7.02–7.20 (m, 2H), 7.25 (d, J=7.7 Hz, 1H), 7.20–7.25 (m, 1H), 7.95–8.20 (m, 2H) ppm.

Example 411

(±)-cis-4-(4,5,6,7,9,10,12,12a-octahydroazepino[3,2,1-hi]pyrido[4,3-b]indol-11(8aH)-yl)-1-(4-fluorophenyl)-1-butanone The title compound (0.17 g, 74%) was prepared by the general method of Example 402 from (±)-cis-4,5,6,7,8a,9,10,11,12,12a-decahydroazepino[3,2,1-hi]pyrido[4,3-b]indole (0.14 g, 0.59 mmol), 4-chloro-4'-fluorobutyrophenone (0.20 g, 1.0 mmol), KI (catalytic) and $K_2CO_3$ (0.14 g, 1.0 mmol) after chromatographic purification as a white amorphous solid. $^1H$ NMR ($CDCl_3$, 300 MHz) δ 1.42–1.62 (m, 1H), 1.62–1.80 (m, 1H), 1.88–2.22 (m, 7H), 2.40–2.70 (m, 5H), 2.80–3.12 (m, 5H), 3.12–3.30 (m, 2H), 3.32–3.50 (m, 1H), 6.69 (t, J=7.5 Hz, 1H), 6.80–7.00 (m, 2H), 7.05–7.20 (m, 2H), 7.90–8.03 (m, 2H) ppm.

Example 412

4-((8aS,12aR-4,5,6,7,9,10,12,12a-octahydroazepino[3,2,1-hi]pyrido[4,3-b]indol-11(8aH)-yl)-1-(4-fluorophenyl)-1-butanone The title compound was prepared by preparative HPLC separation of (±)-cis-4-(4,5,6,7,9,10,12,12a-octahydroazepino[3,2,1-hi]pyrido[4,3-b]indol-11(8aH)-yl)-1-(4-fluorophenyl)-1-butanone on a CHIRALPAK® AD column ($CH_3CN$/Ethanol/DEA =85/15/0.05).

Example 413

4-((8aR,12aS)-4,5,6,7,9,10,12,12a-octahydroazepino[3,2,1-hi]pyrido[4,3-b]indol-11(8aH)-yl)-1-(4-fluorophenyl)-1-butanone The title compound was prepared by preparative HPLC separation of (±)-cis-4-(4,5,6,7,9,10,12,12a-octahydroazepino[3,2,1-hi]pyrido[4,3-b]indol-11(8aH)-yl)-1-(4-fluorophenyl)-1-butanone on a CHIRALPAK® AD column (CH$_3$CN/Ethanol/DEA=85/15/0.05).

Example 414

4-((±)-4,5,6,7,9,10,12,12a-octahydroazepino[3,2,1-hi]pyrido[4,3-b]indol-11(8aH)-yl)-1-(2-amino-4-fluorophenyl)-1-butanone The title compound (0.16 g, 67%) was prepared by the general method of Example 402 from (±)-cis-4,5,6,7,8a,9,10,11,12,12a-decahydroazepino[3,2,1-hi]pyrido[4,3-b]indole (0.14 g, 0.59 mmol), 4-chloro-2'-amino-4'-fluorobutyrophenone (0.22 g, 1.0 mmol), KI (catalytic) and K$_2$CO$_3$ (0.14 g, 1.0 mmol) after chromatographic purification as a white amorphous solid. $^1$H NMR (CDCl$_3$, 300 MHz) δ 1.45–1.62 (m, 2H), 1.62–2.10 (m, 8H), 2.20–2.52 (m, 4H), 2.52–2.72 (m, 2H), 2.72–2.84 (m, 1H), 2.84–3.00 (m, 2H), 3.12–3.30 (m, 3H), 6.20–6.60 (m, 4H), 6.67 (t, J=7.3 Hz, 1H), 6.91 (t, J=7.7 Hz, 2H), 7.77 (dd, J=6.4, 9.0 Hz, 1H) ppm.

Example 415

4-((±)-cis-5,6,8,9,11,11a-hexahydro-4H-pyrido[3',4':4,5]pyrrolo[3,2,1-ij]quinolin-10(7aH)-yl)-1-(2-amino-4-fluorophenyl)-1-butanone The title compound was prepared by the method of Example 402 as a red oil (99 mg, 54%) from (±)-cis-5,6,7a,8,9,10,11,11a-octahydro-4H-pyrido[3',4':4,5]pyrrolo[3,2,1-ij]quinoline (100 mg, 0.47 mmol) and 1-(2-amino-4-fluorophenyl)-4-chloro-1-butanone (152 mg, 0.70 mmol). $^1$H NMR (CDCl$_3$, 300 MHz) δ 1.95–2.15 (m, 7H), 2.37–2.57 (m, 5H), 2.67–2.85 (m, 3H), 2.90–3.05 (m, 3H), 3.24–3.33 (m, 2H), 6.27–6.39 (m, 2H), 6.41–6.50 (br, 2H), 6.64 (t, J=7.3 Hz, 1H), 6.85–6.94 (m, 2H), 7.77 (dd, J=9.2, 6.6 Hz, 1H) ppm.

Example 416

4-((7aS,11aR)-5,6,8,9,11,11a-hexahydro-4H-pyrido[3',4':4,5]pyrrolo[3,2,1-ij]quinolin-10(7aH)-yl)-1-(2-amino-4-fluorophenyl)-1-butanone The title compound was prepared by the method of Example 402 as a yellow oil (35 mg, 20%) from (7aS,11aR)-5,6,7a,8,9,10,11,11a-octahydro-4H-pyrido[3',4':4,5]pyrrolo[3,2,1-ij]quinoline (100 mg, 0.47 mmol) and 1-(2-amino-4-fluorophenyl)-4-chloro-1-butanone (202 mg, 0.93 mmol). The title compound was spectroscopically identical to Example 415.

Example 417

4-((7aR,11aS)-5,6,8,9,11,11a-hexahydro-4H-pyrido[3',4':4,5]pyrrolo[3,2,1-ij]quinolin-10(7aH)-yl)-1-(2-amino-4-fluorophenyl)-1-butanone The title compound was prepared by the method of Example 402 as a yellow oil (95 mg, 34%) from (7aR,11aS)-5,6,7a,8,9,10,11,11a-octahydro-4H-pyrido[3',4':4,5]pyrrolo[3,2,1-ij]quinoline (150 mg, 0.70 mmol) and 1-(2-amino-4-fluorophenyl)-4-chloro-1-butanone (303 mg, 1.40 mmol). The title compound was spectroscopically identical to Example 415.

Example 418

5,6,9,10,11,12-hexahydro-4H,8H-azepino[4',5':4,5]pyrrolo[3,2,1-ij]quinoline

To a solution of 3,4-dihydro-[(2H)-quinolinamine (1.0 g, 14 mmol) and hexahydro-4H-azepin-4-one hydrochloride (1.0 g, 14 mmol) in EtOH (13 mL) was added concentrated HCl (1.2 mL). The reaction was stirred at reflux for 14 h, then cooled to 20° C. A brown precipitate was filtered from the reaction mixture, affording the title compound (800 mg, 45%) as a brown solid. $^1$H NMR (CD$_3$OD, 300 MHz) δ 2.14–2.23 (m, 2H), 2.91 (t, 2H, J=6.0 Hz), 3.16–3.21 (m, 2H), 3.27–3.33 (m, 2H), 3.39–3.50 (m, 4H), 4.04 (t, 2H, J=5.7 Hz), 6.70 (d, 1H, J=6.9 Hz), 6.87–6.93 (m, 1H), 7.22 (d, 1H, J=8.0 Hz) ppm. MS (ESI): 227.2 (base, M+H).

Example 419

(±)-5,6,8,9,10,11,12,12a-octahydro-4H,7aH-azepino[4',5':4,5]pyrrolo[3,2,1-ij]quinoline Step A:

To a solution of 5,6,9,10,11,12-hexahydro-4H,8H-azepino[4',5':4,5]pyrrolo[3,2,1-ij]quinoline (150 mg, 0.65 mmol) in TFA (7.5 mL) was added NaCNBH$_3$ (123 mg, 1.95 mmol) in small portions at 0° C. The reaction mixture was stirred for 1 h. To the reaction mixture was added concentrated HCl (5 mL) and the reaction was heated at reflux for 10 m. The reaction mixture was concentrated in vacuo and basified to pH 14 with 50% NaOH. To this was added 1,4-dioxane (14 mL), and to this solution was added di-tert-butyl dicarbonate (700 mg, 3.2 mmol). The solution was stirred at 20° C. for 16 h. Purification by column chromatography (hexanes:EtOAc 19:1) afforded tert-butyl(±)-5,6,8,9,10,11,12,12a-octahydro-4H,7aH-azepino[4',5':4,5]pyrrolo[3,2,1-ij]quinoline-10-carboxylate as a colorless oil.

Step B:

To a solution of tert-butyl(±)-5,6,8,9,10,11,12,12a-octahydro-4H,7aH-azepino[4',5':4,5]pyrrolo[3,2,1-ij]quinoline-10-carboxylate in CH$_2$Cl$_2$ (2.4 mL) was added TFA (0.6 mL). This was stirred at 20° C. for 3 h. The reaction mixture was diluted with CH$_2$Cl$_2$ (50 mL) and washed with saturated NaHCO$_3$ (50 mL) and brine (50 mL), dried over MgSO$_4$ and concentrated in vacuo to afford the title compound as a yellow oil (87 mg, 59%). $^1$H NMR (CDCl$_3$, 300 MHz) δ 1.77–2.13 (m, 7H), 2.56–2.79 (m, 5H), 2.83–2.93 (m, 1H), 3.00–3.16 (m, 2H), 3.33–3.41 (td, 1H, J=3.7, 9.2 Hz), 3.60 (td, 1H, J=4.4, 9.1 Hz), 6.50 (t, 1H, J=7.3 Hz), 6.76 (t, 2H, 8.0 Hz) ppm.

Example 420

4-[(±)-5,6,8,9,10,11,12,12a-octahydro-4H,7aH-azepino[4',5':4,5]pyrrolo[3,2,1-ij]quinolin-10-yl]-1-(4-fluorophenyl)-1-butanone The title compound was isolated as a yellow oil (55 mg, 37%) according to the method of Example 402 from (±)-5,6,8,9,10,11,12,12a-octahydro-4H,7aH-azepino[4',5':4,5]pyrrolo[3,2,1-ij]quinoline (87 mg, 0.38 mmol) and 4-chloro- 1-(4-fluorophenyl)-1-butanone (153 mg, 0.76 mmol). ¹H NMR (CDCl₃, 300 MHz) δ 2.04–2.36 (m, 6H), 2.65–2.89 (m, 6H), 2.93–3.39 (m, 8H), 3.50–3.59 (m, 1H), 3.71–3.80 (m, 1H), 6.65 (t, 1H, J=7.3 Hz), 6.87 (t, 2H, J=6.9 Hz), 7.09–7.17 (m, 2H), 7.94–8.01 (m, 2H) ppm.

Example 421

4-[(±)-5,6,8,9,10,11,12,12a-octahydro-4H,7aH-azepino[4',5':4,5]pyrrolo[3,2,1-ij]quinolin-10-yl]-1-(2-amino-4-fluorophenyl)-1-butanone The title compound was isolated as a yellow oil (23 mg, 12%) according to the method of Example 402 from (±)-5,6,8,9,10,11,12,12a-octahydro-4H,7aH-azepino[4',5':4,5]pyrrolo[3,2,1-ij]quinoline (111 mg, 0.49 mmol) and 4-chloro-1-(2-amino-4-fluorophenyl)-1-butanone (210 mg, 0.97 mmol). ¹H NMR (CDCl₃, 300 MHz) δ 1.98–2.11(m, 5H), 2.38–2.57 (m, 2H), 2.60–2.69 (m, 3H), 2.71–3.13 (m, 10H), 3.39–3.47 (m, 1H), 3.63–3.70 (m, 1H), 6.20–6.41 (m, 4H), 6.56 (t, 1H, J=7.3 Hz), 6.79 (d, 2H, 7.7 Hz), 7.63–7.69 (m, 1H) ppm.

Example 422

4,5,6,9,10,11,12,13-octahydro-9H-diazepino[4,5-b:3,2,1-hi]indole

The title compound was prepared as a brown solid (287 mg, 65%) according to the method of Example 418 from 2,3,4,5-tetrahydro-1H-1-benzazepin-1-amine (300 mg, 1.85 mmol) and hexahydro-4H-azepin-4-one hydrochloride (277 mg, 1.85 mmol). ¹H NMR (CD₃OD, 300 MHz) δ 1.99–2.16 (m, 4H), 3.04–3.12 (m, 5H), 3.16–3.21 (m, 2), 3.32–3.41 (m, 3H), 4.09–4.15 (m, 2H), 6.80–6.91 (m, 2H), 7.22 (d, 1H, J=6.9 Hz) ppm.

Example 423

(±)-4,5,6,7,9,10,11,12,13,13a-decahydro-8aH-diazepino[4,5-b:3,2,1-hi]indole

The title compound was isolated as a yellow oil (38 mg, 25%) according to the procedure of Example 419, Steps A and B from 4,5,6,9,10,11,12,13-octahydro-9H-diazepino[4,5-b:3,2,1-hi]indole (152 mg, 0.63 mmol). ¹H NMR (CDCl₃, 300 MHz) δ 1.37–1.55 (m, 1H), 1.64–1.80 (m, 1H), 1.85–2.09 (m, 4H), 2.11–2.23 (m, 2H), 2.56–2.97 (m, 6H), 3.12–3.23 (m, 2H), 3.57–3.71 (m, 2H), 6.68 (t, 1H, J=7.4 Hz), 6.87–6.91 (m, 2H) ppm.

Example 424

4-[(±)-4,5,6,7,9,10,11,12,13,13a-decahydro-11H-diazepino[4,5-b:3,2,1-hi]indol-11-yl]-1-(4-fluorophenyl)-1-butanone The title compound was isolated as a yellow oil (20 mg, 60%) according to the method of Example 402 from (±)-4,5,6,7,9,10,11,12,13,13a-decahydro-8aH-diazepino[4,5-b:3,2,1-hi]indole (20 mg, 0.08 mmol) and 4-chloro-1-(4-fluorophenyl)-1-butanone (32 mg, 0.16 mmol). ¹H NMR (CDCl₃, 300 MHz) δ 1.37–1.45 (m, 1H), 1.59–1.77 (m, 1H), 1.91–2.04 (m, 6H), 2.13–2.22 (m, 2H), 2.55–2.71 (m, 6H), 2.85–3.19 (m, 6H), 3.53–3.67 (m, 2H), 6.68 (t, 1H, J=7.3 Hz), 6.88 (d, 2H, J=7.3 Hz), 7.08–7.16 (m, 2H), 7.97–8.03 (m, 2H) ppm.

Example 425

4-[(±)-4,5,6,7,9,10,11,12,13,13a-decahydro-11H-diazepino[4,5-b:3,2,]-hi]indol-11-yl]-1-(2-amino-4-fluorophenyl)-1-butanone The title compound was isolated as a yellow oil (23 mg, 66%) according to the method of Example 402 from (±)-4,5,6,7,9,10,11,12,13,13a-decahydro-8aH-diazepino[4,5-b:3,2,1-hi]indole (20 mg, 0.08 mmol) and 4-chloro-1-(2-amino-4-fluorophenyl)-1-butanone (53 mg, 0.25 mmol). ¹H NMR (CDCl₃, 300 MHz) δ 1.30–1.43 (m, 1H), 1.53–1.64 (m, 1H), 1.88–2.01 (m, 6H), 2.10–2.22 (m, 2H), 2.50–2.70 (m, 6H), 2.70–3.09 (m, 6H), 3.26–3.44 (m, 2H), 6.20–6.30 (m, 2H), 6.36 (br, 2H), 6.62 (t, 1H, J=7.4 Hz), 6.79–6.85 (m, 2H), 7.65–7.70 (m, 1H) ppm.

Example 426

(±)-cis-6,7,8a,9,10,11,12,12a-octahydroazepino[3,2,1-hi]pyrido[4,3-b]indol-4(5H)-one Step A:

To a stirred solution of 1M BCl₃ in toluene (8.8 mL, 8.8 mmol) was added ethyl (±)-cis-1,3,4,4a,5,9b-hexahydro-2H-pyrido[4,3-b]indole-2-carboxylate (984 mg, 4.0 mmol) in benzene (32 mL) at 0° C. To the above solution was added 4-chlorobutanenitrile(0.39 mL, 4.4 mmol), and AlCl₃(587 mg, 4.4 mmol), the reaction mixture was stirred at r.t. for 10 min., then was heated in a sealed tube for 18 h. After cooled down to r.t., was added 5N HCl (32 mL) and heated at 80° C. for 30 min. The reaction mixture was neutralized by 50% NaOH at 0° C., adjusted pH=14, extracted with CH₂Cl₂ (200 mL), the organic layer was dried over MgSO₄, and concentrated in vacuo to afford after chromatographic purification ethyl (±)-cis-6-(4-chlorobutanoyl)-1,3,4,4a,5,9b-hexahydro-2H-pyrido[4,3-b]indole-2-carboxylate (413 mg, 30%).

Step B:

To ethyl (±)-cis-6-(4-chlorobutanoyl)-1,3,4,4a,5,9b-hexahydro-2H-pyrido[4,3-b]indole-2-carboxylate (100 mg, 0.29 mmol) in butanol (3 mL) was added KOH(50 mg) and heated at 109° C. for 5 hr. After cooled down to r.t., KOH(50 mg) and KI(20 mg) were added. The reaction mixture was heated at 109° C. in a sealed tube for 18 h. The reaction mixture was cooled down to r.t., extracted with CH₂Cl₂, dried over MgSO₄ to afford (±)-cis-6,7,8a,9,10,11,12,12a-octahydroazepino[3,2,1-hi]pyrido[4,3-b]indol-4(5H)-one (69 mg, 99%).

Step C:

To (±)-cis-6,7,8a,9,10,11,12,12a-octahydroazepino[3,2,1-hi]pyrido[4,3-b]indol-4(5H)-one (61 mg, 0.25 mmol) in dioxane (1 mL) and 1N NaOH (1 mL) was added Boc₂O (60 mg, 0.27 mmol), stirred at r.t. for 18 h. After extracted with CH₂Cl₂, dried over MgSO₄, concentrated in vacuo to afford tert-butyl(±)-cis-4-oxo-4,5,6,7,9,10,12,12a-octahydroazepino[3,2,1-hi]pyrido[4,3-b]indole-11(8aH)-carboxylate (40 mg, 47%).

Step D:

The title compound was prepared by the method of Example 98 from tert-butyl(±)-cis-4-oxo-4,5,6,7,9,10,12,12a-octahydroazepino[3,2,1-hi]pyrido[4,3-b]indole-11(8aH)-carboxylate to afford the title compound (25 mg, 88%). ¹H NMR (CD₃OD, 300 MHz) δ 7.86–7.89 (m, 1H), 7.34(d, 1H, 6.9 Hz), 6.73–6.78(m, 1H), 4.02–4.04(m, 1H), 3.37–3.39(m, 2H), 3.20–3.27(m, 2H), 2.82–2.92(m, 1H), 2.74–2.80(m, 1H), 2.10–2.14(m, 2H), 0.94–1.07(m, 5H) ppm. MS-ESI: 243 [MH]$^+$.

Example 427 tert-butyl(±)-cis-2-bromo-4-oxo-4,5,6,7,9,10,12,12a-octahydroazepino[3,2,1-hi]pyrido[4,3-b]indole-11(8aH)-carboxylate The title compound was prepared by the method of Example 89 step B from tert-butyl(±)-cis-4-oxo-4,5,6,7,9,10,12,12a-octahydroazepino[3,2,1-hi]pyrido[4,3-b]indole-11(8aH)-carboxylate (88 mg, 0.26 mmol) to afford the title compound (110 mg, 100%).

Example 428 tert-butyl(±)-cis-2-(2,4-dichlorophenyl)-4-oxo-4,5,6,7,9,10,12,12a-octahydroazepino[3,2,1-hi]pyrido[4,3-b]indole-11(8aH)-carboxylate The title compound was prepared by the method of Example 89 step C from tert-butyl(±)-cis-2-bromo-4-oxo-4,5,6,7,9,10,12,12a-octahydroazepino[3,2,1-hi]pyrido[4,3-b]indole-11(8aH)-carboxylate (110 mg, 0.26 mmol) and corresponding 2,4-dichlorophenylboronic acid (60 mg, 0.31 mmol) to afford after chromatographic purification the title compound (70 mg, 55%).

Example 429

(±)-cis-2-(2,4-dichlorophenyl)-6,7,8a,9,10,11,12,12a-octahydroazepino[3,2,1-hi]pyrido[4,3-b]indol-4(5H)-one The title compound was prepared by the method of Example 98 from tert-butyl(±)-cis-2-(2,4-dichlorophenyl)-4-oxo-4,5,6,7,9,10,12,12a-octahydroazepino[3,2,1-hi]pyrido[4,3-b]indole-11(8aH)-carboxylate to afford the title compound (50 mg, 90%). $^1$H NMR (CD$_3$OD, 300 MHz) δ 7.78(d, 1H, 1.4 Hz), 7.48(d, 1H, 1.9 Hz), 7.28–7.32(m, 2H),7.01(s, 1H), 4.06–4.12(m, 1H), 2.59–3.22(m, 6H), 1.71–2.04(m, 3H), 0.95–1.28(m, 4H) ppm. MS-ApCI: 387 [M+H]$^+$.

Example 430

(8aS,12aR)-2-(2,4-dichlorophenyl)-6,7,8a,9,10,11,12,12a-octahydroazepino[3,2,1-hi]pyrido[4,3-b]indol-4(5H)-one The resolution of 2-(2,4-dichlorophenyl)-6,7,8a,9,10,11,12,12a-octahydroazepino[3,2,1-hi]pyrido[4,3-b]indol-4(5H)-one was carried out by High Performance Liquid Chromatography using a chiral column to afford the title compound.

Example 431

(8aR,12aS)-2-(2,4-dichlorophenyl)-6,7,8a,9,10,11,12,12a-octahydroazepino[3,2,1-hi]pyrido[4,3-b]indol-4(5H)-one The resolution of 2-(2,4-dichlorophenyl)-6,7,8a,9,10,11,12,12a-octahydroazepino[3,2,1-hi]pyrido[4,3-b]indol-4(5H)-one was carried out by High Performance Liquid Chromatography using a chiral column to afford the title compound.

Example 432

(8aS,12aR)-2-(2,4-dichlorophenyl)-6,7,8a,9,10,11,12,12a-decahydroazepino[3,2,1-hi]pyrido[4,3-b]indol-4-ol To (8aS,12aR)-2-(2,4-dichlorophenyl)-6,7,8a,9,10,11,12,12a-octahydroazepino[3,2,1-hi]pyrido[4,3-b]indol-4(5H)-one (12 mg, 0.03 mmol) in CH$_3$OH(1 mL) at RT was added NaBH$_4$ (5.4 mg, 0.15 mmol) in three portions. The reaction mixture was stirred at RT for 2 h 2 drops of 1NHCl were added to the reaction mixture, concentrated in vacuo. NH$_4$OH (1 mL) and water (2 mL) were added, extracted with CH$_2$Cl$_2$ (3×3 mL). The combined organic layer was dried over MgSO$_4$, concentrated to afford the title compound (8 mg, 69%). MS-ESI: 389 [MH]$^+$.

Example 433

(8aR,12aS)-2-(2,4-dichlorophenyl)-6,7,8a,9,10,11,12,12a-decahydroazepino[3,2,1-hi]pyrido[4,3-b]indol-4-ol The title compound was prepared by the method of Example 432 from (8aR,12aS)-2-(2,4-dichlorophenyl)-6,7,8a,9,10,11,12,12a-octahydroazepino[3,2,1-hi]pyrido[4,3-b]indol-4(5H)-one (14 mg, 0.04 mmol) to afford the title compound (12 mg, 86%). MS-ESI: 389 [MH]$^+$.

Example 434

(±)-cis-5,6,8,9,10,11,12,12a-octahydro-4H,7aH-azepino[3',4':4,5]pyrrolo[3,2,1-ij]quinoline Step A:
3,4-Dihydro-[(2H)-quinolinamine hydrochloride (5.0 g, 27 mmol) and 1,3-cyclohexanedione (3.1 g, 27 mmol) was mixed in AcOH (4.3 mL) and H$_2$O (4.3 mL). The mixture was heated at 40° C. for 10 min until dissolved completely. The mixture was then concentrated to dryness. The residue was washed with acetonitrile then filtered to yield 3-(3,4-dihydro-1-(2H)-quinolinylimino)-1-cyclohexen-1-ol hydrochloride (5.2 g, 69%) as a yellow solid.

Step B:
3-(3,4-Dihydro-1-(2H)-quinolinylimino)-1-cyclohexen-1-ol hydrochloride (4.78 g, 17 mmol) was mixed with AcOH (37 mL) and conc. HCl (6.1 mL). The reaction mixture was refluxed for 1 h and cooled to RT. The reaction mixture was concentrated in vacuo then the residue was dissolved in CH$_2$Cl$_2$. The organic solution was washed with H$_2$O and brine, dried over MgSO$_4$, filtered and concentrated in vacuo. The residue was chromatographed in silica gel (hex:EtOAc 1:1) to give 5,6,9,10-tetrahydro-4H-pyrido[3,2,1-jk]carbazol-11(8H)-one (1.25 g, 33%) as a light yellow solid.

Step C:
To a solution of 5,6,9,10-tetrahydro-4H-pyrido[3,2,1-jk]carbazol-11(8H)-one (820 mg, 3.6 mmol) in ethanol (7.5 mL) and H$_2$O (3.6 mL) was added hydroxylamine hydrochloride (380 mg, 5.5 mmol) and sodium acetate (452 mg, 5.5 mmol). The reaction mixture was refluxed for 15 h then cooled to RT.

The precipitated solid was filtered and washed with H$_2$O. The solid was dried under vacuum to give 5,6,9,10-tetrahydro-4H-pyrido[3,2,1-jk]carbazol-11(8H)-one oxime (824 mg, 95%) as a gray powder.

Step D:

To a preheated polyphosphoric acid (25 g) was added 5,6,9,10-tetrahydro-4H-pyrido[3,2,1-jk]carbazol-11(8H)-one oxime (810 mg, 3.3 mmol) in one portion at 110° C. The reaction mixture was stirred for 30 min at the same temperature then pour into ice water (100 mL) and triturated to complete the dissolution of the polyphosphoric acid. After 1 h stirring at 20° C., gummy solid was formed, and it was washed with $H_2O$ and $NH_4OH$. The solid was crystallized in EtOAc to give 5,6,8,9,10,11-hexahydro-4H, 12H-azepino [3',4':4,5]pyrrolo[3,2,1-ij]quinolin-12-one (320 mg, 40%) as a yellow solid.

Step E:

To a suspension of $LiAlH_4$ in 1,4-dioxane (26 mL) was added 5,6,8,9,10,11-hexahydro-4H,12H-azepino[3',4':4,5] pyrrolo[3,2,1-ij]quinolin-12-one (300 mg, 1.25 mmol) under $N_2$ at 20° C. The reaction mixture was refluxed for 15 h. The reaction mixture was cooled in an ice bath and added successively with $H_2O$ (0.3 mL), 15% NaOH (0.3 mL) and $H_2O$ (0,8 mL). The mixture was stirred for 1 h at 20° C. then filtered. The filtrate was concentrated in vacuo. The residue was dissolved in dilute AcOH and washed with $Et_2O$. The aqueous solution was basified with 1N NaOH. A white solid was precipitated and filtered to yield 5,6,9,10,11,12-hexahydro-4H,8H-azepino[3',4':4,5]pyrrolo[3,2,1-ij]quinoline (270 mg, 95%).

Step F:

To a solution of 5,6,9,10,11,12-hexahydro-4H,8H-azepino[3',4':4,5]pyrrolo[3,2,1-ij]quinoline (240 mg, 1.06 mmol) in TFA (4.0 ML) was added $Et_3SiH$ (2.0 mL). The mixture was stirred for 3 days then concentrated in vacuo. The residue was dissolved in dilute AcOH and washed with $Et_2O$. The aqueous solution was basified with 1N NaOH. A white solid was precipitated and filtered to yield the title compound as a pale yellow viscous oil (200 mg, 83%). MS (CI, $NH_3$): 229.4 (base, M+H).

Example 435 tert-butyl(±)-cis-5,6,8,9,10,11,12,12a-octahydro-4H, 7aH-azepino[3',4':4,5]pyrrolo[3,2,1-ij]quinoline-11-carboxylate The title compound (114 mg, 99%) was prepared by the method of Example 311 from (±)-cis-5,6,8,9,10,11,12,12a-octahydro-4H,7aH-azepino[3',4':4,5]pyrrolo[3,2,1-ij]quinoline (80 mg, 0.35 mmol) as a viscous colorless oil. MS (ESI): 329.4 (base, M+H).

Example 436 tert-butyl(±)-cis-2-bromo-5,6,8,9,10,11,12,12a-octahydro-4H,7aH-azepino[3',4':4,5]pyrrolo[3,2,1-ij] quinoline-11-carboxylate The title compound (120 mg, 81%) was prepared by the method of Example 314 from tert-butyl(±)-cis-5,6,8,9,10, 11,12,12a-octahydro-4H,7aH-azepino[3',4':4,5]pyrrolo[3,2, 1-ij]quinoline (114 mg, 0.35 mmol) as a viscous colorless oil.

Example 437

(±)-cis-2-[4-methoxy-2-(trifluoromethyl)phenyl]-5,6, 8,9,10,11,12,12a-octahydro-4H,7aH-azepino[3',4':4, 5]pyrrolo[3,2,1-ij]quinoline Step A:

Tert-butyl(±)-cis-2-[4-methoxy-2-(trifluoromethyl)phenyl]-5,6,8,9,10,11,12,12a-octahydro-4H,7aH-azepino[3',4': 4,5]pyrrolo[3,2,1-ij]quinoline-11-carboxylate (56 mg, 91%) was prepared by the general method of Example 319, step A from tert-butyl(±)-cis-2-bromo-5,6,8,9,10,11,12,12a-octahydro-4H,7aH-azepino[3',4':4,5]pyrrolo[3,2,1-ij]quinoline-11-carboxylate (50 mg, 0.12 mmol) and 4-methoxy-2-(trifluoromethyl)phenylboronic acid (54 mg, 0.25 mmol) as a white foam. MS (ESI): 503.6 (base, M+H).

Step B:

The title compound (44 mg, 99%) was prepared by the general method of Example 312, step B from tert-Butyl (±)-cis-2-[4-methoxy-2-(trifluoromethyl)phenyl]-5,6,8,9, 10,11,12,12a-octahydro-4H,7aH-azepino[3',4':4,5]pyrrolo [3,2,1-ij]quinoline-11-carboxylate (54 mg, 0.11 mmol) as a white foam. MS (CI): 403.4 (base, M+H).

Utility

The compounds of the present invention have therapeutic utility for illnesses or disorders involving the neurotransmitter serotonin (5-hydroxy tryptamine or 5-HT) and either agonism or antagonism of 5-HT2 receptors, as demonstrated by the assays described below. Therapeutic utility for these illnesses or disorders could involve numerous biological processes affected by serotonin including, but not limited to, appetite, mood, sleep, sexual activity, and arterial constriction. These biological processes may also be important to numerous central nervous system (CNS) disorders including those related to the affective disorders of depression, anxiety, psychosis, and schizophrenia, as well as, disorders of food intake such as anorexia, bulemia, and obesity. The compounds of the present invention potentially have therapeutic utility in other conditions in which serotonin has been implicated, such as migraine, attention deficit disorder or attention deficit hyperactivity disorder, addictive behavior, and obsessive-compulsive disorder, as well as, conditions associated with cephalic pain, social phobias, and gastrointestinal disorders such as dysfunction of the gastrointestinal tract motility. Lastly, compounds of the present invention potentially have therapeutic utility in neurodegenerative diseases and traumatic conditions represented by the examples of Alzheimer's disease and brain/spinal cord trauma.

The pharmacological analysis of each compound for either antagonism or agonism of at 5-HT2A and 5-HT2C receptors consisted of in vitro and in vivo studies. In vitro analyses included $K_i$ determinations at 5-HT2A and 5-HT2C receptors and an assessment of functional (i.e., agonism or antagonism) activity at each receptor class by IP3 hydrolysis assays. Additional receptor assays were conducted to evaluate receptor specificity of 5-HT2A and 5-HT2C receptors over monoamine and nuisance receptors (e.g. histamine, dopamine, and muscarinic). A compound is considered active as a 5-HT2A antagonist or a 5-HT2C agonist if it has an $IC_{50}$ value or a $K_i$ value of less than about 1 micromolar; preferably less than about 0.1 micromolar; more preferably less than about 0.01 micromolar. Compounds of the invention have been shown to have an $IC_{50}$ value of less than about 1 micromolar for 5-HT2A antagonism or a 5-HT2C agonism.

In vivo assays assessed compound activity in a variety of behavioral paradigms including quipazine head twitch, acute and chronic feeding models, anxiety and depression models (learned-helplessness, elevated plus maze, Geller-Siefter, conditioned taste aversion, taste reactivity, satiety sequence). In aggregate, these models reflect activity as a 5-HT2A antagonist (quipazine head twitch, depression models) or 5-HT2C agonist (feeding models, anxiety models, depression models) and provide some indication as to bioavailability, metabolism and pharmacokinetics.

Radioligand binding experiments were conducted on recombinant human 5-HT2A and 5-HT2C receptors expressed in HEK293E cells. The affinities of compounds of the present invention to bind at these receptors is determined by their capacity to compete for [$^{125}$I]-1-(2,5-dimethoxy-4-iodophenyl)-2-amino-propane (DOI) binding at the 5-HT2A or 5-HT2C. General references for binding assays include 1) Lucaites V L, Nelson D L, Wainscott D B, Baez M (1996) Receptor subtype and density determine the coupling repertoire of the 5-HT2 receptor subfamily. Life Sci., 59(13): 1081–95. J Med Chem 1988 January;31(1):5–7; 2) Glennon R A, Seggel M R, Soine W H, Herrick-Davis K, Lyon R A, Titeler M (1988) [$^{125}$I]-1-(2,5-dimethoxy-4-iodophenyl)-2-amino-propane: an iodinated radioligand that specifically labels the agonist high-affinity state of 5-HT2 serotonin receptors. J. Med. Chem. 31(1):5–7 and 3) Leonhardt S, Gorospe E, Hoffman B J, Teitler M (1992) Molecular pharmacological differences in the interaction of serotonin with 5-hydroxytryptamineIC and 5-hydroxytryptamine2 receptors. Mol Pharmacol., 42(2):328–35.

The functional properties of compounds (efficacy and potency) were determined in whole cells expressing 5-HT2A or 5-HT2C receptors by assessing their ability to stimulate or inhibit receptor-mediated phosphoinositol hydrolysis. The procedures used are described below.

In Vitro Binding Assays

Stable expression of 5-HT2A and 5-HT2C Receptors in HEK293E Cells.

Stable cell lines were generated by transfecting 293EBNA cells with plasmids containing human 5-HT2A, 5-HT2B, or 5-HT2C (VNV edited isoform) cDNA using calcium phosphate. These plasmids also contained the cytomegalovirus (CMV) immediate early promoter to drive receptor expression and EBV oriP for their maintenance as an extrachromosomal element, and the hph gene from *E. Coli* to yield hygromycin B resistance (Horlick et al., 1997). Transfected cells were maintained in Dulbecco's Modified Eagle medium (DMEM) containing dialyzed 10% fetal bovine serum at 37° C. in a humid environment (5% $CO_2$) for 10 days. The 5-HT2A cells were adapted to spinner culture for bulk processing whereas it was necessary to maintain the other lines as adherent cultures. On the day of harvest, cells were washed in phosphate-buffered saline (PBS), counted, and stored at −80° C.

Membrane Preparation

On the day of assay, pellets of whole cells (containing approximately 1×108 cells) expressing the 5-HT2A or 5-HT2C receptor were thawed on ice and homogenized in 50 mM Tris HCl (pH 7.7) containing 1.0 mM EDTA using a Brinkman Polytron (PT-10, setting 6 for 10 sec). The homogenate was centrifuged at 48,000×g for 10 min and the resulting pellet washed twice by repeated homogenization and centrifugation steps. The final pellet was resuspended in tissue buffer and protein determinations were made by the bichichoninic acid (BCA) assay (Pierce Co., Ill.) using bovine serum albumin as the standard.

Radioligand Binding Assays for the 5-HT2A, and 5-HT2C Receptors

Radioligand binding studies were conducted to determine the binding affinities (KI values) of compounds for the human recombinant 5-HT2A, 5-HT2B, and 5-HT2C receptors (Fitzgerald et al., 1999). Assays were conducted in disposable polypropylene 96-well plates (Costar Corp., Cambridge, Mass.) and were initiated by the addition of 5-HT2A, 5-HT2B, or 5-HT2C membrane homogenate in tissue buffer (10–30 (g/well) to assay buffer (50 mM Tris HCl, 0.5 mM EDTA, 10 mM pargyline, 10 mM $MgSO_4$, 0.05% ascorbic acid, pH 7.5) containing [$^{125}$I]DOI for the 5-HT2A and 5-HT2C receptors (0.3–0.5 nM, final) or [$^3$H] LSD (2–2.5 nM, final) for the 5-HT2B receptor, with or without competing drug (i.e, newly synthesized chemical entity). For a typical competition experiment, a fixed concentration of radioligand was competed with duplicate concentrations of ligand (12 concentrations ranging from 10 picomolar to 10 micromolar). The reaction mixtures were incubated to equilibrium for 45 min at 37° C. and terminated by rapid filtration (cell harvestor; Inotech Biosystems Inc., Lansing, Mich.) over GFF glass-fiber filters that had been pre-soaked in 0.3% polyethyleneimine. Filters were washed in ice-cold 50 mM Tris HCl buffer (pH 7.5) and then counted in a gamma counter for the 5-HT2A and 5-HT2C assays, or by liquid scintillation spectroscopy for the 5-HT2B assay.

Phosphoinositide Hydrolysis Studies

The ability of newly synthesized compounds to stimulate phosphoinositide (PI) hydrolysis was monitored in whole cells using a variant (Egan et al., 1998) of a protocol described previously (Berridge et al., 1982). HEK293E cells expressing the human 5-HT2A, 5-HT2B, or 5-HT2C receptor were lifted with 0.5 mM EDTA and plated at a density of 100,000/well onto poly-D-lysine-coated 24-well plates (Biocoat; Becton Dickinson, Bedford, Mass.) in Dulbecco's modified Eagle's serum (DMEM; Gibco BRL) containing high glucose, 2 mM glutamine, 10% dialyzed fetal calf serum, 250 (g/ml hygromycin B, and 250(g/ml G418. Following a 24–48 hr period, the growth media was removed and replaced with DMEM without fetal calf serum and inositol (Gibco BRL). The cells were then incubated with DMEM (without serum and inositol) containing a final concentration of 0.5 uCi/well myo-[$^3$H]inositol for 16–18 hr. Following this incubation, the cells were washed with DMEM (without serum or inositol) containing 10 mM LiCl and 10 (M pargyline and then incubated for 30 min with the same media but now containing one of several test compounds. Reactions were terminated by aspirating the media and lysing the cells by freeze-thaw. [$^3$H]phosphoinositides were extracted with chloroform/methanol (1:2 v/v), separated by anion exchange chromatography (Bio-Rad AG1-X8 resin), and counted by liquid scintillation spectroscopy as described previously (Egan et al., 1998).

Data Analyses

The equilibrium apparent dissociation constants (Ki's) from the competition experiments were calculated using an iterative nonlinear regression curve-fitting program (Graph-Pad Prism; San Diego, Calif.). For the PI hydrolysis experiments, EC50's were calculated using a one-site 'pseudo' Hill model: $y=((Rmax-Rmin)/(1+R/EC50)nH))+Rmax$ where R=response (DeltaGraph, Monterey, Calif.). Emax (maximal response) was derived from the fitted curve maxima (net IP stimulation) for each compound. Intrinsic activity (IA) was determined by expressing the Emax of a compound as a percentage of the Emax of 5-HT (IA=1.0).

In Vivo Experiments for Serotonergic Ligands

Preclinical Efficacy, Potency, and Side Effect Liability a) Anti-Serotonin Efficacy Antagonism of Quipazine-Induced Head Twitch in Rat. Quipazine, an agonist at 5-HT receptors, produces a characteristic head twitch response in rats. 5-HT receptor antagonists effectively antagonize this 5-HT agonist-induced behavioral effect (Lucki et al., 1984). Accordingly, the quipazine-induced head twitch model in rat can function as an in vivo behavioral correlate to 5-HT receptor binding. Compounds are administered 30 minutes before behavioral testing (and 25 minutes before quipazine), and a dose-related antagonism of the quipazine response is determined.

b) Antipsychotic Efficacy

Inhibition of the Conditioned Avoidance Response (CAR) in Rat. Rats are trained to consistently avoid (by climbing onto a pole suspended from the ceiling of the test chamber) an electric foot shock (0.75 mA) delivered to the grid floor of the testing chamber. All antipsychotic drugs effectively inhibit this conditioned avoidance response (Arnt, 1982). The ability of a compound to inhibit this response is used to determine the antipsychotic efficacy of potential drug candidates.

c) Extrapyramidal Side Effect Liability

Induction of Catalepsy in Rat. Typical antipsychotic drugs produce extrapyramidal side effects (EPS) at clinically effective doses. The most widely accepted preclinical indicator of EPS liability in humans is a drug-induced catalepsy syndrome in rat (Costall and Naylor, 1975), a condition whereby the animal will remain immobile in an externally imposed posture (analogous to a catatonic stupor in humans). Rats are tested for induction of catalepsy in a dose-response test after oral administration of compounds.

d) CNS Penetration; In Vivo Brain Receptor Occupancy

In Vivo Binding. To determine the level of in vivo receptor occupancy, an in vivo receptor binding protocol is used. This procedure uses an appropriate radioligand to label the receptor of interest. For example, to measure both Dopamine D2 and 5-HT2A receptors in vivo, one can use $^3$H—N-methyl spiperone ($^3$H-NMSP), (Frost, et. al. 1987) The procedure uses rats (or mice) fasted overnight. To measure the effects of compounds on the receptors of interest, compounds are dosed, usually p.o. for example in 2 microliters/gram body weight in 0.25% Methocel suspension. The radiolabeled compound (in this example, $^3$H-NMSP) is administered by i.v. tail vein injection (10 microcuries label/200 gram rat). Time course experiments are used to determine the optimal time of binding for both the radiolabeled and unlabeled compound. These optimal time frames are used for all subsequent dose-response experiments. After the appropriate time frame of compound/radioligand exposure, the animals are sacrificed and the relevant brain regions dissected (frontal cortex for 5-HT2A and striatum for D2 receptors) and examined for their content of radioactivity. The level of non-specific binding is determined by examining a brain region known not to contain the receptor of interest (in this case the cerebellum) or by administering an excess of compound known pharmacologically to interact with the receptor.

REFERENCES

Arnt, J. Acta Pharmacol. et Toxicol. 1982: 51, 321–329.

Berridge M. J., Downes P. C., Hanley M. R. (1982) Lithium amplifies agonist-dependent phosphotidyinositol response in brain and salivary glands. Biochem. J., 206, 587–595.

Costall, B and Naylor, R J. Psychopharmacology. 1975: 43, 69–74.

Egan C. T., Herrick-Davis K., Miller K., Glennon R. A., and Teitler M. (1998) Agonist activity of LSD and lisuride at cloned 5-HT2A and 5-HT2C receptors. Psychopharmacology, 136, 409–414.

Fitzgerald L W, Conklin D S, Krause C M, Marshall A P, Patterson J P, Tran D P, Iyer G, Kostich W A, Largent B L, Hartig P R (1999) High-affinity agonist binding correlates with efficacy (intrinsic activity) at the human serotonin 5-HT2A and 5-HT2C receptors: evidence favoring the ternary complex and two-state models of agonist action. J. Neurochem., 72, 2127–2134.

Frost, J. J., Smith, A. C., Kuhar, M. J., Dannals, R. F., Wagner, H. N., 1987, In Vivo Binding of 3H-N-Methyl-spiperone to Dopamine and Serotonin Receptors. Life Sciences, 40:987–995.

Horlick, R. A., Sperle, K., Breth, L. A., Reid, C. C., Shen, E. S., Robbinds, A. K., Cooke, G. M., Largent, B. L. (1997) Rapid Generation of stable cell lines expressing corticotrophin-releasing hormone receptor for drug discovery. Protein Expr. Purif. 9,301–308.

Lucki, I, Nobler, M. S., Frazer, A., 1984, Differential actions of serotonin antagonists on two behavioral models of serotonin receptor activation in the rat. J. Pharmacol. Exp. Ther. 228(1):133–139.

Dosage and Formulation

The serotonin agonist and serotonin antagonist compounds of this invention can be administered as treatment for the control or prevention of central nervous system disorders including obesity, anxiety, depression, psychosis, schizophrenia, sleep and sexual disorders, migraine and other conditions associated with cephalic pain, social phobias, and gastrointestinal disorders such as dysfunction of the gastrointestinal tract motility by any means that produces contact of the active agent with the agent's site of action, i.e., 5-HT2 receptors, in the body of a mammal. It can be administered by any conventional means available for use in conjunction with pharmaceuticals, either as an individual therapeutic agent or in a combination of therapeutic agents. It can be administered alone; but preferably is administered with a pharmaceutical carrier selected on the basis of the chosen route of administration and standard pharmaceutical practice.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. By way of general guidance, a daily dosage of active ingredient can be expected to be about 0.001 to about 1000 milligrams per kilogram of body weight, with the preferred dose being about 0.01 to about 100 mg/kg; with the more preferred dose being about 0.1 to about 30 mg/kg. Advantageously, compounds of the present invention may be administered in a single daily dose, or the total daily dosage may be administered in divided doses of two, three, or four times daily.

Dosage forms of compositions suitable for administration contain from about 1 mg to about 100 mg of active ingredient per unit. In these pharmaceutical compositions the active ingredient will ordinarily be present in an amount of about 0.5–95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers are described in *Remington's Pharmaceutical Sciences*, supra, a standard reference text in this field.

Useful pharmaceutical dosage-forms for administration of the compounds of this invention can be illustrated as follows:

Capsules

A large number of unit capsules can be prepared by filling standard two-piece hard gelatin capsules each with 100 mg of powdered active ingredient, 150 mg of lactose, 50 mg of cellulose, and 6 mg magnesium stearic.

Soft Gelatin Capsules

A mixture of active ingredient in a digestible oil such as soybean oil, cottonseed oil or olive oil can be prepared and injected by means of a positive displacement pump into gelatin to form soft gelatin capsules containing 100 mg of the active ingredient. The capsules should then be washed and dried.

Tablets

A large number of tablets can be prepared by conventional procedures so that the dosage unit is 100 mg of active ingredient, 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption.

Suspension

An aqueous suspension can be prepared for oral administration so that each 5 ml contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection can be prepared by stirring 1.5% by weight of active ingredient in 10% by volume propylene glycol and water. The solution is sterilized by commonly used techniques.

The Tables below provide representative Examples, the synthesis of which are described above, of the compounds of Formula (I) of the present invention.

TABLE 1

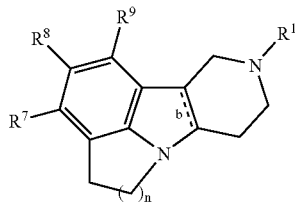

| Ex# | n | R7 | R8 | R9 | b | R1 |
|-----|---|----|----|----|----|----|
| 1 | 1 | H | H | H | dbl | H |
| 2 | 1 | H | H | H | dbl | cycPropyl |
| 3 | 1 | H | H | H | sgl | H |
| 16 | 2 | H | H | H | dbl | H |
| 17 | 2 | H | H | H | sgl | H |
| 37 | 1 | H | H | H | sgl | —C(=O)cycPropyl |
| 38 | 7 | H | H | H | sgl | —C(=O)iPropyl |
| 89 | 1 | H | 2-Cl-phenyl | H | sgl | —CO$_2$-tButyl |
| 90 | 1 | H | 2,4-diCl-phenyl | H | sgl | —CO$_2$-tButyl |
| 91 | 1 | H | 3,4-diCl-phenyl | H | sgl | —CO$_2$-tButyl |
| 92 | 1 | H | 2,3-diCl-phenyl | H | sgl | —CO$_2$-tButyl |
| 93 | 1 | H | 2-Cl-4-CF$_3$-phenyl | H | sgl | —CO$_2$-tButyl |
| 94 | 1 | H | 2-Cl-4-MeO-phenyl | H | sgl | —CO$_2$-tButyl |
| 95 | 1 | H | 2-MeO-4-iPr-phenyl | H | sgl | —CO$_2$-tButyl |
| 96 | 1 | H | 3-F-phenyl | H | sgl | —CO$_2$-tButyl |

TABLE 1-continued

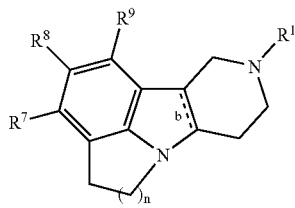

| Ex# | n | R7 | R8 | R9 | b | R1 |
|---|---|---|---|---|---|---|
| 97 | 1 | H | 2,4-diMeO-phenyl | H | sgl | —CO₂-tButyl |
| 98 | 1 | H | 2-Cl-phenyl | H | sgl | H |
| 99 | 1 | H | 2,4-diCl-phenyl | H | sgl | H |
| 100 | 1 | H | 3,4-diCl-phenyl | H | sgl | H |
| 101 | 1 | H | 2,3-diCl-phenyl | H | sgl | H |
| 102 | 1 | H | 2-Cl-4-CF₃-phenyl | H | sgl | H |
| 103 | 1 | H | 2-Cl-4-MeO-phenyl | H | sgl | H |
| 104 | 1 | H | 2-MeO-4-iPr-phenyl | H | sgl | H |
| 105 | 1 | H | 3-F-phenyl | H | sgl | H |
| 106 | 1 | H | 2,4-diMeO-phenyl | H | sgl | H |
| 107 | 2 | H | H | H | sgl | —CO₂-tButyl |
| 108 | 2 | H | Br | H | sgl | —CO₂-tButyl |
| 109 | 2 | H | 2,3-diCl-phenyl | H | sgl | —CO₂-tButyl |
| 110 | 2 | H | 3,4-diCl-phenyl | H | sgl | —CO₂-tButyl |
| 111 | 2 | H | 2-Cl-4-CF₃-phenyl | H | sgl | —CO₂-tButyl |
| 112 | 2 | H | 2,3-diCl-phenyl | H | sgl | H |
| 113 | 2 | H | 3,4-diCl-phenyl | H | sgl | H |
| 114 | 2 | H | 2-Cl-4-CF₃-phenyl | H | sgl | H |
| 189 | 1 | H | 2-Cl-phenyl | H | sgl | —(CH₂)₃C(=O)(4-F-phenyl) |
| 190 | 1 | H | 2,4-diCl-phenyl | H | sgl | —(CH₂)₃C(=O)(4-F-phenyl) |
| 191 | 2 | H | H | H | sgl | —(CH₂)₃C(=O)(4-F-phenyl) |
| 265 | 1 | H | H | H | sgl | —(CH₂)₃C(=O)(4-F-phenyl) |
| 274 | 1 | H | 2-F-4-MeO-phenyl | H | sgl | H |
| 275 | 1 | H | 2-CF₃-4-EtO-phenyl | H | sgl | —CO₂-tButyl |
| 276 | 1 | H | 2-CF₃-4-EtO-phenyl | H | sgl | H |
| 277 | 1 | H | 2-F-4-Cl-phenyl | H | sgl | —CO₂-tButyl |
| 278 | 1 | H | 2-F-4-Cl-phenyl | H | sgl | H |
| 279 | 1 | H | 2-CF₃-4-iPrO-phenyl | H | sgl | —CO₂-tButyl |
| 280 | 1 | H | 2-CF₃-4-iPrO-phenyl | H | sgl | H |
| 281 | 1 | H | 2-CF₃-4-MeO-phenyl | H | sgl | —CO₂-tButyl |
| 282 | 1 | H | 2-CF₃-4-MeO-phenyl | H | sgl | H |
| 283 | 1 | H | phenyl | H | sgl | —CO₂-tButyl |
| 284 | 1 | H | phenyl | H | sgl | H |
| 285 | 1 | H | 2-Me-phenyl | H | sgl | —CO₂-tButyl |
| 286 | 1 | H | 2-Me-phenyl | H | sgl | H |
| 287 | 1 | H | 2-CF₃-phenyl | H | sgl | —CO₂-tButyl |
| 288 | 1 | H | 2-CF₃-phenyl | H | sgl | H |
| 289 | 1 | H | 3,4-diMeO-phenyl | H | sgl | —CO₂-tButyl |
| 290 | 1 | H | 3,4-diMeO-phenyl | H | sgl | H |
| 291 | 1 | H | 2,4-diCl-phenyl | H | sgl | —CO₂-tButyl |
| 292 | 1 | H | 2,4-diCl-phenyl | H | sgl | H |
| 293 | 1 | H | 3,5-diCl-phenyl | H | sgl | —CO₂-tButyl |
| 294 | 1 | H | 3,5-diCl-phenyl | H | sgl | H |
| 295 | 1 | H | 4-MeO-2-iPr-phenyl | H | sgl | —CO₂-tButyl |
| 296 | 1 | H | 4-MeO-2-iPr-phenyl | H | sgl | H |
| 297 | 1 | H | 5-F-4-MeO-2-Me-phenyl | H | sgl | —CO₂-tButyl |
| 298 | 1 | H | 5-F-4-MeO-2-Me-phenyl | H | sgl | H |
| 299 | 1 | H | 4-MeO-2-Me-phenyl | H | sgl | —CO₂-tButyl |
| 300 | 1 | H | 4-MeO-2-Me-phenyl | H | sgl | H |
| 301 | 1 | H | 2-Cl-4-MeO-phenyl | H | sgl | —CO₂-tButyl |
| 302 | 1 | H | 2-Cl-4-MeO-phenyl | H | sgl | H |
| 303 | 1 | H | 4-Cl-2-Me-phenyl | H | sgl | —CO₂-tButyl |
| 304 | 1 | H | 4-Cl-2-Me-phenyl | H | sgl | H |
| 305 | 1 | H | 2-CHO-4-MeO-phenyl | H | sgl | H |
| 306 | 1 | H | 2,6-diCl-phenyl | H | sgl | H |
| 307 | 1 | H | 2-CF₃-4-MeNH-phenyl | H | sgl | H |
| 308 | 1 | H | 2-CF₃-4-NH₂-phenyl | H | sgl | H |
| 309 | 1 | H | 4-MeO-2-CH₃CH(OH)-phenyl | H | sgl | H |
| 310 | 3 | H | H | H | sgl | H |
| 311 | 3 | H | H | H | sgl | —CO₂-tButyl |
| 312 | 3 | H | H | H | sgl | H |
| 313 | 3 | H | H | H | sgl | H |
| 314 | 3 | H | H | H | sgl | —CO₂-tButyl |
| 315 | 3 | H | 2,4-diCl-phenyl | H | sgl | H |
| 316 | 3 | H | 2,3-diCl-phenyl | H | sgl | H |
| 317 | 3 | H | 3,4-diCl-phenyl | H | sgl | H |

TABLE 1-continued

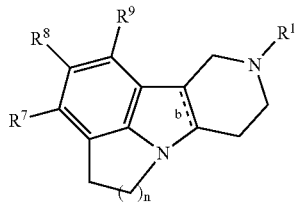

| Ex# | n | R7 | R8 | R9 | b | R1 |
|---|---|---|---|---|---|---|
| 318 | 3 | H | 3,5-diCl-phenyl | H | sgl | H |
| 319 | 3 | H | 2,5-diCl-phenyl | H | sgl | H |
| 320 | 3 | H | 2,6-diCl-phenyl | H | sgl | H |
| 321 | 3 | H | 2-Cl-phenyl | H | sgl | H |
| 322 | 3 | H | 3-Cl-phenyl | H | sgl | H |
| 323 | 3 | H | 4-Cl-phenyl | H | sgl | H |
| 324 | 3 | H | 2,6-diF-phenyl | H | sgl | H |
| 325 | 3 | H | 2,6-diF-phenyl | H | sgl | H |
| 326 | 3 | H | 2,3-diF-phenyl | H | sgl | H |
| 327 | 3 | H | 3,4-diF-phenyl | H | sgl | H |
| 328 | 3 | H | 3-F-phenyl | H | sgl | H |
| 329 | 3 | H | 2-Cl-4-$CF_3$-phenyl | H | sgl | H |
| 330 | 3 | H | 2-Cl-4-MeO-phenyl | H | sgl | H |
| 331 | 3 | H | 2-F-4-MeO-phenyl | H | sgl | H |
| 332 | 3 | H | 4-MeO-2-Me-phenyl | H | sgl | H |
| 333 | 3 | H | 2-$CF_3$-4-MeO-phenyl | H | sgl | H |
| 334 | 3 | H | 2-$CF_3$-phenyl | H | sgl | H |
| 335 | 3 | H | 2-$CF_3$-4-iPrO-phenyl | H | sgl | H |
| 336 | 3 | H | 2,4-di$CF_3$-phenyl | H | sgl | H |
| 337 | 3 | H | 2-F-2-$CF_3$-phenyl | H | sgl | H |
| 338 | 3 | H | 2-$CF_3$-4-$NH_2$-phenyl | H | sgl | H |
| 339 | 3 | H | 2-$CF_3$-4-MeNH-phenyl | H | sgl | H |
| 340 | 3 | H | 2-CHO-phenyl | H | sgl | H |
| 341 | 3 | H | 2-$CH_2$(OH)-phenyl | H | sgl | H |
| 342 | 3 | H | 4-MeO-2-CHO-phenyl | H | sgl | H |
| 343 | 3 | H | 4-MeO-2-$CH_2$(OH)-phenyl | H | sgl | H |
| 344 | 3 | H | 4-CN-2-Me-phenyl | H | sgl | H |
| 345 | 3 | H | 4-MeO-2-$CH_3$CH(OH)-phenyl | H | sgl | H |
| 346 | 2 | H | Br | H | sgl | —$CO_2$-tButyl |
| 347 | 2 | H | 2,4-diCl-phenyl | H | sgl | H |
| 348 | 2 | H | 3,4-diCl-phenyl | H | sgl | H |
| 349 | 2 | H | 3,5-diCl-phenyl | H | sgl | H |
| 350 | 2 | H | 2,5-diCl-phenyl | H | sgl | H |
| 351 | 2 | H | 2,6-diCl-phenyl | H | sgl | H |
| 352 | 2 | H | 2-Cl-phenyl | H | sgl | H |
| 353 | 2 | H | 3-Cl-phenyl | H | sgl | H |
| 354 | 2 | H | 4-Cl-phenyl | H | sgl | H |
| 355 | 2 | H | 2,6-diF-phenyl | H | sgl | H |
| 356 | 2 | H | 2,6-diF-phenyl | H | sgl | Me |
| 357 | 2 | H | 2,3-diF-phenyl | H | sgl | H |
| 358 | 2 | H | 3,4-diF-phenyl | H | sgl | H |
| 359 | 2 | H | 3-F-phenyl | H | sgl | H |
| 360 | 2 | H | 2-Cl-4-MeO-phenyl | H | sgl | H |
| 361 | 2 | H | 2-F-4-MeO-phenyl | H | sgl | H |
| 362 | 2 | H | 4-MeO-2-Me-phenyl | H | sgl | H |
| 363 | 2 | H | 2-$CF_3$-4-MeO-phenyl | H | sgl | H |
| 364 | 2 | H | 2-$CF_3$-4-MeO-phenyl | H | dbl | H |
| 365 | 2 | H | 2-$CF_3$-4-OH-phenyl | H | sgl | H |
| 366 | 2 | H | 2-$CF_3$-phenyl | H | sgl | H |
| 367 | 2 | H | 2-$CF_3$-4-iPrO-phenyl | H | sgl | H |
| 368 | 2 | H | 2,4-di$CF_3$-phenyl | H | sgl | H |
| 369 | 2 | H | 2-$CF_3$-4-F-phenyl | H | sgl | H |
| 370 | 2 | H | 2-$CF_3$-4-$NH_2$-phenyl | H | sgl | H |
| 371 | 2 | H | 2-$CF_3$-4-MeNH-phenyl | H | sgl | H |
| 372 | 2 | H | 4-CN-2-Me-phenyl | H | sgl | H |
| 373 | 2 | H | 2-CHO-phenyl | H | sgl | H |
| 374 | 2 | H | 2-$CH_2$(OH)-phenyl | H | sgl | H |
| 375 | 2 | H | 4-MeO-2-CHO-phenyl | H | sgl | H |
| 376 | 2 | H | 4-MeO-2-$CH_3$CH(OH)-phenyl | H | sgl | H |
| 377 | 3 | H | 2-$CF_3$-4-EtO-phenyl | H | sgl | H |
| 378 | 2 | H | 2-$CF_3$-4-EtO-phenyl | H | sgl | H |
| 379 | 3 | H | 3-Cl-2-Me-phenyl | H | sgl | H |
| 380 | 2 | H | 3-Cl-2-Me-phenyl | H | sgl | H |
| 381 | 2 | H | 5-F-2-Me-phenyl | H | sgl | H |
| 382 | 2 | H | 2,3-diCl-phenyl | H | sgl | Pr |
| 383 | 2 | H | 2,3-diCl-phenyl | H | sgl | Pr |

TABLE 1-continued

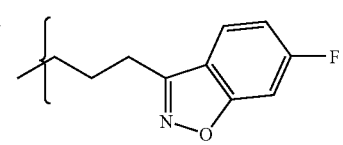

| Ex# | n | R7 | R8 | R9 | b | R1 |
|---|---|---|---|---|---|---|
| 384 | 2 | H | 2,3-diCl-phenyl | H | sgl | Bu |
| 385 | 2 | H | 2,3-diCl-phenyl | H | sgl | Bu |
| 386 | 2 | H | 2,3-diCl-phenyl | H | sgl | 4-pentenyl |
| 387 | 2 | H | 2,3-diCl-phenyl | H | sgl | 3-Me-2-butenyl |
| 388 | 2 | H | 2,4-diCl-phenyl | H | sgl | Pr |
| 389 | 2 | H | 2,4-diCl-phenyl | H | sgl | Bu |
| 390 | 2 | H | 2,4-diCl-phenyl | H | sgl | 4-pentenyl |
| 391 | 2 | H | 2,4-diCl-phenyl | H | sgl | 3-Me-2-butenyl |
| 392 | 2 | H | 2,4-diCl-phenyl | H | sgl | cyclobutylmethyl |
| 393 | 2 | H | 2-$CF_3$-4-MeO-phenyl | H | sgl | Me |
| 394 | 2 | H | 2-$CF_3$-4-MeO-phenyl | H | sgl | Et |
| 395 | 2 | H | 2-$CF_3$-4-MeO-phenyl | H | sgl | Pr |
| 396 | 2 | H | 2-$CF_3$-4-MeO-phenyl | H | sgl | Bu |
| 397 | 2 | H | 2-$CF_3$-4-MeO-phenyl | H | sgl | 4-pentenyl |
| 398 | 2 | H | 2-$CF_3$-4-MeO-phenyl | H | sgl | 3-Me-2-butenyl |
| 399 | 2 | H | 2-$CF_3$-4-MeO-phenyl | H | sgl | 2-F-ethyl |
| 400 | 2 | H | 2-$CF_3$-4-MeO-phenyl | H | sgl | 2,2-diF-ethyl |
| 401 | 2 | H | 2-$CF_3$-4-MeO-phenyl | H | sgl | cyclobutylmethyl |
| 402 | 2 | H | H | H | sgl | —$(CH_2)_3$C(=O)-4-F-phenyl) |
| 403 | 2 | H | H | H | sgl | —$(CH_2)_3$C(=O)(4-F-phenyl) |
| 403 | 2 | H | H | H | sgl | —$(CH_2)_3$C(=O)(4-F-phenyl) |
| 404 | 2 | H | H | H | sgl | —$(CH_2)_3$C(=O)(2-$NH_2$-phenyl) |
| 405 | 2 | H | H | H | sgl | —$(CH_2)_3$C(=O)(2-$NH_2$-phenyl) |
| 406 | 2 | H | H | H | sgl | —$(CH_2)_3$O(4-F-phenyl) |
| 407 | 2 | H | H | H | sgl | —$(CH_2)_3$C(=O)(4-pyridyl) |
| 408 | 2 | H | H | H | sgl | 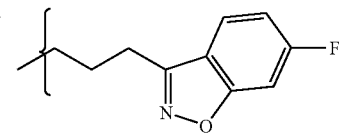 |
| 409 | 2 | H | H | H | sgl | 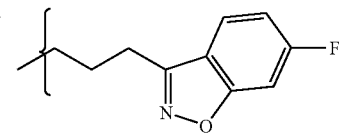 |
| 410 | 2 | H | H | H | dbl | —$(CH_2)_3$C(=O)(4-F-phenyl) |
| 411 | 3 | H | H | H | sgl | —$(CH_2)_3$C(=O)(4-F-phenyl) |
| 412 | 3 | H | H | H | sgl | —$(CH_2)_3$C(=O)(4-F-phenyl) |
| 413 | 3 | H | H | H | sgl | —$(CH_2)_3$C(=O)(4-F-phenyl) |
| 414 | 3 | H | H | H | sgl | —$(CH_2)_3$C(=O)(4-F-2-$NH_2$-phenyl) |
| 415 | 2 | H | H | H | sgl | —$(CH_2)_3$C(=O)(4-F-2-$NH_2$-phenyl) |
| 416 | 2 | H | H | H | sgl | —$(CH_2)_3$C(=O)(4-F-2-$NH_2$-phenyl) |
| 417 | 2 | H | H | H | sgl | —$(CH_2)_3$C(=O)(4-F-2-$NH_2$-phenyl) |

TABLE 2

| Ex# | n | k | R7 | R8 | R9 | b | R1 |
|---|---|---|---|---|---|---|---|
| 418 | 2 | 2 | H | H | H | dbl | H |
| 419 | 2 | 2 | H | H | H | sgl | H |
| 420 | 2 | 2 | H | H | H | sgl | —(CH$_2$)$_3$C(=O)(4-F-phenyl) |
| 421 | 2 | 2 | H | H | H | sgl | —(CH$_2$)$_3$C(=O)(4-F-2-NH$_2$-phenyl) |
| 422 | 3 | 2 | H | H | H | dbl | H |
| 423 | 3 | 2 | H | H | H | sgl | H |
| 424 | 3 | 2 | H | H | H | sgl | —(CH$_2$)$_3$C(=O)(4-F-phenyl) |
| 425 | 3 | 2 | H | H | H | sgl | —(CH$_2$)$_3$C(=O)(4-F-2-NH$_2$-phenyl) |
| 434 | 2 | 1 | H | H | H | sgl | H |
| 435 | 2 | 1 | H | H | H | sgl | —CO$_2$-tButyl |
| 436 | 2 | 1 | H | Br | H | sgl | —CO$_2$-tButyl |
| 437 | 2 | 1 | H | 2-CF$_3$-4-MeO-phenyl | H | sgl | H |

TABLE 3

| Ex# | X | R7 | R8 | R9 | b | R1 |
|---|---|---|---|---|---|---|
| 426 | C=O | H | H | H | sgl | H |
| 427 | C=O | H | H | H | sgl | —CO$_2$-tButyl |
| 428 | C=O | H | 2,4-diCl-phenyl | H | sgl | —CO$_2$-tButyl |
| 429 | C=O | H | 2,4-diCl-phenyl | H | sgl | H |
| 430 | C=O | H | 2,4-diCl-phenyl | H | sgl | H |
| 431 | C=O | H | 2,4-diCl-phenyl | H | sgl | H |
| 432 | CH(OH) | H | 2,4-diCl-phenyl | H | sgl | H |
| 433 | CH(OH) | H | 2,4-diCl-phenyl | H | sgl | H |

TABLE 4

| Ex# | X | n | k | R7 | R8 | R9 | b | R1 |
|---|---|---|---|---|---|---|---|---|
| 196 | NHCO | 1 | 1 | H | H | H | dbl | —(CH$_2$)$_3$C(=O)(4-F-phenyl) |
| 210 | NMe | 2 | 1 | H | H | H | sgl | —(CH$_2$)$_3$C(=O)(4-pyridyl) |
| 211 | NH | 2 | 1 | H | H | H | sgl | H |
| 212 | NH | 2 | 1 | H | H | H | sgl | —(CH$_2$)$_3$C(=O)(4-F-phenyl) |

TABLE 4-continued

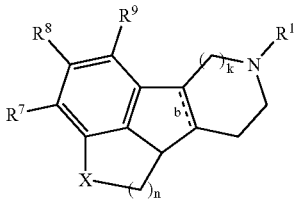

| Ex# | X | n | k | R7 | R8 | R9 | b | R1 |
|---|---|---|---|---|---|---|---|---|
| 217 | NMe | 2 | 1 | H | H | H | sgl | 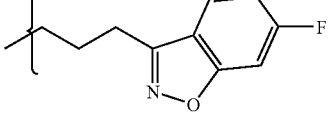 |
| 218 | NMe | 2 | 1 | H | H | H | sgl | 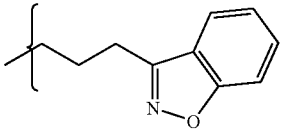 |
| 255 | NMe | 2 | 1 | H | H | H | sgl | H |
| 256 | NEt | 2 | 1 | H | H | H | sgl | H |
| 257 | NPr | 2 | 1 | H | H | H | sgl | H |
| 258 | N(i-Pr) | 2 | 1 | H | H | H | sgl | H |
| 259 | N(n-Bu) | 2 | 1 | H | H | H | sgl | H |
| 260 | N(CH$_2$Ph) | 2 | 1 | H | H | H | sgl | H |
| 261 | NMe | 2 | 1 | H | H | H | sgl | —(CH$_2$)$_3$C(=O)(4-F-phenyl) |
| 262 | NEt | 2 | 1 | H | H | H | sgl | —(CH$_2$)$_3$C(=O)(4-F-phenyl) |
| 263 | N(i-Pr) | 2 | 1 | H | H | H | sgl | —(CH$_2$)$_3$C(=O)(4-F-phenyl) |
| 264 | N(CH$_2$Ph) | 2 | 1 | H | H | H | sgl | —(CH$_2$)$_3$C(=O)(4-F-phenyl) |
| 269 | NMe | 2 | 1 | H | H | H | sgl | —(CH$_2$)$_3$O(4-F-phenyl) |
| N274 | NMe | 2 | 1 | H | 2,4-diCl-phenyl | H | sgl | H |
| N275 | NH | 2 | 1 | H | 2,4-diCl-phenyl | H | sgl | H |
| N276 | NMe | 2 | 1 | H | Br | H | sgl | —(CH$_2$)$_3$C(=O)(4-F-phenyl) |
| N277 | NMe | 7 | 1 | H | MeO | H | sgl | —(CH$_2$)$_3$C(=O)(4-F-phenyl) |
| N278 | NMe | 2 | 1 | H | 2,4-diCl-phenyl | H | sgl | H |
| N279 | NH | 3 | 1 | H | 4-MeO-2-Me-phenyl | H | sgl | H |
| N280 | NHCO | 2 | 1 | H | 2,4-diCl-phenyl | H | sgl | H |
| N281 | NMe | 2 | 2 | H | H | H | sgl | H |
| N282 | NMe | 2 | 2 | H | H | H | sgl | —(CH$_2$)$_3$C(=O)(4-F-phenyl) |
| N283 | NHCH(Me) | 1 | 1 | H | 2,4-diCl-phenyl | H | sgl | H |

TABLE 5

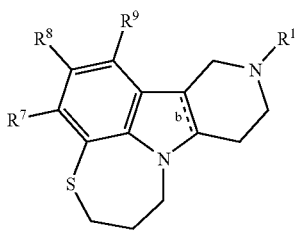

| Ex# | R7 | R8 | R9 | b | R1 |
|---|---|---|---|---|---|
| 4 | H | H | F | dbl | —CO$_2$Et |
| 5 | H | H | F | dbl | H |
| 6 | H | H | Me | dbl | H |
| 7 | H | H | Me | dbl | —CO$_2$—tBu |
| 8 | H | H | Me | sgl | H |
| 9 | H | H | H | sgl | H |
| 10 | H | H | NO$_2$ | dbl | H |
| 11 | H | H | NO$_2$ | sgl | H |
| 12 | Cl | H | H | dbl | H |
| 13 | Cl | H | H | sgl | H |
| 14 | Me | H | H | dbl | H |
| 15 | Me | H | H | sgl | H |

TABLE 5-continued

| Ex# | R7 | R8 | R9 | b | R1 |
|---|---|---|---|---|---|
| 18 | H | H | Br | dbl | H |
| 19 | H | H | Br | sgl | H |
| 25 | H | H | H | sgl | —C(=O)(3,4-diMeO-phenyl) |
| 26 | H | H | H | sgl | —C(=O)(2,5-diMeO-phenyl) |
| 27 | H | H | H | sgl | —C(=O)(3,5-diMeO-phenyl) |
| 28 | H | H | H | sgl | 2,6-diMeO-benzyl |
| 29 | H | H | H | sgl | 2,4-diMeO-benzyl |
| 30 | H | H | H | sgl | 2,4,6-triMeO-benzyl |
| 31 | H | H | H | sgl | 2,3-diMeO-benzyl |
| 32 | H | H | H | sgl | 2,4,5-triMeO-benzyl |
| 33 | H | H | H | sgl | cyclohexylmethyl |
| 34 | H | H | H | sgl | 2,3,4-triMeO-benzyl |
| 35 | H | H | H | sgl | 3,4-diMeO-benzyl |
| 36 | H | H | H | sgl | 3,4,5-triMeO-benzyl |
| 39 | H | H | H | sgl | —CO$_2$Et |
| 40 | H | —C(=O)CH$_3$ | H | sgl | —CO$_2$Et |
| 41 | H | —NHC(=O)CH$_3$ | H | sgl | —CO$_2$Et |
| 42 | H | H | H | sgl | —CH$_2$CH$_2$(4-F-phenyl) |
| 43 | H | H | H | sgl | Et |
| 44 | H | H | H | sgl | Pr |
| 45 | H | H | H | sgl | butyl |
| 46 | H | H | H | sgl | pentyl |
| 47 | H | H | H | sgl | hexyl |
| 48 | H | H | H | sgl | 2-propyl |
| 49 | H | H | H | sgl | 2-butyl |
| 50 | H | H | H | sgl | 2-pentyl |
| 51 | H | H | H | sgl | 2-hexyl |
| 52 | H | H | H | sgl | 2-Me-propyl |
| 53 | H | H | H | sgl | 2-Me-butyl |
| 54 | H | H | H | sgl | 2-Me-pentyl |
| 55 | H | H | H | sgl | 2-Et-butyl |
| 56 | H | H | H | sgl | 3-Me-pentyl |
| 57 | H | H | H | sgl | 3-Me-butyl |
| 58 | H | H | H | sgl | 4-Me-pentyl |
| 59 | H | H | H | sgl | cyclopropylmethyl |
| 60 | H | H | H | sgl | cyclobutylmethyl |
| 61 | H | H | H | sgl | cyclohexylmethyl |
| 62 | H | H | H | sgl | 2-propenyl |
| 63 | H | H | H | sgl | 2-Me-2-propenyl |
| 64 | H | H | H | sgl | trans-2-butenyl |
| 65 | H | H | H | sgl | 3-Me-butenyl |
| 66 | H | H | H | sgl | 3-butenyl |
| 67 | H | H | H | sgl | trans-2-pentenyl |
| 68 | H | H | H | sgl | cis-2-pentenyl |
| 69 | H | H | H | sgl | 4-pentenyl |
| 70 | H | H | H | sgl | 4-Me-3-pentenyl |
| 71 | H | H | H | sgl | 3,3-diCl-2-propenyl |
| 72 | H | H | H | sgl | benzyl |
| 73 | H | H | H | sgl | 2-Me-benzyl |
| 74 | H | H | H | sgl | 3-Me-benzyl |
| 75 | H | H | H | sgl | 4-Me-benzyl |
| 76 | H | H | H | sgl | 2,5-diMe-benzyl |
| 77 | H | H | H | sgl | 2,4-diMe-benzyl |
| 78 | H | H | H | sgl | 3,5-diMe-benzyl |
| 79 | H | H | H | sgl | 2,4,6-triMe-benzyl |
| 80 | H | H | H | sgl | 3-MeO-benzyl |
| 81 | H | H | H | sgl | 3,5-diMeO-benzyl |
| 82 | H | H | H | sgl | pentafluorobenzyl |
| 83 | H | H | H | sgl | 2-phenylethyl |
| 84 | H | H | H | sgl | 1-phenyl-2-propyl |
| 85 | H | H | H | sgl | trnas-3-phenyl-2-propenyl |
| 86 | H | H | H | sgl | 4-phenylbutyl |
| 87 | H | H | H | sgl | 4-phenylbenzyl |
| 88 | H | H | H | sgl | 2-phenylbenzyl |
| 169 | H | Me | H | sgl | H |

TABLE 5-continued

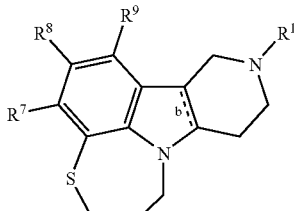

| Ex# | R7 | R8 | R9 | b | R1 |
|---|---|---|---|---|---|
| 170 | H | CN | H | sgl | H |
| 171 | H | Et | H | sgl | H |
| 175 | H | H | H | dbl | Me |
| 176 | H | H | H | sgl | Me |
| 177 | H | H | H | sgl | H |
| 178 | Cl | H | H | sgl | —(CH$_2$)$_3$C(=O)(4-F-phenyl) |
| 179 | Me | H | H | sgl | —(CH$_2$)$_3$C(=O)(4-F-phenyl) |
| 180 | H | H | H | sgl | —(CH$_2$)$_3$S(3-F-phenyl) |
| 181 | H | H | H | sgl | —(CH$_2$)$_3$CH(OH)(4-F-phenyl) |
| 186 | H | H | H | sgl | —(CH$_2$)$_3$C(=O)(4-F-phenyl) |
| 187 | H | MeO | H | sgl | —(CH$_2$)$_3$C(=O)(4-F-phenyl) |
| 192 | H | H | H | sgl | —(CH$_2$)$_3$C(=O)(4-Br-phenyl) |
| 193 | H | H | H | sgl | —(CH$_2$)$_3$SO$_2$(3-F-phenyl) |
| 194 | H | H | H | sgl | —(CH$_2$)$_3$C(=O)(4-(3,4-diCl-phenyl)phenyl) |
| 197 | H | H | H | sgl | —(CH$_2$)$_3$C(=O)(4-Me-phenyl) |
| 198 | H | H | H | sgl | —(CH$_2$)$_3$C(=O)(4-F-phenyl) |
| 199 | H | H | H | sgl | —(CH$_2$)$_3$C(=O)(4-MeO-phenyl) |
| 200 | H | H | H | sgl | —(CH$_2$)$_2$C(=O)(4-F-phenyl) |
| 201 | H | H | H | sgl | —(CH$_2$)$_3$SO$_2$(4-F-phenyl) |
| 202 | H | H | H | sgl | —(CH$_2$)$_3$S(=O)(4-F-phenyl) |
| 203 | H | H | H | sgl | —(CH$_2$)$_3$O(4-F-phenyl) |
| 204 | H | H | H | sgl | —(CH$_2$)$_3$O(phenyl) |
| 205 | H | H | H | sgl | —(CH$_2$)$_3$S(4-F-phenyl) |
| 206 | H | H | H | sgl | —(CH$_2$)$_3$NH(4-F-phenyl) |
| 207 | H | H | H | sgl | —(CH$_2$)$_3$N(CH$_3$)(4-F-phenyl) |
| 208 | H | H | H | sgl | —(CH$_2$)$_3$C(=O)(4-pyridyl) |
| 209 | H | H | H | sgl | —(CH$_2$)$_3$C(=O)(3-pyridyl) |
| 214 | H | H | H | sgl | 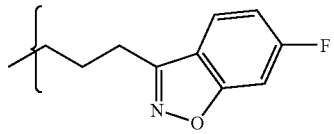 |
| 215 | H | H | H | sgl | 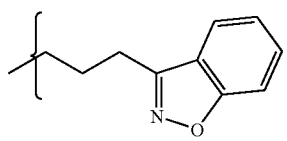 |
| 219 | H | H | H | sgl | —(CH$_2$)$_3$CO$_2$Et |
| 220 | H | H | H | sgl | —(CH$_2$)$_4$CO$_2$Et |
| 221 | H | H | H | sgl | —(CH$_2$)$_3$C(=O)N(CH$_3$)(OCH$_3$) |
| 222 | H | H | H | sgl | —(CH$_2$)$_4$C(=O)N(CH$_3$)(OCH$_3$) |
| 223 | H | H | H | sgl | —(CH$_2$)$_3$C(=O)(3-Me-4-F-phenyl) |
| 224 | H | H | H | sgl | —(CH$_2$)$_3$C(=O)(phenyl) |
| 225 | H | H | H | sgl | —(CH$_2$)$_3$C(=O)(4-Cl-phenyl) |
| 226 | H | H | H | sgl | —(CH$_2$)$_3$C(=O)(3-Me-phenyl) |
| 227 | H | H | H | sgl | —(CH$_2$)$_3$C(=O)(4-tBu-phenyl) |
| 228 | H | H | H | sgl | —(CH$_2$)$_3$C(=O)(3,4-diF-phenyl) |
| 229 | H | H | H | sgl | —(CH$_2$)$_3$C(=O)(2-MeO-5-F-phenyl) |
| 230 | H | H | H | sgl | —(CH$_2$)$_4$C(=O)(phenyl) |
| 231 | H | H | H | sgl | —(CH$_2$)$_3$C(=O)(4-F-1-naphthyl) |
| 232 | H | H | H | sgl | —(CH$_2$)$_3$C(=O)(benzyl) |
| 233 | H | H | H | sgl | —(CH$_2$)$_2$C(=O)NH(4-F-phenyl) |
| 234 | H | H | H | sgl | —(CH$_2$)$_3$C(=O)NH(4-F-phenyl) |
| 235 | H | H | H | sgl | —(CH$_2$)$_3$CH(OH)(4-F-phenyl) |
| 236 | H | H | H | sgl | —(CH$_2$)$_3$CH(OH)(4-pyridyl) |
| 237 | H | H | H | sgl | —(CH$_2$)$_3$CH(OH)(2,3-diMeO-phenyl) |
| 238 | H | H | H | sgl | —(CH$_2$)$_3$C(=O)(2,3-diMeO-phenyl) |
| 239 | H | H | H | sgl | —(CH$_2$)$_4$(cyclohexyl) |

TABLE 5-continued

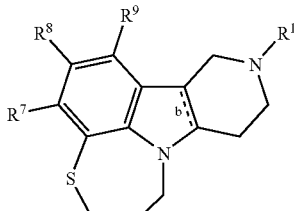

| Ex# | R7 | R8 | R9 | b | R1 |
|---|---|---|---|---|---|
| 240 | H | H | H | sgl | —(CH₂)₃CH(phenyl)₂ |
| 241 | H | H | H | sgl | —CH₂CH₂CH=C(phenyl)₂ |
| 242 | H | H | H | sgl | —(CH₂)₃CH(4-F-phenyl)₂ |
| 243 | H | H | H | sgl | —CH₂CH₂CH=C(4-F-phenyl)₂ |
| 244 | H | H | H | sgl | —(CH₂)₂NHC(=O)(phenyl) |
| 245 | H | H | H | sgl | —(CH₂)₂NHC(=O)(2-F-phenyl) |
| 246 | H | H | H | sgl | —(CH₂)₂NHC(=O)(4-F-phenyl) |
| 247 | H | H | H | sgl | —(CH₂)₃(3-indolyl) |
| 248 | H | H | H | sgl | —(CH₂)₃(1-Me-3-indolyl) |
| 249 | H | H | H | sgl | —CH₂CH₂(3-indolyl) |
| 250 | H | H | H | sgl | —(CH₂)₃(1-indolyl) |
| 251 | H | H | H | sgl | —(CH₂)₃(1-indolinyl) |
| 252 | H | H | H | sgl | —(CH₂)₃(1-benzimidazolyl) |
| 253 | H | H | H | sgl | 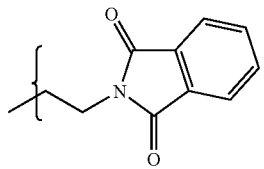 |
| 254 | H | H | H | sgl | 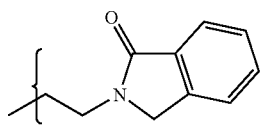 |
| 268 | H | F | H | sgl | —(CH₂)₃C(=O)(4-F-phenyl) |
| 271 | H | H | H | sgl | H |
| 273 | H | F | H | sgl | H |
| S274 | Br | H | H | sgl | H |
| S275 | 2,6-diF-phenyl | H | H | sgl | H |
| S276 | 2-Me-4-MeO-phenyl | H | H | sgl | H |
| S277 | 4-CF₃-phenyl | H | H | sgl | H |
| S278 | 2,3-diCl-phenyl | H | H | sgl | H |
| S279 | 2,4-diCl-phenyl | H | H | sgl | H |
| S280 | 2-Cl-4-CF₃-phenyl | H | H | sgl | H |
| S281 | CN | H | H | sgl | H |
| S282 | CN | Br | H | sgl | H |
| S283 | benzyl | H | H | sgl | H |
| S284 | CHO | H | H | sgl | H |
| S285 | CO₂H | H | H | sgl | H |
| S286 | H | H | H | sgl | —(CH₂)₂NHC(=O)(2,4-diF-phenyl) |
| S287 | H | H | H | sgl | —(CH₂)₂NMeC(=O)-phenyl |
| S288 | H | H | H | sgl | —(CH₂)₂NMeC(=O)(2-F-phenyl) |
| S289 | H | H | H | sgl | —(CH₂)₂NMeC(=O)(2,4-diF-phenyl) |
| S290 | H | H | H | sgl | —(CH₂)₂NMeC(=O)(4-F-phenyl) |
| S291 | H | H | H | sgl | —(CH₂)₃(1H-1,2,3-benzotriazol-1-yl) |
| S292 | H | H | H | sgl | —(CH₂)₃(1H-1,2,3-benzotriazol-2-yl) |
| S293 | H | H | H | sgl | 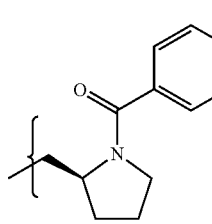 |

TABLE 5-continued

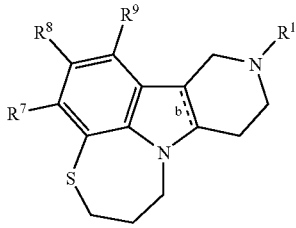

| Ex# | R7 | R8 | R9 | b | R1 |
|---|---|---|---|---|---|
| S294 | H | H | H | sgl | 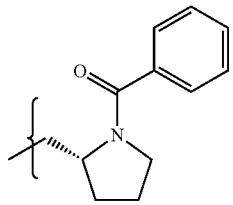 |
| S295 | H | H | H | sgl | 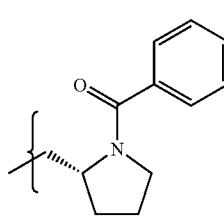 |
| S296 | H | H | H | sgl | —(CH$_2$)$_2$(1H-1,2,3-benzotriazol-1-yl) |
| S297 | H | H | H | sgl | 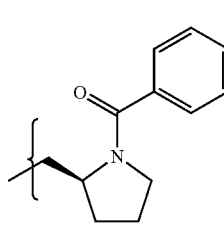 |
| S298 | H | H | H | sgl | —(CH$_2$)$_2$(1H-1,2,3-benzotriazol-2-yl) |
| S299 | H | H | H | sgl | —(CH$_2$)$_3$(3,4-dihydro-1(2H)-quinolinyl) |
| S300 | H | H | H | sgl | —CH$_2$CH$_2$CH=CMe(4-F-phenyl) |
| S301 | H | H | H | sgl | —(CH$_2$)$_2$(2,3-dihydro-1H-inden-2-yl) |
| S302 | H | H | H | sgl | —(CH$_2$)$_3$C(=O)(2-NH$_2$-phenyl) |
| S303 | H | H | H | sgl | —(CH$_2$)$_3$C(=O)(2-NH$_2$-phenyl) |
| S304 | H | H | H | sgl | —(CH$_2$)$_3$C(=O)(2-NH$_2$-5-F-phenyl) |
| S305 | H | H | H | sgl | —(CH$_2$)$_3$C(=O)(2-NH$_2$-3-F-phenyl) |
| S306 | H | H | H | sgl | —(CH$_2$)$_3$C(=O)(2-NH$_2$-4-Cl-phenyl) |
| S307 | H | H | H | sgl | —(CH$_2$)$_3$C(=O)(2-NH$_2$-4-OH-phenyl) |
| S308 | H | H | H | sgl | —(CH$_2$)$_3$C(=O)(2-NH$_2$-4-Br-phenyl) |
| S309 | H | H | H | sgl | —(CH$_2$)$_3$(1H-indazol-3-yl) |
| S310 | H | H | H | sgl | —(CH$_2$)$_3$(5-F-1H-indazol-3-yl) |
| S311 | H | H | H | sgl | —(CH$_2$)$_3$(7-F-1H-indazol-3-yl) |
| S312 | H | H | H | sgl | —(CH$_2$)$_3$(6-Cl-1H-indazol-3-yl) |
| S313 | H | H | H | sgl | —(CH$_2$)$_3$(6-Br-1H-indazol-3-yl) |
| S314 | H | H | H | sgl | —(CH$_2$)$_3$C(=O)(2-NHMe-phenyl) |
| S315 | H | H | H | sgl | —(CH$_2$)$_3$(1-benzothien-3-yl) |
| S355 | H | H | H | sgl | 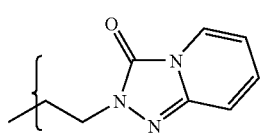 |

TABLE 5-continued

| Ex# | R7 | R8 | R9 | b | R1 |
|---|---|---|---|---|---|
| S356 | H | H | H | sgl | —(CH$_2$)$_3$(6-F-1H-indol-1-yl) |
| S357 | H | H | H | sgl | —(CH$_2$)$_3$(5-F-1H-indol-1-yl) |
| S358 | H | H | H | sgl | —(CH$_2$)$_3$(6-F-2,3-dihydro-1H-indol-1-yl) |
| S359 | H | H | H | sgl | —(CH$_2$)$_3$(5-F-2,3-dihydro-1H-indol-1-yl) |
| S360 | H | H | H | sgl | —(CH$_2$)$_3$(6-F-1H-indol-3-yl) |
| S361 | H | H | H | sgl | —(CH$_2$)$_3$(6-F-1H-indol-3-yl) |
| S362 | H | H | H | sgl | —(CH$_2$)$_3$(5-F-1H-indol-3-yl) |
| S363 | H | H | H | sgl | —(CH$_2$)$_3$(5-F-1H-indol-3-yl) |
| S364 | H | H | H | sgl | —(CH$_2$)$_3$(9H-purin-9-yl) |
| S365 | H | H | H | sgl | —(CH$_2$)$_3$(7H-purin-7-yl) |
| S366 | H | H | H | sgl | (4-cyanophenyl-isoxazolinyl group) |
| S367 | H | H | H | sgl | —(CH$_2$)$_3$(6-F-1H-indazol-3-yl) |
| S368 | H | H | H | sgl | —(CH$_2$)$_3$(6-F-1H-indazol-3-yl) |
| S369 | H | H | H | sgl | —(CH$_2$)$_3$(6-F-1H-indazol-3-yl) |
| S370 | H | H | H | sgl | —(CH$_2$)$_3$C(=O)(2-NH$_2$-4-F-phenyl) |
| S371 | H | H | H | sgl | —(CH$_2$)$_3$C(=O)(2-NH$_2$-4-F-phenyl) |
| S372 | H | H | H | sgl | —(CH$_2$)$_3$C(=O)(2-NHSO$_2$Me-4-F-phenyl) |
| S373 | H | H | H | sgl | —(CH$_2$)$_3$C(=O)(2-NHC(=O)Me-4-F-phenyl) |
| S374 | H | H | H | sgl | —(CH$_2$)$_3$C(=O)(2-NHC(=O)Me-4-F-phenyl) |
| S375 | H | H | H | sgl | —(CH$_2$)$_3$C(=O)(2-NHCO$_2$Et-4-F-phenyl) |
| S376 | H | H | H | sgl | —(CH$_2$)$_3$C(=O)(2-NHC(=O)NHEt-4-F-phenyl) |
| S377 | H | H | H | sgl | —(CH$_2$)$_3$C(=O)(2-NHCHO-4-F-phenyl) |
| S378 | H | H | H | sgl | —(CH$_2$)$_3$C(=O)(2-OH-4-F-phenyl) |
| S379 | H | H | H | sgl | —(CH$_2$)$_3$C(=O)(2-MeS-4-F-phenyl) |
| 442 | H | H | H | sgl | —(CH$_2$)$_3$C(=O)(2-NHSO$_2$Me-4-F-phenyl) |
| 485 | H | H | H | sgl | —(CH$_2$)$_2$C(Me)CO$_2$Me |
| 486 | H | H | H | sgl | —(CH$_2$)$_2$C(Me)C(OH)(4-F-phenyl)$_2$ |
| 487 | H | H | H | sgl | —(CH$_2$)$_2$C(Me)C(OH)(4-Cl-phenyl)$_2$ |
| 489 | H | H | H | sgl | —(CH$_2$)$_2$C(Me)C(=O)(4-F-phenyl) |
| 490 | H | H | H | sgl | —(CH$_2$)$_2$C(Me)C(=O)(2-MeO-4-F-phenyl) |
| 491 | H | H | H | sgl | —(CH$_2$)$_2$C(Me)C(=O)(3-Me-4-F-phenyl) |
| 492 | H | H | H | sgl | —(CH$_2$)$_2$C(Me)C(=O)(2-Me-phenyl) |
| 493 | H | H | H | sgl | —(CH$_2$)$_2$C(Me)C(=O)phenyl |
| 591 | Cl | H | H | sgl | —(CH$_2$)$_3$C(=O)(2-NH$_2$-4-F-phenyl |

TABLE 5A

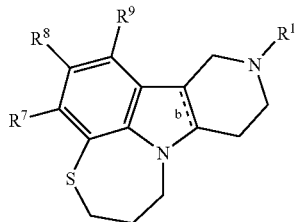

| Ex# | R7 | R8 | R9 | b | R1 |
|---|---|---|---|---|---|
| 115 | H | H | Br | dbl | —CO2—tBu |
| 116 | H | H | 2,3-diCl-phenyl | dbl | —CO2—tBu |
| 117 | H | H | 3,4-diCl-phenyl | dbl | —CO2—tBu |
| 118 | H | H | 2-Cl-4-CF3-phenyl | dbl | —CO2—tBu |
| 119 | H | H | 2,3-diCl-phenyl | dbl | H |
| 120 | H | H | 3,4-diCl-phenyl | dbl | H |
| 121 | H | H | 2-Cl-4-CF3-phenyl | dbl | |
| 122 | H | H | 2,3-diCl-phenyl | sgl | H |
| 123 | H | H | 3,4-diCl-phenyl | sgl | H |
| 124 | H | H | 2-Cl-4-CF3-phenyl | sgl | H |
| 125 | H | H | Br | sgl | —CO2—tBu |
| 126 | H | H | 2,6-diF-phenyl | sgl | —CO2—tBu |
| 127 | H | H | 2,6-diF-phenyl | sgl | H |
| 128 | H | 2,4-diCl-phenyl | H | sgl | H |
| 129 | H | phenyl | H | sgl | H |
| 130 | H | 4-F-phenyl | H | sgl | H |
| 131 | H | 4-Cl-phenyl | H | sgl | H |
| 132 | H | 2-Cl-phenyl | H | sgl | H |
| 133 | H | 2-MeO-phenyl | H | sgl | H |
| 134 | H | 2-Cl-4-CF3-phenyl | H | sgl | H |
| 135 | H | 2,4-diMe-phenyl | H | sgl | H |
| 136 | H | 2-Cl-4-MeO-phenyl | H | sgl | H |
| 137 | H | 4-iPr-phenyl | H | sgl | H |
| 138 | H | 4-Bu-phenyl | H | sgl | H |
| 139 | H | 2-Me-4-MeO-5-F-phenyl | H | sgl | H |
| 140 | H | 2-Me-4-MeO-phenyl | H | sgl | H |
| 141 | H | 2-Cl-4-CF3O-phenyl | H | sgl | H |
| 142 | H | 2,4,5-triMe-phenyl | H | sgl | H |
| 143 | H | 3-Cl-phenyl | H | sgl | H |
| 144 | H | 4-Me-phenyl | H | sgl | H |
| 145 | H | 2-Me-4-Cl-phenyl | H | sgl | H |
| 146 | H | 2,5-diCl-phenyl | H | sgl | H |
| 147 | H | 2-MeO-4-iPr-phenyl | H | sgl | H |
| 148 | H | 2,6-diCl-phenyl | H | sgl | H |
| 149 | H | 2,6-diF-phenyl | H | sgl | H |
| 150 | H | 2-CF3-4-MeO-phenyl | H | sgl | H |
| 151 | H | 2-CF3-phenyl | H | sgl | H |
| 152 | H | 4-pyridyl | H | sgl | H |
| 153 | H | 2-furanyl | H | sgl | H |
| 154 | H | 2-thiophenyl | H | sgl | H |
| 155 | H | 4-F-phenyl | H | sgl | H |
| 156 | H | 2,3-diCl-phenyl | H | sgl | H |
| 157 | H | 4-Et-phenyl | H | sgl | H |
| 158 | H | 2,4-diMeO-phenyl | H | sgl | H |
| 159 | H | 2-F-3-Cl-phenyl | H | sgl | H |
| 160 | H | 4-MeO-phenyl | H | sgl | H |
| 161 | H | 4-MeS-phenyl | H | sgl | H |
| 162 | H | 4-CN-phenyl | H | sgl | H |
| 163 | H | 3-CF3-phenyl | H | sgl | H |
| 164 | H | 2-MeO-phenyl | H | sgl | H |
| 165 | H | 2-naphthyl | H | sgl | H |
| 166 | H | 4-acetylphenyl | H | sgl | H |
| 167 | H | 3-acetamidophenyl | H | sgl | H |
| 168 | H | 2,4-diCl-phenyl | H | sgl | Me |
| S316 | H | 2,3-diMe-phenyl | H | sgl | H |
| S317 | H | 2-Me-5-F-phenyl | H | sgl | H |
| S318 | H | 2-F-5-Me-phenyl | H | sgl | H |
| S319 | H | 2-MeO-5-F-phenyl | H | sgl | H |
| S320 | H | 2-Me-3-Cl-phenyl | H | sgl | H |
| S321 | H | 3-NO2-phenyl | H | sgl | H |
| S322 | H | 2-NO2-phenyl | H | sgl | H |
| S323 | H | 2-Cl-3-Me-phenyl | H | sgl | H |
| S324 | H | 2-MeO-phenyl | H | sgl | H |
| S325 | H | 2,3-diCl-phenyl | H | sgl | H |
| S326 | H | 2-Cl-4-CF3-phenyl | H | sgl | H |

TABLE 5A-continued

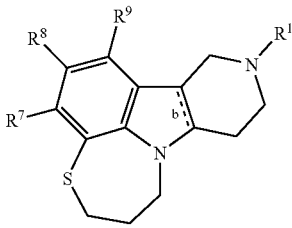

| Ex# | R7 | R8 | R9 | b | R1 |
|---|---|---|---|---|---|
| S327 | H | 2-Me-4-EtO-phenyl | H | sgl | H |
| S328 | H | 2-Me-4-F-phenyl | H | sgl | H |
| S329 | H | 4-Bu-phenyl | H | sgl | H |
| S330 | H | 2-$CF_3$-phenyl | H | sgl | H |
| S331 | H | 2-Cl-6-F-phenyl | H | sgl | H |
| S332 | H | 2-Cl-4-($CHF_2$)O-phenyl | H | sgl | H |
| S333 | H | 4-$CF_3$-phenyl | H | sgl | H |
| S334 | H | 4-Me-phenyl | H | sgl | H |
| S335 | H | 4-$CF_3$O-phenyl | H | sgl | H |
| S336 | H | 2,4-diMeO-6-F-phenyl | H | sgl | H |
| S337 | H | 2-Me-phenyl | H | sgl | H |
| S338 | H | 2-$CF_3$-6-F-phenyl | H | sgl | H |
| S339 | H | 2-MeS-phenyl | H | sgl | H |
| S340 | H | 2,4,6-triF-phenyl | H | sgl | H |
| S341 | H | 2,4,6-triCl-phenyl | H | sgl | H |
| S342 | H | 2,6-diCl-4-MeO-phenyl | H | sgl | H |
| S343 | H | 2,3,4-triF-phenyl | H | sgl | H |
| S344 | H | 2,6-diF-4-Cl-phenyl | H | sgl | H |
| S345 | H | 2,3,4,6-tetraF-phenyl | H | sgl | H |
| S346 | H | 2,3,4,5,6-pentaF-phenyl | H | sgl | H |
| S347 | H | 2,6-di$CF_3$-phenyl | H | sgl | H |
| S348 | H | 2-$CF_3$O-phenyl | H | sgl | H |
| S349 | H | 2-$CF_3$-4-EtO-phenyl | H | sgl | H |
| S350 | H | 2-$CF_3$-4-iPrO-phenyl | H | sgl | H |
| S351 | H | 2-naphtyl | H | sgl | H |
| S352 | H | 2-$CF_3$-4-Cl-phenyl | H | sgl | H |
| S353 | H | 2-$CF_3$-4-F-phenyl | H | sgl | H |
| S354 | H | 2,4-diF-phenyl | H | sgl | Me |
| S380 | H | 2-Cl-4-EtO-phenyl | H | sgl | H |
| S381 | H | 2-Cl-4-iPrO-phenyl | H | sgl | H |
| S382 | H | 2-Et-4-MeO-phenyl | H | sgl | H |
| S383 | H | 2-CHO-4-MeO-phenyl | H | sgl | H |
| S384 | H | 2-CH(OH)Me-4-MeO-phenyl | H | sgl | H |
| S385 | H | 2-CH(OMe)Me-4-MeO-phenyl | H | sgl | H |
| S386 | H | 2-C(=O)Me-4-MeO-phenyl | H | sgl | H |
| S387 | H | 2-$CH_2$(OH)-4-MeO-phenyl | H | sgl | H |
| S388 | H | 2-$CH_2$(OMe)-4-MeO-phenyl | H | sgl | H |
| S389 | H | 2-CH(OH)Et-4-MeO-phenyl | H | sgl | H |
| S390 | H | 2-C(=O)Et-4-MeO-phenyl | H | sgl | H |
| S391 | H | (Z)-2-CH=CH$CO_2$Me-4-MeO-phenyl | H | sgl | H |
| S392 | H | 2-$CH_2CH_2CO_2$Me-4-MeO-phenyl | H | sgl | H |
| S393 | H | (Z)-2-CH=CH$CH_2$(OH)-4-MeO-phenyl | H | sgl | H |
| S394 | H | (E)-2-CH=CH$CO_2$Me-4-MeO-phenyl | H | sgl | H |
| S395 | H | (E)-2-CH=CH$CH_2$(OH)-4-MeO-phenyl | H | sgl | H |
| S396 | H | 2-$CH_2CH_2$OMe-4-MeO-phenyl | H | sgl | H |
| S397 | H | 2-F-4-MeO-phenyl | H | sgl | H |
| S403 | H | 2-Cl-4-F-phenyl | H | sgl | H |
| S405 | H | (2-Cl-phenyl)-CH=CH— | H | sgl | H |
| S406 | H | (3-Cl-phenyl)-CH=CH— | H | sgl | H |
| S407 | H | (2,6-diF-phenyl)-CH=CH— | H | sgl | H |
| S410 | H | cyclohexyl | H | sgl | H |
| S411 | H | cyclopentyl | H | sgl | H |
| S412 | H | cyclohexylmethyl | H | sgl | H |
| S413 | H | —$CH_2CH_2CO_2$Et | H | sgl | H |
| S414 | H | —$(CH_2)_3CO_2$Et | H | sgl | H |
| S415 | H | —$(CH_2)_4CO_2$Et | H | sgl | H |
| S416 | H | —$CH_2$CH=$CH_2$ | H | sgl | H |
| S417 | H | Pr | H | sgl | H |
| S418 | H | benzyl | H | sgl | H |
| S419 | H | 2-F-benzyl | H | sgl | H |

TABLE 5A-continued

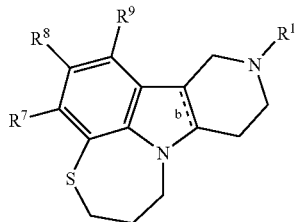

| Ex# | R7 | R8 | R9 | b | R1 |
|---|---|---|---|---|---|
| S420 | H | 3-F-benzyl | H | sgl | H |
| S421 | H | 4-F-benzyl | H | sgl | H |
| S422 | H | 3-MeO-benzyl | H | sgl | H |
| S423 | H | 3-OH-benzyl | H | sgl | H |
| S424 | H | 2-MeO-benzyl | H | sgl | H |
| S425 | H | 2-OH-benzyl | H | sgl | H |
| S426 | H | 2-CO$_2$Me-3-MeO-phenyl | H | sgl | H |
| S427 | H | 2,6-diF-phenyl | H | sgl | H |
| S428 | H | phenyl-CH=CH— | H | sgl | H |
| S429 | H | (2-Me-4-MeO-phenyl)-CH=CH— | H | sgl | H |
| S430 | H | —NMe$_2$ | H | sgl | H |
| S431 | H | 1-pyrrolidinyl | H | sgl | H |
| S432 | H | —NTs$_2$ | H | sgl | H |
| S433 | H | MeO | H | sgl | H |
| 445 | H | 2-Me-4-MeO-phenyl | Me | sgl | H |
| 446 | H | 2-CF$_3$-4-MeO-phenyl | Me | sgl | H |
| 458 | Me | 2-CF$_3$-4-MeO-phenyl | H | sgl | H |
| 459 | Me | 2,4-diCl-phenyl | H | sgl | H |
| 460 | H | 3-CN-phenyl | H | sgl | H |
| 461 | H | 2-Me-4-CN-phenyl | H | sgl | H |
| 462 | H | 2-Me-3-CN-phenyl | H | sgl | H |
| 463 | H | 2-CN-phenyl | H | sgl | H |
| 464 | H | 2-CF$_3$-4-CN-phenyl | Me | sgl | H |
| 465 | H | 3-CHO-phenyl | Me | sgl | H |
| 466 | H | 3-CH$_2$(OH)-phenyl | Me | sgl | H |
| 467 | H | 3-CH$_2$(OMe)-phenyl | Me | sgl | H |
| 468 | H | 3-CH$_2$(NMe$_2$)-phenyl | Me | sgl | H |
| 469 | H | 3-CN-4-F-phenyl | Me | sgl | H |
| 470 | H | 3-CONH$_2$-4-F-phenyl | Me | sgl | H |
| 580 | NH$_2$ | H | H | sgl | H |
| 581 | H | phenyl-NH- | H | sgl | H |
| 582 | phenyl-NH— | H | H | sgl | H |
| 583 | H | (4-F-phenyl)-NH— | H | sgl | H |
| 584 | H | (2,4-diCl-phenyl)-NH— | H | sgl | H |
| 585 | H | phenyl-C(=O)NH— | H | sgl | H |
| 586 | H | benzyl-NH— | H | sgl | H |
| 587 | H | phenyl-S— | H | sgl | H |
| 588 | MeO | H | H | sgl | H |
| 589 | H | 2-CH$_2$(NH$_2$)-4-MeO-phenyl- | H | sgl | H |
| 590 | H | 2-Me-4-MeO-phenyl- | H | sgl | H |
| 592 | H | (2-Me-4-MeO-phenyl)-NH— | H | sgl | H |
| 593 | H | (2-F-4-MeO-phenyl)-NH— | H | sgl | H |
| 595 | H | (2-Me-4-F-phenyl)-NH— | H | sgl | H |

TABLE 6

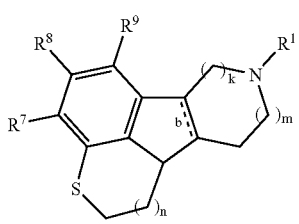

| Ex# | n | k | m | R7 | R8 | R9 | b | R1 |
|---|---|---|---|---|---|---|---|---|
| 471 | 2 | 2 | 1 | H | H | H | sgl | H |
| 472 | 2 | 2 | 1 | H | H | H | sgl | —(CH$_2$)$_3$C(=O)(4-F-phenyl) |

TABLE 6-continued

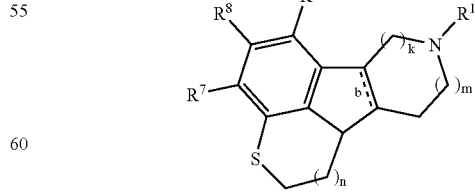

| Ex# | n | k | m | R7 | R8 | R9 | b | R1 |
|---|---|---|---|---|---|---|---|---|
| 473 | 2 | 2 | 1 | H | H | H | sgl | —(CH$_2$)$_3$O(4-F-phenyl) |
| 474 | 2 | 2 | 1 | H | H | H | sgl | —(CH$_2$)$_3$(6-F-benzisoxazol-3-yl) |

TABLE 6-continued

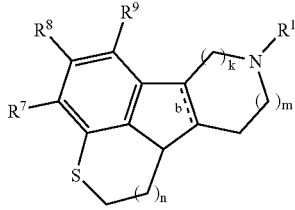

| Ex# | n | k | m | R7 | R8 | R9 | b | R1 |
|---|---|---|---|---|---|---|---|---|
| 475 | 2 | 2 | 1 | H | H | H | sgl | —$(CH_2)_3C(=O)$(4-pyridyl) |
| 476 | 2 | 3 | 0 | H | H | H | sgl | H |
| 477 | 2 | 3 | 0 | H | H | H | sgl | —$(CH_2)_3C(=O)$(4-F-phenyl) |
| 478 | 2 | 3 | 0 | H | H | H | sgl | —$(CH_2)_2$(6-F-benzisoxazol-3-yl) |
| 483 | 2 | 2 | 1 | H | Br | H | sgl | —$(CH_2)_3C(=O)$(4-F-phenyl) |
| 484 | 2 | 2 | 1 | H | Br | H | sgl | —$(CH_2)_2O$(4-F-phenyl) |
| 488 | 1 | 2 | 1 | H | Br | H | sgl | —$CO_2$-tBu |

TABLE 6A

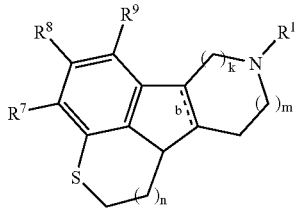

| Ex# | n | k | m | R7 | R8 | R9 | b | R1 |
|---|---|---|---|---|---|---|---|---|
| 479 | 2 | 2 | 1 | H | 2,4-diCl-phenyl | H | sgl | H |
| 480 | 2 | 2 | 1 | H | 2-Cl-4-MeO-phenyl | H | sgl | H |
| 481 | 2 | 2 | 1 | H | 2-Me-4-MeO-phenyl | H | sgl | H |
| 482 | 2 | 2 | 1 | H | Br | H | sgl | H |
| 497 | 1 | 1 | 1 | H | 2-Cl-phenyl | H | sgl | H |
| 498 | 1 | 1 | 1 | H | 3-Cl-phenyl | H | sgl | H |
| 499 | 1 | 1 | 1 | H | 3-F-phenyl | H | sgl | H |
| 500 | 1 | 1 | 1 | H | 4-Cl-phenyl | H | sgl | H |
| 501 | 1 | 1 | 1 | H | 4-F-phenyl | H | sgl | H |
| 502 | 1 | 1 | 1 | H | 2,3-diCl-phenyl | H | sgl | H |
| 503 | 1 | 1 | 1 | H | 2,3-diF-phenyl | H | sgl | H |
| 504 | 1 | 1 | 1 | H | 3,5-diCl-phenyl | H | sgl | H |
| 505 | 1 | 1 | 1 | H | 3,5-diF-phenyl | H | sgl | H |
| 506 | 1 | 1 | 1 | H | 3,4-diCl-phenyl | H | sgl | H |
| 507 | 1 | 1 | 1 | H | 3,4-diF-phenyl | H | sgl | H |
| 508 | 1 | 1 | 1 | H | 3-Cl-4-F-phenyl | H | sgl | H |
| 509 | 1 | 1 | 1 | H | 2-F-4-Cl-phenyl | H | sgl | H |

TABLE 7

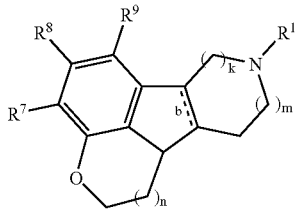

| Ex# | n | k | m | R7 | R8 | R9 | b | R1 |
|---|---|---|---|---|---|---|---|---|
| 172 | 2 | 1 | 1 | H | H | H | sgl | H |
| 173 | 1 | 1 | 1 | H | 2,4-diCl-phenyl | H | sgl | H |
| 174 | 1 | 1 | 1 | H | 2-Cl-4-MeO-phenyl | H | sgl | H |
| 436 | 1 | 1 | 1 | H | 2-Cl-phenyl | H | sgl | H |
| 497 | 1 | 1 | 1 | H | 2-Cl-phenyl | H | sgl | H |

TABLE 7-continued

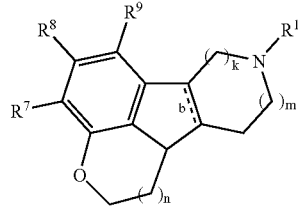

| Ex# | n | k | m | R7 | R8 | R9 | b | R1 |
|---|---|---|---|---|---|---|---|---|
| 498 | 1 | 1 | 1 | H | 3-Cl-phenyl | H | sgl | H |
| 499 | 1 | 1 | 1 | H | 3-F-phenyl | H | sgl | H |
| 500 | 1 | 1 | 1 | H | 4-Cl-phenyl | H | sgl | H |
| 501 | 1 | 1 | 1 | H | 4-F-phenyl | H | sgl | H |
| 502 | 1 | 1 | 1 | H | 2,3-diCl-phenyl | H | sgl | H |
| 503 | 1 | 1 | 1 | H | 2,3-diF-phenyl | H | sgl | H |
| 504 | 1 | 1 | 1 | H | 3,5-diCl-phenyl | H | sgl | H |
| 505 | 1 | 1 | 1 | H | 3,5-diF-phenyl | H | sgl | H |
| 506 | 1 | 1 | 1 | H | 3,4-diCl-phenyl | H | sgl | H |
| 507 | 1 | 1 | 1 | H | 3,4-diF-phenyl | H | sgl | H |
| 508 | 1 | 1 | 1 | H | 3-Cl-4-F-phenyl | H | sgl | H |
| 509 | 1 | 1 | 1 | H | 2-F-4-Cl-phenyl | H | sgl | H |
| 510 | 1 | 1 | 1 | H | 2-Cl-4-F-phenyl | H | sgl | H |
| 511 | 1 | 1 | 1 | H | 2,5-diCl-phenyl | H | sgl | H |
| 512 | 1 | 1 | 1 | H | 2,6-diCl-phenyl | H | sgl | H |
| 513 | 1 | 1 | 1 | H | 2-$CF_3$-phenyl | H | sgl | H |
| 514 | 1 | 1 | 1 | H | 4-$CF_3$-phenyl | H | sgl | H |
| 515 | 1 | 1 | 1 | H | 2,4-di$CF_3$-phenyl | H | sgl | H |
| 516 | 1 | 1 | 1 | H | 2-Cl-4-$CF_3$-phenyl | H | sgl | H |
| 517 | 1 | 1 | 1 | H | 2-MeO-phenyl | H | sgl | H |
| 518 | 1 | 1 | 1 | H | 2,4-diMeO-phenyl | H | sgl | H |
| 519 | 1 | 1 | 1 | H | 2-MeO-5-iPr-phenyl | H | sgl | H |
| 520 | 1 | 1 | 1 | H | 3-$NO_2$-phenyl | H | sgl | H |
| 521 | 1 | 1 | 1 | H | 2-CHO-phenyl | H | sgl | H |
| 522 | 1 | 1 | 1 | H | 2-CH(Me)(OH)-phenyl | H | sgl | H |
| 523 | 1 | 1 | 1 | H | 2-$CH_2$(OH)-phenyl | H | sgl | H |
| 524 | 1 | 1 | 1 | H | 2-CHO-4-MeO-phenyl | H | sgl | H |
| 525 | 1 | 1 | 1 | H | 2-OH-phenyl | H | sgl | H |
| 526 | 1 | 1 | 1 | H | 2-$CF_3$-4-EtO-phenyl | H | sgl | H |
| 527 | 1 | 1 | 1 | H | 2-$CF_3$-4-iPrO-phenyl | H | sgl | H |
| 532 | 1 | 1 | 1 | H | 2-Me-4-MeO-phenyl | H | sgl | H |
| 533 | 1 | 1 | 1 | H | 2-$CF_3$-4-MeO-phenyl | H | sgl | H |
| 534 | 1 | 2 | 1 | H | 3,4,5-triMeO-phenyl | H | sgl | H |
| 535 | 1 | 2 | 1 | H | 1-naphthyl | H | sgl | H |
| 536 | 1 | 2 | 1 | H | 3-MeO-phenyl | H | sgl | H |
| 537 | 1 | 2 | 1 | H | 2,4-diCl-phenyl | H | sgl | H |
| 538 | 1 | 1 | 2 | H | H | H | sgl | H |
| 541 | 2 | 1 | 1 | H | H | H | dbl | H |
| 542 | 2 | 1 | 1 | H | H | H | sgl | H |
| 543 | 2 | 1 | 1 | H | 2,6-diF-phenyl | H | sgl | H |
| 545 | 1 | 2 | 1 | H | H | H | sgl | H |
| 547 | 2 | 1 | 1 | H | 2-$CF_3$-4-MeO-phenyl | H | sgl | H |
| 548 | 2 | 1 | 1 | H | 2-Me-4-MeO-phenyl | H | sgl | H |
| 549 | 2 | 1 | 1 | H | 2-Cl-4-$CF_3$-phenyl | H | sgl | H |
| 550 | 2 | 1 | 1 | H | 2,3-diCl-phenyl | H | sgl | H |
| 551 | 2 | 1 | 1 | H | 2,4-diMeO-phenyl | H | sgl | H |
| 552 | 2 | 1 | 1 | H | 3,4-diMeO-phenyl | H | sgl | H |
| 553 | 2 | 1 | 1 | H | 2,4-diCl-phenyl | H | sgl | H |
| 554 | 2 | 1 | 1 | H | 3,4-diCl-phenyl | H | sgl | H |
| 555 | 2 | 1 | 1 | H | 2,5-diCl-phenyl | H | sgl | H |
| 556 | 2 | 1 | 1 | H | 2-$CF_3$-phenyl | H | sgl | H |
| 557 | 2 | 1 | 1 | H | 2-Me-phenyl | H | sgl | H |
| 558 | 2 | 1 | 1 | H | 2-Cl-phenyl | H | sgl | H |
| 559 | 2 | 1 | 1 | H | 3-F-phenyl | H | sgl | H |
| 560 | 2 | 1 | 1 | H | phenyl | H | sgl | H |
| 561 | 2 | 1 | 1 | H | 2-$CF_3$-4-EtO-phenyl | H | sgl | H |
| 562 | 2 | 1 | 1 | H | 2-$CF_3$-4-iPrO-phenyl | H | sgl | H |
| 563 | 2 | 1 | 1 | H | 2-MeO-4-iPr-phenyl | H | sgl | H |
| 564 | 2 | 1 | 1 | H | 2-F-4-Cl-phenyl | H | sgl | H |
| 565 | 2 | 1 | 1 | H | 2-Cl-4-MeO-phenyl | H | sgl | H |
| 566 | 2 | 1 | 1 | H | 2-CHO-phenyl | H | sgl | H |
| 567 | 2 | 1 | 1 | H | 2-CHO-4-MeO-phenyl | H | sgl | H |
| 568 | 2 | 1 | 1 | H | 2-$CH_2$(OH)-4-MeO-phenyl | H | sgl | H |
| 569 | 2 | 1 | 1 | H | 2-$CH_2$(OH)-phenyl | H | sgl | H |
| 570 | 2 | 1 | 1 | H | 2-$CF_3$-4-NHMe-phenyl | H | sgl | H |

TABLE 7-continued

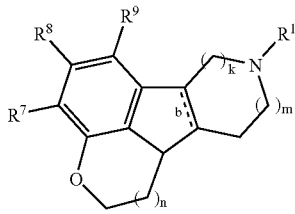

| Ex# | n | k | m | R7 | R8 | R9 | b | R1 |
|---|---|---|---|---|---|---|---|---|
| 571 | 2 | 1 | 1 | H | 2-CF$_3$-4-NH$_2$-phenyl | H | sgl | H |
| 572 | 2 | 1 | 1 | H | 2-C(=O)Me-phenyl | H | sgl | H |
| 573 | 2 | 1 | 1 | H | 2-C(=O)Me-4-MeO-phenyl | H | sgl | H |
| 574 | 2 | 1 | 1 | H | 2-CH(Me)(OH)-phenyl | H | sgl | H |
| 575 | 2 | 1 | 1 | H | 2-CH(Me)(OH)-4-MeO-phenyl | H | sgl | H |
| 576 | 2 | 1 | 1 | H | 2-CF$_3$-4-OH-phenyl | H | sgl | H |
| 577 | 2 | 1 | 1 | H | 2-CF$_3$-4-O(C=O)Me-phenyl | H | sgl | H |

TABLE 7A

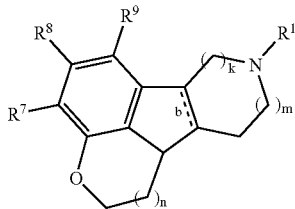

| Ex# | n | k | m | R7 | R8 | R9 | b | R1 |
|---|---|---|---|---|---|---|---|---|
| 182 | 1 | 1 | 1 | H | H | H | sgl | —(CH$_2$)$_3$C(=O)(4-F-phenyl) |
| 266 | 1 | 1 | 1 | H | H | Me | sgl | —(CH$_2$)$_3$C(=O)(4-F-phenyl) |
| 270 | 1 | 1 | 1 | H | H | H | sgl | —(CH$_2$)$_3$O(4-F-phenyl) |
| 272 | 1 | 1 | 1 | H | H | H | sgl | H |
| 494 | 1 | 1 | 1 | H | H | H | sgl | —(CH$_2$)$_3$C(=O)(2-NH$_2$-phenyl) |
| 495 | 1 | 1 | 1 | H | H | H | sgl | —(CH$_2$)$_3$C(=O)(2-NH$_2$-phenyl) |
| 496 | 1 | 1 | 1 | H | H | H | sgl | —(CH$_2$)$_3$(1H-indazol-3-yl) |
| 528 | 1 | 1 | 1 | H | H | H | sgl | —(CH$_2$)$_3$(6-F-1H-indazol-3-yl) |
| 529 | 1 | 1 | 1 | H | H | H | sgl | —(CH$_2$)$_3$C(=O)(2-NH$_2$-4-F-phenyl) |
| 530 | 1 | 1 | 1 | H | H | H | sgl | —(CH$_2$)$_3$C(=O)(2-NH$_2$-4-F-phenyl) |
| 531 | 1 | 1 | 1 | H | H | H | sgl | —(CH$_2$)$_3$C(=O)(2-OH-4-F-phenyl) |
| 539 | 1 | 2 | 1 | H | H | H | sgl | —(CH$_2$)$_3$O(4-F-phenyl) |
| 540 | 1 | 2 | 1 | H | H | H | sgl | —(CH$_2$)$_3$(6-F-1,2-benzisoxazol-3-yl) |
| 544 | 2 | 1 | 1 | H | H | H | sgl | —(CH$_2$)$_3$C(=O)(4-F-phenyl) |
| 546 | 1 | 2 | 1 | H | H | H | sgl | —(CH$_2$)$_3$C(=O)(4-F-phenyl) |

TABLE 8

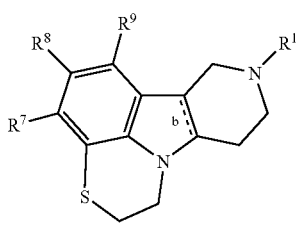

| Ex # | R7 | R8 | R9 | b | R1 |
|---|---|---|---|---|---|
| 183 | H | H | CF$_3$ | cbl | —(CH$_2$)$_3$CH(OH)(4-F-phenyl) |
| 184 | H | H | CF$_3$ | dbl | —(CH$_2$)$_3$C(OCH$_2$CH$_2$O)(4-F-phenyl) |
| 185 | H | H | CF$_3$ | sgl | —(CH$_2$)$_4$(4-F-phenyl) |

TABLE 8-continued

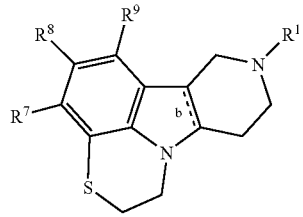

| Ex # | R7 | R8 | R9 | b | R1 |
|---|---|---|---|---|---|
| 188 | H | H | H | sgl | —(CH$_2$)$_3$C(=O)(4-F-phenyl) |
| 195 | H | H | CF$_3$ | dbl | —(CH$_2$)$_3$C(=O)(4-F-phenyl) |
| 213 | H | CH$_3$ | H | sgl | —(CH$_2$)$_3$C(=O)(4-F-phenyl) |
| 438 | H | H | H | sgl | —(CH$_2$)$_3$C(=O)(2-NH$_2$-phenyl) |
| 439 | H | H | H | sgl | —(CH$_2$)$_3$C(=O)(2-NH$_2$-phenyl) |
| 440 | H | H | H | sgl | —(CH$_2$)$_3$C(=O)(2-NH$_2$-4-F-phenyl) |
| 441 | H | H | H | sgl | —(CH$_2$)$_3$C(=O)(2-NH$_2$-4-F-phenyl) |
| 456 | H | H | H | sgl | —(CH$_2$)$_3$C(=O)(4-F-phenyl) |
| 457 | H | H | H | sgl | —(CH$_2$)$_3$C(=O)(4-F-phenyl) |

TABLE 8A

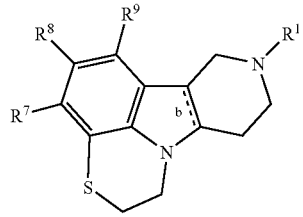

| Ex # | R7 | R8 | R9 | b | R1 |
|---|---|---|---|---|---|
| 443 | 2,3-diCl-phenyl | H | H | sgl | H |
| 444 | 2,3-diF-phenyl | H | H | sgl | H |
| 447 | 2,6-diCl-phenyl | H | H | sgl | H |
| 452 | 2-Me-4-MeO-phenyl | H | H | sgl | H |
| 453 | 2-Cl-6-F-phenyl | H | H | sgl | H |
| 454 | 2,6-diF-phenyl | H | H | sgl | H |
| 455 | 2,4-diCl-phenyl | H | H | sgl | H |

TABLE 9

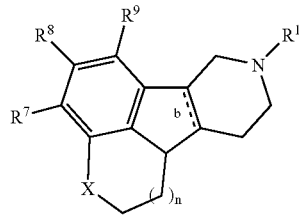

| Ex # | X | n | R7 | R8 | R9 | b | R1 |
|---|---|---|---|---|---|---|---|
| S398 | SO$_2$ | 2 | H | 2,4-diCl-phenyl | H | sgl | H |
| S399 | SO$_2$ | 2 | H | 2,6-diF-phenyl | H | sgl | H |
| S400 | SO$_2$ | 2 | H | 2-Cl-phenyl | H | sgl | H |
| S401 | SO$_2$ | 2 | H | 2-F-4-MeO-phenyl | H | sgl | H |
| S402 | SO$_2$ | 2 | H | 2-Me-4-MeO-phenyl | H | sgl | H |
| S404 | SO | 2 | H | 2-Cl-4-F-phenyl | H | sgl | H |
| S434 | SO | 2 | H | 2,4-diCl-phenyl | H | sgl | H |
| S435 | SO | 2 | H | 2-Me-4-MeO-phenyl | H | sgl | H |
| 448 | SO$_2$ | 1 | H | H | H | sgl | H |
| 449 | SO | 1 | H | H | H | sgl | H |
| 450 | SO$_2$ | 1 | H | 2-CF$_3$-4-MeO-phenyl | H | sgl | H |
| 451 | SO$_2$ | 1 | H | 2,4-diCl-phenyl | H | sgl | H |

What is claimed is:

1. A method for treating a human suffering from sleep disorders associated with 5HT2A receptor modulation, comprising administering to a patient in need thereof a therapeutically effective amount of a compound of formula (I):

(I)

or stereoisomers or pharmaceutically acceptable salt forms thereof, wherein:

b is a single bond;
X is —CHR$^{10}$— or —C(=O)—;
R$^1$ is selected from
  H,
  C(=O)R$^2$,
  C(=O)OR$^2$,
  C$_{1-8}$ alkyl,
  C$_{2-8}$ alkenyl,
  C$_{2-8}$ alkynyl,
  C$_{3-7}$ cycloalkyl,
  C$_{1-6}$ alkyl substituted with Z,
  C$_{2-6}$ alkenyl substituted with Z,
  C$_{2-6}$ alkynyl substituted with Z,
  C$_{3-6}$ cycloalkyl substituted with Z,
  aryl substituted with Z,
  5–6 membered heterocyclic ring system containing at least one heteroatom selected from the group consisting of N, O, and S, said heterocyclic ring system substituted with Z;
  C$_{1-3}$ alkyl substituted with Y,
  C$_{2-3}$ alkenyl substituted with Y,
  C$_{2-3}$ alkynyl substituted with Y,
  C$_{1-6}$ alkyl substituted with 0–2 R$^2$,
  C$_{2-6}$ alkenyl substituted with 0–2 R$^2$,
  C$_{2-6}$ alkynyl substituted with 0–2 R$^2$,
  aryl substituted with 0–2 R$^2$, and
  5–6 membered heterocyclic ring system containing at least one heteroatom selected from the group consisting of N, O, and S, said heterocyclic ring system substituted with 0–2 R$^2$;

Y is selected from
  C$_{3-6}$ cycloalkyl substituted with Z,
  aryl substituted with Z,
  5–6 membered heterocyclic ring system containing at least one heteroatom selected from the group consisting of N, O, and S, said heterocyclic ring system substituted with Z;
  C$_{3-6}$ cycloalkyl substituted with —(C$_{1-3}$ alkyl)-Z,
  aryl substituted with —(C$_{1-3}$ alkyl)-Z, and
  5–6 membered heterocyclic ring system containing at least one heteroatom selected from the group consisting of N, O, and S, said heterocyclic ring system substituted with —(C$_{1-3}$ alkyl)-Z;

Z is selected from H,
  —CH(OH)R$^2$,
  —C(ethylenedioxy)R$^2$,
  —OR$^2$,
  —SR$^2$,
  —NR$^2$R$^3$,
  —C(O)R$^2$,
  —C(O)NR$^2$R$^3$,
  —NR$^3$C(O)R$^2$,
  —C(O)OR$^2$,
  —OC(O)R$^2$,
  —CH(=NR$^4$)NR$^2$R$^3$,
  —NHC(=NR$^4$)NR$^2$R$^3$,
  —S(O)R$^2$,
  —S(O)$_2$R$^2$,
  —S(O)$_2$NR$^2$R$^3$, and —NR$^3$S(O)$_2$R$^2$;

R$^2$, at each occurrence, is independently selected from
  halo,
  C$_{1-3}$ haloalkyl,
  C$_{1-4}$ alkyl,
  C$_{2-4}$ alkenyl,
  C$_{2-4}$ alkynyl,
  C$_{3-6}$ cycloalkyl,
  aryl substituted with 0–5 R$^{42}$;
  C$_{3-10}$ carbocyclic group substituted with 0–3 R$^{41}$, and
  5–10 membered heterocyclic ring system containing from 1–4 heteroatoms selected from the group consisting of N, O, and S substituted with 0–3 R$^{41}$;

R$^3$, at each occurrence, is independently selected from
  H, C$_{1-4}$ alkyl, C$_{2-4}$ alkenyl, C$_{2-4}$ alkynyl, and
  C$_{1-4}$ alkoxy;

alternatively, R$^2$ and R$^3$ join to form a 5- or 6-membered ring optionally substituted with —O— or —N(R$^4$)—;

R$^4$, at each occurrence, is independently selected from H and C$_{1-4}$ alkyl;

R$^5$ is H or C$_{1-4}$ alkyl;

R$^{6a}$ and R$^{6b}$, at each occurrence, are independently selected from
  H, —OH, —NR$^{46}$R$^{47}$, —CF$_3$, C$_{1-4}$ alkyl, C$_{2-4}$ alkenyl, C$_{2-4}$ alkynyl, C$_{1-4}$ alkoxy, C$_{1-4}$ haloalkyl, C$_{3-6}$ cycloalkyl, and
  aryl substituted with 0–3 R$^{44}$;

R$^7$ and R$^9$, at each occurrence, are independently selected from
  H, halo, —CF$_3$, —OCF$_3$, —OH, —CN, —NO$_2$, —NR$^{46}$R$^{47}$,
  C$_{1-8}$ alkyl, C$_{2-8}$ alkenyl, C$_{2-8}$ alkynyl, C$_{1-4}$ haloalkyl, C$_{1-8}$ alkoxy, (C$_{1-4}$ haloalkyl)oxy,
  C$_{3-0}$ cycloalkyl substituted with 0–2 R$^{33}$,
  C$_{1-4}$ alkyl substituted with 0–2 R$^{11}$,
  C$_{3-10}$ carbocyclic group substituted with 0–3 R$^{33}$,
  aryl substituted with 0–5 R$^{33}$,
  5–10 membered heterocyclic ring system containing from 1–4 heteroatoms selected from the group consisting of N, O, and S substituted with 0–3 R$^{31}$;
  OR$^{12}$, SR$^{12}$, NR$^{12}$R$^{13}$, C(O)H, C(O)R$^{12}$, C(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(O)OR$^{15}$, NR$^{12}$S(O)$_2$R$^{15}$, and NR$^{12}$C(O)NHR$^{15}$;

R$^8$ is selected from
  H, halo, —CF$_3$, —OCF$_3$, —OH, —CN, —NO$_2$,
  C$_{1-8}$ alkyl, C$_{2-8}$ alkenyl, C$_{2-8}$ alkynyl, C$_{1-14}$ haloalkyl, C$_{1-8}$ alkoxy, (C$_{1-4}$ haloalkyl)oxy,
  C$_{3-10}$ cycloalkyl substituted with 0–2 R$^{33}$,
  C$_{1-4}$ alkyl substituted with 0–2 R$^{11}$,
  C$_{2-4}$ alkenyl substituted with 0–2 R$^{11}$,
  C$_{2-4}$ alkynyl substituted with 0–1 R$^{11}$, $C_{3-10}$ carbocyclic group substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, $C(O)H$, $C(O)R^{12}$, $C(O)NR^{12}R^{13}$, $NR^{14}C(O)R^{12}$, $C(O)OR^{12}$, $OC(O)R^{12}$, $OC(O)OR^{12}$, $CH(=NR^{14})NR^{12}R^{13}$, $NHC(=NR^{14})NR^{12}R^{13}$, $S(O)R^{12}$, $S(O)_2R^{12}$, $S(O)NR^{12}R^{13}$, $S(O)_2NR^{12}R^{13}$, $NR^{14}S(O)R^{12}$, $NR^{14}S(O)_2R^{12}$, $NR^{12}C(O)R^{15}$, $NR^{12}C(O)OR^{15}$, $NR^{12}S(O)_2R^{15}$, and $NR^{12}C(O)NHR^{15}$;

$R^{10}$ is selected from H, —OH,
$C_{1-6}$ alkyl substituted with 0–1 $R^{10B}$,
$C_{2-6}$ alkenyl substituted with 0–1 $R^{10B}$,
$C_{2-6}$ alkynyl substituted with 0–1 $R^{10B}$, and
$C_{1-6}$ alkoxy;

$R^{10B}$ is selected from
$C_{1-4}$ alkoxy,
$C_{3-6}$ cycloalkyl,
$C_{3-10}$ carbocyclic group substituted with 0–3 $R^{33}$,
phenyl substituted with 0–3 $R^{33}$, and
5–6 membered heterocyclic ring system containing 1, 2, or 3 heteroatoms selected from the group consisting of N, O, and S substituted with 0–2 $R^{44}$;

$R^{11}$ is selected from
H, halo, —$CF_3$, —CN, —$NO_2$,
$C_{3-10}$ carbocyclic group substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, $C(O)H$, $C(O)R^{12}$, $C(O)NR^{12}R^{13}$, $NR^{14}C(O)R^{12}$, $C(O)OR^{12}$, $OC(O)R^{12}$, $OC(O)OR^{12}$, $CH(NR^{14})NR^{12}R^{13}$, $NHC(=NR^{14})NR^{12}R^{13}$, $S(O)R^{12}$, $S(O)_2R^{12}$, $S(O)NR^{12}R^{13}$, $S(O)_2NR^{12}R^{13}$, $NR^{14}S(O)R^{12}$, $NR^{14}S(O)_2R^{12}$, $NR^{12}C(O)R^{15}$, $NR^{12}C(O)OR^{15}$, $NR^{12}S(O)_2R^{15}$, and $NR^{12}C(O)NHR^{15}$;

$R^{12}$, at each occurrence, is independently selected from
$C_{1-4}$ alkyl substituted with 0–1 $R^{12a}$,
$C_{2-4}$ alkenyl substituted with 0–1 $R^{12a}$,
$C_{2-4}$ alkynyl substituted with 0–1 $R^{12a}$,
$C_{3-6}$ cycloalkyl substituted with 0–3 $R^{33}$,
phenyl substituted with 0–5 $R^{33}$;
$C_{3-10}$ carbocyclic group substituted with 0–3 $R^{33}$, and
5–10 membered heterocyclic ring system containing from 1–4 heteroatoms selected from the group consisting of N, O, and S substituted with 0–3 $R^{31}$;

$R^{12a}$, at each occurrence, is independently selected from
phenyl substituted with 0–5 $R^{33}$;
$C_{3-10}$ carbocyclic group substituted with 0–3 $R^{33}$, and
5–10 membered heterocyclic ring system containing from 1–4 heteroatoms selected from the group consisting of N, O, and S substituted with 0–3 $R^{31}$;

$R^{13}$, at each occurrence, is independently selected from H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —$N(R^{14})$—;

alternatively, $R^{12}$ and $R^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;

$R^{14}$, at each occurrence, is independently selected from H and $C_{1-4}$ alkyl;

$R^{15}$, at each occurrence, is independently selected from H, $C_{1-4}$ alkyl, $C_{2-4}$ alkenyl, and $C_{2-4}$ alkynyl;

$R^{16}$, at each occurrence, is independently selected from H, OH, halo, CN, $NO_2$, $CF_3$, $SO_2R^{45}$, $NR^{46}R^{47}$,
—C(=O)H,
$C_{1-4}$ alkyl, $C_{2-4}$ alkenyl, $C_{2-4}$ alknyl, $C_{1-4}$ haloalkyl,
$C_{1-3}$ haloalkyl-oxy-, and $C_{1-3}$ alkyloxy-;

$R^{31}$, at each occurrence, is independently selected from H, OH, halo, $CF_3$, $SO_2R^{45}$, $NR^{46}R^{47}$, and $C_{1-4}$ alkyl;

$R^{33}$, at each occurrence, is independently selected from H, OH, halo, CN, $NO_2$, $CF_3$, $SO_2R^{45}$, $NR^{46}R^{47}$,
—C(=O)H,
$C_{1-6}$ alkyl, $C_{2-6}$ alkenyl, $C_{2-6}$ alkynyl,
$C_{3-6}$ cycloalkyl, $C_{1-4}$ haloalkyl, $C_{1-4}$ haloalkyl-oxy-, $C_{1-4}$ alkyloxy-,
$C_{1-4}$ alkylthio-, $C_{1-4}$ alkyl-C(=O)—, $C_{1-4}$ alkyl-C(=O)NH—, $C_{1-4}$ alkyl-OC(=O)—,
$C_{1-4}$ alkyl-C(=O)O—, $C_{3-6}$ cycloalkyl-oxy-, $C_{3-6}$ cycloalkylmethyl-oxy-;
$C_{1-6}$ alkyl substituted with OH, methoxy, ethoxy, propoxy, or butoxy; and
$C_{2-6}$ alkenyl substituted with OH, methoxy, ethoxy, propoxy, or butoxy;

$R^{41}$, at each occurrence, is independently selected from H, $CF_3$, halo, OH, $CO_2H$, $SO_2R^{45}$, $NR^{46}R^{47}$, $NO_2$, CN, =O;
$C_{2-8}$ alkenyl, $C_{2-8}$ alkynyl, $C_{1-4}$ alkoxy, $C_{1-4}$ haloalkyl
$C_{1-4}$ alkyl substituted with 0–1 $R^{43}$,
aryl substituted with 0–3 $R^{42}$, and
5–10 membered heterocyclic ring system containing from 1–4 heteroatoms selected from the group consisting of N, O, and S substituted with 0–3 $R^{44}$;

$R^{42}$, at each occurrence, is independently selected from
H, $CF_3$, halo, OH, $CO_2H$, $SO_2R^{45}$, $SOR^{45}$, $SR^{45}$, $NR^{46}SO_2R^{45}$, $NR^{46}COR^{45}$, $NR^{46}R^{47}$, $NO_2$, CN, CH(=NH)$NH_2$, NHC(=NH)$NH_2$,
$C_{2-6}$ alkenyl, $C_{2-6}$ alkynyl, $C_{1-4}$ alkoxy, $C_{1-4}$ haloalkyl, $C_{3-6}$ cycloalkyl,
$C_{1-4}$ alkyl substituted with 0–1 $R^{43}$,
aryl substituted with 0–3 $R^{44}$, and
5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-4}$ alkyl;

$R^{47}$, at each occurrence, is independently selected from H, $C_{1-4}$ alkyl,
—C(=O)NH($C_{1-14}$ alkyl), —$SO_2$($C_{1-4}$ alkyl),
—C(=O)O($C_{1-4}$ alkyl), —C(=O)($C_{1-4}$ alkyl), and
—C(=O)H;

k is 1 or 2;

m is 0, 1, or 2;

n is 0, 1, 2, or 3;

provided when m is 0 or 1 then k is 1 or 2;

provided when m is 2 then k is 1;

provided that when $R^6$ or $R^{6a}$ is $NH_2$, then X is not —CH($R^{10}$); and provided that when n=0, then $R^6$ or $R^{6a}$ is not $NH_2$ or —OH.

2. The method as defined in claim 1 where in the compound administered:

X is —CHR$^{10}$— or —C(=O)—;

R$^1$ is selected from
- H,
- C(=O)R$^2$,
- C(=O)OR$^2$,
- C$_{1-8}$ alkyl,
- C$_{2-8}$ alkenyl,
- C$_{2-8}$ alkynyl,
- C$_{3-7}$ cycloalkyl,
- C$_{1-6}$ alkyl substituted with 0–2 R$^2$,
- C$_{2-6}$ alkenyl substituted with 0–2 R$^2$,
- C$_{2-6}$ alkynyl substituted with 0–2 R$^2$,
- aryl substituted with 0–2 R$^2$, and
- 5–6 membered heterocyclic ring system containing at least one heteroatom selected from the group consisting of N, O, and S, said heterocyclic ring system substituted with 0–2 R$^2$;

R$^2$, at each occurrence, is independently selected from
- F, Cl, CH$_2$F, CHF$_2$, CF$_3$,
- C$_{1-4}$ alkyl,
- C$_{2-4}$ alkenyl,
- C$_{2-4}$ alkynyl,
- C$_{3-6}$ cycloalkyl,
- phenyl substituted with 0–5 R$^{42}$;
- C$_{3-10}$ carbocyclic group substituted with 0–3 R$^{41}$, and
- 5–10 membered heterocyclic ring system containing from 1–4 heteroatoms selected from the group consisting of N, O, and S substituted with 0–3 R$^{41}$;

R$^5$ is H, methyl, ethyl, propyl, or butyl;

R$^{6a}$ is selected from
- H, —OH, —NR$^{46}$R$^{47}$, —CF$_3$,
- C$_{1-4}$ alkyl, C$_{1-4}$ alkoxy, C$_{1-4}$ haloalkyl, and
- aryl substituted with 0–3 R$^{44}$;

R$^{6b}$ is H;

R$^7$ and R$^9$, at each occurrence, are independently selected from
- H, halo, —CF$_3$, —OCF$_3$, —OH, —CN, —NO$_2$, —NR$^{46}$R$^{47}$,
- C$_{1-8}$ alkyl, C$_{2-8}$ alkenyl, C$_{2-8}$ alkynyl, C$_{1-4}$ haloalkyl, C$_{1-8}$ alkoxy, (C$_{1-4}$ haloalkyl)oxy,
- C$_{3-10}$ cycloalkyl substituted with 0–2 R$^{33}$,
- C$_{1-4}$ alkyl substituted with 0–2 R$^{11}$,
- C$_{3-10}$ carbocyclic group substituted with 0–3 R$^{33}$,
- aryl substituted with 0–5 R$^{33}$,
- 5–10 membered heterocyclic ring system containing from 1–4 heteroatoms selected from the group consisting of N, O, and S substituted with 0–3 R$^{31}$;
- OR$^{12}$, SR$^{12}$, NR$^{12}$R$^{13}$, C(O)H, C(O)R$^{12}$, C(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(O)OR$^{15}$, NR$^{12}$S(O)$_2$R$^{15}$, and NR$^{12}$C(O)NHR$^{15}$;

R$^8$ is selected from
- H, halo, —CF$_3$, —OCF$_3$, —OH, —CN, —NO$_2$,
- C$_{1-8}$ alkyl, C$_{2-8}$ alkenyl, C$_{2-8}$ alkynyl, C$_{1-4}$ haloalkyl, C$_{1-8}$ alkoxy, (C$_{1-4}$ haloalkyl)oxy,
- C$_{3-10}$ cycloalkyl substituted with 0–2 R$^{33}$,
- C$_{1-4}$ alkyl substituted with 0–2 R$^{11}$,
- C$_{2-4}$ alkenyl substituted with 0–2 R$^{11}$,
- C$_{2-4}$ alkynyl substituted with 0–1 R$^{11}$,
- C$_{3-10}$ carbocyclic group substituted with 0–3 R$^{33}$,
- aryl substituted with 0–5 R$^{33}$,
- 5–10 membered heterocyclic ring system containing from 1–4 heteroatoms selected from the group consisting of N, O, and S substituted with 0–3 R$^{31}$;
- OR$^{12}$, SR$^{12}$, NR$^{12}$R$^{13}$, C(O)H, C(O)R$^{12}$, C(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(O)OR$^{15}$, NR$^{12}$S(O)$_2$R$^{15}$, and NR$^{12}$C(O)NHR$^{15}$;

R$^{10}$ is selected from H, —OH,
- C$_{1-6}$ alkyl substituted with 0–1 R$^{10B}$,
- C$_{2-6}$ alkenyl substituted with 0–1 R$^{10B}$,
- C$_{2-6}$ alkynyl substituted with 0–1 R$^{10B}$, and
- C$_{1-6}$ alkoxy;

R$^{10B}$ is selected from
- C$_{1-4}$ alkoxy,
- C$_{3-6}$ cycloalkyl,
- C$_{3-10}$ carbocyclic group substituted with 0–3 R$^{33}$,
- phenyl substituted with 0–3 R$^{33}$, and
- 5–6 membered heterocyclic ring system containing 1, 2, or 3 heteroatoms selected from the group consisting of N, O, and S substituted with 0–2 R$^{44}$;

R$^{11}$ is selected from
- H, halo, —CF$_3$, —CN, —NO$_2$,
- C$_{1-8}$ alkyl, C$_{2-8}$ alkenyl, C$_{2-8}$ alkynyl, C$_{1-4}$ haloalkyl, C$_{1-8}$ alkoxy, C$_{3-10}$ cycloalkyl,
- C$_{3-10}$ carbocyclic group substituted with 0–3 R$^{33}$,
- aryl substituted with 0–5 R$^{33}$,
- 5–10 membered heterocyclic ring system containing from 1–4 heteroatoms selected from the group consisting of N, O, and S substituted with 0–3 R$^{31}$;
- OR$^{12}$, SR$^{12}$, NR$^{12}$R$^{13}$, C(O)H, C(O)R$^{12}$, C(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(O)OR$^{15}$, NR$^{12}$S(O)$_2$R$^{15}$, and NR$^{12}$C(O)NHR$^{15}$;

R$^{12}$, at each occurrence, is independently selected from
- C$_{1-4}$ alkyl substituted with 0–1 R$^{12a}$,
- C$_{2-4}$ alkenyl substituted with 0–1 R$^{12a}$,
- C$_{2-4}$ alkynyl substituted with 0–1 R$^{12a}$,
- C$_{3-6}$ cycloalkyl substituted with 0–3 R$^{33}$,
- phenyl substituted with 0–5 R$^{33}$;
- C$_{3-10}$ carbocyclic group substituted with 0–3 R$^{33}$, and
- 5–10 membered heterocyclic ring system containing from 1–4 heteroatoms selected from the group consisting of N, O, and S substituted with 0–3 R$^{31}$;

R$^{12a}$, at each occurrence, is independently selected from
- phenyl substituted with 0–5 R$^{33}$;
- C$_{3-10}$ carbocyclic group substituted with 0–3 R$^{33}$, and
- 5–10 membered heterocyclic ring system containing from 1–4 heteroatoms selected from the group consisting of N, O, and S substituted with 0–3 R$^{31}$;

R$^{13}$, at each occurrence, is independently selected from
H, C$_{1-4}$ alkyl, C$_{2-4}$ alkenyl, and C$_{2-4}$ alkynyl;

alternatively, R$^{12}$ and R$^{13}$ join to form a 5- or 6-membered ring optionally substituted with —O— or —N(R$^{14}$)—;

alternatively, R$^{12}$ and R$^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 R$^{16}$;

$R^{14}$, at each occurrence, is independently selected from H and $C_{1-4}$ alkyl;
$R^{15}$, at each occurrence, is independently selected from H, $C_{1-4}$ alkyl, $C_{2-4}$ alkenyl, and $C_{2-4}$ alkynyl;
$R^{16}$, at each occurrence, is independently selected from
  H, OH, halo, CN, $NO_2$, $CF_3$, $SO_2R^{45}$, $NR^{46}R^{47}$, —C(=O)H,
  $C_{1-4}$ alkyl, $C_{2-4}$ alkenyl, $C_{2-4}$ alkynyl, $C_{1-4}$ haloalkyl, $C_{1-3}$ haloalkyl-oxy-, and $C_{1-3}$ alkyloxy-;
$R^{31}$, at each occurrence, is independently selected from H, OH, halo, $CF_3$, $SO_2R^{45}$, $NR^{46}R^{47}$, and $C_{1-4}$ alkyl;
$R^{33}$, at each occurrence, is independently selected from
  H, OH, halo, CN, $NO_2$, $CF_3$, $SO_2R^{45}$, $NR^{46}R^{47}$, —C(=O)H,
  $C_{1-6}$ alkyl, $C_{2-6}$ alkenyl, $C_{2-6}$ alkynyl,
  $C_{3-6}$ cycloalkyl, $C_{1-14}$ haloalkyl, $C_{1-14}$ haloalkyl-oxy-, $C_{1-4}$ alkyloxy-,
  $C_{1-4}$ alkylthio-, $C_{1-4}$ alkyl-C(=O)—, $C_{1-4}$ alkyl-C(=O)NH—, $C_{1-4}$ alkyl-OC(=O)—,
  $C_{1-4}$ alkyl-C(=O)O—, $C_{3-6}$ cycloalkyl-oxy-, $C_{3-6}$ cycloalkylmethyl-oxy-;
  $C_{1-6}$ alkyl substituted with OH, methoxy, ethoxy, propoxy, or butoxy; and
  $C_{2-6}$ alkenyl substituted with OH, methoxy, ethoxy, propoxy, or butoxy;
$R^{41}$, at each occurrence, is independently selected from
  H, $CF_3$, halo, OH, $CO_2H$, $SO_2R^{45}$, $NR^{46}R^{47}$, $NO_2$, CN;
  $C_{2-8}$ alkenyl, $C_{2-8}$ alkynyl, $C_{1-4}$ alkoxy, $C_{1-4}$ haloalkyl
  $C_{1-4}$ alkyl substituted with 0–1 $R^{43}$,
  aryl substituted with 0–3 $R^{42}$, and
  5–10 membered heterocyclic ring system containing from 1–4 heteroatoms selected from the group consisting of N, O, and S substituted with 0–3 $R^{44}$;
$R^{42}$, at each occurrence, is independently selected from
  H, $CF_3$, halo, OH, $CO_2H$, $SO_2R^{45}$, $NR^{46}R^{47}$, $NO_2$, CN, CH(=NH)$NH_2$, NHC(=NH)$NH_2$,
  $C_{2-6}$ alkenyl, $C_{2-6}$ alkynyl, $C_{1-4}$ alkoxy, $C_{1-4}$ haloalkyl, $C_{3-6}$ cycloalkyl,
  $C_{1-4}$ alkyl substituted with 0–1 $R^{43}$,
  aryl substituted with 0–3 $R^{44}$, and
  5–10 membered heterocyclic ring system containing from 1–4 heteroatoms selected from the group consisting of N, O, and S substituted with 0–3 $R^{44}$;
$R^{43}$ is $C_{3-6}$ cycloalkyl or aryl substituted with 0–3 $R^{44}$;
$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;
$R^{45}$ is $C_{1-4}$ alkyl;
$R^{46}$, at each occurrence, is independently selected from H and $C_{1-4}$ alkyl;
$R^{47}$, at each occurrence, is independently selected from H and $C_{1-4}$ alkyl;
k is 1 or 2;
m is 0, 1, or 2; and
n is 0, 1, 2, or 3.

3. The method as defined in claim 2 where in the compound administered:
X is —$CHR^{10}$—;
$R^1$ is selected from
  H,
  C(=O)$R^2$,
  C(=O)O$R^2$,
  $C_{1-6}$ alkyl,
  $C_{2-6}$ alkenyl,
  $C_{2-6}$ alkynyl,
  $C_{3-6}$ cycloalkyl,
  $C_{1-4}$ alkyl substituted with 0–2 $R^2$,
  $C_{2-4}$ alkenyl substituted with 0–2 $R^2$, and
  $C_{2-4}$ alkynyl substituted with 0–2 $R^2$;
$R^2$, at each occurrence, is independently selected from
  $C_{1-4}$ alkyl,
  $C_{2-4}$ alkenyl,
  $C_{2-4}$ alkynyl,
  $C_{3-6}$ cycloalkyl,
  phenyl substituted with 0–5 $R^{42}$;
  $C_{3-10}$ carbocyclic group substituted with 0–3 $R^{41}$, and
  5–10 membered heterocyclic ring system containing from 1–4 heteroatoms selected from the group consisting of N, O, and S substituted with 0–3 $R^{41}$;
$R^5$ is H, methyl, ethyl, propyl, or butyl;
$R^{6a}$ is selected independently from
  H, —OH, —$NR^{46}R^{47}$, —$CF_3$, $C_{1-3}$ alkyl, and $C_{1-3}$ alkoxy;
$R^{6b}$ is H;
$R^7$ and $R^9$, at each occurrence, are independently selected from
  H, halo, —$CF_3$, —$OCF_3$, —OH, —CN, —$NO_2$, —$NR^{46}R^{47}$,
  $C_{1-6}$ alkyl, $C_{2-6}$ alkenyl, $C_{2-6}$ alkynyl, $C_{1-6}$ haloalkyl, $C_{1-6}$ alkoxy, ($C_{1-4}$ haloalkyl)oxy,
  $C_{3-10}$ cycloalkyl substituted with 0–2 $R^{33}$,
  $C_{1-4}$ alkyl substituted with 0–2 $R^{11}$,
  $C_{3-10}$ carbocyclic group substituted with 0–3 $R^{33}$,
  aryl substituted with 0–5 $R^{33}$,
  5–10 membered heterocyclic ring system containing from 1–4 heteroatoms selected from the group consisting of N, O, and S substituted with 0–3 $R^{31}$;
  $OR^{12}$, $SR^{12}$, $NR^{12}R^{13}$, C(O)H, C(O)$R^{12}$, C(O)$NR^{12}R^{13}$, $NR^{14}C(O)R^{12}$, C(O)O$R^{12}$, OC(O)$R^{12}$, OC(O)O$R^{12}$, CH(=$NR^{14}$)$NR^{12}R^{13}$, NHC(=$NR^{14}$)$NR^{12}R^{13}$, S(O)$R^{12}$, S(O)$_2R^{12}$, S(O)$NR^{12}R^{13}$, S(O)$_2NR^{12}R^{13}$, $NR^{14}S(O)R^{12}$, and $NR^{14}S(O)_2R^{12}$;
$R^8$ is selected from
  H, halo, —$CF_3$, —$OCF_3$, —OH, —CN, —$NO_2$,
  $C_{1-6}$ alkyl, $C_{2-6}$ alkenyl, $C_{2-6}$ alkynyl, $C_{1-6}$ haloalkyl, $C_{1-6}$ alkoxy, ($C_{1-4}$ haloalkyl)oxy,
  $C_{3-10}$ cycloalkyl substituted with 0–2 $R^{33}$,
  $C_{1-4}$ alkyl substituted with 0–2 $R^1$,
  $C_{2-4}$ alkenyl substituted with 0–2 $R^{11}$,
  $C_{2-4}$ alkynyl substituted with 0–1 $R^{11}$,
  $C_{3-10}$ carbocyclic group substituted with 0–3 $R^{33}$,
  aryl substituted with 0–5 $R^{33}$,
  5–10 membered heterocyclic ring system containing from 1–4 heteroatoms selected from the group consisting of N, O, and S substituted with 0–3 $R^{31}$;
  $OR^{12}$, $SR^{12}$, $NR^{12}R^{13}$, C(O)H, C(O)$R^{12}$, C(O)$NR^{12}R^{13}$, $NR^{14}C(O)R^{12}$, C(O)O$R^{12}$, OC(O)$R^{12}$, OC(O)O$R^{12}$, CH(=$NR^{14}$)$NR^{12}R^{13}$, NHC(=$NR^{14}$)$NR^{12}R^{13}$, S(O)$R^{12}$, S(O)$_2R^{12}$, S(O)$NR^{12}R^{13}$, S(O)$_2NR^{12}R^{13}$, $NR^{14}S(O)R^{12}$, $NR^{14}S(O)_2R^{12}$, $NR^{12}C(O)R^{15}$, $NR^{12}C(O)OR^{15}$, $NR^{12}S(O)_2R^{15}$, and $NR^{12}C(O)NHR^{15}$;
$R^{10}$ is selected from H, —OH,
  $C_{1-6}$ alkyl substituted with 0–1 $R^{10B}$,
  $C_{2-6}$ alkenyl substituted with 0–1 $R^{10B}$,
  $C_{2-6}$ alkynyl substituted with 0–1 $R^{10B}$, and
  $C_{1-6}$ alkoxy;
$R^{10B}$ is selected from
  $C_{1-4}$ alkoxy,
  $C_{3-6}$ cycloalkyl,
  $C_{3-10}$ carbocyclic group substituted with 0–3 $R^{33}$,
  phenyl substituted with 0–3 $R^{33}$, and 5–6 membered heterocyclic ring system containing 1, 2, or 3 heteroatoms selected from the group consisting of N, O, and S substituted with 0–2 $R^{44}$;

$R^{11}$ is selected from
H, halo, —$CF_3$, —CN, —$NO_2$, $C_{1-6}$ alkyl,
$C_{2-6}$ alkenyl, $C_{2-6}$ alkynyl, $C_{1-4}$ haloalkyl, $C_{1-6}$ alkoxy,
$C_{3-10}$ cycloalkyl,
$C_{3-10}$ carbocyclic group substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, C(O)H, C(O)$R^{12}$, C(O)$NR^{12}R^{13}$, $NR^{14}$C(O)$R^{12}$, C(O)$OR^{12}$, OC(O)$R^{12}$, OC(O)$OR^{12}$, CH(=$NR^{14}$)$NR^{12}R^{13}$, NHC(=$NR^{14}$)$NR^{12}R^{13}$, S(O)$R^{12}$, S(O)$_2R^{12}$, S(O)$NR^{12}R^{13}$, S(O)$_2NR^{12}R^{13}$, $NR^{14}$S(O)$R^{12}$, and $NR^{14}$S(O)$_2R^{12}$;

$R^{12}$, at each occurrence, is independently selected from
$C_{1-4}$ alkyl substituted with 0–1 $R^{12a}$,
$C_{2-4}$ alkenyl substituted with 0–1 $R^{12a}$,
$C_{2-4}$ alkynyl substituted with 0–1 $R^{12a}$,
$C_{3-6}$ cycloalkyl substituted with 0–3 $R^{33}$,
phenyl substituted with 0–5 $R^{33}$;
$C_{3-10}$ carbocyclic group substituted with 0–3 $R^{33}$, and
5–10 membered heterocyclic ring system containing from 1–4 heteroatoms selected from the group consisting of N, O, and S substituted with 0–3 $R^{31}$;

$R^{12a}$, at each occurrence, is independently selected from
phenyl substituted with 0–5 $R^{33}$;
$C_{3-10}$ carbocyclic group substituted with 0–3 $R^{33}$, and
5–10 membered heterocyclic ring system containing from 1–4 heteroatoms selected from the group consisting of N, O, and S substituted with 0–3 $R^{31}$;

$R^{13}$, at each occurrence, is independently selected from
H, $C_{1-4}$ alkyl, $C_{2-4}$ alkenyl, and $C_{2-4}$ alkynyl;
alternatively, $R^{12}$ and $R^{13}$ join to form a 5- or 6-membered ring optionally substituted with —O— or —N($R^{14}$)—;
alternatively, $R^{12}$ and $R^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;

$R^{14}$, at each occurrence, is independently selected from H, methyl, ethyl, propyl, and butyl;

$R^{15}$, at each occurrence, is independently selected from
H, $C_{1-4}$ alkyl, $C_{2-4}$ alkenyl, and $C_{2-4}$ alkynyl;

$R^{16}$, at each occurrence, is independently selected from
H, OH, F, Cl, CN, $NO_2$, $CF_3$, $SO_2R^{45}$, $NR^{46}R^{47}$,
—C(=O)H,
methyl, ethyl, methoxy, ethoxy, trifluoromethyl, and trifluoromethoxy;

$R^{31}$, at each occurrence, is independently selected from
H, OH, halo, $CF_3$, $SO_2R^{45}$, $NR^{46}R^{47}$, and $C_{1-4}$ alkyl;

$R^{33}$, at each occurrence, is independently selected from
H, OH, halo, CN, $NO_2$, $CF_3$, $SO_2R^{45}$, $NR^{46}R^{47}$,
—C(=O)H,
$C_{1-6}$ alkyl, $C_{2-6}$ alkenyl, $C_{2-6}$ alkynyl,
$C_{3-6}$ cycloalkyl, $C_{1-4}$ haloalkyl, $C_{1-14}$ haloalkyl-oxy-, $C_{1-4}$ alkyloxy-,
$C_{1-4}$ alkylthio-, $C_{1-4}$ alkyl-C(=O)—, $C_{1-4}$ alkyl-C(=O)NH—, $C_{1-4}$ alkyl-OC(=O)—,
$C_{1-4}$ alkyl-C(=O)O—, $C_{3-6}$ cycloalkyl-oxy-, $C_{3-6}$ cycloalkylmethyl-oxy-;
$C_{1-6}$ alkyl substituted with OH, methoxy, ethoxy, propoxy, or butoxy; and $C_{2-6}$ alkenyl substituted with OH, methoxy, ethoxy, propoxy, or butoxy;

$R^{41}$, at each occurrence, is independently selected from
H, $CF_3$, halo, OH, $CO_2H$, $SO_2R^{45}$, $NR^{46}R^{47}$, $NO_2$, CN,
$C_{2-8}$ alkenyl, $C_{2-8}$ alkynyl, $C_{1-4}$ alkoxy, $C_{1-4}$ haloalkyl
$C_{1-4}$ alkyl substituted with 0–1 $R^{43}$,
aryl substituted with 0–3 $R^{42}$, and
5–10 membered heterocyclic ring system containing from 1–4 heteroatoms selected from the group consisting of N, O, and S substituted with 0–3 $R^{44}$;

$R^{42}$, at each occurrence, is independently selected from
H, $CF_3$, halo, OH, $CO_2H$, $SO_2R^{45}$, $NR^{46}R^{47}$, $NO_2$, CN,
CH(=NH)$NH_2$, NHC(=NH)$NH_2$,
$C_{2-6}$ alkenyl, $C_{2-6}$ alkynyl, $C_{1-4}$ alkoxy, $C_{1-4}$ haloalkyl,
$C_{3-6}$ cycloalkyl,
$C_{1-4}$ alkyl substituted with 0–1 $R^{43}$,
aryl substituted with 0–3 $R^{44}$, and
5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-4}$ alkyl;

$R^{47}$, at each occurrence, is independently selected from H and $C_{1-4}$ alkyl;

k is 1 or 2;
m is 0 or 1; and
n is 0, 1 or 2.

4. The method as defined in claim 2 where in the compound administered:
X is —$CH_2$—;
$R^1$ is selected from
H,
$C_{1-4}$ alkyl,
$C_{2-4}$ alkenyl,
$C_{2-4}$ alkynyl,
$C_{3-4}$ cycloalkyl,
$C_{1-3}$ alkyl substituted with 0–1 $R^2$,
$C_{2-3}$ alkenyl substituted with 0–1 $R^2$, and
$C_{2-3}$ alkynyl substituted with 0–1 $R^2$;

$R^2$, at each occurrence, is independently selected from
$C_{1-4}$ alkyl,
$C_{2-4}$ alkenyl,
$C_{2-4}$ alkynyl,
$C_{3-6}$ cycloalkyl,
phenyl substituted with 0–5 $R^{42}$;
$C_{3-6}$ carbocyclic group substituted with 0–3 $R^{41}$, and
5–6 membered heterocyclic ring system containing 1, 2, or 3 heteroatoms selected from the group consisting of N, O, and S substituted with 0–3 $R^{41}$;

$R^5$ is H, methyl, ethyl, propyl, or butyl;
$R^{6a}$ is H, methyl, ethyl, methoxy, —OH, or —$CF_3$;
$R^{6b}$ is H;
$R^7$ and $R^9$, at each occurrence, are independently selected from
H, halo, —$CF_3$, —$OCF_3$, —OH, —CN, —$NO_2$, —$NR^{46}R^{47}$,
$C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{3-10}$ carbocyclic group substituted with 0–3 $R^{33}$,
aryl substituted with 0–5 $R^{33}$, and 5–6 membered heterocyclic ring system containing 1, 2, or 3 heteroatoms selected from the group consisting of N, O, and S substituted with 0–3 $R^{31}$;

$R^8$ is selected from
H, halo, —$CF_3$, —$OCF_3$, —OH, —CN, —$NO_2$,
$C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{2-4}$ alkenyl substituted with 0–2 $R^{11}$,
$C_{2-4}$ alkynyl substituted with 0–1 $R^{11}$,
$C_{3-10}$ carbocyclic group substituted with 0–3 $R^{33}$,
aryl substituted with 0–5 $R^{33}$,
5–6 membered heterocyclic ring system containing 1, 2, or 3 heteroatoms selected from the group consisting of N, O, and S substituted with 0–3 $R^{31}$;
$OR^{12}$, $SR^{12}$, $NR^{12}R^{13}$, $NR^{12}C(O)R^{15}$, $NR^{12}C(O)OR^{15}$, $NR^{12}S(O)_2R^{15}$, and $NR^{12}C(O)NHR^{15}$;

$R^{11}$ is selected from
H, halo, —$CF_3$, —CN, —$NO_2$,
$C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
$C_{3-10}$ cycloalkyl substituted with 0–2 $R^{33}$,
$C_{3-10}$ carbocyclic group substituted with 0–3 $R^{33}$,
aryl substituted with 0–5 $R^{33}$, and
5–6 membered heterocyclic ring system containing 1, 2, or 3 heteroatoms selected from the group consisting of N, O, and S substituted with 0–3 $R^{31}$;

$R^{12}$, at each occurrence, is independently selected from
$C_{1-4}$ alkyl substituted with 0–1 $R^{12a}$,
$C_{2-4}$ alkenyl substituted with 0–1 $R^{12a}$,
$C_{2-4}$ alkynyl substituted with 0–1 $R^{12a}$,
$C_{3-6}$ cycloalkyl substituted with 0–3 $R^{33}$,
phenyl substituted with 0–5 $R^{33}$;
$C_{3-10}$ carbocyclic group substituted with 0–3 $R^{33}$, and
5–10 membered heterocyclic ring system containing from 1–4 heteroatoms selected from the group consisting of N, O, and S substituted with 0–3 $R^{31}$;

$R^{12a}$, at each occurrence, is independently selected from
phenyl substituted with 0–5 $R^{33}$;
$C_{3-10}$ carbocyclic group substituted with 0–3 $R^{33}$, and
5–10 membered heterocyclic ring system containing from 1–4 heteroatoms selected from the group consisting of N, O, and S substituted with 0–3 $R^{31}$;

$R^{13}$, at each occurrence, is independently selected from
H, $C_{1-4}$ alkyl, $C_{2-4}$ alkenyl, and $C_{2-4}$ alkynyl;
alternatively, $R^{12}$ and $R^{13}$ join to form a 5- or 6-membered ring optionally substituted with —O— or —N($R^{14}$)—;
alternatively, $R^{12}$ and $R^{13}$ when attached to N may be combined to form a 9- or 10-membered bicyclic heterocyclic ring system containing from 1–3 heteroatoms selected from the group consisting of one N, two N, three N, one N one O, and one N one S; wherein said bicyclic heterocyclic ring system is unsaturated or partially saturated, wherein said bicyclic heterocyclic ring system is substituted with 0–2 $R^{16}$;

$R^{14}$, at each occurrence, is independently selected from H, methyl, ethyl, propyl, and butyl;

$R^{15}$, at each occurrence, is independently selected from H, methyl, ethyl, propyl, and butyl;

$R^{16}$, at each occurrence, is independently selected from H, OH, F, Cl, CN, $NO_2$, methyl, ethyl, methoxy, ethoxy, trifluoromethyl, and trifluoromethoxy;

$R^{31}$, at each occurrence, is independently selected from H, OH, halo, $CF_3$, methyl, ethyl, and propyl;

$R^{33}$, at each occurrence, is independently selected from H, OH, halo, CN, $NO_2$, $CF_3$, $SO_2R^{45}$, $NR^{46}R^{47}$, —C(=O)H,
$C_{1-6}$ alkyl, $C_{2-6}$ alkenyl, $C_{2-6}$ alkynyl,
$C_{3-6}$ cycloalkyl, $C_{1-4}$ haloalkyl, $C_{1-4}$ haloalkyl-oxy-, $C_{1-4}$ alkyloxy-,
$C_{1-4}$ alkylthio-, $C_{1-4}$ alkyl-C(=O)—, $C_{1-4}$ alkyl-C(=O)NH—, $C_{1-4}$ alkyl-OC(=O)—,
$C_{1-4}$ alkyl-C(=O)O—, $C_{3-6}$ cycloalkyl-oxy-, $C_{3-6}$ cycloalkylmethyl-oxy-;
$C_{1-6}$ alkyl substituted with OH, methoxy, ethoxy, propoxy, or butoxy; and
$C_{2-6}$ alkenyl substituted with OH, methoxy, ethoxy, propoxy, or butoxy;

$R^{41}$, at each occurrence, is independently selected from
H, $CF_3$, halo, OH, $CO_2H$, $SO_2R^{45}$, $NR^{46}R^{47}$, $NO_2$, CN,
$C_{2-4}$ alkenyl, $C_{2-4}$ alkynyl, $C_{1-3}$ alkoxy, $C_{1-3}$ haloalkyl, and $C_{1-3}$ alkyl;

$R^{42}$, at each occurrence, is independently selected from
H, $CF_3$, halo, OH, $CO_2H$, $SO_2R^{45}$, $NR^{46}R^{47}$, $NO_2$, CN,
CH(=NH)$NH_2$, NHC(=NH)$NH_2$,
$C_{2-4}$ alkenyl, $C_{2-4}$ alkynyl, $C_{1-3}$ alkoxy, $C_{1-3}$ haloalkyl, $C_{3-6}$ cycloalkyl, and $C_{1-3}$ alkyl;

$R^{43}$ is cyclopropyl, cyclobutyl, cyclopentyl, cyclohexyl, phenyl, or pyridyl, each substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, methyl, ethyl, propyl, butyl, methoxy, ethoxy, propoxy, and butoxy;

$R^{45}$ is methyl, ethyl, propyl, or butyl;

$R^{46}$, at each occurrence, is independently selected from H, methyl, ethyl, propyl, and butyl;

$R^{47}$, at each occurrence, is independently selected from from H, methyl, ethyl, propyl, and butyl;

k is 1;
m is 1; and
n is 0, 1 or 2.

5. The method as defined in claim 2 where in the compound administered:
X is —$CH_2$—;
$R^1$ is selected from
H,
$C_{1-4}$ alkyl,
$C_{2-4}$ alkenyl,
$C_{2-4}$ alkynyl,
$C_{3-4}$ cycloalkyl,
$C_{1-3}$ alkyl substituted with 0–1 $R^2$,
$C_{2-3}$ alkenyl substituted with 0–1 $R^2$, and
$C_{2-3}$ alkynyl substituted with 0–1 $R^2$;
$R^2$, at each occurrence, is independently selected from
$C_{1-4}$ alkyl,
$C_{2-4}$ alkenyl,
$C_{2-4}$ alkynyl,
$C_{3-6}$ cycloalkyl,
phenyl substituted with 0–5 $R^{42}$;
$C_{3-6}$ carbocyclic group substituted with 0–3 $R^{41}$, and
5–6 membered heterocyclic ring system containing 1, 2, or 3 heteroatoms selected from the group consisting of N, O, and S substituted with 0–3 $R^{41}$;

$R^5$ is H, methyl, ethyl, propyl, or butyl;
$R^{6a}$ is H, methyl, ethyl, methoxy, —OH, or —$CF_3$;
$R^{6b}$ is H;
$R^7$ and $R^9$, at each occurrence, are independently selected from
H, F, Cl, —$CH_3$, —$OCH_3$, —$CF_3$, —$OCF_3$, —CN, and —$NO_2$, $R^8$ is selected from
H, F, Cl, Br, —$CF_3$, —$OCF_3$, —OH, —CN, —$NO_2$,
$C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{2-4}$ alkenyl substituted with 0–2 $R^{11}$,
$C_{2-4}$ alkynyl substituted with 0–1 $R^{11}$,
$C_{3-10}$ carbocyclic group substituted with 0–3 $R^{33}$,
aryl substituted with 0–5 $R^{33}$,
5–6 membered heterocyclic ring system containing 1, 2, or 3 heteroatoms selected from the group consisting of N, O, and S substituted with 0–3 $R^{31}$;
$OR^{12}$, $SR^{12}$, $NR^{12}R^{13}$, $NR^{12}C(O)R^{15}$, $NR^{12}C(O)OR^{15}$, $NR^{12}S(O)_2R^{15}$, and $NR^{12}C(O)NHR^{15}$;

$R^{11}$ is selected from
H, halo, —$CF_3$, —CN, —$NO_2$,
$C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
$C_{3-10}$ cycloalkyl substituted with 0–2 $R^{33}$,
$C_{3-10}$ carbocyclic group substituted with 0–3 $R^{33}$,
aryl substituted with 0–5 $R^{33}$, and
5–6 membered heterocyclic ring system containing 1, 2, or 3 heteroatoms selected from the group consisting of N, O, and S substituted with 0–3 $R^{31}$;

$R^{12}$, at each occurrence, is independently selected from
$C_{1-4}$ alkyl substituted with 0–1 $R^{12a}$,
$C_{2-4}$ alkenyl substituted with 0–1 $R^{12a}$,
$C_{2-4}$ alkynyl substituted with 0–1 $R^{12a}$,
$C_{3-6}$ cycloalkyl substituted with 0–3 $R^{33}$,
phenyl substituted with 0–5 $R^{33}$;
$C_{3-10}$ carbocyclic group substituted with 0–3 $R^{33}$, and
5–10 membered heterocyclic ring system containing from 1–4 heteroatoms selected from the group consisting of N, O, and S substituted with 0–3 $R^{31}$;

$R^{12a}$, at each occurrence, is independently selected from
phenyl substituted with 0–5 $R^{33}$;
$C_{3-10}$ carbocyclic group substituted with 0–3 $R^{33}$, and
5–10 membered heterocyclic ring system containing from 1–4 heteroatoms selected from the group consisting of N, O, and S substituted with 0–3 $R^{31}$;

$R^{13}$, at each occurrence, is independently selected from
H, $C_{1-4}$ alkyl, $C_{2-4}$ alkenyl, and $C_{2-4}$ alkynyl;
alternatively, $R^{12}$ and $R^{13}$ join to form a 5- or 6-membered ring optionally substituted with —O— or —N($R^{14}$)—;
alternatively, $R^{12}$ and $R^{13}$ when attached to N may be combined to form a 9- or 10-membered bicyclic heterocyclic ring system containing from 1–3 heteroatoms selected from the group consisting of N, O, and S; wherein said bicyclic heterocyclic ring system is selected from indolyl, indolinyl, indazolyl, benzimidazolyl, benzimidazolinyl, benztriazolyl, benzoxazolyl, benzoxazolinyl, benzthiazolyl, and dioxobenzthiazolyl; wherein said bicyclic heterocyclic ring system is substituted with 0–1 $R^{16}$;

$R^{14}$, at each occurrence, is independently selected from H, methyl, ethyl, propyl, and butyl;
$R^{15}$, at each occurrence, is independently selected from H, methyl, ethyl, propyl, and butyl;
$R^{16}$, at each occurrence, is independently selected from H, OH, F, Cl, CN, $NO_2$, methyl, ethyl, methoxy, ethoxy, trifluoromethyl, and trifluoromethoxy;
$R^{31}$, at each occurrence, is independently selected from H, OH, halo, $CF_3$, methyl, ethyl, and propyl;
$R^{33}$, at each occurrence, is independently selected from H, OH, halo, CN, $NO_2$, $CF_3$, $SO_2R^{45}$, $NR^{46}R^{47}$, —C(=O)H, $C_{1-6}$ alkyl, $C_{2-6}$ alkenyl, $C_{2-6}$ alkynyl,
$C_{3-6}$ cycloalkyl, $C_{1-4}$ haloalkyl, $C_{1-4}$ haloalkyl-oxy-, $C_{1-14}$ alkyloxy-,
$C_{1-4}$ alkylthio-, $C_{1-4}$ alkyl-C(=O)—, $C_{1-4}$ alkyl-C(=O)NH—, $C_{1-4}$ alkyl-OC(=O)—,
$C_{1-4}$ alkyl-C(=O)O—, $C_{3-6}$ cycloalkyl-oxy-, $C_{3-6}$ cycloalkylmethyl-oxy-;
$C_{1-6}$ alkyl substituted with OH, methoxy, ethoxy, propoxy, or butoxy; and
$C_{2-6}$ alkenyl substituted with OH, methoxy, ethoxy, propoxy, or butoxy;
$R^{41}$, at each occurrence, is independently selected from H, $CF_3$, halo, OH, $CO_2H$, $SO_2R^{45}$, $NR^{46}R^{47}$, $NO_2$, CN, $C_{2-4}$ alkenyl, $C_{2-4}$ alkynyl, $C_{1-3}$ alkoxy, $C_{1-3}$ haloalkyl, and $C_{1-3}$ alkyl;
$R^{42}$, at each occurrence, is independently selected from H, $CF_3$, halo, OH, $CO_2H$, $SO_2R^{45}$, $NR^{46}R^{47}$, $NO_2$, CN, CH(=NH)$NH_2$, NHC(=NH)$NH_2$, $C_{2-4}$ alkenyl, $C_{2-4}$ alkynyl, $C_{1-3}$ alkoxy, $C_{1-3}$ haloalkyl, $C_{3-6}$ cycloalkyl, and $C_{1-3}$ alkyl;
$R^{43}$ is cyclopropyl, cyclobutyl, cyclopentyl, cyclohexyl, phenyl, or pyridyl, each substituted with 0–3 $R^{44}$;
$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, methyl, ethyl, propyl, butyl, methoxy, ethoxy, propoxy, and butoxy;
$R^{45}$ is methyl, ethyl, propyl, or butyl;
$R^{46}$, at each occurrence, is independently selected from H, methyl, ethyl, propyl, and butyl;
$R^{47}$, at each occurrence, is independently selected from from H, methyl, ethyl, propyl, and butyl;
k is 1;
m is 1; and
n is 0, 1 or 2.

6. The method as defined in claim 2 where in the compound administered:
X is —$CH_2$—;
$R^1$ is selected from H,
$C_{1-5}$ alkyl substituted with 0–1 $R^2$,
$C_{2-5}$ alkenyl substituted with 0–1 $R^2$, and
$C_{2-3}$ alkynyl substituted with 0–1 $R^2$;
$R^2$ is $C_{3-6}$ cycloalkyl;
$R^5$ is H, methyl, ethyl, or propyl;
$R^{6a}$ is H, methyl, or ethyl;
$R^{6b}$ is H;
$R^7$ and $R^9$, at each occurrence, are independently selected from
H, F, Cl, —$CH_3$, —$OCH_3$, —$CF_3$, —$OCF_3$, —CN, and —$NO_2$,
$R^8$ is selected from
methyl substituted with $R^{11}$;
ethenyl substituted with $R^{11}$;
$OR^{12}$, $SR^{12}$, $NR^{12}R^{13}$, $NR^{12}C(O)R^{15}$, $NR^{12}C(O)OR^{15}$, $NR^{12}S(O)_2R^{15}$, and $NR^{12}C(O)NHR^{15}$;
$R^{11}$ is selected from
phenyl-substituted with 0–5 fluoro;
2-($H_3CCH_2C(=O)$)-phenyl-substituted with $R^{33}$;
2-($H_3CC(=O)$)-phenyl-substituted with $R^{33}$;
2-(HC(=O))-phenyl-substituted with $R^{33}$;
2-($H_3CCH(OH)$)-phenyl-substituted with $R^{33}$;
2-($H_3CCH_2CH(OH)$)-phenyl-substituted with $R^{33}$;
2-(HOCH$_2$)-phenyl-substituted with $R^{33}$;
2-(HOCH$_2$CH$_2$)-phenyl-substituted with $R^{33}$;
2-($H_3COCH_2$)-phenyl-substituted with $R^{33}$;
2-($H_3COCH_2CH_2$)-phenyl-substituted with $R^{33}$;
2-($H_3CCH(OMe)$)-phenyl-substituted with $R^{33}$;
2-($H_3COC(=O)$)-phenyl-substituted with $R^{33}$;

2-(HOCH$_2$CH=CH)-phenyl-substituted with R$^{33}$;
2-((MeOC=O)CH=CH)-phenyl-substituted with R$^{33}$;
2-(methyl)-phenyl-substituted with R$^{33}$;
2-(ethyl)-phenyl-substituted with R$^{33}$;
2-(i-propyl)-phenyl-substituted with R$^{33}$;
2-(F$_3$C)-phenyl-substituted with R$^{33}$;
2-(NC)-phenyl-substituted with R$^{33}$;
2-(H$_3$CO)-phenyl-substituted with R$^{33}$;
2-(fluoro)-phenyl-substituted with R$^{33}$;
2-(chloro)-phenyl-substituted with R$^{33}$;
3-(NC)-phenyl-substituted with R$^{33}$;
3-(H$_3$CO)-phenyl-substituted with R$^{33}$;
3-(fluoro)-phenyl-substituted with R$^{33}$;
3-(chloro)-phenyl-substituted with R$^{33}$;
4-(NC)-phenyl-substituted with R$^{33}$;
4-(fluoro)-phenyl-substituted with R$^{33}$;
4-(chloro)-phenyl-substituted with R$^{33}$;
4-(H$_3$CS)-phenyl-substituted with R$^{33}$;
4-(H$_3$CO)-phenyl-substituted with R$^{33}$;
4-(ethoxy)-phenyl-substituted with R$^{33}$;
4-(i-propoxy)-phenyl-substituted with R$^{33}$;
4-(i-butoxy)-phenyl-substituted with R$^{33}$;
4-(H$_3$CCH$_2$CH$_2$C(=O))-phenyl-substituted with R$^{33}$;
4-((H$_3$C)$_2$CHC(=O))-phenyl-substituted with R$^{33}$;
4-(H$_3$CCH$_2$C(=O))-phenyl-substituted with R$^{33}$;
4-(H$_3$CC(=O))-phenyl-substituted with R$^{33}$;
4-(H$_3$CCH$_2$CH$_2$CH(OH))-phenyl-substituted with R$^{33}$;
4-((H$_3$C)$_2$CHCH(OH))-phenyl-substituted with R$^{33}$;
4-(H$_3$CCH$_2$CH(OH))-phenyl-substituted with R$^{33}$;
4-(H$_3$CCH(OH))-phenyl-substituted with R$^{33}$;
4-(cyclopropyloxy)-phenyl-substituted with R$^{33}$;
4-(cyclobutyloxy)-phenyl-substituted with R$^{33}$; and
4-(cyclopentyloxy)-phenyl-substituted with R$^{33}$;
R$^{12}$ is selected from
phenyl-substituted with 0–5 fluoro;
2-(H$_3$CCH$_2$C(=O))-phenyl-substituted with R$^{33}$;
2-(H$_3$CC(=O))-phenyl-substituted with R$^{33}$;
2-(HC(=O))-phenyl-substituted with R$^{33}$;
2-(H$_3$CCH(OH))-phenyl-substituted with R$^{33}$;
2-(H$_3$CCH$_2$CH(OH))-phenyl-substituted with R$^{33}$;
2-(HOCH$_2$)-phenyl-substituted with R$^{33}$;
2-(HOCH$_2$CH$_2$)-phenyl-substituted with R$^{33}$;
2-(H$_3$COCH$_2$)-phenyl-substituted with R$^{33}$;
2-(H$_3$COCH$_2$CH$_2$)-phenyl-substituted with R$^{33}$;
2-(H$_3$CCH(OMe))-phenyl-substituted with R$^{33}$;
2-(H$_3$COC(=O))-phenyl-substituted with R$^{33}$;
2-(HOCH$_2$CH=CH)-phenyl-substituted with R$^{33}$;
2-((MeOC=O)CH=CH)-phenyl-substituted with R$^{33}$;
2-(methyl)-phenyl-substituted with R$^{33}$;
2-(ethyl)-phenyl-substituted with R$^{33}$;
2-(i-propyl)-phenyl-substituted with R$^{33}$;
2-(F$_3$C)-phenyl-substituted with R$^{33}$;
2-(NC)-phenyl-substituted with R$^{33}$;
2-(H$_3$CO)-phenyl-substituted with R$^{33}$;
2-(fluoro)-phenyl-substituted with R$^{33}$;
2-(chloro)-phenyl-substituted with R$^{33}$;
3-(NC)-phenyl-substituted with R$^{33}$;
3-(H$_3$CO)-phenyl-substituted with R$^{33}$;
3-(fluoro)-phenyl-substituted with R$^{33}$;
3-(chloro)-phenyl-substituted with R$^{33}$;
4-(NC)-phenyl-substituted with R$^{33}$;
4-(fluoro)-phenyl-substituted with R$^{33}$;
4-(chloro)-phenyl-substituted with R$^{33}$;
4-(H$_3$CS)-phenyl-substituted with R$^{33}$;
4-(H$_3$CO)-phenyl-substituted with R$^{33}$;
4-(ethoxy)-phenyl-substituted with R$^{33}$;
4-(i-propoxy)-phenyl-substituted with R$^{33}$;
4-(i-butoxy)-phenyl-substituted with R$^{33}$;
4-(H$_3$CCH$_2$CH$_2$C(=O))-phenyl-substituted with R$^{33}$;
4-((H$_3$C)$_2$CHC(=O))-phenyl-substituted with R$^{33}$;
4-(H$_3$CCH$_2$C(=O))-phenyl-substituted with R$^{33}$;
4-(H$_3$CC(=O))-phenyl-substituted with R$^{33}$;
4-(H$_3$CCH$_2$CH$_2$CH(OH))-phenyl-substituted with R$^{33}$;
4-((H$_3$C)$_2$CHCH(OH))-phenyl-substituted with R$^{33}$;
4-(H$_3$CCH$_2$CH(OH))-phenyl-substituted with R$^{33}$;
4-(H$_3$CCH(OH))-phenyl-substituted with R$^{33}$;
4-(cyclopropyloxy)-phenyl-substituted with R$^{33}$;
4-(cyclobutyloxy)-phenyl-substituted with R$^{33}$; and
4-(cyclopentyloxy)-phenyl-substituted with R$^{33}$;

R$^{13}$ is H, methyl, or ethyl;
alternatively, R$^{12}$ and R$^{13}$ join to form a 5- or 6-membered ring selected from pyrrolyl, pyrrolidinyl, imidazolyl, piperidinyl, piperizinyl, methylpiperizinyl, and morpholinyl;
alternatively, R$^{12}$ and R$^{13}$ when attached to N may be combined to form a 9- or 10-membered bicyclic heterocyclic ring system containing from 1–3 heteroatoms selected from the group consisting of N, O, and S; wherein said bicyclic heterocyclic ring system is selected from indolyl, indolinyl, indazolyl, benzimidazolyl, benzimidazolinyl, benztriazolyl, benzoxazolyl, benzoxazolinyl, benzthiazolyl, and dioxobenzthiazolyl; wherein said bicyclic heterocyclic ring system is substituted with 0–1 R$^{16}$;
R$^{15}$ is H, methyl, ethyl, propyl, or butyl;
R$^{16}$, at each occurrence, is independently selected from H, OH, F, Cl, CN, NO$_2$, methyl, ethyl, methoxy, ethoxy, trifluoromethyl, and trifluoromethoxy;
R$^{33}$, at each occurrence, is independently selected from H, F, Cl, —CH$_3$, —OCH$_3$, —CF$_3$, —OCF$_3$, —CN, and —NO$_2$;
k is 1;
m is 1; and
n is 1 or 2.

7. The method as defined in claim 2 where the compound administered is a compound of Formula (I-a):

(I-a)

wherein:
b is a single bond;
X is —CH$_2$—, —CH(OH)—, or °C(=O)—;
R$^1$ is selected from
hydrogen, methyl, ethyl, n-propyl, n-butyl, s-butyl, t-butyl, n-pentyl, n-hexyl, 2-propyl, 2-butyl, 2-pentyl, 2-hexyl, 2-methylpropyl, 2-methylbutyl, 2-methylpentyl, 2-ethylbutyl, 3-methylpentyl, 3-methylbutyl, 4-methylpentyl, 2-fluoroethyl, 2,2-difluoroethyl, 2,2,2-trifluoroethyl,
2-propenyl, 2-methyl-2-propenyl, trans-2-butenyl, 3-methyl-butenyl, 3-butenyl, trans-2-pentenyl, cis-2-pentenyl, 4-pentenyl, 4-methyl-3-pentenyl, 3,3-dichloro-2-propenyl, trans-3-phenyl-2-propenyl,
cyclopropyl, cyclobutyl, cyclopentyl, cyclohexyl, cyclopropylmethyl, cyclobutylmethyl, cyclopentylmethyl, cyclohexylmethyl,
benzyl, 2-methylbenzyl, 3-methylbenzyl, 4-methylbenzyl, 2,5-dimethylbenzyl, 2,4-dimethylbenzyl, 3,5-dimethylbenzyl,
2,4,6-trimethyl-benzyl, 3-methoxy-benzyl, 3,5-dimethoxy-benzyl, pentafluorobenzyl, 2-phenyl-ethyl, 1-phenyl-2-propyl, 4-phenylbutyl, 4-phenylbenzyl, 2-phenylbenzyl,
(2,3-dimethoxy-phenyl)C(=O)—, (2,5-dimethoxy-phenyl)C(=O)—, (3,4-dimethoxy-phenyl)C(=O)—,
(3,5-dimethoxy-phenyl)C(=O)—, cyclopropyl-C(=O)—,
isopropyl-C(=O)—, ethyl-$CO_2$—, propyl-$CO_2$—, t-butyl-$CO_2$—,
2,6-dimethoxy-benzyl, 2,4-dimethoxy-benzyl, 2,4,6-trimethoxy-benzyl, 2,3-dimethoxy-benzyl, 2,4,5-trimethoxy-benzyl, 2,3,4-trimethoxy-benzyl, 3,4-dimethoxy-benzyl, 3,4,5-trimethoxy-benzyl, (4-fluoro-phenyl)ethyl,
—CH=$CH_2$, —$CH_2$—CH=$CH_2$, —CH=CH—$CH_3$, —C—CH, —C≡C—$CH_3$, and —$CH_2$—C≡CH;

$R^7$, $R^8$, and $R^9$, at each occurrence, are independently selected from
hydrogen, fluoro, chloro, bromo, cyano, methyl, ethyl, propyl, isopropyl, butyl, t-butyl, nitro, trifluoromethyl, methoxy, ethoxy, isopropoxy, trifluoromethoxy, phenyl,
methylC(=O)—, ethylC(=O)—, propylC(=O)—, isopropylC(=O)—, butylC(=O)—, phenylC(=O)—,
methyl$CO_2$—, ethyl$CO_2$—, propyl$CO_2$—, isopropyl$CO_2$—, butyl$CO_2$—, phenyl$CO_2$—,
dimethylamino-S(=O)—, diethylamino-S(=O)—, dipropylamino-S(=O)—, di-isopropylamino-S(=O)—, dibutylamino-S(=O)—, diphenylamino-S(=O)—,
dimethylamino-$SO_2$—, diethylamino-$SO_2$—, dipropylamino-$SO_2$—, di-isopropylamino-$SO_2$—, dibutylamino-$SO_2$—, diphenylamino-$SO_2$—,
dimethylamino-C(=O)—, diethylamino-C(=O)—, dipropylamino-C(=O)—, di-isopropylamino-C(=O)—, dibutylamino-C(=O)—, diphenylamino-C(=O)—,
2-chlorophenyl, 2-fluorophenyl, 2-bromophenyl, 2-cyanophenyl, 2-methylphenyl, 2-trifluoromethylphenyl,
2-methoxyphenyl, 2-trifluoromethoxyphenyl,
3-chlorophenyl, 3-fluorophenyl, 3-bromophenyl, 3-cyanophenyl, 3-methylphenyl, 3-ethylphenyl, 3-propylphenyl, 3-isopropylphenyl, 3-butylphenyl, 3-trifluoromethylphenyl, 3-methoxyphenyl, 3-isopropoxyphenyl, 3-trifluoromethoxyphenyl, 3-thiomethoxyphenyl,
4-chlorophenyl, 4-fluorophenyl, 4-bromophenyl, 4-cyanophenyl, 4-methylphenyl, 4-ethylphenyl, 4-propylphenyl, 4-isopropylphenyl, 4-butylphenyl, 4-trifluoromethylphenyl, 4-methoxyphenyl, 4-isopropoxyphenyl, 4-trifluoromethoxyphenyl, 4-thiomethoxyphenyl,
2,3-dichlorophenyl, 2,3-difluorophenyl, 2,3-dimethylphenyl,
2,3-ditrifluoromethylphenyl, 2,3-dimethoxyphenyl, 2,3-ditrifluoromethoxyphenyl,
2,4-dichlorophenyl, 2,4-difluorophenyl, 2,4-dimethylphenyl,
2,4-ditrifluoromethylphenyl, 2,4-dimethoxyphenyl, 2,4-ditrifluoromethoxyphenyl,
2,5-dichlorophenyl, 2,5-difluorophenyl, 2,5-dimethylphenyl,
2,5-ditrifluoromethylphenyl, 2,5-dimethoxyphenyl, 2,5-ditrifluoromethoxyphenyl,
2,6-dichlorophenyl, 2,6-difluorophenyl, 2,6-dimethylphenyl,
2,6-ditrifluoromethylphenyl, 2,6-dimethoxyphenyl, 2,6-ditrifluoromethoxyphenyl,
3,4-dichlorophenyl, 3,4-difluorophenyl, 3,4-dimethylphenyl,
3,4-ditrifluoromethylphenyl, 3,4-dimethoxyphenyl, 3,4-ditrifluoromethoxyphenyl,
2,4,6-trichlorophenyl, 2,4,6-trifluorophenyl,
2,4,6-trimethylphenyl, 2,4,6-tritrifluoromethylphenyl,
2,4,6-trimethoxyphenyl, 2,4,6-tritrifluoromethoxyphenyl,
2-chloro-4-$CF_3$-phenyl, 2-fluoro-3-chloro-phenyl,
2-chloro-4-$CF_3$-phenyl, 2-chloro-4-methoxy-phenyl,
2-methoxy-4-isopropyl-phenyl, 2-$CF_3$-4-methoxy-phenyl,
2-methyl-4-methoxy-5-fluoro-phenyl,
2-methyl-4-methoxy-phenyl, 2-chloro-4-$CF_3$O-phenyl,
2,4,5-trimethyl-phenyl, 2-methyl-4-chloro-phenyl,
methyl-C(=O)NH—, ethyl-C(=O)NH—, propyl-C(=O)NH—,
isopropyl-C(=O)NH—, butyl-C(=O)NH—, phenyl-C(=O)NH—,
4-acetylphenyl, 3-acetamidophenyl, 4-pyridyl, 2-furanyl,
2-thiophenyl, 2-naphthyl;
2-Me-5-F-phenyl, 2-F-5-Me-phenyl, 2-MeO-5-F-phenyl,
2-Me-3-Cl-phenyl, 3-$NO_2$-phenyl, 2-$NO_2$-phenyl,
2-Cl-3-Me-phenyl, 2-Me-4-EtO-phenyl, 2-Me-4-F-phenyl,
2-Cl-6-F-phenyl, 2-Cl-4-($CHF_2$)O-phenyl,
2,4-diMeO-6-F-phenyl, 2-$CF_3$-6-F-phenyl,
2-MeS-phenyl, 2,6-diCl-4-MeO-phenyl,
2,3,4-triF-phenyl, 2,6-diF-4-Cl-phenyl,
2,3,4,6-tetraF-phenyl, 2,3,4,5,6-pentaF-phenyl,
2-$CF_3$-4-EtO-phenyl, 2-$CF_3$-4-iPrO-phenyl,
2-$CF_3$-4-Cl-phenyl, 2-$CF_3$-4-F-phenyl, 2-Cl-4-EtO-phenyl,
2-Cl-4-iPrO-phenyl, 2-Et-4-MeO-phenyl,
2-CHO-4-MeO-phenyl, 2-CH(OH)Me-4-MeO-phenyl,
2-CH(OMe)Me-4-MeO-phenyl, 2-C(=O)Me-4-MeO-phenyl,
2-$CH_2$(OH)-4-MeO-phenyl, 2-$CH_2$(OMe)-4-MeO-phenyl,
2-CH(OH)Et-4-MeO-phenyl, 2-C(=O)Et-4-MeO-phenyl,
(Z)-2-CH=CH$CO_2$Me-4-MeO-phenyl,
2-$CH_2CH_2CO_2$Me-4-MeO-phenyl,
(Z)-2-CH=CH$CH_2$(OH)-4-MeO-phenyl,
(E)-2-CH=CH$CO_2$Me-4-MeO-phenyl,
(E)-2-CH=CH$CH_2$(OH)-4-MeO-phenyl,
2-$CH_2CH_2$OMe-4-MeO-phenyl,
2-F-4-MeO-phenyl, 2-Cl-4-F-phenyl,
(2-Cl-phenyl)-CH=CH—, (3-Cl-phenyl)-CH=CH—,
(2,6-diF-phenyl)-CH=CH—, —$CH_2$CH=$CH_2$, phenyl-CH=CH—, (2-Me-4-MeO-phenyl)-CH=CH—,
cyclohexyl, cyclopentyl, cyclohexylmethyl,
—CH$_2$CH$_2$CO$_2$Et, —(CH$_2$)$_3$CO$_2$Et, —(CH$_2$)$_4$CO$_2$Et,
benzyl, 2-F-benzyl, 3-F-benzyl, 4-F-benzyl,
3-MeO-benzyl, 3-OH-benzyl, 2-MeO-benzyl,
2-OH-benzyl, 2-CO$_2$Me-3-MeO-phenyl,
2-Me-4-CN-phenyl, 2-Me-3-CN-phenyl, 2-CF$_3$-4-CN-phenyl,
3-CHO-phenyl, 3-CH$_2$(OH)-phenyl, 3-CH$_2$(OMe)-phenyl,
3-CH$_2$(NMe$_2$)-phenyl, 3-CN-4-F-phenyl,
3-CONH$_2$-4-F-phenyl, 2-CH$_2$(NH$_2$)-4-MeO-phenyl-,
phenyl-NH—, (4-F-phenyl)-NH—, (2,4-diCl-phenyl)-NH—,
phenyl-C(=O)NH—, benzyl-NH—, (2-Me-4-MeO-phenyl)-NH—,
(2-F-4-MeO-phenyl)-NH—, (2-Me-4-F-phenyl)-NH—,
phenyl-S—, —NMe2,1-pyrrolidinyl, and
—N(tosylate)$_2$,
provided that two of R$^7$, R$^8$, and R$^9$, are independently selected from hydrogen, fluoro, chloro, bromo, cyano, methyl, ethyl, propyl, isopropyl, butyl, t-butyl, nitro, trifluoromethyl, methoxy, ethoxy, isopropoxy, and trifluoromethoxy;
m is 1, and
n is 0, 1 or 2.

8. The method as defined in claim 7 where the compound administered is a compound of Formula (V):

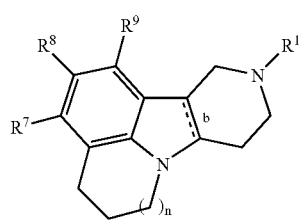

(V)

wherein:
b is a single bond, wherein the bridge hydrogens are in a cis position;
R$^1$ is selected from
hydrogen, methyl, ethyl, n-propyl, n-butyl, s-butyl, t-butyl, n-pentyl, n-hexyl, 2-propyl, 2-butyl, 2-pentyl, 2-hexyl, 2-methylpropyl, 2-methylbutyl, 2-methylpentyl, 2-ethylbutyl, 3-methylpentyl, 3-methylbutyl, 4-methylpentyl, 2-fluoroethyl, 2,2-difluoroethyl, 2,2,2-trifluoroethyl, 2-propenyl, 2-methyl-2-propenyl, trans-2-butenyl, 3-methyl-butenyl, 3-butenyl, trans-2-pentenyl, cis-2-pentenyl, 4-pentenyl, 4-methyl-3-pentenyl, 3,3-dichloro-2-propenyl,
trans-3-phenyl-2-propenyl, cyclopropyl, cyclobutyl, cyclopentyl, cyclohexyl, cyclopropylmethyl, cyclobutylmethyl, cyclopentylmethyl, cyclohexylmethyl,
—CH=CH$_2$, —CH$_2$—CH=CH$_2$, —CH=CH—CH$_3$, —C≡CH, —C≡C—CH$_3$,
and —CH$_2$—C≡CH;
R$^7$ and R$^9$, at each occurrence, are independently selected from hydrogen, fluoro, methyl, trifluoromethyl, and methoxy;

R$^8$ is selected from
hydrogen, fluoro, chloro, bromo, cyano, methyl, ethyl, propyl, isopropyl, butyl, t-butyl, nitro, trifluoromethyl, methoxy, ethoxy, isopropoxy, trifluoromethoxy, phenyl,
methylC(=O)—, ethylC(=O)—, propylC(=O)—, isopropylC(=O)—, butylC(=O)—, phenylC(=O)—,
methylCO$_2$—, ethylCO$_2$—, propylCO$_2$—, isopropylCO$_2$—, butylCO$_2$—, phenylCO$_2$—,
dimethylamino-S(=O)—, diethylamino-S(=O)—,
dipropylamino-S(=O)—, di-isopropylamino-S(=O)—, dibutylamino-S(=O)—, diphenylamino-S(=O)—,
dimethylamino-SO$_2$—, diethylamino-SO$_2$—, dipropylamino-SO$_2$—, di-isopropylamino-SO$_2$—, dibutylamino-SO$_2$—,
diphenylamino-SO$_2$—,
dimethylamino-C(=O)—, diethylamino-C(=O)—,
dipropylamino-C(=O)—, di-isopropylamino-C(=O)—, dibutylamino-C(=O)—, diphenylamino-C(=O)—,
2-chlorophenyl, 2-fluorophenyl, 2-bromophenyl, 2-cyanophenyl, 2-methylphenyl, 2-trifluoromethylphenyl,
2-methoxyphenyl, 2-trifluoromethoxyphenyl,
3-chlorophenyl, 3-fluorophenyl, 3-bromophenyl,
3-cyanophenyl, 3-methylphenyl, 3-ethylphenyl,
3-propylphenyl, 3-isopropylphenyl, 3-butylphenyl,
3-trifluoromethylphenyl, 3-methoxyphenyl,
3-isopropoxyphenyl, 3-trifluoromethoxyphenyl,
3-thiomethoxyphenyl,
4-chlorophenyl, 4-fluorophenyl, 4-bromophenyl,
4-cyanophenyl, 4-methylphenyl, 4-ethylphenyl,
4-propylphenyl, 4-isopropylphenyl, 4-butylphenyl,
4-trifluoromethylphenyl, 4-methoxyphenyl,
4-isopropoxyphenyl, 4-trifluoromethoxyphenyl,
4-thiomethoxyphenyl,
2,3-dichlorophenyl, 2,3-difluorophenyl, 2,3-dimethylphenyl,
2,3-ditrifluoromethylphenyl, 2,3-dimethoxyphenyl,
2,3-ditrifluoromethoxyphenyl,
2,4-dichlorophenyl, 2,4-difluorophenyl, 2,4-dimethylphenyl,
2,4-ditrifluoromethylphenyl, 2,4-dimethoxyphenyl,
2,4-ditrifluoromethoxyphenyl,
2,5-dichlorophenyl, 2,5-difluorophenyl, 2,5-dimethylphenyl,
2,5-ditrifluoromethylphenyl, 2,5-dimethoxyphenyl,
2,5-ditrifluoromethoxyphenyl,
2,6-dichlorophenyl, 2,6-difluorophenyl, 2,6-dimethylphenyl,
2,6-ditrifluoromethylphenyl, 2,6-dimethoxyphenyl,
2,6-ditrifluoromethoxyphenyl,
3,4-dichlorophenyl, 3,4-difluorophenyl, 3,4-dimethylphenyl,
3,4-ditrifluoromethylphenyl, 3,4-dimethoxyphenyl,
3,4-ditrifluoromethoxyphenyl,
2,4,6-trichlorophenyl, 2,4,6-trifluorophenyl,
2,4,6-trimethylphenyl, 2,4,6-tritrifluoromethylphenyl,
2,4,6-trimethoxyphenyl, 2,4,6-tritrifluoromethoxyphenyl,
2-chloro-4-CF$_3$-phenyl, 2-fluoro-3-chloro-phenyl,
2-chloro-4-CF$_3$-phenyl, 2-chloro-4-methoxy-phenyl,
2-methoxy-4-isopropyl-phenyl, 2-CF$_3$-4-methoxy-phenyl,
2-methyl-4-methoxy-5-fluoro-phenyl, 2-methyl-4-methoxy-phenyl, 2-chloro-4-$CF_3$O-phenyl,
2,4,5-trimethyl-phenyl, 2-methyl-4-chloro-phenyl,
methyl-C(=O)NH—, ethyl-C(=O)N-H—, propyl-C(=O)NH—,
isopropyl-C(=O)NH—, butyl-C(=O)NH—, phenyl-C(=O)NH—,
4-acetylphenyl, 3-acetamidophenyl, 4-pyridyl, 2-furanyl,
2-thiophenyl, 2-naphthyl;
2-Me-5-F-phenyl, 2-F-5-Me-phenyl, 2-MeO-5-F-phenyl,
2-Me-3-Cl-phenyl, 3-$NO_2$-phenyl, 2-$NO_2$-phenyl,
2-Cl-3-Me-phenyl, 2-Me-4-EtO-phenyl, 2-Me-4-F-phenyl,
2-Cl-6-F-phenyl, 2-C1–4-($CHF_2$)O-phenyl,
2,4-diMeO-6-F-phenyl, 2-$CF_3$-6-F-phenyl,
2-MeS-phenyl, 2,6-diCl-4-MeO-phenyl,
2,3,4-triF-phenyl, 2,6-diF-4-Cl-phenyl,
2,3,4,6-tetraF-phenyl, 2,3,4,5,6-pentaF-phenyl,
2-$CF_3$-4-EtO-phenyl, 2-$CF_3$-4-iPrO-phenyl,
2-$CF_3$-4-Cl-phenyl, 2-$CF_3$-4-F-phenyl, 2-Cl-4-EtO-phenyl,
2-Cl-4-iPrO-phenyl, 2-Et-4-MeO-phenyl,
2-CHO-4-MeO-phenyl, 2-CH(OH)Me-4-MeO-phenyl,
2-CH(OMe)Me-4-MeO-phenyl, 2-C(=O)Me-4-MeO-phenyl,
2-$CH_2$(OH)-4-MeO-phenyl, 2-$CH_2$(OMe)-4-MeO-phenyl,
2-CH(OH)Et-4-MeO-phenyl, 2-C(=O)Et-4-MeO-phenyl,
(Z)-2-CH=CH$CO_2$Me-4-MeO-phenyl,
2-$CH_2CH_2CO_2$Me-4-MeO-phenyl,
(Z)-2-CH=CH$CH_2$(OH)-4-MeO-phenyl,
(E)-2-CH=CH$CO_2$Me-4-MeO-phenyl,
(E)-2-CH=CH$CH_2$(OH)-4-MeO-phenyl,
2-$CH_2CH_2$OMe-4-MeO-phenyl,
2-F-4-MeO-phenyl, 2-Cl-4-F-phenyl,
(2-Cl-phenyl)-CH=CH—, (3-Cl-phenyl)-CH=CH—,
(2,6-diF-phenyl)-CH=CH—, —$CH_2$CH=$CH_2$,
phenyl-CH=CH—, (2-Me-4-MeO-phenyl)-CH=CH—,
cyclohexyl, cyclopentyl, cyclohexylmethyl,
—$CH_2CH_2CO_2$Et, —($CH_2$)$_3CO_2$Et, —($CH_2$)$_4CO_2$Et,
benzyl, 2-F-benzyl, 3-F-benzyl, 4-F-benzyl,
3-MeO-benzyl, 3-OH-benzyl, 2-MeO-benzyl,
2-OH-benzyl, 2-$CO_2$Me-3-MeO-phenyl,
2-Me-4-CN-phenyl, 2-Me-3-CN-phenyl, 2-$CF_3$-4-CN-phenyl,
3-CHO-phenyl, 3-$CH_2$(OH)-phenyl, 3-$CH_2$(OMe)-phenyl,
3-$CH_2$(N$Me_2$)-phenyl, 3-CN-4-F-phenyl,
3-$CONH_2$-4-F-phenyl, 2-$CH_2$($NH_2$)-4-MeO-phenyl-,
phenyl-NH—, (4-F-phenyl)-NH—, (2,4-diCl-phenyl)-NH—,
phenyl-C(=O)NH—, benzyl-NH—, (2-Me-4-MeO-phenyl)-NH—,
(2-F-4-MeO-phenyl)-NH—, (2-Me-4-F-phenyl)-NH—,
phenyl-S—, —N$Me_2$, 1-pyrrolidinyl, and
—N(tosylate)$_2$; and
n is 0, 1 or 2.

9. The method as defined in claim 1 where in the compound administered:

X is —CHR$^{10}$— or —C(=O)—;
R$^1$ is selected from
C$_{1-6}$ alkyl substituted with Z,
C$_{2-6}$ alkenyl substituted with Z,
C$_{2-6}$ alkynyl substituted with Z,
C$_{3-6}$ cycloalkyl substituted with Z,
aryl substituted with Z,
5–6 membered heterocyclic ring system containing at least one heteroatom selected from the group consisting of N, O, and S, said heterocyclic ring system substituted with Z;
C$_{1-6}$ alkyl substituted with 0–2 R$^2$,
C$_{2-6}$ alkenyl substituted with 0–2 R$^2$,
C$_{2-6}$ alkynyl substituted with 0–2 R$^2$,
aryl substituted with 0–2 R$^2$, and
5–6 membered heterocyclic ring system containing at least one heteroatom selected from the group consisting of N, O, and S, said heterocyclic ring system substituted with 0–2 R$^2$;

Z is selected from H,
—CH(OH)R$^2$,
—C(ethylenedioxy)R$^2$,
—SR$^2$,
—NR$^2$R$^3$,
—C(O)R$^2$,
—C(O)NR$^2$R$^3$,
—NR$^3$C(O)R$^2$,
—C(O)OR$^2$,
—OC(O)R$^2$,
—CH(=NR$^4$)NR$^2$R$^3$,
—NHC(=NR$^4$)NR$^2$R$^3$,
—S(O)R$^2$,
—S(O)$_2$R$^2$,
—S(O)$_2$NR$^2$R$^3$, and —NR$^3$S(O)$_2$R$^2$;

R$^2$, at each occurrence, is independently selected from
C$_{1-4}$ alkyl,
C$_{2-4}$ alkenyl,
C$_{2-4}$ alkynyl,
C$_{3-6}$ cycloalkyl,
aryl substituted with 0–5 R$^{42}$;
C$_{3-10}$ carbocyclic group substituted with 0–3 R$^{41}$, and
5–10 membered heterocyclic ring system containing from 1–4 heteroatoms selected from the group consisting of N, O, and S substituted with 0–3 R$^{41}$;

R$^3$, at each occurrence, is independently selected from
H, C$_{1-4}$ alkyl, C$_{2-4}$ alkenyl, C$_{2-4}$ alkynyl, and
C$_{1-4}$ alkoxy;

alternatively, R$^2$ and R$^3$ join to form a 5- or 6-membered ring optionally substituted with —O— or —N(R$^4$)—;

R$^4$, at each occurrence, is independently selected from H, methyl, ethyl, propyl, and butyl;

R$^5$ is H, methyl, ethyl, propyl, or butyl;

R$^{6a}$ is selected from
H, —OH, —NR$^{46}$R$^{47}$, —CF$_3$,
C$_{1-4}$ alkyl, C$_{2-4}$ alkenyl, C$_{2-4}$ alkynyl, C$_{1-4}$ alkoxy, C$_{1-4}$ haloalkyl, C$_{3-6}$ cycloalkyl, and
aryl substituted with 0–3 R$^{44}$;

R$^{6b}$ is H;

R$^7$, R$^8$, and R$^9$, at each occurrence, are independently selected from
H, halo, —CF$_3$, —OCF$_3$, —OH, —CN, —NO$_2$, —NR$^{46}$R$^{47}$,
C$_{1-8}$ alkyl, C$_{2-8}$ alkenyl, C$_{2-8}$ alkynyl, C$_{1-4}$ haloalkyl, C$_{1-8}$ alkoxy, (C$_{1-4}$ haloalkyl)oxy,
C$_{1-4}$ alkyl substituted with 0–2 R$^{11}$,
C$_{3-10}$ carbocyclic group substituted with 0–3 R$^{33}$,
aryl substituted with 0–5 R$^{33}$,
5–10 membered heterocyclic ring system containing from 14 heteroatoms selected from the group consisting of N, O, and S substituted with 0–3 R$^{31}$;

OR$^{12}$, SR$^{12}$, NR$^{12}$R$^{13}$, C(O)H, C(O)R$^{12}$, C(O)
NR$^{12}$R$^{13}$, NR$^{14}$C(O)R$^{12}$, C(O)OR$^{12}$, OC(O)R$^{12}$,
OC(O)OR$^{12}$, CH(=NR$^{14}$)NR$^{12}$R$^{13}$, NHC(=NR$^{14}$)
NR$^{12}$R$^{13}$, S(O)R$^{12}$, S(O)$_2$R$^{12}$, S(O)NR$^{12}$R$^{13}$, S(O)$_2$
NR$^{12}$R$^{13}$, NR$^{14}$S(O)R$^{12}$, NR$^{14}$S(O)$_2$R$^{12}$, NR$^{12}$C(O)
R$^{15}$, NR$^{12}$C(O)OR$^{15}$, NR$^{12}$S(O)$_2$R$^{15}$, and NR$^{12}$C(O)
NHR$^{15}$;

R$^{10}$ is selected from H, —OH,
C$_{1-6}$ alkyl substituted with 0–1 R$^{10B}$,
C$_{2-6}$ alkenyl substituted with 0–1 R$^{10B}$,
C$_{2-6}$ alkynyl substituted with 0–1 R$^{10B}$, and
C$_{1-6}$ alkoxy;

R$^{10B}$ is selected from
C$_{1-4}$ alkoxy,
C$_{3-6}$ cycloalkyl,
C$_{3-10}$ carbocyclic group substituted with 0–3 R$^{33}$,
phenyl substituted with 0–3 R$^{33}$, and
5–6 membered heterocyclic ring system containing 1, 2, or 3 heteroatoms selected from the group consisting of N, O, and S substituted with 0–2 R$^{44}$;

R$^{11}$ is selected from
H, halo, —CF$_3$, —CN, —NO$_2$,
C$_{1-8}$ alkyl, C$_{2-8}$ alkenyl, C$_{2-8}$ alkynyl, C$_{1-4}$ haloalkyl, C$_{1-8}$ alkoxy, C$_{3-10}$ cycloalkyl,
C$_{3-10}$ carbocyclic group substituted with 0–3 R$^{33}$,
aryl substituted with 0–5 R$^{33}$,
5–10 membered heterocyclic ring system containing from 1–4 heteroatoms selected from the group consisting of N, O, and S substituted with 0–3 R$^{31}$;
OR$^{12}$, SR$^{12}$, NR$^{12}$R$^{13}$, C(O)H, C(O)R$^{12}$, C(O)
NR$^{12}$R$^{13}$, NR$^{14}$C(O)R$^{12}$, C(O)OR$^{12}$, OC(O)R$^{12}$,
OC(O)OR$^{12}$, CH(=NR$^{14}$)NR$^{12}$R$^{13}$, NHC(=NR$^{14}$)
NR$^{12}$R$^{13}$, S(O)R$^{12}$, S(O)$_2$R$^{12}$, S(O)NR$^{12}$R$^{13}$, S(O)$_2$
NR$^{12}$R$^{13}$, NR$^{14}$S(O)R$^{12}$, and NR$^{14}$S(O)$_2$R$^{12}$;

R$^{12}$, at each occurrence, is independently selected from
C$_{1-4}$ alkyl,
C$_{2-4}$ alkenyl,
C$_{2-4}$ alkynyl,
C$_{3-6}$ cycloalkyl,
phenyl substituted with 0–5 R$^{33}$;
C$_{3-10}$ carbocyclic group substituted with 0–3 R$^{33}$, and
5–10 membered heterocyclic ring system containing from 1–4 heteroatoms selected from the group consisting of N, O, and S substituted with 0–3 R$^{31}$;

R$^{13}$, at each occurrence, is independently selected from
H, C$_{1-4}$ alkyl, C$_{2-4}$ alkenyl, and C24 alknyl;
alternatively, R$^{12}$ and R$^{13}$ join to form a 5- or 6-membered ring optionally substituted with —O— or —N(R$^{14}$)—;

R$^{14}$, at each occurrence, is independently selected from H and C$_{1-4}$ alkyl;

R$^{31}$, at each occurrence, is independently selected from
H, OH, halo, CF$_3$, SO$_2$R$^{45}$, NR$^{46}$R$^{47}$, methyl, ethyl, and propyl;

R$^{33}$, at each occurrence, is independently selected from
H, OH, halo, CN, NO$_2$, CF$_3$, SO$_2$R$^{45}$, NR$^{46}$R$^{47}$,
C$_{1-3}$ alkyl, C$_{2-3}$ alkenyl, C$_{2-3}$ alkynyl, C$_{3-5}$ cycloalkyl, C$_{1-3}$ haloalkyl, C$_{1-3}$ haloalkyl-oxy-, C$_{1-3}$ alkyloxy-, C$_{1-3}$ alkylthio-, C$_{1-3}$ alkyl-C(=O)—, and C$_{1-3}$ alkyl-C(=O)NH—;

R$^{41}$, at each occurrence, is independently selected from
H, CF$_3$, halo, OH, CO$_2$H, SO$_2$R$^{45}$, NR$^{46}$R$^{47}$, NO$_2$, CN,
=O,
C$_{2-8}$ alkenyl, C$_{2-8}$ alkynyl, C$_{1-4}$ alkoxy, C$_{1-4}$ haloalkyl
C$_{1-4}$ alkyl substituted with 0–1 R$^{43}$,
aryl substituted with 0–3 R$^{42}$, and
5–10 membered heterocyclic ring system containing from 1–4 heteroatoms selected from the group consisting of N, O, and S substituted with 0–3 R$^{44}$;

R$^{42}$, at each occurrence, is independently selected from
H, CF$_3$, halo, OH, CO$_2$H, SO$_2$R$^{45}$, SR$^{45}$, NR$^{46}$R$^{47}$, OR$^{48}$, NO$_2$, CN, CH(=NH)NH$_2$, NHC(=NH)NH$_2$,
C$_{2-6}$ alkenyl, C$_{2-6}$ alkynyl, C$_{1-4}$ alkoxy, C$_{1-4}$ haloalkyl,
C$_{3-6}$ cycloalkyl,
C$_{1-4}$ alkyl substituted with 0–1 R$^{43}$,
aryl substituted with 0–3 R$^{44}$, and
5–10 membered heterocyclic ring system containing from 1–4 heteroatoms selected from the group consisting of N, O, and S substituted with 0–3 R$^{44}$;

R$^{43}$ is C$_{3-6}$ cycloalkyl or aryl substituted with 0–3 R$^{44}$;

R$^{44}$, at each occurrence, is independently selected from H,
halo, —OH, NR$^{46}$R$^{47}$, CO$_2$H, SO$_2$R$^{45}$, —CF$_3$,
—OCF$_3$, —CN, —NO$_2$, C$_{1-4}$ alkyl, and C$_{1-4}$ alkoxy;

R$^{45}$ is C$_{1-4}$ alkyl;

R$^{46}$, at each occurrence, is independently selected from H and C$_{1-4}$ alkyl;

R$^{47}$, at each occurrence, is independently selected from H,
C$_{1-4}$ alkyl,
—C(=O)NH(C$_{1-4}$ alkyl), —SO$_2$(C$_{1-4}$ alkyl),
—SO$_2$(phenyl), —C(=O)O(C$_{1-4}$ alkyl), —C(=O)
(C$_{1-4}$ alkyl), and —C(=O)H;

R$^{48}$, at each occurrence, is independently selected from H,
C$_{1-4}$ alkyl,
—C(=O)NH(C$_{1-4}$ alkyl), —C(=O)O(C$_{1-4}$ alkyl),
—C(=O)(C$_{1-4}$ alkyl), and —C(=O)H;

k is 1 or 2;
m is 0, 1, or 2; and
n is 0, 1 or 2.

10. The method as defined in claim 9 where in the compound administered:

X is —CHR$^{10}$— or —C(=O)—;
R$^{1}$ is selected from
C$_{2-5}$ alkyl substituted with Z,
C$_{2-5}$ alkenyl substituted with Z,
C$_{2-5}$ alkynyl substituted with Z,
C$_{3-6}$ cycloalkyl substituted with Z,
aryl substituted with Z,
5–6 membered heterocyclic ring system containing at least one heteroatom selected from the group consisting of N, O, and S, said heterocyclic ring system substituted with Z;
C$_{1-5}$ alkyl substituted with 0–2 R$^2$,
C$_{2-5}$ alkenyl substituted with 0–2 R$^2$, and
C$_{2-5}$ alkynyl substituted with 0–2 R$^2$;

Z is selected from H,
—CH(OH)R$^2$,
—C(ethylenedioxy)R$^2$,
—SR$^2$,
—NR$^2$R$^3$,
—C(O)R$^2$,
—C(O)NR$^2$R$^3$,
—NR$^3$C(O)R$^2$,
—C(O)OR$^2$,
—OC(O)R$^2$,
—CH(=NR$^4$)NR$^2$R$^3$,
—NHC(=NR$^4$)NR$^2$R$^3$,
—S(O)R$^2$,
—S(O)$_2$R$^2$,
—S(O)$_2$NR$^2$R$^3$, and —NR$^3$S(O)$_2$R$^2$;

R$^2$, at each occurrence, is independently selected from
C$_{1-4}$ alkyl,
C$_{2-4}$ alkenyl,
C$_{2-4}$ alkynyl, $C_{3-6}$ cycloalkyl,
aryl substituted with 0–5 $R^{42}$;
$C_{3-10}$ carbocyclic group substituted with 0–3 $R^{41}$, and
5–10 membered heterocyclic ring system containing from 1–4 heteroatoms selected from the group consisting of N, O, and S substituted with 0–3 $R^{41}$;

$R^3$, at each occurrence, is independently selected from
H, $C_{1-4}$ alkyl, $C_{2-4}$ alkenyl, $C_{2-4}$ alkynyl, and
$C_{1-4}$ alkoxy;
alternatively, $R^2$ and $R^3$ join to form a 5- or 6-membered ring optionally substituted with —O— or —N($R^4$)—;

$R^4$, at each occurrence, is independently selected from H, methyl, ethyl, propyl, and butyl;

$R^5$ is H, methyl, or ethyl;

$R^{6a}$ is selected from
H, —OH, —N$R^{46}R^{47}$, —$CF_3$,
$C_{1-4}$ alkyl, $C_{2-4}$ alkenyl, $C_{2-4}$ alkynyl, $C_{1-4}$ alkoxy, $C_{1-4}$ haloalkyl, and $C_{3-6}$ cycloalkyl;

$R^{6b}$ is H;

$R^7$, $R^8$, and $R^9$, at each occurrence, are independently selected from
H, halo, —$CF_3$, —$OCF_3$, —OH, —$OCH_3$, —CN, —$NO_2$, —N$R^{46}R^{47}$,
$C_{1-6}$ alkyl, $C_{2-6}$ alkenyl, $C_{2-6}$ alkynyl, $C_{1-4}$ haloalkyl, $C_{1-6}$ alkoxy, ($C_{1-4}$ haloalkyl)oxy,
$C_{1-4}$ alkyl substituted with 0–2 $R^{11}$,
$C_{3-10}$ carbocyclic group substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
O$R^{12}$, S$R^{12}$, N$R^{12}R^{13}$, C(O)H, C(O)$R^{12}$, C(O)N$R^{12}R^{13}$, N$R^{14}$C(O)$R^{12}$, C(O)O$R^{12}$, OC(O)$R^{12}$, CH(=N$R^{14}$)N$R^{12}R^{13}$, NHC(=N$R^{14}$)N$R^{12}R^{13}$, S(O)$R^{12}$, S(O)$_2R^{12}$, S(O)$_2$N$R^{12}R^{13}$, N$R^{14}$S(O)$_2R^{12}$, N$R^{14}$S(O)$R^{12}$, N$R^{14}$S(O)$_2R^{12}$, N$R^{12}$C(O)$R^{15}$, N$R^{12}$C(O)O$R^{15}$, N$R^{12}$S(O)$_2R^{15}$, and N$R^{12}$C(O)NH$R^{15}$;

$R^{10}$ is selected from H, —OH, $C_{1-6}$ alkyl, $C_{1-4}$ alkoxy, and $C_{1-2}$ alkyl substituted with 0–1 $R^{10B}$;

$R^{10B}$ is $C_{3-6}$ cycloalkyl or
phenyl substituted with 0–3 $R^{33}$;

$R^{11}$ is selected from
H, halo, —$CF_3$, —$OCF_3$, —OH, —$OCH_3$, —CN, —$NO_2$, —N$R^{46}R^{47}$,
$C_{1-6}$ alkyl, $C_{2-6}$ alkenyl, $C_{2-6}$ alkynyl, $C_{1-4}$ haloalkyl, $C_{1-6}$ alkoxy, ($C_{1-4}$ haloalkyl)oxy,
$C_{3-10}$ carbocyclic group substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
O$R^{12}$, S$R^{12}$, N$R^{12}R^{13}$, C(O)H, C(O)$R^{12}$, C(O)N$R^{12}R^{13}$, N$R^{14}$C(O)$R^{12}$, C(O)O$R^{12}$, OC(O)$R^{12}$, CH(=N$R^{14}$)N$R^{12}R^{13}$, NHC(=N$R^{14}$)N$R^{12}R^{13}$, S(O)$R^{12}$, S(O)$_2R^{12}$, S(O)$_2$N$R^{12}R^{13}$, and N$R^{14}$S(O)$_2R^{12}$;

$R^{12}$, at each occurrence, is independently selected from
$C_{1-4}$ alkyl,
$C_{2-4}$ alkenyl,
$C_{2-4}$ alkynyl,
$C_{3-6}$ cycloalkyl,
phenyl substituted with 0–5 $R^{33}$;
$C_{3-10}$ carbocyclic group substituted with 0–3 $R^{33}$, and
5–10 membered heterocyclic ring system containing from 1–4 heteroatoms selected from the group consisting of N, O, and S substituted with 0–3 $R^{31}$;

$R^{13}$, at each occurrence, is independently selected from
H, $C_{1-4}$ alkyl, $C_{2-4}$ alkenyl, and $C_{2-4}$ alkynyl;
alternatively, $R^{12}$ and $R^{13}$ join to form a 5- or 6-membered ring optionally substituted with —O— or —N($R^{14}$)—;

$R^{14}$, at each occurrence, is independently selected from H and $C_{1-4}$ alkyl;

$R^{31}$, at each occurrence, is independently selected from
H, OH, halo, $CF_3$, methyl, and ethyl;

$R^{33}$, at each occurrence, is independently selected from
H, OH, halo, CN, $NO_2$, $CF_3$, methyl, and ethyl;

$R^{41}$, at each occurrence, is independently selected from
H, $CF_3$, halo, OH, $CO_2$H, $SO_2R^{45}$, N$R^{46}R^{47}$, $NO_2$, CN, =O,
$C_{2-8}$ alkenyl, $C_{2-8}$ alkynyl, $C_{1-4}$ alkoxy, $C_{1-4}$ haloalkyl,
$C_{1-4}$ alkyl substituted with 0–1 $R^{43}$,
aryl substituted with 0–3 $R^{42}$, and
5–10 membered heterocyclic ring system containing from 1–4 heteroatoms selected from the group consisting of N, O, and S substituted with 0–3 $R^{44}$;

$R^{42}$, at each occurrence, is independently selected from
H, $CF_3$, halo, OH, $CO_2$H, $SO_2R^{45}$, S$R^{45}$, N$R^{46}R^{47}$, O$R^{48}$, $NO_2$, CN, CH(=NH)$NH_2$, NHC(=NH)$NH_2$,
$C_{2-6}$ alkenyl, $C_{2-6}$ alkynyl, $C_{1-4}$ alkoxy, $C_{1-4}$ haloalkyl, $C_{3-6}$ cycloalkyl,
$C_{1-4}$ alkyl substituted with 0–1 $R^{43}$,
aryl substituted with 0–3 $R^{44}$, and
5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, —OH, N$R^{46}R^{47}$, $CO_2$H, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-3}$ alkyl;

$R^{47}$, at each occurrence, is independently selected from H, $C_{1-4}$ alkyl,
—C(=O)NH($C_{1-4}$ alkyl), —$SO_2$($C_{1-4}$ alkyl),
—$SO_2$(phenyl), —C(=O)O($C_{1-4}$ alkyl), —C(=O)($C_{1-4}$ alkyl), and —C(=O)H;

$R^{48}$, at each occurrence, is independently selected from H, $C_{1-4}$ alkyl,
—C(=O)NH($C_{1-4}$ alkyl), —C(=O)O($C_{1-4}$ alkyl),
—C(=O)(C1A alkyl), and —C(=O)H;

k is 1 or 2;
m is 0, 1, 2; and
n is 0, 1 or 2.

11. The method as defined in claim 9 where in the compound administered:

X is —$CH_2$—;

$R^1$ is selected from
$C_{2-4}$ alkyl substituted with Z,
$C_{2-4}$ alkenyl substituted with Z,
$C_{2-4}$ alkynyl substituted with Z,
$C_{3-6}$ cycloalkyl substituted with Z,
aryl substituted with Z,
5–6 membered heterocyclic ring system containing at least one heteroatom selected from the group consisting of N, O, and S, said heterocyclic ring system substituted with Z;
$C_{2-4}$ alkyl substituted with 0–2 $R^2$, and
$C_{2-4}$ alkenyl substituted with 0–2 $R^2$;

Z is selected from H,
—CH(OH)$R^2$,
—C(ethylenedioxy)$R^2$,
—S$R^2$,

—NR$^2$R$^3$,
—C(O)R$^2$,
—C(O)NR$^2$R$^3$,
—NR$^3$C(O)R$^2$,
—C(O)OR$^2$,
—S(O)R$^2$,
—S(O)$_2$R$^2$,
—S(O)$_2$NR$^2$R$^3$, and —NR$^3$S(O)$_2$R$^2$;

R$^2$, at each occurrence, is independently selected from
  phenyl substituted with 0–5 R$^{42}$;
  C$_{3-10}$ carbocyclic group substituted with 0–3 R$^{41}$, and
  5–10 membered heterocyclic ring system containing from 1–4 heteroatoms selected from the group consisting of N, O, and S substituted with 0–3 R$^{41}$;

R$^3$, at each occurrence, is independently selected from
  H, C$_{1-4}$ alkyl, C$_{2-4}$ alkenyl, C$_{2-4}$ alkynyl, and
  C$_{1-4}$ alkoxy;

alternatively, R$^2$ and R$^3$ join to form a 5- or 6-membered ring optionally substituted with —O— or —N(R$^4$)—;

R$^4$, at each occurrence, is independently selected from H, methyl, ethyl, propyl, and butyl;

R$^5$ is H;

R$^{6a}$ is selected from H, —OH, —CF$_3$, methyl, ethyl, propyl, butyl, methoxy, and, ethoxy;

R$^{6b}$ is H;

R$^7$, R$^8$, and R$^9$, at each occurrence, are independently selected from
  H, halo, —CF$_3$, —OCF$_3$, —OH, —OCH$_3$, —CN, —NO$_2$,
  C$_{1-4}$ alkyl, C$_{1-4}$ haloalkyl, C$_{1-4}$ alkoxy, (C$_{1-3}$ haloalkyl)oxy, and
  C$_{1-4}$ alkyl substituted with 0–2 R$^{11}$;

R$^{11}$ is selected from
  H, halo, —CF$_3$, —OCF$_3$, —OH, —OCH$_3$, —CN, —NO$_2$,
  C$_{1-4}$ alkyl, C$_{1-4}$ haloalkyl, C$_{1-4}$ alkoxy, and (C$_{1-3}$ haloalkyl)oxy;

R$^{33}$, at each occurrence, is independently selected from
  H, OH, halo, CF$_3$, and methyl;

R$^{41}$, at each occurrence, is independently selected from
  H, CF$_3$, halo, OH, CO$_2$H, SO$_2$R$^{45}$, NR$^{46}$R$^{47}$, NO$_2$, CN, =O,
  C$_{2-8}$ alkenyl, C$_{2-8}$ alkynyl, C$_{1-4}$ alkoxy, C$_{1-4}$ haloalkyl,
  C$_{1-4}$ alkyl substituted with 0–1 R$^{43}$,
  aryl substituted with 0–3 R$^{42}$, and
  5–10 membered heterocyclic ring system containing from 1–4 heteroatoms selected from the group consisting of N, O, and S substituted with 0–3 R$^{44}$;

R$^{42}$, at each occurrence, is independently selected from
  H, CF$_3$, halo, OH, CO$_2$H, SO$_2$R$^{45}$, SR$^{45}$, NR$^{46}$R$^{47}$, OR$^{48}$, NO$_2$, CN, CH(=NH)NH$_2$, NHC(=NH)NH$_2$,
  C$_{2-6}$ alkenyl, C$_{2-6}$ alkynyl, C$_{1-4}$ alkoxy, C$_{1-4}$ haloalkyl, C$_{3-6}$ cycloalkyl,
  C$_{1-4}$ alkyl substituted with 0–1 R$^{43}$,
  aryl substituted with 0–3 R$^{44}$, and
  5–10 membered heterocyclic ring system containing from 1–4 heteroatoms selected from the group consisting of N, O, and S substituted with 0–3 R$^{44}$;

R$^{43}$ is cyclopropyl, cyclobutyl, cyclopentyl, cyclohexyl, phenyl, or pyridyl, each substituted with 0–3 R$^{44}$;

R$^{44}$, at each occurrence, is independently selected from H, halo, —OH, NR$^{46}$R$^{47}$, CO$_2$H, SO$_2$R$^{45}$, —CF$_3$, —OCF$_3$, —CN, —NO$_2$, methyl, ethyl, propyl, butyl, methoxy, ethoxy, propoxy, and butoxy;

R$^{45}$ is methyl, ethyl, propyl, or butyl;

R$^{46}$, at each occurrence, is independently selected from H, methyl, ethyl, propyl, and butyl;

R$^{47}$, at each occurrence, is independently selected from
  H, methyl, ethyl, n-propyl, i-propyl, n-butyl,
  i-butyl, —C(=O)NH(methyl), —C(=O)NH(ethyl),
  —SO$_2$(methyl), —SO$_2$(ethyl), —SO$_2$(phenyl),
  —C(=O)O(methyl), —C(=O)O(ethyl), —C(=O)(methyl),
  —C(=O)(ethyl), and —C(=O)H;

R$^{48}$, at each occurrence, is independently selected from
  H, methyl, ethyl, n-propyl, i-propyl, —C(=O)NH(methyl), —C(=O)NH(ethyl), —C(=O)O(methyl), —C(=O)O(ethyl), —C(=O)(methyl), —C(=O)(ethyl), and —C(=O)H:

k is 1;
m is 0, 1, or 2; and
n is 0, 1 or 2.

12. The method as defined in claim 9 where in the compound administered:

X is —CH$_2$—;

R$^1$ is selected from
  ethyl substituted with Z,
  propyl substituted with Z,
  butyl substituted with Z,
  propenyl substituted with Z,
  butenyl substituted with Z,
  ethyl substituted with R$^2$,
  propyl substituted with R$^2$,
  butyl substituted with R$^2$,
  propenyl substituted with R$^2$, and
  butenyl substituted with R$^2$;

Z is selected from H,
  —CH(OH)R$^2$,
  —OR$^2$,
  —SR$^2$,
  —NR$^2$R$^3$,
  —C(O)R$^2$,
  —C(O)NR$^2$R$^3$,
  —NR$^3$C(O)R$^2$,
  —C(O)OR$^2$,
  —S(O)R$^2$,
  —S(O)$_2$R$^2$,
  —S(O)$_2$NR$^2$R$^3$, and —NR$^3$S(O)$_2$R$^2$;

R$^2$, at each occurrence, is independently selected from
  phenyl substituted with 0–3 R$^{42}$;
  naphthyl substituted with 0–3 R$^{42}$;
  cyclopropyl substituted with 0–3 R$^{41}$;
  cyclobutyl substituted with 0–3 R$^{41}$;
  cyclopentyl substituted with 0–3 R$^{41}$;
  cyclohexyl substituted with 0–3 R$^{41}$;
  pyridyl substituted with 0–3 R$^{41}$;
  indolyl substituted with 0–3 R$^{41}$;
  indolinyl substituted with 0–3 R$^{41}$;
  benzimidazolyl substituted with 0–3 R$^{41}$;
  benzotriazolyl substituted with 0–3 R$^{41}$;
  benzothienyl substituted with 0–3 R$^{41}$;
  benzofuranyl substituted with 0–3 R$^{41}$;
  phthalimid-1-yl substituted with 0–3 R$^{41}$;
  inden-2-yl substituted with 0–3 R$^{41}$;
  2,3-dihydro-1H-inden-2-yl substituted with 0–3 R$^{41}$;
  indazolyl substituted with 0–3 R$^{41}$;
  tetrahydroquinolinyl substituted with 0–3 R$^{41}$; and
  tetrahydro-isoquinolinyl substituted with 0–3 R$^{41}$;

R$^3$, at each occurrence, is independently selected from
  H, methyl, and ethyl;

R$^5$ is H;

R$^{6a}$ is selected from H, —OH, methyl, and methoxy;

R$^{6b}$ is H;

R[7], R[8], and R[9], at each occurrence, are independently selected from H, F, Cl, methyl, ethyl, methoxy, —CF$_3$, and —OCF$_3$;

R[41], at each occurrence, is independently selected from H, F, Cl, Br, OH, CF$_3$, NO$_2$, CN, =O, methyl, ethyl, propyl, butyl, methoxy, and ethoxy;

R[42], at each occurrence, is independently selected from H, F, Cl, Br, OH, CF$_3$, SO$_2$R[45], SR[45], NR[46]R[47], OR[48], NO$_2$, CN, =O, methyl, ethyl, propyl, butyl, methoxy, and ethoxy;

R[45] is methyl, ethyl, propyl, or butyl;

R[46], at each occurrence, is independently selected from H, methyl, ethyl, propyl, and butyl;

R[47], at each occurrence, is independently selected from H, methyl, ethyl, n-propyl, i-propyl, n-butyl, i-butyl, —C(=O)NH(methyl), —C(=O)NH(ethyl), —SO$_2$(methyl), —SO$_2$(ethyl), —SO$_2$(phenyl), —C(=O)O(methyl), —C(=O)O(ethyl), —C(=O)(methyl), —C(=O)(ethyl), and —C(=O)H;

R[48], at each occurrence, is independently selected from H, methyl, ethyl, n-propyl, i-propyl, —C(=O)NH(methyl), —C(=O)NH(ethyl), —C(=O)O(methyl), —C(=O)O(ethyl), —C(=O)(methyl), —C(=O)(ethyl), and —C(=O)H;

k is 1;
m is 0, 1, or 2; and
n is 0, 1 or 2.

13. The method as defined in claim 9 where the compound administered is a compound of Formula (I-a):

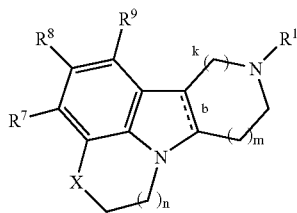

(I-a)

wherein:
b is a single bond;
X is —CH$_2$—, CH(OH)—, or —C(=O)—
R[1] is selected from
—(CH$_2$)$_3$C(=O)(4-fluoro-phenyl),
—(CH$_2$)$_3$C(=O)(4-bromo-phenyl),
—(CH$_2$)$_3$C(=O)(4-methyl-phenyl),
—(CH$_2$)$_3$C(=O)(4-methoxy-phenyl),
—(CH$_2$)$_3$C(=O)(4-(3,4-dichloro-phenyl)phenyl),
—(CH$_2$)$_3$C(=O)(3-methyl-4-fluoro-phenyl),
—(CH$_2$)$_3$C(=O)(2,3-dimethoxy-phenyl),
—(CH$_2$)$_3$C(=O)(phenyl),
—(CH$_2$)$_3$C(=O)(4-chloro-phenyl),
—(CH$_2$)$_3$C(=O)(3-methyl-phenyl),
—(CH$_2$)$_3$C(=O)(4-t-butyl-phenyl),
—(CH$_2$)$_3$C(=O)(3,4-difluoro-phenyl),
—(CH$_2$)$_3$C(=O)(2-methoxy-5-fluoro-phenyl),
—(CH$_2$)$_3$C(=O)(4-fluoro-1-naphthyl),
—(CH$_2$)$_3$C(=O)(benzyl),
—(CH$_2$)$_3$C(=O)(4-pyridyl),
—(CH$_2$)$_3$C(=O)(3-pyridyl),
—(CH$_2$)$_3$CH(OH)(4-fluoro-phenyl),
—(CH$_2$)$_3$CH(OH)(4-pyridyl),
—(CH$_2$)$_3$CH(OH)(2,3-dimethoxy-phenyl),
—(CH$_2$)$_3$S(3-fluoro-phenyl),
—(CH$_2$)$_3$S(4-fluoro-phenyl),
—(CH$_2$)$_3$S(=O)(4-fluoro-phenyl),
—(CH$_2$)$_3$SO$_2$(3-fluoro-phenyl),
—(CH$_2$)$_3$SO$_2$(4-fluoro-phenyl),
—(CH$_2$)$_3$O(4-fluoro-phenyl),
—(CH$_2$)$_3$O(phenyl),
—(CH$_2$)$_3$O(3-pyridyl),
—(CH$_2$)$_3$O(4-pyridyl),
—(CH$_2$)$_3$O(2-NH$_2$-phenyl),
—(CH$_2$)$_3$O(2-NH$_2$-5-F-phenyl),
—(CH$_2$)$_3$O(2-NH$_2$-4-F-phenyl),
—(CH$_2$)$_3$O(2-NH$_2$-3-F-phenyl),
—(CH$_2$)$_3$O(2-NH$_2$-4-Cl-phenyl),
—(CH$_2$)$_3$O(2-NH$_2$-4-OH-phenyl),
—(CH$_2$)$_3$O(2-NH$_2$-4-Br-phenyl),
—(CH$_2$)$_3$O(2-NHC(=O)Me-4-F-phenyl),
—(CH$_2$)$_3$O(2-NHC(=O)Me-phenyl),
—(CH$_2$)$_3$NH(4-fluoro-phenyl),
—(CH$_2$)$_3$N(methyl)(4-fluoro-phenyl),
—(CH$_2$)$_3$CO$_2$(ethyl),
—(CH$_2$)$_3$C(=O)N(methyl)(methoxy),
—(CH$_2$)$_3$C(=O)NH(4-fluoro-phenyl),
—(CH$_2$)$_2$NHC(=O)(phenyl),
—(CH$_2$)$_2$NMeC(=O)(phenyl),
—(CH$_2$)$_2$NHC(=O)(2-fluoro-phenyl),
—(CH$_2$)$_2$NMeC(=O)(2-fluoro-phenyl),
—(CH$_2$)$_2$NHC(=O)(4-fluoro-phenyl),
—(CH$_2$)$_2$NMeC(=O)(4-fluoro-phenyl),
—(CH$_2$)$_2$NHC(=O)(2,4-difluoro-phenyl),
—(CH$_2$)$_2$NMeC(=O)(2,4-difluoro-phenyl),
—(CH$_2$)$_3$(3-indolyl),
—(CH$_2$)$_3$(1-methyl-3-indolyl),
—(CH$_2$)$_3$(1-indolyl),
—(CH$_2$)$_3$(1-indolinyl),
—(CH$_2$)$_3$(1-benzimidazolyl),
—(CH$_2$)$_3$(1H-1,2,3-benzotriazol-1-yl),
—(CH$_2$)$_3$(1H-1,2,3-benzotriazol-2-yl),
—(CH$_2$)$_2$(1H-1,2,3-benzotriazol-1-yl),
—(CH$_2$)$_2$(1H-1,2,3-benzotriazol-2-yl),
—(CH$_2$)$_3$(3,4 dihydro-1(2H)-quinolinyl),
—(CH$_2$)$_2$C(=O)(4-fluoro-phenyl),
—(CH$_2$)$_2$C(=O)NH(4-fluoro-phenyl),
—CH$_2$CH$_2$(3-indolyl),
—CH$_2$CH$_2$(1-phthalimidyl),
—(CH$_2$)$_4$C(=O)N(methyl)(methoxy),
—(CH$_2$)$_4$CO$_2$(ethyl),
—(CH$_2$)$_4$C(=O)(Phenyl),
—(CH$_2$)$_4$(cyclohexyl),
—(CH$_2$)$_3$CH(phenyl)$_2$,
—CH$_2$CH$_2$CH=C(phenyl)$_2$,
—CH$_2$CH$_2$CH=CMe(4-F-phenyl),
—(CH$_2$)$_3$CH(4-fluoro-phenyl)$_2$,
—CH$_2$CH$_2$CH=C(4-fluoro-phenyl)$_2$,
—(CH$_2$)$_2$(2,3-dihydro-1H-inden-2-yl),
—(CH$_2$)$_3$C(=O)(2-NH$_2$-phenyl),
—(CH$_2$)$_3$C(=O)(2-NH$_2$-5-F-phenyl),
—(CH$_2$)$_3$C(=O)(2-NH$_2$-4-F-phenyl),
—(CH$_2$)$_3$C(=O)(2-NH$_2$-3-F-phenyl),
—(CH$_2$)$_3$C(=O)(2-NH$_2$-4-Cl-phenyl),
—(CH$_2$)$_3$,C(=O)(2-NH$_2$-4-OH-phenyl),
—(CH$_2$)$_3$C(=O)(2-NH$_2$-4-Br-phenyl),
—(CH$_2$)$_3$(1H-indazol-3-yl),
—(CH$_2$)$_3$(5-F-1H-indazol-3-yl),
—(CH$_2$)$_3$(7-F-1H-indazol-3-yl),
—(CH$_2$)$_3$(6-Cl-1-H-indazol-3-yl),
—(CH$_2$)$_3$(6-Br-1H-indazol-3-yl), —(CH₂)₃C(=O)(2-NHMe-phenyl),
—(CH₂)₃(1-benzothien-3-yl),
—(CH₂)₃(6-F-1H-indol-1-yl),
—(CH₂)₃(5-F-1H-indol-1-yl),
—(CH₂)₃(6-F-2,3-dihydro-1H-indol-1-yl),
—(CH₂)₃(5-F-2,3-dihydro-1H-indol-1-yl),
—(CH₂)₃(6-F-1H-indol-3-yl),
—(CH₂)₃(5-F-1H-indol-3-yl),
—(CH₂)₃(5-F-1H-indol-3-yl),
—(CH₂)₃(9H-purin-9-yl),
—(CH₂)₃(7H-purin-7-yl),
—(CH₂)₃(6-F-1H-indazol-3-yl),
—(CH₂)₃C(=O)(2-NHSO₂Me-4-F-phenyl),
—(CH₂)₃C(=O)(2-NHC(=O)Me-4-F-phenyl),
—(CH₂)₃C(=O)(2-NHC(=O)Me-phenyl),
(CH₂)₃C(=O)(2-NHCO₂Et-4-F-phenyl),
—(CH₂)₃C(=O)(2-NHC(=O)NHEt-4-F-phenyl),
—(CH₂)₃C(=O)(2-NHCHO-4-F-phenyl),
—(CH₂)₃C(=O)(2-OH-4-F-phenyl),
—(CH₂)₃C(=O)(2-MeS-4-F-phenyl),
—(CH₂)₃C(=O)(2-NHSO₂Me-4-F-phenyl),
—(CH₂)₂C(Me)CO₂Me,
—(CH₂)₂C(Me)CH(OH)(4-F-phenyl)₂,
—(CH₂)₂C(Me)CH(OH)(4-Cl-phenyl)₂,
—(CH₂)₂C(Me)C(=O)(4-F-phenyl),
—(CH₂)₂C(Me)C(=O)(2-MeO-4-F-phenyl),
—(CH₂)₂C(Me)C(=O)(3-Me-4-F-phenyl),
—(CH₂)₂C(Me)C(=O)(2-Me-phenyl),
—(CH₂)₂C(Me)C(=O)phenyl,

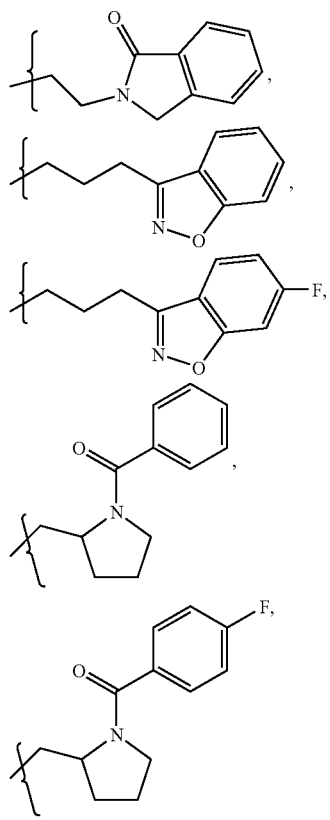

-continued

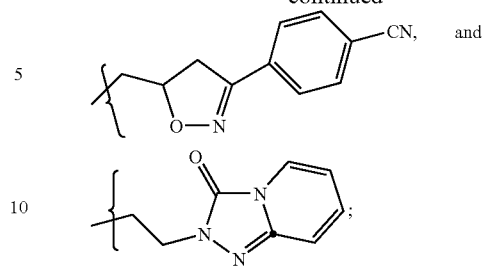

R⁷, R⁸, and R⁹, at each occurrence, are independently selected from
hydrogen, fluoro, chloro, bromo, cyano, methyl, ethyl, propyl, isopropyl, butyl, t-butyl, nitro, trifluoromethyl, methoxy, ethoxy, isopropoxy, trifluoromethoxy, phenyl, benzyl,
HC(=O)—, methylC(=O)—, ethylC(=O)—, propylC(=O)—, isopropylC(=O)—, n-butylC(=O)—, isobutylC(=O)—, secbutylC(=O)—, tertbutylC(=O)—, phenylC(=O)—,
methylC(=O)NH—, ethylC(=O)NH—, propylC(=O)NH—, isopropylC(=O)NH—, n-butylC(=O)NH—, isobutylC(=O)NH—, secbutylC(=O)NH—, tertbutylC(=O)NH—, phenylC(=O)NH—,
methylamino-, ethylamino-, propylamino-, isopropylamino-, n-butylamino-, isobutylamino-, secbutylamino-, tertbutylamino-, phenylamino-,
provided that two of substituents R⁷, R⁸, and R⁹, are independently selected from hydrogen, fluoro, chloro, bromo, cyano, methyl, ethyl, propyl, isopropyl, butyl, t-butyl, nitro, trifluoromethyl, methoxy, ethoxy, isopropoxy, and trifluoromethoxy;
k is 1 or 2;
m is 1 or 2; and
n is 0, 1 or 2.

14. The method as defined in claim 13 where the compound administered is a compound of Formula (V-a):

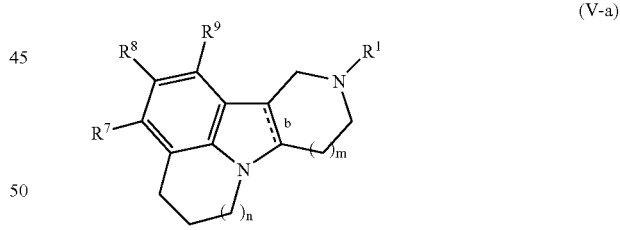

(V-a)

wherein:
b is a single bond, wherein the bridge hydrogens are in a cis position;
R¹ is selected from
—(CH₂)₃C(=O)(4-fluoro-phenyl),
—(CH₂)₃C(=O)(4-bromo-phenyl),
—(CH₂)₃C(=O)(4-methyl-phenyl),
—(CH₂)₃C(=O)(4-methoxy-phenyl),
—(CH₂)₃C(=O)(4-(3,4-dichloro-phenyl)phenyl),
—(CH₂)₃C(=O)(3-methyl-4-fluoro-phenyl),
—(CH₂)₃C(=O)(2,3-dimethoxy-phenyl),
—(CH₂)₃C(=O)(phenyl),
—(CH₂)₃C(=O)(4-chloro-phenyl),
—(CH₂)₃C(=O)(3-methyl-phenyl), —(CH$_2$)$_3$C(=O)(4-t-butyl-phenyl),
—(CH$_2$)$_3$C(=O)(3,4-difluoro-phenyl),
—(CH$_2$)$_3$C(=O)(2-methoxy-5-fluoro-phenyl),
—(CH$_2$)$_3$C(=O)(4-fluoro-1-naphthyl),
—(CH$_2$)$_3$C(=O)(benzyl),
—(CH$_2$)$_3$C(=O)(4-pyridyl),
—(CH$_2$)$_3$C(=O)(3-pyridyl),
—(CH$_2$)$_3$CH(OH)(4-fluoro-phenyl),
—(CH$_2$)$_3$CH(OH)(4-pyridyl),
—(CH$_2$)$_3$CH(OH)(2,3-dimethoxy-phenyl),
—(CH$_2$)$_3$S(3-fluoro-phenyl),
—(CH$_2$)$_3$S(4-fluoro-phenyl),
—(CH$_2$)$_3$S(=O)(4-fluoro-phenyl),
—(CH$_2$)$_3$SO$_2$(3-fluoro-phenyl),
—(CH$_2$)$_3$SO$_2$(4-fluoro-phenyl),
—(CH$_2$)$_3$O(4-fluoro-phenyl),
—(CH$_2$)$_3$O(phenyl),
—(CH$_2$)$_3$NH(4-fluoro-phenyl),
—(CH$_2$)$_3$N(methyl)(4-fluoro-phenyl),
—(CH$_2$)$_3$CO$_2$(ethyl),
—(CH$_2$)$_3$C(=O)N(methyl)(methoxy),
—(CH$_2$)$_3$C(=O)NH(4-fluoro-phenyl),
—(CH$_2$)$_2$NHC(=O)(phenyl),
—(CH$_2$)$_2$NMeC(=O)(phenyl),
—(CH$_2$)$_2$NHC(=O)(2-fluoro-phenyl),
—(CH$_2$)$_2$NMeC(=O)(2-fluoro-phenyl),
—(CH$_2$)$_2$NHC(=O)(4-fluoro-phenyl),
—(CH$_2$)$_2$NMeC(=O)(4-fluoro-phenyl),
—(CH$_2$)$_2$NHC(=O)(2,4-difluoro-phenyl),
—(CH$_2$)$_2$NMeC(=O)(2,4-difluoro-phenyl),
—(CH$_2$)$_3$(3-indolyl),
—(CH$_2$)$_3$(1-methyl-3-indolyl),
—(CH$_2$)$_3$(1-indolyl),
—(CH$_2$)$_3$(1-indolinyl),
—(CH$_2$)$_3$(1-benzimidazolyl),
—(CH$_2$)$_3$(1H-1,2,3-benzotriazol-1-yl),
—(CH$_2$)$_3$(1H-1,2,3-benzotriazol-2-yl),
—(CH$_2$)$_2$(1H-1,2,3-benzotriazol-1-yl),
—(CH$_2$)$_2$(1H-1,2,3-benzotriazol-2-yl),
—(CH$_2$)$_3$(3,4 dihydro-1(2H)-quinolinyl),
—(CH$_2$)$_2$C(=O)(4-fluoro-phenyl),
—(CH$_2$)$_2$C(=O)NH(4-fluoro-phenyl),
—CH$_2$CH$_2$(3-indolyl),
—CH$_2$CH$_2$(1-phthalimidyl),
—(CH$_2$)$_4$C(=O)N(methyl)(methoxy),
—(CH$_2$)$_4$CO$_2$(ethyl),
—(CH$_2$)$_4$C(=O)(phenyl),
—(CH$_2$)$_4$(cyclohexyl),
—(CH$_2$)$_3$CH(phenyl)$_2$,
—CH$_2$CH$_2$CH=C(Phenyl)$_2$,
—CH$_2$CH$_2$CH=CMe(4-F-phenyl),
—(CH$_2$)$_3$CH(4-fluoro-phenyl)$_2$,
—CH$_2$CH$_2$CH=C(4-fluoro-phenyl)$_2$,
—(CH$_2$)$_2$(2,3-dihydro-1H-inden-2-yl),
—(CH$_2$)$_3$C(=O)(2-NH$_2$-phenyl),
—(CH$_2$)$_3$C(=O)(2-NH$_2$-5-F-phenyl),
—(CH$_2$)$_3$C(=O)(2-NH$_2$-4-F-phenyl),
—(CH$_2$)$_3$C(=O)(2-NH$_2$-3-F-phenyl),
—(CH$_2$)$_3$C(=O)(2-NH$_2$-4-Cl-phenyl),
—(CH$_2$)$_3$C(=O)(2-NH$_2$4-OH-phenyl),
—(CH$_2$)$_3$C(=O)(2-NH$_2$-4-Br-phenyl),
—(CH$_2$)$_3$(1H-indazol-3-yl),
—(CH$_2$)$_3$(5-F-1H-indazol-3-yl),
—(CH$_2$)$_3$(7-F-1H-indazol-3-yl),
—(CH$_2$)$_3$(6-Cl-1H-indazol-3-yl),
—(CH$_2$)$_3$(6-Br-1H-indazol-3-yl),
—(CH$_2$)$_3$C(=O)(2-NHMe-phenyl),
—(CH$_2$)$_3$(1-benzothien-3-yl),
—(CH$_2$)$_3$(6-F-1H-indol-1-yl),
—(CH$_2$)$_3$(5-F-1H-indol-1-yl),
—(CH$_2$)$_3$(6-F-2,3-dihydro-1H-indol-1-yl),
—(CH$_2$)$_3$(5-F-2,3-dihydro-1H-indol-1-yl),
—(CH$_2$)$_3$(6-F-1H-indol-3-yl),
—(CH$_2$)$_3$(5-F-1H-indol-3-yl),
—(CH$_2$)$_3$(5-F-1H-indol-3-yl),
—(CH$_2$)$_3$(9H-purin-9-yl),
—(CH$_2$)$_3$(7H-purin-7-yl),
—(CH$_2$)$_3$(6-F-1H-indazol-3-yl),
—(CH$_2$)$_3$C(=O)(2-NHSO$_2$Me-4-F-phenyl),
—(CH$_2$)$_3$C(=O)(2-NHC(=O)Me-4-F-phenyl),
—(CH$_2$)$_3$C(=O)(2-NHC(=O)Me-4-F-phenyl),
—(CH$_2$)$_3$C(=O)(2-NHCO$_2$Et-4-F-phenyl),
—(CH$_2$)$_3$C(=O)(2-NHC(=O)NHEt-4-F-phenyl),
—(CH$_2$)$_3$C(=O)(2-NHCHO-4-F-phenyl),
—(CH$_2$)$_3$C(=O)(2-OH-4-F-phenyl),
—(CH$_2$)$_3$C(=O)(2-MeS-4-F-phenyl),
—(CH$_2$)$_3$C(=O)(2-NHSO$_2$Me-4-F-phenyl),
—(CH$_2$)$_2$C(Me)CO$_2$Me,
—(CH$_2$)$_2$C(Me)CH(OH)(4-F-phenyl)$_2$,
—(CH$_2$)$_2$C(Me)CH(OH)(4-Cl-phenyl)$_2$,
—(CH$_2$)$_2$C(Me)C(=O)(4-F-phenyl),
—(CH$_2$)$_2$C(Me)C(=O)(2-MeO-4-F-phenyl),
—(CH$_2$)$_2$C(Me)C(=O)(3-Me-4-F-phenyl),
—(CH$_2$)$_2$C(Me)C(=O)(2-Me-phenyl),
—(CH$_2$)$_2$C(Me)C(=O)phenyl,

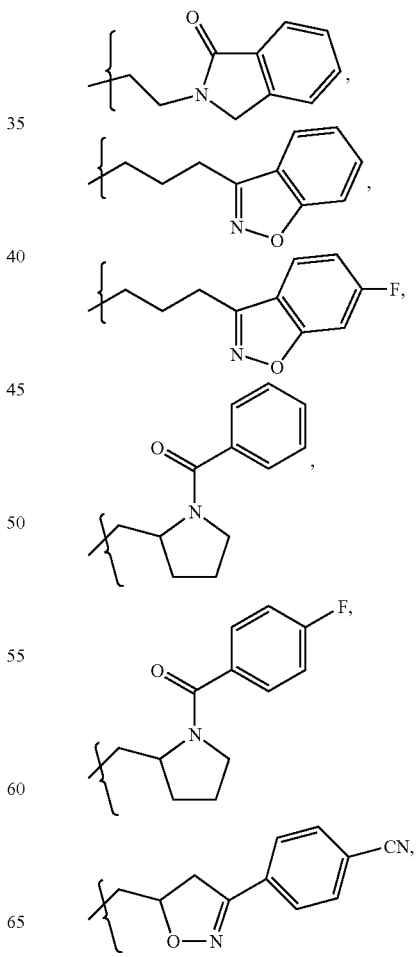

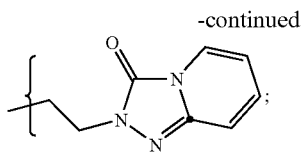

R[7], R[8], and R[9], at each occurrence, are independently selected from hydrogen, fluoro, chloro, bromo, cyano, methyl, ethyl, propyl, isopropyl, butyl, t-butyl, nitro, trifluoromethyl, methoxy, ethoxy, isopropoxy, trifluoromethoxy, methylC(=O)—, ethylC(=O)—, propylC(=O)—, isopropylC(=O)—, methylC(=O)NH—, ethylC(=O)NH—, propylC(=O)NH—, isopropylC(=O)NH, methylamino-, ethylamino-, propylamino-, and isopropylamino-, provided that two of substituents R[7], R[8], and R[9], are independently selected from hydrogen, fluoro, chloro, methyl, trifluoromethyl, methoxy, and trifluoromethoxy;

m is 1 or 2; and n is 0, 1 or 2.

15. The method as defined in claim 1 where the compound administered is selected from the group:

(±)-cis-9-(cyclopropylcarbonyl)-4,5,6a,7,8,9,10,10a-octahydropyrido[4,3-b]pyrrolo[3,2,1-hi]indole;

(±)-cis-9-isobutyryl-4,5,6a,7,8,9,10,10a-octahydropyrido[4,3-b]pyrrolo[3,2,1-hi]indole;

tert-butyl(±)-cis-2-(2-chlorophenyl)-4,5,7,8,10,10a-hexahydropyrido[4,3-b]pyrrolo[3,2,1-hi]indole-9(6aH)-carboxylate;

tert-butyl(±)-cis-2-(2,4-dichlorophenyl)-4,5,7,8,10,10a-hexahydropyrido[4,3-b]pyrrolo[3,2,1-hi]indole-9(6aH)-carboxylate;

tert-butyl(±)-cis-2-(3,4-dichlorophenyl)-4,5,7,8,10,10a-hexahydropyrido[4,3-b]pyrrolo[3,2,1-hi]indole-9(6aH)-carboxylate;

tert-butyl(±)-cis-2-(2,3-dichlorophenyl)-4,5,7,8,10,10a-hexahydropyrido[4,3-b]pyrrolo[3,2,1-hi]indole-9(6aH)-carboxylate;

tert-butyl(±)-cis-2-[2-chloro-4-(trifluoromethyl)phenyl]-4,5,7,8,10,10a-hexahydropyrido[4,3-b]pyrrolo[3,2,1-hi]indole-9(6aH)-carboxylate;

tert-butyl(±)-cis-2-(2-chloro-4-methoxyphenyl)-4,5,7,8,10,10a-hexahydropyrido[4,3-b]pyrrolo[3,2,1-hi]indole-9(6aH)-carboxylate;

tert-butyl(±)-cis-2-(5-isopropyl-2-methoxyphenyl)-4,5,7,8,10,10a-hexahydropyrido[4,3-b]pyrrolo[3,2,1-hi]indole-9(6aH)-carboxylate;

tert-butyl(±)-cis-2-(3-fluorophenyl)-4,5,7,8,10,10a-hexahydropyrido[4,3-b]pyrrolo[3,2,1-hi]indole-9(6aH)-carboxylate;

tert-butyl(±)-cis-2-(2,4-dimethoxyphenyl)-4,5,7,8,10,10a-hexahydropyrido[4,3-b]pyrrolo[3,2,1-hi]indole-9(6aH7)-carboxylate;

(±)-cis-2-(2-chlorophenyl)-4,5,6a,7,8,9,10,10a-octahydropyrido[4,3-b]pyrrolo[3,2,1-hi]indole;

(±)-cis-2-(2,4-dichlorophenyl)-4,5,6a,7,8,9,10,10a-octahydropyrido[4,3-b]pyrrolo[3,2,1-hi]indole;

(±)-cis-2-(3,4-dichlorophenyl)-4,5,6a,7,8,9,10,10a-octahydropyrido[4,3-b]pyrrolo[3,2,1-hi]indole;

(±)-cis-2-(2,3-dichlorophenyl)-4,5,6a,7,8,9,10,10a-octahydropyrido[4,3-b]pyrrolo[3,2,1-hi]indole;

(±)-cis-2-[2-chloro-4-(trifluoromethyl)phenyl]-4,5,6a,7,8,9,10,10a-octahydropyrido[4,3-b]pyrrolo[3,2,1-hi]indole;

(±)-cis-2-(2-chloro-4-methoxyphenyl)-4,5,6a,7,8,9,10,10a-octahydropyrido [4,3-b]pyrrolo[3,2,1-hi]indole;

(±)-cis-2-(4-isopropyl-2-methoxyphenyl)-4,5,6a,7,8,9,10,10a-octahydropyrido[4,3-b]pyrrolo[3,2,1-hi]indole;

(±)-cis-2-(3-fluorophenyl)-4,5,6a,7,8,9,10,10a-octahydropyrido[4,3-b]pyrrolo[3,2,1-hi]indole;

(±)-cis-2-(2,4-dimethoxyphenyl)-4,5,6a,7,8,9,10,10a-octahydropyrido[4,3-b]pyrrolo[3,2,1-hi]indole;

tert-butyl(±)-cis-5,6,8,9,11,11a-hexahydro-4H-pyrido[3',4':4,5]pyrrolo[3,2,1-ij]quinoline-10(7aH)-carboxylate;

tert-butyl(±)-cis-2-bromo-5,6,8,9,11,11a-hexahydro-4H-pyrido [3',4':4,5]pyrrolo[3,2,1-ij]quinoline-10(7aH)-carboxylate;

tert-butyl(±)-cis-2-(2,3-dichlorophenyl)-5,6,8,9,11,11a-hexahydro-4H-pyrido[3',4':4,5]pyrrolo[3,2,1-ij]quinoline-10(7aH)-carboxylate;

tert-butyl(±)-cis-2-(3,4-dichlorophenyl)-5,6,8,9,11,11a-hexahydro-4H-pyrido[3',4':4,5]pyrrolo[3,2,1-ij]quinoline-10(7aH)-carboxylate;

tert-butyl(±)-cis-2-[2-chloro-4-(trifluoromethyl)phenyl]-5,6,8,9,11,11a-hexahydro-4H-pyrido[3',4':4,5]pyrrolo[3,2,1-ij]quinoline-10(7aH)-carboxylate;

(±)-cis-2-(2,3-dichlorophenyl)-5,6,7a,8,9,10,11,11a-octahydro-4H-pyrido[3',4':4,5]pyrrolo[3,2,1-ij]quinoline;

(±)-cis-2-(3,4-dichlorophenyl)-5,6,7a,8,9,10,11,11a-octahydro-4H-pyrido[3',4':4,5]pyrrolo[3,2,1-ij]quinoline;

(±)-cis-2-[2-chloro-4-(trifluoromethyl)phenyl]-5,6,7a,8,9,10,11,11a-octahydro-4H-pyrido[3',4':4,5]pyrrolo[3,2,1-ij]quinoline;

4-((±)-cis-2-(2-chlorophenyl)-4,5,7,8,10,10a-hexahydropyrido[4,3-b]pyrrolo[3,2,1-hi]indol-9(6aH)-yl)-1-(4-fluorophenyl)-1-butanone;

4-((±)-cis-2-(2,4-dichlorophenyl)-4,5,7,8,10,11a-hexahydropyrido[4,3-b]pyrrolo[3,2,1-hi]indol-9(6aH)-yl)-1-(4-fluorophenyl)-1-butanone;

4-((±)-cis-5,6,8,9,11,11a-hexahydro-4H-pyrido[3',4':4,5]pyrrolo[3,2,1-ij]qionolin-10(7aH)-yl)-1-(4-fluorophenyl)-1-butanone;

4-((±)-cis-4,5,7,8,10,10a-hexahydropyrido[4,3-b]pyrrolo[3,2,1-hi]indol-9(6aH)-yl)-1-(4-fluorophenyl)-1-butanone;

(6aS,10aR)-2-(2-fluoro-4-methoxyphenyl)-4,5,6a,7,8,9,10,10a-octahydropyrido[4,3-b]pyrrolo[3,2,1-hi]indole;

tert-butyl(6aS,10aR)-2-[4-ethoxy-2-(trifluoromethyl)phenyl]-4,5,7,8,10,10a-hexahydropyrido [4,3-b]pyrrolo[3,2,1-hi]indole-9(6aH)-carboxylate;

(6aS,10aR)-2-[4-ethoxy-2-(trifluoromethyl)phenyl]-4,5,6a,7,8,9,10,10a-octahydropyrido [4,3-b]pyrrolo[3,2,1-hi]indole;

tert-butyl(6aS,10aR)-2-(4-chloro-2-fluorophenyl)-4,5,7,8,10,10a-hexahydropyrido[4,3-b]pyrrolo[3,2,1-hi]indole-9(6aH)-carboxylate;

(6aS,10aR)-2-(4-chloro-2-fluorophenyl)-4,5,6a,7,8,9,10,10a-octahydropyrido[4,3-b]pyrrolo[3,2,1-hi]indole;

tert-butyl(6aS,10aR)-2-[4-isopropoxy-2-(trifluoromethyl)phenyl]-4,5,7,8,10,10a-hexahydropyrido[4,3-b]pyrrolo[3,2,1-hi]indole-9(6aH)-carboxylate;

(6aS,10aR)-2-[4-isopropoxy-2-(trifluoromethyl)phenyl]-4,5,6a,7,8,9,10,10a-octahydropyrido[4,3-b]pyrrolo[3,2,1-hi]indole;

tert-butyl(6aS,10aR)-2-[4-methoxy-2-(trifluoromethyl)phenyl]-4,5,7,8,10,10a-hexahydropyrido[4,3-b]pyrrolo[3,2,1-hi]indole-9(6aH)-carboxylate;

(6aS,10aR)-2-[4-methoxy-2-(trifluoromethyl)phenyl]-4,5,6a,7,8,9,10,10a-octahydropyrido[4,3-b]pyrrolo[3,2,1-hi]indole;

tert-butyl(6aS,10aR)-2-phenyl-4,5,7,8,10,10a-hexahydropyrido[4,3-b]pyrrolo[3,2,1-hi]indole-9(6aH)-carboxylate;

(6aS,10aR)-2-phenyl-4,5,6a,7,8,9,10,10a-octahydropyrido[4,3-b]pyrrolo[3,2,1-hi]indole;

tert-butyl(6aS,10aR)-2-(2-methylphenyl)-4,5,7,8,10,10a-hexahydropyrido[4,3-b]pyrrolo[3,2,1-hi]indole-9(6aH)-carboxylate;

(6aS,10aR)-2-(2-methylphenyl)-4,5,6a,7,8,9,10,10a-octahydropyrido[4,3-b]pyrrolo[3,2,1-hi]indole;

tert-butyl(6aS,10aR)-2-[2-(trifluoromethyl)phenyl]-4,5,7,8,10,10a-hexahydropyrido[4,3-b]pyrrolo[3,2,1-hi]indole-9(6aH)-carboxylate;

(6aS,10aR)-2-[2-(trifluoromethyl)phenyl]-4,5,6a,7,8,9,10,10a-octahydropyrido[4,3-b]pyrrolo[3,2,1-hi]indole;

tert-butyl(6aS,10aR)-2-(3,4-dimethoxyphenyl)-4,5,7,8,10,10a-hexahydropyrido[4,3-b]pyrrolo[3,2,1-hi]indole-9(6aH)-carboxylate;

(6aS,10aR)-2-(3,4-dimethoxyphenyl)-4,5,6a,7,8,9,10,10a-octahydropyrido[4,3-b]pyrrolo[3,2,1-hi]indole;

tert-butyl(6aS,10aR)-2-(2,5-dichlorophenyl)-4,5,7,8,10,10a-hexahydropyrido[4,3-b]pyrrolo[3,2,1-hi]indole-9(6aH)-carboxylate;

(6aS,10aR)-2-(2,5-dichlorophenyl)-4,5,6a,7,8,9,10,10a-octahydropyrido[4,3-b]pyrrolo[3,2,1-hi]indole;

tert-butyl(6aS,10aR)-2-(3,5-dichlorophenyl)-4,5,7,8,10,10a-hexahydropyrido[4,3-b]pyrrolo[3,2,1-hi]indole-9(6aH)-carboxylate;

(6aS,10aR)-2-(3,5-dichlorophenyl)-4,5,6a,7,8,9,10,10a-octahydropyrido[4,3-b]pyrrolo[3,2,1-hi]indole;

tert-butyl(6aS,10aR)-2-(2-isopropyl-4-methoxyphenyl)-4,5,7,8,10,10a-hexahydropyrido[4,3-b]pyrrolo[3,2,1-hi]indole-9(6aH)-carboxylate;

(6aS,10aR)-2-(2-isopropyl-4-methoxyphenyl)-4,5,6a,7,8,9,10,10a-octahydropyrido[4,3-b]pyrrolo[3,2,1-hi]indole;

tert-butyl(6aS,10aR)-2-(5-fluoro-4-methoxy-2-methylphenyl)-4,5,7,8,10,10a-hexahydropyrido[4,3-b]pyrrolo[3,2,1-hi]indole-9(6aH)-carboxylate;

(6aS,10aR)-2-(5-fluoro-4-methoxy-2-methylphenyl)-4,5,6a,7,8,9,10,10a-octahydropyrido[4,3-b]pyrrolo[3,2,1-hi]indole;

tert-butyl(6aS,10aR)-2-(4-methoxy-2-methylphenyl)-4,5,7,8,10,10a-hexahydropyrido[4,3-b]pyrrolo[3,2,1-hi]indole-9(6aH)-carboxylate;

(6aS,10aR)-2-(4-methoxy-2-methylphenyl)-4,5,6a,7,8,9,10,10a-octahydropyrido[4,3-b]pyrrolo[3,2,1-hi]indole;

tert-butyl(6aS,10aR)-2-(2-chloro-4-methoxyphenyl)-4,5,7,8,10,10a-hexahydropyrido[4,3-b]pyrrolo[3,2,1-hi]indole-9(6aH)-carboxylate;

(6aS,10aR)-2-(2-chloro-4-methoxyphenyl)-4,5,6a,7,8,9,10,10a-octahydropyrido[4,3-b]pyrrolo[3,2,1-hi]indole;

tert-butyl(6aS,10aR)-2-(3-chloro-2-methylphenyl)-4,5,7,8,10,10a-hexahydropyrido[4,3-b]pyrrolo[3,2,1-hi]indole-9(6aH)-carboxylate;

(6aS,10aR)-2-(3-chloro-2-methylphenyl)-4,5,6a,7,8,9,10,10a-octahydropyrido[4,3-b]pyrrolo[3,2,1-hi]indole;

2-[(6aS,10aR)-4,5,6a,7,8,9,10,10a-octahydropyrido[4,3-b]pyrrolo[3,2,1-hi]-2-yl]-5-methoxybenzaldehyde;

(6aS,10aR)-2-(2,6-dichlorophenyl)-4,5,6a,7,8,9,10,10a-octahydropyrido[4,3-b]pyrrolo[3,2,1-hi]indole;

N-[4-[(6aS,10aR)-4,5,6a,7,8,9,10,10a-octahydropyrido[4,3-b]pyrrolo[3,2,1-hi]indol-2-yl]-3-(trifluoromethyl)phenyl]-N-methylamine;

4-[(6aS,10aR)-4,5,6a,7,8,9,10,10a-octahydropyrido[4,3-b]pyrrolo[3,2,1-hi]indol-2-yl]-3-(trifluoromethyl)phenylamine;

1-(2-[(6aS,10aR)-4,5,6a,7,8,9,10,10a-octahydropyrido[4,3-b]pyrrolo[3,2,1-hi]indol-2-yl]-5-methoxyphenyl)ethanol;

tert-butyl(±)-cis-4,5,6,7,8a,9,10,11,12,12a-decahydroazepino[3,2,1-hi]pyrido[4,3-b]indole-11(8aH)-carboxylate;

tert-butyl(8aS,12aR)-2-bromo-4,5,6,7,8a,9,10,11,12,12a-decahydroazepino[3,2,1-hi]pyrido[4,3-b]indole-11(8aH)-carboxylate;

(8aS,12aR)-2-(2,4-dichlorophenyl)-4,5,6,7,8a,9,10,11,12,12a-decahydroazepino[3,2,1-hi]pyrido[4,3-b]indole;

(8aS,12aR)-2-(2,3-dichlorophenyl)-4,5,6,7,8a,9,10,11,12,12a-decahydroazepino[3,2,1-hi]pyrido[4,3-b]indole;

(8aS,12aR)-2-(3,4-dichlorophenyl)-4,5,6,7,8a,9,10,11,12,12a-decahydroazepino[3,2,1-hi]pyrido[4,3-b]indole;

(8aS,12aR)-2-(3,5-dichlorophenyl)-4,5,6,7,8a,9,10,11,12,12a-decahydroazepino[3,2,1-hi]pyrido[4,3-b]indole;

(8aS,12aR)-2-(2,5-dichlorophenyl)-4,5,6,7,8a,9,10,11,12,12a-decahydroazepino[3,2,1-hi]pyrido[4,3-b]indole;

(8aS,12aR)-2-(2,6-dichlorophenyl)-4,5,6,7,8a,9,10,11,12,12a-decahydroazepino[3,2,1-hi]pyrido[4,3-b]indole;

(8aS,12aR)-2-(2-chlorophenyl)-4,5,6,7,8a,9,10,11,12,12a-decahydroazepino[3,2,1-hi]pyrido[4,3-b]indole;

(8aS,12aR)-2-(3-chlorophenyl)-4,5,6,7,8a,9,10,11,12,12a-decahydroazepino[3,2,1-hi]pyrido[4,3-b]indole;

(8aS,12aR)-2-(4-chlorophenyl)-4,5,6,7,8a,9,10,11,12,12a-decahydroazepino[3,2,1-hi]pyrido[4,3-b]indole;

(±)-cis-2-(2,6-difluorophenyl)-4,5,6,7,8a,9,10,11,12,12a-decahydroazepino[3,2,1-hi]pyrido[4,3-b]indole;

(8aS,12aR)-2-(2,6-difluorophenyl)-4,5,6,7,8a,9,10,11,12,12a-decahydroazepino[3,2,1-hi]pyrido[4,3-b]indole;

(8aS,12aR)-2-(2,3-difluorophenyl)-4,5,6,7,8a,9,10,11,12,12a-decahydroazepino[3,2,1-hi]pyrido[4,3-b]indole;

(8aS,12aR)-2-(3,4-difluorophenyl)-4,5,6,7,8a,9,10,11,12,12a-decahydroazepino[3,2,1-hi]pyrido[4,3-b]indole;

(8aS,12aR)-2-(3-fluorophenyl)-4,5,6,7,8a,9,10,11,12,12a-decahydroazepino[3,2,1-hi]pyrido[4,3-b]indole;

(8aS,12aR)-2-[2-chloro-4-(trifluoromethyl)phenyl]-4,5,6,7,8a,9,10,11,12,12a-decahydroazepino[3,2,1-hi]pyrido[4,3-b]indole;

(8aS,12aR)-2-(2-chloro-4-methoxyphenyl)-4,5,6,7,8a,9,10,11,12,12a-decahydroazepino[3,2,1-hi]pyrido[4,3-b]indole;

(8aS,12aR)-2-(2-fluoro-4-methoxyphenyl)-4,5,6,7,8a,9,10,11,12,12a-decahydroazepino[3,2,1-hi]pyrido[4,3-b]indole;

(8aS,12aR)-2-(4-methoxy-2-methylphenyl)-4,5,6,7,8a,9,10,11,12,12a-decahydroazepino[3,2,1-hi]pyrido[4,3-b]indole;

(8aS,12aR)-2-[4-methoxy-2-(trifluoromethyl)phenyl]-4,5,6,7,8a,9,10,11,12,12a-decahydroazepino[3,2,1-hi]pyrido[4,3-b]indole;

(8aS,12aR)-2-[2-(trifluoromethyl)phenyl]-4,5,6,7,8a,9,10,11,12,12a-decahydroazepino[3,2,1-hi]pyrido[4,3-b]indole;

(8aS,12aR)-2-[4-isopropoxy-2-(trifluoromethyl)phenyl]-4,5,6,7,8a,9,10,11,12,12a-decahydroazepino[3,2,1-hi]pyrido[4,3-b]indole;

(8aS,12aR)-2-[2,4-bis(trifluoromethyl)phenyl]-4,5,6,7,8a,9,10,11,12,12a-decahydroazepino[3,2,1-hi]pyrido[4,3-b]indole;

(8aS,12aR)-2-[4-fluoro-2-(trifluoromethyl)phenyl]-4,5,6,7,8a,9,10,11,12,12a-decahydroazepino[3,2,1-hi]pyrido[4,3-b]indole;

4-[(8aS,12aR)-4,5,6,7,8a,9,10,11,12,12a-decahydroazepino[3,2,1-hi]pyrido[4,3-b]indol-2-yl]-3-(trifluoromethyl)aniline;
4-[(8aS,12aR)-4,5,6,7,8a,9,10,11,12,12a-decahydroazepino[3,2,1-hi]pyrido[4,3-b]indol-2-yl]-N-methyl-3-(trifluoromethyl)aniline;
2-[(8aS,12aR)-4,5,6,7,8a,9,10,11,12,12a-decahydroazepino[3,2,1-hi]pyrido[4,3-b]indol-2-yl]benzaldehyde;
{2-[(8aS,12aR)-4,5,6,7,8a,9,10,11,12,12a-decahydroazepino[3,2,1-hi]pyrido[4,3-b]indol-2-yl]phenyl}methanol;
2-[(8aS,12aR)-4,5,6,7,8a,9,10,11,12,12a-decahydroazepino[3,2,1-hi]pyrido[4,3-b]indol-2-yl]-5-methoxybenzaldehyde;
{2-[(8aS,12aR)-4,5,6,7,8a,9,10,11,12,12a-decahydroazepino[3,2,1-hi]pyrido[4,3-b]indol-2-yl]-5-methoxyphenyl}methanol;
4-[(8aS,12aR)-4,5,6,7,8a,9,10,11,12,12a-decahydroazepino[3,2,1-hi]pyrido[4,3-b]indol-2-yl]-3-methylbenzonitrile;
1-{2-[(8aS,12aR)-4,5,6,7,8a,9,10,11,12,12a-decahydroazepino[3,2,1-hi]pyrido[4,3-b]indol-2-yl]-5-methoxyphenyl}ethanol;
tert-butyl(7aS,11aR)-2-bromo-5,6,7a,8,9,10,11,11a-octahydro-4H-pyrido[3',4':4,5]pyrrolo[3,2,1-ij]quinoline-10(7aH)-carboxylate;
(7aS,11aR)-2-(2,4-dichlorophenyl)-5,6,7a,8,9,10,11,11a-octahydro-4H-pyrido[3',4':4,5]pyrrolo[3,2,1-ij]quinoline;
(7aS,11aR)-2-(3,4-dichlorophenyl)-5,6,7a,8,9,10,11,11a-octahydro-4H-pyrido[3',4':4,5]pyrrolo[3,2,1-ij]quinoline;
(7aS,11aR)-2-(3,5-dichlorophenyl)-5,6,7a,8,9,10,11,11a-octahydro-4H-pyrido[3',4':4,5]pyrrolo[3,2,1-ij]quinoline;
(7aS,11aR)-2-(2,5-dichlorophenyl)-5,6,7a,8,9,10,11,11a-octahydro-4H-pyrido[3',4':4,5]pyrrolo[3,2,1-ij]quinoline;
(7aS,11aR)-2-(2,6-dichlorophenyl)-5,6,7a,8,9,10,11,11a-octahydro-4H-pyrido[3',4':4,5]pyrrolo[3,2,1-ij]quinoline;
(7aS,11aR)-2-(2-chlorophenyl)-5,6,7a,8,9,10,11,11a-octahydro-4H-pyrido[3',4':4,5]pyrrolo[3,2,1-ij]quinoline;
(7aS,11aR)-2-(3-chlorophenyl)-5,6,7a,8,9,10,11,11a-octahydro-4H-pyrido[3',4':4,5]pyrrolo[3,2,1-ij]quinoline;
(7aS,11aR)-2-(4-chlorophenyl)-5,6,7a,8,9,10,11,11a-octahydro-4H-pyrido[3',4':4,5]pyrrolo[3,2,1-ij]quinoline;
(7aS,11aR)-2-(2,6-difluorophenyl)-5,6,7a,8,9,10,11,11a-octahydro-4H-pyrido[3',4':4,5]pyrrolo[3,2,1-ij]quinoline;
(7aS,11aR)-2-(2,6-difluorophenyl)-10-methyl-5,6,7a,8,9,10,11,11a-octahydro-4H-pyrido[3',4':4,5]pyrrolo[3,2,1-ij]quinoline;
(7aS,11aR)-2-(2,3-difluorophenyl)-5,6,7a,8,9,10,11,11a-octahydro-4H-pyrido[3',4':4,5]pyrrolo[3,2,1-ij]quinoline;
(7aS,11aR)-2-(3,4-difluorophenyl)-5,6,7a,8,9,10,11,11a-octahydro-4H-pyrido[3',4':4,5]pyrrolo[3,2,1-ij]quinoline;
(7aS,11aR)-2-(3-fluorophenyl)-5,6,7a,8,9,10,11,11a-octahydro-4H-pyrido[3',4':4,5]pyrrolo[3,2,1-ij]quinoline;
(7aS,11aR)-2-[2-chloro-4-methoxyphenyl)-5,6,7a,8,9,10,11,11a-octahydro-4H-pyrido[3',4':4,5]pyrrolo[3,2,1-ij]quinoline;
(7aS,11aR)-2-[2-fluoro-4-methoxyphenyl)-5,6,7a,8,9,10,11,11a-octahydro-4H-pyrido[3',4':4,5]pyrrolo[3,2,1-ij]quinoline;
(7aS,111aR)-2-(4-methoxy-2-methylphenyl)-5,6,7a,8,9,10,11,11a-octahydro-4H-pyrido[3',4':4,5]pyrrolo[3,2,1-ij]quinoline;
(7aS,11aR)-2-[4-methoxy-2-(trifluoromethyl)phenyl]-5,6,7a,8,9,10,11,11a-octahydro-4H-pyrido[3',4':4,5]pyrrolo[3,2,1-ij]quinoline;
4-[(7aS,11aR)-5,6,7a,8,9,10,11,11a-octahydro-4H-pyrido[3',4':4,5]pyrrolo[3,2,1-ij]quinolin-2-yl]-3-(trifluoromethyl)phenol;
(7aS,11aR)-2-[2-(trifluoromethyl)phenyl]-5,6,7a,8,9,10,11,11a-octahydro-4H-pyrido[3',4':4,5]pyrrolo[3,2,1-ij]quinoline;
(7aS,11aR)-2-[4-isopropoxy-2-(trifluoromethyl)phenyl]-5,6,7a,8,9,10,11,11a-octahydro-4H-pyrido[3',4':4,5]pyrrolo[3,2,1-ij]quinoline;
(7aS,11aR)-2-[2,4-bis(trifluoromethyl)phenyl]-5,6,7a,8,9,10,11,11a-octahydro-4H-pyrido[3',4':4,5]pyrrolo[3,2,1-ij]quinoline;
(7aS,11aR)-2-[4-fluoro-2-(trifluoromethyl)phenyl]-5,6,7a,8,9,10,11,11a-octahydro-4H-pyrido[3',4':4,5]pyrrolo[3,2,1-ij]quinoline;
4-[(7aS,11aR)-5,6,7a,8,9,10,11,11a-octahydro-4H-pyrido[3',4':4,5]pyrrolo[3,2,1-ij]quinolin-2-yl]-3-(trifluoromethyl)aniline;
4-[(7aS,11aR)-5,6,7a,8,9,10,11,11a-octahydro-4H-pyrido[3',4':4,5]pyrrolo[3,2,1-ij]quinolin-2-yl]-N-methyl-3-(trifluoromethyl)aniline;
4-[(7aS,1 aR)-5,6,7a,8,9,10,11,11a-octahydro-4H-pyrido[3',4':4,5]pyrrolo[3,2,1-ij]quinolin-2-yl]-3-methylbenzonitrile;
2-[(7aS,11aR)-5,6,7a,8,9,10,11,11a-octahydro-4H-pyrido[3',4':4,5]pyrrolo[3,2,1-ij]quinolin-2-yl]benzaldehyde;
{2-[(7aS,11aR)-5,6,7a,8,9,10,11,11a-octahydro-4H-pyrido[3',4':4,5]pyrrolo[3,2,1-ij]quinolin-2-yl]phenyl}methanol;
2-[(7aS,11aR)-5,6,7a,8,9,10,11,11a-octahydro-4H-pyrido[3',4':4,5]pyrrolo[3,2,1-ij]quinolin-2-yl]-5-methoxybenzaldehyde;
{2-[(7aS,11aR)-5,6,7a,8,9,10,11,11a-octahydro-4H-pyrido[3',4':4,5]pyrrolo[3,2,1-ij]quinolin-2-yl]-5-methoxyphenyl}methanol;
(8aS,12aR)-2-[4-ethoxy-2-(trifluoromethyl)phenyl]-4,5,6,7,8a,9,10,11,12,12a-decahydroazepino[3,2,1-hi]pyrido[4,3b]indole;
(7aS,11aR)-2-[4-ethoxy-2-(trifluoromethyl)phenyl]-5,6,7a,8,9,10,11,11a-octahydro-4H-pyrido[3',4':4,5]pyrrolo[3,2,1-ij]quinoline;
(8aS,12aR)-2-[3-chloro-2-methylphenyl]-4,5,6,7,8a,9,10,11,12,12a-decahydroazepino[3,2,1-hi]pyrido[4,3b]indole;
(7aS,11aR)-2-[3-chloro-2-methylphenyl]-5,6,7a,8,9,10,11,11a-octahydro-4H-pyrido[3',4':4,5]pyrrolo[3,2,1-ij]quinoline;
(7aS,11aR)-2-[5-fluoro-2-methylphenyl]-5,6,7a,8,9,10,11,11a-octahydro-4H-pyrido[3',4':4,5]pyrrolo[3,2,1-ij]quinoline;
(±)-cis-2-(2,3-dichlorophenyl)-10-propyl-5,6,7a,8,9,10,11,11a-octahydro-4H-pyrido[3',4':4,5]pyrrolo[3,2,1-ij]quinoline;
(7aS,11aR)-2-(2,3-dichlorophenyl)-10-propyl-5,6,7a,8,9,10,11,11a-octahydro-4H-pyrido[3',4':4,5]pyrrolo[3,2,1-ij]quinoline;
(±)-cis-10-butyl-2-(2,3-dichlorophenyl)-5,6,7a,8,9,10,11,11a-octahydro-4H-pyrido[3',4':4,5]pyrrolo[3,2,1-ij]quinoline;
(7aS,11aR)-10-butyl-2-(2,3-dichlorophenyl)-5,6,7a,8,9,10,11,11a-octahydro-4H-pyrido[3',4':4,5]pyrrolo[3,2,1-ij]quinoline;
(7aS,11aR)-2-(2,3-dichlorophenyl)-10-(4-pentenyl)-5,6,7a,8,9,10,11,11a-octahydro-4H-pyrido[3',4':4,5]pyrrolo[3,2,1-ij]quinoline;

(7aS,11aR)-2-(2,3-dichlorophenyl)-10-(3-methyl-2-butenyl)-5,6,7a,8,9,10,11,11a-octahydro-4H-pyrido[3',4':4,5]pyrrolo[3,2,1-ij]quinoline;

(7aS,11aR)-2-(2,4-dichlorophenyl)-10-propyl-5,6,7a,8,9,10,11,11a-octahydro-4H-pyrido[3',4':4,5]pyrrolo[3,2,1-ij]quinoline;

(7aS,11aR)-10-butyl-2-(2,4-dichlorophenyl)-5,6,7a,8,9,10,11,11a-octahydro-4H-pyrido[3',4':4,5]pyrrolo[3,2,1-ij]quinoline;

(7aS,11aR)-2-(2,4-dichlorophenyl)-10-(4-pentenyl)-5,6,7a,8,9,10,11,11a-octahydro-4H-pyrido[3',4':4,5]pyrrolo[3,2,1-ij]quinoline;

(7aS,11aR)-2-(2,4-dichlorophenyl)-10-(3-methyl-2-butenyl)-5,6,7a,8,9,10,11,11a-octahydro-4H-pyrido[3',4':4,5]pyrrolo[3,2,1-ij]quinoline;

(7aS,11aR)-10-(cyclobutylmethyl)-2-(2,3-dichlorophenyl)-5,6,7a,8,9,10,11,11a-octahydro-4H-pyrido[3',4':4,5]pyrrolo[3,2,1-ij]quinoline;

(7aS,11aR)-2-[4-methoxy-2-(trifluoromethyl)phenyl]-10-methyl-5,6,7a,8,9,10,11,11a-octahydro-4H-pyrido[3',4':4,5]pyrrolo[3,2,1-ij]quinoline;

(7aS,11aR)-10-ethyl-2-[4-methoxy-2-(trifluoromethyl)phenyl]-5,6,7a,8,9,10,11,11a-octahydro-4H-pyrido[3',4':4,5]pyrrolo[3,2,1-ij]quinoline;

(7aS,11aR)-2-[4-methoxy-2-(trifluoromethyl)phenyl]-10-propyl-5,6,7a,8,9,10,11,11a-octahydro-4H-pyrido[3',4':4,5]pyrrolo[3,2,1-ij]quinoline;

(7aS,11aR)-10-butyl-2-[4-methoxy-2-(trifluoromethyl)phenyl]-10-methyl-5,6,7a,8,9,10,11,11a-octahydro-4H-pyrido[3',4':4,5]pyrrolo[3,2,1-ij]quinoline;

(7aS,11aR)-2-[4-methoxy-2-(trifluoromethyl)phenyl]-10-(4-pentenyl)-5,6,7a,8,9,10,11,11a-octahydro-4H-pyrido[3',4':4,5]pyrrolo[3,2,1-ij]quinoline;

(7aS,11aR)-2-[4-methoxy-2-(trifluoromethyl)phenyl]-10-(3-methyl-2-butenyl)-5,6,7a,8,9,10,11,11a-octahydro-4H-pyrido[3',4':4,5]pyrrolo[3,2,1-ij]quinoline;

(7aS,11aR)-10-(2-fluoroethyl)-2-[4-methoxy-2-(trifluoromethyl)phenyl]-5,6,7a,8,9,10,11,11a-octahydro-4H-pyrido[3',4':4,5]pyrrolo[3,2,1-ij]quinoline;

(7aS,11aR)-10-(2,2-difluoroethyl)-2-[4-methoxy-2-(trifluoromethyl)phenyl]-5,6,7a,8,9,10,11,11a-octahydro-4H-pyrido[3',4':4,5]pyrrolo[3,2,1-ij]quinoline;

(7aS,11aR)-10-(cyclobutylmethyl)-2-[4-methoxy-2-(trifluoromethyl)phenyl]-5,6,7a,8,9,10,11,11a-octahydro-4H-pyrido[3',4':4,5]pyrrolo[3,2,1-ij]quinoline;

4-((7aS,11aR)-5,6,8,9,11,11a-hexahydro-4H-pyrido[3',4':4,5]pyrrolo[3,2,1-ij]quinolin-10(7aH)-yl)-1-(4-fluorophenyl)-1-butanone;

4-((7aR,11aS)-5,6,8,9,11,11a-hexahydro-4H-pyrido[3',4':4,5]pyrrolo[3,2,1-ij]quinolin-10(7aH)-yl)-1-(4-fluorophenyl)-1-butanone;

4-((7aS,11aR)-5,6,8,9,11,11a-hexahydro-4H-pyrido[3',4':4,5]pyrrolo[3,2,1-ij]quinolin-10(7ah)-yl)-1-(2-aminophenyl)-1-butanone;

4-((7aR,11aS)-5,6,8,9,11,11a-hexahydro-4H-pyrido[3',4':4,5]pyrrolo[3,2,1-ij]quinolin-10(7aH)-yl)-1-(2-aminophenyl)-1-butanone;

(±)-cis-3-(5,6,8,9,11,11a-hexahydro-4H-pyrido[3',4':4,5]pyrrolo[3,2,1-ij]quinolin-10(7aH)-yl)propyl 4-fluorophenyl ether;

4-((±)-cis-5,6,8,9,11,11a-hexahydro-4H-pyrido[3',4':4,5]pyrrolo[3,2,1-ij]quinolin-10(7aH)-yl)-1-(4-pyridinyl)-1-butanone;

(±)-cis-10-[3-(6-fluoro-1,2-benzisoxazol-3-yl)propyl]-5,6,7a,8,9,10,11,11a-octahydro-4H-pyrido[3',4':4,5]pyrrolo[3,2,1-ij]quinoline;

(7aS,11aR)-10-[3-(6-fluoro-1,2-benzisoxazol-3-yl)propyl]-5,6,7a,8,9,10,11,11a-octahydro-4H-pyrido[3',4':4,5]pyrrolo[3,2,1-ij]quinoline;

(±)-cis-4-(4,5,6,7,9,10,12,12a-octahydroazepino[3,2,1-hi]pyrido[4,3-b]indol-11(8aH)-yl)-1-(4-fluorophenyl)-1-butanone;

4-((8aS,12aR)-4,5,6,7,9,10,12,12a-octahydroazepino[3,2,1-hi]pyrido[4,3-b]indol-11(8aH)-yl)-1-(4-fluorophenyl)-1-butanone;

4-((8aR,12aS)-4,5,6,7,9,10,12,12a-octahydroazepino[3,2,1-hi]pyrido[4,3-b]indol-11(8aH)-yl)-1-(4-fluorophenyl)-1-butanone;

4-((±)4,5,6,7,9,10,12,12a-octahydroazepino[3,2,1-hi]pyrido[4,3-b]indol-11(8aH)-yl)-1-(2-amino-4-fluorophenyl)-1-butanone;

4-((±)-cis-5,6,8,9,11,11a-hexahydro-4H-pyrido[3',4':4,5]pyrrolo[3,2,1-ij]quinolin-10(7aH)-yl)-1-(2-amino-4-fluorophenyl)-1-butanone;

4-((7aS,11aR)-5,6,8,9,11,11a-hexahydro-4H-pyrido[3',4':4,5]pyrrolo[3,2,1-ij]quinolin-10(7aH)-yl)-1-(2-amino-4-fluorophenyl)-1-butanone; and 4-((7aR,11aS)-5,6,8,9,11,11a-hexahydro-4H-pyrido[3',4':4,5]pyrrolo[3,2,1-ij]quinolin-10(7aH)-yl)-1-(2-amino-4-fluorophenyl)-1-butanone.

16. The method as defined in claim 1 where the compound administered is selected from the group:

4-[(±)-5,6,8,9,10,11,12,12a-octahydro-4H,7aH-azepino[4',5':4,5]pyrrolo[3,2,1-ij]quinolin-10-yl]-1-(4-fluorophenyl)-1-butanone;

4-[(±)-5,6,8,9,10,11,12,12a-octahydro-4H,7aH-azepino[4',5':4,5]pyrrolo[3,2,1-ij]quinolin-10-yl]-1-(2-amino-4-fluorophenyl)-1-butanone;

4-[(±)-4,5,6,7,9,10,11,12,13,13a-decahydro-11H-diazepino[4,5-b:3,2,1-hi]indol-11-yl]-1-(4-fluorophenyl)-1-butanone;

4-[(±)-4,5,6,7,9,10,11,12,13,13a-decahydro-11H-diazepino[4,5-b:3,2,1-hi]indol-11-yl]-1-(2-amino-4-fluorophenyl)-1-butanone;

tert-butyl(±)-cis-5,6,8,9,10,11,12,12a-octahydro-4H,7aH-azepino[3',4':4,5]pyrrolo[3,2,1-ij]quinoline-11-carboxylate;

tert-butyl(±)-cis-2-bromo-5,6,8,9,10,11,12,12a-octahydro-4H,7aH-azepino[3',4':4,5]pyrrolo[3,2,1-ij]quinoline-11-carboxylate; and (±)-cis-2-[4-methoxy-2-(trifluoromethyl)phenyl]-5,6,8,9,10,11,12,12a-octahydro-4H,7aH-azepino[3',4':4,5]pyrrolo[3,2,1-ij]quinoline.

17. The method as defined in claim 1 where the compound administered is selected from the group:

tert-butyl(±)-cis-2-bromo-4-oxo-4,5,6,7,9,10,12,12a-octahydroazepino[3,2,1-hi]pyrido[4,3-b]indole-11(8aH)-carboxylate;

tert-butyl(±)-cis-2-(2,4-dichlorophenyl)-4-oxo-4,5,6,7,9,10,12,12a-octahydroazepino[3,2,1-hi]pyrido[4,3-b]indole-11(8aH)-carboxylate;

(±)-cis-2-(2,4-dichlorophenyl)-6,7,8a,9,10,11,12,12a-octahydroazepino[3,2,1-hi]pyrido[4,3-b]indol-4(5H)-one;

(8aS,12aR)-2-(2,4-dichlorophenyl)-6,7,8a,9,10,11,12,12a-octahydroazepino[3,2,1-hi]pyrido[4,3-b]indol-4(5H)-one;

(8aR,12aS)-2-(2,4-dichlorophenyl)-6,7,8a,9,10,11,12,12a-octahydroazepino[3,2,1-hi]pyrido[4,3-b]indol-4(5H)-one;

(8aS,12aR)-2-(2,4-dichlorophenyl)-6,7,8a,9,10,11,12,12a-decahydroazepino[3,2,1-hi]pyrido[4,3-b]indol-4-ol; and (8aR,12aS)-2-(2,4-dichlorophenyl)-6,7,8a,9,10,11,12,12a-decahydroazepino[3,2,1-hi]pyrido[4,3-b]indol-4-ol.

* * * * *

UNITED STATES PATENT AND TRADEMARK OFFICE
CERTIFICATE OF CORRECTION

PATENT NO.            : 7,081,455 B2                                Page 1 of 1
APPLICATION NO.       : 10/786935
DATED                 : July 25, 2006
INVENTOR(S)           : Rajagopalan et al.

It is certified that error appears in the above-identified patent and that said Letters Patent is hereby corrected as shown below:

Title page, item 75

The inventorship should be amended to read as follows:

--Parthasarathi Rajagopalan, Madras (IN); Albert J. Robichaud, Ringoes, NJ (US); Taekyu Lee, Doylestown, PA (US); Wei Deng, Lexington, MA (US); Ian S. Mitchell, Lafayette, CO (US); Wenting Chen, Langhorne, PA (US); Christopher D. McClung, Chicago, IL (US); Emilie J. Calvello, Baltimore, MD (US); David M. Zawrotny, Ann Arbor, MI (US)--

Signed and Sealed this
Twenty-fourth Day of November, 2015

Michelle K. Lee
*Director of the United States Patent and Trademark Office*